(12) United States Patent
Bigot et al.

(10) Patent No.: US 10,941,139 B2
(45) Date of Patent: Mar. 9, 2021

(54) CRYPTOPHYCIN COMPOUNDS AND CONJUGATES, THEIR PREPARATION AND THEIR THERAPEUTIC USE

(71) Applicant: SANOFI, Paris (FR)

(72) Inventors: Antony Bigot, Paris (FR); Hervé Bouchard, Paris (FR); Marie-Priscille Brun, Paris (FR); François Clerc, Paris (FR); Jidong Zhang, Paris (FR)

(73) Assignee: SANOFI, Paris (FR)

( * ) Notice: Subject to any disclaimer, the term of this patent is extended or adjusted under 35 U.S.C. 154(b) by 118 days.

(21) Appl. No.: 15/768,792

(22) PCT Filed: Nov. 3, 2016

(86) PCT No.: PCT/EP2016/076603
§ 371 (c)(1),
(2) Date: Apr. 16, 2018

(87) PCT Pub. No.: WO2017/076998
PCT Pub. Date: May 11, 2017

(65) Prior Publication Data
US 2019/0382391 A1 Dec. 19, 2019

(30) Foreign Application Priority Data
Nov. 5, 2015 (EP) ..................................... 15306751

(51) Int. Cl.
*C07D 413/06* (2006.01)
*C07D 413/14* (2006.01)
*A61P 35/00* (2006.01)

(52) U.S. Cl.
CPC ............ *C07D 413/06* (2013.01); *A61P 35/00* (2018.01); *C07D 413/14* (2013.01)

(58) Field of Classification Search
CPC ...... A61P 35/00; C07D 413/06; C07D 413/14
See application file for complete search history.

(56) References Cited

U.S. PATENT DOCUMENTS

| 6,013,626 A * | 1/2000 | Moore | C07D 273/00 514/19.2 |
|---|---|---|---|
| 7,230,101 B1 | 6/2007 | Murthi et al. | |
| 2002/0128185 A1 | 9/2002 | Shih | |

FOREIGN PATENT DOCUMENTS

| WO | 2005077090 A2 | 8/2005 |
| WO | 2007127440 A2 | 11/2007 |
| WO | 2008010101 A2 | 1/2008 |
| WO | 2011001052 A1 | 1/2011 |
| WO | 2011039724 A1 | 4/2011 |
| WO | 2017076998 A1 | 5/2017 |

OTHER PUBLICATIONS

Kotoku et al., (2006) "Synthesis of 15,20-triamide analogue with polar substituent on the phenyl ring of arenastatin A, an extremely potent cytotoxic spongean depsipeptide," Bioorganic and Medicinal Chemistry, 14:7446-7457.

Vishal A. Verma et al., (2015) "The cryptophycins as potent payloads for antibody drug conjugates," Bioorganic and Medicinal Chemistry Letters, 25(4):864-868.

McCombs et al. (2015) "Antibody Drug Conjugates: Design and Selection of Linker, Payload and Conjugation Chemistry," The AAPS Journal, 17(2):339-351.

International Search Report for International Application No. PCT/EP2016/076603, dated Dec. 6, 2016, 4 pages.

Al-Awar et al., (2003) "A Convergent Approach to Cryptophycin 52 Analogues: Synthesis and biological Evaluation of a Novel Series of Fragment a Epoxides and Chlorohydrins," J. Med. Chem., 46:2985-3007.

Boinpally et al., (2003) "Pharmacokinetics and tissue distribution of cryptophycin 52 (C-52) epoxide and cryptophycin 55 (C-55) chlorohydrin in mice with subcutaneous tumors," Cancer Chemother Pharmacol, 52:25-33.

Edelman et al., (2003) "Phase 2 study of cryptophycin 52 (LY355703) in patients previously treated with platinum based chemotherapy for advanced non-small cell lung cancer," Lung Cancer, 39:197-199.

Eibler et al., (2006) "The Synthesis of Cryptophycins," Synthesis, 22:3747-3789.

Sessa et al., (2002) "Phase 1 and pharmacological studies of the cryptophycin analogue LY355703 administered on a single intermittent or weekly schedule," European Journal of Cancer, 38:2388-2396.

Argawal et al., (2013) "Hydrazine-Pictet-Spengler Ligation as Biocompatible Method for the Generation of Stable Protein Conjugates," Bioconjugate Chemistry, 24:846-851.

Garnett et al., (2001) "Targeted drug conjugates: principles and progress," Advanced Drug Delivery Reviews, 53:171-216.

(Continued)

*Primary Examiner* — Erich A Leeser
(74) *Attorney, Agent, or Firm* — Lathrop GPM LLP; James H. Velema, Esq.

(57) ABSTRACT

The present invention relates to cryptophycin compounds of formula (I). The invention also relates to cryptophycin payloads, to cryptophycin conjugates, to compositions containing them and to their therapeutic use, especially as anticancer agents. The invention also relates to the process for preparing these conjugates.

(I)

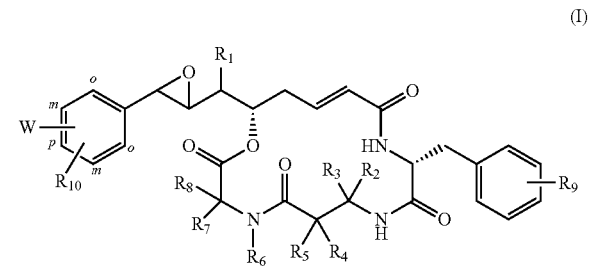

53 Claims, 25 Drawing Sheets

(56) References Cited

OTHER PUBLICATIONS

Argawal et al., (2015) "Site-Specific Antibody-Drug Conjugates: The Nexus of Bioothogonal Chemistry, Protein Engineering, and Drug Development," Biconjugate Chem., 26:176-192.
Axup et al., (2012) "Syntheis of site-specific antibody-drug conjugates using unnatural amino acids," PNAS, 109 (40)16101-16106.
Hudak et al., (2012) "Synthesis of Heterobifunctional Protein Fusions Using Copper-Free Click Chemistry and the Aldehyde Tag," Angew. Chem. Int. Ed., 51:4161-4165.
Jeger et al., (2010) "Site-Specific and Stoichiometric Modification of Antibodies by Bacterial Transglutaminase," Angew. Chem. Int. Ed., 49:9995-9997.
Junutula et al., (2008) "Site-specific conjugation of a cytotoxic drug to an antibody improves the therapeutic index," Nature Biotechnology, 26(8):925-932.
Strop et al., (2013) "Location Matters: Site of Conjugation Modulates Stability and Pharmacokinetics of Antibody Drug Conjugates," Chem. Biol., 20:161-167.
Zhou et al., (2014) "Site-Specific Antibody-Drug Conjugation through Glycoengineering," Bioconjugate Chem., 25:510-520.
Hu et al., (1999) "A Convenient Trimethylsilylthioxy-Dehalogenation Reaction for the Preparation of Functionalized Thiols," J. Org. Chem., 64:4959-4961.
Bal et al., (1981) "Oxidation of alpha-beta-unstaturated aldehydes," Tetrahedron, 37:2091-2096.
Richard et al., (2005) "Internalization of a Peptide into Multilamellar Vesicles Assisted by the Formation of an alpha-Oxo Oxime Bond," Chem. Eur. J., 11:7315-7321.
Sakellariou et al., (2003) "Novel peripherally functionalized seco-porphyrazines: synthesis, characterization and spectroscopic evaluation," Tetrahedron, 59:9083-9090.
Cromwell et al., (2006) "Protein Aggregation and Bioprocessing," The AAPS Journal, Article 66, E572-E579.
Litzen et al., (1993) "Separation and Quantitation of Monoclonal Antibody Aggregates by Asymmetrical Flow Field-Flow Fractionation and Comparison to Gel Permeation Chromatography," Analytical Biochemistry, 212:469-480.
Wang et al., (2008) "Fractionation of monoclonal antibody aggregates using membrane chromatography," Journal of Membrane Science, 318:311-316.
Carter et al., (2008) "Antibody-Drug Conjugates for Cancer Therapy," Cancer, 14:154-169.
Chari et al., (2008) "Targeted Cancer Therapy: Conferring Specificity to Cytotoxic Drugs," Chem. Res., 41:98-107.

\* cited by examiner

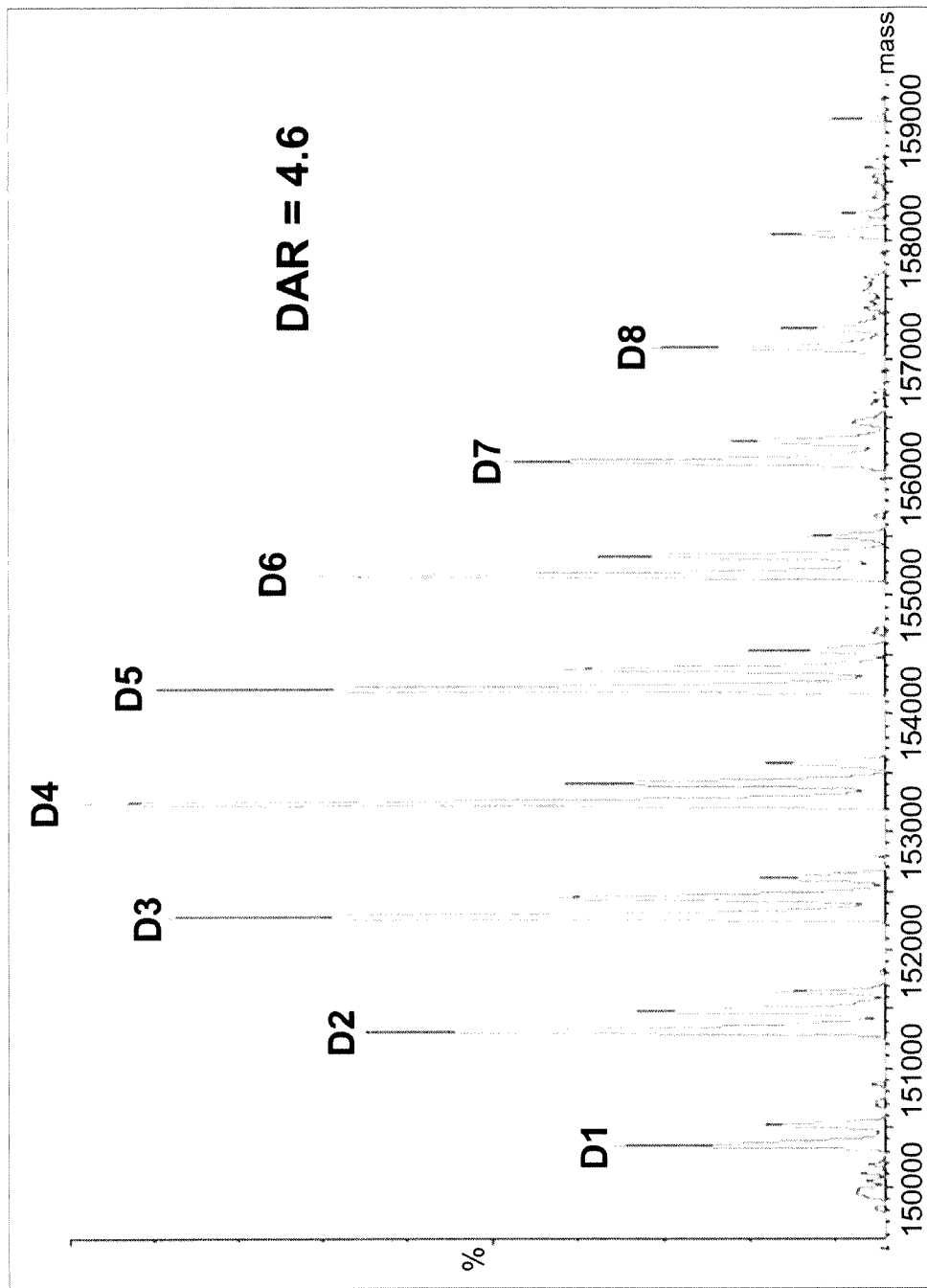
Figure 1: High resolution mass spectrum of Ex.3 (method B1)

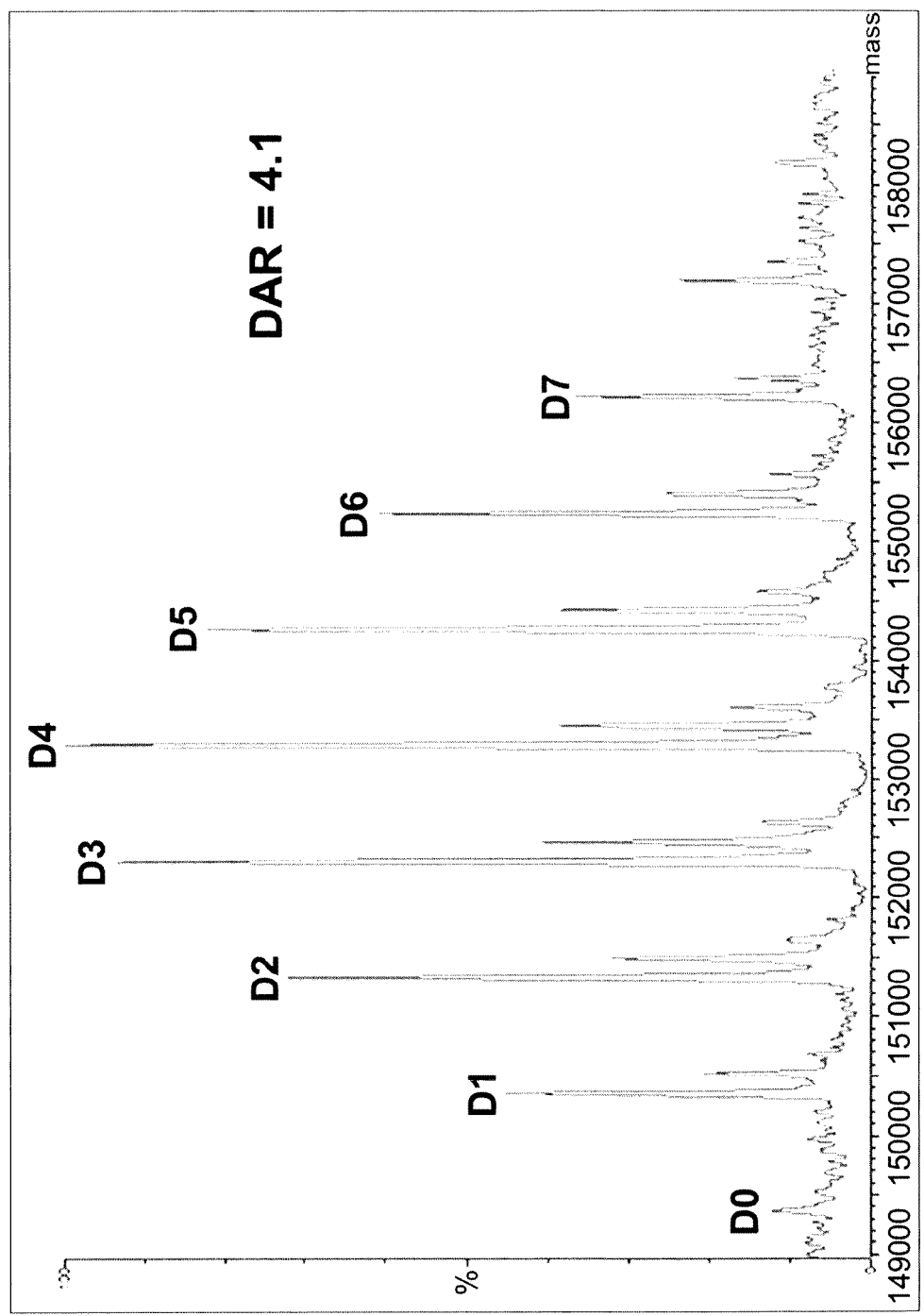
Figure 2: High resolution mass spectrum of Ex.7 (method B1)

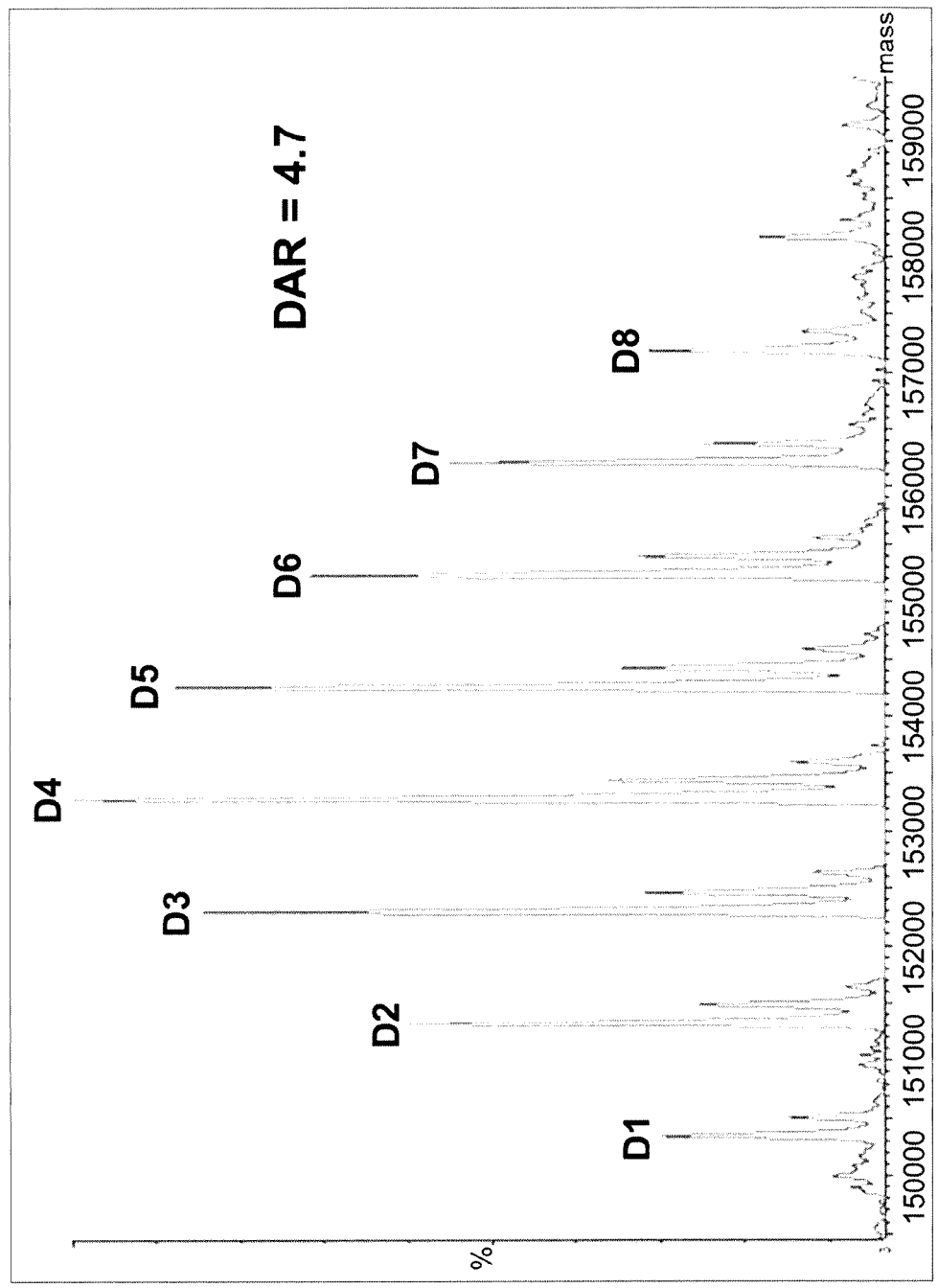
Figure 3: High resolution mass spectrum of Ex.10 (method B1)

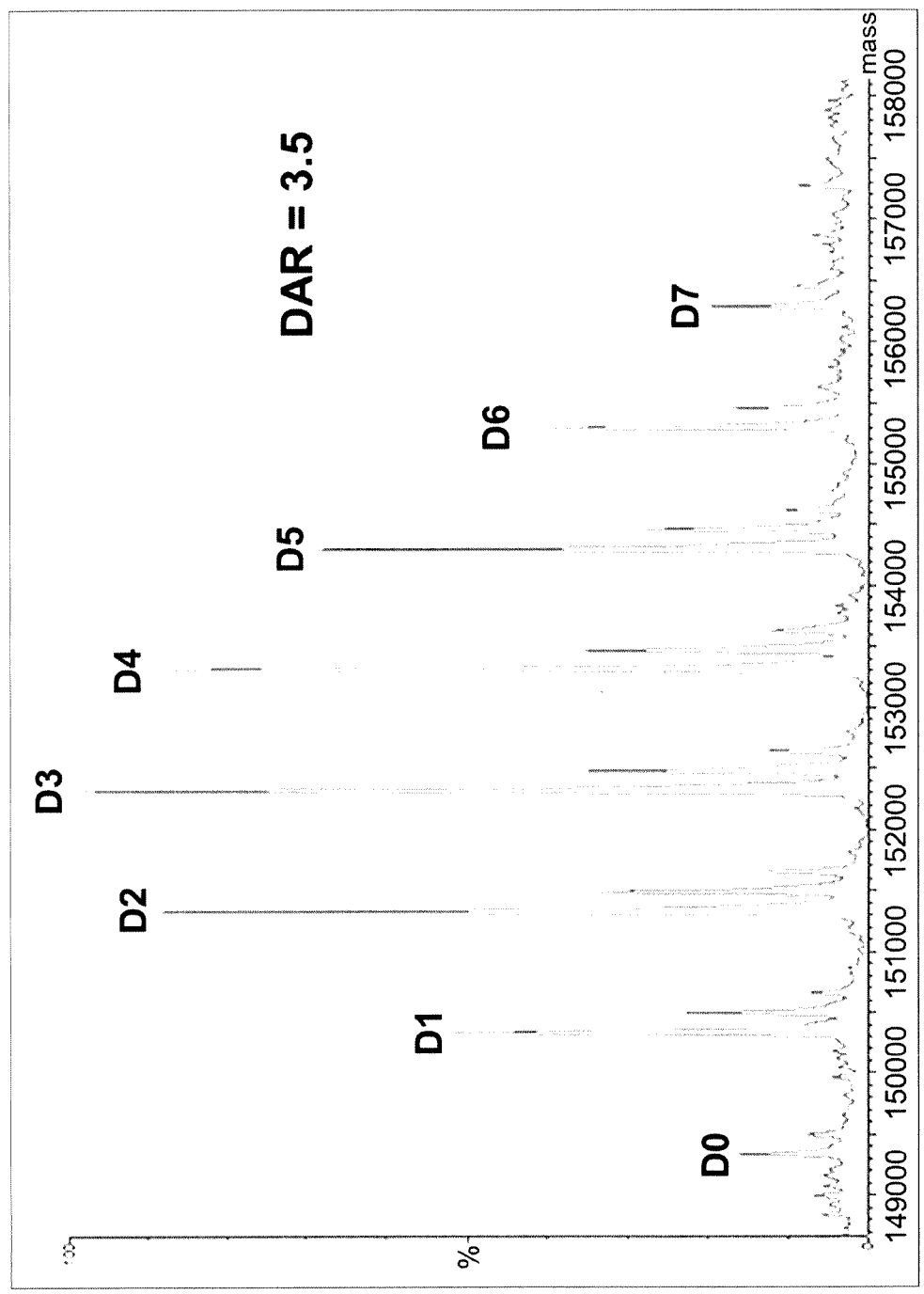
Figure 4: High resolution mass spectrum of Ex.14 (method B1)

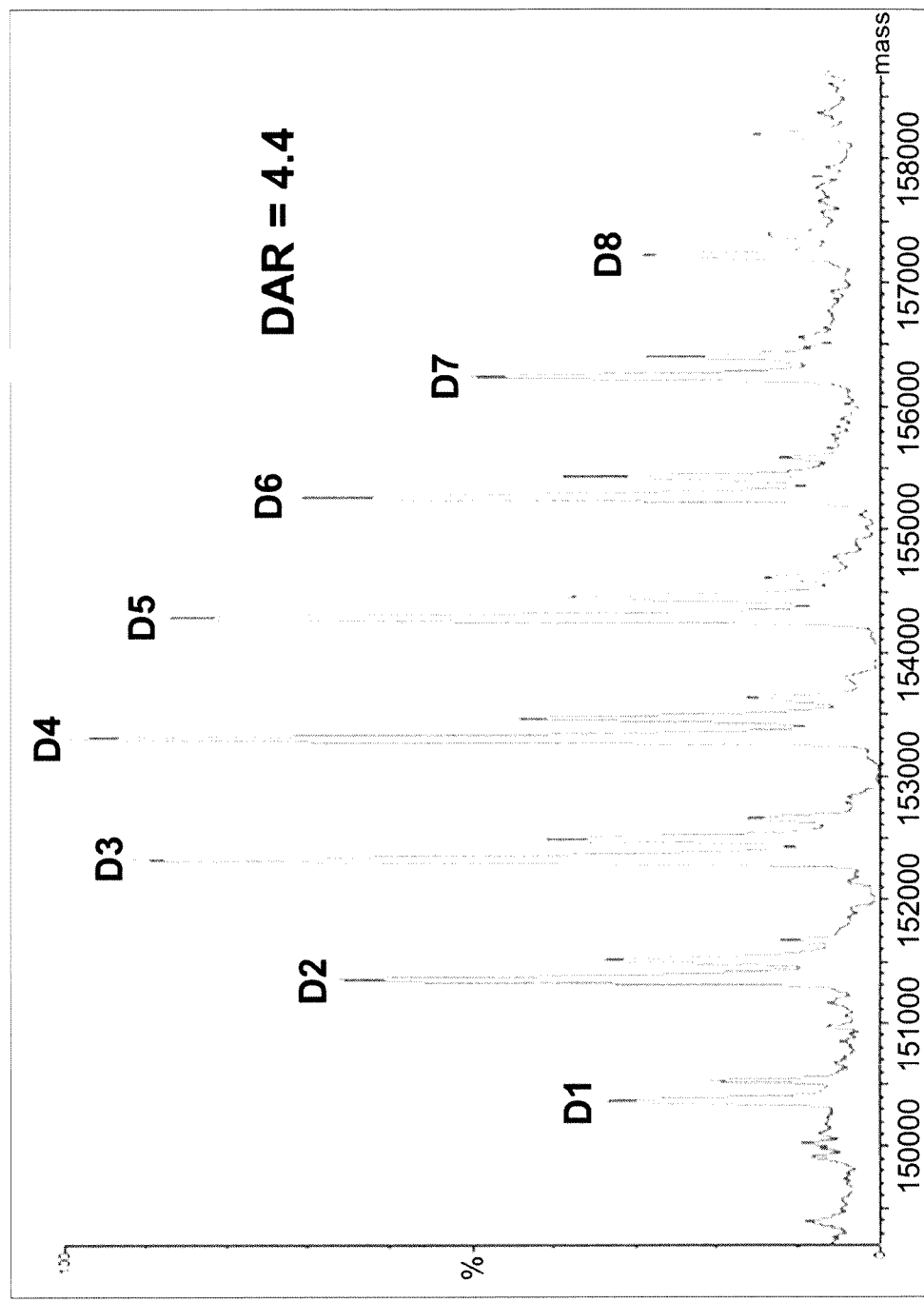
Figure 5: High resolution mass spectrum of Ex.20 (method B1)

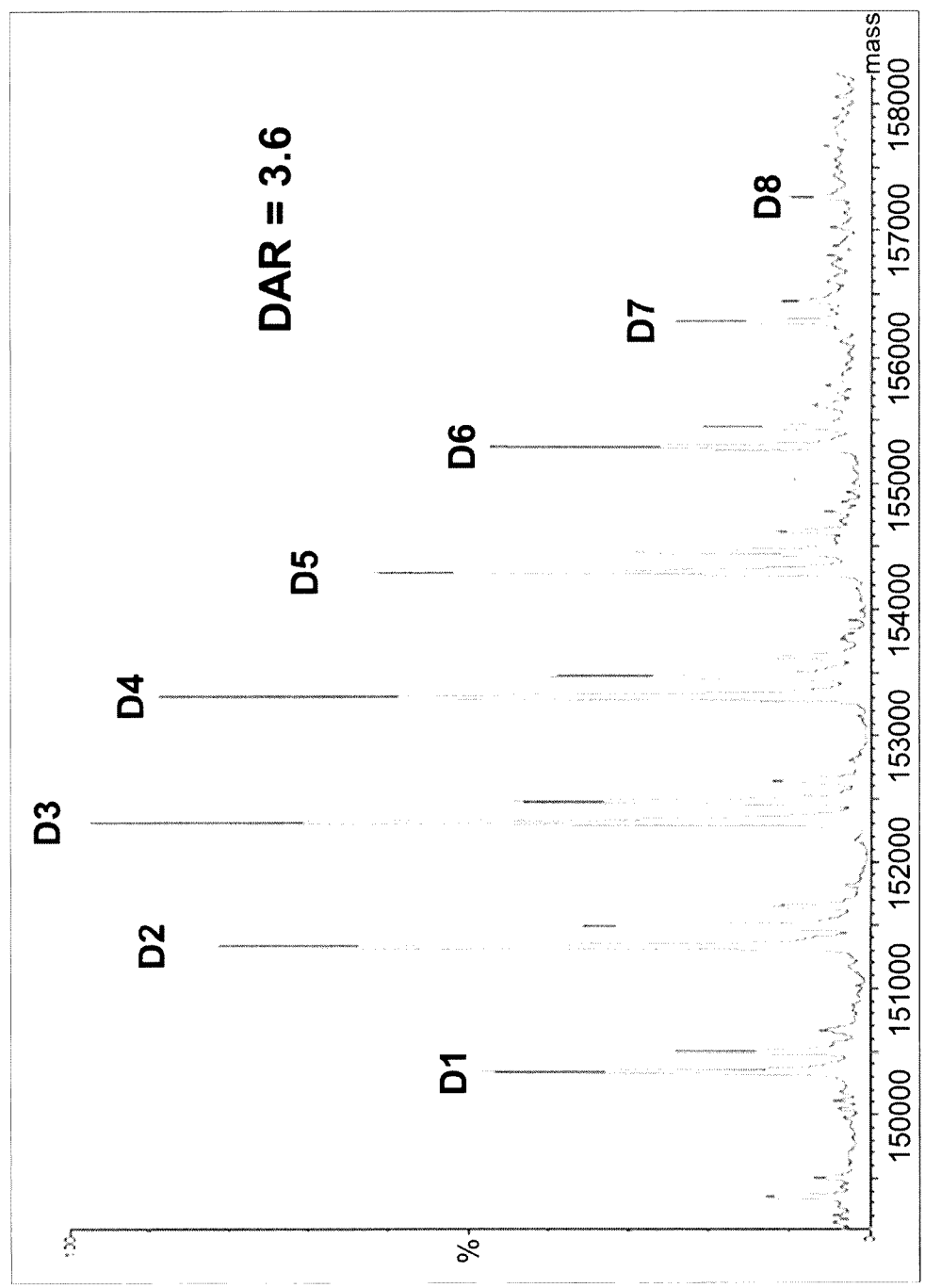
Figure 6: High resolution mass spectrum of Ex.23 (method B1)

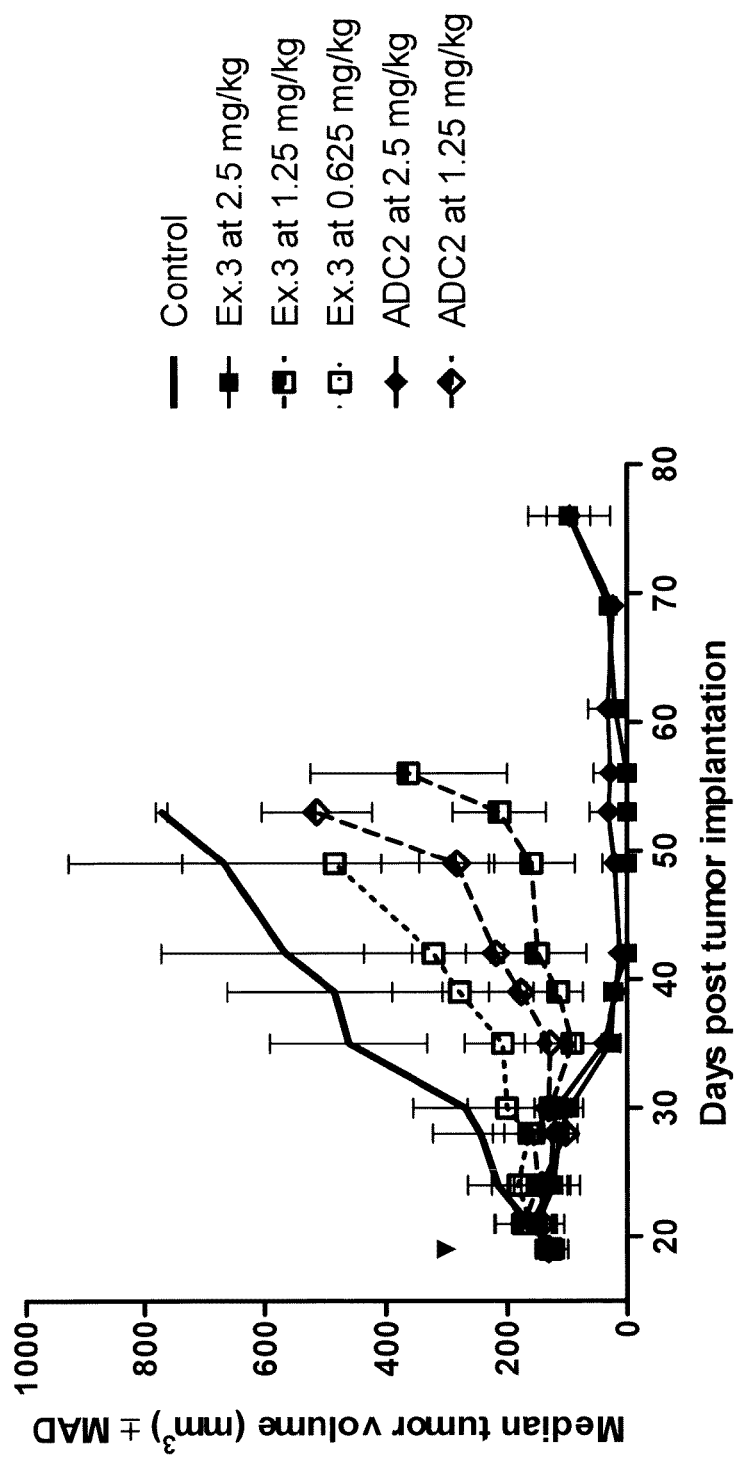
Figure 7: *In vivo* efficacy of Ex.3 against MDA-MB-231 xenograft in SCID mice

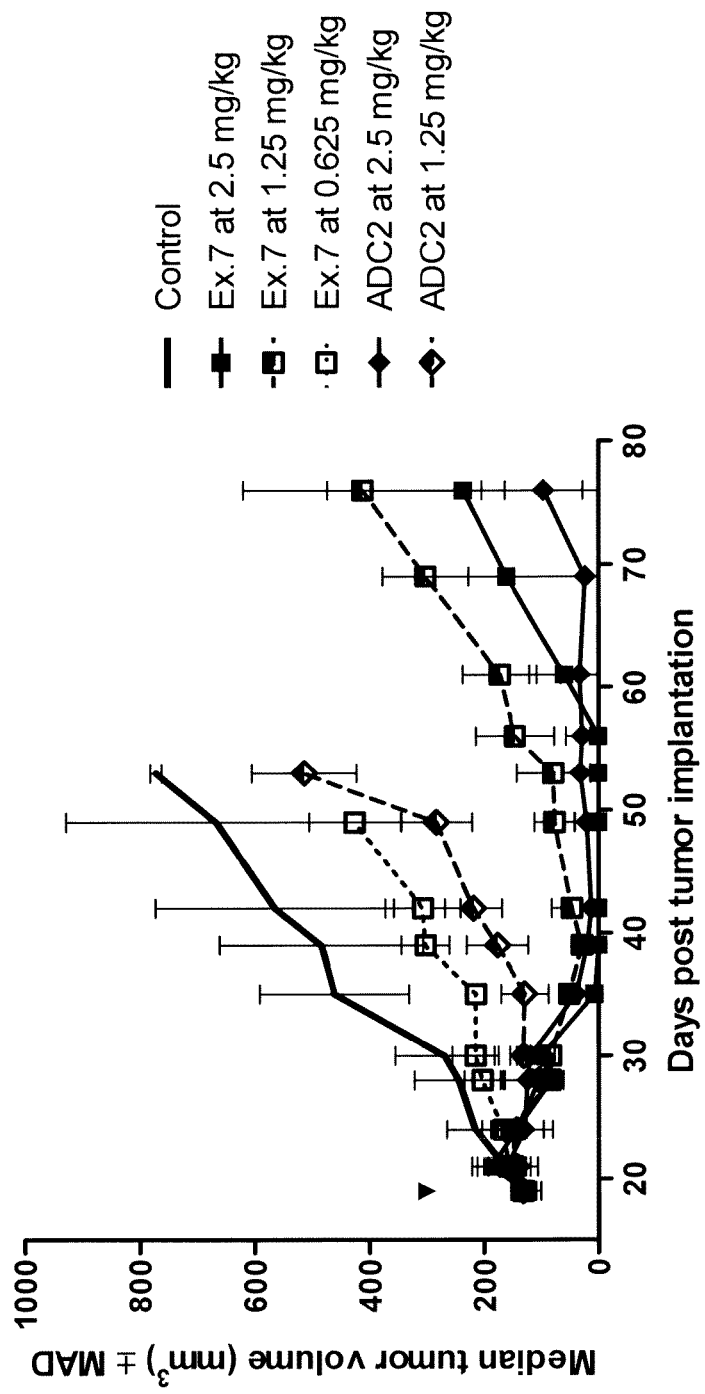
Figure 8: *In vivo* efficacy of Ex.7 against MDA-MB-231 xenograft in SCID mice

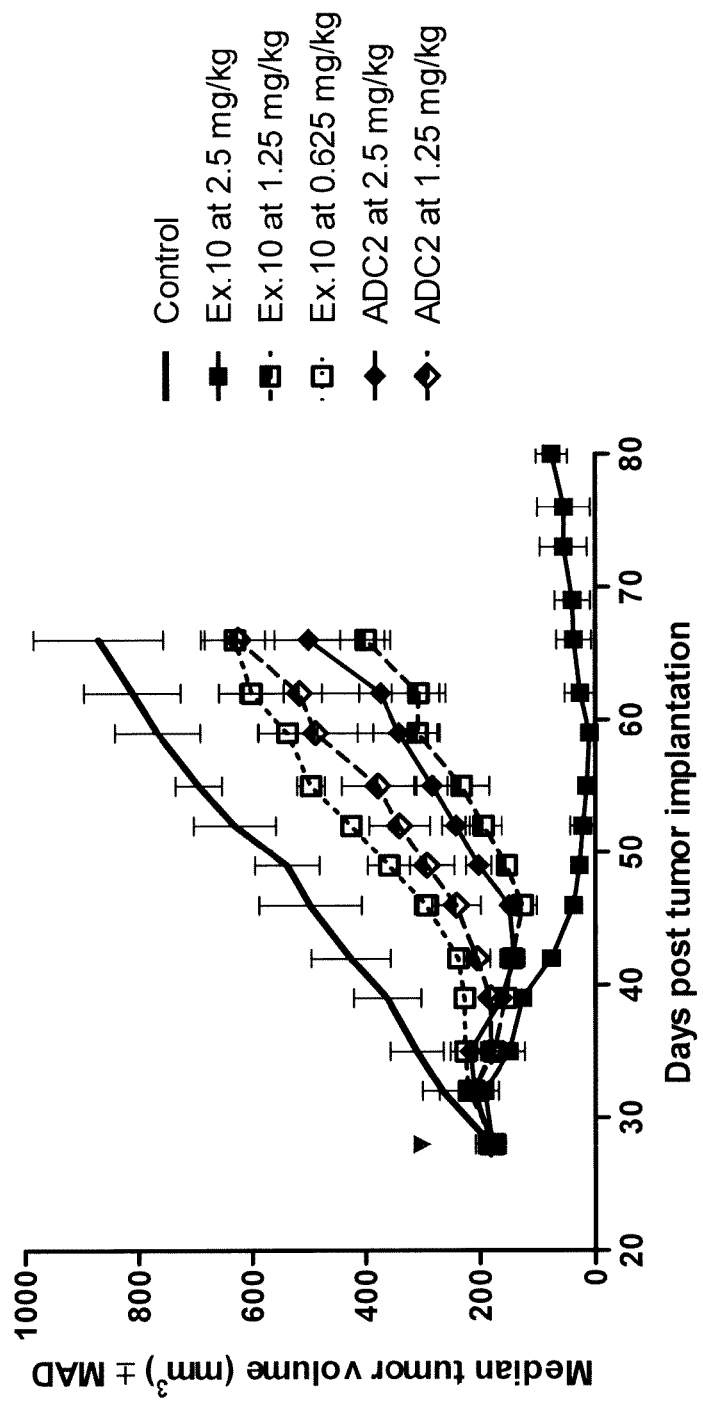
Figure 9: *In vivo* efficacy of Ex.10 against MDA-MB-231 xenograft in SCID mice

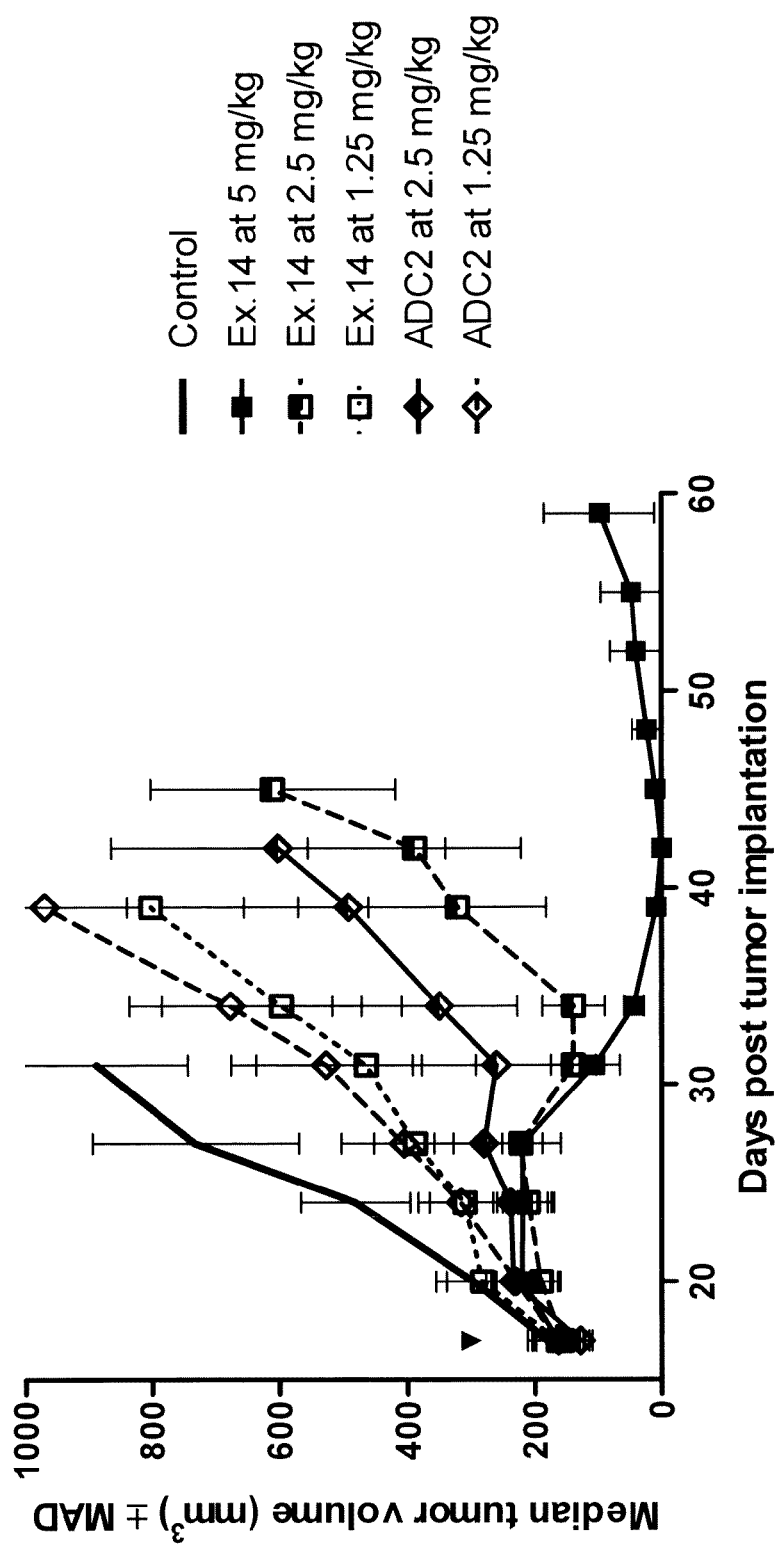
Figure 10: *In vivo* efficacy of Ex.14 against MDA-MB-231 xenograft in SCID mice

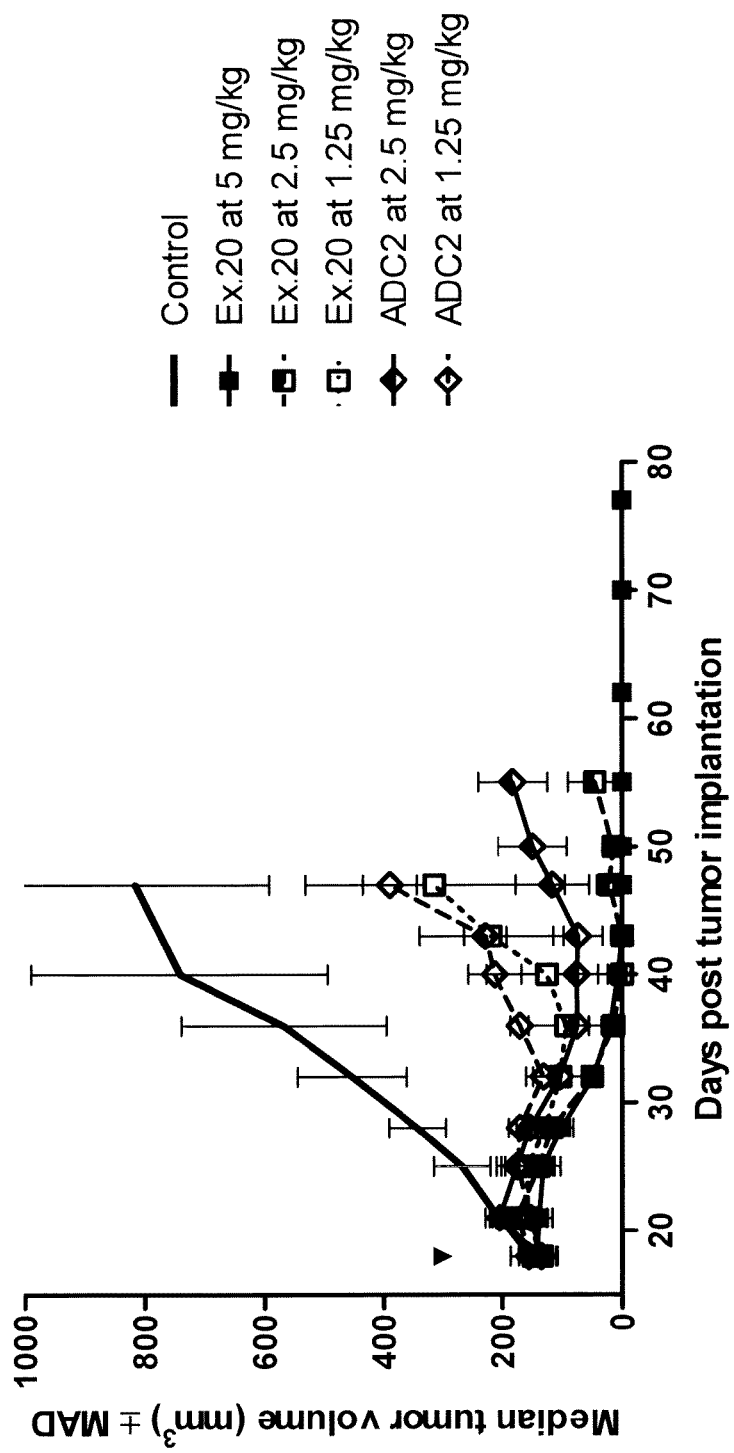
Figure 11: *In vivo* efficacy of Ex.20 against MDA-MB-231 xenograft in SCID mice

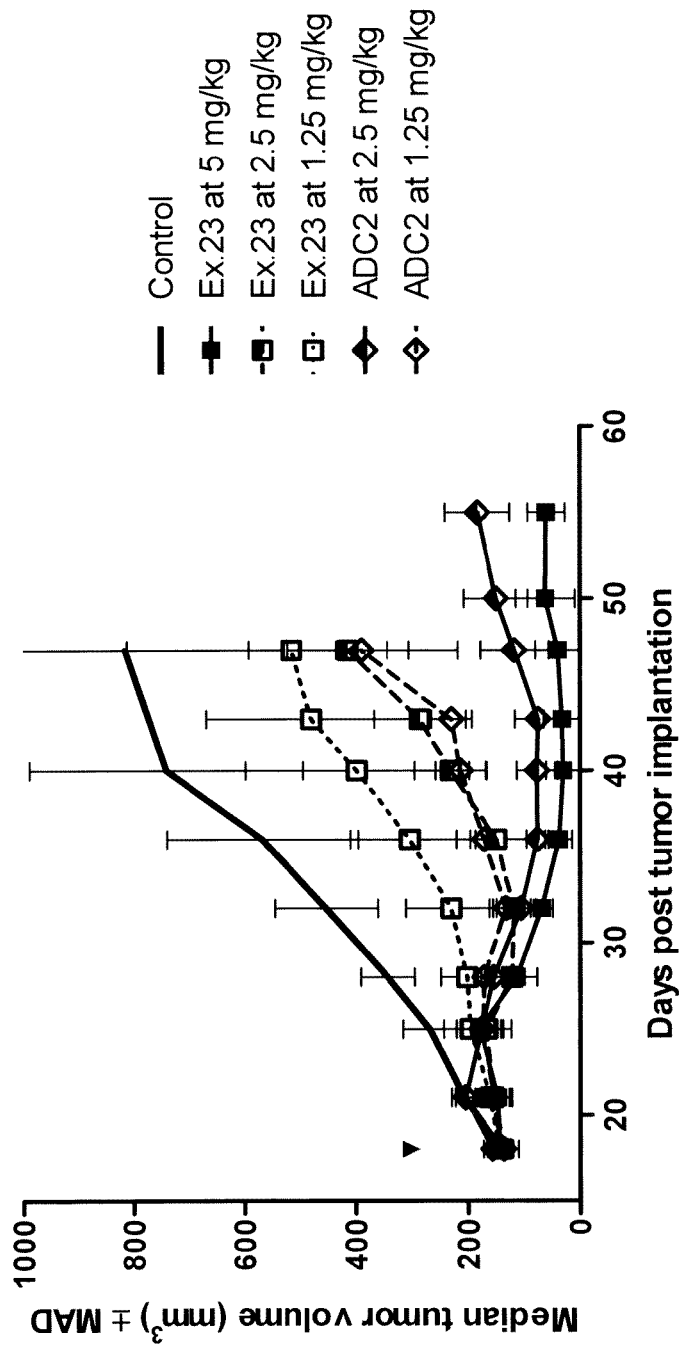
Figure 12: *In vivo* efficacy of Ex.23 against MDA-MB-231 xenograft in SCID mice

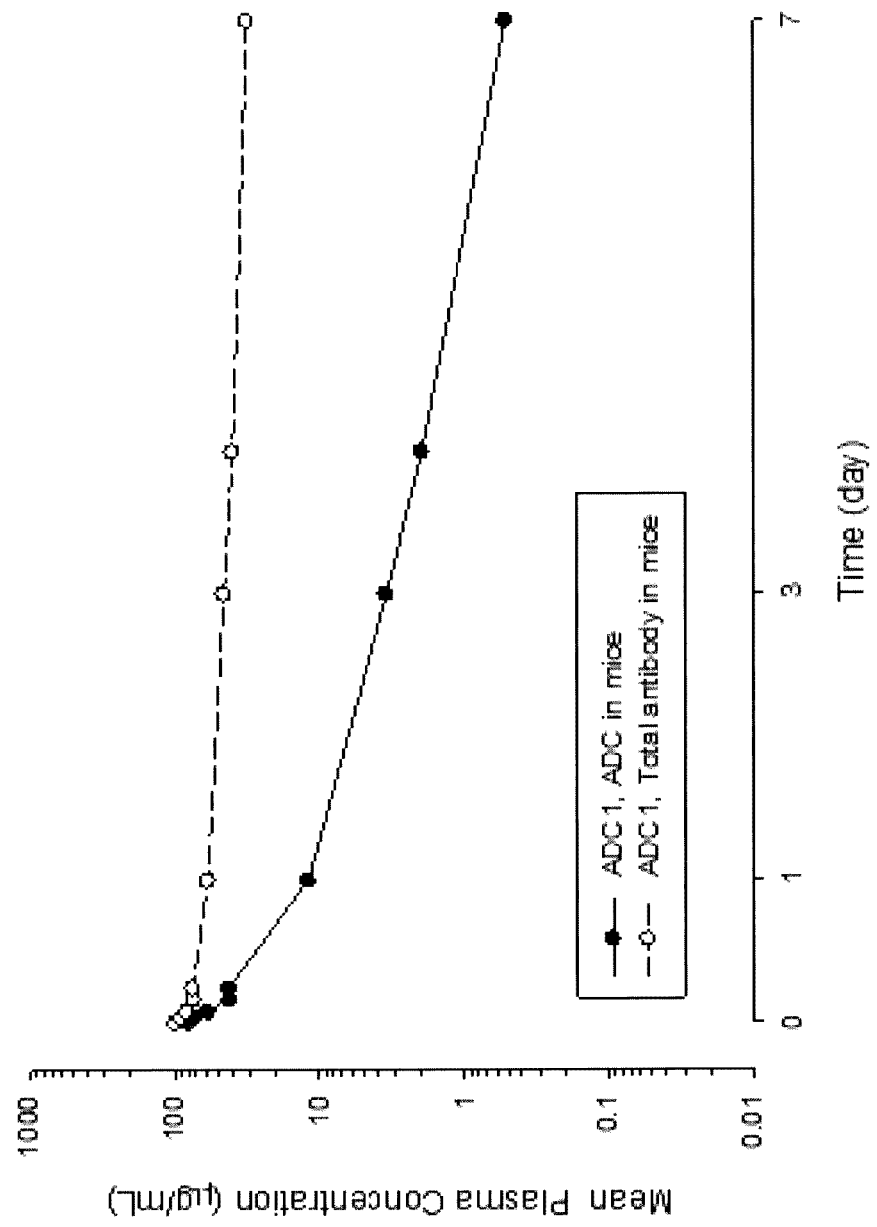
Figure 13: *In vivo* PK profile of ADC1 following a single i.v. administration in SCID mice (10 mg/kg)

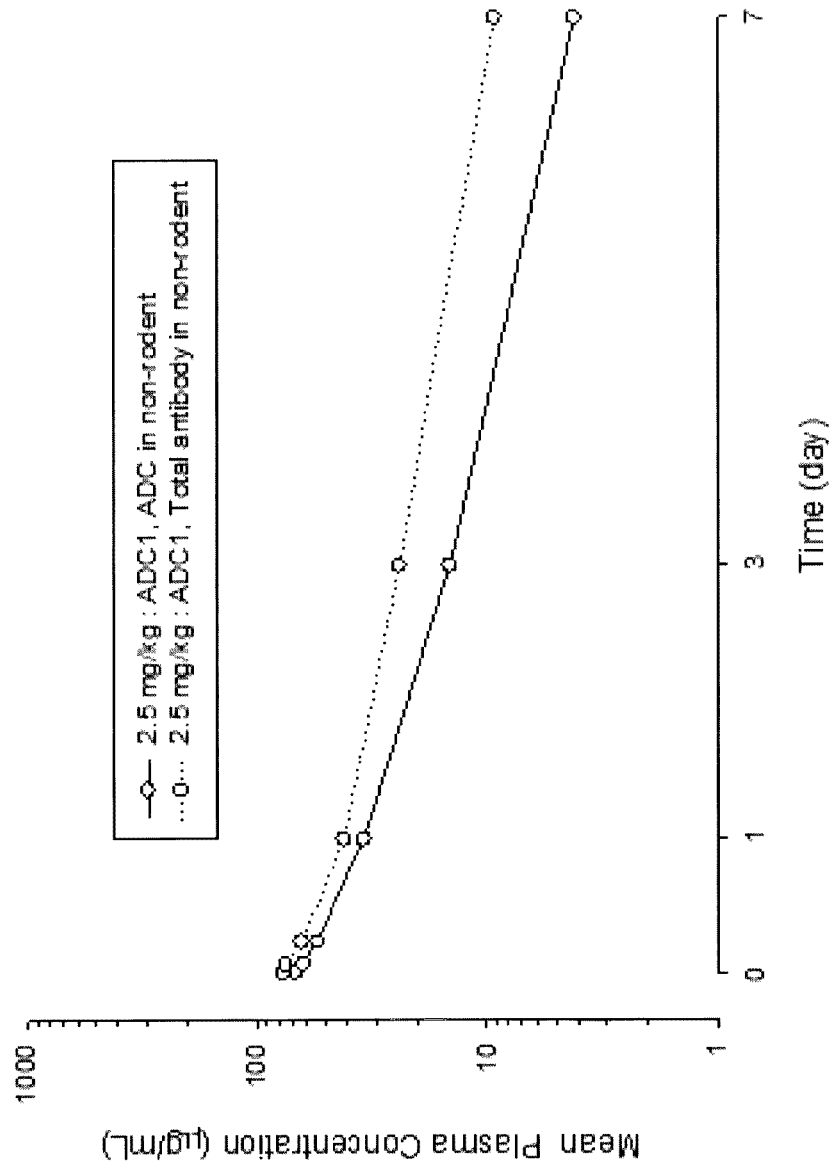
Figure 14: *In vivo* PK profile of ADC1 following a single i.v. administration in non-rodent species (2.5 mg/kg)

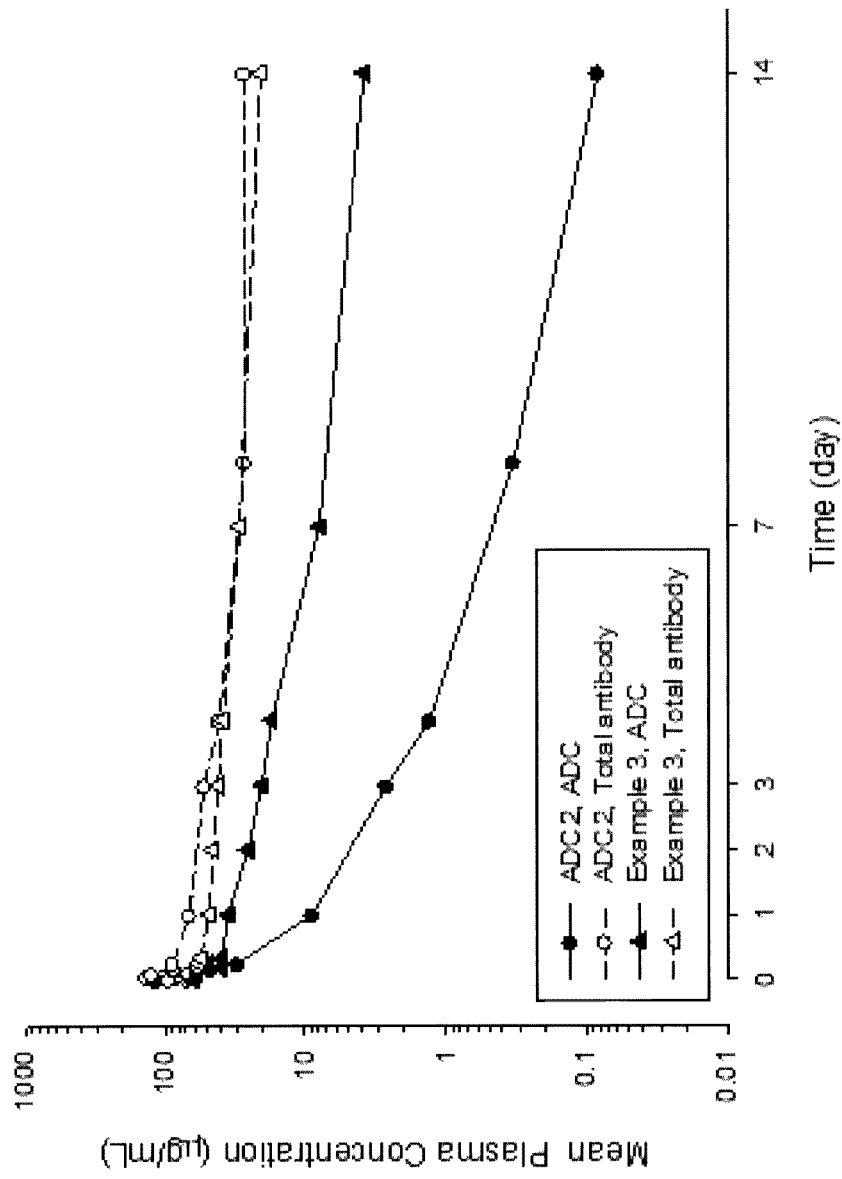
Figure 15: *In vivo* PK profile of Ex.3 following a single i.v. administration in SCID mice (5 mg/kg)

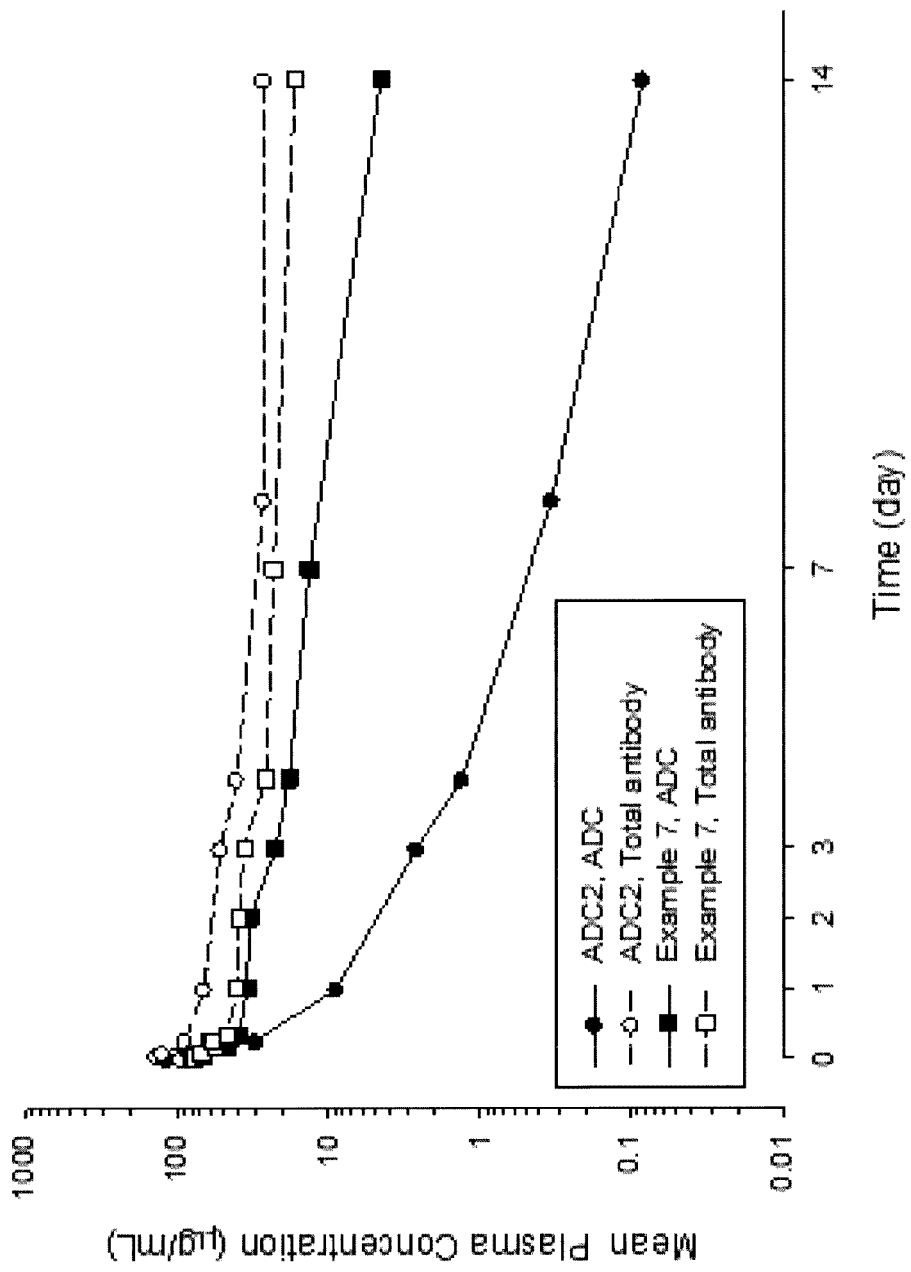
Figure 16: *In vivo* PK profile of Ex.7 following a single i.v. administration in SCID mice (5 mg/kg)

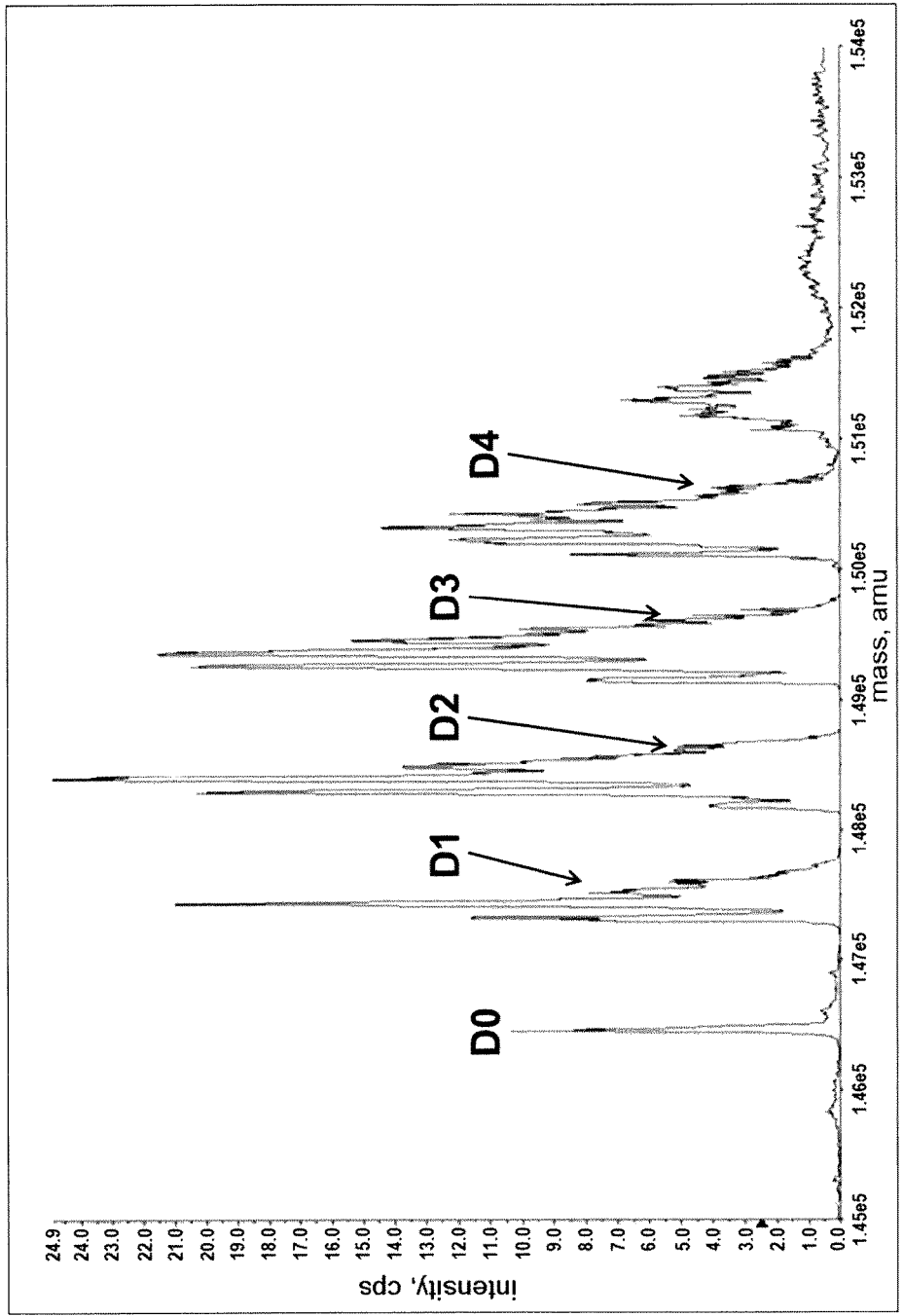
Figure 17: HRMS spectrum of deglycosylated ADC1 at 96 h following a single i.v. administration in SCID mice at 10 mg/kg (method B2)

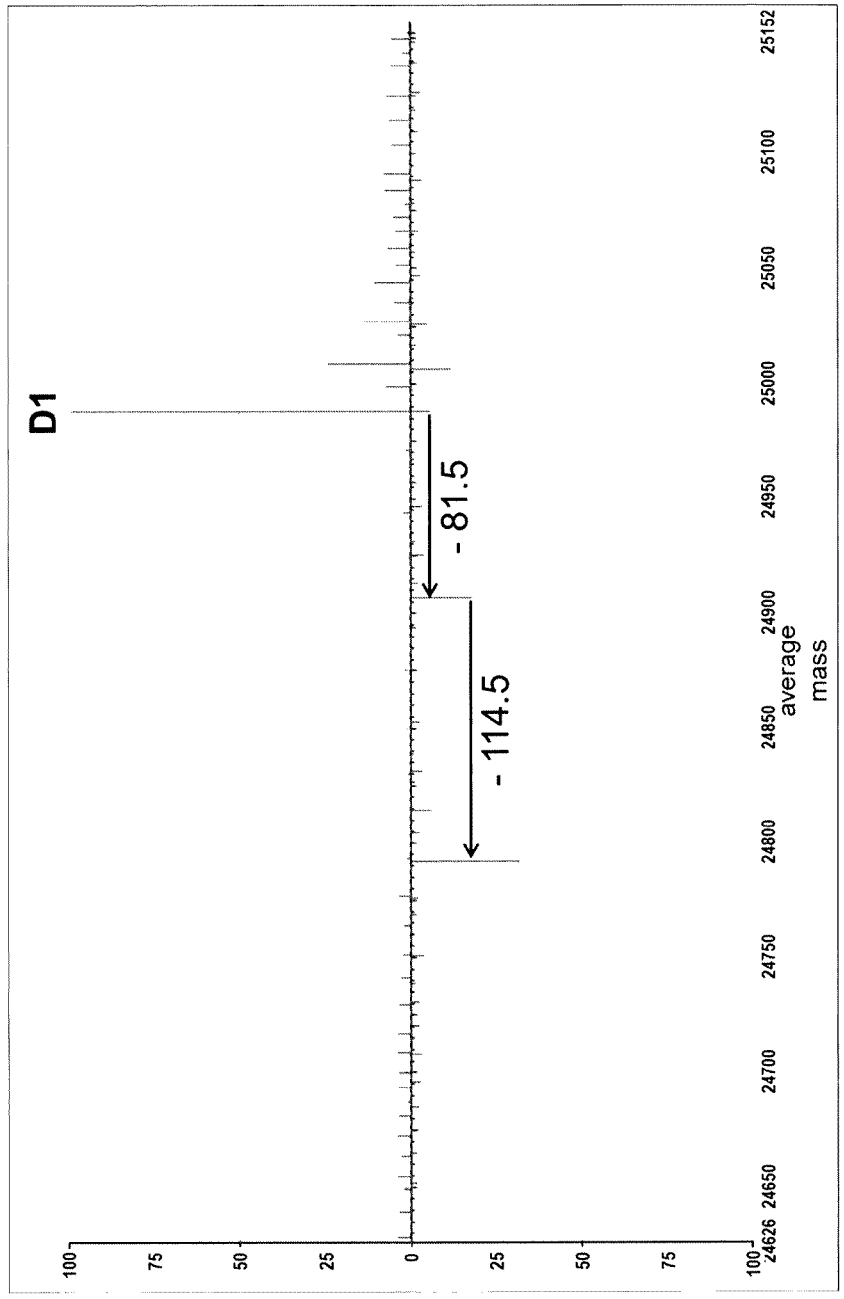
Figure 18: HRMS spectrum of ADC2 light chain at 96 h following a single i.v. administration in SCID mice at 10 mg/kg (method B2)

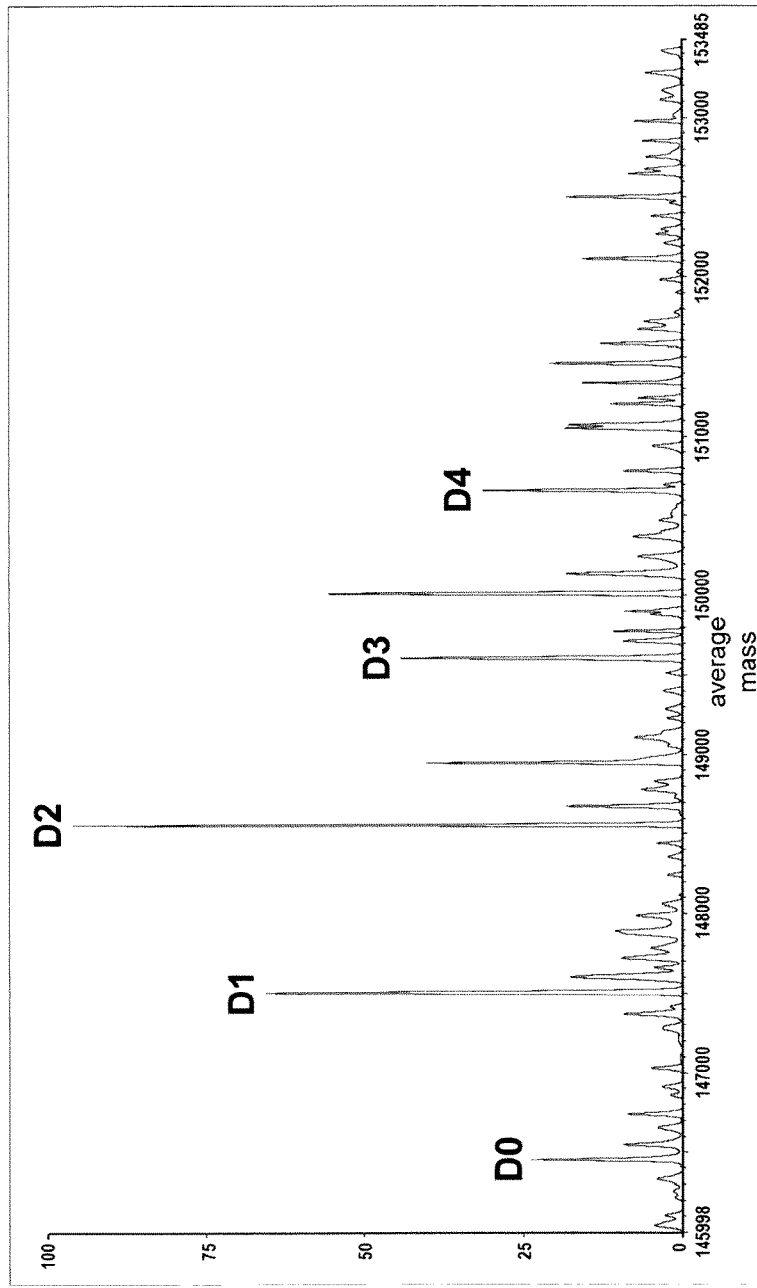
Figure 19: HRMS spectrum of deglycosylated ADC1 at 6 d following a single i.v. administration in non-rodent species at 5 mg/kg (method B2)

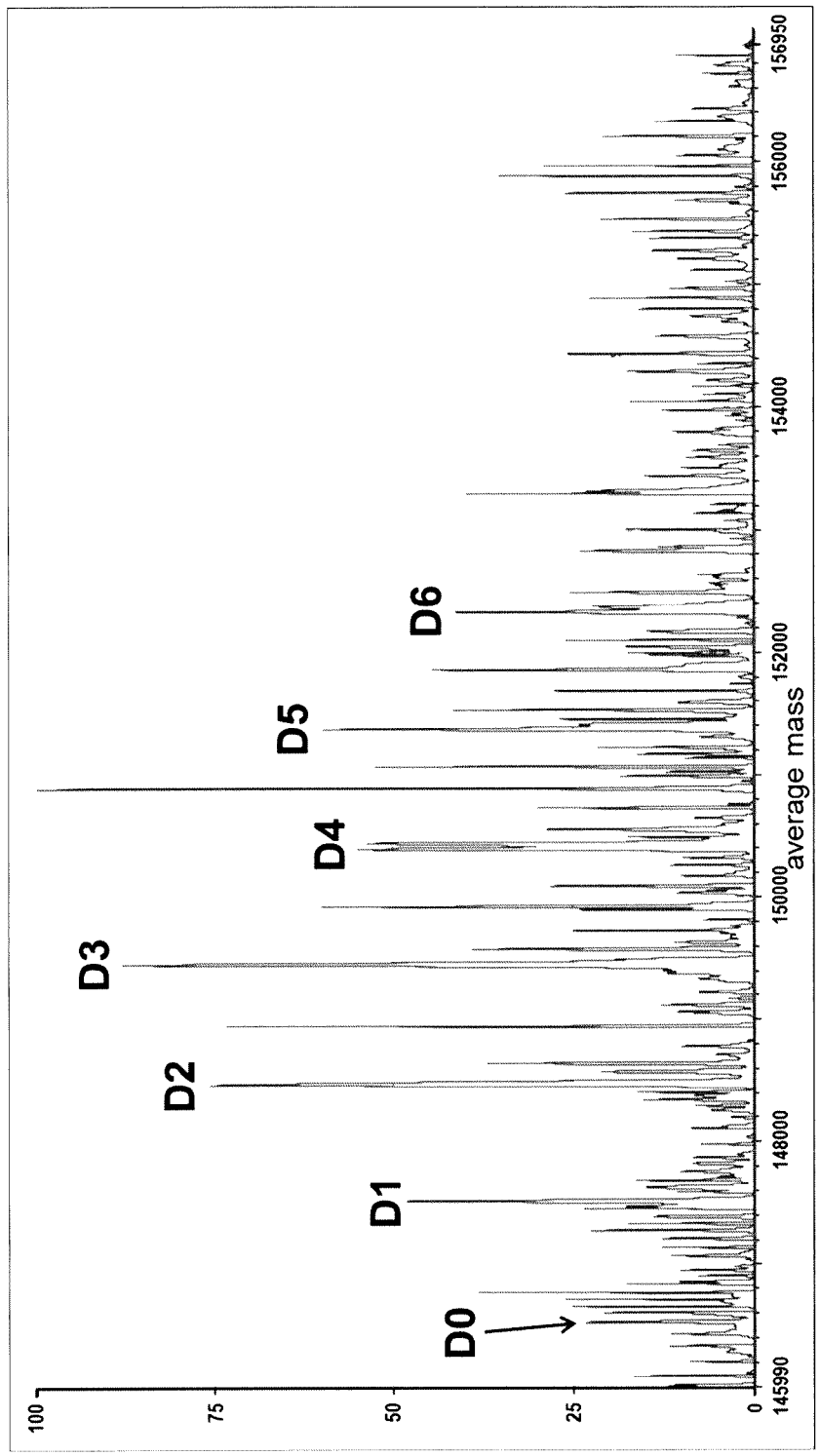
Figure 20: HRMS spectrum of Ex.3 at 96 h following a single i.v. administration in SCID mice at 5 mg/kg (method B2)

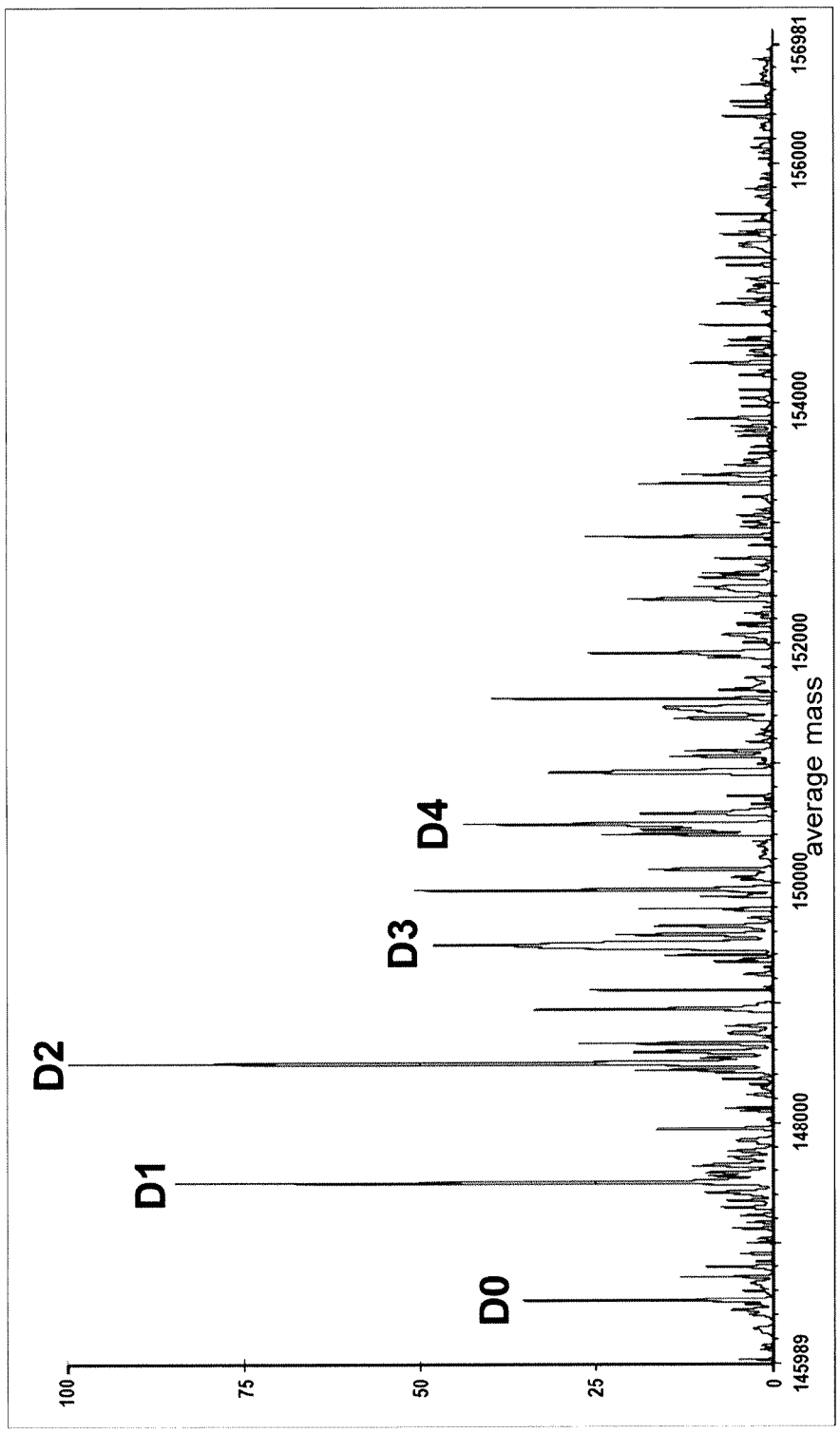
Figure 21: HRMS spectrum of Ex.7 at 96 h following a single i.v. administration in SCID mice at 5 mg/kg (method B2)

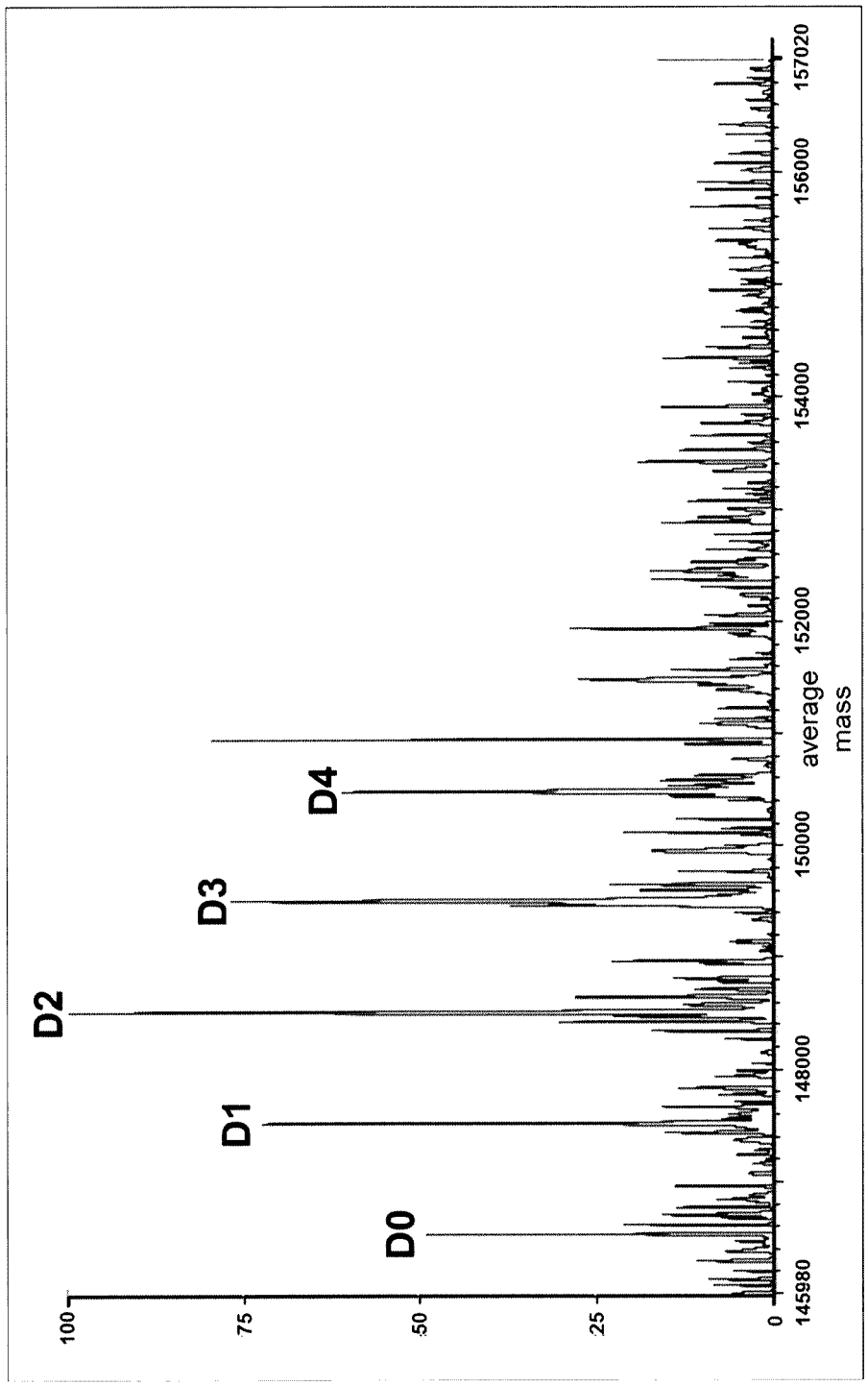
Figure 22: HRMS spectrum of Ex.10 at 96 h following a single i.v. administration in SCID mice at 5 mg/kg (method B2)

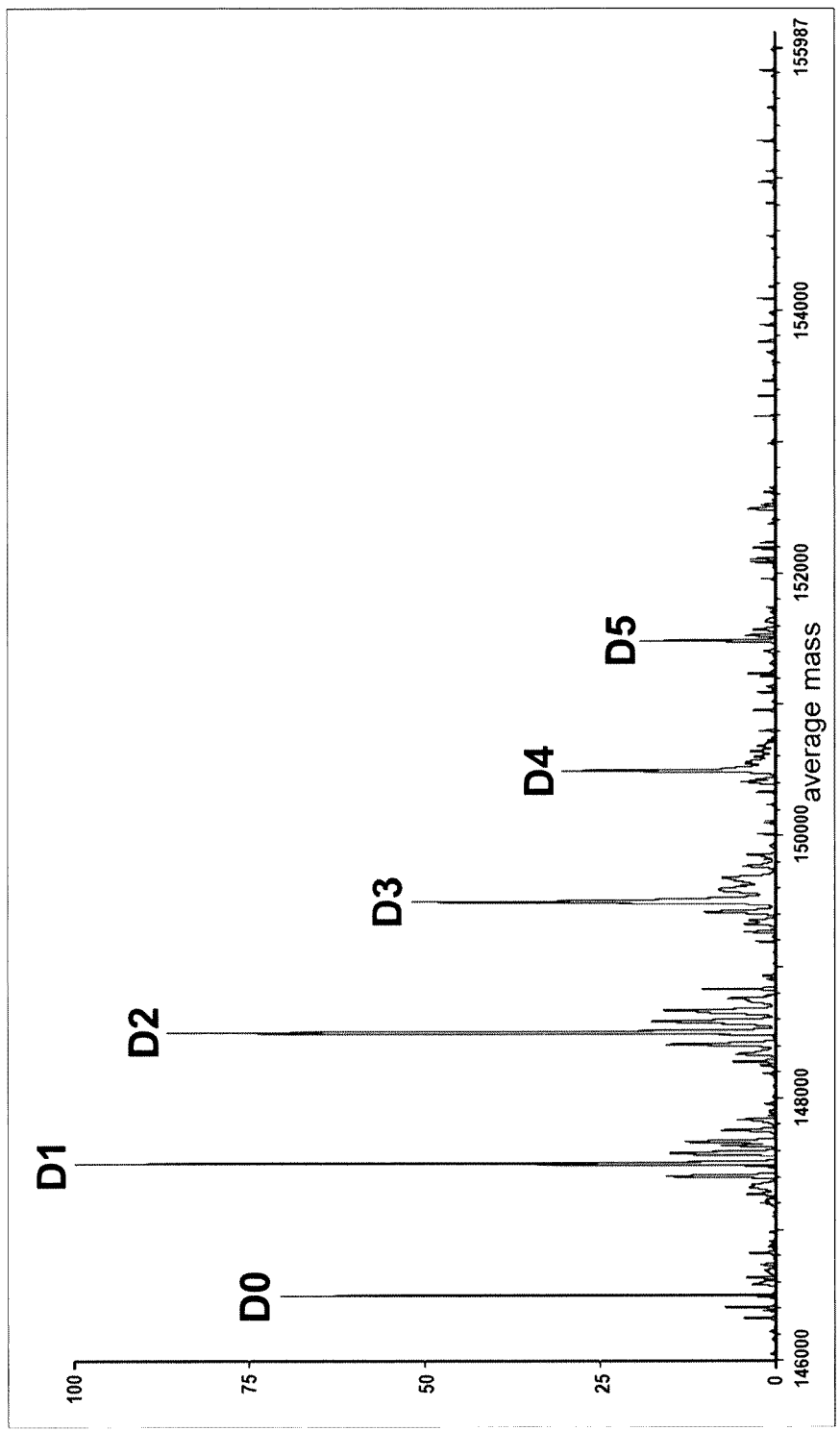
Figure 23: HRMS spectrum of Ex.14 at 96 h following a single i.v. administration in SCID mice at 5 mg/kg (method B2)

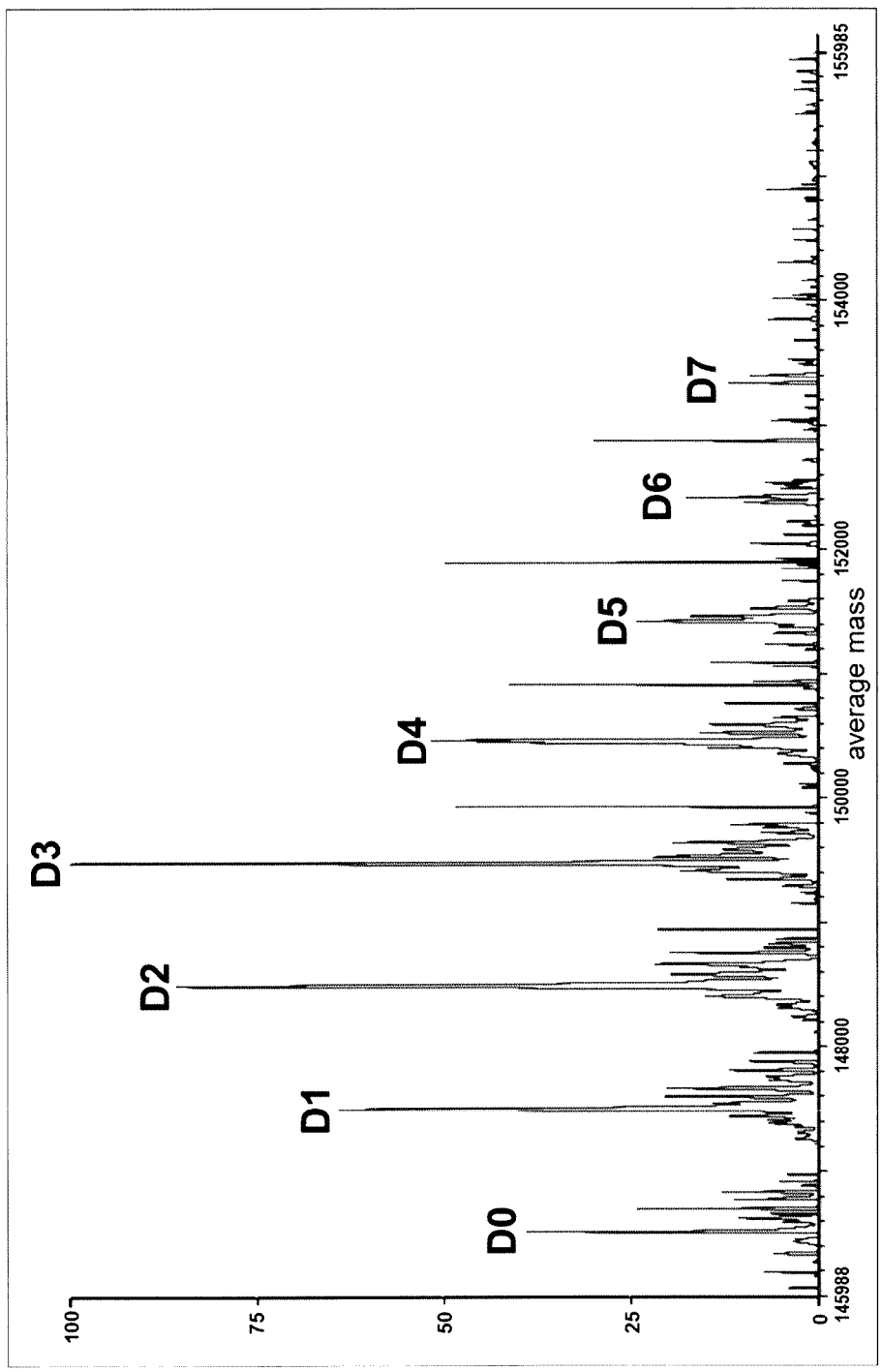
Figure 24: HRMS spectrum of Ex.20 at 96 h following a single i.v. administration in SCID mice at 5 mg/kg (method B2)

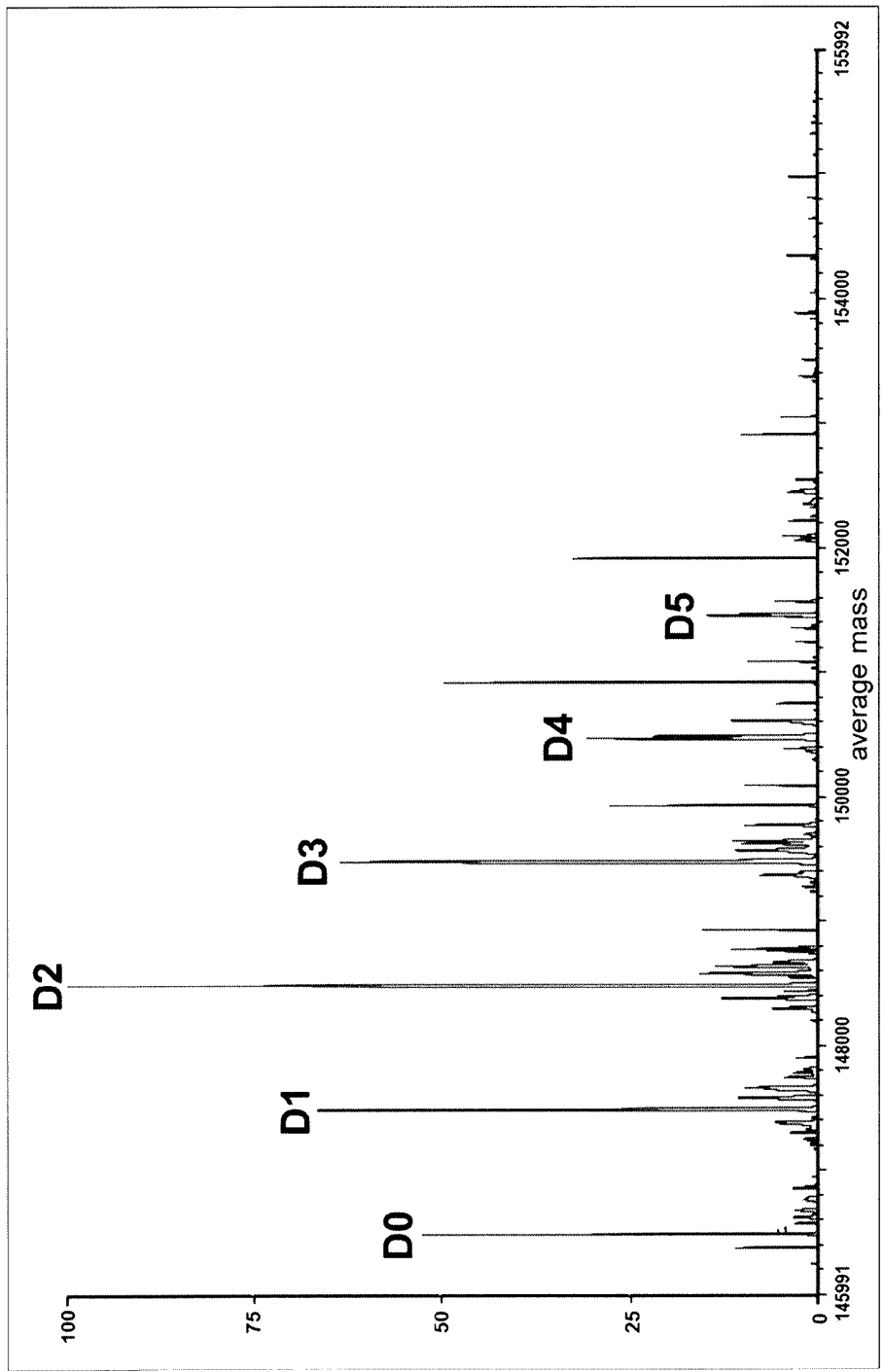
Figure 25: HRMS spectrum of Ex.23 at 96 h following a single i.v. administration in SCID mice at 5 mg/kg (method B2)

CRYPTOPHYCIN COMPOUNDS AND CONJUGATES, THEIR PREPARATION AND THEIR THERAPEUTIC USE

CROSS-REFERENCE TO RELATED APPLICATIONS

This application is a 35 U.S.C. § 371 filing of International Patent Application No. PCT/EP2016/076603, filed Nov. 3, 2016, which claims priority to European Patent Application No. 15306751.7, filed Nov. 5, 2015, the entire contents of which are incorporated herein by reference.

The present invention relates to new cryptophycin compounds, to new cryptophycin payloads, to new cryptophycin conjugates, to compositions containing them and to their therapeutic use, especially as anticancer agents. The invention also relates to the process for preparing these conjugates.

Cryptophycins are secondary metabolites belonging to the class of depsipeptide macrocycles produced by cyanobacteria of the genus *Nostoc*. The first representative of this class of molecules, cryptophycin-1 (C-1), was isolated in 1990 from cyanobacterium *Nostoc* sp (ATCC 53789; see Eißler S., et al., *Synthesis* 2006, 22, 3747-3789). Cryptophycins C-1 and C-52, which are characterized by an epoxide function, were discovered to have in vitro and in vivo antitumor activity in the early 1990s. The chlorohydrins of these, C-8 and C-55, were markedly more active but could not be formulated as stable solutions (Bionpally R. R., et al., *Cancer Chemother Pharmacol* 2003, 52, 25-33). Their higher activity was correlated by their putative ability to generate the corresponding epoxides in cells. With no method to adequately stabilize the chlorohydrins at the time, cryptophycin C-52 (LY355703) entered clinical trials, produced marginal antitumor activity in two phase II lung cancer trials with 30-40% stable disease and was thus discontinued (Edelman M. J., et al., *Lung Cancer* 2003, 39, 197-99 and Sessa C., et al., *Eur J Cancer* 2002, 38, 2388-96).

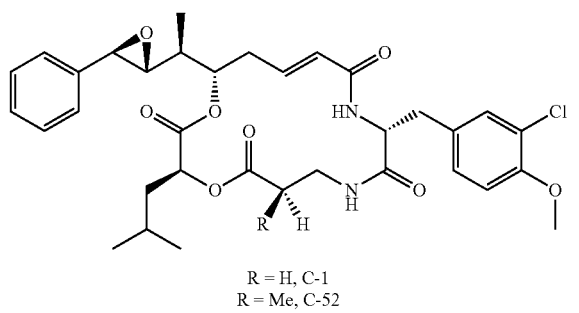

R = H, C-1
R = Me, C-52

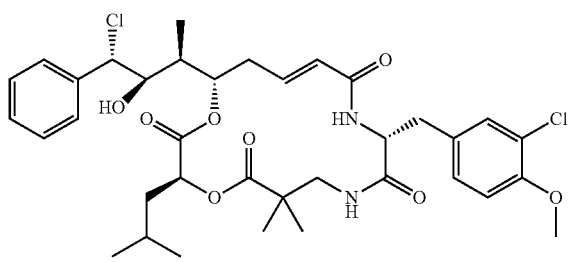

C-55

Considering their high potency and common mechanism of action with maytansinoids and auristatins, the two cytotoxic molecules validated in the clinic for antibody-drug conjugates (ADC), this series was considered as a potential tubulin binder for ADC. Therefore conjugates in the cryptophycin series were developed starting from derivatization at the para-benzylic position of the macrocycle (Al-Awar R. S., et al., *J Med Chem* 2003, 46, 2985-3007).

WO2011/001052 describes cryptophycin antibody-drug conjugates for which the cytotoxic moiety is linked to the antibody through the para-benzylic position using various kinds of linkers. They might be cleavable, disulfide or protease-sensitive, or non-cleavable.

Further optimization of cryptophycin antibody-drug conjugates described in WO2011/001052 led to potent cryptophycin conjugates which displayed promising antitumor activity but were found unstable in the plasma of mice while being stable in the plasma of non-rodent species. Therefore, there was a need for cryptophycin conjugates exhibiting improved stability properties.

The purpose of this invention is that of proposing new cryptophycin macrocycles which once conjugated to an antibody are stable in mice plasma and new cryptophycin conjugates composed of those stable macrocycles.

SUMMARY OF THE INVENTION

In this respect, the invention relates to cryptophycin compounds of formula (I):

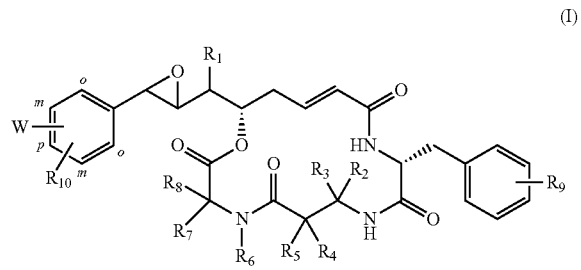

(I)

wherein:
$R_1$ represents a $(C_1\text{-}C_6)$alkyl group;
$R_2$ and $R_3$ represent, independently of each other, a hydrogen atom or a $(C_1\text{-}C_6)$alkyl group;
or alternatively $R_2$ and $R_3$ form together with the carbon atom to which they are attached a $(C_3\text{-}C_6)$cycloalkyl or a $(C_3\text{-}C_6)$heterocycloalkyl group;
$R_4$ and $R_5$ represent, independently of each other, a hydrogen atom or a $(C_1\text{-}C_6)$alkyl group or a $(C_1\text{-}C_6)$alkyl-NH($R_{12}$) group or a $(C_1\text{-}C_6)$alkyl-OH group or a $(C_1\text{-}C_6)$alkyl-SH group or a $(C_1\text{-}C_6)$alkyl-CO$_2$H group;
or alternatively $R_4$ and $R_5$ form together with the carbon atom to which they are attached a $(C_3\text{-}C_6)$cycloalkyl or a $(C_3\text{-}C_6)$heterocycloalkyl group;
$R_6$ represents a hydrogen atom or a $(C_1\text{-}C_6)$alkyl group;
$R_7$ and $R_8$ represent, independently of each other, a hydrogen atom or a $(C_1\text{-}C_6)$alkyl group or a $(C_1\text{-}C_6)$alkyl-CO$_2$H group or a $(C_1\text{-}C_6)$alkyl-N$(C_1\text{-}C_6)$alkyl$_2$ group;
or alternatively $R_7$ and $R_8$ form together with the carbon atom to which they are attached a $(C_3\text{-}C_6)$cycloalkyl group or a $(C_3\text{-}C_6)$heterocycloalkyl group;
$R_9$ represents one or more substituents of the phenyl nucleus chosen, independently of each other, from: a hydrogen atom, —OH, $(C_1\text{-}C_4)$alkoxy, a halogen atom, —NH$_2$, —NH(C$_1$-C$_6$)alkyl, —N(C$_1$-C$_6$)alkyl$_2$, —NH(C$_1$-C$_6$)cycloalkyl or (C$_3$-C$_6$)heterocycloalkyl;

R$_{10}$ represents at least one substituent of the phenyl nucleus chosen from a hydrogen atom and a group (C$_1$-C$_4$)alkyl;

W represents (C$_1$-C$_6$)alkyl-NH(R$_{11}$), more particularly (CH$_2$)$_n$NHR$_{11}$;

(C$_1$-C$_6$)alkyl-OH, more particularly (CH$_2$)$_n$OH;

(C$_1$-C$_6$)alkyl-SH, more particularly (CH$_2$)$_n$SH;

CO$_2$H or C(=O)NH$_2$;

(C$_1$-C$_6$)alkyl-CO$_2$H or (C$_1$-C$_6$)alkyl-C(=O)NH$_2$; or (C$_1$-C$_6$)alkyl-N$_3$.

W being positioned in an ortho (o), meta (m) or para (p) position of the phenyl nucleus;

R$_{11}$ and R$_{12}$ represent, independently of each other, a hydrogen atom or (C$_1$-C$_6$)alkyl, more particularly a methyl group;

n represents an integer between 1 and 6.

The invention further relates to cryptophycin payloads of formula (II):

or alternatively Y represents (C$_1$-C$_6$)alkyl-triazole-like

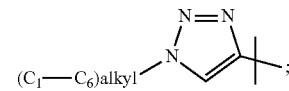

Y being positioned in an ortho (o), meta (m) or para (p) position of the phenyl nucleus;

R$_{11}$ represents a hydrogen atom or a (C$_1$-C$_6$)alkyl group;

L represents a linker;

RCG1 represents a reactive chemical group present at the end of the linker, RCG1 being reactive towards a reactive chemical group present on an antibody.

The invention also relates to conjugates of formula (III):

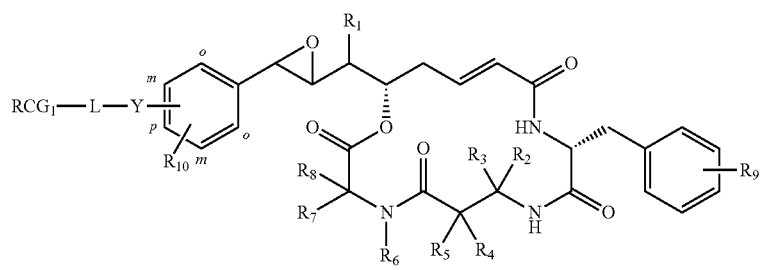

(II)

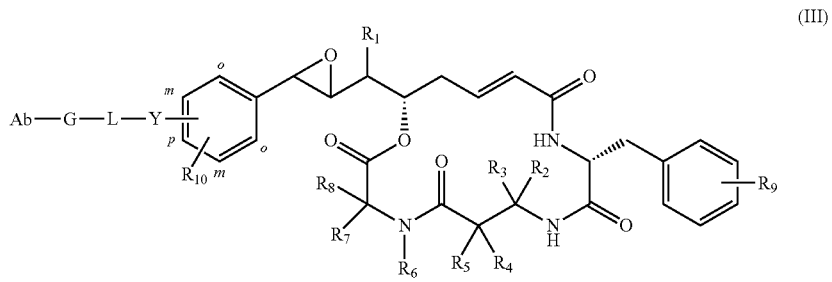

(III)

wherein:

R$_1$, R$_2$, R$_3$, R$_4$, R$_5$, R$_6$, R$_7$, R$_8$, R$_9$ and R$_{10}$ are as defined in formula (I);

Y represents (C$_1$-C$_6$)alkyl-NR$_{11}$ or (C$_1$-C$_6$)alkyl-O or (C$_1$-C$_6$)alkyl-S;

or alternatively Y represents C(=O)O, C(=O)NH, (C$_1$-C$_6$)alkyl-C(=O)O or (C$_1$-C$_6$)alkyl-C(=O)NH;

wherein:

R$_1$, R$_2$, R$_3$, R$_4$, R$_5$, R$_6$, R$_7$, R$_8$, R$_9$ and R$_{10}$ are as defined in formula (I);

Y and L are as defined in formula (II);

G represents the product of reaction between RCG1, a reactive chemical group present at the end of the linker and RCG2, an orthogonal reactive chemical group present on the antibody (Ab);

Ab represents an antibody.

Each substituent $R_1$ to $R_{11}$ may also adopt one of the spatial configurations (e.g. R or S or alternatively Z or E) as described in the examples.

The compounds of formula (I), (II) and (III) may contain one or more asymmetric carbon atoms. They may therefore exist in the form of enantiomers or diastereoisomers. These enantiomers and diastereoisomers, and also mixtures thereof, including racemic mixtures, form part of the invention.

The compounds of formula (I), including those that are illustrated, may exist in the form of bases or of acid-addition salts, especially of pharmaceutically acceptable acids.

Definitions

In the context of the present invention, certain terms have the following definitions:

alkenyl group: a hydrocarbon group obtained by removing one hydrogen atom from an alkene. The alkenyl group may be linear or branched. Examples that may be mentioned include ethenyl (—CH=CH$_2$, also named vinyl) and propenyl (—CH$_2$—CH=CH$_2$, also named allyl).

alkoxy group: a group —O-alkyl, in which the alkyl group is as defined below;

alkyl group: a linear or branched saturated aliphatic hydrocarbon-based group obtained by removing a hydrogen atom from an alkane. Examples that may be mentioned include methyl, ethyl, propyl, isopropyl, butyl, isobutyl, tert-butyl, pentyl, neopentyl, 2,2-dimethylpropyl and hexyl groups;

alkylene group: a saturated divalent group of empirical formula —C$_n$H$_{2n}$—, obtained by removing two hydrogen atoms from an alkane. The alkylene group may be linear or branched. Examples that may be mentioned include methylene (—CH$_2$—), ethylene (—CH$_2$CH$_2$—), propylene (—CH$_2$CH$_2$CH$_2$—), butylene (—CH$_2$CH$_2$CH$_2$CH$_2$—) and hexylene (—CH$_2$CH$_2$CH$_2$CH$_2$CH$_2$CH$_2$—) groups or the following branched groups

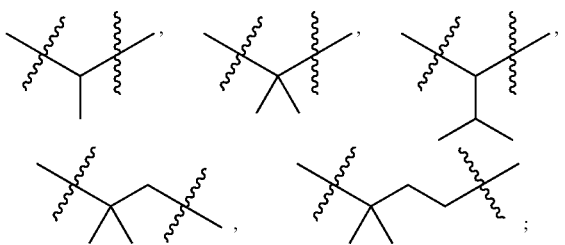

preferably, the alkylene group is of the formula —(CH$_2$)$_n$—, n representing an integer; in the ranges of values, the limits are included (e.g. a range of the type "n ranging from 1 to 6" or "between 1 and 6" includes limits 1 and 6);

antibody: an antibody with affinity for a biological target, more particularly a monoclonal antibody. The function of the antibody is to direct the biologically active compound as a cytotoxic compound towards the biological target. The antibody may be monoclonal, polyclonal or multispecific; it may also be an antibody fragment; it may also be a murine, chimeric, humanized or human antibody. An "antibody" may be a natural or conventional antibody in which two heavy chains are linked to each other by disulfide bonds and each heavy chain is linked to a light chain by a disulfide bond (also referred to as a "full-length antibody"). The terms "conventional (or full-length) antibody" refers both to an antibody comprising the signal peptide (or propeptide, if any), and to the mature form obtained upon secretion and proteolytic processing of the chain(s). There are two types of light chain, lambda (l) and kappa (κ). There are five main heavy chain classes (or isotypes) which determine the functional activity of an antibody molecule: IgM, IgD, IgG, IgA and IgE. Each chain contains distinct sequence domains. The light chain includes two domains or regions, a variable domain (VL) and a constant domain (CL). The heavy chain includes four domains, a variable domain (VH) and three constant domains (CH1, CH2 and CH3, collectively referred to as CH). The variable regions of both light (VL) and heavy (VH) chains determine binding recognition and specificity to the antigen. The constant region domains of the light (CL) and heavy (CH) chains confer important biological properties such as antibody chain association, secretion, transplacental mobility, complement binding, and binding to Fc receptors (FcR). The Fv fragment is the N-terminal part of the Fab fragment of an immunoglobulin and consists of the variable portions of one light chain and one heavy chain. The specificity of the antibody resides in the structural complementarity between the antibody combining site and the antigenic determinant. Antibody combining sites are made up of residues that are primarily from the hypervariable or complementarity determining regions (CDRs). Occasionally, residues from nonhypervariable or framework regions (FR) influence the overall domain structure and hence the combining site. Complementarity Determining Regions or CDRs refer to amino acid sequences which together define the binding affinity and specificity of the natural Fv region of a native immunoglobulin binding site. The light and heavy chains of an immunoglobulin each have three CDRs, designated CDR1-L, CDR2-L, CDR3-L and CDR1-H, CDR2-H, CDR3-H, respectively. A conventional antibody antigen-binding site, therefore, includes six CDRs, comprising the CDR set from each of a heavy and a light chain V region. As used herein, the term "antibody" denotes both conventional (full-length) antibodies and fragments thereof, as well as single domain antibodies and fragments thereof, in particular variable heavy chain of single domain antibodies. Fragments of (conventional) antibodies typically comprise a portion of an intact antibody, in particular the antigen binding region or variable region of the intact antibody, and retain the biological function of the conventional antibody. Examples of such fragments include Fv, Fab, F(ab')2, Fab', dsFv, (dsFv)2, scFv, sc(Fv)2 and diabodies.

The function of the antibody is to direct the biologically active compound as a cytotoxic compound towards the biological target.

aryl group: a cyclic aromatic group containing between 5 to 10 carbon atoms. Examples of aryl groups include phenyl, tolyl, xylyl, naphtyl;

biological target: an antigen (or group of antigens) preferably located at the surface of cancer cells or stromal cells associated with this tumour; these antigens may be, for example, a growth factor receptor, an oncogene product or a mutated "tumor suppressant" gene product, an angiogenesis-related molecule or an adhesion molecule;

conjugate: an antibody-drug conjugate or ADC, i.e. an antibody to which is covalently attached via a linker at least one molecule of a cytotoxic compound;

cycloalkyl group: a cyclic alkyl group comprising between 3 and 6 carbon atoms engaged in the cyclic structure. Examples that may be mentioned include cyclopropyl, cyclobutyl, cyclopentyl and cyclohexyl groups;

DAR (drug-to-antibody ratio): an average number of cytotoxic molecules attached via a linker to an antibody;

halogen: any of the four elements fluorine, chlorine, bromine and iodine;

heteroaryl group: an aryl group containing between 2 to 10 carbon atoms and between 1 to 5 heteroatoms such as nitrogen, oxygen or sulphur engaged in the ring and connected to the carbon atoms forming the ring. Examples of heteroaryl groups include pyridyl, pyrimidyl, thienyl, imidazolyl, triazolyl, indolyl, imidazopyridyl, pyrazolyl;

heterocycloalkyl group: a cycloalkyl group containing between 2 to 8 carbon atoms and between 1 to 3 heteroatoms, such as nitrogen, oxygen or sulphur engaged in the ring and connected to the carbon atoms forming the ring. Examples include aziridinyl, pyrrolidinyl, piperidinyl, piperazinyl, morpholinyl, thiomorpholinyl, tetrahydrofuranyl, tetrahydrothiofuranyl, tetrahydropyranyl, azetidinyl, oxetanyl and pyranyl;

linker: a group of atoms or a single bond that can covalently attach a cytotoxic compound to an antibody in order to form a conjugate;

fragment: simpler molecules that allow the total synthesis of cryptophycin compounds;

payload: a cytotoxic compound to which is covalently attached a linker;

reactive chemical group: group of atoms that can promote or undergo a chemical reaction.

Abbreviations

ADC: antibody-drug conjugate; AcOH: acetic acid; AIBN: azobisisobutyronitrile; ALK: $(C_1-C_{12})$alkylene group, more particularly $(C_1-C_6)$alkylene, more particularly of the form $—(CH_2)_n—$, n being an integer from 1 to 12 and preferably from 1 to 6; aq.: aqueous; Ar: argon; AUC: area under the curve; BEMP: 2-tert-butylimino-2-diethylamino-1,3-dimethylperhydro-1,3,2-diazaphosphorine; $BF_3$: boron trifluoride; $Boc_2O$: di-tert-butyl-dicarbonate; BuLi: butyl lithium; CAN: ceric ammonium nitrate; Cbz: carboxybenzyl; $CHCl_3$: chloroform; $CH_3CN$: acetonitrile; $CH_3I$: methyl iodide; $CO_2$: carbon dioxide; CL: clearance; m-CPBA: m-chloroperbenzoic acid; CR: complete response; crypto denotes the unit of formula

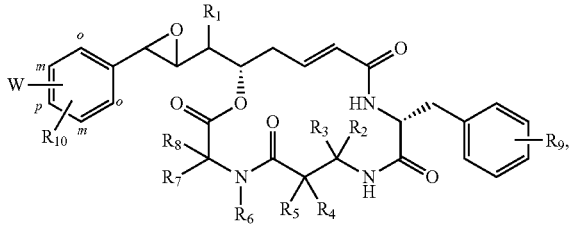

crypto especially denoting one of the $D_1$-$D_{19}$ cryptophycin compounds described later or a cryptophycin compound of an example; D1 refers to an ADC with a DAR of 1, D2 to an ADC with a DAR of 2, etc.; d: day; DAR: drug-to-antibody ratio; DBU: 8-diazabycyclo[5.4.0]undec-7-ene; DCC: N,N'-dicyclohexylcarbodiimide; DCE: dichloroethane; DCM: dichloromethane; DDQ: 2,3-dichloro-5,6-dicyano-1,4-benzoquinone; DIC: N,N'-diisopropylcarbodiimide; DIAD: diisopropylazodicarboxylate; DIEA: N,N-diisopropylethylamine; DMA: dimethylacetamide; DMAP: 4-(dimethylamino)pyridine; DME: dimethoxyethane; DMEM: Dulbecco's Modified Eagle Medium; DMEM/F12: Dulbecco's Modified Eagle Medium Nutrient Mixture F-12; DMF: dimethylformamide; DMSO: dimethylsulfoxide; DPBS: Dulbecco's phosphate-buffered saline; DPPA: diphenylphosphorazide $(PhO)_2P(=O)N_3$; DSC: N,N'-disuccinimidyl carbonate; EDA: ethylenediamine; EDC: 1-(3-dimethylaminopropyl)-3-ethylcarbodiimide; EDTA: ethylenediaminetetraacetic acid; EEDQ: N-ethoxycarbonyl-2-ethoxy-1,2-dihydroquinoline; ELSD: evaporating light scattering detector; eq.: equivalent; ES: electrospray; EtOAc: ethyl acetate; $Et_2O$: diethyl ether; EtOH: ethanol; Ex.: example; FCS: foetal calf serum; Fmoc: 9-fluorenylmethoxycarbonyl; FmocOSu: N-(9-fluorenylmethoxycarbonyloxy) succinimide; GI: electroinductive group; Grubbs I: benzylidene-bis(tricyclohexylphosphine)dichlororuthenium; Grubbs II: (1,3-bis(2,4,6-trimethylphenyl)-2-imidazolidinylidene)dichloro(phenylmethylene)(tricyclohexylphosphine)ruthenium; h: hour; $H_2O$: water; Hal: halogen; HATU: 1-[bis(dimethylamino)methylene]-1H-1,2,3-triazolo[4,5-b]pyridinium 3-oxid hexafluorophosphate; HCl: chlorohydric acid; HEPES: 4-(2-hydroxyethyl)-1-piperazineethanesulfonic acid; HIC: hydrophobic interaction chromatography; HOAt: 1-hydroxy-7-azabenzotriazole; HOBt: 1-hydroxy-benzotriazole; HPLC: high performance liquid chromtography; HRMS: high resolution mass spectrometry; $IC_{50}$: median inhibitory concentration; i.e.: id est meaning that is; IEC: ion exchange chromatography; iPrOH: 2-propanol; $iPr_2O$: diisopropyl ether; i.v.: intravenous; $K_2CO_3$: potassium carbonate; LDA: lithium diisopropylamide; LiOH: lithium hydroxide; marg.: marginally; MeOH: methanol; MeTHF: 2-methyl-tetrahydrofuran; $MgSO_4$: magnesium sulfate; min: minute; MNBA: 2-methyl-6-nitrobenzoic anhydride; MTBE: methyl tert-butyl ether; MTD: maximum tolerated dose; NaH: sodium hydride; $NaHSO_4$: sodium bisulfate; $Na_2S_2O_3$: sodium thiosulfate; NaCl: sodium chloride; $NaHCO_3$: sodium hydrogen carbonate; $NaHSO_3$: sodium bisulfite; $NaHSO_4$: sodium hydrogen sulfate; NaOH: sodium hydroxide; $NH_4Cl$: ammonium chloride; NHS: N-hydroxysuccinimide; NMP: 1-methyl-2-pyrrolidone; NMR: nuclear magnetic resonance; $P_2$-Et: 1-ethyl-2,2,4,4,4-pentakis(dimethylamino)-2λ5,4λ5-catenadi(phosphazene); PBS: phosphate-buffered saline; PEG: polyethylene glycol; PK: pharmacokinetics; PMB: para-methoxybenzyl; PNGase F: Peptide-N-Glycosidase F; $PPh_3$: triphenylphosphine; ppm: parts per million; PR: partial response; QS: quantum satis meaning the amount what is needed; Q-Tof: quadrupole time-of-flight; quant.: quantitative yield; RCG: reactive chemical group; RT: room temperature; sat.: saturated; s.c.: subcutaneously; SCID: severe combined immunodeficiency; SEC: size exclusion chromatography; TBAF: tetrabutylammonium fluoride; tBuOK: potassium tert-butoxide; TCEP: tris(2-carboxyethyl)phosphine hydrochloride; TEA: triethylamine; TEMPO: (2,2,6,6-tetramethylpiperidin-1-yl)oxyl; TFA: trifluoroacetic acid; TFS: tumor-free survivor; THF: tetrahydrofuran; THP: tetrahydropyran; TLC: thin layer chromatography; $t_{1/2}$: half-life; $t_R$: retention time; p-TsOH: para-toluenesulfonic acid; UPLC: Ultra Performance Liquid Chromatography; UV: ultra-violet; $V_{ss}$: apparent volume of distribution at steady state.

FIGURES

FIG. 1: High resolution mass spectrum of Ex. 3
FIG. 2: High resolution mass spectrum of Ex. 7
FIG. 3: High resolution mass spectrum of Ex. 10
FIG. 4: High resolution mass spectrum of Ex. 14
FIG. 5: High resolution mass spectrum of Ex. 20
FIG. 6: High resolution mass spectrum of Ex. 23
FIG. 7: In vivo efficacy of Ex. 3 against MDA-MB-231 xenograft in SCID mice
FIG. 8: In vivo efficacy of Ex. 7 against MDA-MB-231 xenograft in SCID mice
FIG. 9: In vivo efficacy of Ex. 10 against MDA-MB-231 xenograft in SCID mice
FIG. 10: In vivo efficacy of Ex. 14 against MDA-MB-231 xenograft in SCID mice
FIG. 11: In vivo efficacy of Ex. 20 against MDA-MB-231 xenograft in SCID mice
FIG. 12: In vivo efficacy of Ex. 23 against MDA-MB-231 xenograft in SCID mice
FIG. 13: In vivo PK profile of $ADC_1$ following a single i.v. administration in SCID mice
FIG. 14: In vivo PK profile of $ADC_1$ following a single i.v. administration in non-rodent species
FIG. 15: In vivo PK profile of Ex. 3 following a single i.v. administration in SCID mice
FIG. 16: In vivo PK profile of Ex. 7 following a single i.v. administration in SCID mice
FIG. 17: HRMS spectrum of deglycosylated $ADC_1$ at 96 h following a single i.v. administration in SCID mice
FIG. 18: HRMS spectrum of $ADC_2$ light chain at 96 h following a single i.v. administration in SCID mice
FIG. 19: HRMS spectrum of deglycosylated $ADC_1$ at 6 d following a single i.v. administration in non-rodent species
FIG. 20: HRMS spectrum of Ex. 3 at 96 h following a single i.v. administration in SCID mice
FIG. 21: HRMS spectrum of Ex. 7 at 96 h following a single i.v. administration in SCID mice
FIG. 22: HRMS spectrum of Ex. 10 at 96 h following a single i.v. administration in SCID mice
FIG. 23: HRMS spectrum of Ex. 14 at 96 h following a single i.v. administration in SCID mice
FIG. 24: HRMS spectrum of Ex. 20 at 96 h following a single i.v. administration in SCID mice
FIG. 25: HRMS spectrum of Ex. 23 at 96 h following a single i.v. administration in SCID mice

DETAILED DESCRIPTION OF THE INVENTION

The invention relates to cryptophycin compounds of formula (I):

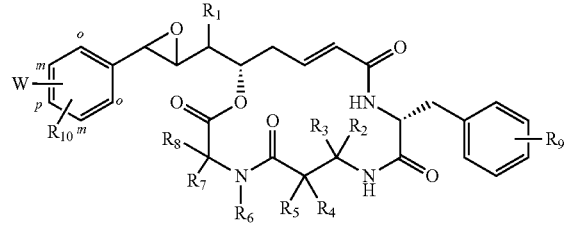

(I)

wherein:
$R_1$ represents a $(C_1-C_6)$alkyl group;
$R_2$ and $R_3$ represent, independently of each other, a hydrogen atom or a $(C_1-C_6)$alkyl group;
or alternatively $R_2$ and $R_3$ form together with the carbon atom to which they are attached a $(C_3-C_6)$cycloalkyl or a $(C_3-C_6)$heterocycloalkyl group;
$R_4$ and $R_5$ represent, independently of each other, a hydrogen atom or a $(C_1-C_6)$alkyl group or a $(C_1-C_6)$alkyl-NH$(R_{12})$ group or a $(C_1-C_6)$alkyl-OH group or a $(C_1-C_6)$alkyl-SH group or a $(C_1-C_6)$alkyl-$CO_2$H group;
or alternatively $R_4$ and $R_5$ form together with the carbon atom to which they are attached a $(C_3-C_6)$cycloalkyl or a $(C_3-C_6)$heterocycloalkyl group;
$R_6$ represents a hydrogen atom or a $(C_1-C_6)$alkyl group;
$R_7$ and $R_8$ represent, independently of each other, a hydrogen atom or a $(C_1-C_6)$alkyl group or a $(C_1-C_6)$alkyl-$CO_2$H group or a $(C_1-C_6)$alkyl-N$(C_1-C_6)$alkyl$_2$ group;
or alternatively $R_7$ and $R_8$ form together with the carbon atom to which they are attached a $(C_3-C_6)$cycloalkyl group or a $(C_3-C_6)$heterocycloalkyl group;
$R_9$ represents one or more substituents of the phenyl nucleus chosen, independently of each other, from: a hydrogen atom, —OH, $(C_1-C_4)$alkoxy, a halogen atom, —NH$_2$, —NH$(C_1-C_6)$alkyl or —N$(C_1-C_6)$alkyl$_2$ or —NH$(C_1-C_6)$cycloalkyl or $(C_3-C_6)$heterocycloalkyl group;
$R_{10}$ represents at least one substituent of the phenyl nucleus chosen from a hydrogen atom and a group $(C_1-C_4)$alkyl;
W represents
$(C_1-C_6)$alkyl-NH$(R_{11})$, more particularly $(CH_2)_n$NHR$_{11}$;
$(C_1-C_6)$alkyl-OH, more particularly $(CH_2)_n$OH;
$(C_1-C_6)$alkyl-SH, more particularly $(CH_2)_n$SH;
$CO_2$H or C(=O)NH$_2$;
$(C_1-C_6)$alkyl-$CO_2$H or $(C_1-C_6)$alkyl-C(=O)NH$_2$; or
$(C_1-C_6)$alkyl-N$_3$.
W is positioned in an ortho (o), meta (m) or para (p) position of the phenyl nucleus;
$R_{11}$ and $R_{12}$ represent, independently of each other, a hydrogen atom or a group $(C_1-C_6)$alkyl, more particularly a methyl group;
n represents an integer between 1 and 6.

The cryptophycin compound may be one of the following $D_1$-$D_{19}$:

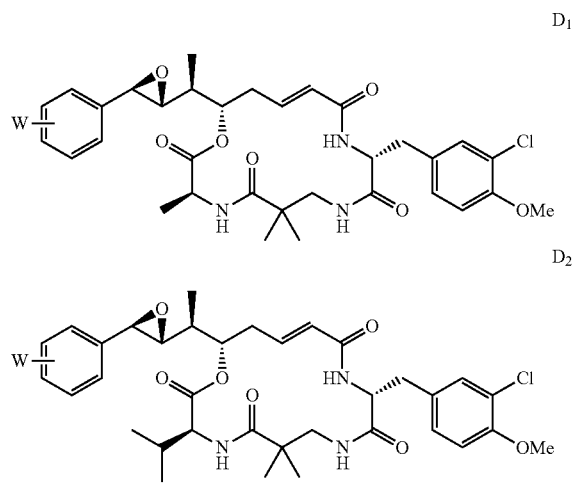

D3
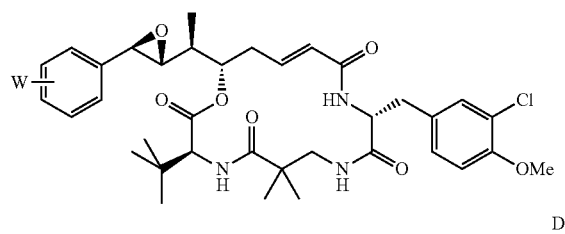
D4
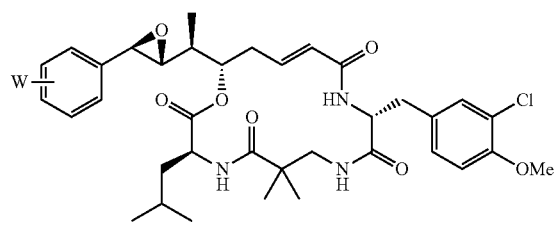
D5
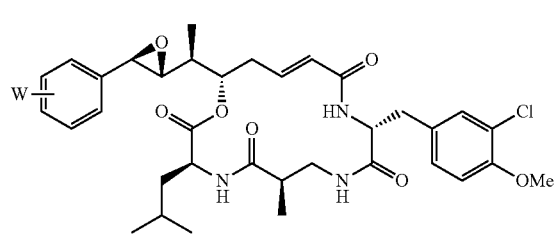
D6
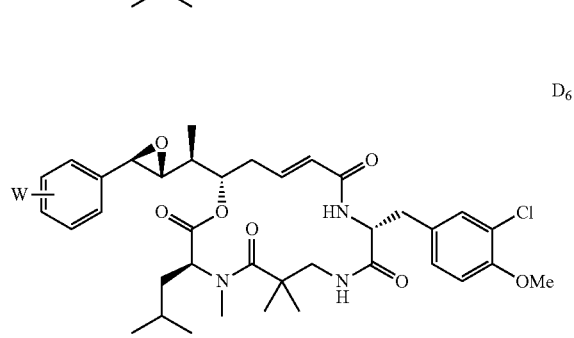
D7
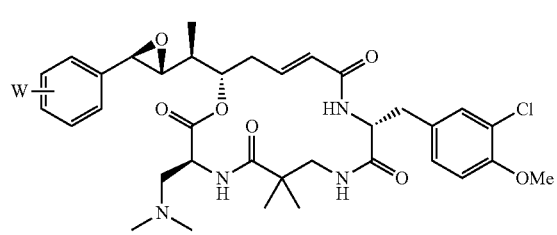
D8
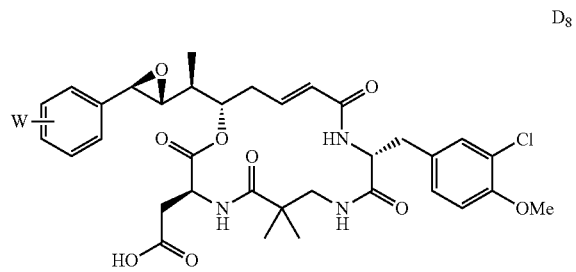
D9
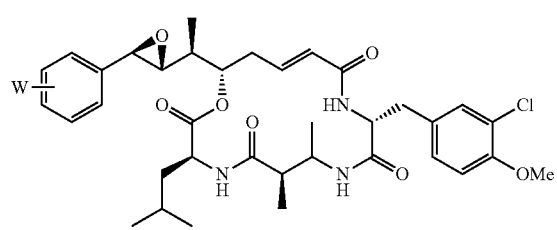
D10
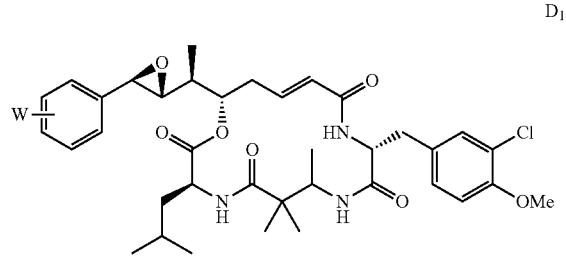
D11
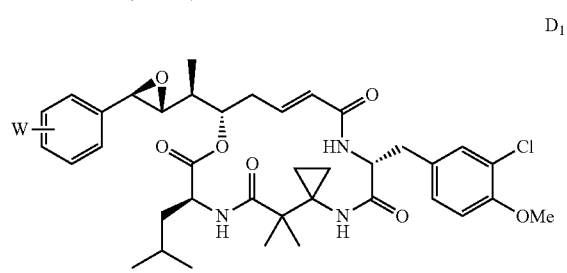
D12
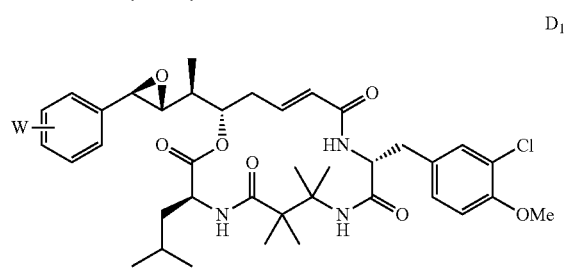
D13
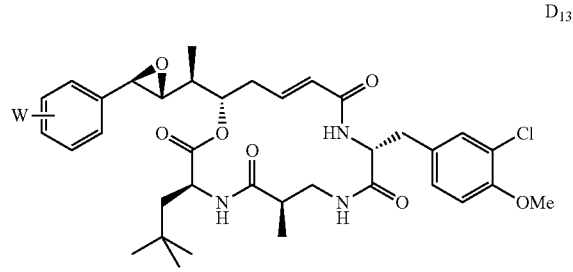
D14
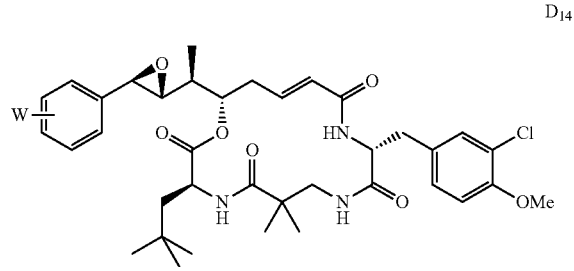

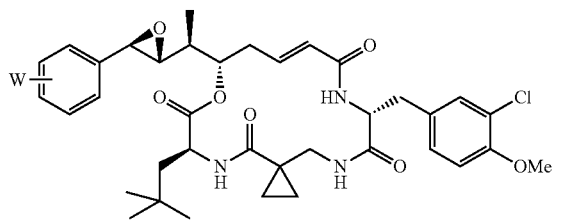

D15

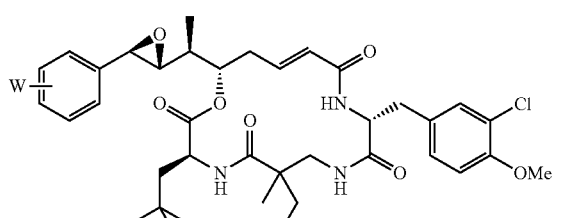

D16

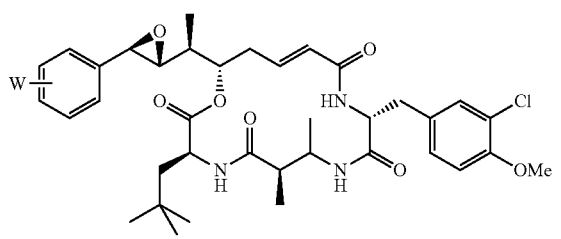

D17

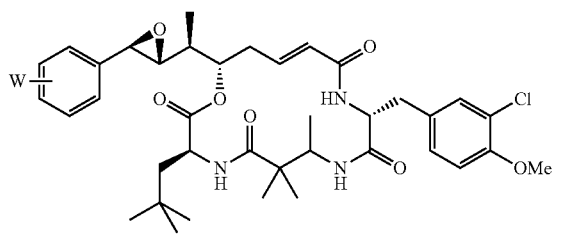

D18

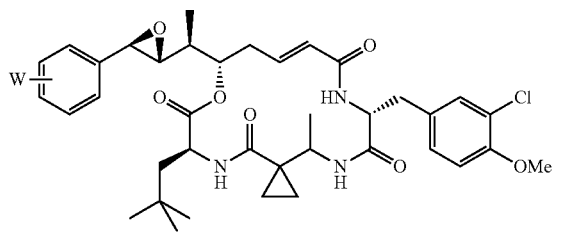

D19 wherein:

W and $R_{12}$ are as defined in formula (I);

Or the cryptophycin compound may be an equivalent unit described in one of the examples.

Among the compounds of formula (I) that are subject matter of the invention, a first group of compounds is composed of the compounds for which $R_1$ represents a $(C_1-C_6)$alkyl, in particular a methyl group.

Among the compounds of formula (I) that are subject matter of the invention, a second group of compounds is composed of the compounds for which each of $R_2$ and $R_3$ represents a hydrogen atom.

Among the compounds of formula (I) that are subject matter of the invention, a third group of compounds is composed of the compounds for which one of $R_2$ and $R_3$ represents a $(C_1-C_6)$alkyl, in particular a methyl group, and the other one represents a hydrogen atom.

Among the compounds of formula (I) that are subject matter of the invention, a fourth group of compounds is composed of the compounds for which $R_2$ and $R_3$ form together with the carbon atom to which they are attached a $(C_3-C_6)$cycloalkyl group, in particular a cyclopropyl group.

Among the compounds of formula (I) that are subject matter of the invention, a fifth group of compounds is composed of the compounds for which each of $R_4$ and $R_5$ represents a $(C_1-C_6)$alkyl, in particular a methyl group.

Among the compounds of formula (I) that are subject matter of the invention, a sixth group of compounds is composed of the compounds for which $R_6$ represents a hydrogen atom.

Among the compounds of formula (I) that are subject matter of the invention, a seventh group of compounds is composed of the compounds for which $R_7$ and $R_8$ represent independently of each other an hydrogen atom or a $(C_1-C_6)$ alkyl group.

Among the compounds of formula (I) that are subject matter of the invention, an eighth group of compounds is composed of the compounds for which $R_9$ represents two substituents selected from a methoxy group and a chlorine atom. More particularly, the phenyl nucleus comprises two substituents in positions 3 and 4 on the phenyl nucleus. Preferably, it is 3-Cl and 4-methoxy.

Among the compounds of formula (I) that are subject matter of the invention, a ninth group of compounds is composed of the compounds for which $R_{10}$ represents a hydrogen atom.

Among the compounds of formula (I) that are subject matter of the invention, a tenth group of compounds is composed of the compounds for which W is positioned in the para position of the phenyl nucleus.

Among the compounds of formula (I) that are subject matter of the invention, a eleventh group of compounds is composed of the compounds for which W is selected from $(C_1-C_6)$alkyl-NHR$_{11}$, in particular $(C_1-C_3)$alkyl-NHR$_{11}$, particularly a CH$_2$—NH$_2$ group, $(C_1-C_6)$alkyl-OH, in particular $(C_1-C_3)$alkyl-OH, particularly a CH$_2$—OH group, $(C_1-C_6)$alkyl-SH, in particular $(C_1-C_3)$alkyl-SH and $(C_1-C_6)$alkyl-CO$_2$H, in particular $(C_1-C_3)$alkyl-CO$_2$H.

Among the compounds of formula (I) that are subject matter of the invention, a twelfth group of compounds is composed of the compounds for which $R_1$ represents a $(C_1-C_6)$alkyl, in particular a methyl group, each of $R_2$ and $R_3$ represents a hydrogen atom, $R_6$ represents a hydrogen atom, $R_9$ represents two substituents selected from a methoxy group and a chlorine atom, more particularly, the phenyl nucleus comprises two substituents in positions 3 and 4 on the phenyl nucleus, preferably, it is 3-Cl and 4-methoxy and $R_{10}$ represents a hydrogen atom.

Among the compounds of formula (I) that are subject matter of the invention, a thirteenth group of compounds is composed of the compounds for which $R_1$ represents a $(C_1-C_6)$alkyl, in particular a methyl group, $R_2$ and $R_3$ represents a $(C_1-C_6)$alkyl, in particular a methyl group, and the other one represents a hydrogen atom, $R_6$ represents a hydrogen atom, $R_9$ represents two substituents selected from a methoxy group and a chlorine atom, more particularly, the phenyl nucleus comprises two substituents in positions 3 and 4 on the phenyl nucleus, preferably, it is 3-Cl and 4-methoxy and $R_{10}$ represents a hydrogen atom.

Alternatively, W is selected from $(CH_2)_nNHR_{11}$, $(CH_2)_nSH$ from $(CH_2)_nOH$, wherein n represents an integer between 1 and 6.

Among the compounds of formula (I) that are subject matter of the invention, a fourteenth group of compounds is composed of the compounds of the following structure (beta epoxide configuration):

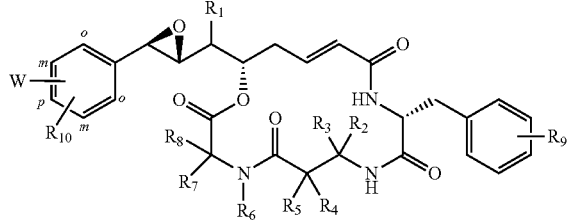

All these sub-groups taken alone or in combination are part of the invention.

Among the compounds of formula (I) that are the subject matter of the invention, mention may be made in particular of the following compounds:

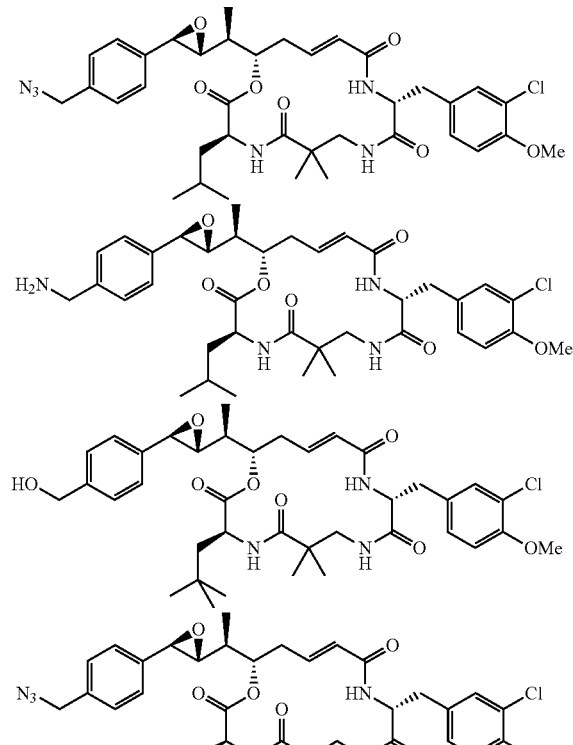

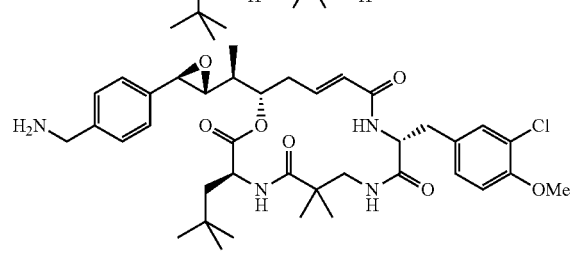

-continued

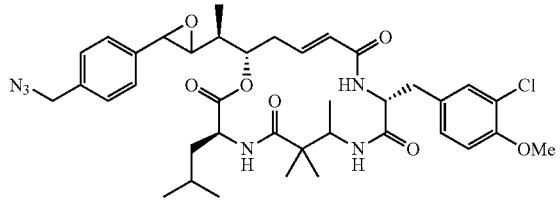

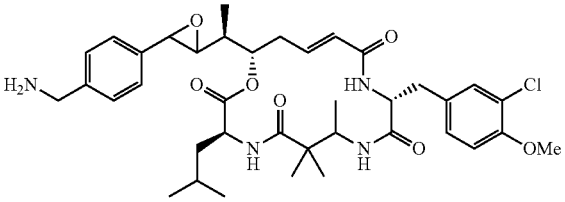

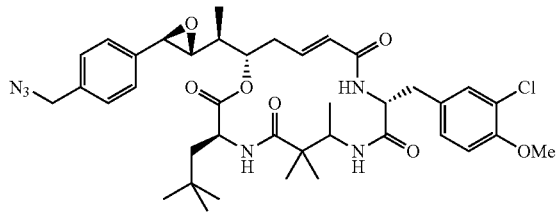

-continued

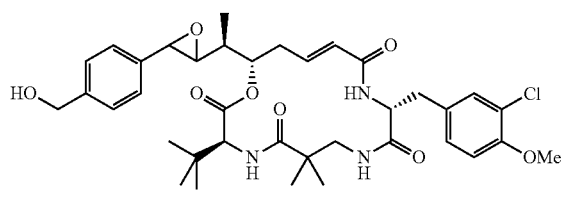

-continued

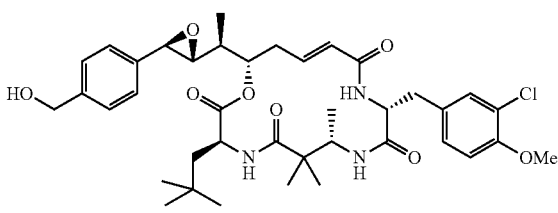

stereomer 2

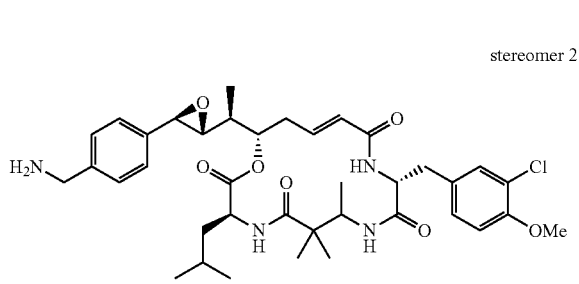

The invention further relates to cryptophycin payloads of formula (II):

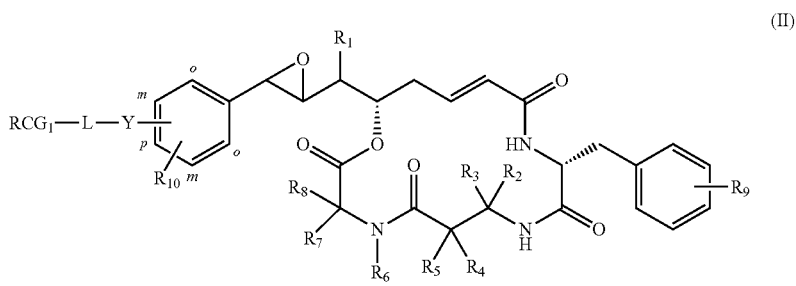

-continued

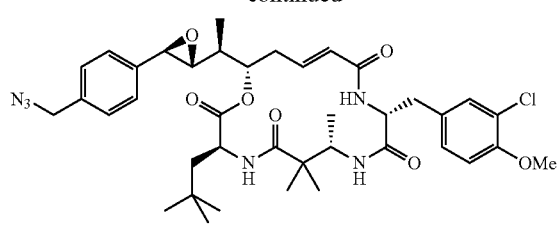

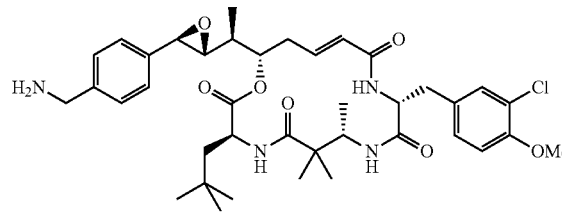

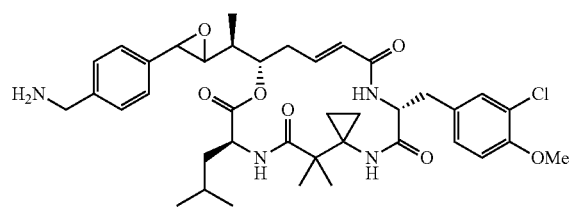

wherein:

$R_1$, $R_2$, $R_3$, $R_4$, $R_5$, $R_6$, $R_7$, $R_7$, $R_9$ and $R_{10}$ are as defined in formula (I);

Y represents $(C_1-C_6)$alkyl-$NR_{11}$ or $(C_1-C_6)$alkyl-O or $(C_1-C_6)$alkyl-S;

or alternatively Y represents C(=O)O, C(=O)NH, $(C_1-C_6)$alkyl-C(=O)O or $(C_1-C_6)$alkyl-C(=O)NH;

or alternatively Y represents $(C_1-C_6)$alkyl-triazole-like

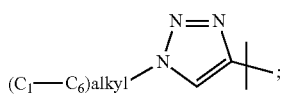

Y is positioned in an ortho (o), meta (m) or para (p) position of the phenyl nucleus;

$R_{11}$ represents a hydrogen atom or a $(C_1-C_6)$alkyl group;

L represents a linker;

RCG1 represents a reactive chemical group present at the end of the linker, RCG1 being reactive towards a reactive chemical group present on an antibody.

Among the compounds of formula (II) that are subject matter of the invention, a first group of compounds is composed of the compounds for which $R_1$ represents a $(C_1-C_6)$alkyl, in particular a methyl group.

Among the compounds of formula (II) that are subject matter of the invention, a second group of compounds is composed of the compounds for which each of $R_2$ and $R_3$ represents a hydrogen atom.

Among the compounds of formula (II) that are subject matter of the invention, a third group of compounds is composed of the compounds for which one of $R_2$ and $R_3$ represents a ($C_1$-$C_6$)alkyl group, in particular a methyl group and the other one represents a hydrogen atom.

Among the compounds of formula (II) that are subject matter of the invention, a fourth group of compounds is composed of the compounds for which $R_2$ and $R_3$ form together with the carbon atom to which they are attached a ($C_3$-$C_6$)cycloalkyl group, in particular a cyclopropyl group.

Among the compounds of formula (II) that are subject matter of the invention, a fifth group of compounds is composed of the compounds for which each of $R_4$ and $R_5$ represents a ($C_1$-$C_6$)alkyl group, in particular a methyl group.

Among the compounds of formula (II) that are subject matter of the invention, a sixth group of compounds is composed of the compounds for which $R_6$ represents a hydrogen atom.

Among the compounds of formula (II) that are subject matter of the invention, a seventh group of compounds is composed of the compounds for which $R_7$ and $R_8$ represent independently of each other an hydrogen atom or a ($C_1$-$C_6$) alkyl group.

Among the compounds of formula (II) that are subject matter of the invention, an eighth group of compounds is composed of the compounds for which $R_9$ represents two substituents selected from a methoxy group and a chlorine atom. More particularly, the phenyl nucleus comprises two substituents in positions 3 and 4 on the phenyl nucleus. Preferably, it is 3-Cl and 4-methoxy.

Among the compounds of formula (II) that are subject matter of the invention, a ninth group of compounds is composed of the compounds for which $R_{10}$ represents a hydrogen atom.

Among the compounds of formula (II) that are subject matter of the invention, a tenth group of compounds is composed of the compounds for which Y is positioned in the para position of the phenyl nucleus.

Among the compounds of formula (II) that are subject matter of the invention, an eleventh group of compounds is composed of the compounds for which Y represents ($C_1$-$C_6$)alkyl-$NR_{11}$ in particular ($C_1$-$C_3$)alkyl-$NR_{11}$ more particularly $CH_2$—NH.

Among the compounds of formula (I) that are subject matter of the invention, a twelfth group of compounds is composed of the compounds for which $R_1$ represents a ($C_1$-$C_6$)alkyl, in particular a methyl group, each of $R_2$ and $R_3$ represents a hydrogen atom, $R_6$ represents a hydrogen atom, $R_9$ represents two substituents selected from a methoxy group and a chlorine atom, more particularly, the phenyl nucleus comprises two substituents in positions 3 and 4 on the phenyl nucleus, preferably, it is 3-Cl and 4-methoxy and $R_{10}$ represents a hydrogen atom.

Among the compounds of formula (I) that are subject matter of the invention, a thirteenth group of compounds is composed of the compounds for which $R_1$ represents a ($C_1$-$C_6$)alkyl, in particular a methyl group, $R_2$ and $R_3$ represents a ($C_1$-$C_6$)alkyl, in particular a methyl group, and the other one represents a hydrogen atom, $R_6$ represents a hydrogen atom, $R_9$ represents two substituents selected from a methoxy group and a chlorine atom, more particularly, the phenyl nucleus comprises two substituents in positions 3 and 4 on the phenyl nucleus, preferably, it is 3-Cl and 4-methoxy and $R_{10}$ represents a hydrogen atom.

Among the compounds of formula (II) that are subject matter of the invention, a fourteenth group of compounds is composed of the compounds of the following structure (beta epoxide configuration):

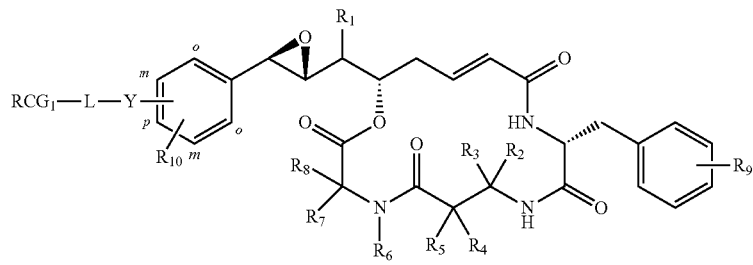

All these sub-groups taken alone or in combination are part of the invention.

Among the compounds of formula (II) that are the subject matter of the invention, mention may be made in particular of the following compounds:

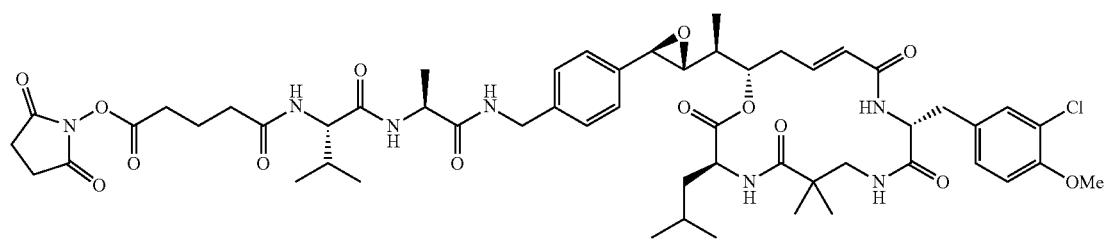

-continued
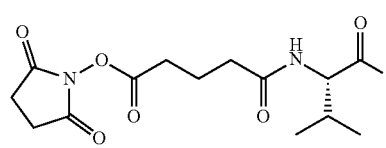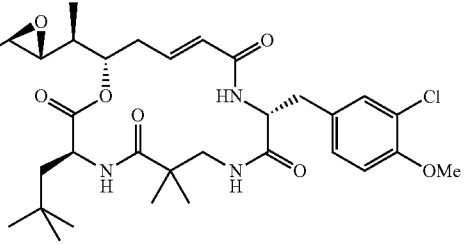
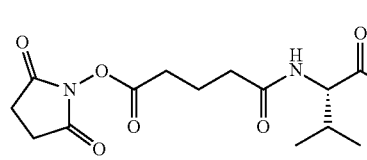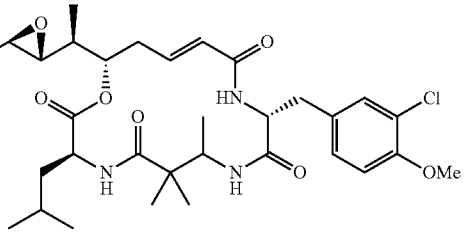
stereomer 1
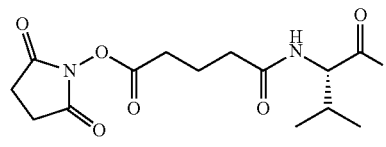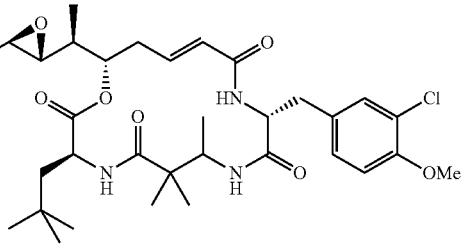
stereomer 1
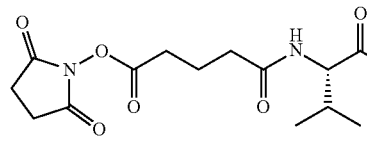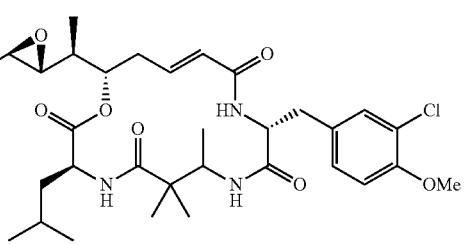
stereomer 2
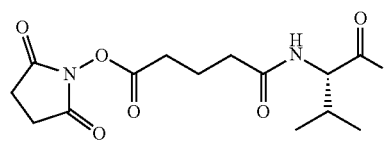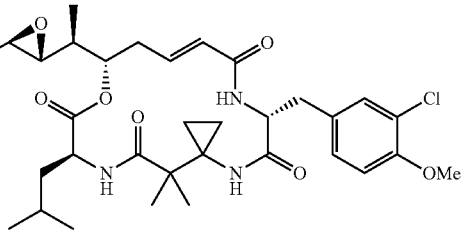
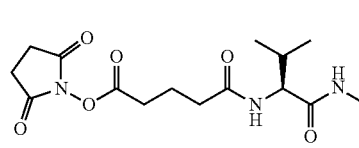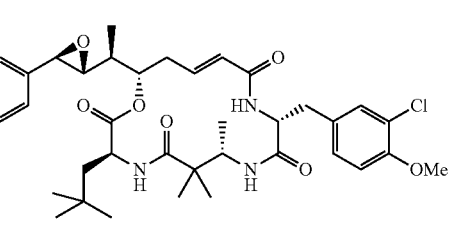

-continued

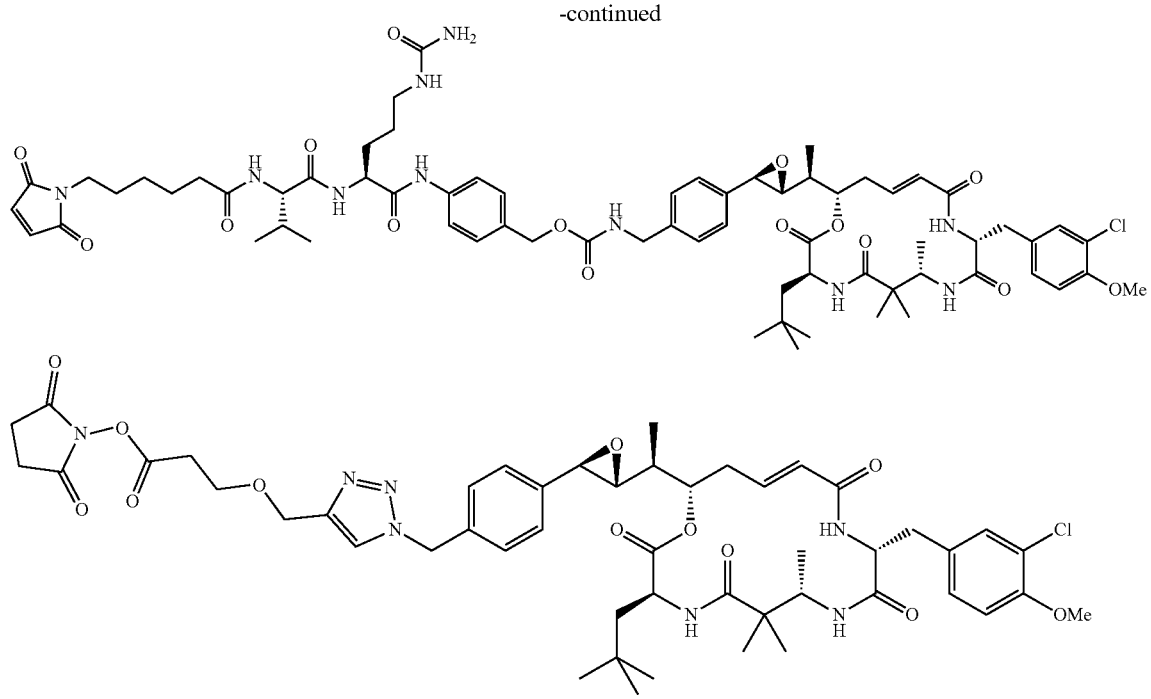

The invention also relates to conjugates of formula (III):

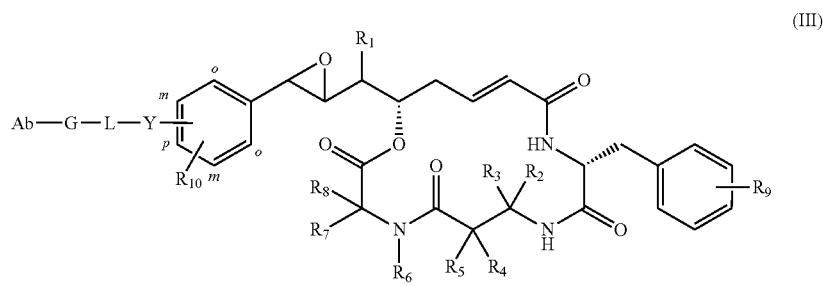

(III)

wherein:
R$_1$, R$_2$, R$_3$, R$_4$, R$_5$, R$_6$, R$_7$, R$_8$, R$_9$ and R$_{10}$ are as defined in formula (I);
Y and L are as defined in formula (II);
G represents the product of reaction between RCG1, a reactive chemical group present at the end of the linker and RCG2, an orthogonal reactive chemical group present on the antibody (Ab);
Ab represents an antibody.

Among the compounds of formula (III) that are subject matter of the invention, a first group of compounds is composed of the compounds for which R$_1$ represents a (C$_1$-C$_6$)alkyl, in particular a methyl group.

Among the compounds of formula (III) that are subject matter of the invention, a second group of compounds is composed of the compounds for which each of R$_2$ and R$_3$ represents a hydrogen atom.

Among the compounds of formula (III) that are subject matter of the invention, a third group of compounds is composed of the compounds for which one of R$_2$ and R$_3$ represents a (C$_1$-C$_6$)alkyl group, in particular a methyl group and the other one represents a hydrogen atom.

Among the compounds of formula (III) that are subject matter of the invention, a fourth group of compounds is composed of the compounds for which R$_2$ and R$_3$ form together with the carbon atom to which they are attached a (C$_3$-C$_6$)cycloalkyl group, in particular a cyclopropyl group.

Among the compounds of formula (III) that are subject matter of the invention, a fifth group of compounds is composed of the compounds for which each of R$_4$ and R$_5$ represents a (C$_1$-C$_6$)alkyl group, in particular a methyl group.

Among the compounds of formula (III) that are subject matter of the invention, a sixth group of compounds is composed of the compounds for which R$_6$ represents a hydrogen atom.

Among the compounds of formula (III) that are subject matter of the invention, a seventh group of compounds is composed of the compounds for which R$_7$ and R$_8$ represent independently of each other an hydrogen atom or a (C$_1$-C$_6$) alkyl group.

Among the compounds of formula (III) that are subject matter of the invention, an eighth group of compounds is composed of the compounds for which R$_9$ represents two substituents selected from a methoxy group and a chlorine atom. More particularly, the phenyl nucleus comprises two substituents in positions 3 and 4 on the phenyl nucleus. Preferably, it is 3-Cl and 4-methoxy.

Among the compounds of formula (III) that are subject matter of the invention, a ninth group of compounds is composed of the compounds for which $R_{10}$ represents a hydrogen atom.

Among the compounds of formula (II) that are subject matter of the invention, a tenth group of compounds is composed of the compounds for which Y is positioned in the para position of the phenyl nucleus.

Among the compounds of formula (III) that are subject matter of the invention, an eleventh group of compounds is composed of the compounds for which Y represents ($C_1$-$C_6$)alkyl-$NR_{11}$ in particular ($C_1$-$C_3$)alkyl-$NR_{11}$ more particularly $CH_2$—NH.

Among the compounds of formula (I) that are subject matter of the invention, a twelfth group of compounds is composed of the compounds of the following structure (beta epoxide configuration):

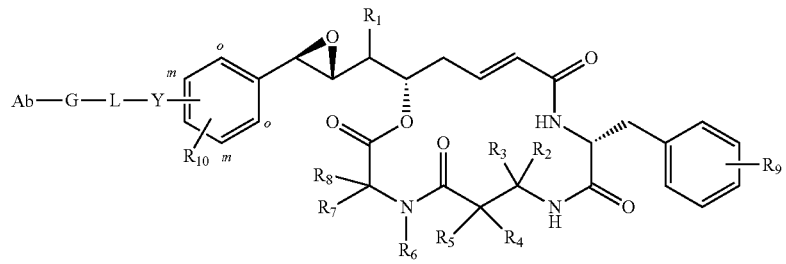

All these sub-groups taken alone or in combination are part of the invention.

Among the compounds of formula (III) that are the subject matter of the invention, mention may be made in particular of the following compounds:

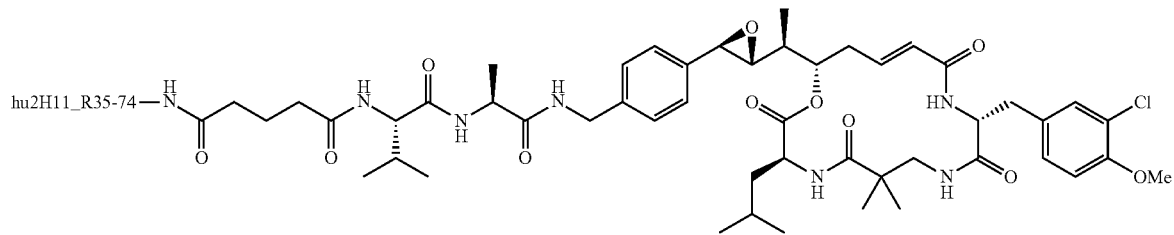

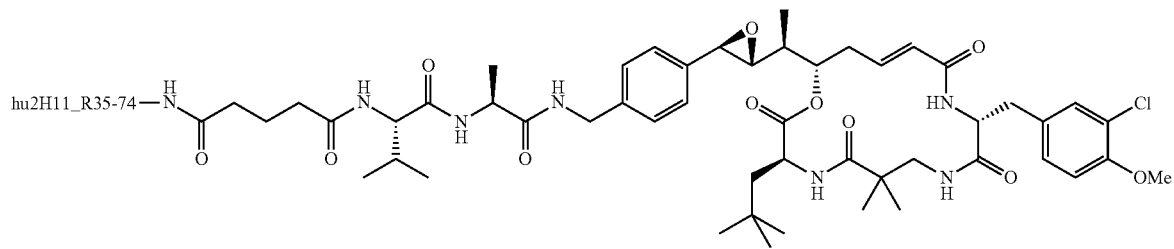

stereomer 1

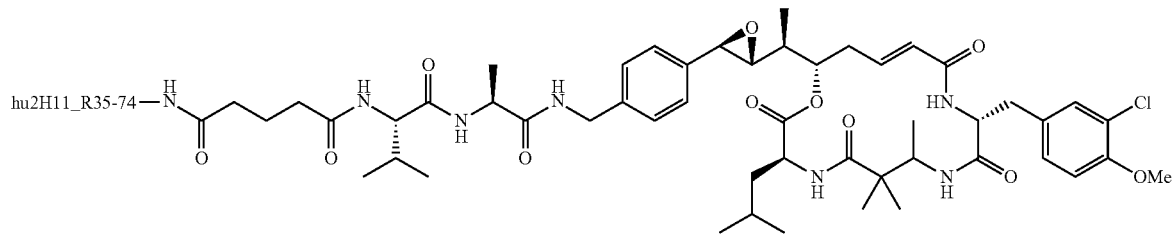

-continued stereomer 1 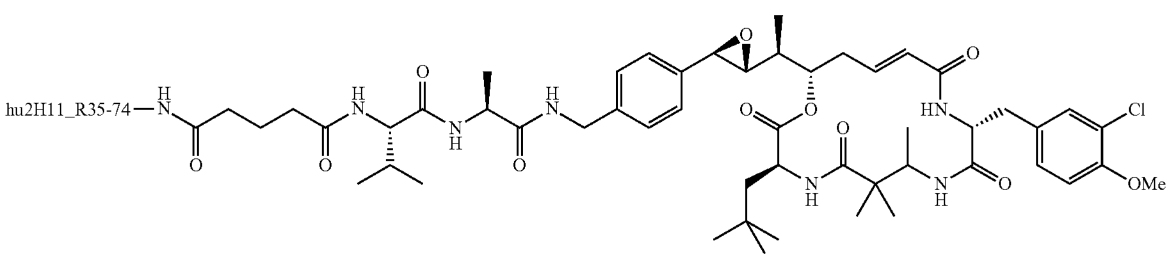 stereomer 2

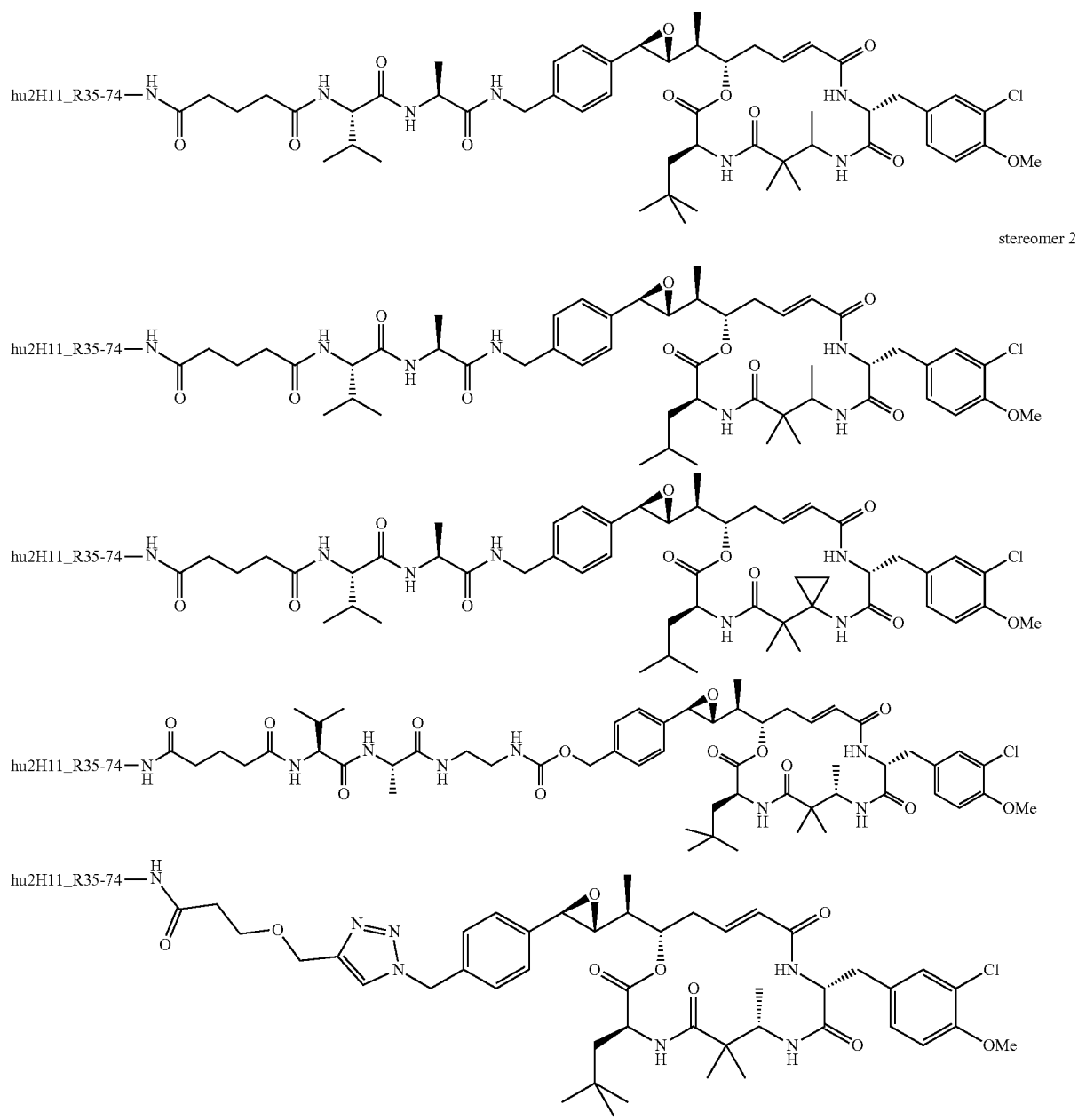

The attachment between the cryptophycin payload of formula (II) and the antibody, in order to obtain the conjugate of formula (III), is produced by means of a reactive chemical group RCG1 present on the payload that is reactive towards a reactive group RCG2 present on the antibody. The reaction between RCG1 and RCG2 ensures the attachment of the compound of formula (II) to the antibody by formation of a covalent bond. In the conjugate of formula (III), parts of RCG1 and RCG2 can remain forming the attachment between the linker and the antibody.

Examples of RCG1 that may be mentioned include:

(i) the —C(═O)—$Z_aR_a$ reactive group for which $Z_a$ represents a single bond, O or NH, more particularly O, and $R_a$ represents a hydrogen atom or a $(C_1-C_6)$alkyl, $(C_3-C_7)$cycloalkyl, alkenyl, aryl, heteroaryl or $(C_3-C_7)$heterocycloalkyl group. The aryl group may be substituted by 1 to 5 groups chosen from halogen, in particular F, alkyl, alkoxy, nitro and cyano groups;

(ii) one of the following reactive groups: the maleimido group; the haloacetamido

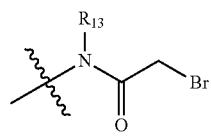

group with $R_{13}$ representing a hydrogen atom or a $(C_1\text{-}C_6)$ alkyl group, more particularly Me; —Cl; —$N_3$; —OH; —SH; —$NH_2$; —C≡CH or an activated C≡C such as a cyclooctyne moiety like

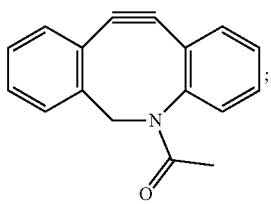 [SMILES: CC(=O)N1Cc2ccccc2C#Cc2ccccc21]

an O-alkyl hydroxylamine or a Pictet-Spengler reaction substrate such as

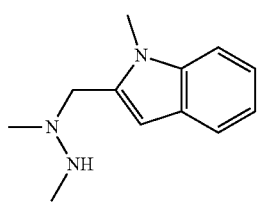

described in Agarwal P., et al., *Bioconjugate Chem* 2013, 24, 846-851.

More particularly, —$Z_aR_a$ may represent —OH, —$OCH_3$, —$OCH_2CH=CH_2$, (O-NHS)

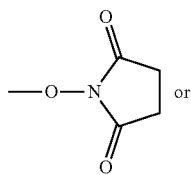 or

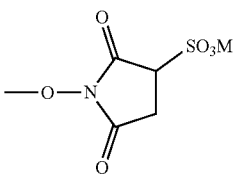

M = H or cation where cation represents for example sodium, potassium or cesium or

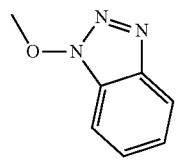

or the

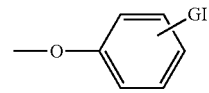

group in which GI represents at least one electroinductive group such as —$NO_2$ or -Hal, especially —F. They may be, for example, the following groups:

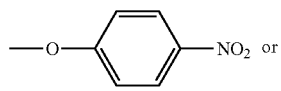 or

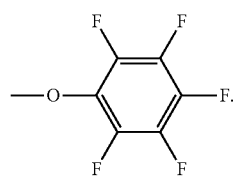

Another type of —C(=O)$Z_aR_a$ group is the following:

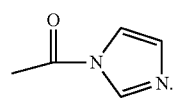

More particularly, RCG1 may be chosen from one of those described in the examples.

Examples of RCG2 that may be mentioned include (Garnett M. C., et al., *Advanced Drug Delivery Reviews* 2001, 53, 171-216):
(i) ε-amino groups of lysines borne by the side chains of the lysine residues that are present at the surface of an antibody;
(ii) α-amino groups of N-terminal amino acids of antibody heavy and light chains;
(iii) the saccharide groups of the hinge region;
(iv) the thiols of cysteines generated by reducing intra-chain disulfide bonds or the thiols of engineered cysteines;
(v) amide groups borne by the side chains of some glutamine residues that are present at the surface of an antibody;
(vi) aldehyde groups introduced using formylglycine generating enzyme.

More recently, other conjugation approaches have been considered, for instance the introduction of cysteines by mutation (Junutula J. R., et al., *Nature Biotechnology* 2008, 26, 925-932), the introduction of unnatural amino acids allowing other types of chemistry (Axup J. Y., et al., *PNAS* 2012, 109, 40, 16101-16106) or the conjugation on antibody glycans (Zhou Q., et al., *Bioconjugate Chem.* 2014, 25, 510-520). Another approach for site-specific modifications of antibodies is based on enzymatic labeling using for example bacterial transglutaminase (Jeger S., et al., *Angew. Chem. Int. Ed.* 2010, 49, 9995-9997; Strop P., et al., *Chem. Biol.* 2013, 20, 161-167) or formylglycine generating enzyme (Hudak J. E., et al., *Angew. Chem. Int. Ed.* 2012, 51, 4161-4165). For a review of site-specific conjugation strategies, see Agarwal P. and Bertozzi C. R., *Bioconjugate Chem* 2015, 26, 176-192. These conjugation technologies may also be applied to cryptophycin payloads described in the present invention.

It is also possible to chemically modify the antibody so as to introduce novel reactive chemical groups RCG2. Thus, it is well known to those skilled in the art how to modify an antibody with the aid of a modifying agent introducing for example activated disulfide, thiol, maleimido or haloacetamido groups (see especially WO2005/077090 page 14 and WO2011/001052). The modification makes it possible to improve the conjugation reaction and to use a wider variety of groups RCG1.

More particularly, in the case where RCG1 is of the type (ii) above, it is possible to chemically modify the antibody using an adequate modifying agent or to introduce one or more unnatural amino acids so as to introduce the adequate functions RCG2. For example:
when RCG1 represents a N-hydroxysuccinimidyl ester, RCG2 represents a —NH2 group;
when RCG1 represents a maleimido or haloacetamido function or a —Cl group, RCG2 may be a —SH group;
when RCG1 represents a —N$_3$ group, RCG2 may be a —C≡CH group or an activated CC such as a cyclooctyne moiety;
when RCG1 represents a —OH or —NH$_2$ group, RCG2 may be a carboxylic acid or amide function;
when RCG1 represents a —SH group, RCG2 may be a maleimido or haloacetamido function;
when RCG1 represents a —C≡CH function or an activated C≡C, RCG2 may be a —N$_3$ group;
when RCG1 represents a —O-alkyl hydroxylamine function or a Pictet-Spengler reaction substrate, RCG2 may be an aldehyde or ketone function.

Examples of G that may be mentioned include:

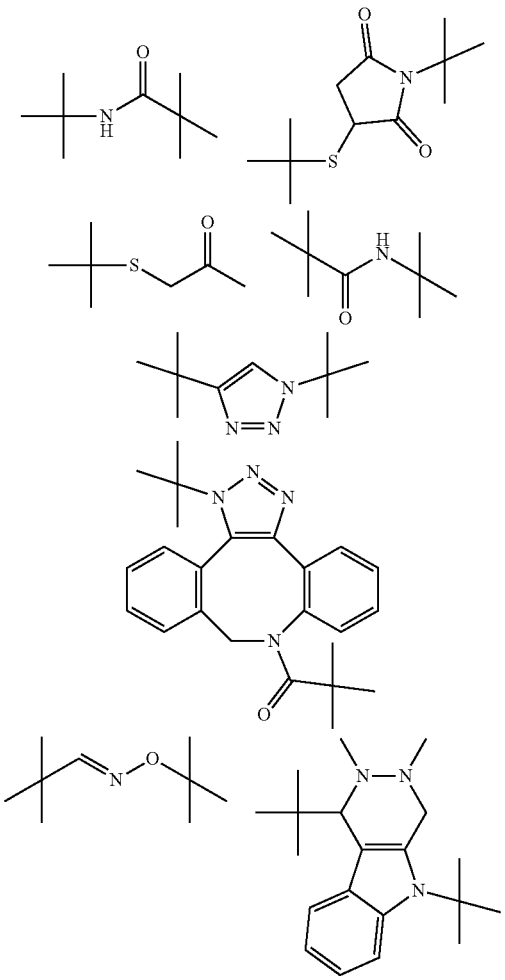

The invention relates to cryptophycin payloads of formula (II) and to conjugates of formula (III):

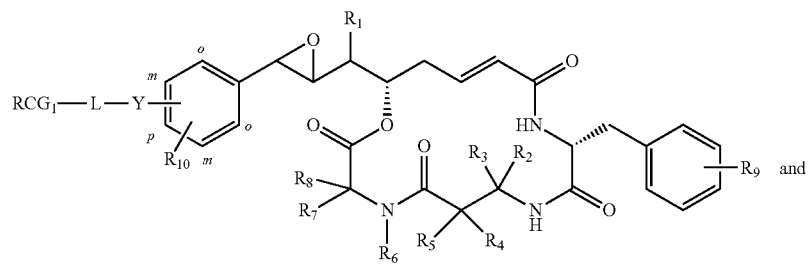

(II)

-continued

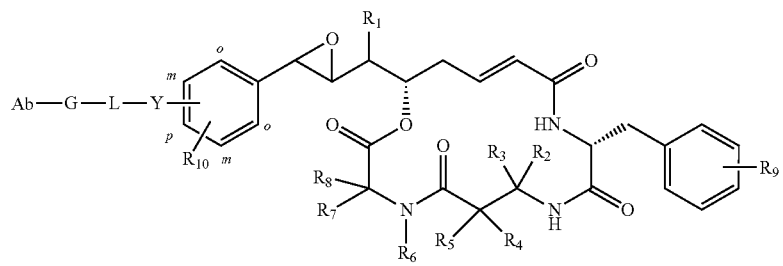

(III)

in which the linker L is of formula (IV):

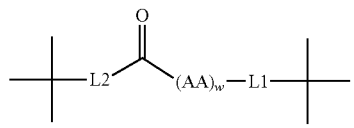

(IV)

in which:
L1 represents
  a single bond or a $NR_{16}$(hetero)aryl-$CR_{15}R_{14}$—O—C(=O) group if Y=$(C_1$-$C_6)$alkyl-$N(R_{11})$;
  a $NR_{18}$—$(C_2$-$C_6)$alkyl-$NR_{17}$—C(=O) group or a $NR_{16}$(hetero)aryl-$CR_{15}R_{14}$—O—C(=O)$NR_{18}$—$(C_2$-$C_6)$alkyl-$NR_{17}$—C(=O) group if Y=$(C_1$-$C_6)$ alkyl-O— or $(C_1$-$C_6)$alkyl-S;
  a $NR_{16}$(hetero)aryl-$CR_{15}R_{14}$ group if Y=C(=O)O, C(=O)NH, $(C_1$-$C_6)$alkyl-C(=O)O or $(C_1$-$C_6)$alkyl-C(=O)NH;
$R_{11}$, $R_{14}$, $R_{15}$, $R_{16}$, $R_{17}$ and $R_{18}$ represent, independently of each other, H or a $(C_1$-$C_6)$alkyl group;
$(AA)_w$ represents a sequence of w amino acids AA connected together via peptide bonds;
w represents an integer ranging from 1 to 12, preferably from 1 to 6 and more particularly 2 or 3;
L2 represents a single bond or a $(C_1$-$C_6)$alkyl group or a $(C_1$-$C_6)$alkyl-$(OCH_2CH_2)_i$ group or a $(C_1$-$C_6)$alkyl-$(OCH_2CH_2)_i$—O$(C_1$-$C_6)$alkyl group or a $(CH_2CH_2O)_i$ $(C_1$-$C_6)$alkyl group or a CH($SO_3H$)—$(C_1$-$C_6)$alkyl group or a $(C_1$-$C_6)$alkyl-CH($SO_3H$) group or a $(C_1$-$C_6)$alkyl-cyclohexyl group or a $NR_{19}$—$(C_1$-$C_6)$alkyl group or a $NR_{20}$—$(CH_2CH_2O)_i(C_1$-$C_6)$alkyl group or a $NR_{21}$-aryl group or a $NR_{21}$-heteroaryl group or a $(C_1$-$C_6)$alkyl-$NR_{22}$C(=O)—$(C_1$-$C_6)$alkyl group or a$(C_1$-$C_6)$alkyl-$NR_{22}$C(=O)—$(C_1$-$C_6)$alkyl-$(OCH_2CH_2)_i$ group. More particularly L2 represents a (C1-C6)alkyl group or a (C1-C6)alkyl-$(OCH_2CH_2)_i$ group or a CH($SO3H$)—(C1-C6)alkyl group;
$R_{19}$, $R_{20}$, $R_{21}$ and $R_{22}$ represent, independently of each other, H or a $(C_1$-$C_6)$alkyl group;
i represents an integer between 1 and 50 and preferably between 1 and 10 (i may take all the values between 1 and 50).

AA denotes a natural or unnatural amino acid, of configuration D or L, more particularly chosen from: alanine (Ala), β-alanine, γ-aminobutyric acid, 2-amino-2-cyclohexylacetic acid, 2-amino-2-phenylacetic acid, arginine (Arg), asparagine (Asn), aspartic acid (Asp), citrulline (Cit), cysteine (Cys), α,αdimethyl-γ-aminobutyric acid, β,β-dimethyl-γ-aminobutyric acid, glutamine (Gln), glutamic acid (Glu), glycine (Gly), histidine (His), isoleucine (Ile), leucine (Leu), lysine (Lys), ε-acetyl-lysine (AcLys), methionine (Met), ornithine (Orn), phenylalanine (Phe), proline (Pro), serine (Ser), threonine (Thr), tryptophan (Trp), tyrosine (Tyr), valine (Val). More particularly, AA is chosen from alanine (Ala), citrulline (Cit), glutamine (Gln), glycine (Gly), ε-acetyl-lysine (AcLys), valine (Val).

The sequence $(AA)_w$ has the formula:

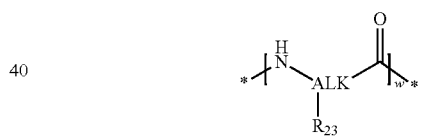

in which $R_{23}$ represents the side chain of one of the amino acids described above. Examples of sequences are as follows: Gly-Gly, Phe-Lys, Val-Lys, Val-AcLys, Val-Cit, Phe-Phe-Lys, D-Phe-Phe-Lys, Gly-Phe-Lys, Ala-Lys, Val-Ala, Phe-Cit, Leu-Cit, Ile-Cit, Trp-Cit, Phe-Ala, Ala-Phe, Gly-Gly-Gly, Gly-Ala-Phe, Gly-Val-Cit, Gly-Phe-Leu-Cit, Gly-Phe-Leu-Gly, Ala-Leu-Ala-Leu.

For Y=$(C_1$-$C_6)$alkyl-$N(R_{11})$ and more particularly $CH_2NH$, RCG1-L may be one of the following (IV1-17):

| RCG1 | Examples of RCG1-L |
|---|---|
| 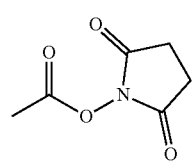 | 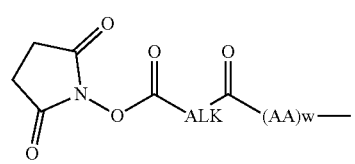 |
| | (IV1) |

| RCG1 | Examples of RCG1-L |
|---|---|
| | 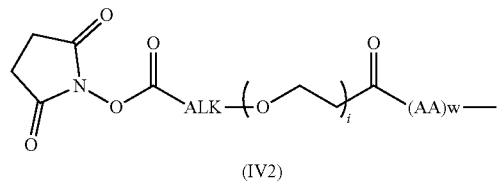<br>(IV2) |
| | 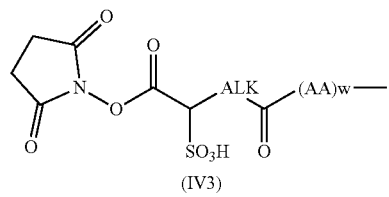<br>(IV3) |
| 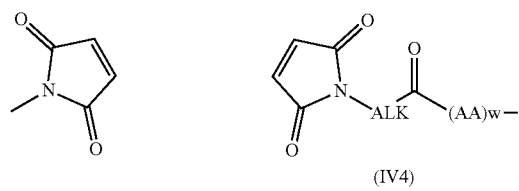 | |
| | (IV4) |
| | 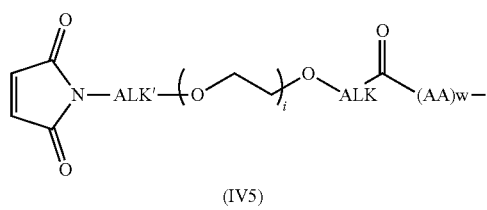<br>(IV5) |
| | 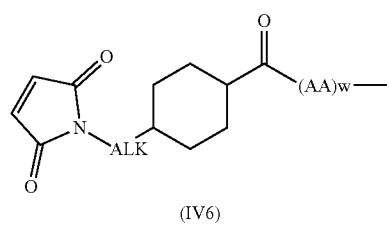<br>(IV6) |
| | 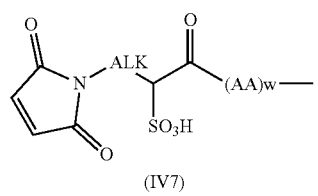<br>(IV7) |
| 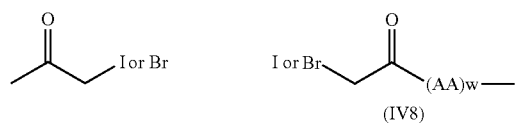 | |
| | (IV8) |
| | 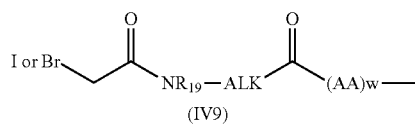<br>(IV9) |

| RCG1 | Examples of RCG1-L |
|---|---|
| | 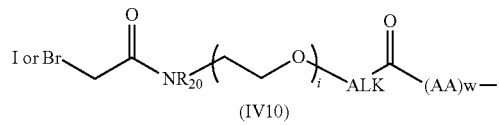<br>(IV10) |
| | 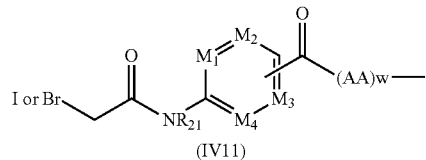<br>(IV11) |
| —NH$_2$ | 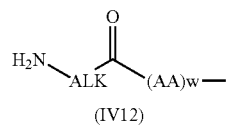<br>(IV12) |
| | 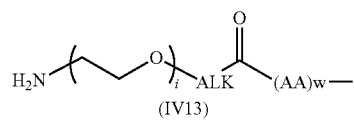<br>(IV13) |
| —N$_3$ | 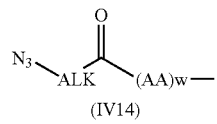<br>(IV14) |
| | 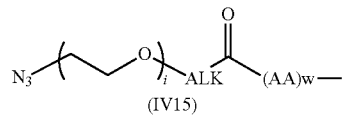<br>(IV15) |
| | 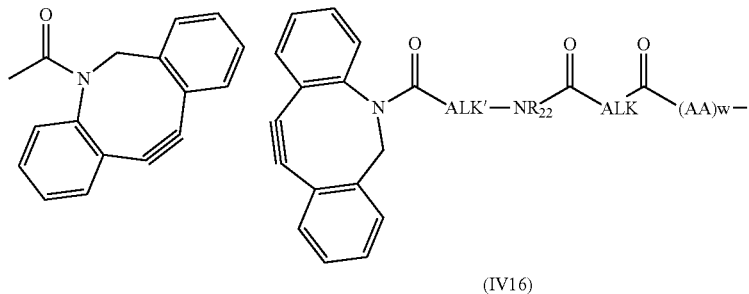<br>(IV16) |
| | 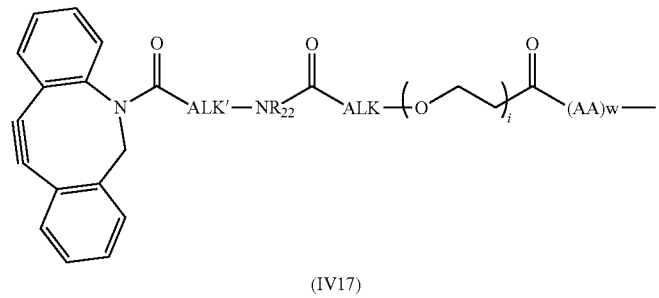<br>(IV17) | in which:
 (AA)$_w$ represents a sequence of w amino acids AA connected together via peptide bonds as described above;
 w represents an integer ranging from 1 to 12, preferably from 1 to 6 and more particularly 2 or 3;
 i represents an integer between 1 and 50 and preferably between 1 and 10 (i may take all the values between 1 and 50);
 $M_1$, $M_2$, $M_3$ and $M_4$ are chosen, independently of each other, from $CR_{24}$ and N;

$R_{19}$, $R_{20}$, $R_{21}$, $R_{22}$ and $R_{24}$ represent, independently of each other, a hydrogen atom or a $(C_1-C_6)$alkyl group, more particularly a hydrogen atom or a methyl group.
For Y=$(C_1-C_6)$alkyl-O or $(C_1-C_6)$alkyl-S and more particularly $CH_2O$ or $CH_2S$, RCG1-L may be one of the following (IV18-34):
| RCG1 | Examples of RCG1-L |
|---|---|
| 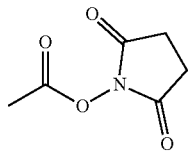 | 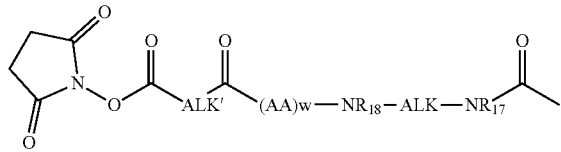<br>(IV18) |
| | 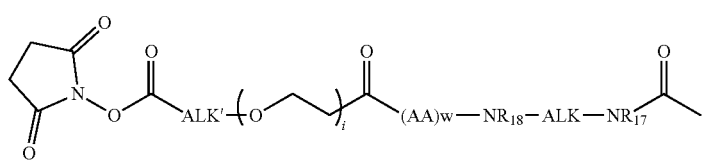<br>(IV19) |
| | 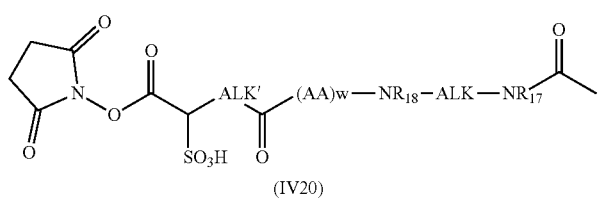<br>(IV20) |
| 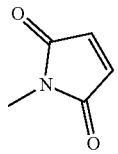 | 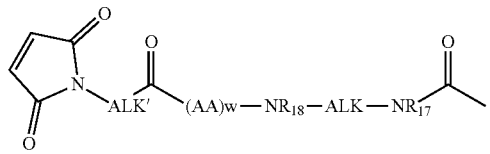<br>(IV21) |
| | 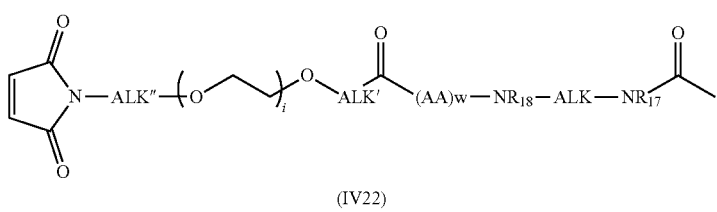<br>(IV22) |
| | 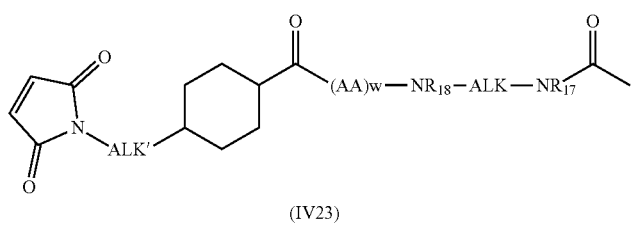<br>(IV23) |
| | 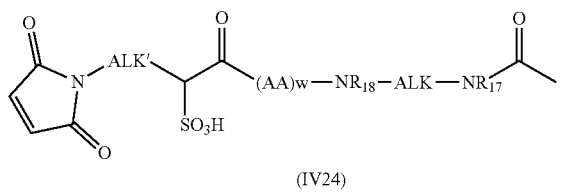<br>(IV24) |

-continued
| RCG1 | Examples of RCG1-L |
|---|---|
| 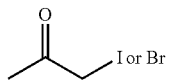 | 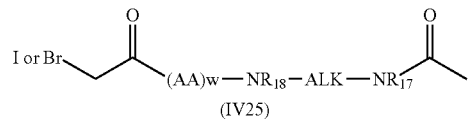(IV25) |
| | 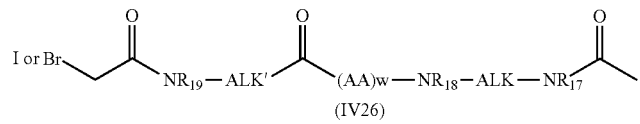(IV26) |
| | 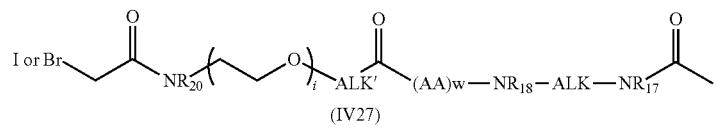(IV27) |
| | 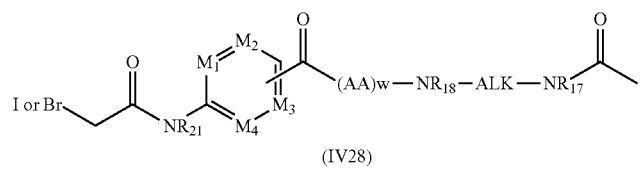(IV28) |
| —NH₂ | 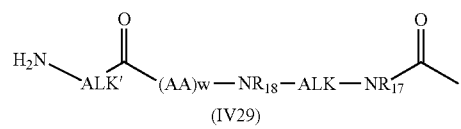(IV29) |
| | 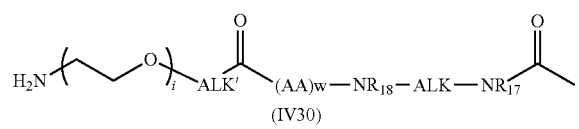(IV30) |
| —N₃ | 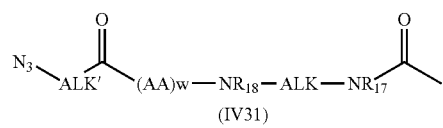(IV31) |
| | 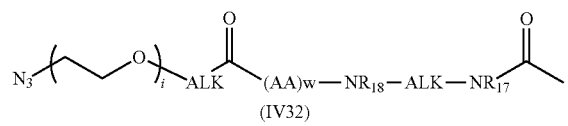(IV32) |
| 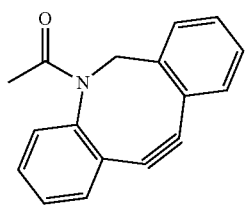 | 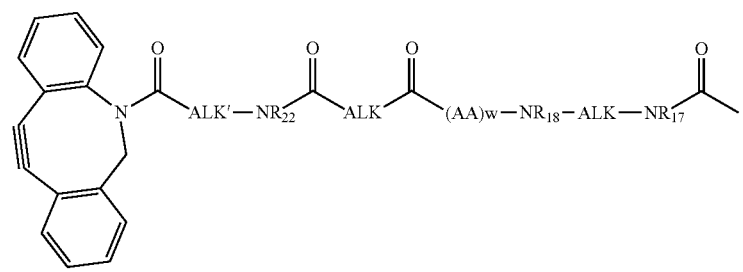(IV33) |

| RCG1 | Examples of RCG1-L |
|---|---|
| | 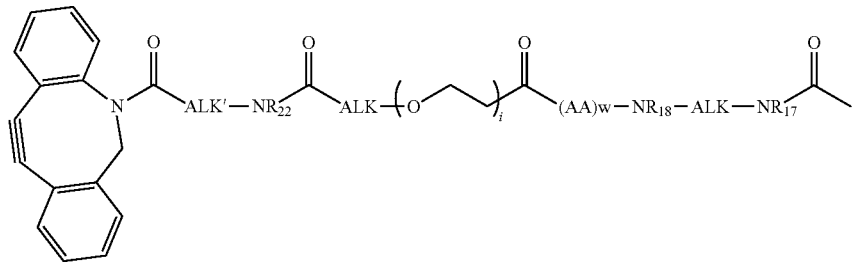 |
| | (IV34) | in which:
- $(AA)_w$ represents a sequence of w amino acids AA connected together via peptide bonds as described above;
- w represents an integer ranging from 1 to 12, preferably from 1 to 6 and more particularly 2 or 3;
- i represents an integer between 1 and 50 and preferably between 1 and 10 (i may take all the values between 1 and 50);

$M_1$, $M_2$, $M_3$ and $M_4$ are chosen, independently of each other, from $CR_{24}$ and N;

$R_{17}$, $R_{18}$, $R_{19}$, $R_{20}$, $R_{21}$, $R_{22}$ and $R_{24}$ represent, independently of each other, a hydrogen atom or a $(C_1-C_6)$alkyl group, more particularly a hydrogen atom or a methyl group.

For $Y=(C_1-C_6)$alkyl-$N(R_{11})$ and more particularly $CH_2NH$, RCG1-L may also be one of the following (IV35-51):

| RCG1 | Examples of RCG1-L |
|---|---|
| 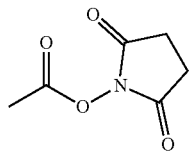 | 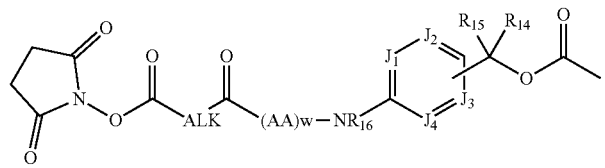 |
| | (IV35) |
| | 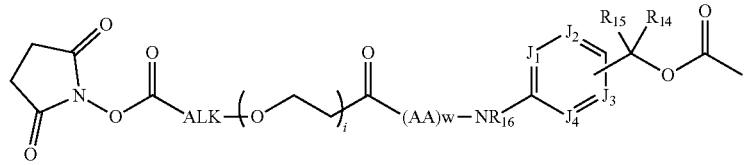 |
| | (IV36) |
| | 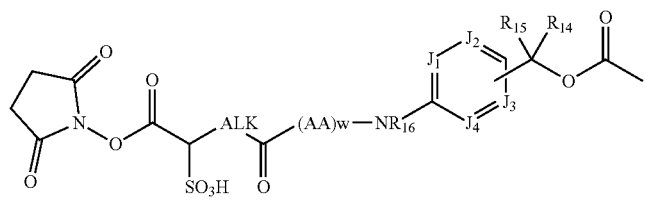 |
| | (IV37) |
| 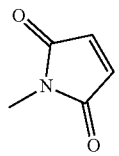 | 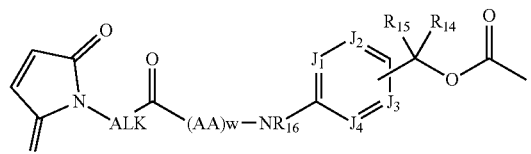 |
| | (IV38) |

-continued
| RCG1 | Examples of RCG1-L |
|------|---------------------|
|      | 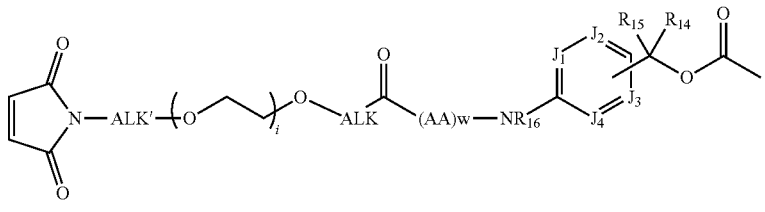 (IV39) |
|      | 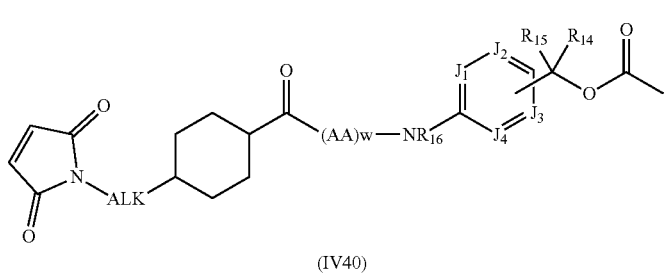 (IV40) |
|      | 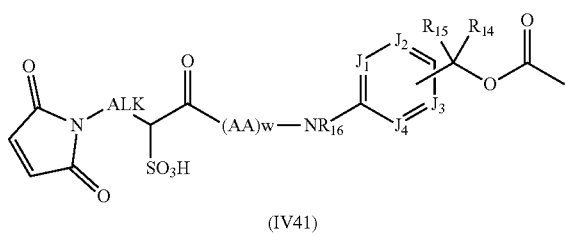 (IV41) |
| 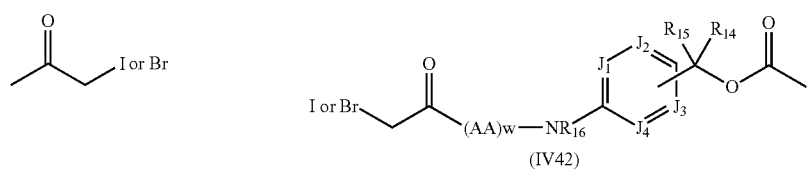 | (IV42) |
|      | 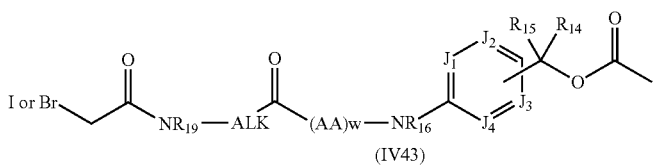 (IV43) |
|      | 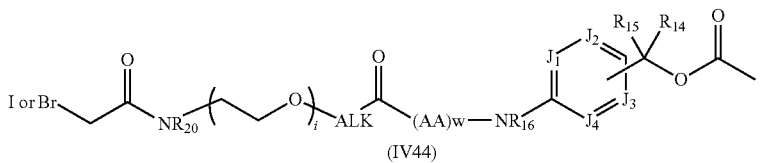 (IV44) |
|      | 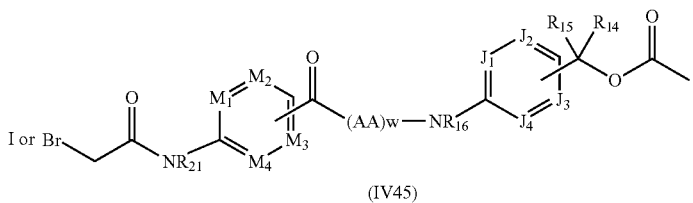 (IV45) |

-continued
| RCG1 | Examples of RCG1-L |
|---|---|
| —NH$_2$ | 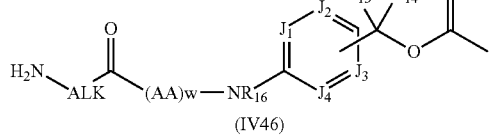<br>(IV46)<br><br>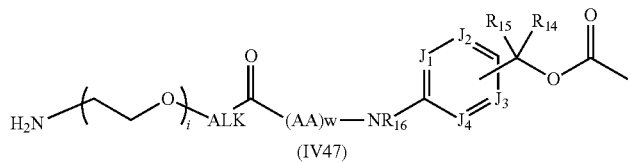<br>(IV47) |
| —N$_3$ | 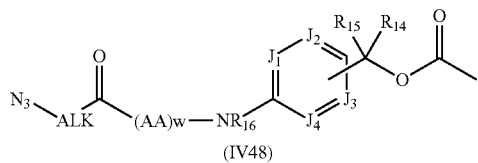<br>(IV48)<br><br>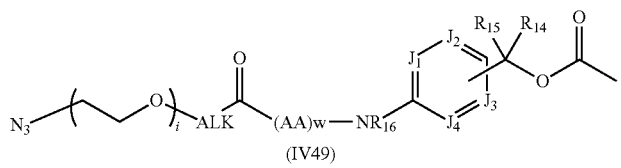<br>(IV49) |
| 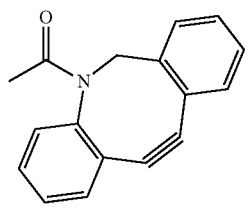 | 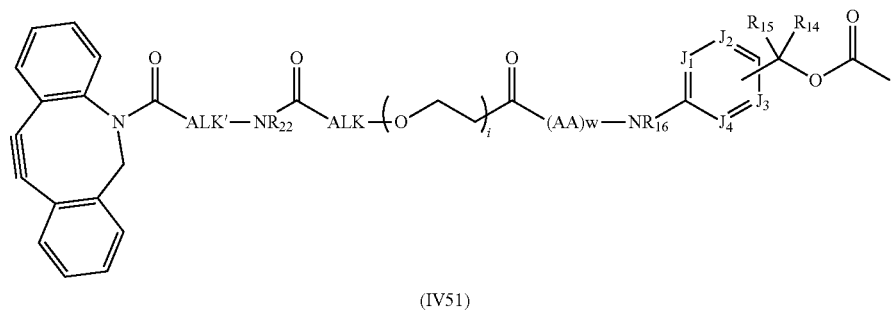<br>(IV50)<br><br>(IV51) | in which:
- $(AA)_w$ represents a sequence of w amino acids AA connected together via peptide bonds as described above;
- w represents an integer ranging from 1 to 12, preferably from 1 to 6 and more particularly 2 or 3;
- i represents an integer between 1 and 50 and preferably between 1 and 10 (i may take all the values between 1 and 50);
- $J_1$, $J_2$, $J_3$ and $J_4$ are chosen, independently of each other, from $CR_{24}$ and N;

$M_1$, $M_2$, $M_3$ and $M_4$ are chosen, independently of each other, from $CR_{24}$ and N;

$R_{14}$, $R_{15}$, $R_{16}$, $R_{19}$, $R_{20}$, $R_{21}$, $R_{22}$ and $R_{24}$ represent, independently of each other, a hydrogen atom or a $(C_1-C_6)$alkyl group, more particularly a hydrogen atom or a methyl group.

For $Y=(C_1-C_6)$alkyl-O or $(C_1-C_6)$alkyl-S and more particularly $CH_2O$ or $CH_2S$, RCG1-L may also be one of the following (IV52-68):

| RCG1 | Examples of RCG1-L |
|---|---|
| 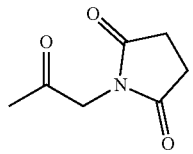 | 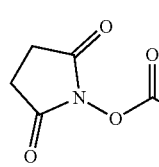 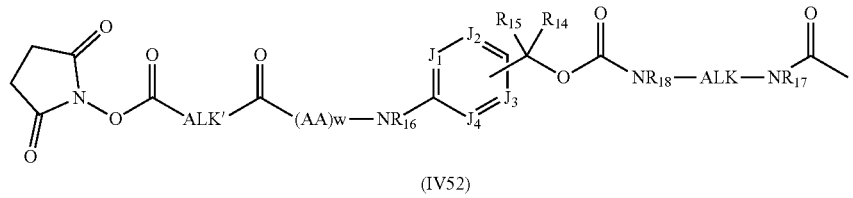 <br> (IV52) |
| | 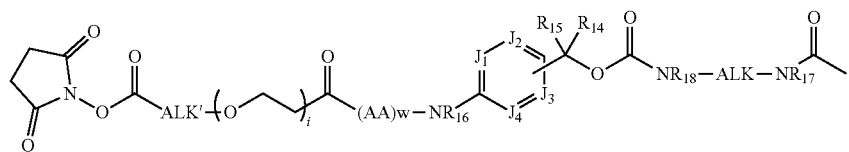 <br> (IV53) |
| | 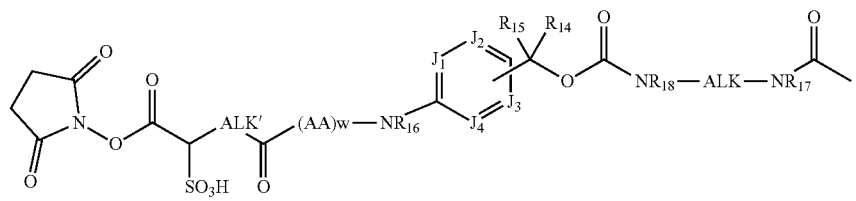 <br> (IV54) |
| 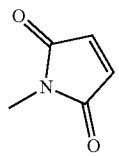 | 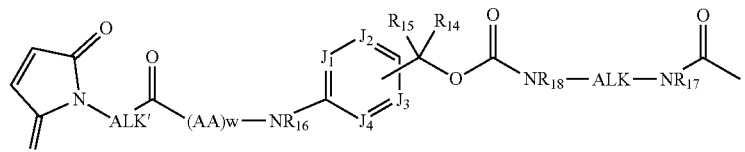 <br> (IV55) |
| | 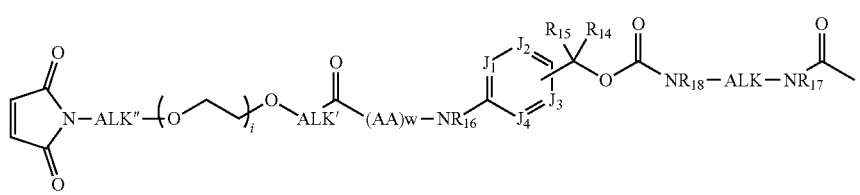 <br> (IV56) |
| | 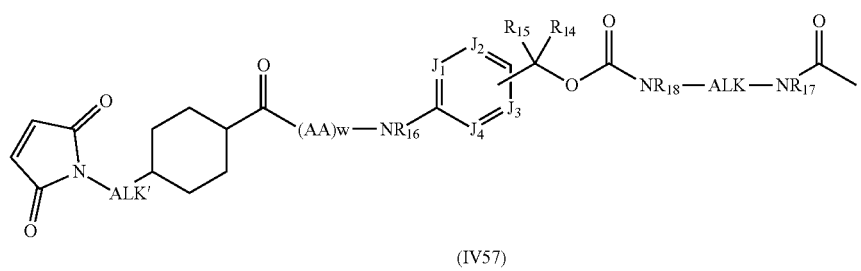 <br> (IV57) |

| RCG1 | Examples of RCG1-L |
|---|---|
| | 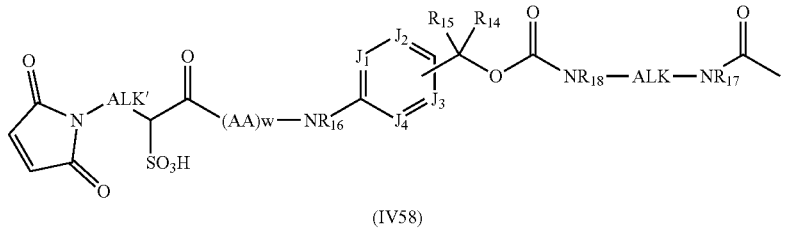<br>(IV58) |
| 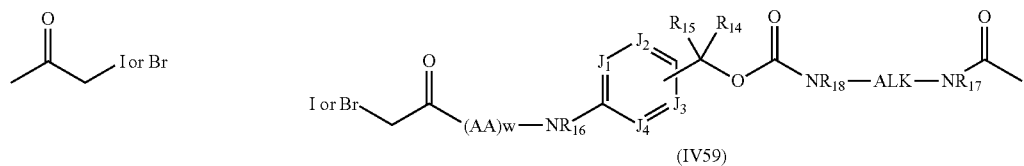 | 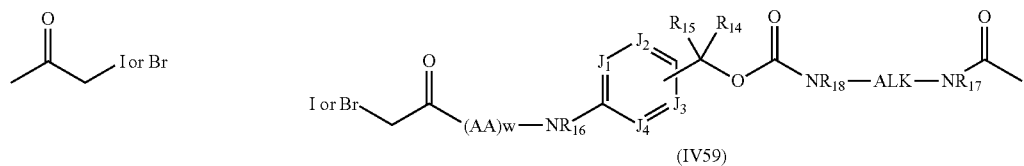<br>(IV59) |
| | 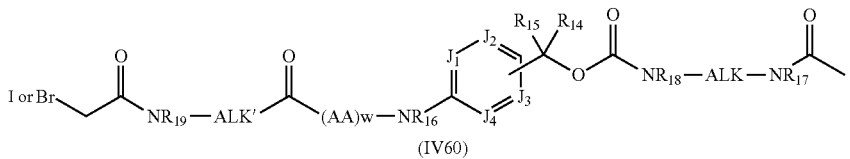<br>(IV60) |
| | 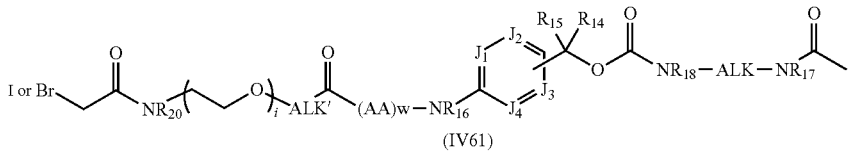<br>(IV61) |
| | 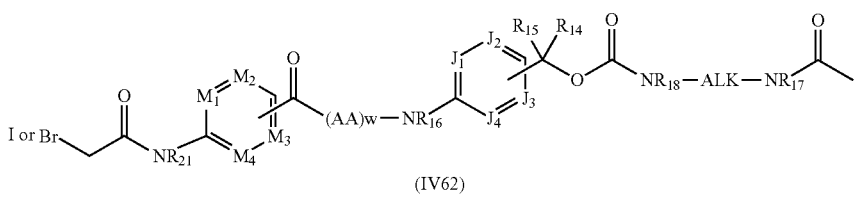<br>(IV62) |
| —NH$_2$ | 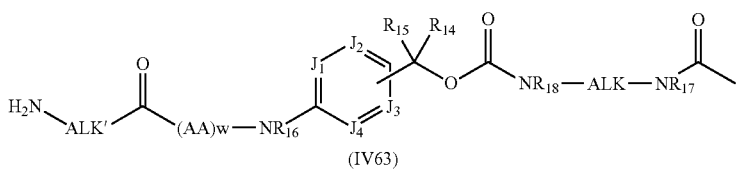<br>(IV63) |
| | 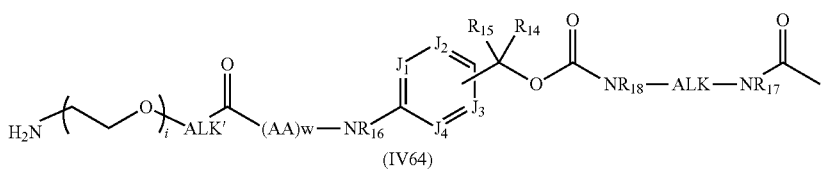<br>(IV64) |
| —N$_3$ | 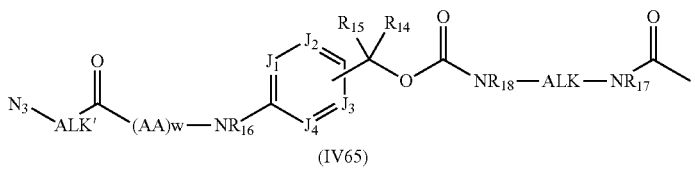<br>(IV65) |

| RCG1 | Examples of RCG1-L |
|---|---|
| | 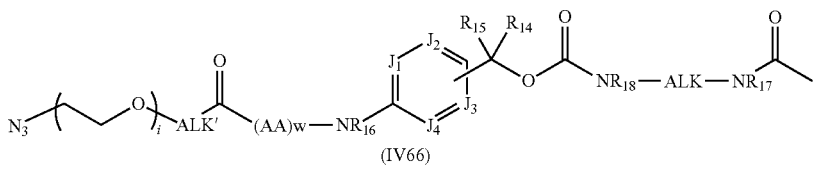 (IV66) |
| | 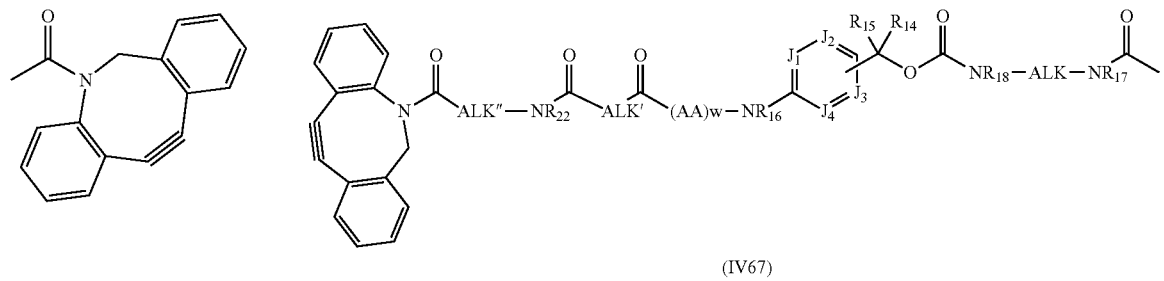 (IV67) |
| | 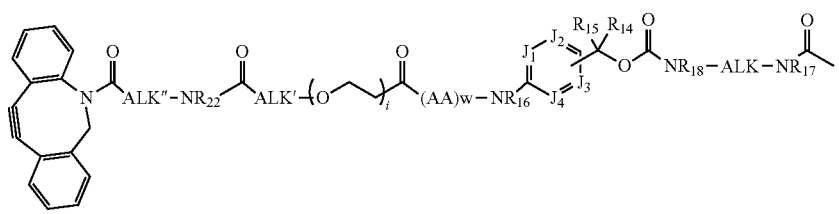 (IV68) | in which:
- $(AA)_w$ represents a sequence of w amino acids AA connected together via peptide bonds as described above;
- w represents an integer ranging from 1 to 12, preferably from 1 to 6 and more particularly 2 or 3;
- i represents an integer between 1 and 50 and preferably between 1 and 10 (i may take all the values between 1 and 50);
- $J_1$, $J_2$, $J_3$ and $J_4$ are chosen, independently of each other, from $CR_{24}$ and N;
- $M_1$, $M_2$, $M_3$ and $M_4$ are chosen, independently of each other, from $CR_{24}$ and N;
- $R_{14}$, $R_{15}$, $R_{16}$, $R_{17}$, $R_{18}$, $R_{19}$, $R_{20}$, $R_{21}$, $R_{22}$ and $R_{24}$ represent, independently of each other, a hydrogen atom or a $(C_1$-$C_6)$alkyl group, more particularly a hydrogen atom or a methyl group.

For $Y=C(=O)O$, $C(=O)NH$, $(C_1$-$C_6)$alkyl-$C(=O)O$ or $(C_1$-$C_6)$alkyl-$C(=O)NH$ and more particularly $C(=O)O$ or $CH_2$—$C(=O)O$, RCG1-L may be one of the following (IV69-85):

| RCG1 | Examples of RCG1-L |
|---|---|
| | 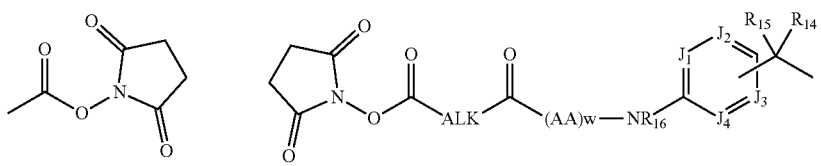  (IV69) |
| | 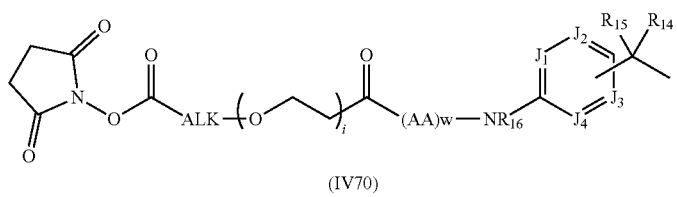 (IV70) |

| RCG1 | Examples of RCG1-L |
|---|---|
| | 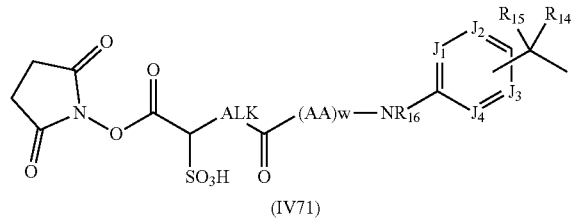 (IV71) |
| 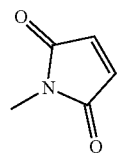 | 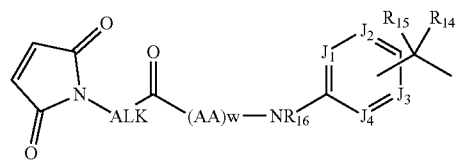 (IV72) |
| | 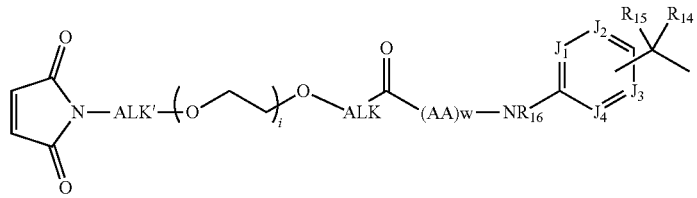 (IV73) |
| | 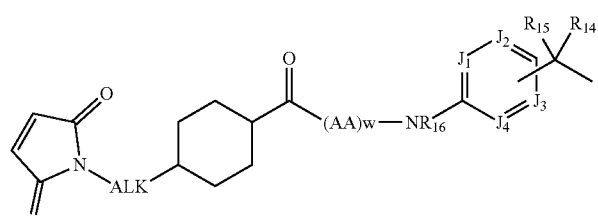 (IV74) |
| | 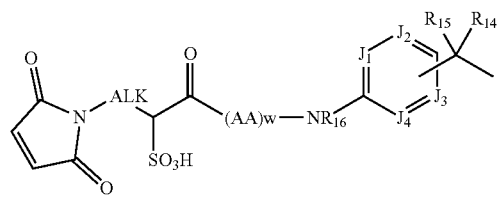 (IV75) |
| 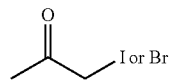 | 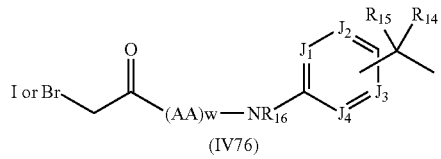 (IV76) |
| | 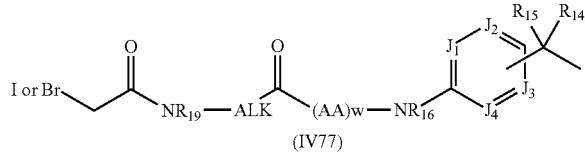 (IV77) |

| RCG1 | Examples of RCG1-L |
|---|---|
|  | 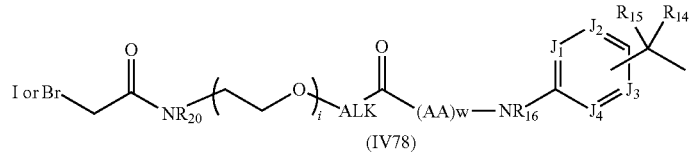<br>(IV78) |
|  | 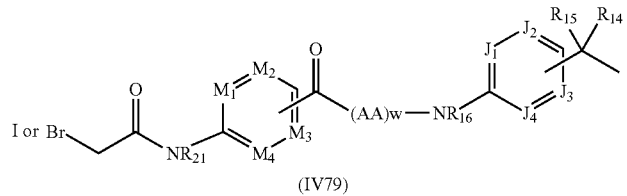<br>(IV79) |
| —NH$_2$ | 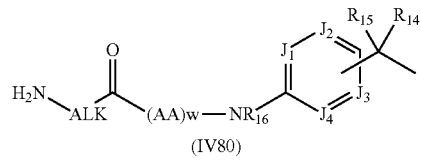<br>(IV80) |
|  | 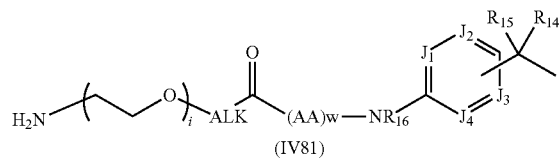<br>(IV81) |
| —N$_3$ | 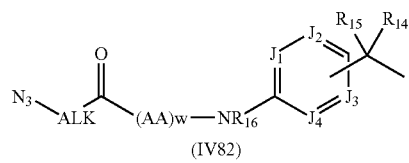<br>(IV82) |
|  | 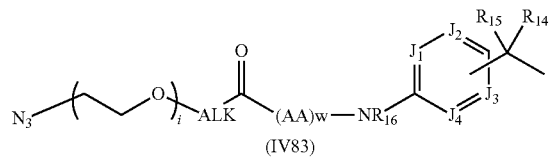<br>(IV83) |
|  | 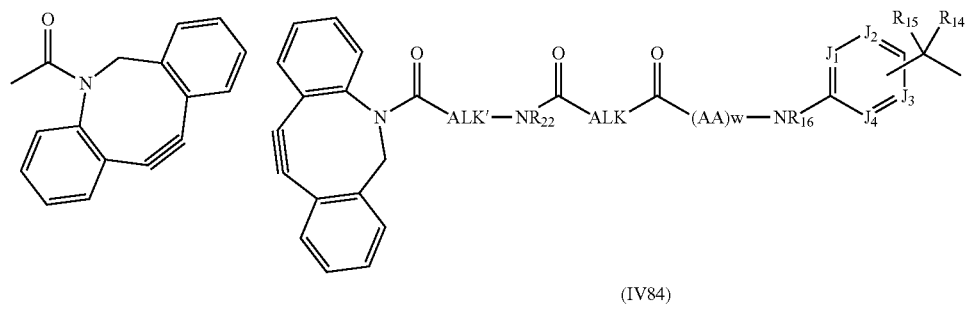<br>(IV84) |

| RCG1 | Examples of RCG1-L |
|---|---|
| 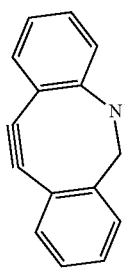 | 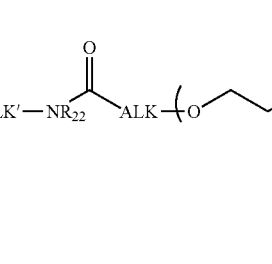 (IV85) | in which:
- $(AA)_w$ represents a sequence of w amino acids AA connected together via peptide bonds as described above;
- w represents an integer ranging from 1 to 12, preferably from 1 to 6 and more particularly 2 or 3;
- i represents an integer between 1 and 50 and preferably between 1 and 10 (i may take all the values between 1 and 50);
- $J_1$, $J_2$, $J_3$ and $J_4$ are chosen, independently of each other, from $CR_{24}$ and N;
- $M_1$, $M_2$, $M_3$ and $M_4$ are chosen, independently of each other, from $CR_{24}$ and N;
- $R_{14}$, $R_{15}$, $R_{16}$, $R_{19}$, $R_{20}$, $R_{21}$, $R_{22}$ and $R_{24}$ represent, independently of each other, a hydrogen atom or a $(C_1-C_6)$alkyl group, more particularly a hydrogen atom or a methyl group.

For Y=C(=O) or $(C_1-C_6)$alkyl-C(=O), the invention also relates to cryptophycin payloads of formula (II) and to conjugates of formula (III):

in which the linker L is of formula (V):

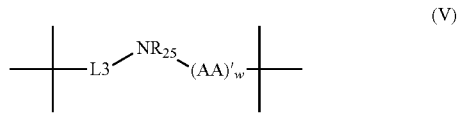 (V)

in which:
- $(AA)'_w$ represents a sequence of w amino acids AA connected together via peptide bonds;
- w represents an integer ranging from 1 to 12, preferably from 1 to 6 and more particularly 2 or 3;
- $R_{25}$ represents a hydrogen atom or a $(C_1-C_6)$alkyl group;
- L3 represents a $(C_1-C_6)$alkyl group or a $(CH_2CH_2O)_i$—$(C_1-C_6)$alkyl group or a $(C_1-C_6)$alkyl-$(OCH_2CH_2)_i$ group or a $CH(SO_3H)$—$(C_1-C_6)$alkyl group or or a $(C_1-C_6)$alkyl-$(OCH_2CH_2)_i$—$O(C_1-C_6)$alkyl group or a

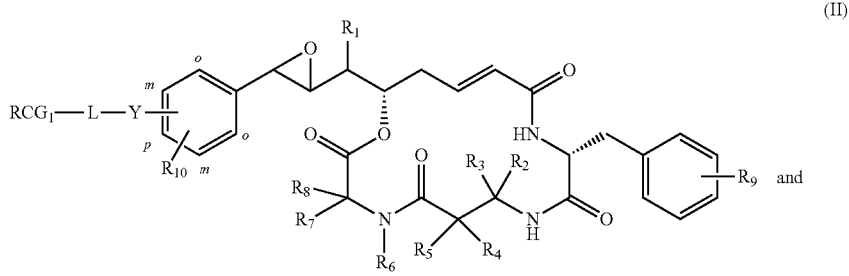 (II)

and

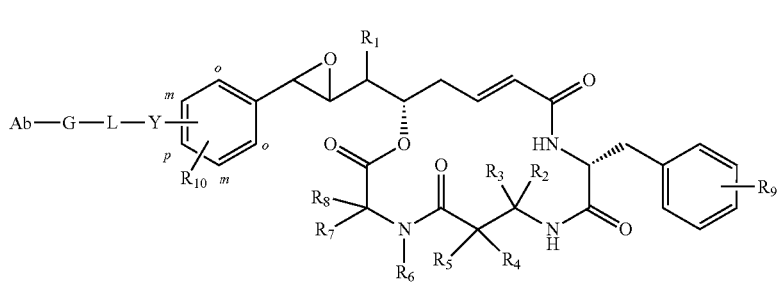 (III)

$NR_{19}$—$(C_1-C_6)$alkyl group or a $NR_{20}$—$(CH_2CH_2O)_iCH_2CH_2$ group or a $(C_1-C_6)$alkyl-cyclohexyl-C(=O)$NR_{19}$—$(C_1-C_6)$alkyl group or a $(C_1-C_6)$alkyl-cyclohexyl-C(=O)$NR_{20}$—$(CH_2CH_2O)_i$—$CH_2CH_2$ group or a $NR_{21}$-aryl-C(=O)$NR_{19}$—$(C_1-C_6)$alkyl group or a $NR_{21}$-heteroaryl-C(=O)$NR_{19}$—$(C_1-C_6)$alkyl group or a $(C_1-C_6)$alkyl-$NR_{22}$C(=O)$(CH_2CH_2O)_i$—$(C_1-C_6)$alkyl group;

$R_{19}$, $R_{20}$, $R_{21}$, $R_{22}$ and $R_{25}$ represents a hydrogen atom or a $(C_1-C_6)$alkyl group;

RCG1 represents a reactive chemical group that is reactive towards a reactive chemical group present on the antibody, as defined above;

$R_1$, $R_2$, $R_3$, $R_4$, $R_5$, $R_6$, $R_7$, $R_8$, $R_9$ and $R_{10}$ are as defined above.

AA denotes a natural or unnatural amino acid, of configuration D or L, more particularly chosen from: alanine (Ala), β-alanine, γ-aminobutyric acid, 2-amino-2-cyclohexylacetic acid, 2-amino-2-phenylacetic acid, arginine (Arg), asparagine (Asn), aspartic acid (Asp), citrulline (Cit), cysteine (Cys), α,α-dimethyl-γ-aminobutyric acid, β,β-dimethyl-γ-aminobutyric acid, glutamine (Gln), glutamic acid (Glu), glycine (Gly), histidine (His), isoleucine (Ile), leucine (Leu), lysine (Lys), ε-acetyl-lysine (AcLys), methionine (Met), ornithine (Orn), phenylalanine (Phe), proline (Pro), serine (Ser), threonine (Thr), tryptophan (Trp), tyrosine (Tyr), valine (Val). More particularly, AA is chosen from alanine (Ala), citrulline (Cit), glutamine (Gln), glycine (Gly), ε-acetyl-lysine (AcLys), valine (Val)

The sequence $(AA)'_w$ has the formula:

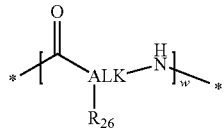

in which $R_{26}$ represents the side chain of one of the amino acids described above. Examples of sequences are as follows: Gly-Gly, Lys-Phe, Lys-Val, AcLys-Val, Cit-Val, Lys-Phe-Phe, Lys-Phe-DPhe, Lys-Phe-Gly, Lys-Ala, Ala-Val, Cit-Phe, Cit-Leu, Cit-Ile, Cit-Trp, Ala-Phe, Phe-Ala, Gly-Gly-Gly, Phe-Ala-Gly, Cit-Val-Gly, Cit-Leu-Phe-Gly, Gly-Leu-Phe-Gly, Leu-Ala-Leu-Ala.

For Y=C(=O) or $(C_1-C_6)$alkyl-C(=O) and more particularly C(=O) or $CH_2$—C(=O), RCG1-L may be one of the following (V86-101):

| RCG1 | Examples of RCG1-L |
|---|---|
| 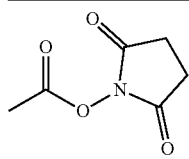 | 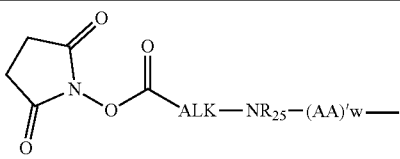<br>(V86) |
| | 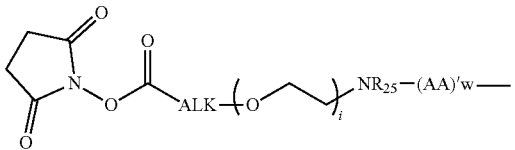<br>(V87) |
| | 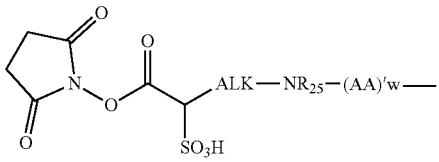<br>(V88) |
| 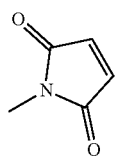 | 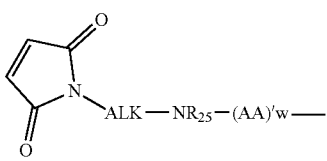<br>(V89) |
| | 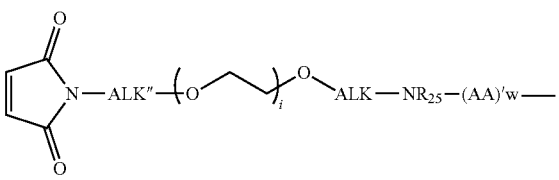<br>(V90) |

| RCG1 | Examples of RCG1-L |
|---|---|
| | 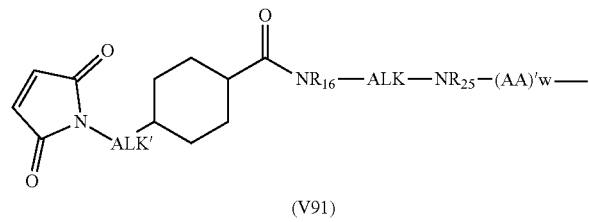<br>(V91)<br>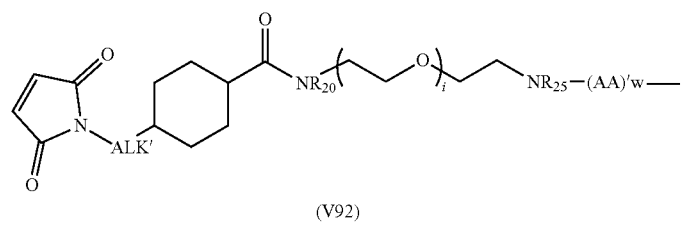<br>(V92) |
| 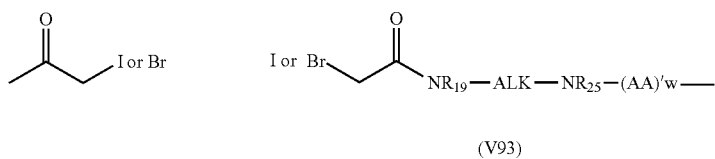 | 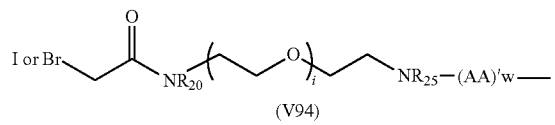<br>(V93)<br>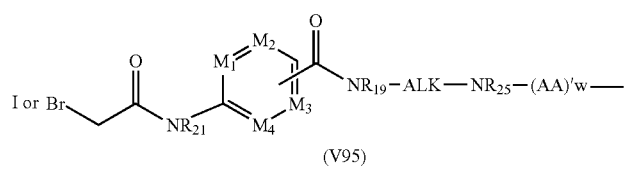<br>(V94)<br>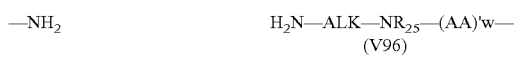<br>(V95) |
| —NH$_2$ | H$_2$N—ALK—NR$_{25}$—(AA)'w—<br>(V96)<br>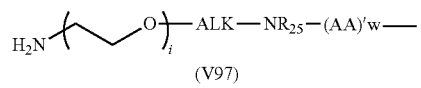<br>(V97) |
| —N$_3$ | N$_3$—ALK—NR$_{25}$—(AA)'w—<br>(V98)<br>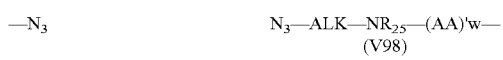<br>(V99) |
| 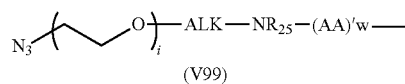 | 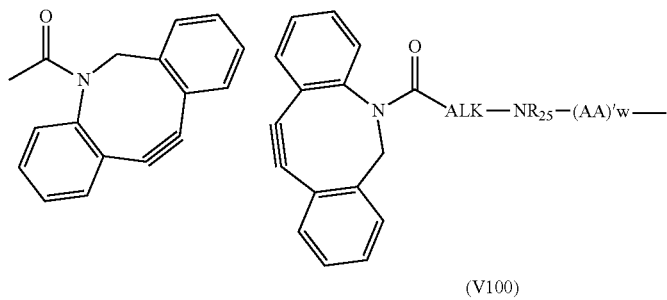<br>(V100) |

| RCG1 | Examples of RCG1-L |
|---|---|
| | 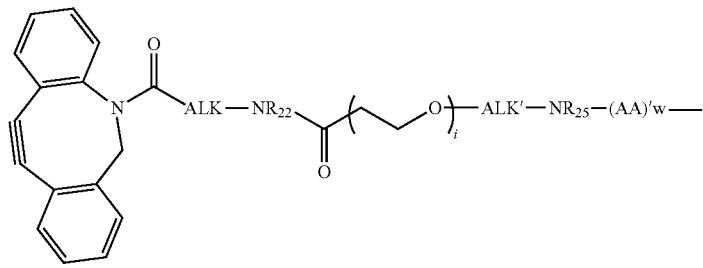<br>(V101) | in which:
- $(AA)'_w$ represents a sequence of w amino acids AA connected together via peptide bonds as described above;
- w represents an integer ranging from 1 to 12, preferably from 1 to 6 and more particularly 2 or 3;
- i represents an integer between 1 and 50 and preferably between 1 and 10 (i may take all the values between 1 and 50);
- $M_1$, $M_2$, $M_3$ and $M_4$ are chosen, independently of each other, from $CR_{24}$ and N;
- $R_{19}$, $R_{20}$, $R_{21}$, $R_{22}$, $R_{24}$ and $R_{25}$ represent, independently of each other, a hydrogen atom or a ($C_1$-$C_6$)alkyl group, more particularly a hydrogen atom or a methyl group.

The linker L may also be chosen from the illustrated compounds.

In accordance with the invention, the compounds of general formula (I), (II) and (III) can be prepared by the following processes.

Process for Preparing the Cryptophycin Compounds

General Route A for the Preparation of the Compounds of Formula (I) in the Case where $W=CH_2N_3$ or $CH_2NH_2$ Scheme 1

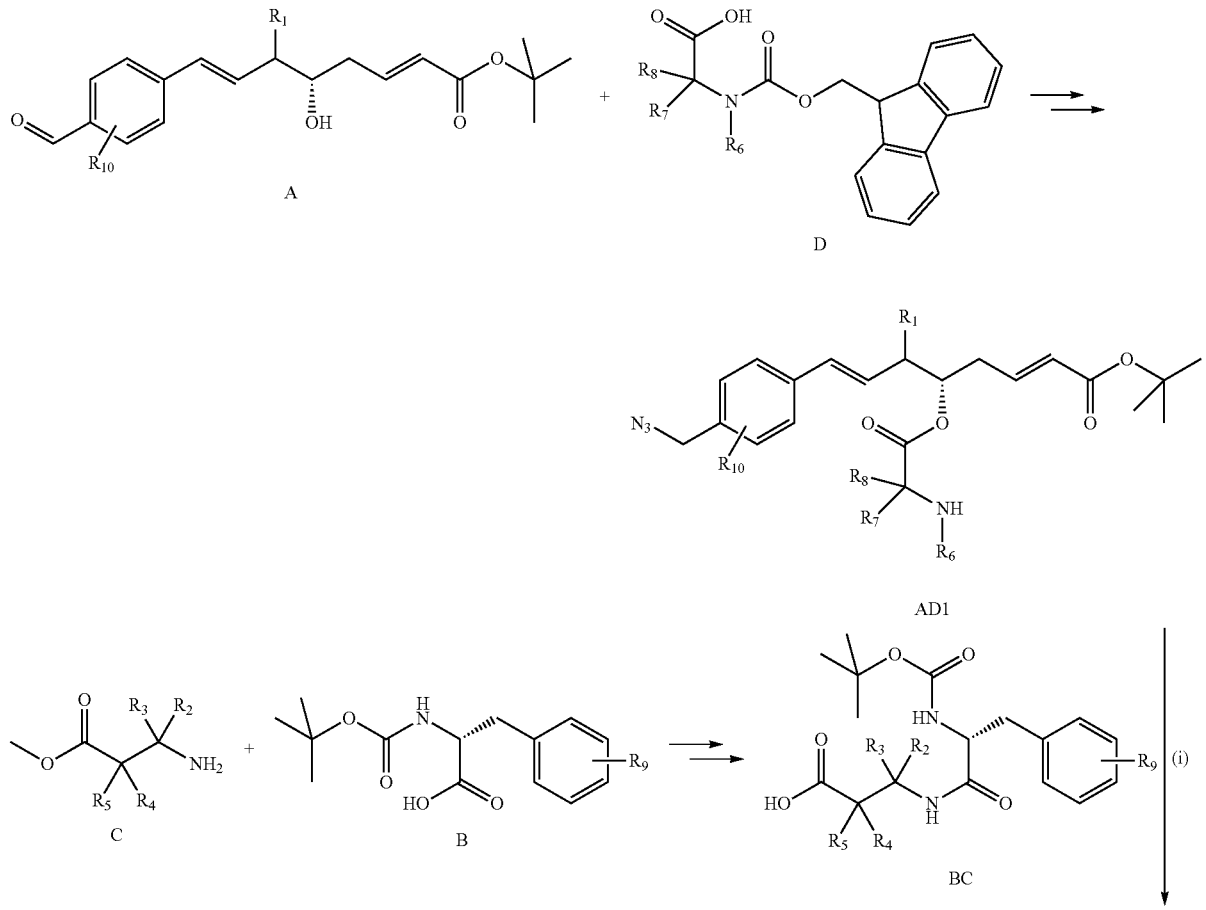

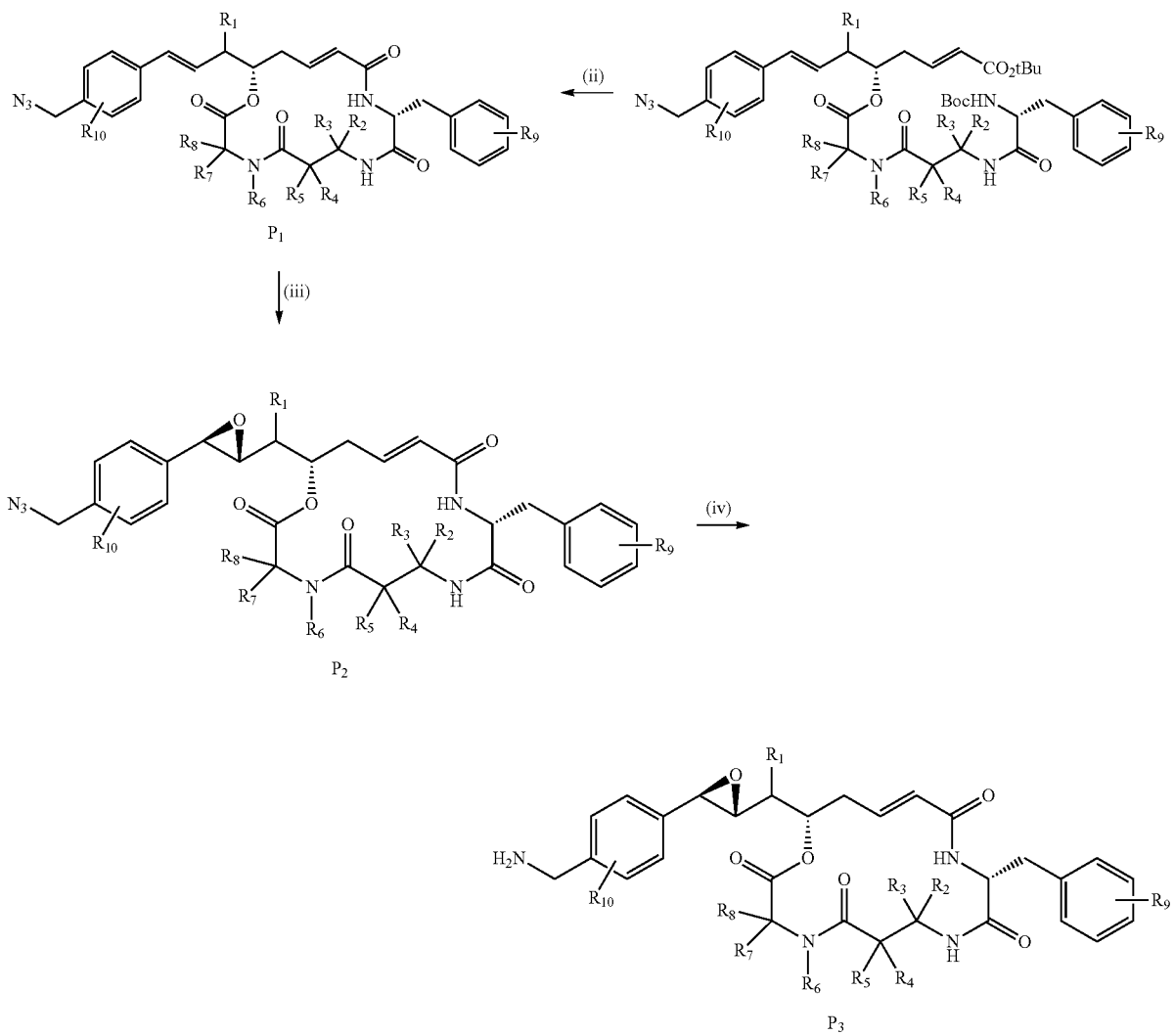

Fragments A, B, C and D allow the preparation of cryptophycin compounds $P_1$ to $P_3$ with the aid of the steps detailed below:

Step (i): peptidic coupling between fragments AD1 and BC in the presence of coupling reagents such as, for example, HOAt and HATU;

Step (ii): deprotection in acidic conditions using for example TFA and macrocyclization in the presence of coupling reagents such as, for example, HOAt and HATU;

Step (iii): oxidation of the olefine to form the epoxide using, for example, m-CPBA;

Step (v): reduction of the azido group using, for example, TCEP.

Fragments A and B were prepared according to the synthesis described below. Fragments C protected as methyl esters are commercially available for $R_4$=H, $R_5$=Me (R), $R_2$=$R_3$=H (CAS number [92535-26-7]); $R_4$=H, $R_5$=Me (S), $R_2$=$R_3$=H (CAS number [118138-56-0]); $R_4$=$R_5$=Me, $R_2$=$R_3$=H (CAS number [25307-82-8]); $R_2$=H, $R_3$=Me (R), $R_4$=H, $R_5$=Me (R) (CAS number [86544-92-5]); $R_2$=H, $R_3$=Me (S), $R_4$=H, $R_5$=Me (R) (CAS number [86544-93-6]); $R_2$=H, $R_3$=Me (R), $R_4$=$R_5$=Me (CAS number [1315052-25-5]); $R_2$=H, $R_3$=Me (S), $R_4$=$R_5$=Me (CAS number [1315050-96-4]); $R_2$=H, $R_3$=iPr (R), $R_4$=$R_5$=Me (CAS number [1314999-06-8]); $R_2$=H, $R_3$=iPr (S), $R_4$=$R_5$=Me (CAS number [1315054-33-1]); $R_2$=$R_3$=$R_4$=$R_5$=Me (CAS number [90886-53-6]); $R_4$ and $R_5$ form together with the carbon atom to which they are attached a cyclopropyl group (CAS number [914226-26-9]). They may also be prepared as described in the examples. Non-commercially available fragments C were prepared as described in the examples. All fragments D are commercially available: L-Fmoc-Ala-OH (CAS number [35661-39-3]); L-Fmoc-Val-OH (CAS number [68858-20-8]); L-Fmoc-tert-Leu-OH (CAS number [132684-60-7]); L-Fmoc-Leu-OH (CAS number [35661-60-0]); L-Fmoc-NMe-Leu-OH (CAS number [103478-62-2]); L-Fmoc-3-dimethylamino-Ala-OH (CAS number [587880-86-2]); L-Fmoc-(Oallyl)Asp-OH (CAS number [146982-24-3]); L-Fmoc-4-methyl-Leu-OH (CAS number [139551-74-9]). Building blocks AD1 and BC were prepared according to the synthesis described below.

General Route B for the Preparation of the Compounds of Formula (I) in the Case where W=CH$_2$OH or CH$_2$N$_3$ or CH$_2$NH$_2$
Scheme 2
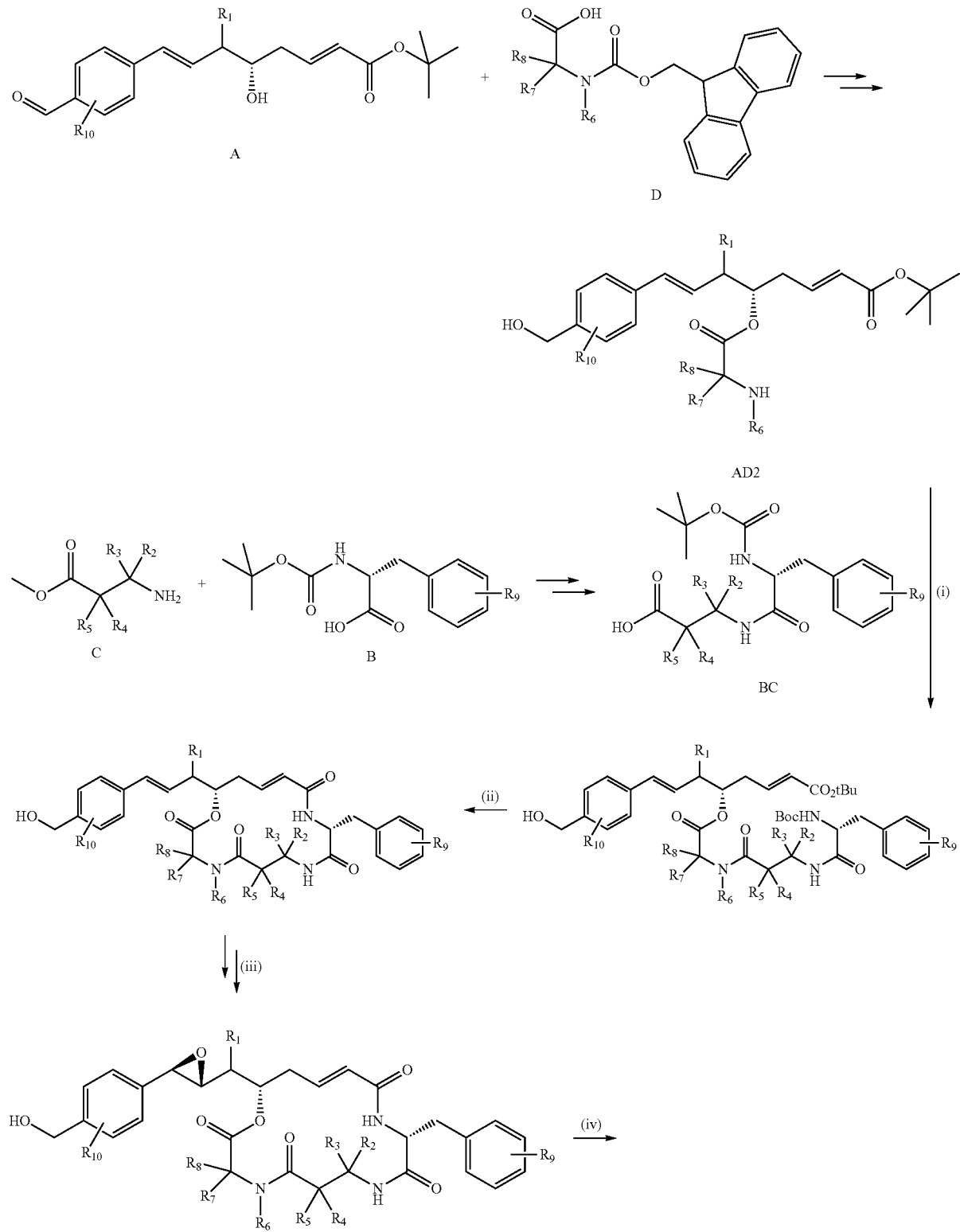

-continued

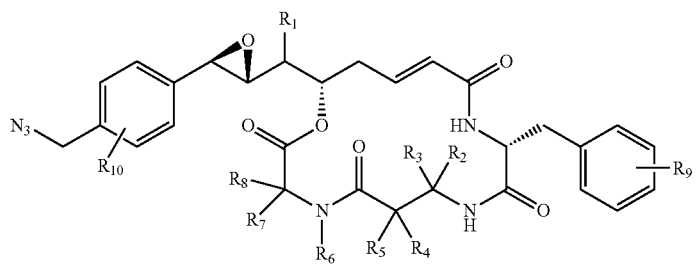

P₂

↓ (v)

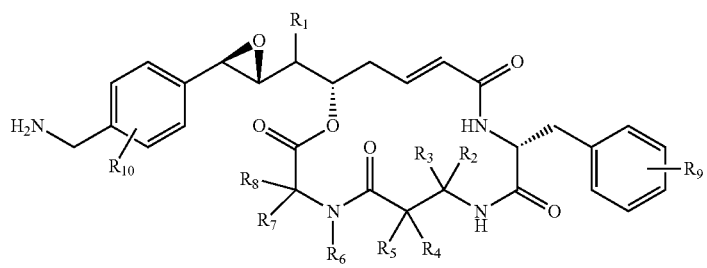

P₃

Fragments A, B, C and D allow the preparation of cryptophycin compounds P₂ to P₄ with the aid of the steps detailed below:

Step (i): peptidic coupling between fragments AD1 and BC in the presence of coupling reagents such as, for example, HOAt and HATU;

Step (ii): deprotection in acidic conditions using for example TFA, macrocyclization in the presence of coupling reagents such as, for example, HOAt and HATU and acetate hydrolysis at pH 6-7 using for example NaOH in a mixture of water and AcOEt;

Step (iii): benzylic alcohol protection as a silyl ether using for example chlorotriisopropylsilane in the presence of a base such as, for example, imidazole; oxidation of the olefine to form the epoxide using, for example, m-CPBA; deprotection of the silyl ether using, for example, a TBAF solution.

Step (iv): azidation in the presence of DPPA and a base such as, for example, DBU;

Step (v): reduction of the azido group using, for example, TCEP.

Fragments A and B were prepared according to the synthesis described below. Fragments C were either commercially available as reported in the previous section or prepared as described in the examples. All fragments D are commercially available as reported in the previous section. Building blocks AD2 and BC were prepared according to the synthesis described below.

General Route C for the Preparation of the Compounds of Formula (I) in the Case where W=CH₂OH or CH₂N₃ or CH₂NH₂

Scheme 3

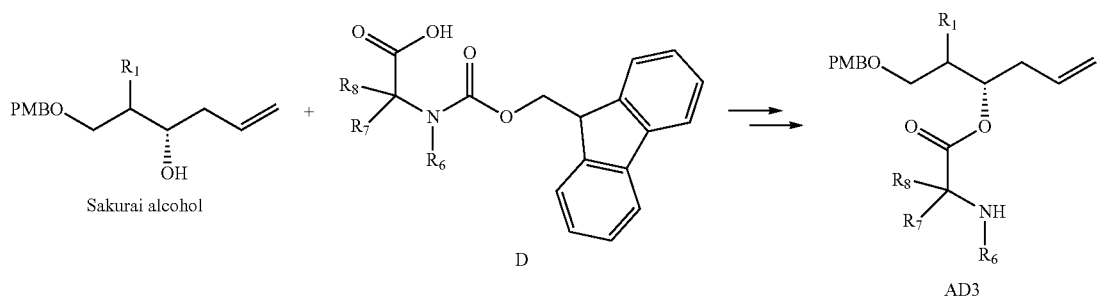

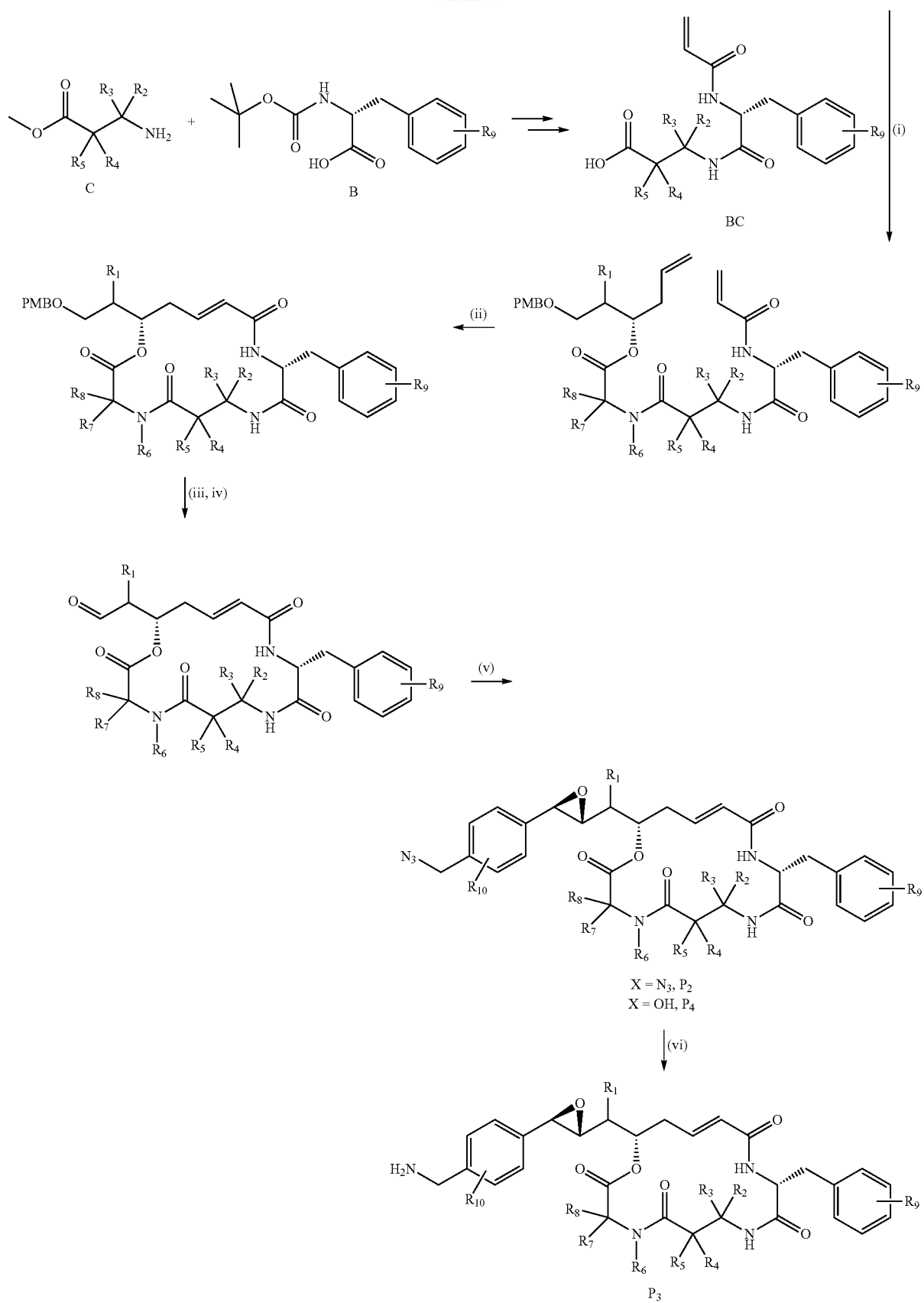

Sakurai alcohol and fragments B, C and D allow the preparation of cryptophycin compounds $P_2$ to $P_4$ with the aid of the steps detailed below:

Step (i): peptidic coupling between fragments AD3 and alternative BC in the presence of coupling reagents such as, for example, HOAt and HATU;

Step (ii): macrocyclization by ring closing metathesis in the presence of a catalyst such as, for example, Grubbs I catalyst;

Step (iii): deprotection of the p-methoxybenzyl ether in acidic conditions such as, for example, 10% TFA;

Step (iv): oxidation of the alcohol using an oxidizing agent such as, for example, TEMPO in the presence of sodium hypochlorite;

Step (v): introduction of the epoxide by asymmetric Corey-Chaykovsky reaction using appropriately substituted isothiocineole-derived chiral sulfonium in the presence of a base such as, for example, phosphazene base $P_2$-Et;

Step (vi): reduction of the azido group using, for example, TCEP.

Sakurai alcohol and fragment B were prepared according to the synthesis described below. Fragments C were either commercially available as reported in the previous section or prepared as described in the examples. All fragments D are commercially available as reported in the previous section. Building blocks AD3 and alternative BC were prepared according to the synthesis described below.

Preparation of the Compounds of Formula (I) in the Case where W=$CH_2SH$

Scheme 4

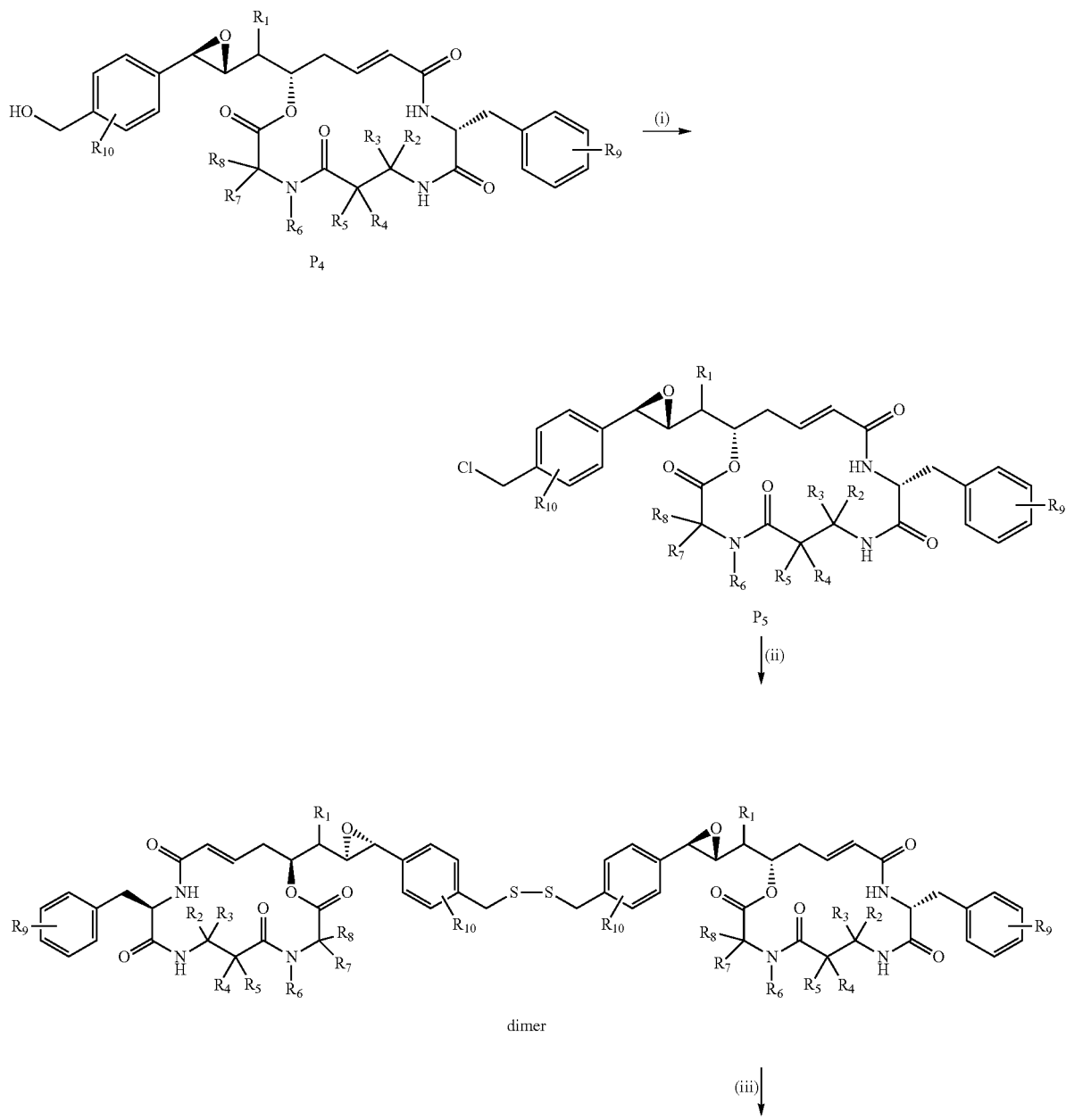

-continued

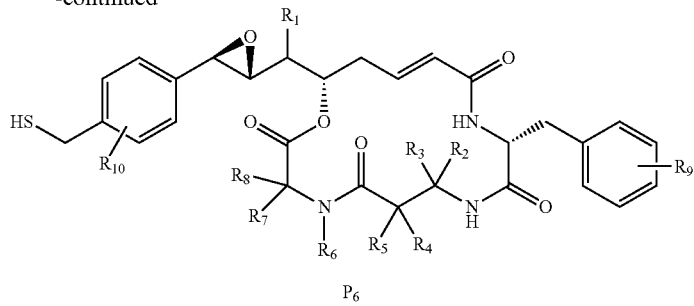

P₆

P₄ allows the preparation of other cryptophycin compounds P₅ and P₆ with the aid of the steps detailed below:

Step (i): introduction of the chloro group using methanesulfonyl chloride in the presence of a base such as, for example, DIEA;

Step (ii): functionalization using tetrabutylammonium trimethylsilylthiolate prepared in situ from TBAF and hexamethyldisilathiane according to Hu J., et al., *J. Org. Chem.* 1999, 64, 4959-496: in the course of this reaction, the intermediate dimer depicted in Scheme 3 is usually formed;

Step (iii): reduction of the dimer using a phosphine such as, for example, TCEP.

Schemes 1, 2, 3 and 4 describe the cases n=1 but may also apply for the preparation of compounds of formula (I) in the case where n>1 starting from P₂, P₃ or P₄ with the aid of the steps detailed below and described in Scheme 2 of WO2011/001052:

Scheme 5

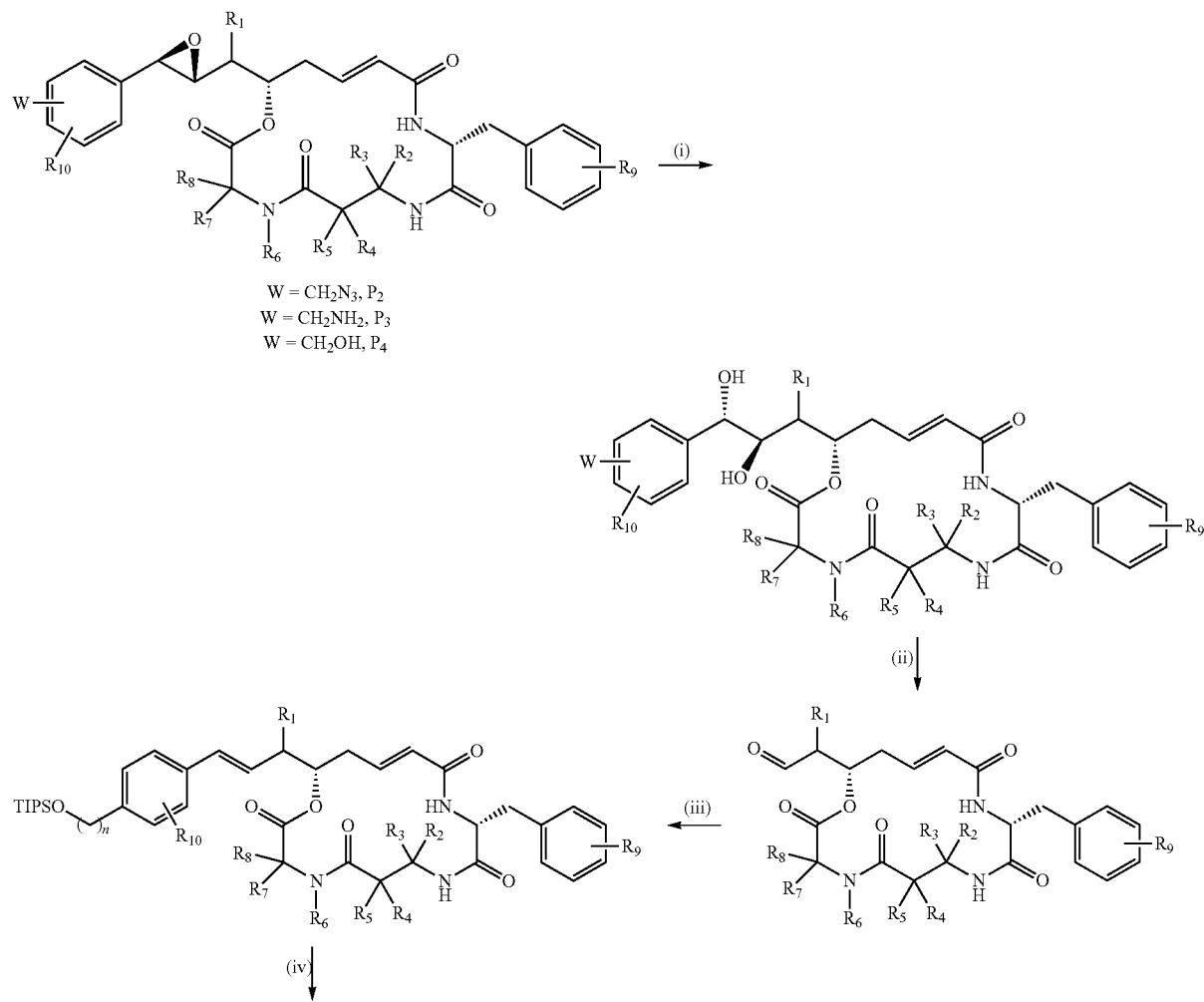

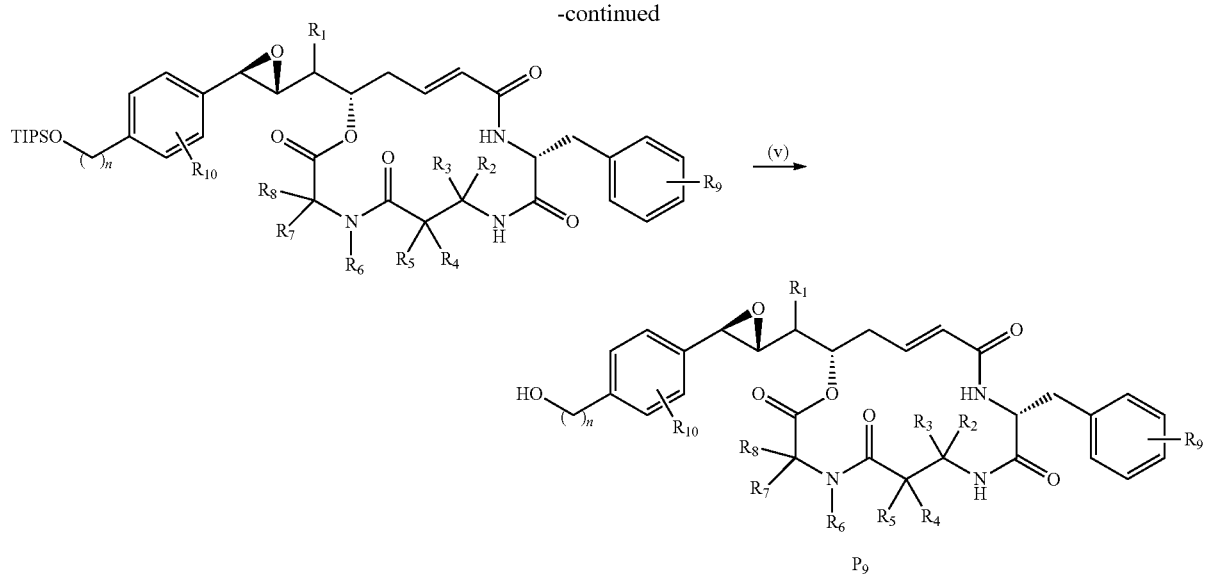

Step (i): opening of the epoxide ring in acidic medium so as to obtain the diol function; concentrated perchloric acid may be used, for example;

Step (ii): oxidative cleavage of the diol using, for example, sodium periodate;

Step (iii): Wittig reaction using a suitable phosphonium halide, for example a bromide, and a strong base, for instance BuLi;

Step (iv): oxidation of the olefine to form the epoxide using, for example, m-CPBA;

Step (v): deprotection of the silyl ether using, for example, a TBAF solution.

Preparation of the Compounds of Formula (I) in the Case where $W=CO_2H$

Scheme 6

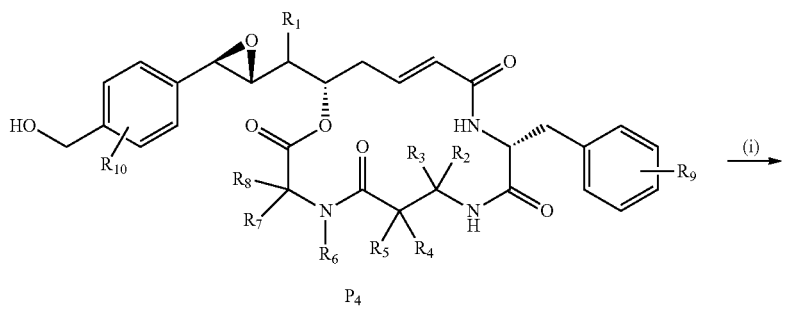

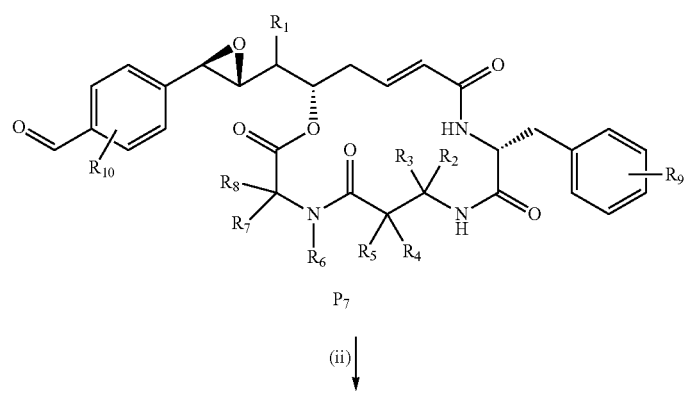

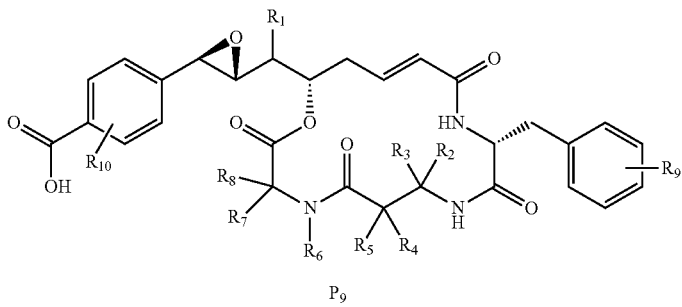

P$_4$ allows the preparation of other cryptophycin compounds P$_7$ and P$_8$ with the aid of the steps detailed below:

Step (i): oxidation using the Dess-Martin reagent;

Step (ii): oxidation of Pinnick type in the presence of 2 methyl-2-butene (Pinnick H. W., *Tetrahedron* 1981, 37, 2091-2096).

Scheme 6 describes the case n=0 but may also apply for the preparation of compounds of formula (I) in the case where W=(CH$_2$)$_n$CO$_2$H starting from an analog of P$_4$ bearing a (CH$_2$)$_{n+1}$OH group. Schemes 1, 2, 3, 4, 5 and 6 are given for a linker in the para position, but may identically apply for the ortho or meta positions. Similarly, they are given for a cryptophycin compound, but may also apply to the preparation of other compounds of formula (I), especially D$_1$-D$_{19}$.

Process for Preparing the Cryptophycin Payloads

The compounds of formula (II) might be prepared according to Scheme 7 starting with a cryptophycin compound of formula (I) and a linker precursor (LP):

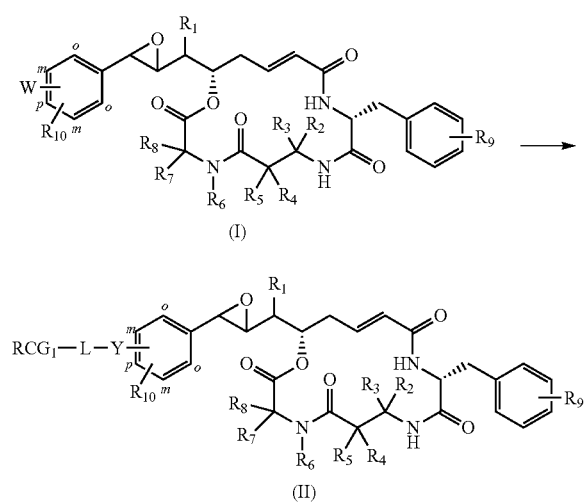

W represents (C$_1$-C$_6$)alkyl-NH(R$_{11}$), more particularly (CH$_2$)$_n$NHR$_{11}$;

(C$_1$-C$_6$)alkyl-OH, more particularly (CH$_2$)$_n$OH;

(C$_1$-C$_6$)alkyl-SH, more particularly (CH$_2$)$_n$SH;

CO$_2$H;

(C$_1$-C$_6$)alkyl-CO$_2$H, more particularly (CH$_2$)$_n$CO$_2$H; or (C$_1$-C$_6$)alkyl-N$_3$.

in which R$_{11}$ represents a hydrogen atom or a group (C$_1$-C$_6$)alkyl, more particularly a methyl group.

The linker precursor LP has the function of introducing a precursor of the linker L into the cryptophycin compound after reaction between the group W and a chemical function present on LP.

In Scheme 7, several steps and/or reactions may be necessary to prepare the cryptophycin payload (II) starting from the cryptophycin compound (I). For example, in the case where Z$_a$R$_a$=—O—NHS, a linker L for which Z$_a$R$_a$=—O-allyl may be introduced using the corresponding linker precursor, followed by deprotecting the ester function and introducing —O—NHS. Deprotection may be performed by treatment with a palladium catalyst, for example Pd(PPh$_3$)$_4$ in the presence of a scavenger amine, for example morpholine; the activation may be performed with DSC in the presence of a base such as, for example, DIEA or with NHS in the presence of a coupling agent such as, for example, DCC. This conversion of a group Z$_a$R$_a$ into another group Z$_a$R$_a$ (e.g. —O-allyl→—O—NHS) may be applied to obtain other groups Z$_a$R$_a$, especially those described previously.

Scheme 7' similarly illustrates the preparation of a cryptophycin compound comprising a linker bearing respectively, a maleimido, a haloacetamido, an amino or an azido group (L* represents a fragment of a linker such that L=-L*-maleimido or L=-L*-haloacetamido or L=-L*—NH$_2$— or L=-L*—N$_3$).

Scheme 7'

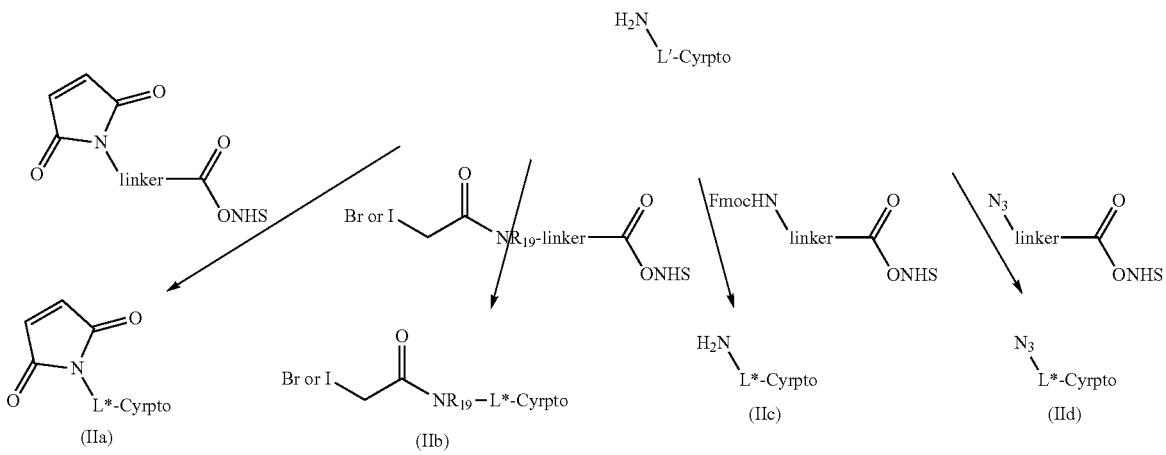

These compounds are obtained by reaction between a cryptophycin compound comprising a linker L' comprising an amino group and a modifying agent for introducing, respectively, a maleimido, a haloacetamido, an amino or an azido group.

The compounds of formula (II) might alternatively be prepared according to Scheme 8 starting with the same cryptophycin compound of formula (I) and another linker precursor (LP'):

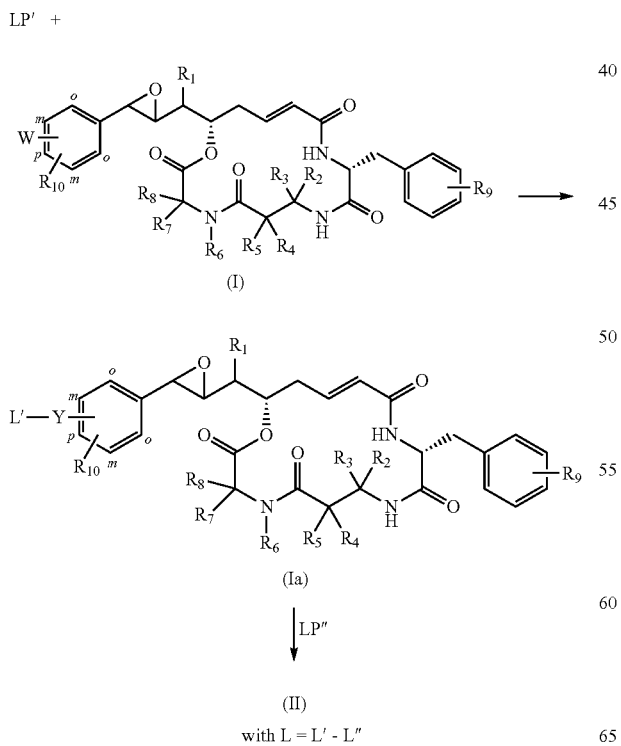

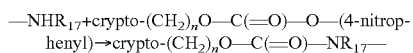

with L = L' - L''

In Scheme 8, several steps and/or reactions may be necessary to arrive at the cryptophycin payload (II) starting from the cryptophycin compound (I). For example, in the case where $Z_aR_a$=—O—NHS, a protected linker precursor L' may be introduced, followed by deprotection and coupling to a linker precursor L'' to introduce the carboxylic acid function that may be directly activated to $Z_aR_a$=—O—NHS or first deprotected and subsequently activated (L' and L'' represent fragments of linker such that L=L'-L''). Deprotection may be performed by treatment with a base, for example, piperidine; coupling to a linker L'' may proceed through opening of a cyclic anhydride, for example, glutaric anhydride; the activation may be performed with DSC in the presence of a base such as, for example, DIEA or with NHS in the presence of a coupling agent such as, for example, DCC.

An example of reaction between the group W and a chemical function present on LP is an amidation either between a linker precursor LP bearing a carboxylic acid function and W=$(CH_2)_nNH_2$ or between a linker precursor LP bearing an amine function and W=$CO_2H$ or $(CH_2)_nCO_2H$: this reaction may be performed in the presence of a coupling agent such as, for example, EDCl or HOBt. It is also possible to react a linker precursor LP bearing an amine function and W'=$(CH_2)_nO—C(=O)—O$—(4-nitrophenyl) obtained from W=$(CH_2)_nOH$ and p-nitrophenyl chloroformate (activation of the alcohol in the form of carbonate) according to the scheme below ($R_{17}$=H or $(C_1-C_6)$alkyl):

—$NHR_{17}$+crypto-$(CH_2)_nO—C(=O)—O$—(4-nitrophenyl)→crypto-$(CH_2)_nO—C(=O)—NR_{17}$—

The same kind of reaction can also be performed between a linker precursor LP bearing an alcohol function activated as a carbonate and W=$(CH_2)_nNH_2$. Another example of reaction is an esterification between a linker precursor bearing an alcohol function and W=$CO_2H$ or $(CH_2)_nCO_2H$: this reaction may be performed in the presence of a coupling agent such as, for example, MNBA. Another example of reaction is a copper-catalyzed azide-alkyne cycloaddition between a linker precursor bearing an alkyne function and W=$(CH_2)N_3$: this reaction may be performed in the presence of copper sulfate and sodium ascorbate.

Preparation of the Compounds of Formula (II) in the Case where W=$(CH_2)_n NH_2$ and L=(IV1) with n=1, $R_{15}$=H and ALK=$(CH_2)_3$ Based on Scheme 7
Scheme 9
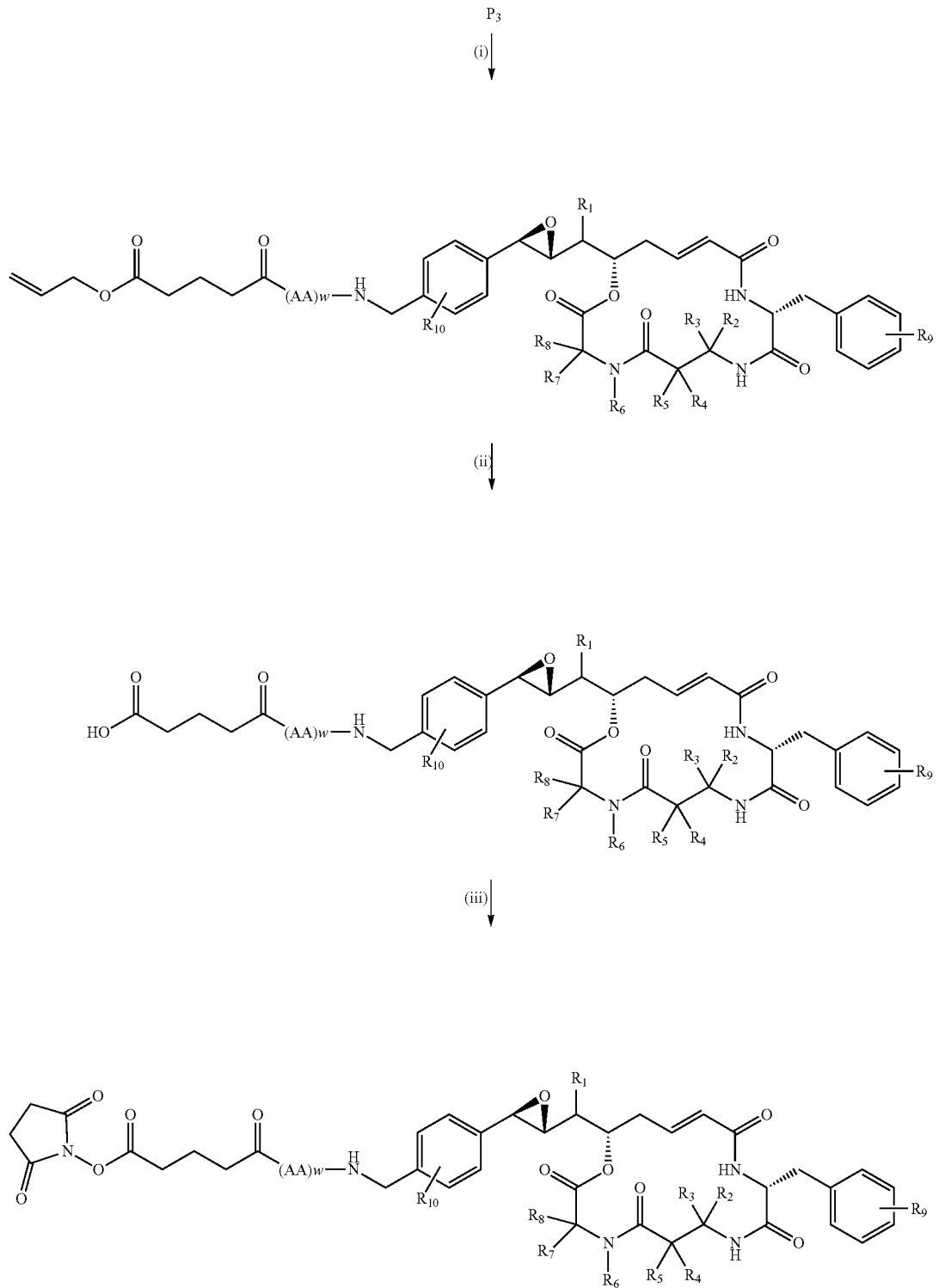

Step (i): peptidic coupling in the presence of coupling reagents such as, for example, EDC and HOBt, and a base such as, for example, DIEA;

Step (ii): deprotection of the allyl ester in the presence of a catalyst such as, for example, tetrakis-(triphenylphosphine)palladium;

Step (iii): activation of the carboxylic acid as a NHS ester by treatment with DSC in the presence of a base such as, for example, DIEA.

Preparation of the Compounds of Formula (II) in the Case where W=$(CH_2)_nNH_2$ and L=(IV1) with n=1, $R_{11}$=H and ALK=$(CH_2)_3$ Based on Scheme 8

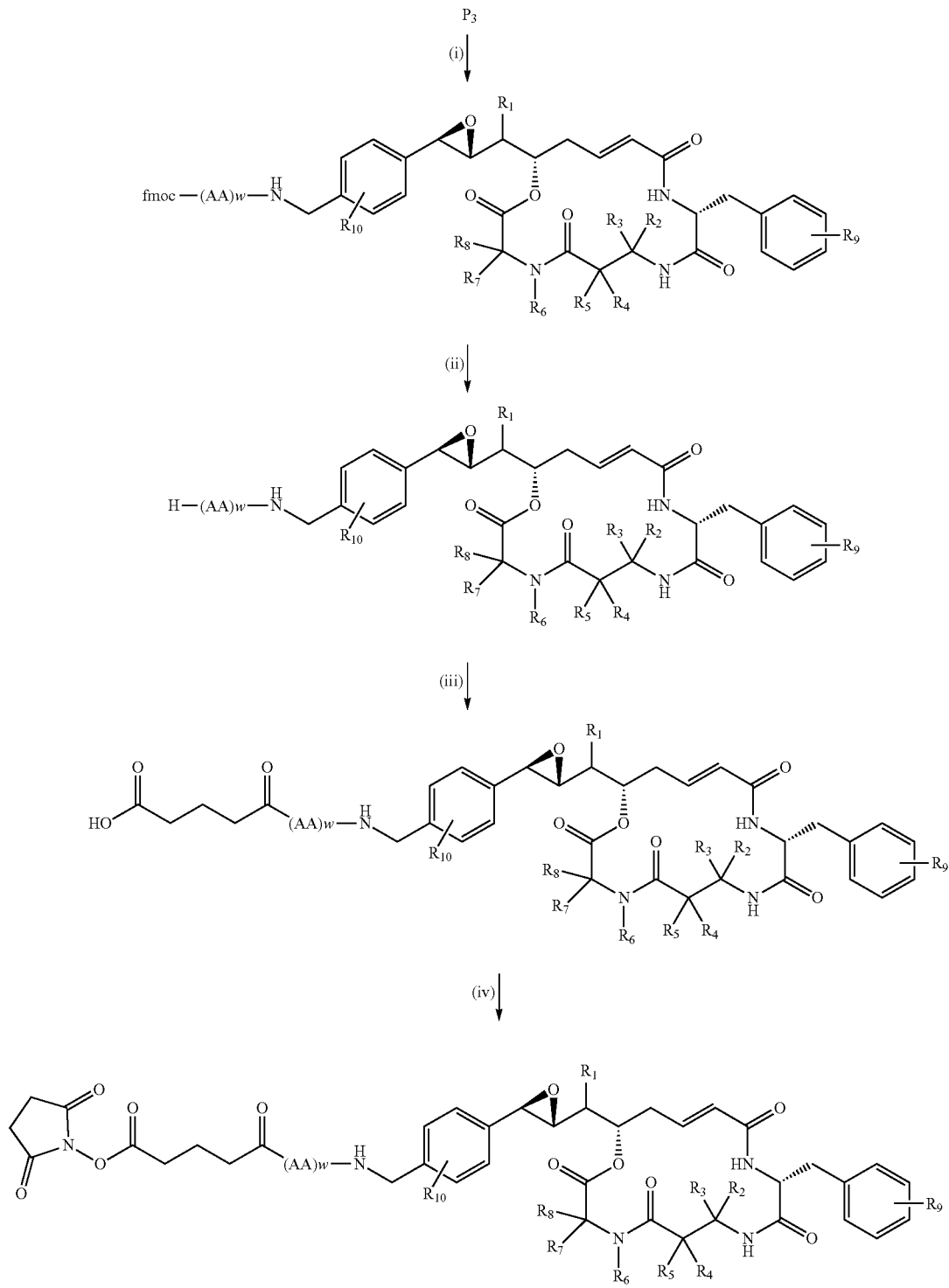

Scheme 10

Step (i): peptidic coupling in the presence of coupling reagents such as, for example, EDC and HOBt and a base such as, for example, DIEA;

Step (ii): deprotection of the Fmoc amine in the presence of a base such as, for example, piperidine;

Step (iii): coupling to glutaric anhydride;

Step (iv): activation of the carboxylic acid as a NHS ester by treatment with DSC in the presence of a base such as, for example, DIEA.

Schemes 9 and 10 describe the case L(IV1) with n=1, $R_{11}$=H and ALK=$(CH_2)_3$ but they may also apply to other linkers L with RCG1=C(=O)ONHS, namely the case L(IV1) with n≠1 and/or $R_{11}$≠H and/or ALK≠$(CH_2)_3$ and the cases L(IV2) and L(IV3). They are given for a linker in the para position, but may identically apply for the ortho or meta positions. Similarly, they are given for a cryptophycin compound, but may also apply to the preparation of other compounds of formula (I), especially $D_1$-$D_{19}$.

Preparation of the Compounds of Formula (II) in the Case where W=$(CH_2)_N$H2 with n=1, $R_{11}$=H and RCG1=Maleimido, Haloacetamido, $NH_2$, $N_3$ or Cyclooctyne Namely Linkers L(IV4) to L(IV17)

Scheme 11

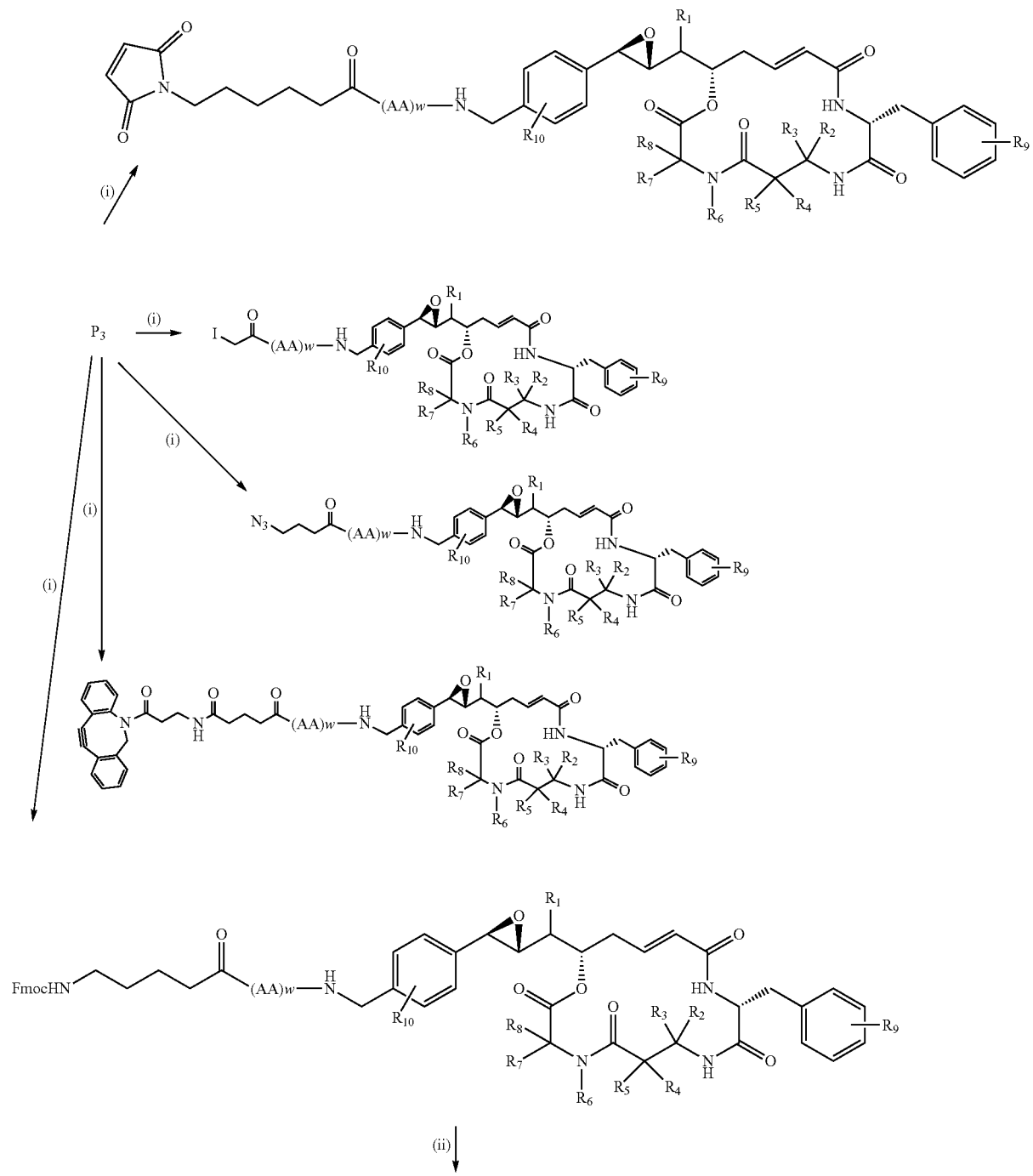

-continued

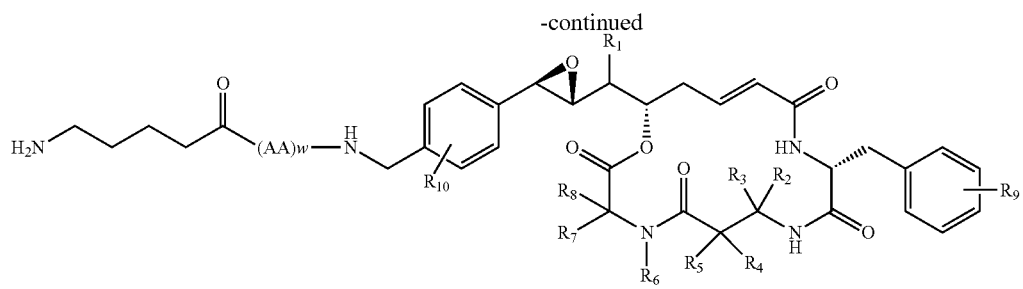

Step (i): peptidic coupling in the presence of coupling reagents such as, for example, EDC and HOBt and a base such as, for example, DIEA;

Step (ii): deprotection of the Fmoc amine in the presence of a base such as, for example, piperidine.

Scheme 11 describes the cases L(IV4) with n=1, $R_{11}$=H and ALK=$(CH_2)_5$, L(IV8) with n=1 and $R_{11}$=H, L(IV12) with n=1, $R_{11}$=H and ALK=$(CH_2)_4$, L(IV14) with n=1, $R_{11}$=H and ALK=$(CH_2)_3$ and L(IV16) with n=1, $R_{11}$=H, ALK=$(CH_2)_3$ and ALK'=$(CH_2)_2$ but it may also apply to other linkers L(IV4) to L(IV17) with RCG1=maleimido, iodoacetamido, $NH_2$, $N_3$ or cyclooctyne. It is depicted for an iodoacetamido reactive group but may identically apply for a bromoacetamido reactive group. It is given for a linker in the para position, but may identically apply for the ortho or meta positions. Similarly, it is given for a cryptophycin compound, but may also apply to the preparation of other compounds of formula (I), especially $D_1$-$D_{19}$.

Preparation of the Compounds of Formula (II) in the Case where W=$(CH_2)_nX$ with X=O or S and L=(IV18) with n=1, $R_{17}$ and $R_{18}$=H and ALK=$(CH_2)_3$ Based on Scheme 7

Scheme 12

$P_4$ or $P_6$ (i) ↓

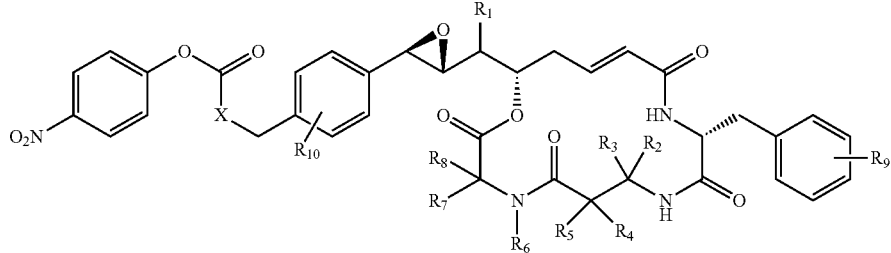

$P_{10}$ (ii) ↓

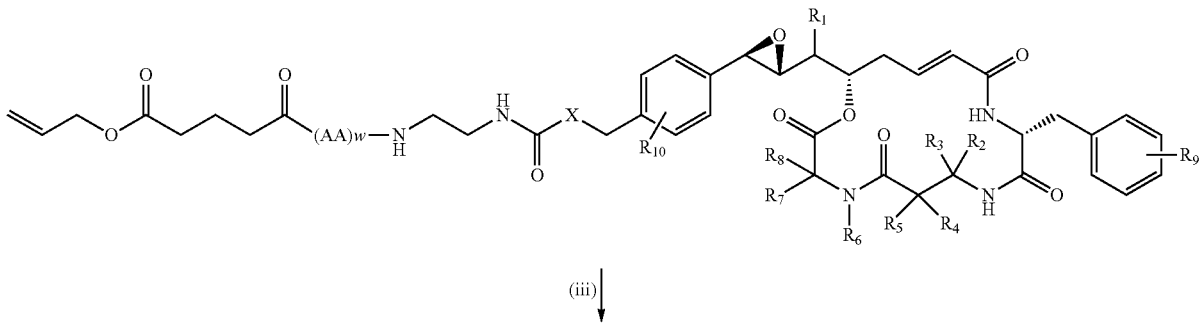

(iii) ↓

-continued

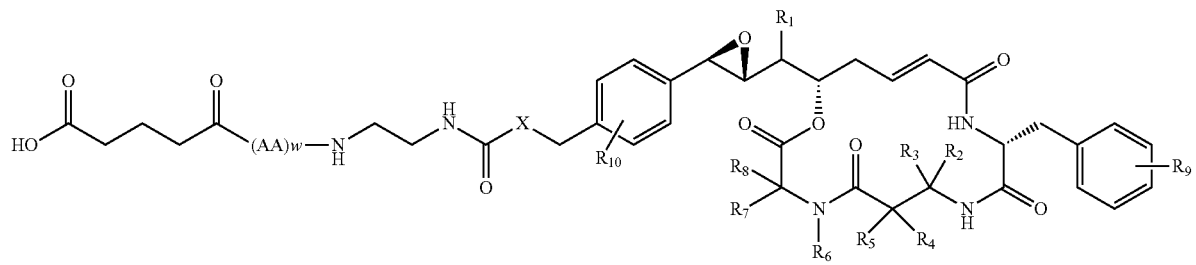

(iv) ↓

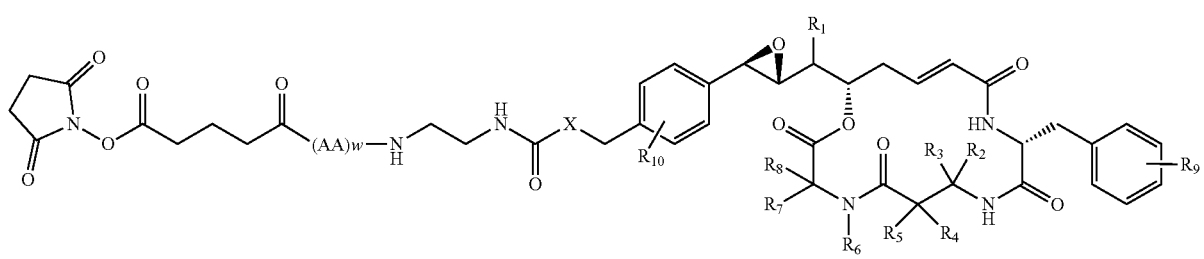

Step (i): activation of the benzylic alcohol or benzylic thiol as a p-nitrophenyl-(thio)carbonate by treatment with p-nitrophenyl-chloroformate in the presence of a base such as, for example, DIEA;

Step (ii): formation of the (thio)carbamate by reacting with an amine in the presence of a base such as, for example, DIEA;

Step (iii): deprotection of the allyl ester in the presence of a catalyst such as, for example, tetrakis(triphenylphosphine) palladium;

Step (iv): activation of the carboxylic acid as a NHS ester by treatment with DSC in the presence of a base such as, for example, DIEA.

Preparation of the Compounds of Formula (II) in the Case where $W=(CH_2)_nX$ with $X=O$ or S and $L=(IV18)$ with $n=1$, $R_{17}$ and $R_{18}=H$ and $ALK=(CH_2)_3$ Based on Scheme 8

Scheme 13

$P_{10}$ (i) ↓

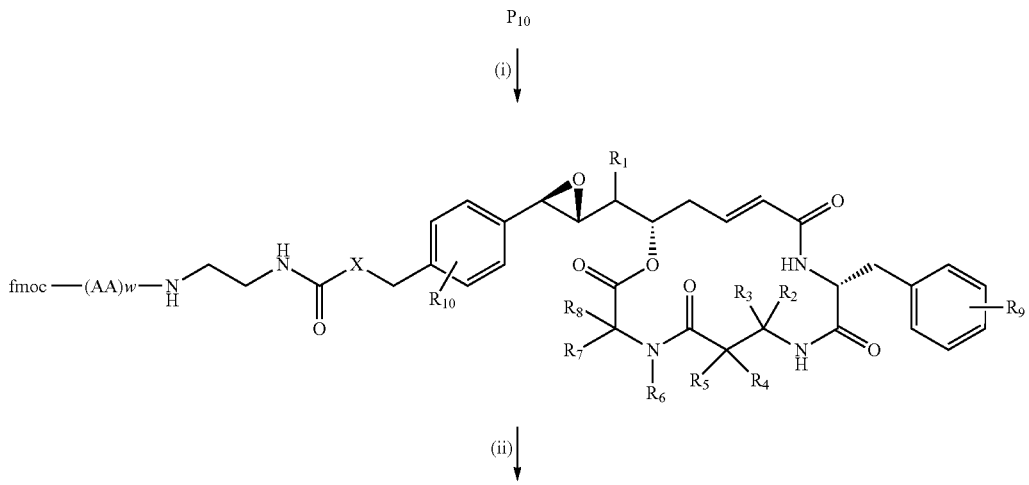

(ii) ↓

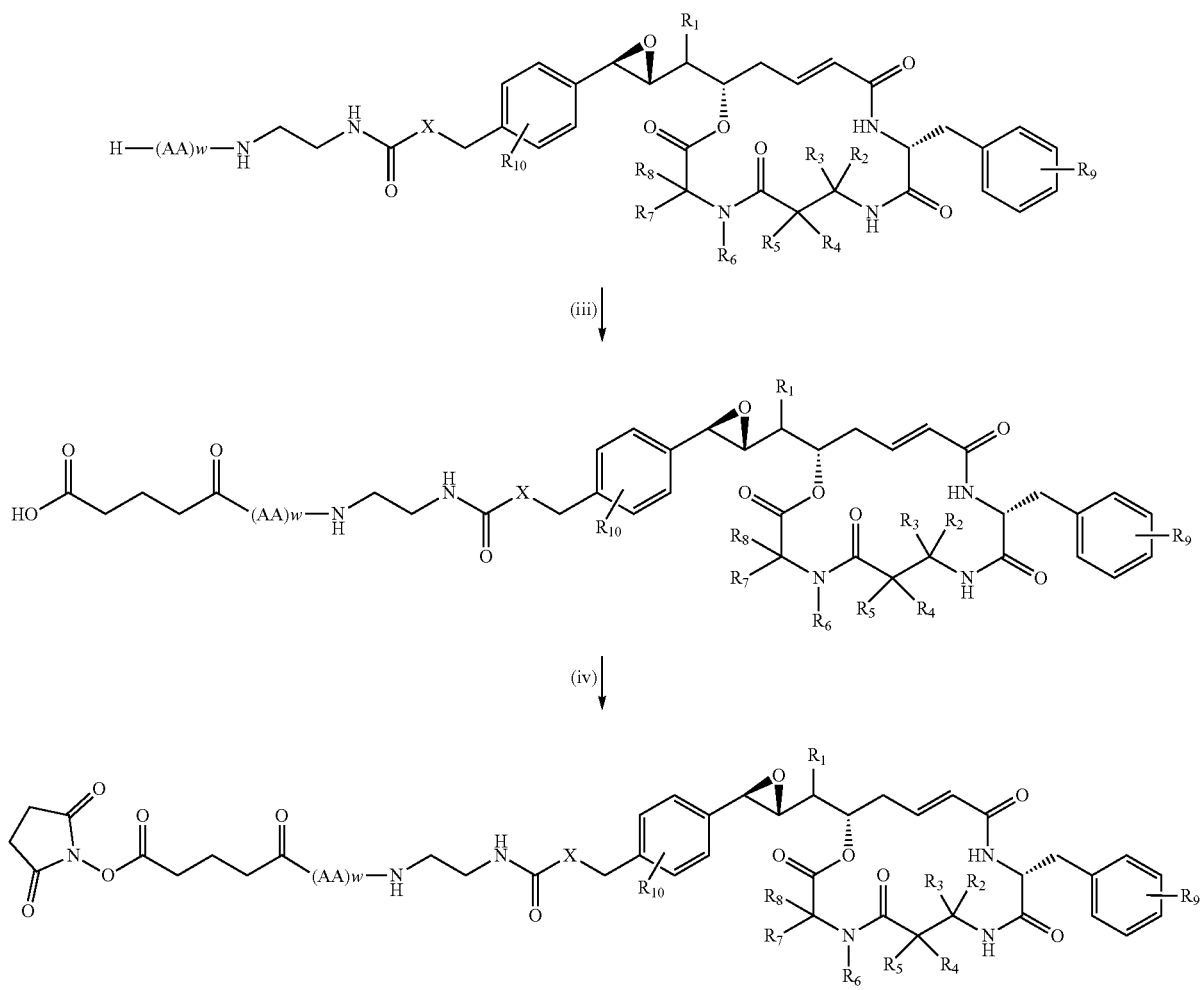

Step (i): formation of the (thio)carbamate by reacting with an amine in the presence of a base such as, for example, DIEA;

Step (ii): deprotection of the Fmoc amine in the presence of a base such as, for example, piperidine;

Step (iii): coupling to glutaric anhydride;

Step (iv): activation of the carboxylic acid as a NHS ester by treatment with DSC in the presence of a base such as, for example, DIEA.

Schemes 12 and 13 describe the case L(IV18) with n=1, $R_{17}$ and $R_{18}$=H and ALK=$(CH_2)_3$ but they may also apply to other linkers L with RCG1=C(=O)ONHS, namely the case L(IV18) with n≠1 and/or $R_{17}$, $R_{18}$≠H and/or ALK≠$(CH_2)_3$ and the cases L(IV19) and L(IV20). They are given for a linker in the para position, but may identically apply for the ortho or meta positions. Similarly, they are given for a cryptophycin compound, but may also apply to the preparation of other compounds of formula (I), especially $D_1$-$D_{19}$. Preparation of the Compounds of Formula (II) in the Case where W=$(CH_2)_n$X with X=O or S and RCG1=Maleimido, Haloacetamido, $NH_2$, $N_3$ or Cyclooctyne Namely Linkers L(IV21) to (IV34)

Scheme 14

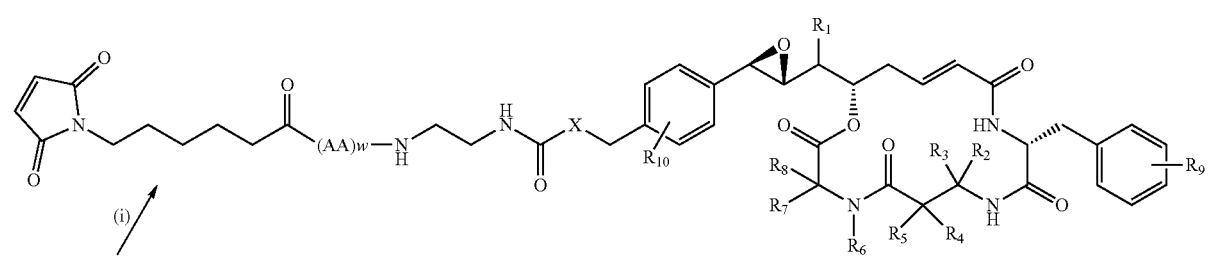

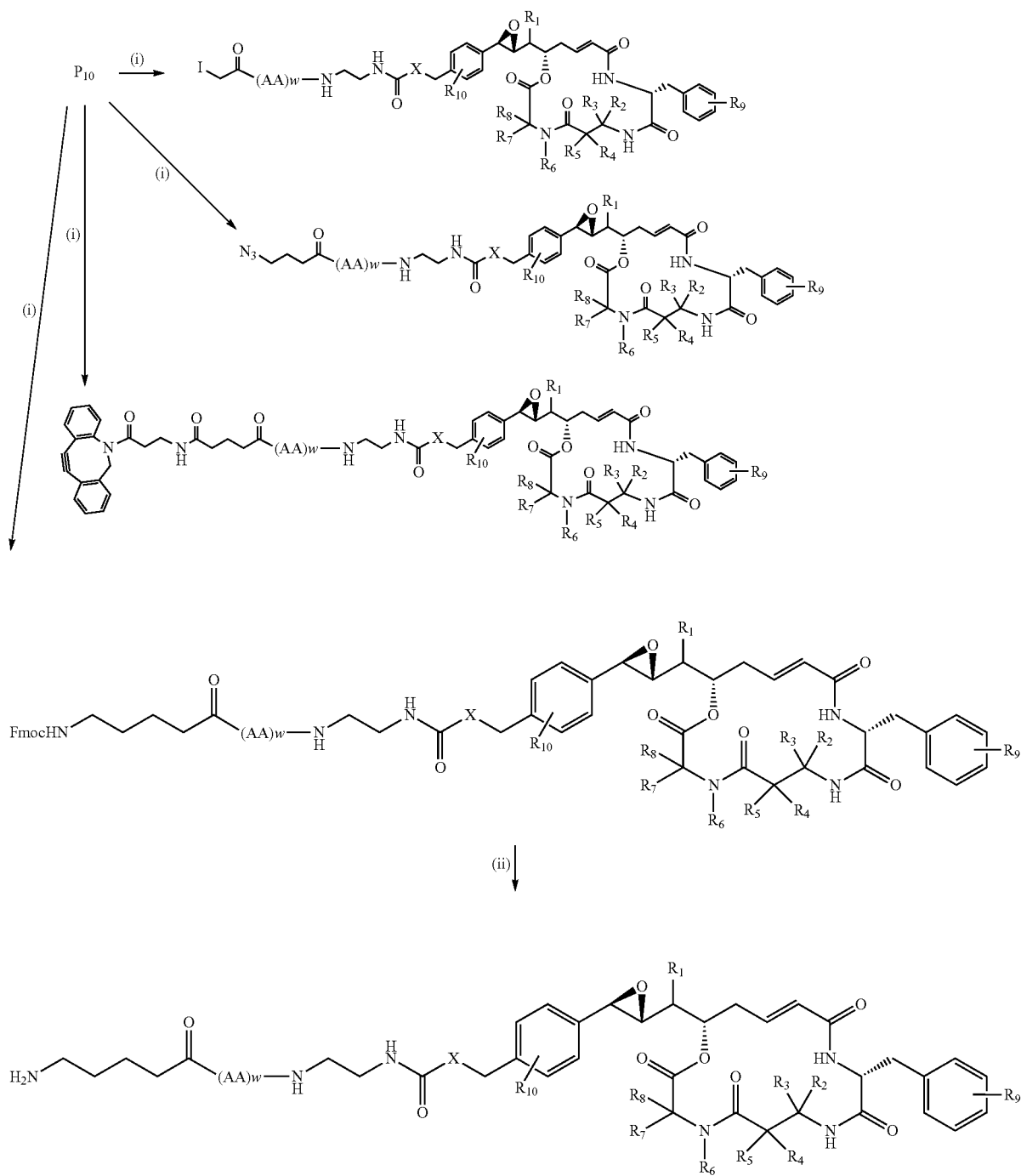

Step (i): formation of the (thio)carbamate, the reaction is performed in the presence of a base such as, for example, DIEA;

Step (ii): deprotection of the Fmoc amine in the presence of a base such as, for example, piperidine.

Scheme 14 describes the case L(IV21) with n=1, $R_{17}$ and $R_{18}$=H and ALK=$(CH_2)_5$, the case L(IV25) with n=1 and $R_{17}$ and $R_{18}$=H, the case L(IV29) with n=1, $R_{17}$ and $R_{18}$=H and ALK=$(CH_2)_4$, the case L(IV31) with n=1, $R_{17}$ and $R_{18}$=H and ALK=$(CH_2)_3$ and the case L(IV33) with n=1, $R_{17}$, $R_{18}$ and $R_{22}$=H, ALK=$(CH_2)_3$ and ALK'=$(CH_2)_2$ but it may also apply to other linkers L(IV21 to 34) with RCG1=maleimido, iodoacetamido, $NH_2$, $N_3$ or cyclooctyne. It is depicted for an iodoacetamido reactive group but may identically apply for a bromoacetamido reactive group. It is given for a linker in the para position, but may identically apply for the ortho or meta positions. Similarly, it is given for a cryptophycin compound, but may also apply to the preparation of other compounds of formula (I), especially $D_1$-$D_{19}$.

Preparation of the Compounds of Formula (II) in the Case where W=(CH$_2$)$_n$NH$_2$ and L=(IV35) with n=1, R$_{11}$=R$_{14}$=R$_{15}$=R$_{16}$=H, J$_1$=J$_2$=J$_3$=J$_4$=CH and ALK=(CH$_2$)$_3$ Based on Scheme 7
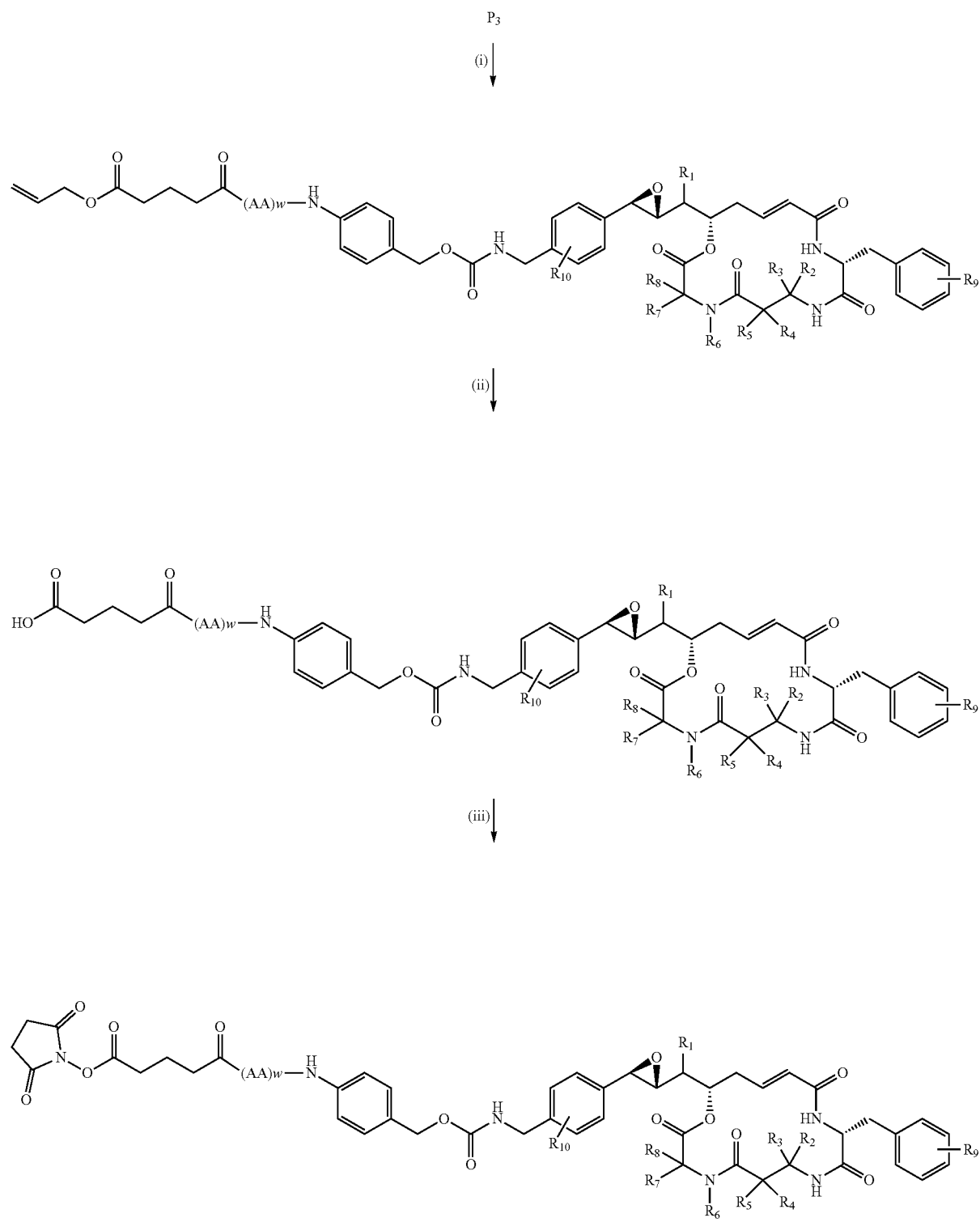

Step (i): formation of the carbamate, the reaction is performed in the presence of a base such as, for example, DIEA;

Step (ii): deprotection of the allyl ester in the presence of a catalyst such as, for example, tetrakis-(triphenylphosphine)palladium;

Step (iii): activation of the carboxylic acid as a NHS ester by treatment with DSC in the presence of a base such as, for example, DIEA.

Preparation of the Compounds of Formula (II) in the Case where W=$(CH_2)_nNH_2$ and L=(IV35) with n=1, $R_{11}$=$R_{14}$=$R_{15}$=$R_{16}$=H, $J_1$=$J_2$=$J_3$=$J_4$=CH and ALK=$(CH_2)_3$ Based on Scheme 8

Scheme 16

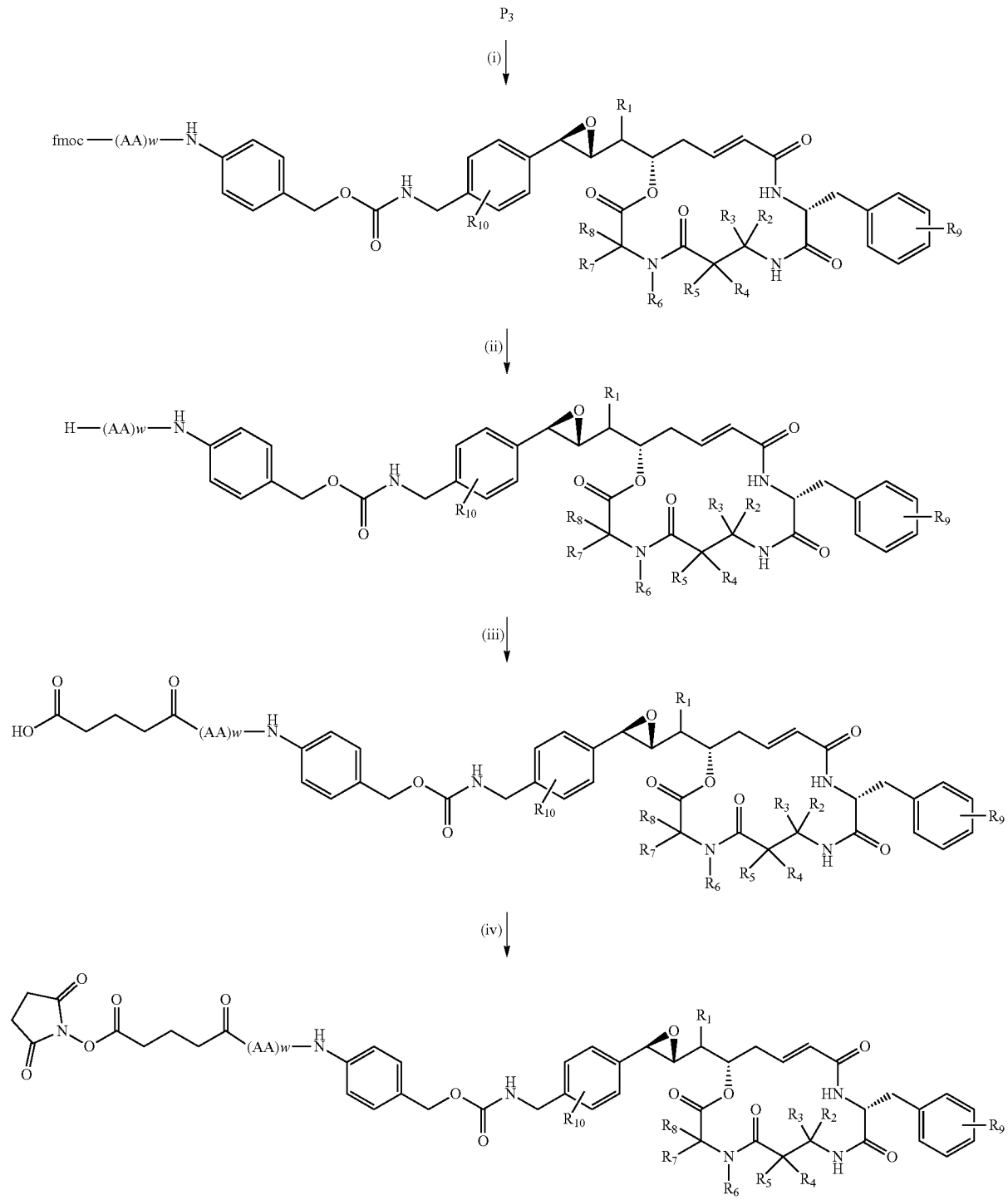

Step (i): formation of the carbamate, the reaction is performed in the presence of a base such as, for example, DIEA in the presence of a suitable p-nitrophenylcarbonate reagent;

Step (ii): deprotection of the Fmoc amine in the presence of a base such as, for example, piperidine;

Step (iii): coupling to glutaric anhydride;

Step (iv): activation of the carboxylic acid as a NHS ester by treatment with DSC in the presence of a base such as, for example, DIEA.

Schemes 15 and 16 describe the case L(IV35) with n=1, $R_{11}=R_{14}=R_{15}=R_{16}=H$, $J_1=J_2=J_3=J_4=CH$, a para-benzylic alcohol and ALK=$(CH_2)_3$ but they may also apply to other linkers L with RCG1=C(=O)ONHS, namely the case L(IV35) with n≠1 and/or $R_{11}$, $R_{14}$, $R_{15}$, $R_{16}$≠H and/or $J_1$, $J_2$, $J_3$, $J_4$≠CH and/or an ortho-benzylic alcohol and/or ALK≠$(CH_2)_3$ and the cases L(IV36) and L(IV37). They are given for a linker in the para position, but may identically apply for the ortho or meta positions. Similarly, they are given for a cryptophycin compound, but may also apply to the preparation of other compounds of formula (I), especially $D_1$-$D_{19}$.

Preparation of the Compounds of Formula (II) in the Case where W=$(CH_2)_n NH_2$ with n=1, $R_{11}=R_{14}=R_{15}=R_{16}=H$, $J_1=J_2=J_3=J_4=CH$ and RCG1=Maleimido, Haloacetamido, $NH_2$, $N_3$ or Cyclooctyne Namely Linkers L(IV38) to L(IV151)

Scheme 17

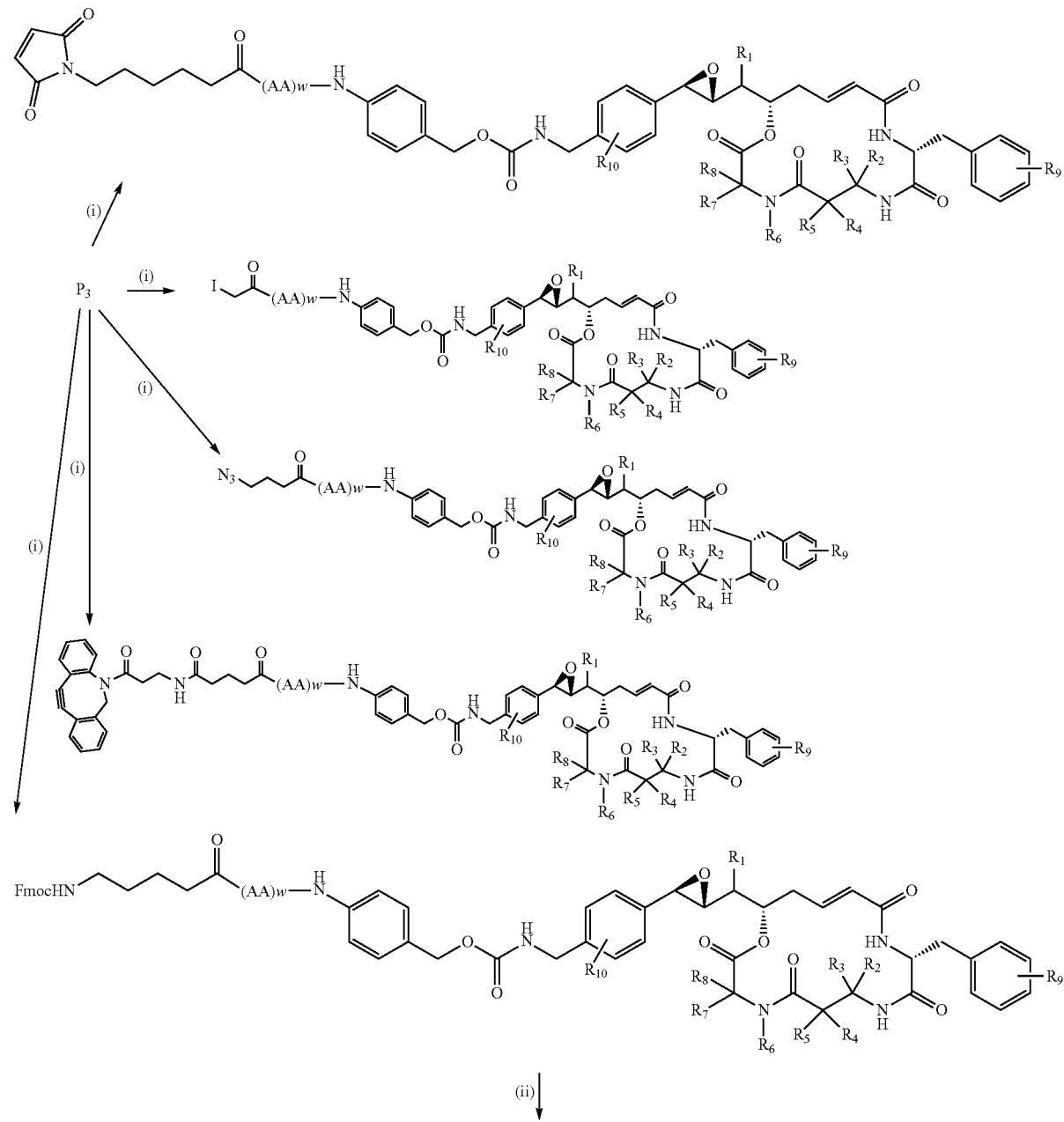

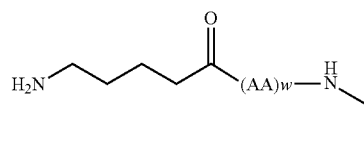
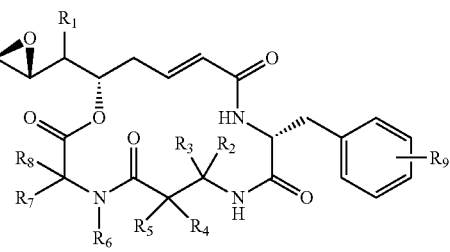

Step (i): formation of the carbamate, the reaction is performed in the presence of a base such as, for example, DIEA in the presence of a suitable p-nitrophenylcarbonate reagent;

Step (ii): deprotection of the Fmoc amine in the presence of a base such as, for example, piperidine.

Scheme 17 describes the cases L(IV38) with n=1, $R_{11}=R_{14}=R_{15}=R_{16}=H$, $J_1=J_2=J_3=J_4=CH$, a para- benzylic alcohol and $ALK=(CH_2)_5$, L(IV42) with n=1, $R_{11}=R_{14}=R_{15}=R_{16}=H$ and $J_1=J_2=J_3=J_4=CH$ and a para-benzylic alcohol, L(IV46) with n=1, $R_{11}=R_{14}=R_{15}=R_{16}=H$, $J_1=J_2=J_3=J_4=CH$, a para-benzylic alcohol and $ALK=(CH_2)_4$, L(IV48) with n=1, $R_{11}=R_{14}=R_{15}=R_{16}=H$, $J_1=J_2=J_3=J_4=CH$, a para-benzylic alcohol and $ALK=(CH_2)_3$ and L(IV50) with n=1, $R_{11}=R_{14}=R_{15}=R_{16}=R_{22}=H$, $J_1=J_2=J_3=J_4=CH$, a para-benzylic alcohol, $ALK=(CH_2)_3$ and $ALK'=(CH_2)_2$ but it may also apply to other linkers L(IV38) to L(IV51) with RCG1=maleimido, iodoacetamido, $NH_2$, $N_3$ or cyclooctyne. It is given with a para-benzylic alcohol but it may also apply to an ortho-benzylic alcohol. It is depicted for an iodoacetamido reactive group but may identically apply for a bromoacetamido reactive group. It is given for a linker in the para position, but may identically apply for the ortho or meta positions. Similarly, it is given for a cryptophycin compound, but may also apply to the preparation of other compounds of formula (I), especially $D_1$-$D_{19}$.

Preparation of the Compounds of Formula (II) in the Case where $W=(CH_2)_nX$ with $X=O$ or S and L=(IV52) with n=1, $R_{14}=R_{15}=R_{16}=R_{17}=R_{18}=H$, $J_1=J_2=J_3=J_4=CH$ and $ALK=(CH_2)_3$ Based on Scheme 7

Scheme 18

P$_{10}$ (i) ↓

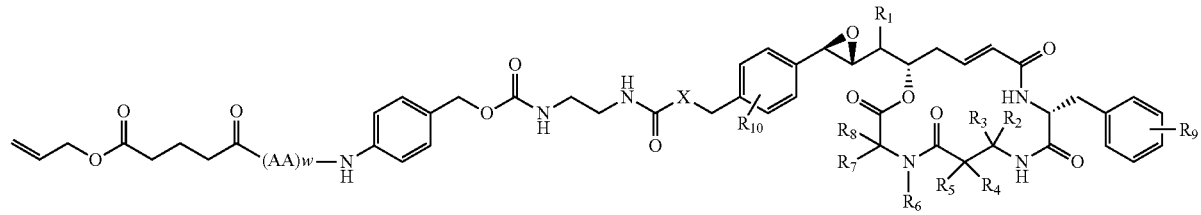

(ii) ↓

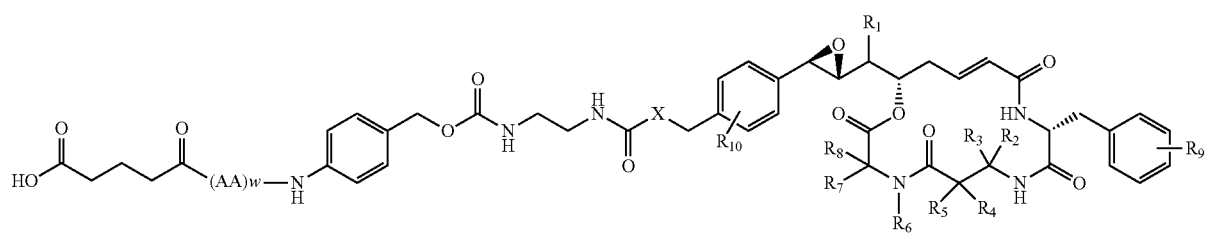

(iii) ↓

-continued

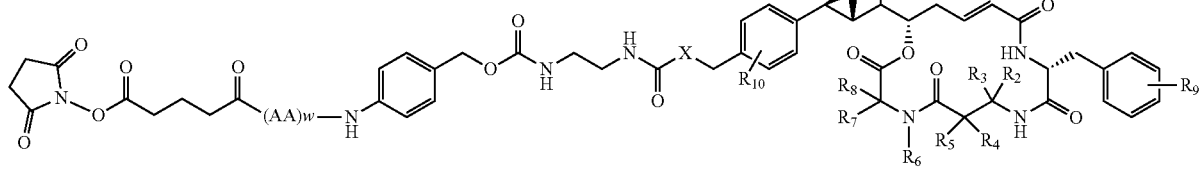

Step (i): formation of the (thio)carbamate by reacting with an amine in the presence of a base such as, for example, DIEA;

Step (ii): deprotection of the allyl ester in the presence of a catalyst such as, for example, tetrakis(triphenylphosphine) palladium;

Step (iii): activation of the carboxylic acid as a NHS ester by treatment with DSC in the presence of a base such as, for example, DIEA.

Preparation of the Compounds of Formula (II) in the Case where W=(CH$_2$)$_n$X with X=O or S and L=(IV52) with n=1, R$_{14}$=R$_{15}$=R$_{16}$=R$_{17}$=R$_{18}$=H, J$_1$=J$_2$=J$_3$=J$_4$=CH and ALK=(CH$_2$)$_3$ Based on Scheme 8

Scheme 19

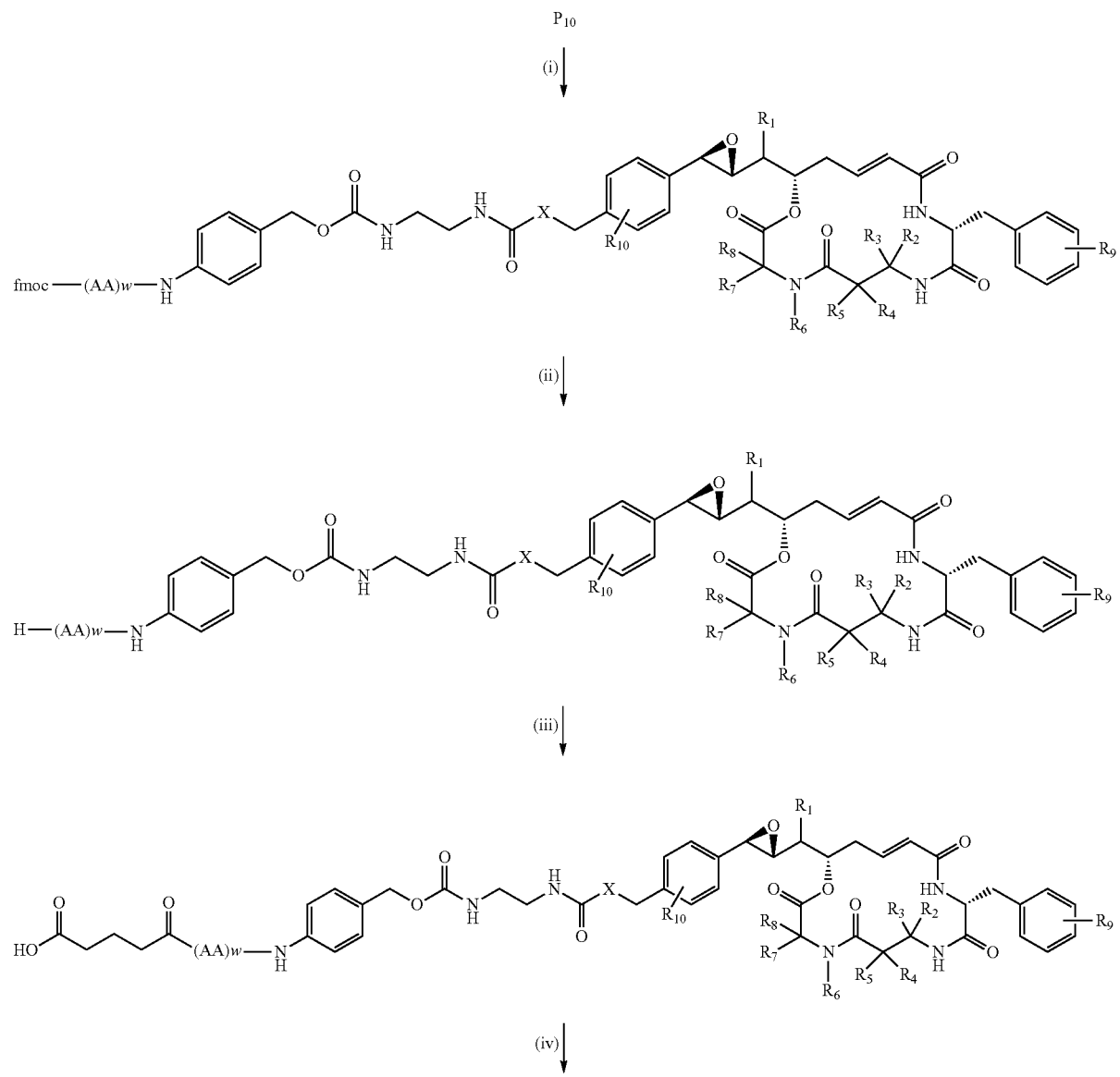

-continued

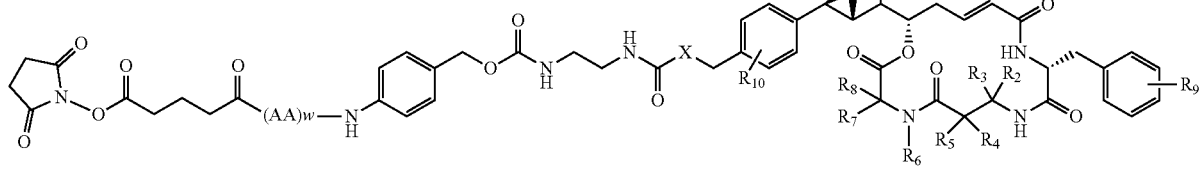

Step (i): formation of the (thio)carbamate by reacting with an amine in the presence of a base such as, for example, DIEA;

Step (ii): deprotection of the Fmoc amine in the presence of a base such as, for example, piperidine;

Step (iii): coupling to glutaric anhydride;

Step (iv): activation of the carboxylic acid as a NHS ester by treatment with DSC in the presence of a base such as, for example, DIEA.

Schemes 18 and 19 describe the case L(IV52) with n=1, $R_{14}=R_{15}=R_{16}=R_{17}=R_{18}=H$, $J_1=J_2=J_3=J_4=CH$, a para-benzylic alcohol and $ALK=(CH_2)_3$ but they may also apply to other linkers L with RCG1=C(=O)ONHS, namely the case L(IV52) with n≠1 and/or $R_{14}$, $R_{15}$, $R_{16}$, $R_{17}$, $R_{18}$≠H and/or $J_1$, $J_2$, $J_3$, $J_4$≠CH and/or an ortho-benzylic alcohol and/or ALK≠$(CH_2)_3$ and the cases L(IV53) and L(IV54). They are given for a linker in the para position, but may identically apply for the ortho or meta positions. Similarly, they are given for a cryptophycin compound, but may also apply to the preparation of other compounds of formula (I), especially $D_1$-$D_{19}$.

Preparation of the Compounds of Formula (II) in the Case where W=$(CH_2)_nX$ with X=O or S and RCG1=Maleimido, Haloacetamido, $NH_2$, $N_3$ or Cyclooctyne Namely Linkers L(IV55) to (IV68)

Scheme 20

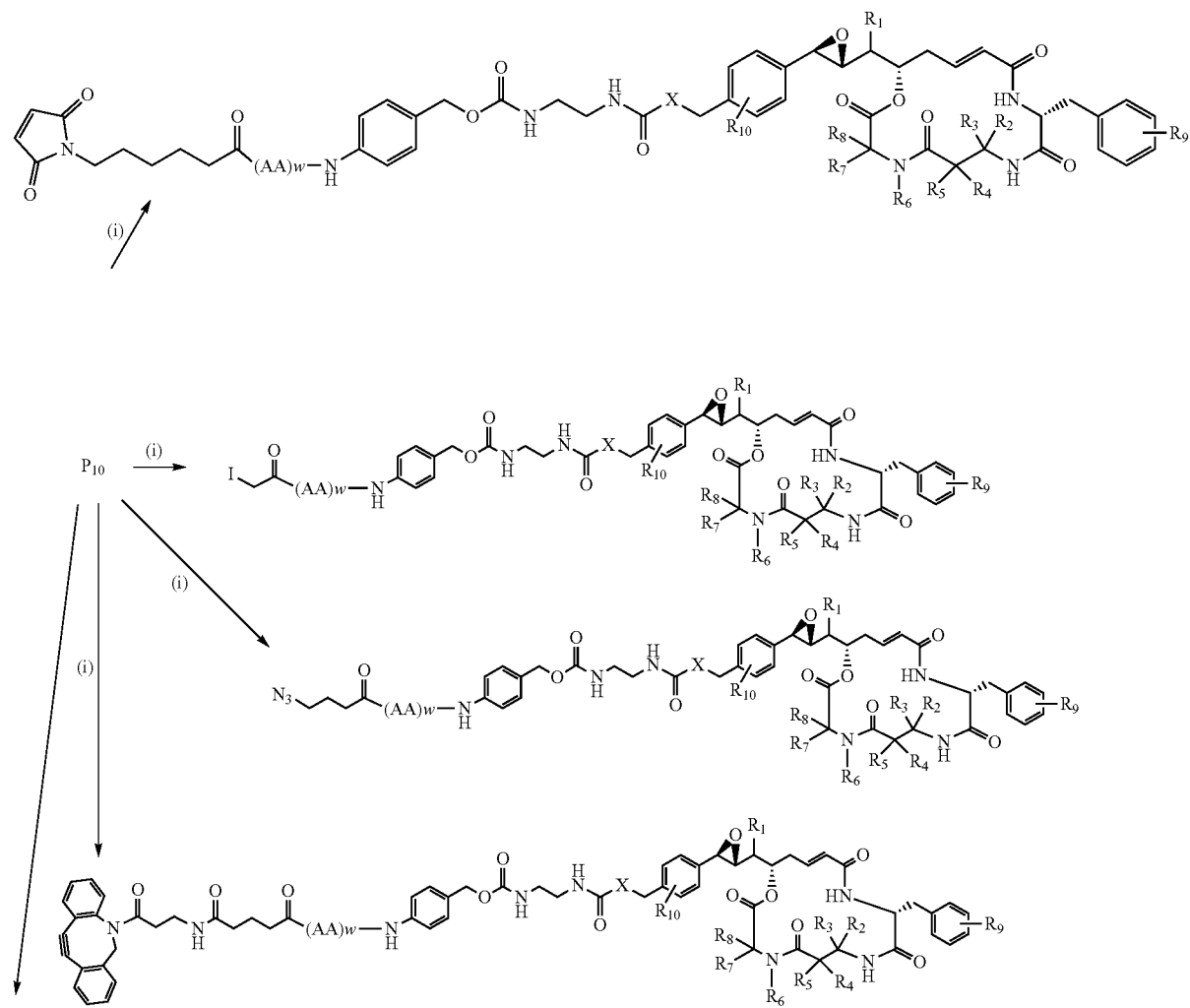

-continued

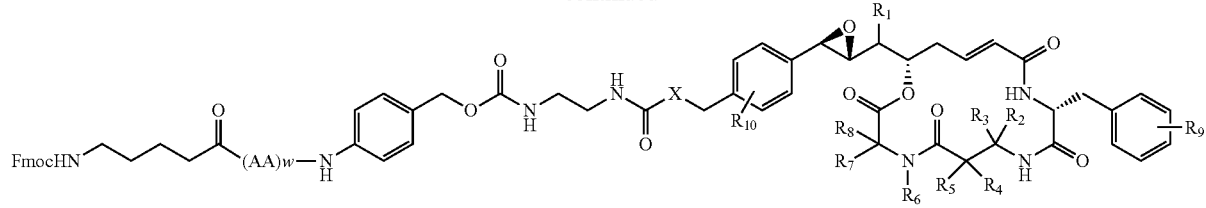

(ii) ↓

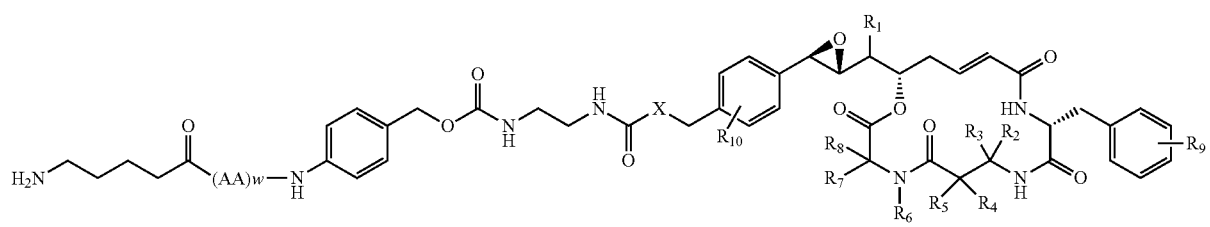

Step (i): formation of the (thio)carbamate by reacting with an amine in the presence of a base such as, for example, DIEA;

Step (ii): deprotection of the Fmoc amine in the presence of a base such as, for example, piperidine.

Scheme 20 describes the case L(IV55) with n=1, $R_{14}=R_{15}=R_{16}=R_{17}=R_{18}=H$, $J_1=J_2=J_3=J_4=CH$, a para-benzylic alcohol, $ALK=(CH_2)_2$ and $ALK'=(CH_2)_5$, the case L(IV59) with n=1, $R_{14}=R_{15}=R_{16}=R_{17}=R_{18}=H$, $J_1=J_2=J_3=J_4=CH$, a para-benzylic alcohol and $ALK=(CH_2)_2$, the case L(IV63) with n=1, $R_{14}=R_{15}=R_{16}=R_{17}=R_{18}=H$, $J_1=J_2=J_3=J_4=CH$, a para-benzylic alcohol, $ALK=(CH_2)_2$ and $ALK'=(CH_2)_4$, the case L(IV65) with n=1, $R_{14}=R_{15}=R_{16}=R_{17}=R_{18}=H$, $J_1=J_2=J_3=J_4=CH$, a para-benzylic alcohol, $ALK=(CH_2)_2$ and $ALK'=(CH_2)_3$ and the case L(IV67) with n=1, $R_{14}=R_{15}=R_{16}=R_{17}=R_{18}=R_{22}=H$, $J_1=J_2=J_3=J_4=CH$, a para-benzylic alcohol, $ALK=(CH_2)_2$, $ALK'=(CH_2)_5$ and $ALK''=(CH_2)_2$ but it may also apply to other linkers L(IV55 to 68) with RCG1=maleimido, iodoacetamido, $NH_2$, $N_3$ or cyclooctyne. It is depicted for an iodoacetamido reactive group but may identically apply for a bromoacetamido reactive group. It is given for a linker in the para position, but may identically apply for the ortho or meta positions. Similarly, it is given for a cryptophycin compound, but may also apply to the preparation of other compounds of formula (I), especially $D_1$-$D_{19}$.

Preparation of the Compounds of Formula (II) in the Case where W=C(=O)O and L=(IV69) with $R_{14}=R_{15}=R_{16}=H$, $J_1=J_2=J_3=J_4=CH$ and $ALK=(CH_2)_3$ Based on Scheme 7

Scheme 21

$P_8$ (i) ↓

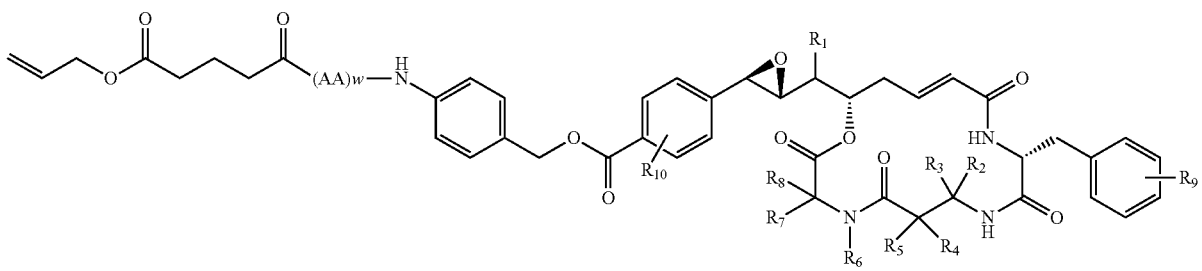

(ii) ↓

-continued

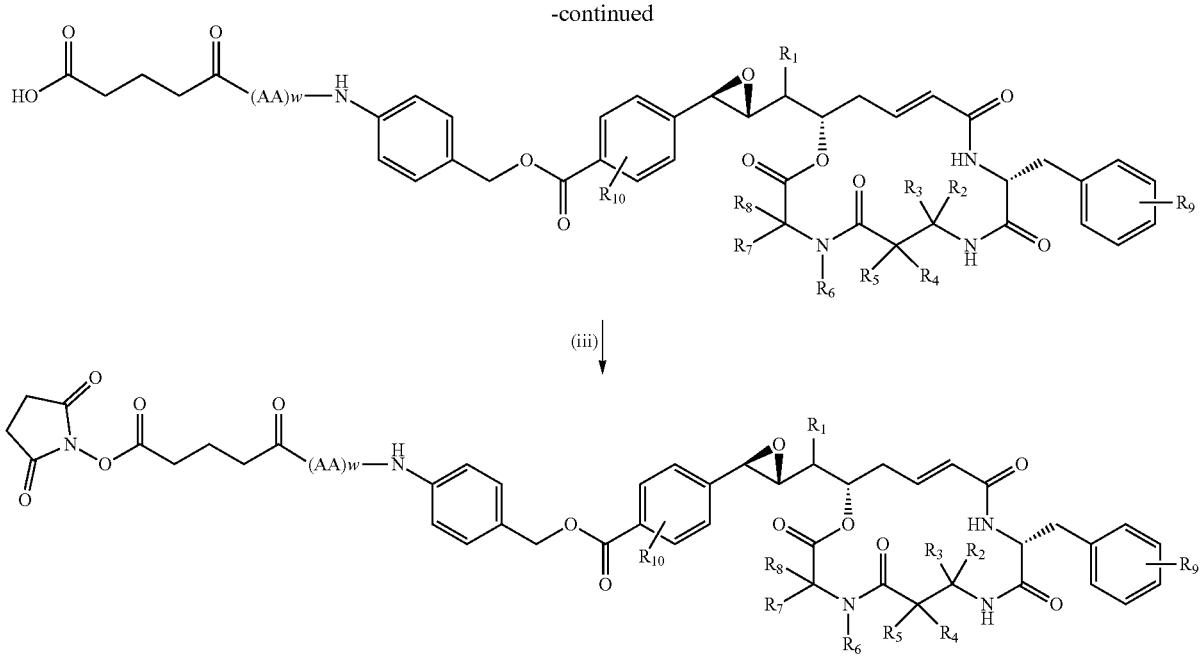

Step (i): esterification in the presence of a coupling reagent such as, for example, MNBA and a base such as, for example, DMAP and DIEA;

Step (ii): deprotection of the allyl ester in the presence of a catalyst such as, for example, tetrakis-(triphenylphosphine)palladium;

Step (iii): activation of the carboxylic acid as a NHS ester by treatment with DSC in the presence of a base such as, for example, DIEA.

Preparation of the Compounds of Formula (II) in the Case where W=C(=O)O and L=(IV69) with $R_{14}=R_{15}=R_{16}=H$, $J_1=J_2=J_3=J_4=CH$ and $ALK=(CH_2)_3$ Based on Scheme 8

Scheme 22

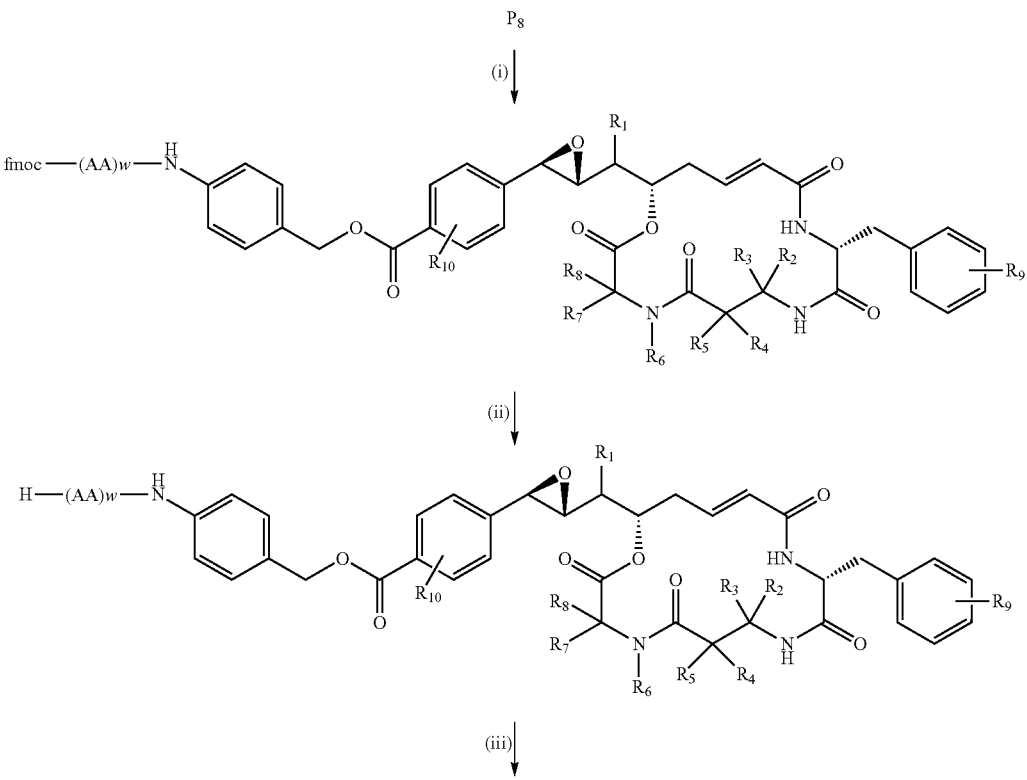

-continued

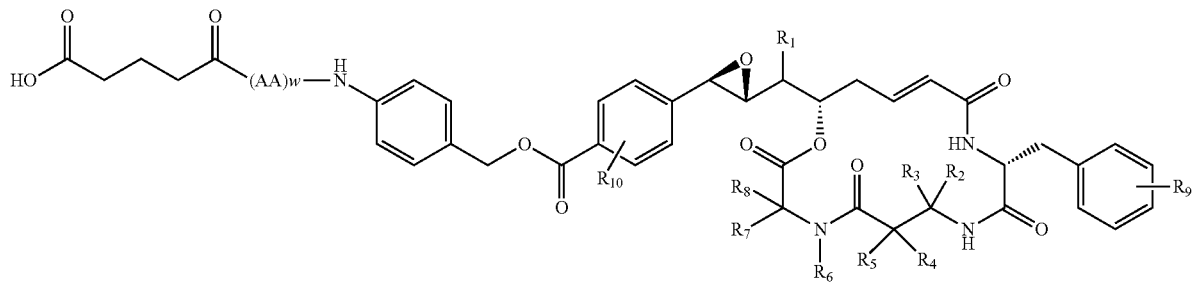

(iv) ↓

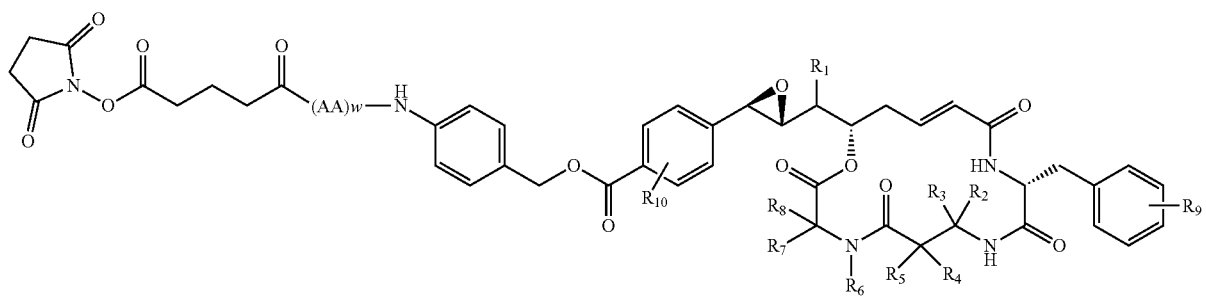

Step (i): esterification in the presence of a coupling reagent such as, for example, MNBA and a base such as, for example, DMAP and DIEA;

Step (ii): deprotection of the Fmoc amine in the presence of a base such as, for example, piperidine;

Step (iii): coupling to glutaric anhydride;

Step (iv): activation of the carboxylic acid as a NHS ester by treatment with DSC in the presence of a base such as, for example, DIEA.

Schemes 21 and 22 describe the case L(IV69) with $R_{14}=R_{15}=R_{16}=H$, $J_1=J_2=J_3=J_4=CH$, a para-benzylic alcohol and ALK=$(CH_2)_3$ but they may also apply to other linkers L with RCG1=C(=O)ONHS, namely the case L(IV69) with $R_{14}$, $R_{15}$, $R_{16}\neq H$ and/or $J_1$, $J_2$, $J_3$, $J_4\neq CH$ and/or an ortho-benzylic alcohol and/or ALK$\neq(CH_2)_3$ and the cases L(IV70) and L(IV71). They are given for a linker in the para position, but may identically apply for the ortho or meta positions.

Similarly, they are given for a cryptophycin compound, but may also apply to the preparation of other compounds of formula (I), especially $D_1$-$D_{19}$.

Preparation of the Compounds of Formula (II) in the Case where W=C(=O)O with $R_{14}=R_{15}=R_{16}=H$, $J_1=J_2=J_3=J_4=CH$ and RCG1=Maleimido, Haloacetamido, $NH_2$, $N_3$ or Cyclooctyne Namely Linkers L(IV72) to L(IV85)

Scheme 23

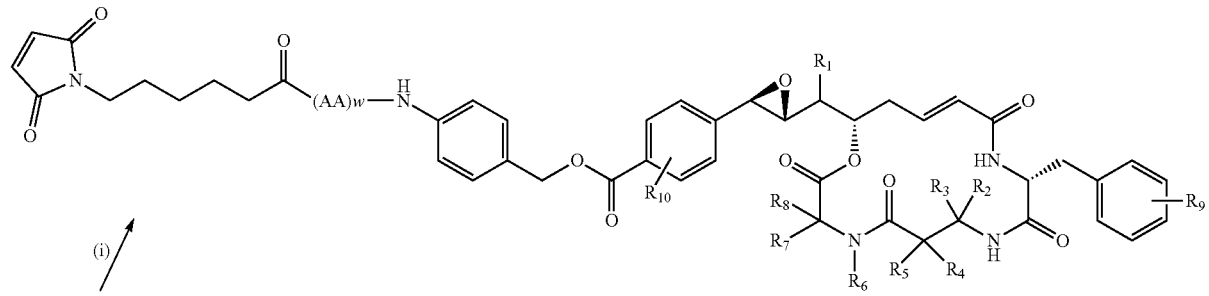

(i) ↗

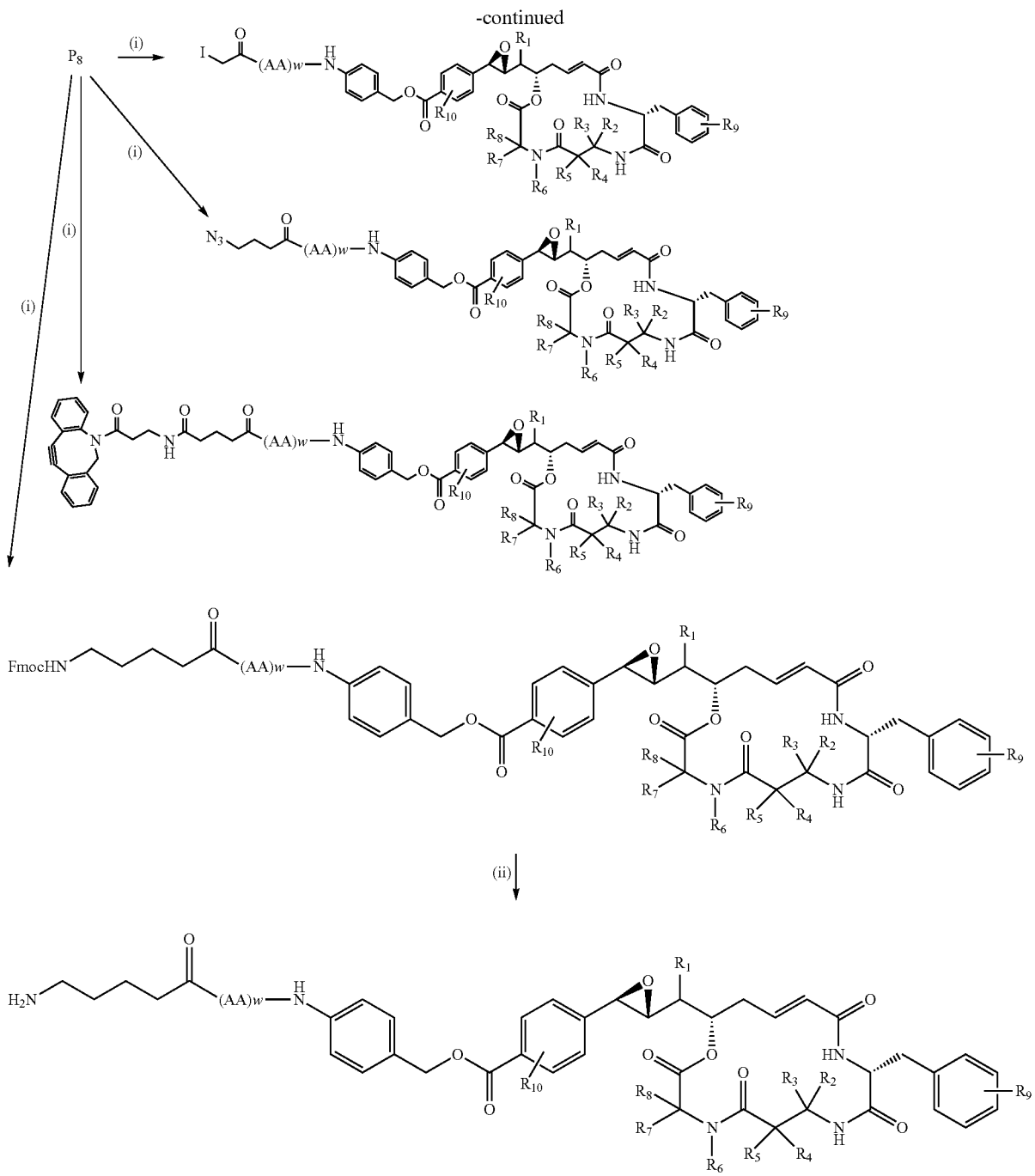

Step (i): esterification in the presence of a coupling reagent such as, for example, MNBA and a base such as, for example, DMAP and DIEA;

Step (ii): deprotection of the Fmoc amine in the presence of a base such as, for example, piperidine.

Scheme 23 describes the cases L(IV72) with n=1, $R_{14}=R_{15}=R_{16}=H$, $J_1=J_2=J_3=J_4=CH$, a para-benzylic alcohol and $ALK=(CH_2)_5$, L(IV76) with n=1, $R_{14}=R_{15}=R_{16}=H$ and $J_1=J_2=J_3=J_4=CH$ and a para-benzylic alcohol, L(IV80) with n=1, $R_{14}=R_{15}=R_{16}=H$, $J_1=J_2=J_3=J_4=CH$, a para-benzylic alcohol and $ALK=(CH_2)_4$, L(IV82) with n=1, $R_{14}=R_{15}=R_{16}=H$, $J_1=J_2=J_3=J_4=CH$, a para-benzylic alcohol and $ALK=(CH_2)_3$ and L(IV84) with n=1, $R_{14}=R_{15}=R_{16}=R_{22}=H$, $J_1=J_2=J_3=J_4=CH$, a para-benzylic alcohol, $ALK=(CH_2)_3$ and $ALK'=(CH_2)_2$ but it may also apply to other linkers L(IV72) to L(IV85) with RCG1=maleimido, iodoacetamido, $NH_2$, $N_3$ or cyclooctyne. It is given with a para-benzylic alcohol but it may also apply to an ortho-benzylic alcohol. It is depicted for an iodoacetamido reactive group but may identically apply for a bromoacetamido reactive group. It is given for a linker in the para position, but may identically apply for the ortho or meta positions. Similarly, it is given for a cryptophycin compound, but may also apply to the preparation of other compounds of formula (I), especially $D_1$-$D_{19}$.

Preparation of the Compounds of Formula (II) in the Case where W=C(=O)O and L=(V86) with $R_{25}$=H and ALK=$(CH_2)_7$ Scheme 24 describes the case L(V86) with $R_{25}$=H and ALK=$(CH_2)_7$ but they may also apply to other linkers L with RCG1=C(=O)ONHS, namely the case L(V86) with $R_{25} \neq H$

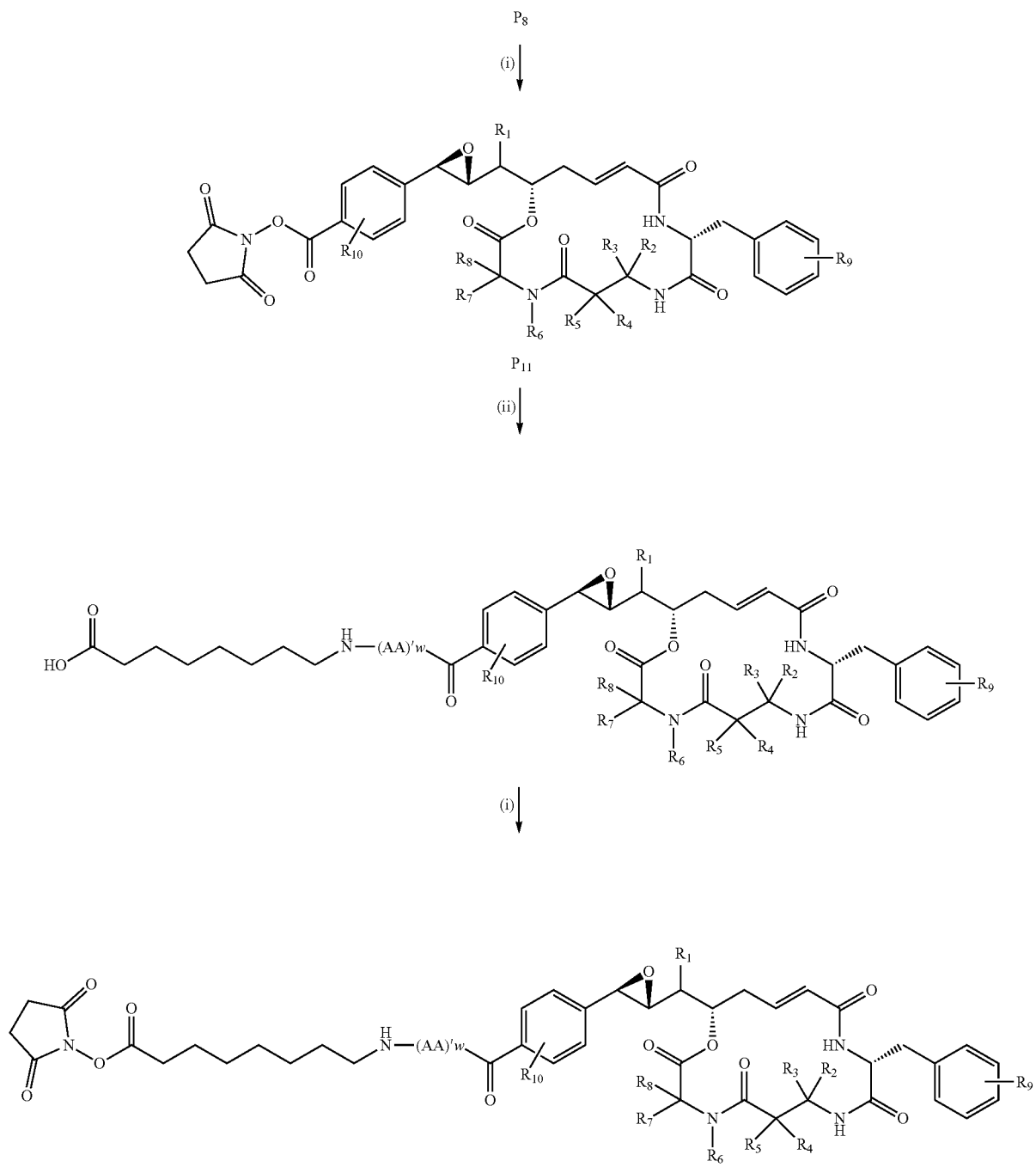

Step (i): activation of the carboxylic acid as a NHS ester by treatment with DSC in the presence of a base such as, for example, DIEA;
Step (ii): peptidic coupling in the presence of a base such as, for example, DIEA;
Step (iii): activation of the carboxylic acid as a NHS ester by treatment with DSC in the presence of a base such as, for example, DIEA.

and/or ALK$\neq(CH_2)_7$ and the cases L(V87) and L(V88). They are given for a linker in the para position, but may identically apply for the ortho or meta positions. Similarly, they are given for a cryptophycin compound, but may also apply to the preparation of other compounds of formula (I), especially $D_1$-$D_{19}$.

Preparation of the Compounds of Formula (II) in the Case where W=C(=O)O with $R_{30}$=H and RCG1=Maleimido, Haloacetamido, $NH_2$, $N_3$ or Cyclooctyne Namely Linkers L(V89) to L(V101)

$R_{25}$=H and ALK=$(CH_2)_3$ and L(V100) with $R_{22}$=$R_{25}$=H, ALK=$(CH_2)_3$ and ALK'=$(CH_2)_2$ but it may also apply to other linkers L(V89) to L(V101) with RCG1=maleimido, iodoacetamido, $NH_2$, $N_3$ or cyclooctyne. It is depicted for an Scheme 25

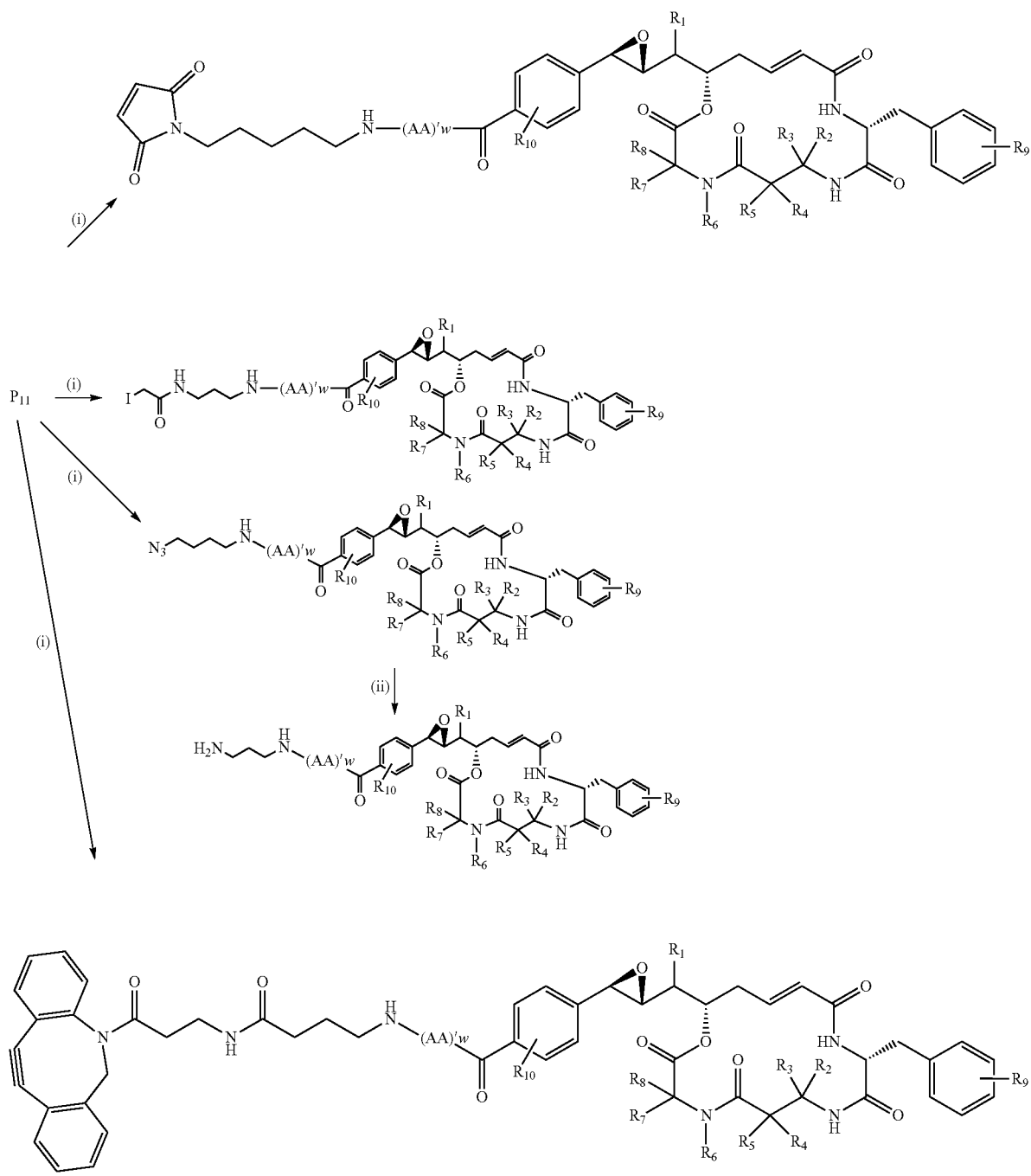

Step (i): peptidic coupling in the presence of a base such as, for example, DIEA;
Step (ii): reduction of the azido by treatment with a reducing agent such as, for example, TCEP.
Scheme 25 describes the cases L(V89) with $R_{25}$=H and ALK=$(CH_2)_5$, L(V93) with $R_{25}$=H and ALK=$(CH_2)_3$, L(V96) with $R_{25}$=H and ALK=$(CH_2)_4$, L(V98) with iodoacetamido reactive group but may identically apply for a bromoacetamido reactive group. It is given for a linker in the para position, but may identically apply for the ortho or meta positions. Similarly, it is given for a cryptophycin compound, but may also apply to the preparation of other compounds of formula (I), especially $D_1$-$D_{19}$.

Process for Preparing the Cryptophycin Conjugates

The compounds of formula (III) might be prepared according to Scheme 26 starting with a cryptophycin payload of formula (II) and an antibody (Ab):

Scheme 26

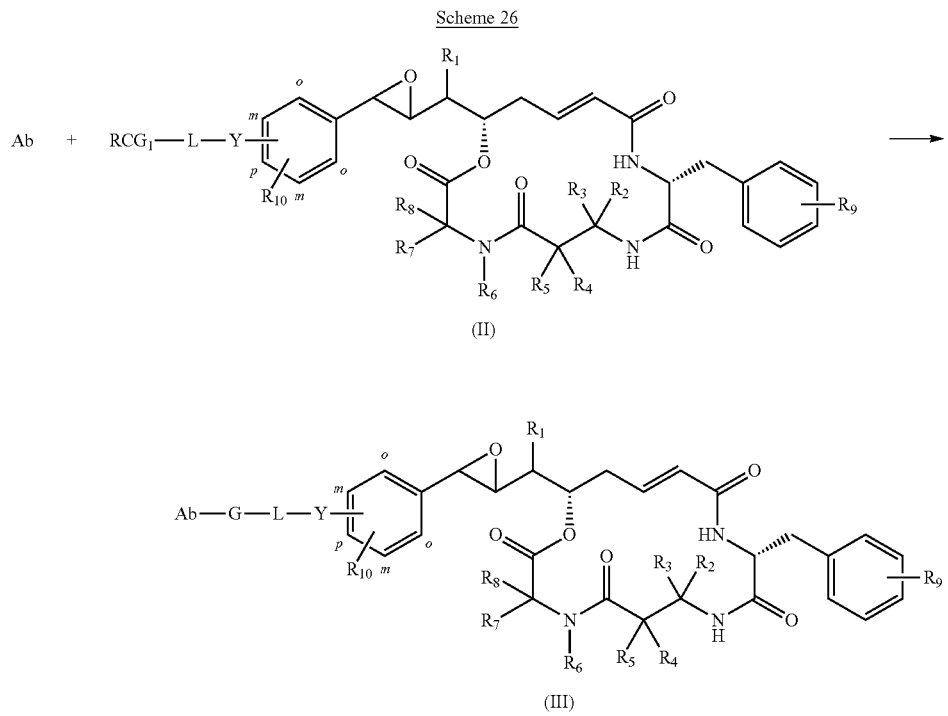

in which:
- Y represents $(C_1-C_6)$alkyl-$NR_{11}$ or $(C_1-C_6)$alkyl-O or $(C_1-C_6)$alkyl-S;
- or alternatively Y represents C(=O)O or O $(C_1-C_6)$alkyl-C(=O)O;
- or alternatively Y represents $(C_1-C_6)$alkyl-triazole-like

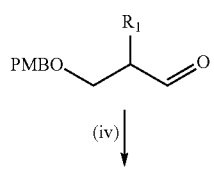

- Y is positioned in an ortho (o), meta (m) or para (p) position of the phenyl nucleus;
- $R_{11}$ represents a hydrogen atom or a $(C_1-C_6)$alkyl group;
- L represents a linker positioned in an ortho (o), meta (m) or para (p) position of the phenyl nucleus, as defined above;
- RCG1 represents a reactive chemical group that is reactive towards a reactive chemical group present on the antibody, as defined above;
- Ab represents an antibody.

Process for Preparing the Building Blocks for the Synthesis of Cryptophycin Compounds of Formula (I)

General Synthesis of Fragment A

Scheme 27

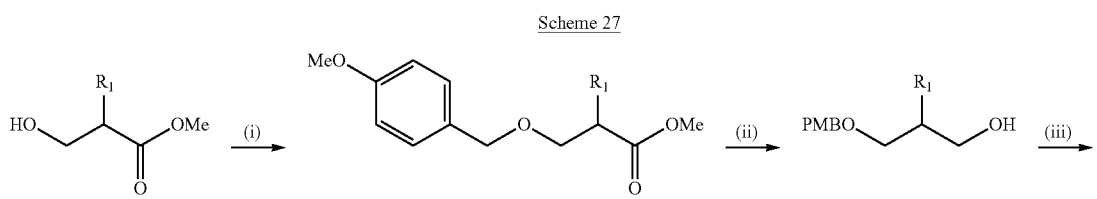

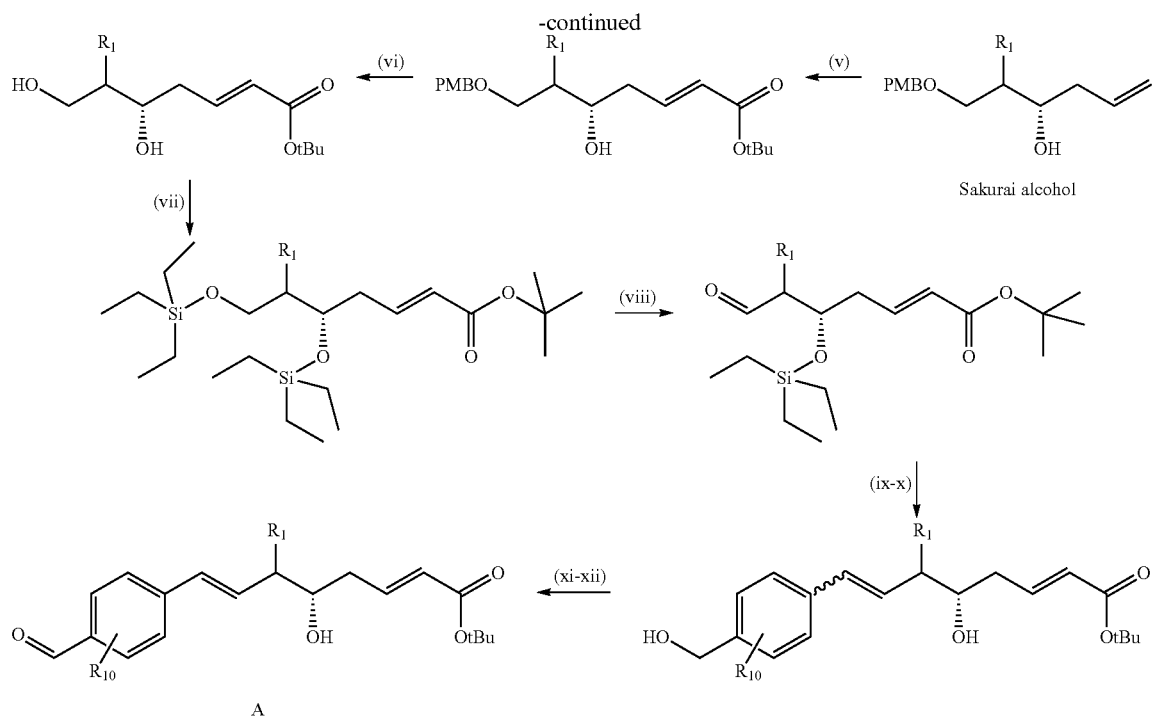

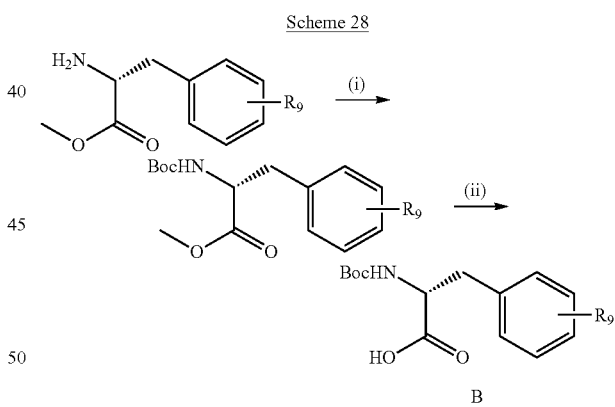

Fragment A may be prepared in 12 steps starting from appropriate hydroxy esters with the aid of the steps detailed below:

Step (i): protection of the alcohol as a p-methoxybenzyl ether using p-methoxybenzyl alcohol activated as a trichloroacetimidate in the presence of a catalytic amount of acid such as, for example, p-TsOH;

Step (ii): reduction of the ester using a reducing agent such as, for example, lithium borohydride;

Step (iii): oxidation of the alcohol using an oxidizing agent such as, for example, TEMPO in the presence of sodium hypochlorite;

Step (iv): diastereoselective allylation using allyltributyltin in the presence of tin tetrachloride;

Step (v): cross metathesis using tert-butylacrylate in the presence of a catalyst such as, for example, Grubbs II catalyst;

Step (vi): deprotection of the p-methoxybenzyl ether using CAN and subsequent treatment with ethanedithiol in the presence of a catalytic amount of acid such as, for example, p-TsOH;

Step (vii): protection of the alcohols as silyl ethers using chlorotriethylsilane in the presence of a base such as, for example, imidazole;

Step (viii): Swern oxidation using DMSO and oxalyl chloride in the presence of a base such as, for example, DIEA;

Step (ix): Wittig reaction using a suitable phosphonium halide, for example a bromide, and a strong base such as, for example, BuLi;

Step (x): deprotection of the silyl ether using, for example, a TBAF solution.

Step (xi): oxidation of the benzylic alcohol using an oxidizing agent such as, for example, manganese oxide;

Step (xii): isomerization of the double bond using AIBN in the presence of benzenethiol.

Hydroxy esters are commercially available for $R_1$=Me (CAS number [72657-23-9]), Et (CAS number [72604-81-0]) and iPr (CAS number [72604-82-1]). Preparation of phosphonium halides is described in WO2011/001052.

General Synthesis of Fragment B

Scheme 28

Fragment B may be prepared in 2 steps starting from appropriate amino acids with the aid of the steps detailed below:

Step (i): protection of the amine by treatment with $Boc_2O$ in the presence of a base such as, for example, TEA;

Step (ii): saponification of the methyl ester using a base such as, for example, LiOH.

Amino acids protected as methyl esters are commercially available for $R_9$=3-Cl, 4-OMe (CAS number [704870-54-2]); 3-Cl, 4-OEt (CAS number [1256963-00-9]); 3-Cl, 4-OPr (CAS number [1259709-59-9]); 3-Cl, 4-OMe, 5-F (CAS number [1213670-98-4]); 3-Cl, 4-OMe, 5-Cl (CAS number [1259701-42-2]); 3-Cl, 4-OMe, 5-OMe (CAS number [1212820-34-2]); 3-Cl, 4-OH, 5-OMe (CAS number

[1213426-93-7]); 3-Cl, 4-NH$_2$ (CAS number [1213672-64-0]); 2-Cl, 3-Cl, 4-NH$_2$ (CAS number [1213607-49-8]); 3-Cl, 4-NH$_2$, 5-F (CAS number [1213400-66-8]); 3-Cl, 4-NH$_2$, 5-Cl (CAS number [1213480-30-8]).

General Synthesis of Building Block AD1

Step (ii): reduction of the aldehyde into an alcohol using a reducing agent such as, for example, sodium trimethoxyborohydride;

Step (iii): activation of the alcohol as a mesylate by treatment with methanesulfonyl chloride in the presence of Scheme 29

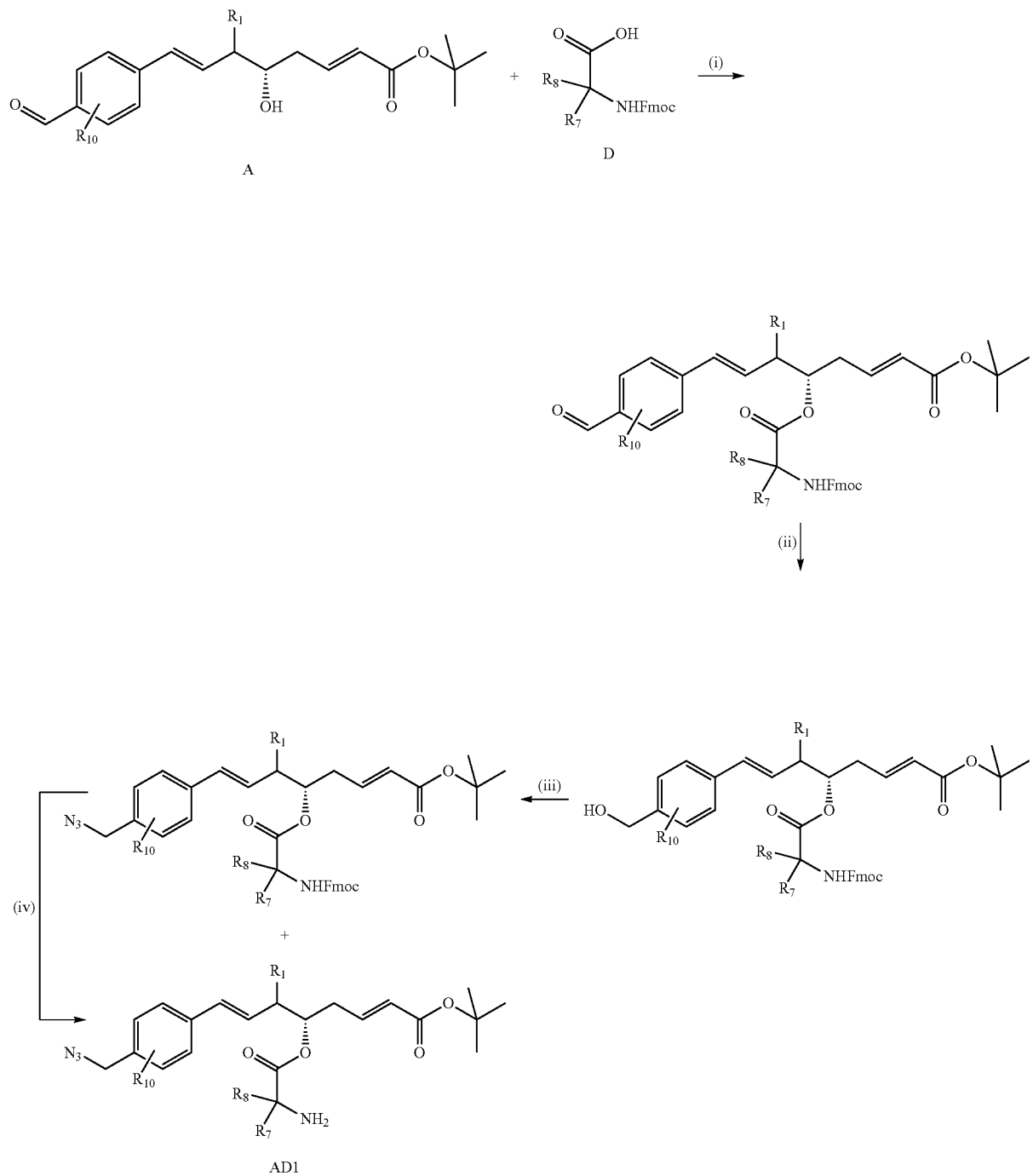

Fragments A and D allow the preparation of building block AD1 with the aid of the steps detailed below:

Step (i): esterification of fragment D with fragment A in the presence of a coupling reagent such as, for example, MNBA and a base such as, for example, DMAP and DIEA;

a base such as, for example, TEA; substitution of the mesylate by an azido group by treatment with sodium azide;

Step (iv): deprotection of the amine by treatment with a base such as, for example, piperidine.

General Synthesis of Building Block AD2

Scheme 30

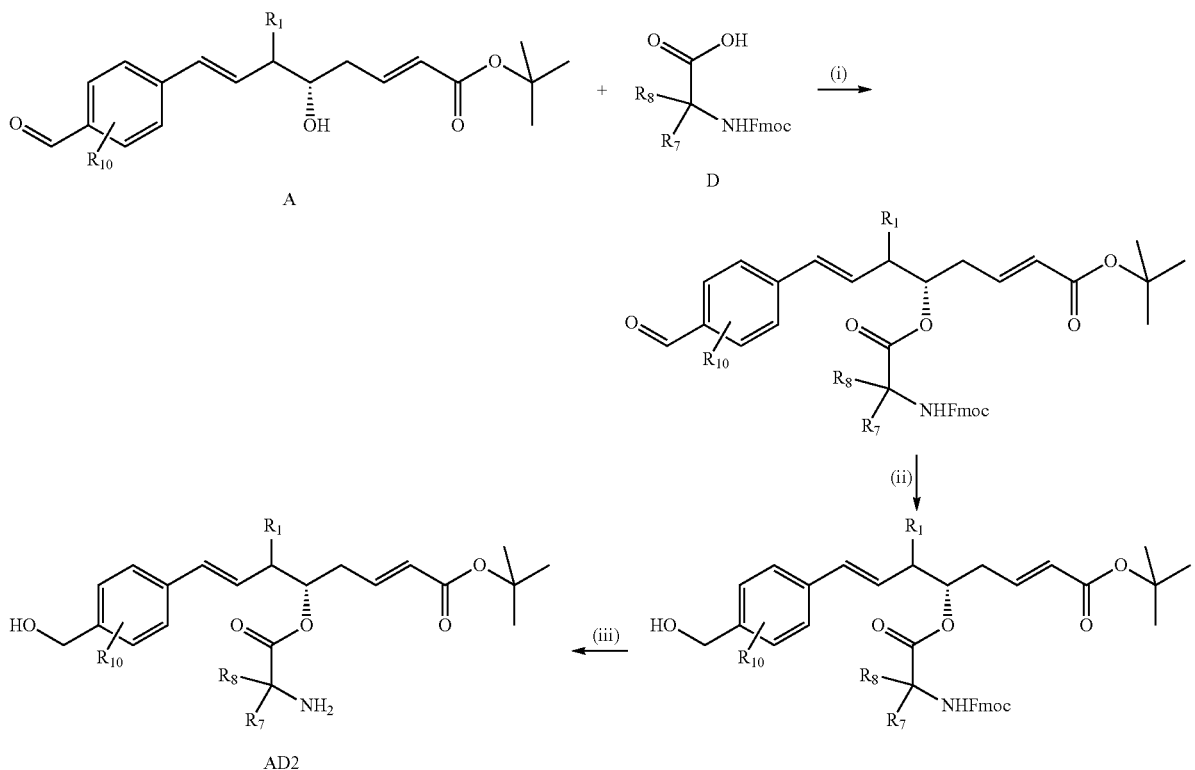

Fragments A and D allow the preparation of building block AD2 with the aid of the steps detailed below:

Step (i): esterification of fragment D with fragment A in the presence of a coupling reagent such as, for example, MNBA and a base such as, for example, DMAP and DIEA;

Step (ii): reduction of the aldehyde into an alcohol using a reducing agent such as, for example, sodium trimethoxyborohydride;

Step (iii): deprotection of the amine by treatment with a base such as, for example, piperidine.

General Synthesis of Building Block AD3

Scheme 31

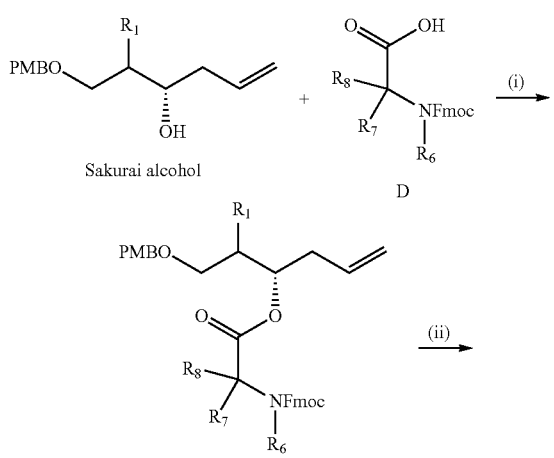

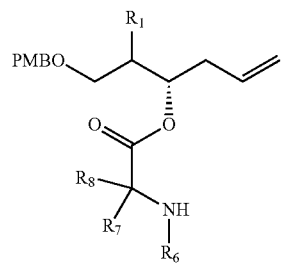

Step (i): esterification of fragment D with Sakurai alcohol in the presence of a coupling reagent such as, for example, MNBA and a base such as, for example, DMAP and DIEA;

Step (ii): deprotection of the amine by treatment with a base such as, for example, piperidine.

General Synthesis of Building Block BC

Scheme 32

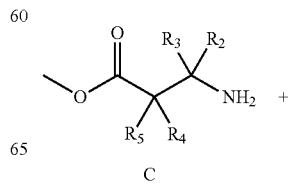

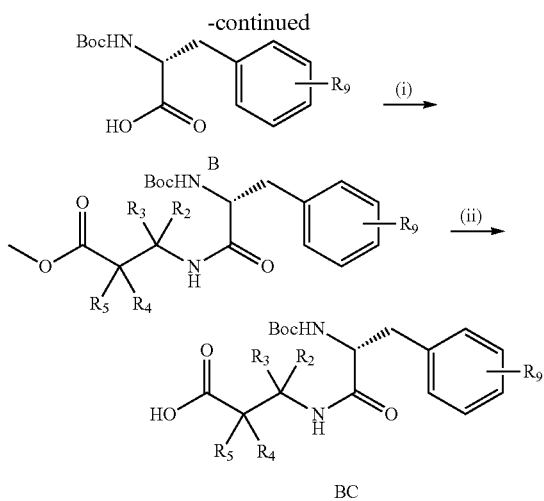

Fragments B and C allow the preparation of building block BC with the aid of the steps detailed below:

Step (i): peptidic coupling of fragment B with fragment C in the presence of coupling reagents such as, for example, HOBt and EDC and a base such as, for example, DIEA;

Step (ii): saponification of the methyl ester using a base such as, for example, LiOH.

General Synthesis of an Alternative Building Block BC

Fragments B and C allow the preparation of an alternative building block BC with the aid of the steps detailed below:

Step (i): peptidic coupling of fragment B with fragment C in the presence of coupling reagents such as, for example, HOBt and EDC and a base such as, for example, DIEA;

Step (ii): deprotection of the Boc group in acidic conditions using, for example, TFA;

Step (iii): formation of the acrylamide by treatment with acryloyle chloride in the presence of a base such as, for example, DIEA;

Step (iv): saponification of the methyl ester using a base such as, for example, tBuOK.

Preparation of the Linker Precursors LP

LP may be one of the following; $LP_1$ to $LP_{101}$ are described using L amino acids but may also apply to D amino acids. They are given for w=2 but may similarly apply to w>2 by repeating as many times as required the peptide coupling step.

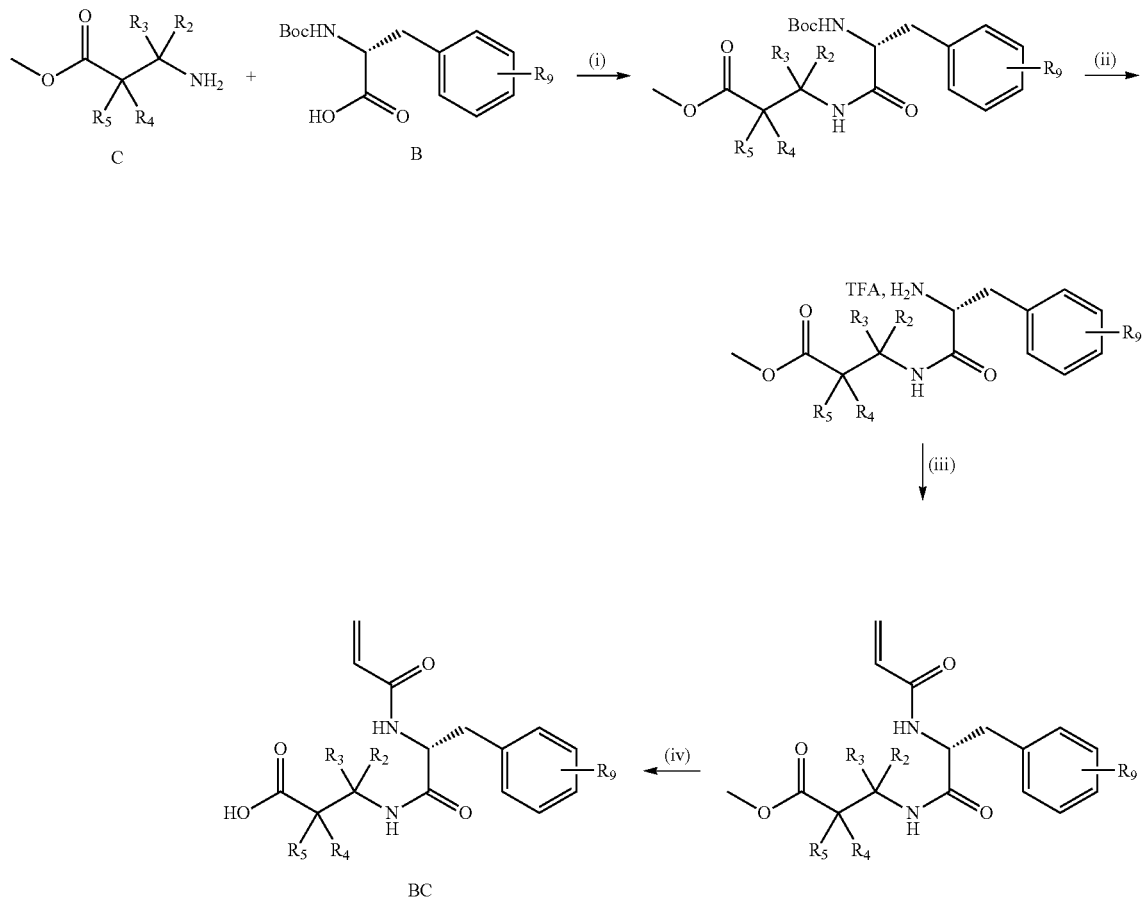

Scheme 33 prepared according to the scheme below:

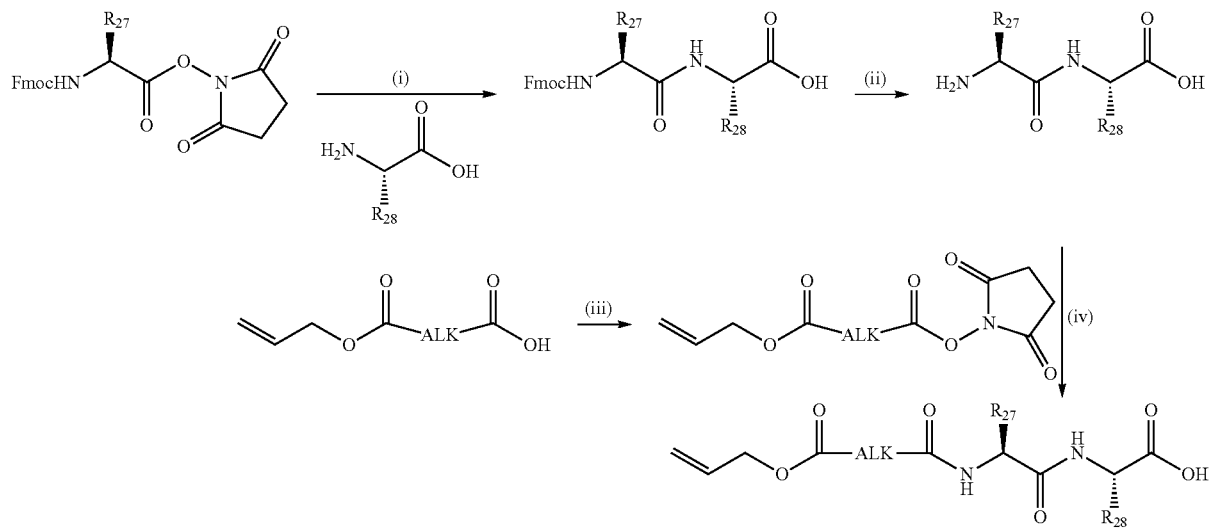

Step (i): peptide coupling between Fmoc-L-amino acid-ONHS and L-amino acid; the reaction is performed in a polar solvent such as a DME/THF/H$_2$O mixture in the presence of a base such as, for example, sodium bicarbonate;

Step (ii): deprotection of the amine; the reaction is performed in a polar solvent such as a DCM/MeOH mixture in the presence of a base such as, for example, piperidine;

Step (iii): activation of the carboxylic acid as a NHS ester; the reaction is performed in a polar aprotic solvent such as DCM by treatment with NHS in the presence of a coupling agent such as, for example, EDC;

Step (iv): peptide coupling between the dipeptide and the NHS ester; the reaction is performed at RT in a polar aprotic solvent such as a DCM/CH$_3$CN mixture.

NHS esters of Fmoc-L-amino acids are commercially available; the diacids monoprotected as allyl esters are commercially available for n=2 (monoallyl succinate) or may be prepared by transesterification of the methyl or tert-butyl monoesters, which are commercially available for n=2 to 6.

LP$_2$

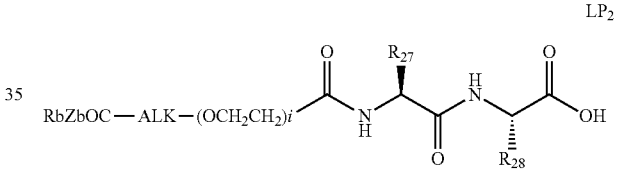

prepared according to the scheme below:

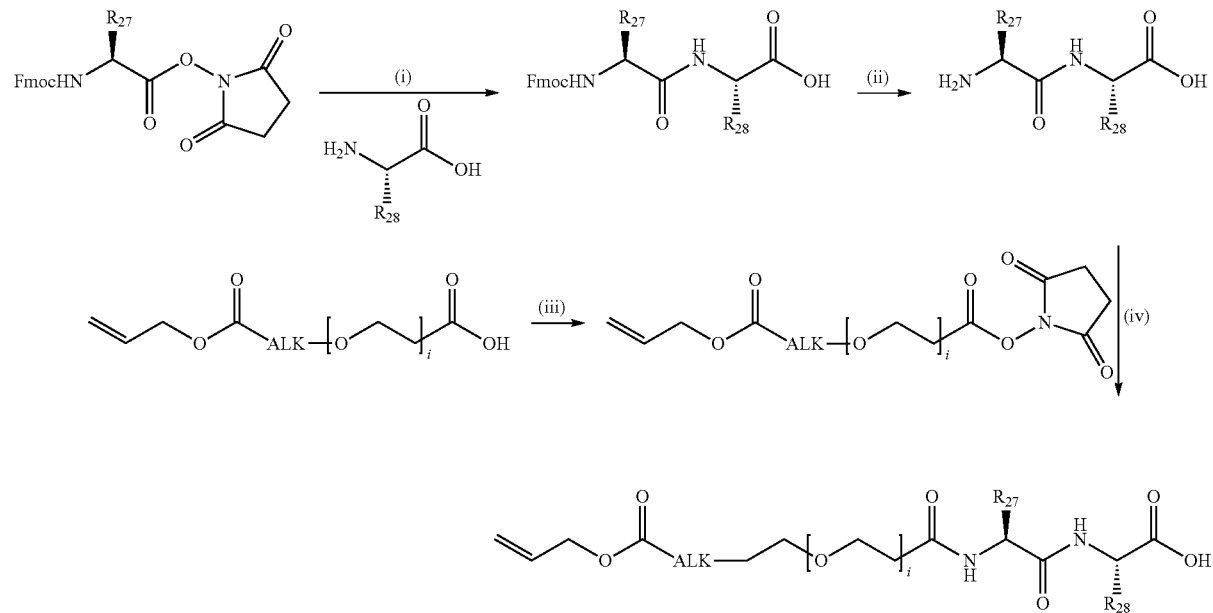

Step (i): peptide coupling between Fmoc-L-amino acid-ONHS and L-amino acid; the reaction is performed in a polar solvent such as a DME/THF/H$_2$O mixture in the presence of a base such as, for example, sodium bicarbonate;

Step (ii): deprotection of the amine; the reaction is performed in a polar solvent such as a DCM/MeOH mixture in the presence of a base such as, for example, piperidine;

Step (iii): activation of the carboxylic acid as a NHS ester; the reaction is performed in a polar aprotic solvent such as DCM by treatment with NHS in the presence of a coupling agent such as, for example, supported DCC;

Step (iv): peptide coupling between the dipeptide and the NHS ester; the reaction is performed in a polar aprotic solvent such as a DCM/CH$_3$CN mixture.

NHS esters of Fmoc-L-amino acids are commercially available; the PEG diacids monoprotected as allyl esters may be prepared according to the scheme below:

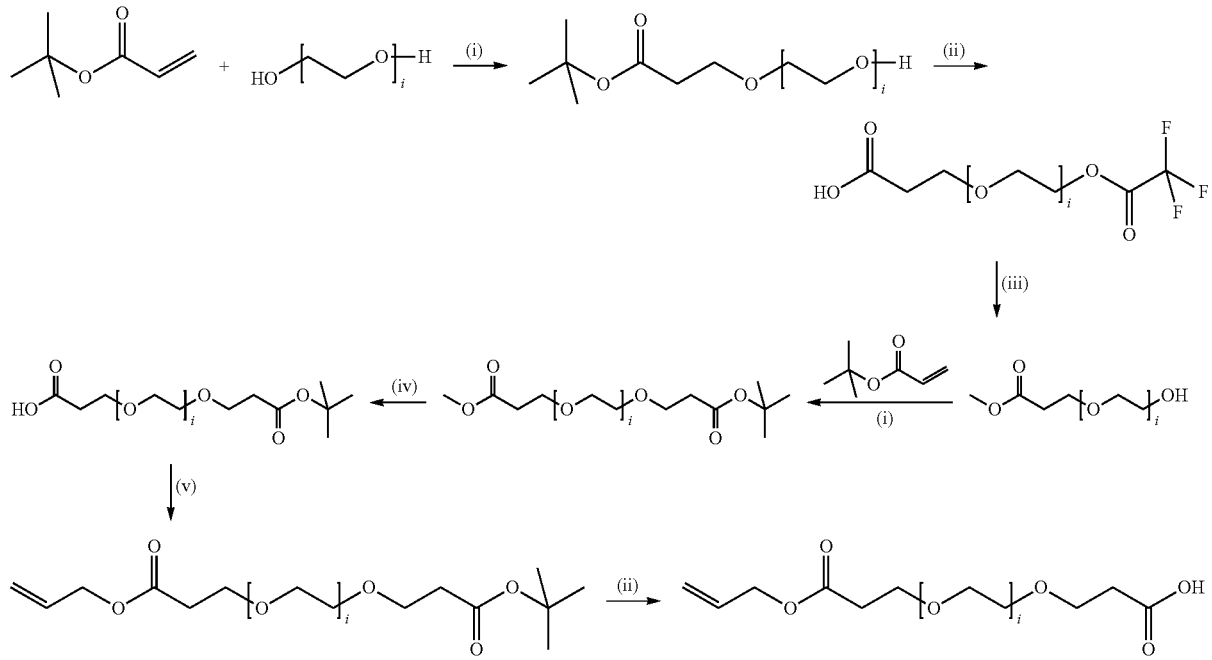

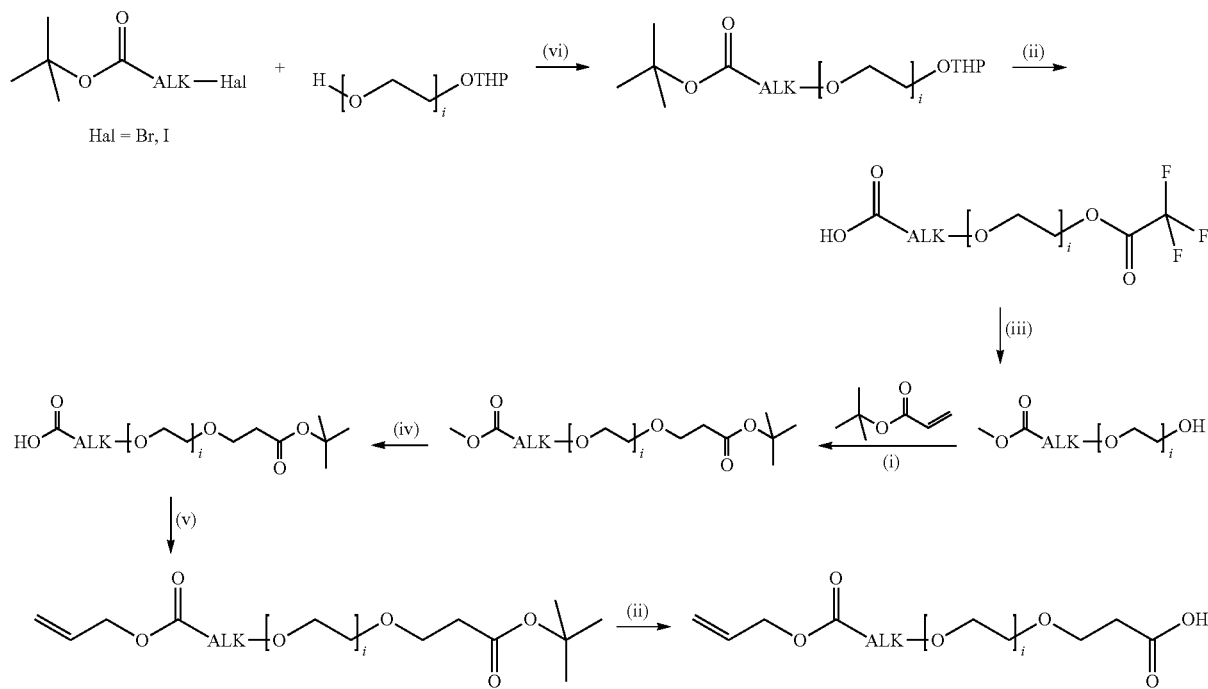

Step (i): elongation of the PEG chain; the reaction is performed in an anhydrous polar aprotic solvent such as THF or DMF by treatment of an unsaturated protected acid with the alkoxyde generated by the action of sodium in catalytic amount;

Step (ii): deprotection using a solution of hydrochloric acid (for example solution in dioxane) or of trifluoroacetic acid. In the latter case, trifluoroacetate of the alcohol function present on the structure may be formed. This trifluoroacetate is cleaved during the following step (iii);

Step (iii): protection of the carboxylic acid as a methyl ester; the reaction is performed in a polar aprotic solvent such as MeOH, by treatment with trimethylsilyldiazomethane;

Step (iv): saponification of the methyl ester; the reaction is performed in a mixture of polar solvents such as a THF/H$_2$O mixture in the presence of LiOH;

Step (v): protection of the carboxylic acid as an allyl ester; the reaction is performed in a polar aprotic solvent such as DCM in the presence of allyl alcohol, a coupling agent such as, for example, EDC and a base such as, for example, DMAP;

Step (vi): elongation of the PEG chain; the reaction is performed in an anhydrous polar aprotic solvent such as THF or DMF by treatment of a halogenated ester with the alkoxyde of the PEG diol monoprotected as a THP ether. The preparation of this type of monoprotected PEG diol is well described in the literature: see, for example, Richard A., et al., *Chem. Eur. J.* 2005, 11, 7315-7321 or Sakellariou E. G., et al., *Tetrahedron* 2003, 59, 9083-9090.

The starting PEG diols are commercially available for i=3 to 12.

LP$_3$

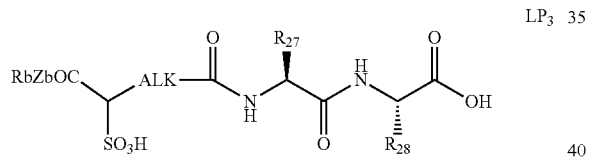

Step (i): peptide coupling between Fmoc-L-amino acid-ONHS and L-amino acid; the reaction is performed in a polar solvent such as a DME/THF/H$_2$O mixture in the presence of a base such as, for example, sodium bicarbonate;

Step (ii): deprotection of the amine; the reaction is performed in a polar solvent such as a DCM/MeOH mixture in the presence of a base such as, for example, piperidine;

Step (iii): activation of the carboxylic acid as a NHS ester; the reaction is performed in a polar solvent such as a mixture DMF/H$_2$O by treatment with N,N'-disuccinimidyl carbonate in the presence of a base such as, for example, DIEA;

Step (iv): peptide coupling between the dipeptide and the NHS ester; the reaction is performed at RT in a polar aprotic solvent such as a DCM/CH$_3$CN mixture.

NHS esters of Fmoc-L-amino acids are commercially available; the sulfo diacids monoprotected as allyl ester may be prepared according to the scheme below:

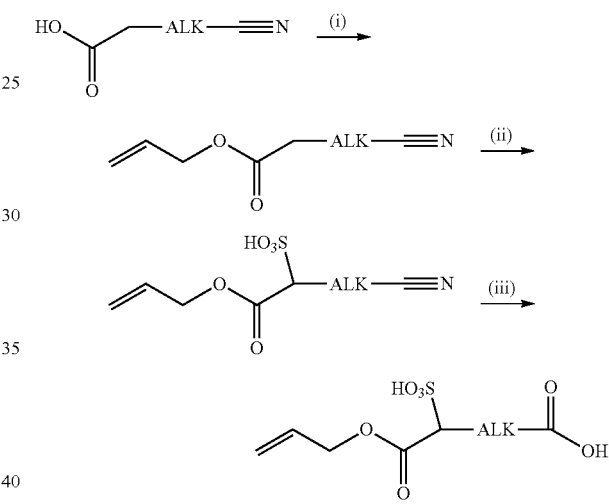

prepared according to the scheme below:

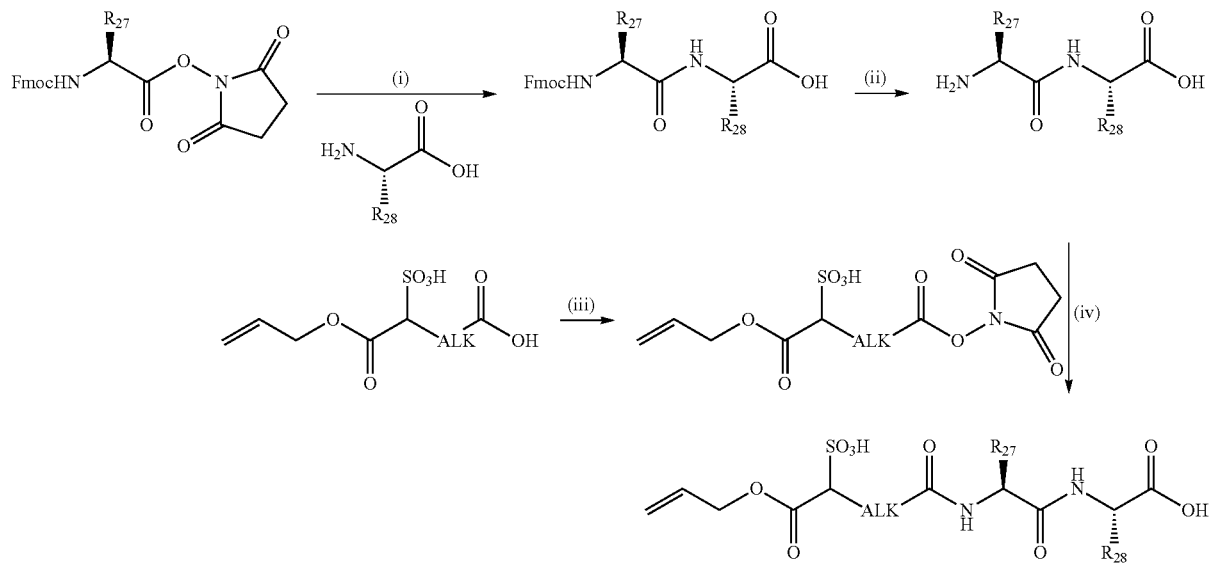

alternative when ALK=CH$_2$CH$_2$

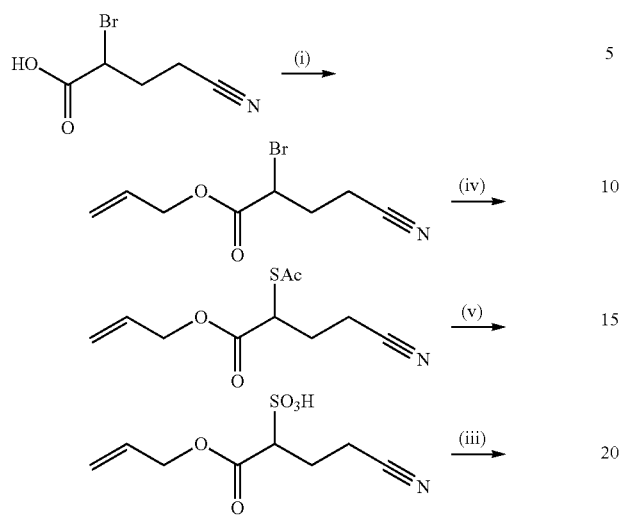

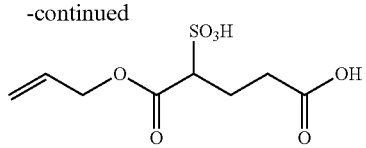

Step (i): protection of the carboxylic acid as an allyl ester; the reaction is performed in a polar aprotic solvent such as DCM in the presence of allyl alcohol, a coupling agent such as, for example, EDC and a base such as, for example, DMAP;

Step (ii): α-sulfonation of the carboxylic acid; the reaction is performed at 75° C. in a polar aprotic solvent like DCE by treatment with chlorosulfonic acid in the presence of a base such as, for example, DIEA.

Step (iii): formation of the carboxylic acid moiety; the reaction is performed by treatment with sodium hydroxide;

Step (iv): substitution of the bromide by a thioacetyle; the reaction is performed at −20° C. in a polar aprotic solvent such as THF using thioacetic acid in the presence of a base such as, for example, DIEA;

Step (v): formation of the sulfonic acid moiety; the reaction is performed at RT by treatment with hydrogen peroxide and acetic acid.

Cyano carboxylic acids are commercially available for n=1 to 12.

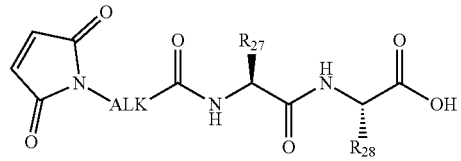

LP$_4$ prepared according to the scheme below:

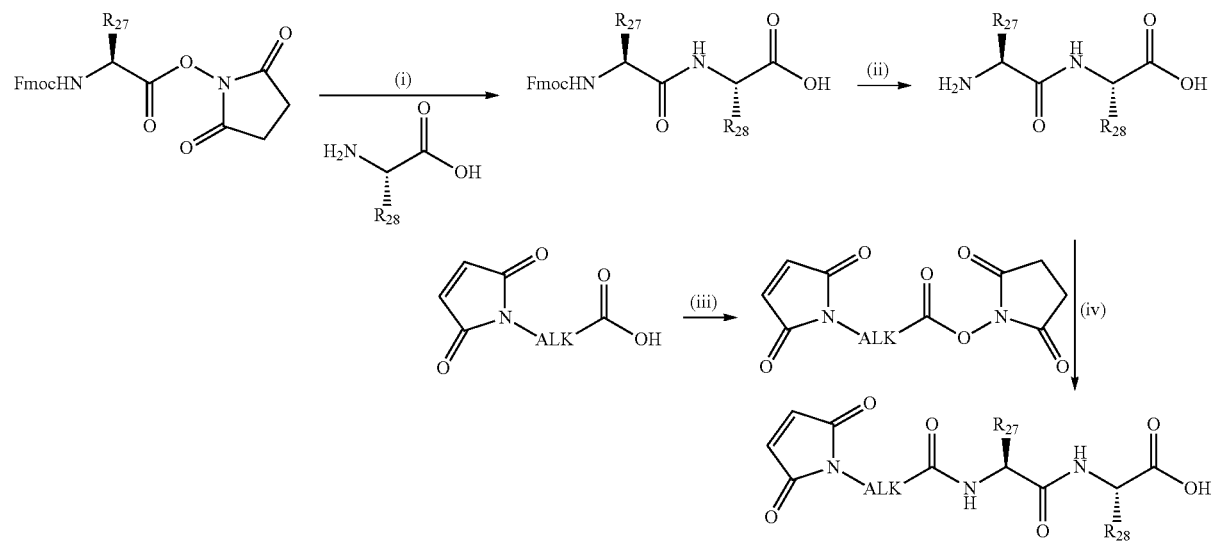

Step (i): peptide coupling between Fmoc-L-amino acid-ONHS and L-amino acid; the reaction is performed in a polar solvent such as a DME/THF/H$_2$O mixture in the presence of a base such as, for example, sodium bicarbonate;

Step (ii): deprotection of the amine; the reaction is performed in a polar solvent such as a DCM/MeOH mixture in the presence of a base such as, for example, piperidine;

Step (iii): activation of the carboxylic acid as a NHS ester; the reaction is performed in a polar aprotic solvent such as DCM by treatment with NHS in the presence of a coupling agent such as, for example, EDC;

Step (iv): peptide coupling between the dipeptide and the NHS ester; the reaction is performed in a polar aprotic solvent such as a DCM/CH$_3$CN mixture.

NHS esters of Fmoc-L-amino acids are commercially available; the maleimido carboxylic acids are commercially available for n=1 to 12.

LP$_5$

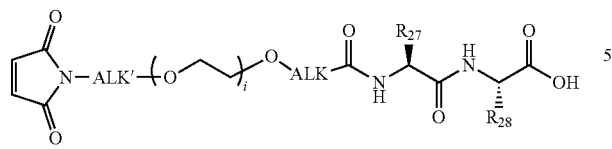

prepared according to the scheme below:

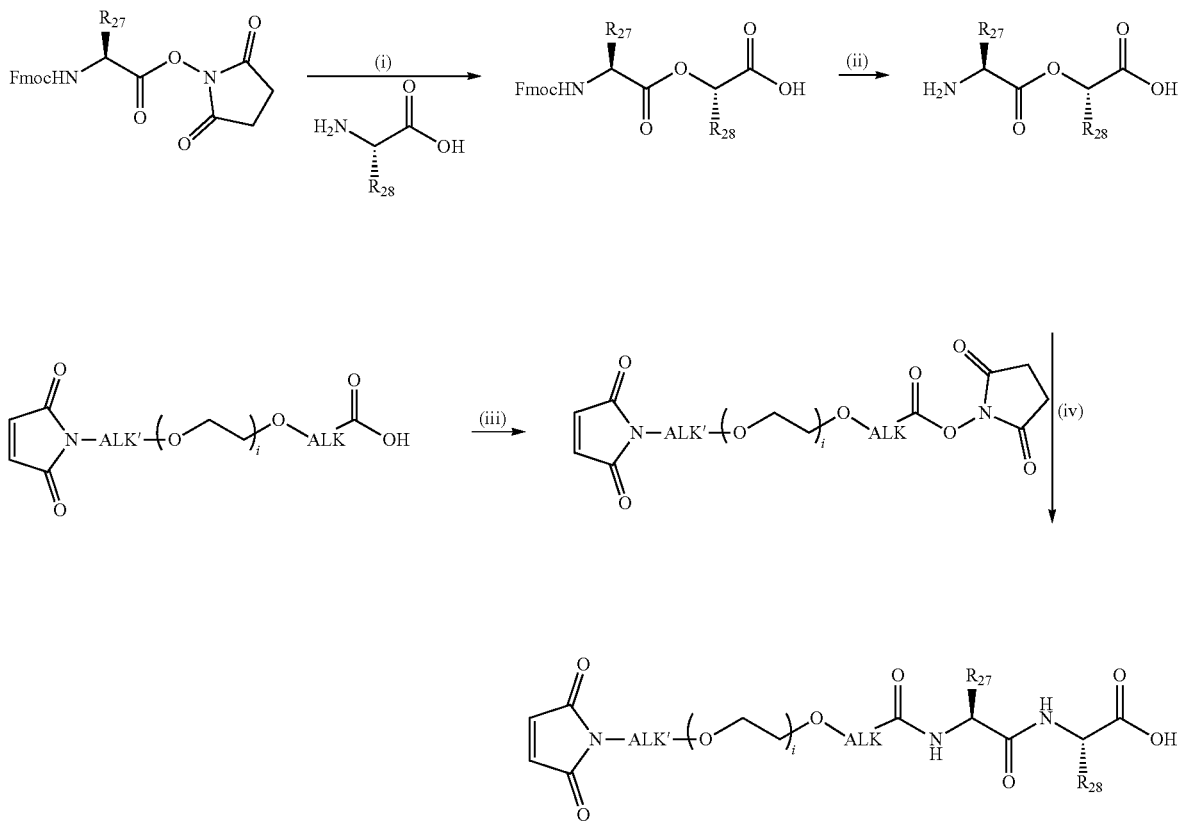

Step (i): peptide coupling between Fmoc-L-amino acid-ONHS and L-amino acid; the reaction is performed in a polar solvent such as a DME/THF/H$_2$O mixture in the presence of a base such as, for example, sodium bicarbonate;

Step (ii): deprotection of the amine; the reaction is performed in a polar solvent such as a DCM/MeOH mixture in the presence of a base such as, for example, piperidine;

Step (iii): activation of the carboxylic acid as a NHS ester; the reaction is performed in a polar aprotic solvent such as DCM by treatment with NHS in the presence of a coupling agent such as, for example, supported DCC;

Step (iv): peptide coupling between the dipeptide and the NHS ester; the reaction is performed in a polar aprotic solvent such as a DCM/CH$_3$CN mixture.

NHS esters of Fmoc-L-amino acids are commercially available; the maleimido acids are commercially available for ALK=ALK'=CH$_2$CH$_2$ and i=1 to 7 and may be otherwise prepared according to the scheme below:

when ALK = ALK' = CH$_2$CH$_2$ and i > 7

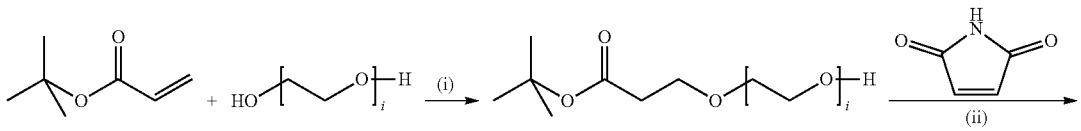

-continued
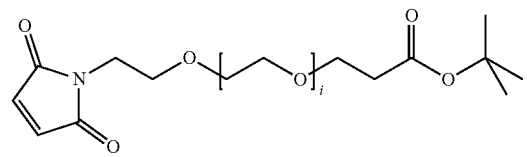
↓(iii)
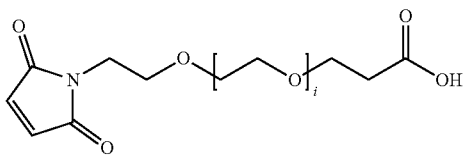
when ALK ≠ CH₂CH₂ and ALK' = CH₂CH₂
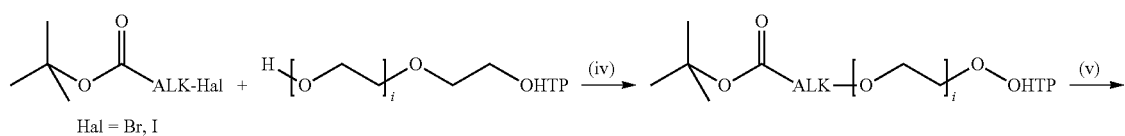
Hal = Br, I
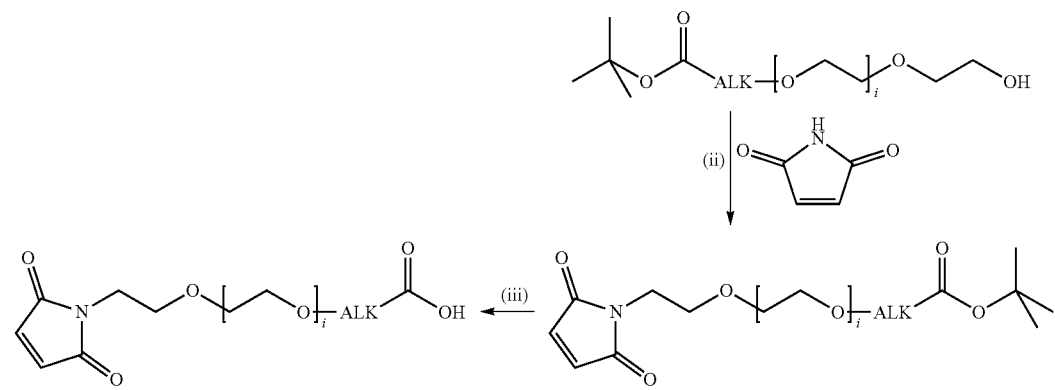
when ALK = CH₂CH₂ and ALK' ≠ CH₂CH₂
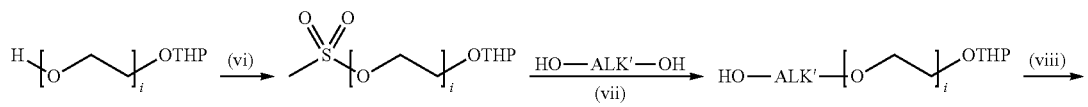
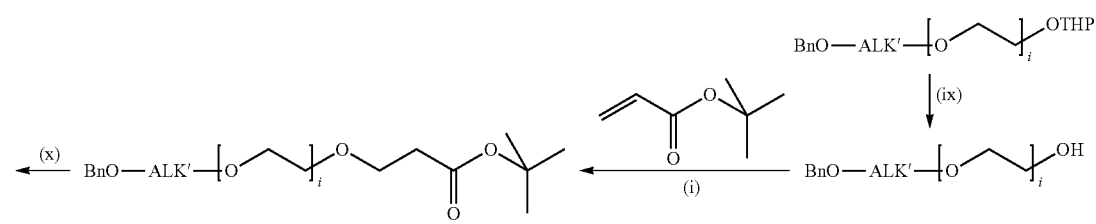

-continued
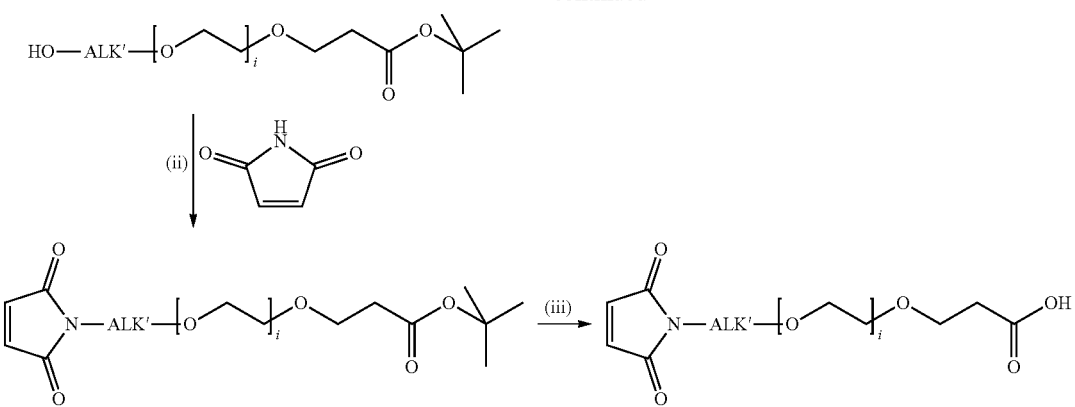
when ALK and ALK' ≠ CH$_2$CH$_2$
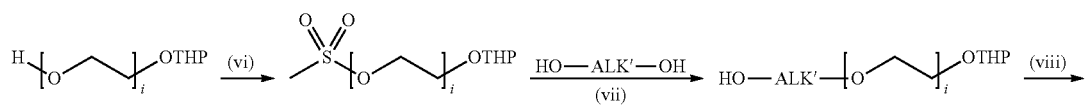
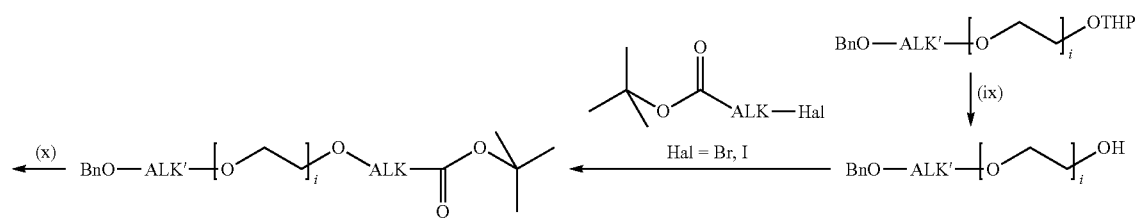
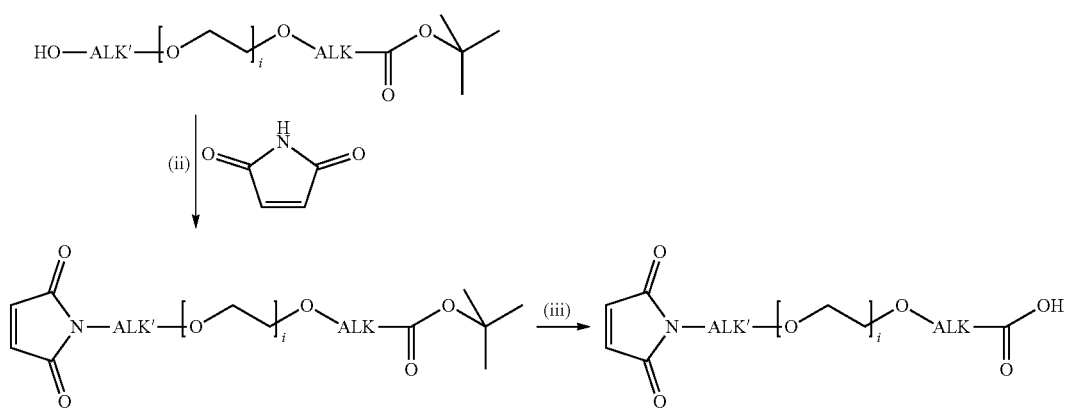

Step (i): elongation of the PEG chain; the reaction is performed in an anhydrous polar aprotic solvent such as THF or DMF by treatment of an unsaturated protected acid with the alkoxyde generated by the action of sodium in catalytic amount;

Step (ii): Mitsunobu reaction on maleimide; the reaction is performed in a polar aprotic solvent such as THF by treatment of maleimide by the PEG hydroxy acid in the presence of $PPh_3$ and DIAD;

Step (iii): deprotection using a solution of hydrochloric acid (for example solution in dioxane) or of trifluoroacetic acid;

Step (iv): elongation of the PEG chain; the reaction is performed in an anhydrous polar aprotic solvent such as THF or DMF by treatment of a halogenated ester with the alkoxyde of the PEG diol monoprotected as the THP ether. The preparation of this type of monoprotected PEG diol is well described in the literature: see, for example, Richard A., et al., *Chem. Eur. J.* 2005, 11, 7315-7321 or Sakellariou E. G., et al., *Tetrahedron* 2003, 59, 9083-9090;

Step (v): selective deprotection of THP ether; the reaction is performed in a polar protic solvent such as MeOH using a catalytic amount of acetyl chloride;

Step (vi): activation of the alcohol as a mesylate; the reaction is performed in a polar aprotic solvent such as DCM by treatment with methanesulfonyl chloride in the presence of a base such as, for example, TEA;

Step (vii): nucleophilic substitution; the reaction is performed in a polar aprotic solvent such as DMF in the presence of a base such as, for example, sodium hydride;

Step (viii): protection of the alcohol as a benzyl ether; the reaction is performed in a polar aprotic solvent such as THF by treatment with benzyl bromide in the presence of a base such as, for example, sodium hydride;

Step (ix): deprotection of the alcohol using a solution of hydrochloric acid (for example solution in dioxane);

Step (x): deprotection of the alcohol by hydrogenolysis in the presence of a catalyst such as, for example, palladium on carbon.

The starting PEG diols are commercially available for i=3 to 12. The starting ALK diols are commercially available for n=1 to 12.

$LP_6$

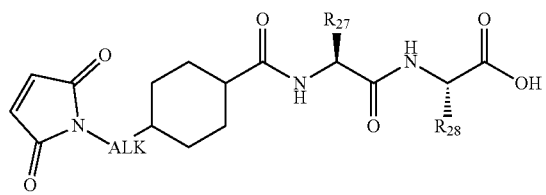

prepared according to the scheme below:

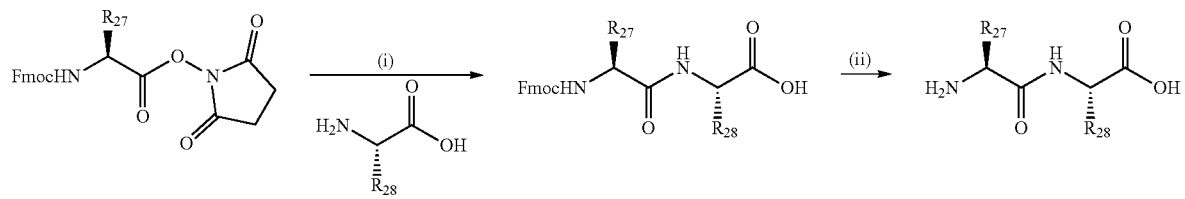

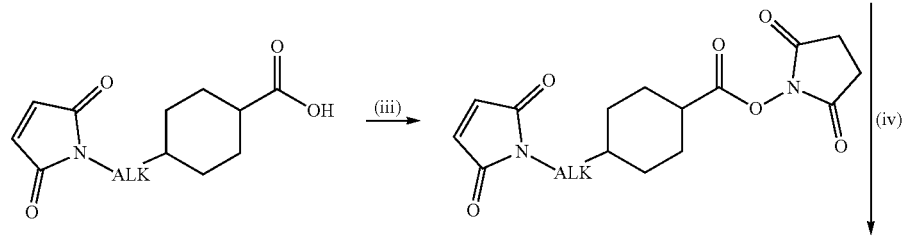

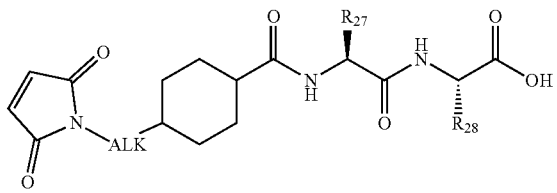

Step (i): peptide coupling between Fmoc-L-amino acid-ONHS and L-amino acid; the reaction is performed in a polar solvent such as a DME/THF/H$_2$O mixture in the presence of a base such as, for example, sodium bicarbonate;

Step (ii): deprotection of the amine; the reaction is performed in a polar solvent such as a DCM/MeOH mixture in the presence of a base such as, for example, piperidine;

Step (iii): activation of the carboxylic acid as a NHS ester; the reaction is performed in a polar solvent such as a mixture DMF/H$_2$O by treatment with N,N'-disuccinimidyl carbonate in the presence of a base such as, for example, DIEA;

Step (iv): peptide coupling between the dipeptide and the NHS ester; the reaction is performed in a polar aprotic solvent such as a DCM/CH$_3$CN mixture.

NHS esters of Fmoc-L-amino acids are commercially available; the maleimido cyclohexanecarboxylic acid is commercially available for ALK=CH$_2$ and may be otherwise prepared according to the scheme below:

Step (iv): deprotection of the amine; the reaction is performed by hydrogenolysis in a polar protic solvent such as MeOH in the presence of a catalyst such as, for example, palladium;

Step (v): introduction of the maleimido moiety; the reaction is performed in a polar aprotic solvent such as DMF by treatment with maleic anhydride in the presence of NHS and a coupling reagent such as, for example, EDC;

Step (vi): deprotection using a solution of hydrochloric acid (for example solution in dioxane) or of trifluoroacetic acid;

Step (vii): palladium-catalyzed coupling; the reaction is performed in a polar aprotic solvent such as THF by treatment with the bromo-ALK-cyano derivative in the presence of lithium chloride, zinc and trimethylchlorosilane and a catalyst such as, for example, tetrakis(triphenylphosphine)palladium.

When n = 2 to 4

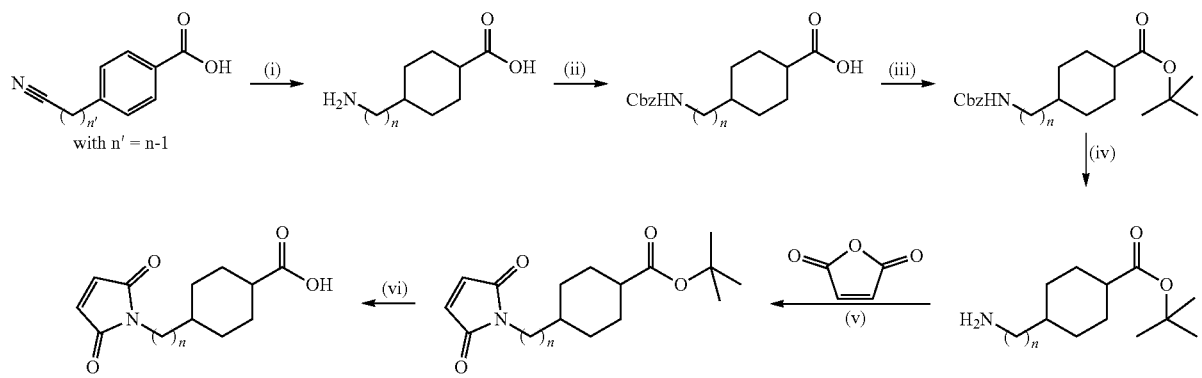

When n > 4

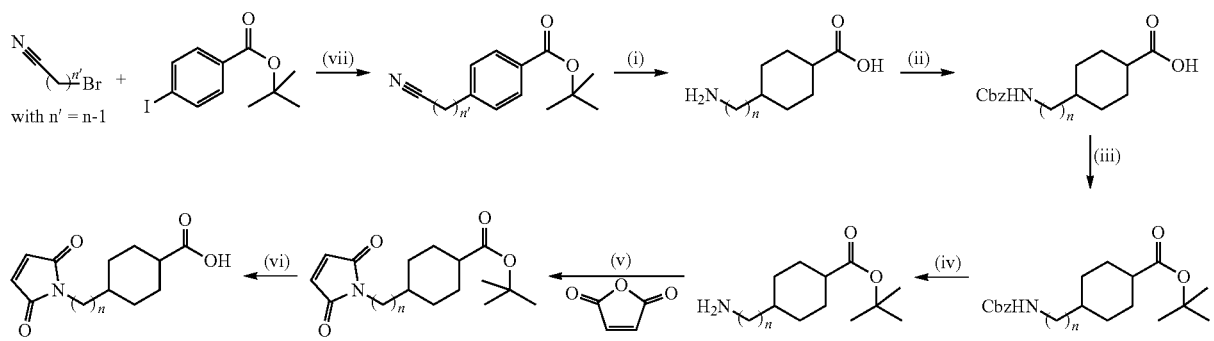

Step (i): hydrogenation; the reaction is performed at 60° C. in acetic acid in the presence of a catalyst such as platinum oxide under pressure of hydrogen, for example 60 psi;

Step (ii): protection of the amine; the reaction is performed in a polar protic solvent such as a dioxane/H$_2$O mixture by treatment with benzylchloroformate in the presence of a base such as, for example, NaOH;

Step (iii): protection of the carboxylic acid; the reaction is performed in a polar aprotic solvent such as DCM by treatment with tert-butanol in the presence of a coupling reagent such as, for example, EDC and a base such as, for example, DMAP;

The suitable bromo-ALK-cyano derivatives are commercially available for n=1 to 12.

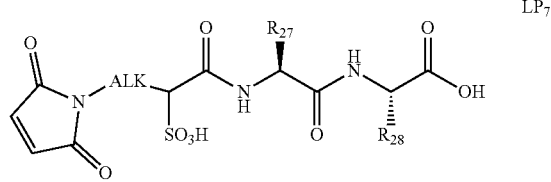

LP$_7$ prepared according to the scheme below:

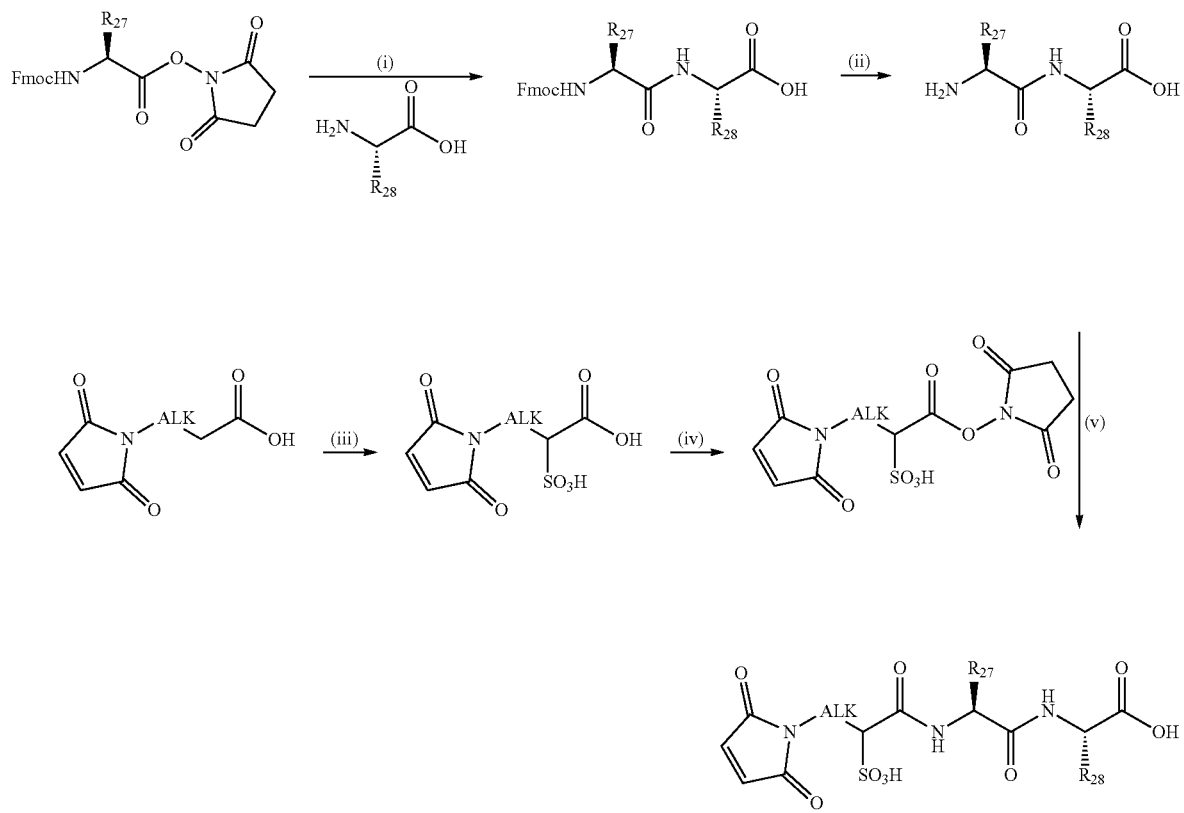

Step (i): peptide coupling between Fmoc-L-amino acid-ONHS and L-amino acid; the reaction is performed in a polar solvent such as a DME/THF/H$_2$O mixture in the presence of a base such as, for example, sodium bicarbonate;

Step (ii): deprotection of the amine; the reaction is performed in a polar solvent such as a DCM/MeOH mixture in the presence of a base such as, for example, piperidine;

Step (iii): α-sulfonation of the carboxylic acid; the reaction is performed at 75° C. in a polar aprotic solvent like DCE by treatment with chlorosulfonic acid in the presence of a base such as, for example, DIEA;

Step (iv): activation of the carboxylic acid as a NHS ester; the reaction is performed at RT in a polar solvent such as a mixture DMF/H$_2$O by treatment with N,N'-disuccinimidyl carbonate in the presence of a base such as, for example, DIEA;

Step (v): peptide coupling between the dipeptide and the NHS ester; the reaction is performed at RT in a polar aprotic solvent such as a DCM/CH$_3$CN mixture.

NHS esters of Fmoc-L-amino acids are commercially available; the maleimido acids are commercially available for n=1 to 12.

LP$_8$

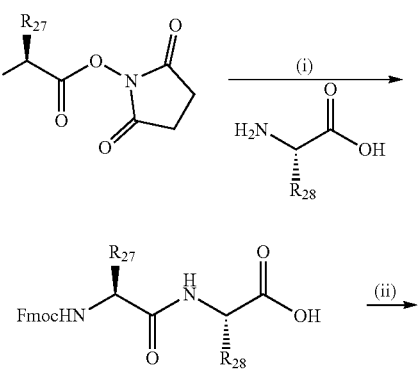

prepared according to the scheme below:

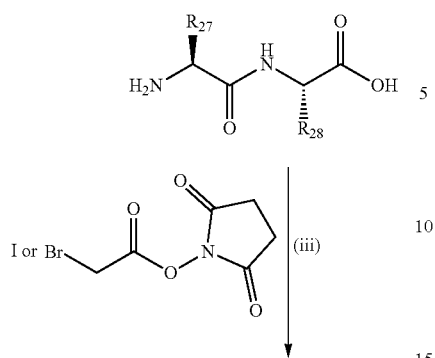

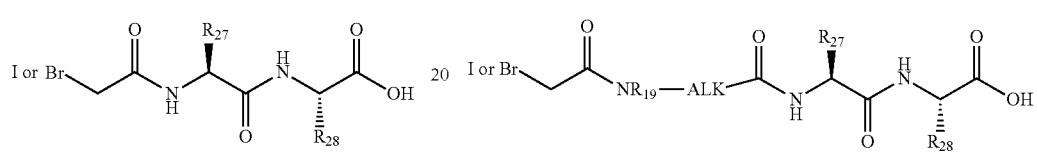

Step (i): peptide coupling between Fmoc-L-amino acid-ONHS and L-amino acid; the reaction is performed in a polar solvent such as a DME/THF/H₂O mixture in the presence of a base such as, for example, sodium bicarbonate;

Step (ii): deprotection of the amine; the reaction is performed in a polar solvent such as a DCM/MeOH mixture in the presence of a base such as, for example, piperidine;

Step (iii): peptide coupling between the dipeptide and the NHS ester; the reaction is performed in a polar aprotic solvent such as a DCM/CH₃CN mixture.

NHS esters of Fmoc-L-amino acids are commercially available; N-succinimidyl bromo- and iodo-acetates are commercially available.

LP₉ prepared according to the scheme below:

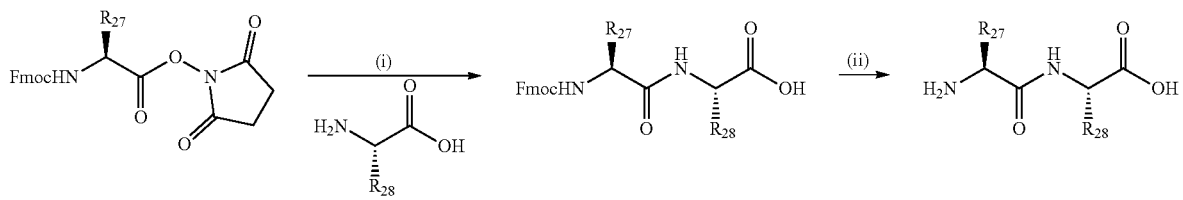

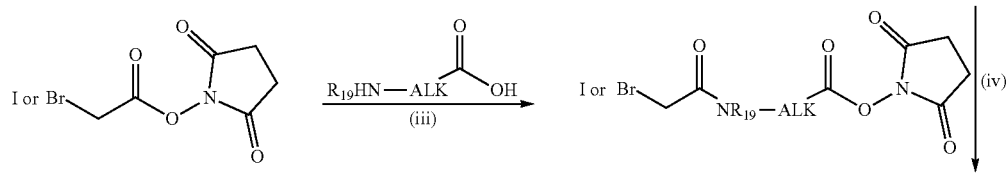

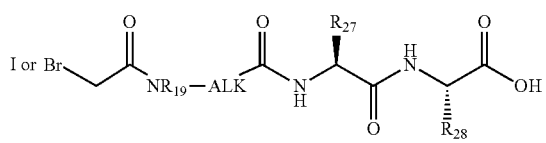

Step (i): peptide coupling between Fmoc-L-amino acid-ONHS and L-amino acid; the reaction is performed in a polar solvent such as a DME/THF/H$_2$O mixture in the presence of a base such as, for example, sodium bicarbonate;

Step (ii): deprotection of the amine; the reaction is performed in a polar solvent such as a DCM/MeOH mixture in the presence of a base such as, for example, piperidine;

Step (iii): coupling and activation of the carboxylic acid as a NHS ester; the coupling of N-succinimidyl bromo- and iodo-acetate with the amino carboxylic acid is performed at RT in a polar aprotic solvent such as a DCM/DMF mixture followed by the addition of N,N'-disuccinimidyl carbonate and a base, such as, for example, DIEA;

Step (iv): peptide coupling between the dipeptide and the NHS ester; the reaction is performed in a polar aprotic solvent such as a DCM/CH$_3$CN mixture.

NHS esters of Fmoc-L-amino acids are commercially available; N-succinimidyl bromo- and iodo-acetates are commercially available, the amino carboxylic acids also for n=1 to 12 and the N-methylated amino carboxylic acids for n=1 to 7.

LP$_{10}$

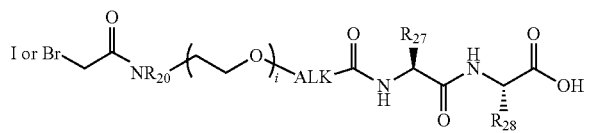

prepared according to the scheme below:

Step (i): peptide coupling between Fmoc-L-amino acid-ONHS and L-amino acid; the reaction is performed in a polar solvent such as a DME/THF/H$_2$O mixture in the presence of a base such as, for example, sodium bicarbonate;

Step (ii): deprotection of the amine; the reaction is performed in a polar solvent such as a DCM/MeOH mixture in the presence of a base such as, for example, piperidine;

Step (iii): coupling and activation of the carboxylic acid as a NHS ester; the coupling of N-succinimidyl bromo- and iodo-acetate with the amino carboxylic acid is performed in a polar aprotic solvent such as a DCM/DMF mixture followed by the addition of N,N'-disuccinimidyl carbonate and a base such as, for example, DIEA;

Step (iv): peptide coupling between the dipeptide and the NHS ester; the reaction is performed in a polar aprotic solvent such as a DCM/CH$_3$CN mixture.

NHS esters of Fmoc-L-amino acids are commercially available; N-succinimidyl bromo- and iodo-acetate are commercially available; in the case where ALK=CH$_2$CH$_2$ and R$_{20}$=H, the amino PEG carboxylic acids are commercially available for i=1 to 6 and otherwise may be prepared from tert-butyl acrylate and the corresponding amino-PEG-alco

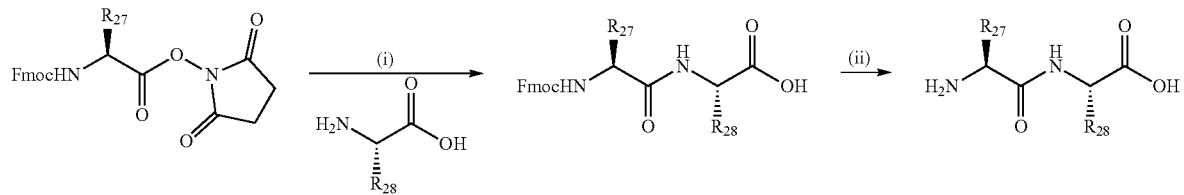

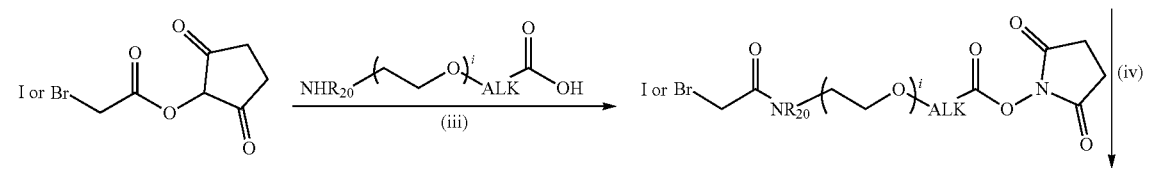

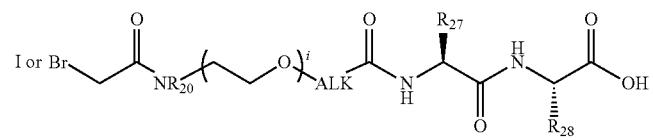

hol; in the case where ALK≠CH$_2$CH$_2$, they may be prepared according to the schemes below:
in the case where ALK=CH$_2$CH$_2$ and R$_{20}$H
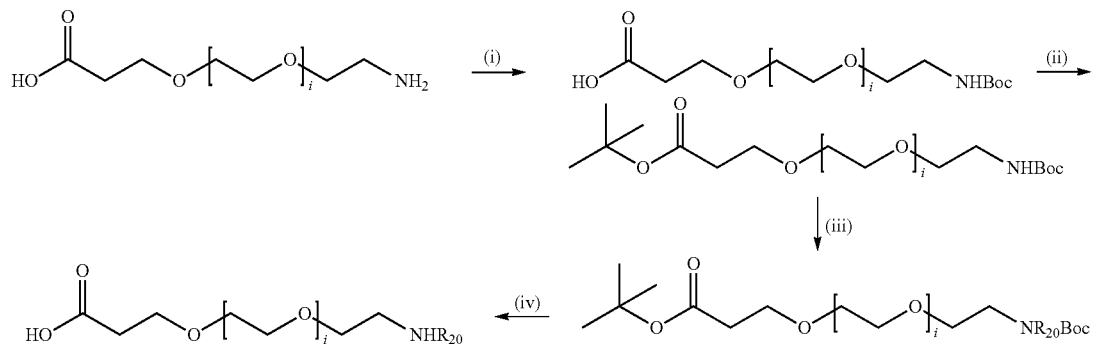
in the case where ALK≠CH$_2$CH$_2$
in the case where R$_{20}$≠H
-continued
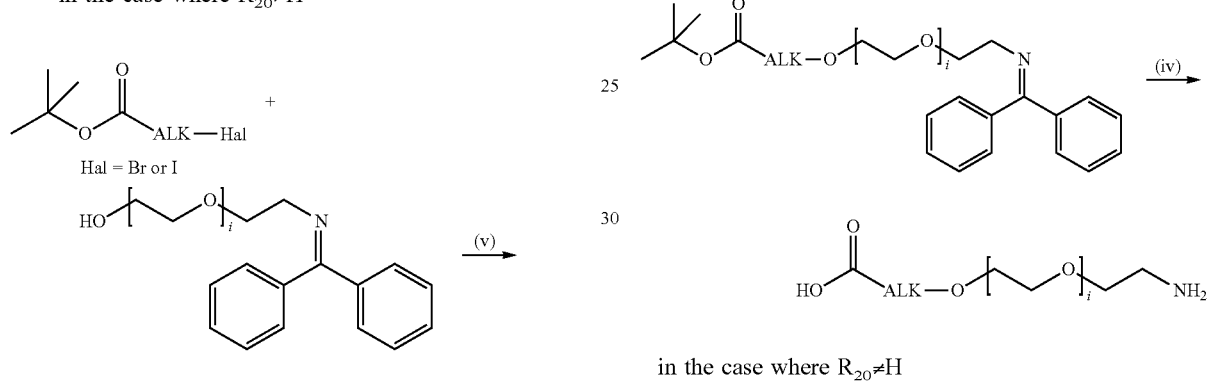
in the case where R$_{20}$≠H
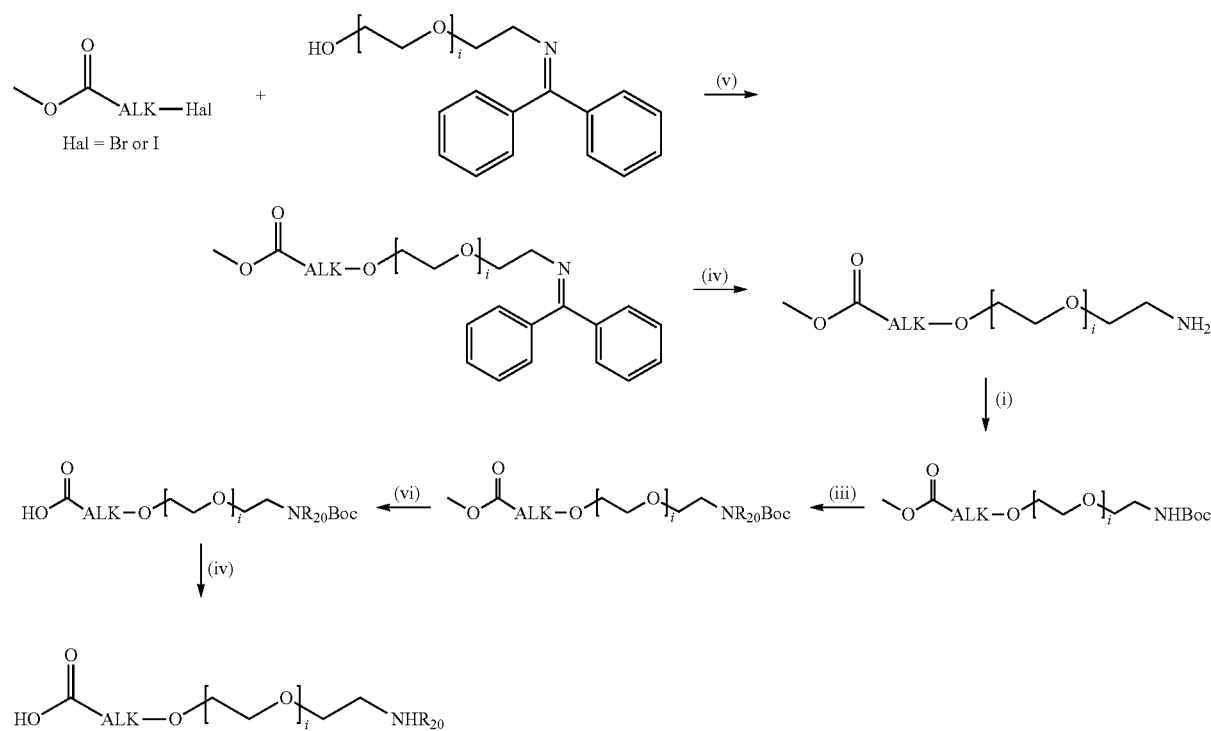

Step (i): protection of the amine; the reaction is performed in a polar aprotic solvent such as DCM by treating the amine with di-tert-butyl dicarbonate in the presence of a base such as, for example, TEA;

Step (ii): protection of the carboxylic acid; the reaction is performed in a polar aprotic solvent such as DCM by treatment with tert-butanol in the presence of a coupling reagent such as, for example, EDC and a base such as, for example, DMAP;

Step (iii): alkylation of the nitrogen atom; the reaction is performed in an anhydrous polar aprotic solvent such as THF by treatment with a base such as sodium hydride in the presence of a reagent bearing a leaving group such as a halide;

Step (iv): deprotection using a solution of hydrochloric acid (for example solution in dioxane) or of trifluoroacetic acid;

Step (v): elongation of the PEG chain; the reaction is performed in an anhydrous polar aprotic solvent such as THF or DMF by treatment of a halogenated ester with the alkoxyde of a benzophenone-imine-PEG-alcohol generated via the action of sodium hydride or potassium naphthalenide as described in WO2007/127440;

Step (vi): saponification of the ester; the reaction is performed by reacting the ester with LiOH in the presence of $H_2O$.

The amino-PEG-alcohols are commercially available, for example for i=3, 4, 7, 8 or may be prepared from the PEG diols, which are commercially available for i=3 to 12, according to the procedure described in U.S. Pat. No. 7,230,101. The protection of the amine function with benzophenone may be performed by azeotropic dehydration in the presence of a Lewis acid such as $BF_3$ etherate.

$LP_{11}$

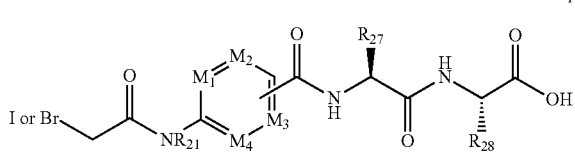

prepared according to the scheme below:

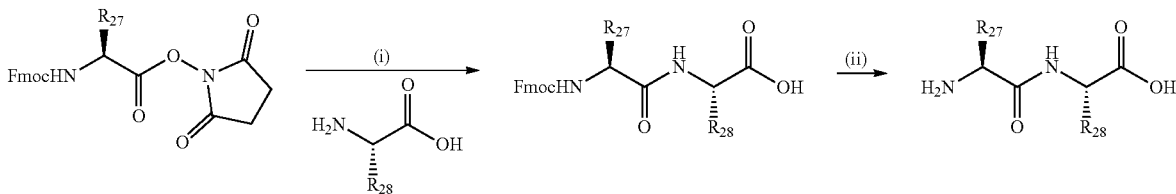

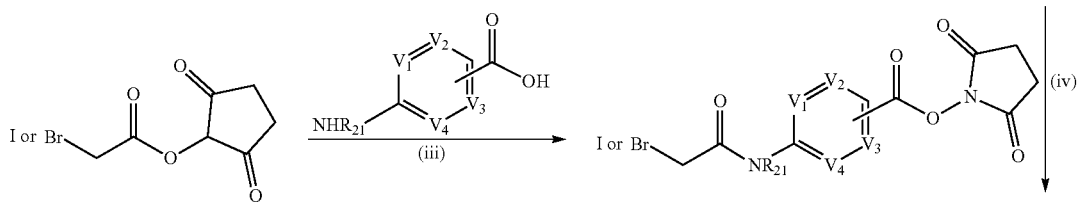

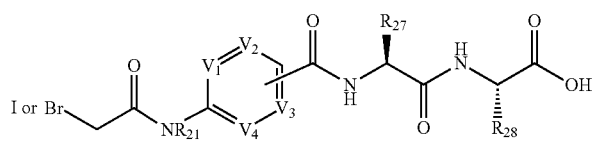

Step (i): peptide coupling between Fmoc-L-amino acid-NHS and L-amino acid; the reaction is performed in a polar solvent such as a DME/THF/H₂O mixture in the presence of a base such as, for example, sodium bicarbonate;

Step (ii): deprotection of the amine Fmoc; the reaction is performed in a polar solvent such as a DCM/MeOH mixture in the presence of a base such as, for example, piperidine;

Step (iii): coupling and activation of the carboxylic acid as a NHS ester; the coupling of N-succinimidyl bromo- and iodo-acetate with the amino carboxylic acid is performed at RT in a polar aprotic solvent such as a DCM/DMF mixture followed by the addition of N,N'-disuccinimidyl carbonate and a base such as, for example, DIEA;

Step (iv): peptide coupling between the dipeptide and the NHS ester; the reaction is performed at RT in a polar aprotic solvent such as a DCM/CH₃CN mixture.

NHS esters of Fmoc-L-amino acids are commercially available; N-succinimidyl bromo- and iodo-acetate are commercially available; the amino-(hetero)aryl-carboxylic acids are commercially available, like for example 4-amino-2-benzoic acid, 6-amino-3-pyridine carboxylic acid, 5-amino-2-pyrazine carboxylic acid, 2-amino-5-pyrimidine carboxylic acid or 6-amino-1,2,4,5-tetrazine carboxylic acid.

Step (i): peptide coupling between Fmoc-L-amino acid-ONHS and L-amino acid; the reaction is performed in a polar solvent such as a DME/THF/H₂O mixture in the presence of a base such as, for example, sodium bicarbonate;

Step (ii): deprotection of the amine; the reaction is performed in a polar solvent such as a DCM/MeOH mixture in the presence of a base such as, for example, piperidine;

Step (iii): activation of the carboxylic acid as a NHS ester; the reaction is performed in a polar aprotic solvent such as DCM by treatment with NHS in the presence of a coupling agent such as, for example, EDC;

Step (iv): peptide coupling between the dipeptide and the NHS ester; the reaction is performed in a polar aprotic solvent such as a DCM/CH₃CN mixture.

NHS esters of Fmoc-L-amino acids are commercially available; the amino carboxylic acids are commercially available for n=1 to 11.

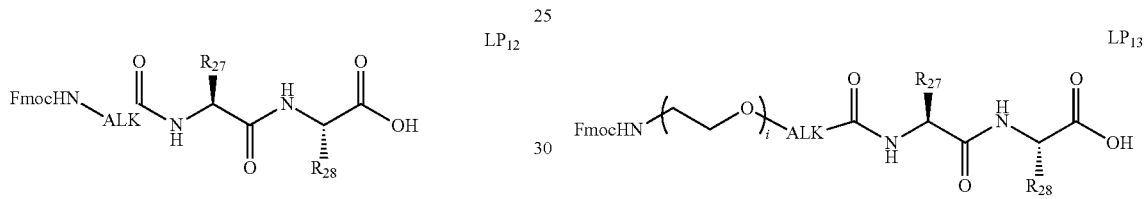

prepared according to the scheme below:

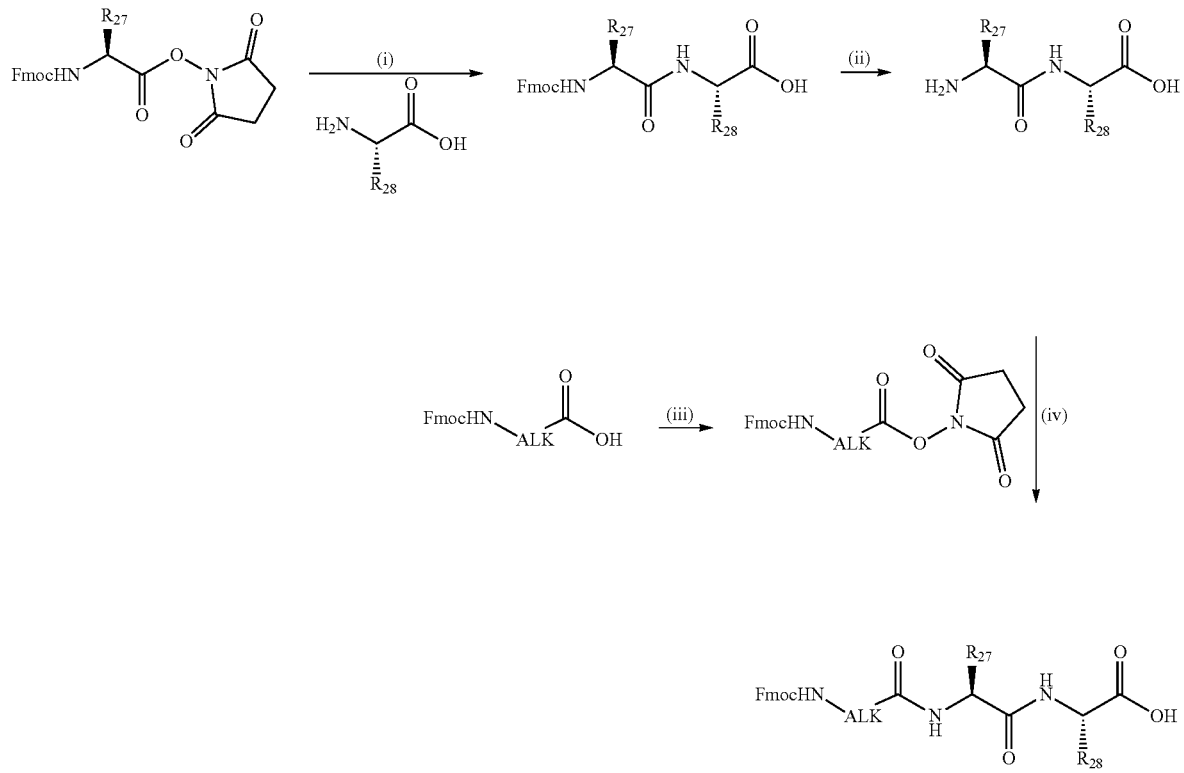

prepared according to the scheme below:

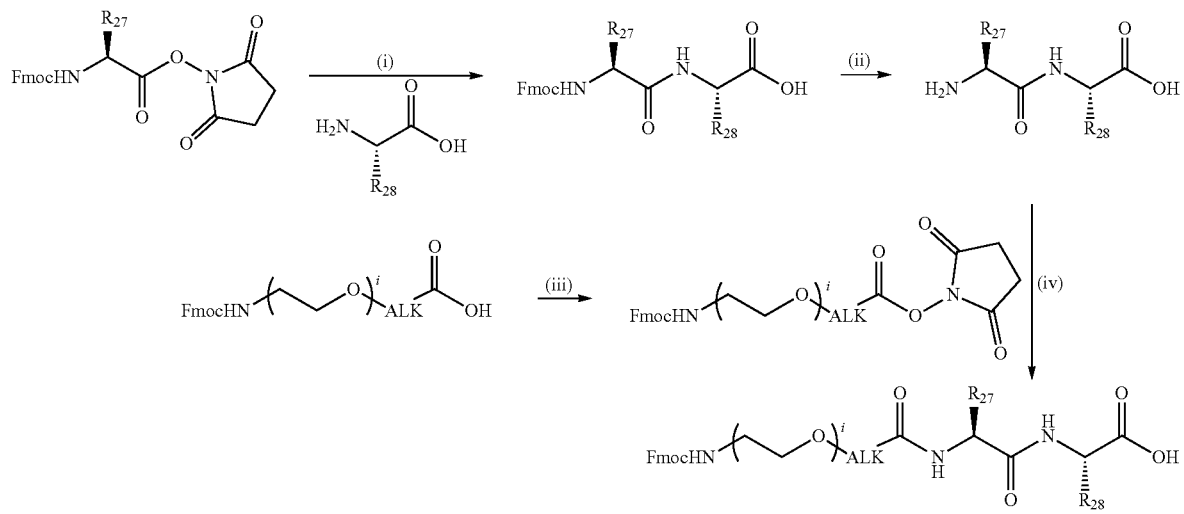

Step (i): peptide coupling between Fmoc-L-amino acid-ONHS and L-amino acid; the reaction is performed in a polar solvent such as a DME/THF/H$_2$O mixture in the presence of a base such as, for example, sodium bicarbonate;

Step (ii): deprotection of the amine; the reaction is performed in a polar solvent such as a DCM/MeOH mixture in the presence of a base such as, for example, piperidine;

Step (iii): activation of the carboxylic acid as a NHS ester; the reaction is performed in a polar aprotic solvent such as DCM by treatment with NHS in the presence of a coupling agent such as, for example, supported DCC;

Step (iv): peptide coupling between the dipeptide and the NHS ester; the reaction is performed in a polar aprotic solvent such as a DCM/CH$_3$CN mixture.

NHS ester of Fmoc-L-amino acids are commercially available; in the case where ALK=CH$_2$CH$_2$, Fmoc-protected amino PEG carboxylic acids are commercially available for i=1 to 6 and otherwise may be prepared from tert-butyl acrylate and the corresponding amino-PEG-alcohol; in the case where ALK≠CH$_2$CH$_2$, they may be prepared according to the schemes described for linker precursor LP$_{10}$. Protection of the amine function with a Fmoc group may be realized by treatment with FmocOSu (CAS number [82911-69-1]) in the presence of a base such as, for example, DIEA.

LP$_{14}$

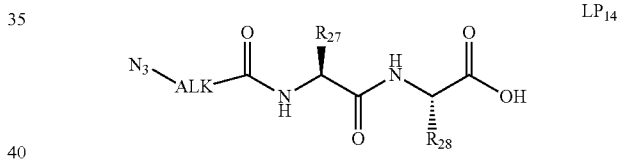

prepared according to the scheme below:

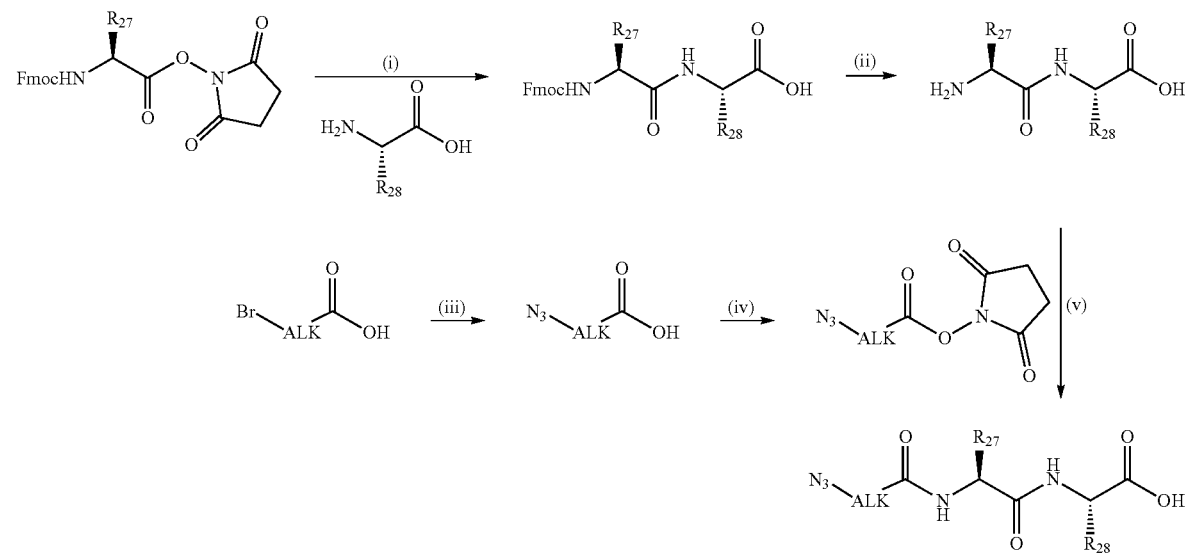

Step (i): peptide coupling between Fmoc-L-amino acid-ONHS and L-amino acid; the reaction is performed in a polar solvent such as a DME/THF/H$_2$O mixture in the presence of a base such as, for example, sodium bicarbonate;

Step (ii): deprotection of the amine; the reaction is performed in a polar solvent such as a DCM/MeOH mixture in the presence of a base such as, for example, piperidine;

Step (iii): introduction of the azido group; the reaction is performed in a polar solvent such as an acetone/H$_2$O mixture by treatment with sodium azide;

Step (iv): activation of the carboxylic acid as a NHS ester; the reaction is performed in a polar aprotic solvent such as DCM by treatment with NHS in the presence of a coupling agent such as, for example, EDC;

Step (v): peptide coupling between the dipeptide and the NHS ester; the reaction is performed in a polar aprotic solvent such as a DCM/CH$_3$CN mixture.

NHS esters of Fmoc-L-amino acids are commercially available; bromo carboxylic acids are commercially available for n=1 to 11.

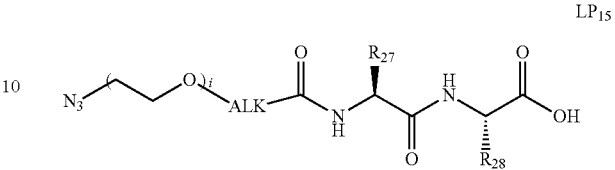

prepared according to the scheme below:

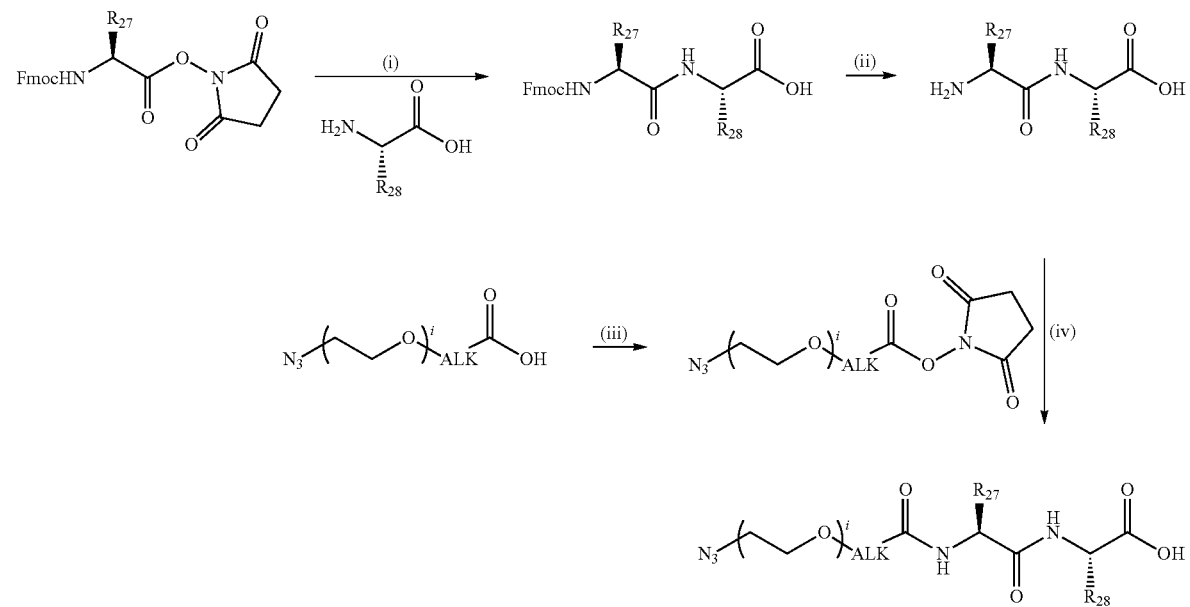

Step (i): peptide coupling between Fmoc-L-amino acid-ONHS and L-amino acid; the reaction is performed in a polar solvent such as a DME/THF/H$_2$O mixture in the presence of a base such as, for example, sodium bicarbonate;

Step (ii): deprotection of the amine; the reaction is performed in a polar solvent such as a DCM/MeOH mixture in the presence of a base such as, for example, piperidine;

Step (iii): activation of the carboxylic acid as a NHS ester; the reaction is performed in a polar aprotic solvent such as DCM by treatment with NHS in the presence of a coupling agent such as, for example, supported DCC;

Step (iv): peptide coupling between the dipeptide and the NHS ester; the reaction is performed in a polar aprotic solvent such as a DCM/CH$_3$CN mixture.

NHS esters of Fmoc-L-amino acids are commercially available; azido PEG acids may be prepared according to the schemes below:

when ALK=CH$_2$CH$_2$

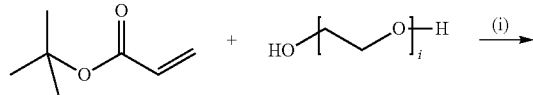

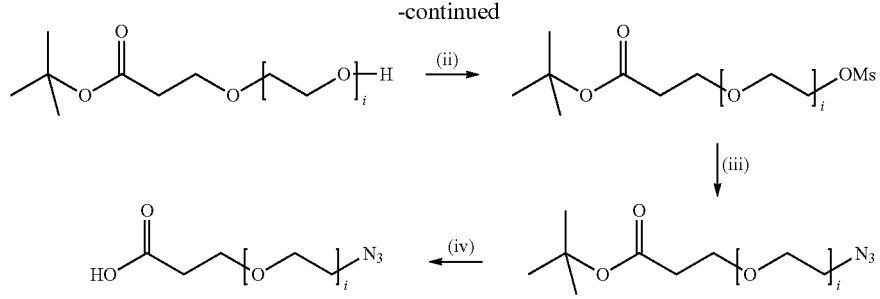

when ALK≠CH₂CH₂

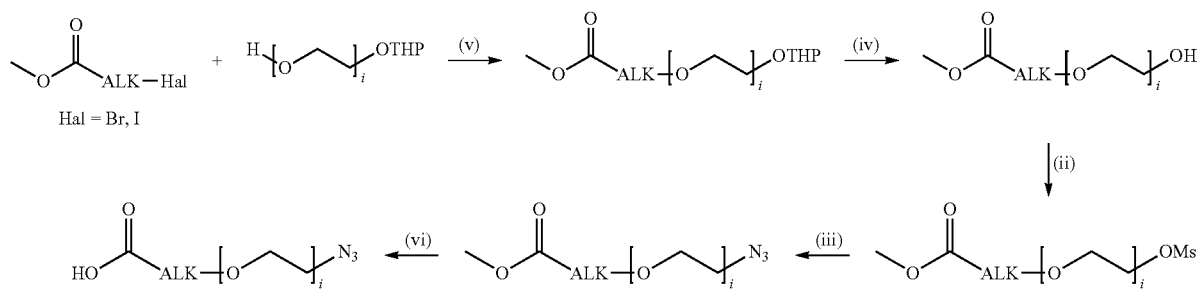

Step (i): elongation of the PEG chain; the reaction is performed in an anhydrous polar aprotic solvent such as THF or DMF by treatment of an unsaturated protected acid with the alkoxyde generated by the action of sodium in catalytic amount;

Step (ii): activation of the alcohol function; the reaction is performed in a polar solvent such as DCM using methanesulfonyl chloride in the presence of a base such as, for example, TEA;

Step (iii): substitution of the mesylate by an azido group; the reaction is performed in a polar solvent such as an acetone/H₂O mixture by treatment with sodium azide;

Step (iv): deprotection using a solution of hydrochloric acid (for example solution in dioxane);

Step (v): elongation of the PEG chain; the reaction is performed in an anhydrous polar aprotic solvent such as THF or DMF by treatment of a halogenated ester with the alkoxyde of the PEG diol monoprotected as a THP ether, alkoxyde generated for example with sodium hydride. The preparation of this type of monoprotected PEG diol is well described in the literature:

see, for example, Richard A. et al. *Chem. Eur. J.* 2005, 11, 7315-7321 or Sakellariou E. G., et al. *Tetrahedron* 2003, 59, 9083-9090;

Step (vi): saponification of the methyl ester; the reaction is performed at RT in a mixture of polar solvents such as a THF/H₂O mixture in the presence of LiOH.

The starting PEG diols are commercially available for i=3 to 12; the bromo methyl esters are commercially available for n=1 to 12.

$LP_{16}$

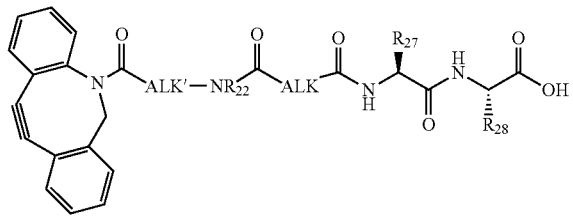

prepared according to the scheme below:

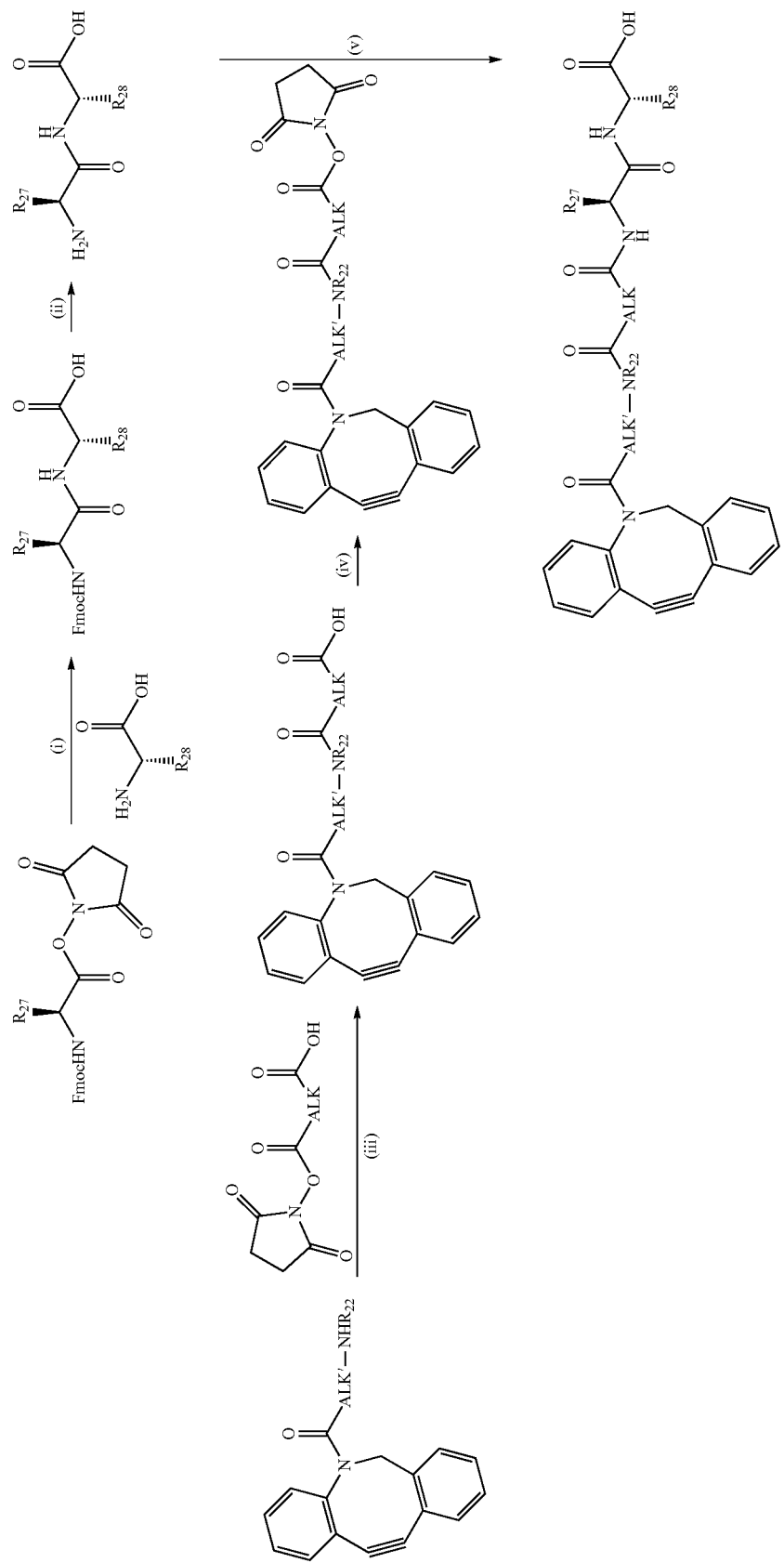

Step (i): peptide coupling between Fmoc-L-amino acid-ONHS and L-amino acid; the reaction is performed in a polar solvent such as a DME/THF/H$_2$O mixture in the presence of a base such as, for example, sodium bicarbonate;

Step (ii): deprotection of the amine; the reaction is performed in a polar solvent such as a DCM/MeOH mixture in the presence of a base such as, for example, piperidine;

Step (iii): cyclooctyne coupling; the reaction is performed in a polar solvent such as DCM;

Step (iv): activation of the carboxylic acid as a NHS ester; the reaction is performed in a polar aprotic solvent such as DCM by treatment with NHS in the presence of a coupling agent such as, for example, EDC;

Step (v): peptide coupling between the dipeptide and the NHS ester; the reaction is performed in a polar aprotic solvent such as DCM.

NHS esters of Fmoc-L-amino acids are commercially available; cyclooctynes are commercially available for n'=1, 2, 3 and 5; diacids monoactivated as NHS ester are commercially available for n=1 to 3 and for n=4 to 10 they may be prepared by activating commercially available diacids with NHS in the presence of a coupling agent such as, for example, DCC and a base such as, for example, DMAP.

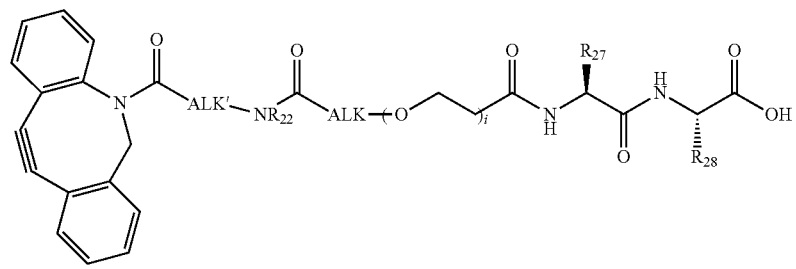

LP$_{17}$ prepared according to the scheme below:

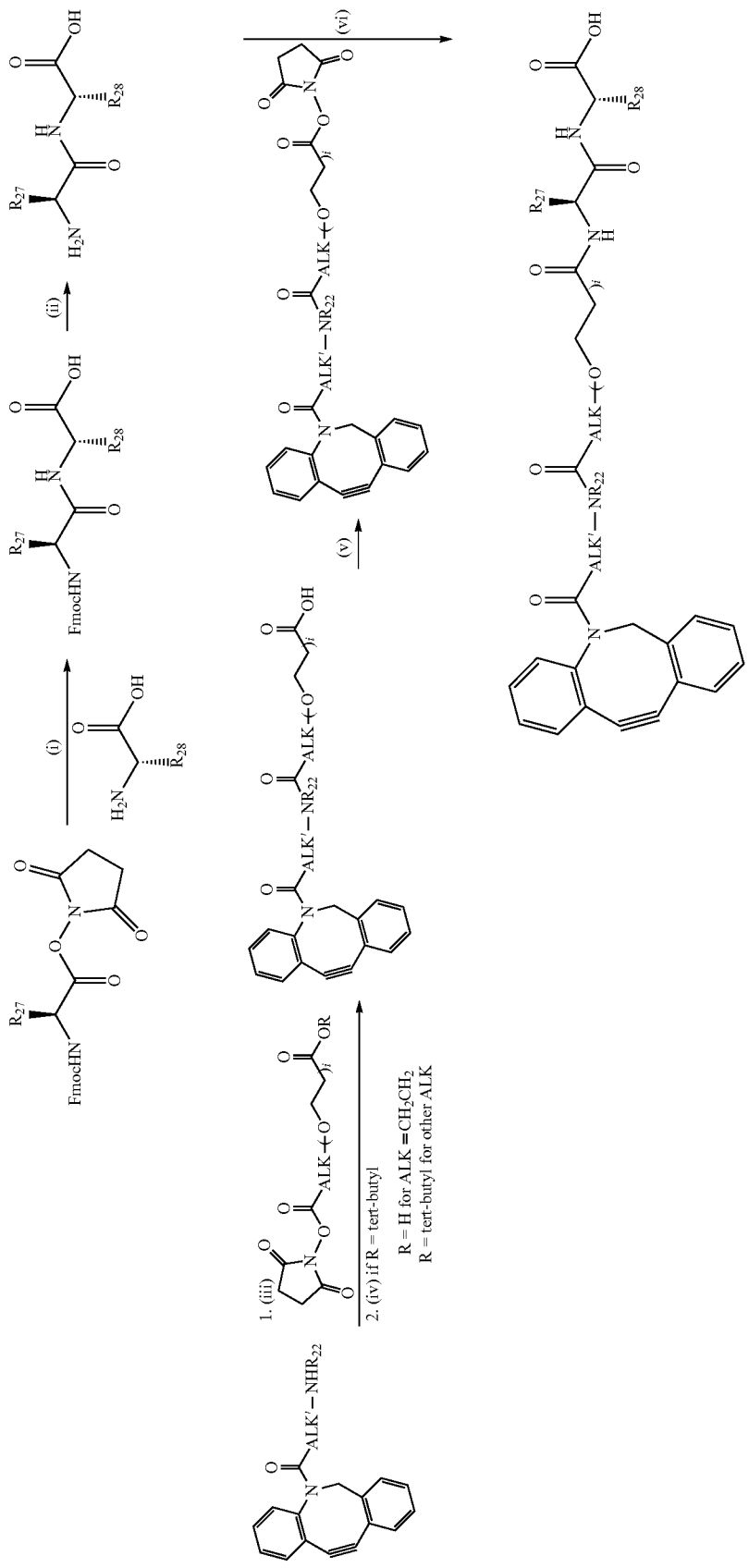

Step (i): peptide coupling between Fmoc-L-amino acid-ONHS and L-amino acid; the reaction is performed in a polar solvent such as a DME/THF/H₂O mixture in the presence of a base such as, for example, sodium bicarbonate;

Step (ii): deprotection of the amine; the reaction is performed in a polar solvent such as a DCM/MeOH mixture in the presence of a base such as, for example, piperidine;

Step (iii): cyclooctyne coupling; the reaction is performed in a polar solvent such as DCM;

Step (iv): deprotection using a solution of hydrochloric acid (for example solution in dioxane);

Step (v): activation of the cyclooctyne-PEG carboxylic acid as a NHS ester; the reaction is performed in a polar aprotic solvent such as DCM by treatment with NHS in the presence of a coupling agent such as, for example, EDC;

Step (vi): peptide coupling between the dipeptide and the NHS ester; the reaction is performed in a polar aprotic solvent such as DCM.

NHS esters of Fmoc-L-amino acids are commercially available; cyclooctynes are commercially available for n'=1, 2, 3 and 5; the PEG diacids mono-activated as NHS ester are prepared according to the scheme below:

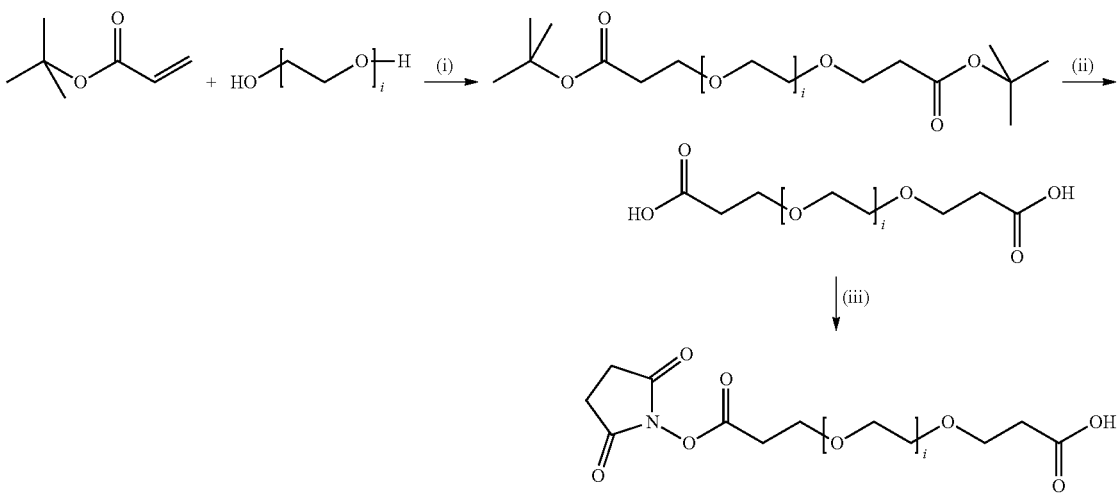

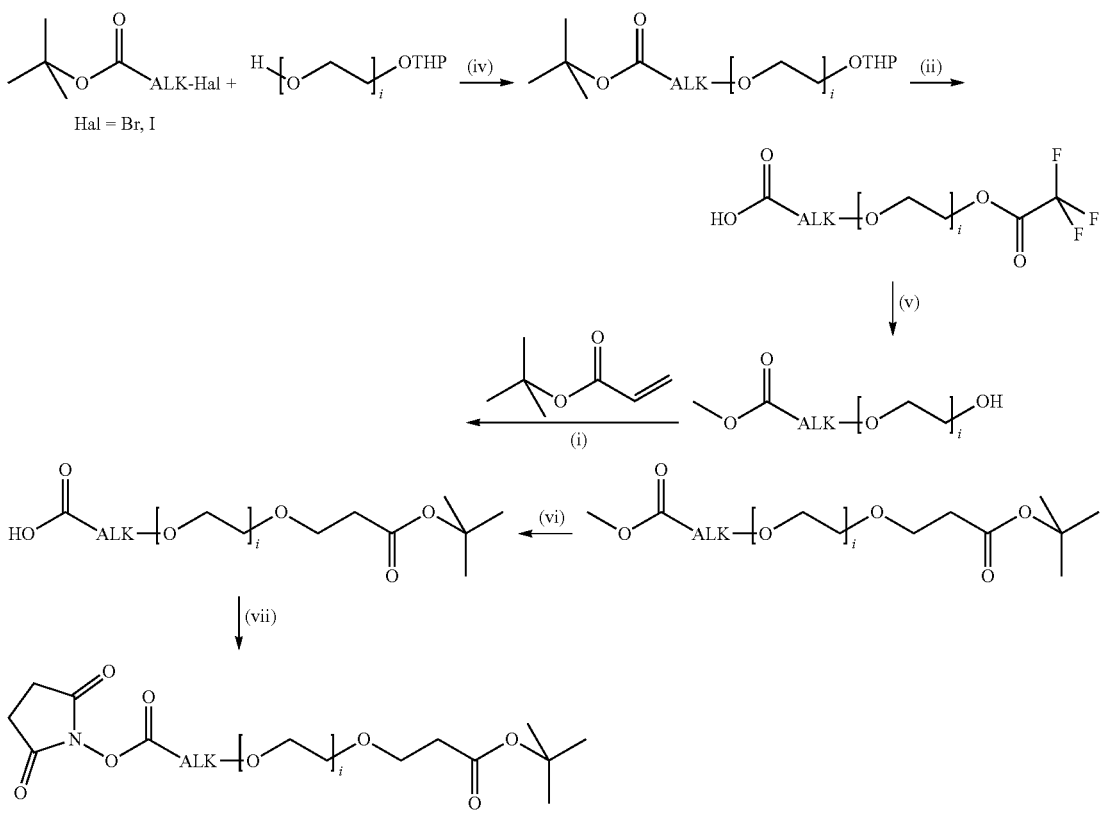

Step (i): elongation of the PEG chain; the reaction is performed in an anhydrous polar aprotic solvent such as THF or DMF by treatment of an unsaturated protected acid with the alkoxyde generated by the action of sodium in catalytic amount;

Step (ii): deprotection using a solution of hydrochloric acid (for example solution in dioxane) or of trifluoroacetic acid;

Step (iii): mono-activation of one acid as a NHS ester; the reaction is performed in a polar solvent such as THF using NHS in the presence of a coupling agent such as, for example, DCC and a base such as, for example, DMAP;

Step (iv): elongation of the PEG chain; the reaction is performed in an anhydrous polar aprotic solvent such as THF or DMF by treatment of a halogenated ester with the alkoxyde of the PEG diol monoprotected as a THP ether. The preparation of this type of monoprotected PEG diol is well described in the literature: see, for example, Richard A., et al., *Chem. Eur. J.* 2005, 11, 7315-7321 or Sakellariou E. G., et al., *Tetrahedron* 2003, 59, 9083-9090;

Step (v): protection of the carboxylic acid as a methyl ester; the reaction is performed in a polar aprotic solvent such as MeOH, by treatment with trimethylsilyldiazomethane;

Step (vi): saponification of the methyl ester; the reaction is performed in a mixture of polar solvents such as a THF/H$_2$O mixture in the presence of LiOH;

Step (vii): activation of the acid as a NHS ester; the reaction is performed in a polar solvent such as THF using NHS in the presence of a coupling agent such as, for example, DCC and a base such as, for example, DMAP.

The starting PEG diols are commercially available for i=3 to 12.

$LP_{18}$

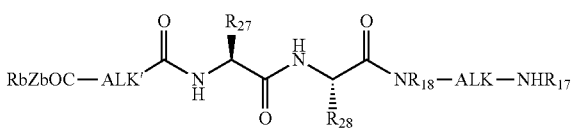

prepared according to the scheme below:

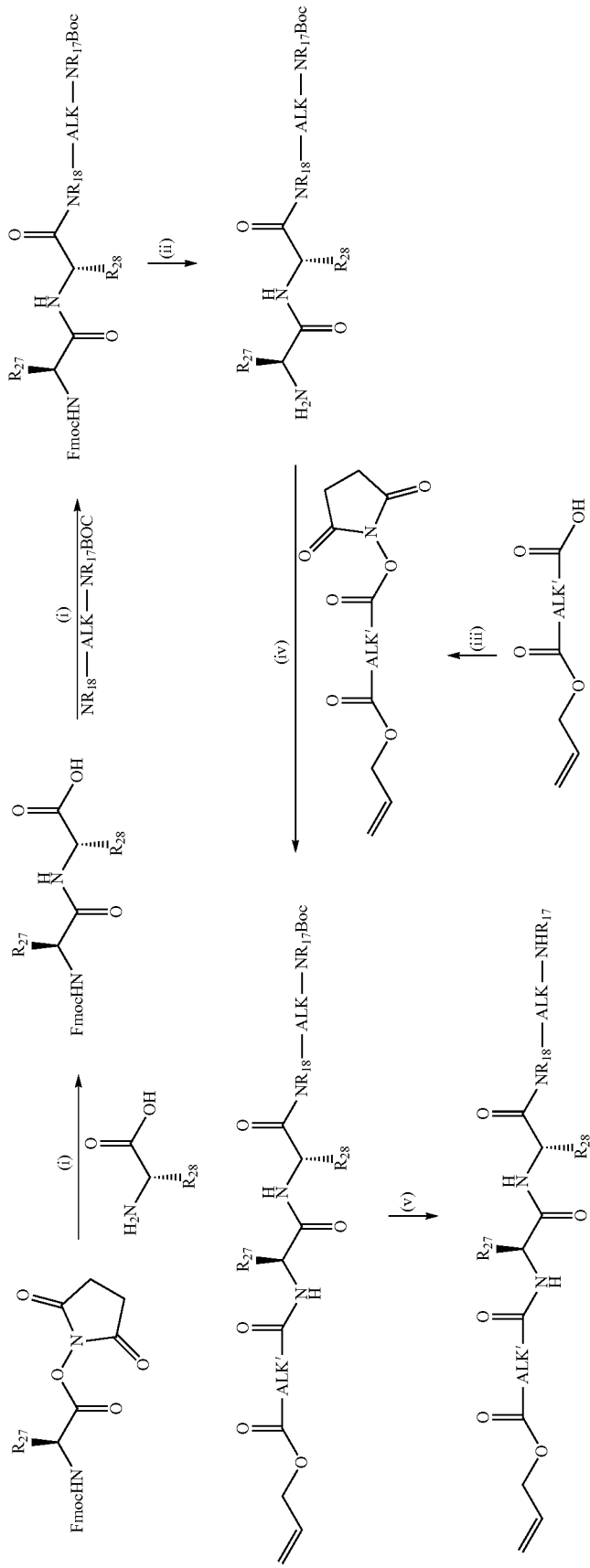

Step (i): peptide coupling; the reaction is performed in a polar solvent such as a DME/THF/H$_2$O mixture in the presence of a base such as sodium bicarbonate or in a polar solvent such as DCM in the presence of a coupling reagent such as propylphosphonic anhydride and a base such as, for example, TEA;

Step (ii): deprotection of the amine; the reaction is performed in a polar solvent such as a DCM/MeOH mixture in the presence of a base such as, for example, piperidine;

Step (iii): activation of the carboxylic acid as a NHS ester; the reaction is performed in a polar aprotic solvent such as DCM by treatment with NHS in the presence of a coupling agent such as, for example, EDC;

Step (iv): peptide coupling between the dipeptide and the NHS ester; the reaction is performed in a polar aprotic solvent such as a DCM/CH$_3$CN mixture;

Step (v): deprotection using a solution of hydrochloric acid (for example solution in dioxane) or of trifluoroacetic acid.

NHS esters of Fmoc-L-amino acids are commercially available; the mono-protected diamines are commercially available for n=2 to 4 and R$_{17}$ and R$_{18}$=H or Me independently of each other. The diacids monoprotected as allyl esters are commercially available for n=2 (monoallyl succinate) or may be prepared by transesterification of the methyl or tert-butyl monoesters, which are commercially available for n'=2 to 6.

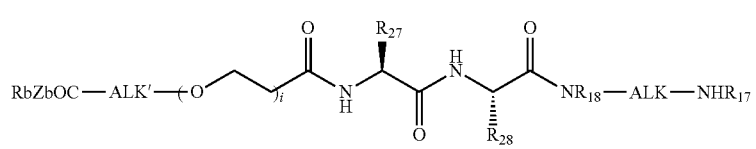

LP$_{19}$ prepared according to the scheme below:

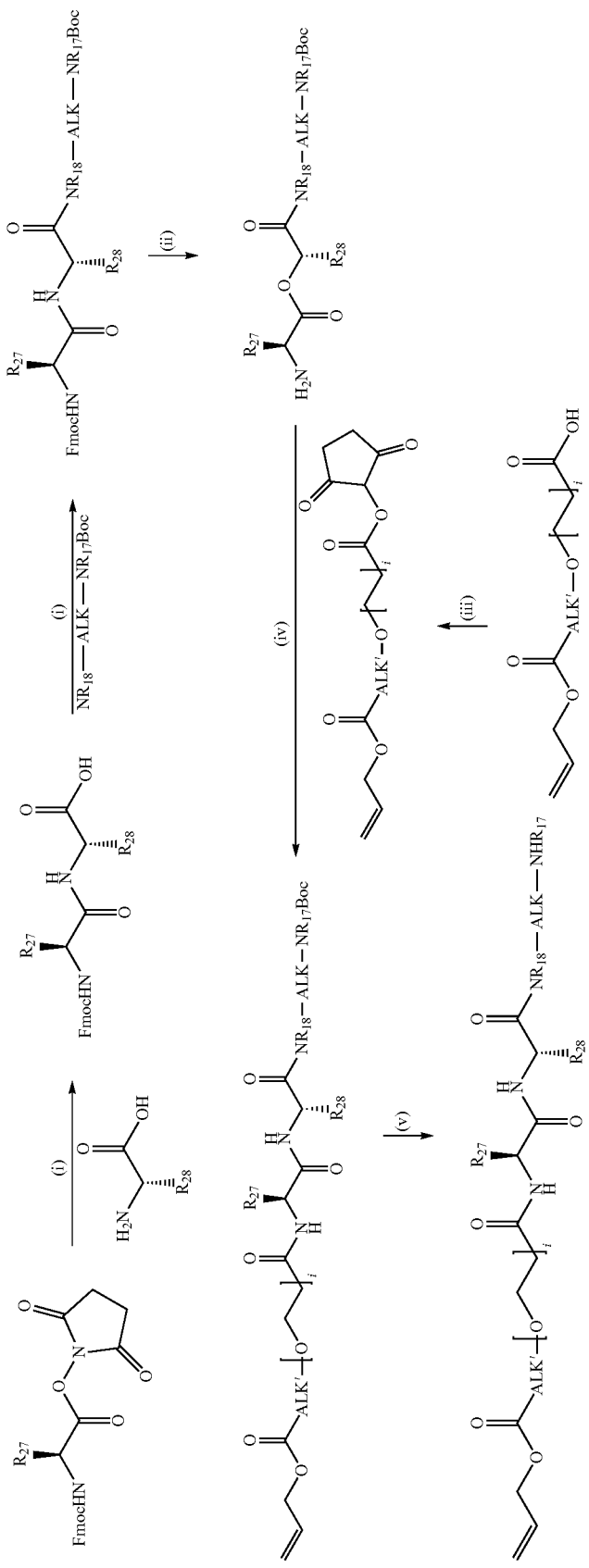

Step (i): peptide coupling; the reaction is performed in a polar solvent such as a DME/THF/H$_2$O mixture in the presence of a base such as sodium bicarbonate or in a polar solvent such as DCM in the presence of a coupling reagent such as propylphosphonic anhydride and a base such as, for example, TEA;

Step (ii): deprotection of the amine; the reaction is performed in a polar solvent such as a DCM/MeOH mixture in the presence of a base such as, for example, piperidine;

Step (iii): activation of the carboxylic acid as a NHS ester; the reaction is performed in a polar aprotic solvent such as DCM by treatment with NHS in the presence of a coupling agent such as, for example, EDC;

Step (iv): peptide coupling between the dipeptide and the NHS ester; the reaction is performed in a polar aprotic solvent such as a DCM/CH$_3$CN mixture;

Step (v): deprotection using a solution of hydrochloric acid (for example solution in dioxane) or of trifluoroacetic acid.

NHS esters of Fmoc-L-amino acids are commercially available; the mono-protected diamines are commercially available for n=2 to 4 and R$_{17}$ and R$_{18}$=H or Me independently of each other; the PEG diacids monoprotected as allyl esters are prepared according to the schemes described for linker precursor LP$_2$.

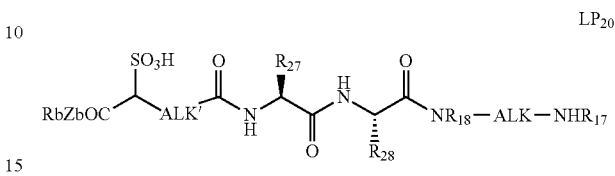

LP$_{20}$ prepared according to the scheme below:

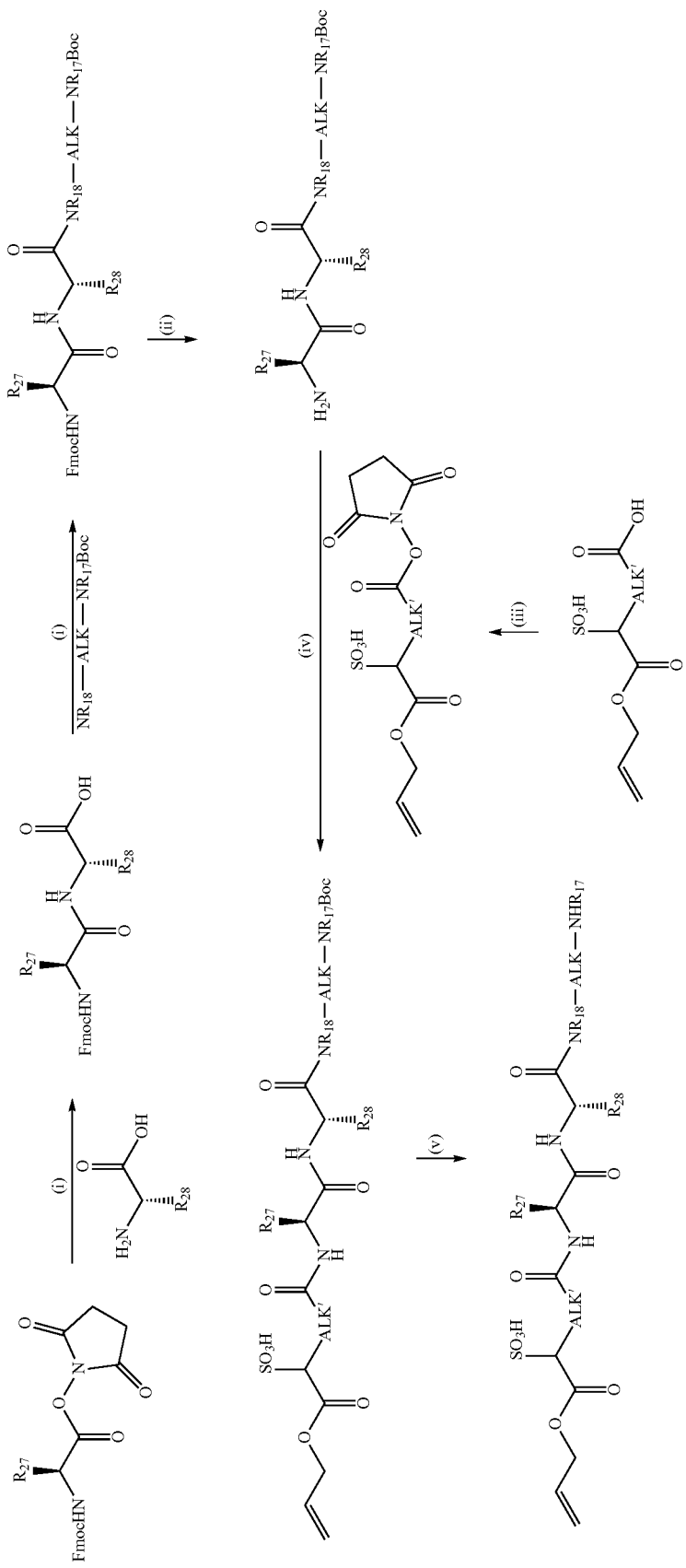

Step (i): peptide coupling; the reaction is performed in a polar solvent such as a DME/THF/H$_2$O mixture in the presence of a base such as sodium bicarbonate or in a polar solvent such as DCM in the presence of a coupling reagent such as propylphosphonic anhydride and a base such as, for example, TEA;

Step (ii): deprotection of the amine; the reaction is performed in a polar solvent such as a DCM/MeOH mixture in the presence of a base such as, for example, piperidine;

Step (iii): activation of the carboxylic acid as a NHS ester; the reaction is performed in a polar aprotic solvent such as DCM by treatment with NHS in the presence of a coupling agent such as, for example, EDC;

Step (iv): peptide coupling between the dipeptide and the NHS ester; the reaction is performed in a polar aprotic solvent such as a DCM/CH$_3$CN mixture;

Step (v): deprotection using a solution of hydrochloric acid (for example solution in dioxane) or of trifluoroacetic acid.

NHS esters of Fmoc-L-amino acids are commercially available; the mono-protected diamines are commercially available for n=2 to 4 and $R_{17}$ and $R_{18}$=H or Me independently of each other; the sulfo diacids monoprotected as allyl ester are prepared according to the schemes described for linker precursor $LP_3$.

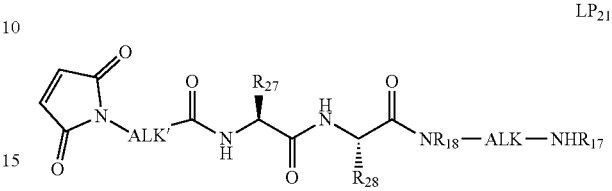

LP$_{21}$ prepared according to the scheme below:

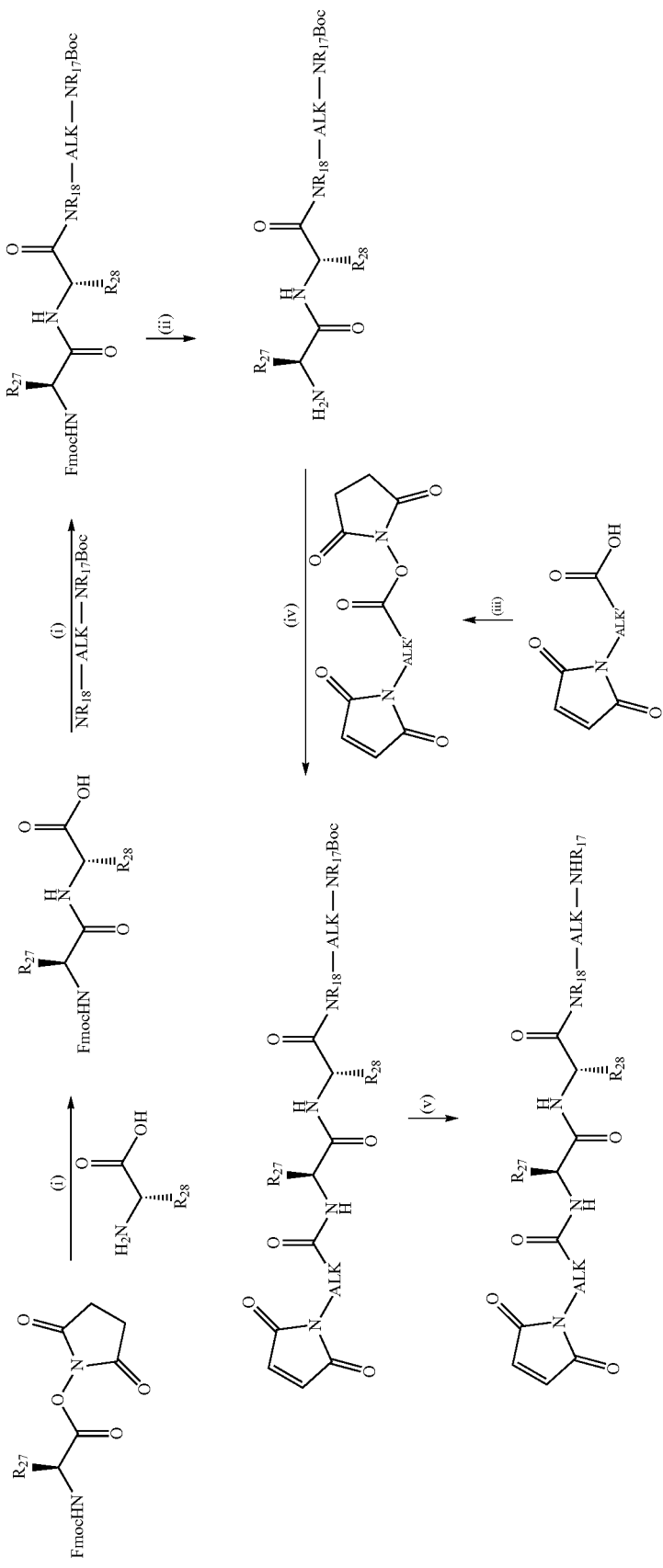

Step (i): peptide coupling; the reaction is performed in a polar solvent such as a DME/THF/H$_2$O mixture in the presence of a base such as sodium bicarbonate or in a polar solvent such as DCM in the presence of a coupling reagent such as propylphosphonic anhydride and a base such as, for example, TEA.

Step (ii): deprotection of the amine; the reaction is performed in a polar solvent such as a DCM/MeOH mixture in the presence of a base such as, for example, piperidine;

Step (iii): activation of the carboxylic acid as a NHS ester; the reaction is performed in a polar aprotic solvent such as DCM by treatment with NHS in the presence of a coupling agent such as, for example, EDC;

Step (iv): peptide coupling between the dipeptide and the NHS ester; the reaction is performed in a polar aprotic solvent such as a DCM/CH$_3$CN mixture;

Step (v): deprotection using a solution of hydrochloric acid (for example solution in dioxane) or of trifluoroacetic acid.

NHS esters of Fmoc-L-amino acids are commercially available; the mono-protected diamines are commercially available for n=2 to 4 and R$_{17}$ and R$_{18}$=H or Me independently of each other; the maleimido carboxylic acids are commercially available for n=1 to 12.

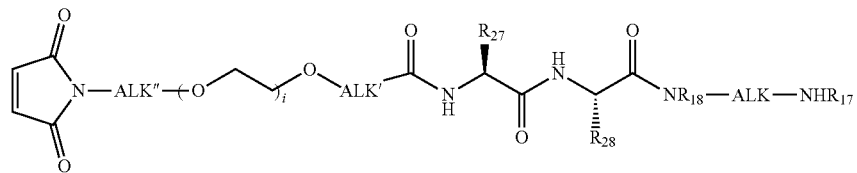

LP$_{22}$ prepared according to the scheme below:

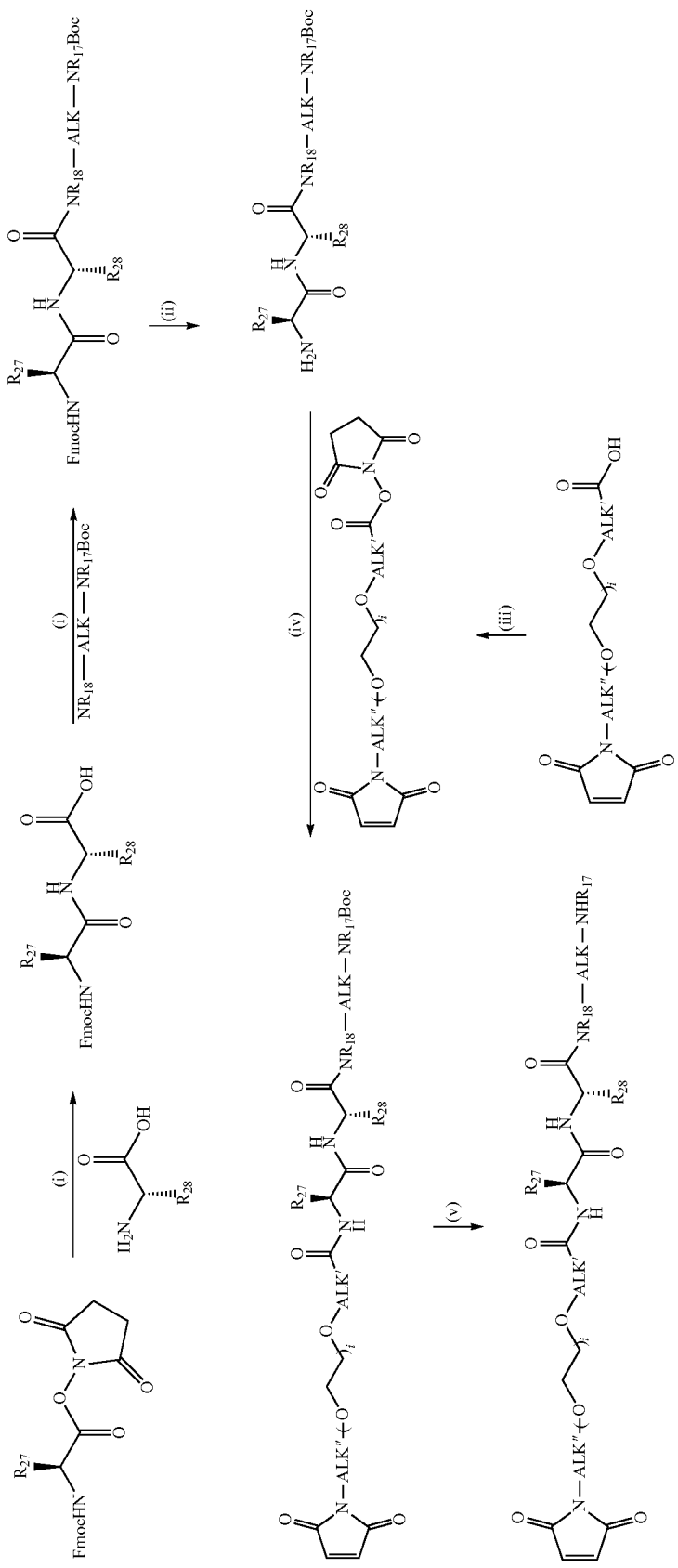

Step (i): peptide coupling; the reaction is performed in a polar solvent such as a DME/THF/H$_2$O mixture in the presence of a base such as sodium bicarbonate or in a polar solvent such as DCM in the presence of a coupling reagent such as propylphosphonic anhydride and a base such as, for example, TEA;

Step (ii): deprotection of the amine; the reaction is performed in a polar solvent such as a DCM/MeOH mixture in the presence of a base such as, for example, piperidine;

Step (iii): activation of the carboxylic acid as a NHS ester; the reaction is performed in a polar aprotic solvent such as DCM by treatment with NHS in the presence of a coupling agent such as, for example, supported DCC;

Step (iv): peptide coupling between the dipeptide and the NHS ester; the reaction is performed in a polar aprotic solvent such as a DCM/CH$_3$CN mixture;

Step (v): deprotection using a solution of hydrochloric acid (for example solution in dioxane) or of trifluoroacetic acid.

NHS esters of Fmoc-L-amino acids are commercially available; the mono-protected diamines are commercially available for n=2 to 4 and $R_{17}$ and $R_{18}$=H or Me independently of each other; the maleimido PEG acids are commercially available for ALK=ALK'=CH$_2$CH$_2$ and i=1 to 7 and are otherwise prepared according to the schemes described for linker precursor LP$_5$.

LP$_{23}$

prepared according to the scheme below:

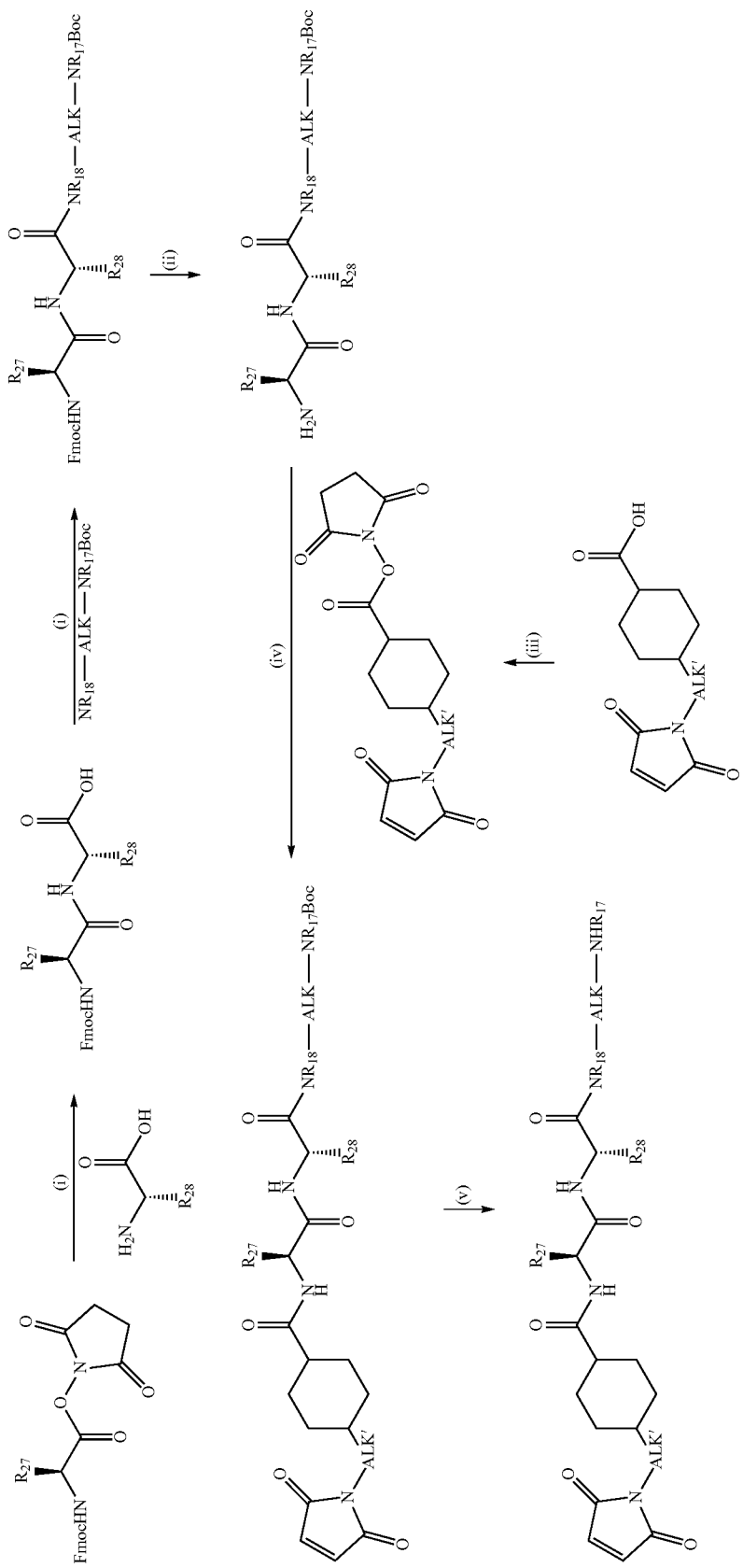

Step (i): peptide coupling; the reaction is performed in a polar solvent such as a DME/THF/H$_2$O mixture in the presence of a base such as sodium bicarbonate or in a polar solvent such as DCM in the presence of a coupling reagent such as propylphosphonic anhydride and a base such as, for example, TEA;

Step (ii): deprotection of the amine; the reaction is performed in a polar solvent such as a DCM/MeOH mixture in the presence of a base such as, for example, piperidine;

Step (iii): activation of the carboxylic acid as a NHS ester; the reaction is performed in a polar aprotic solvent such as DCM by treatment with NHS in the presence of a coupling agent such as, for example, EDC;

Step (iv): peptide coupling between the dipeptide and the NHS ester; the reaction is performed in a polar aprotic solvent such as a DCM/CH$_3$CN mixture;

Step (v): deprotection using a solution of hydrochloric acid (for example solution in dioxane) or of trifluoroacetic acid.

NHS esters of Fmoc-L-amino acids are commercially available; the mono-protected diamines are commercially available for n=2 to 4 and $R_{17}$ and $R_{18}$=H or Me independently of each other; the maleimido cyclohexanecarboxylic acid is commercially available for ALK=CH$_2$ and may otherwise be prepared according to the schemes described for linker precursor LP$_6$.

LP$_{24}$

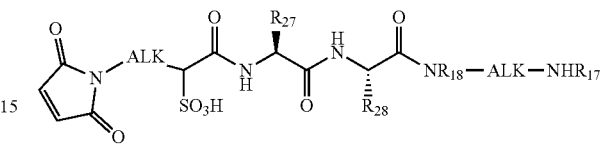

prepared according to the scheme below:

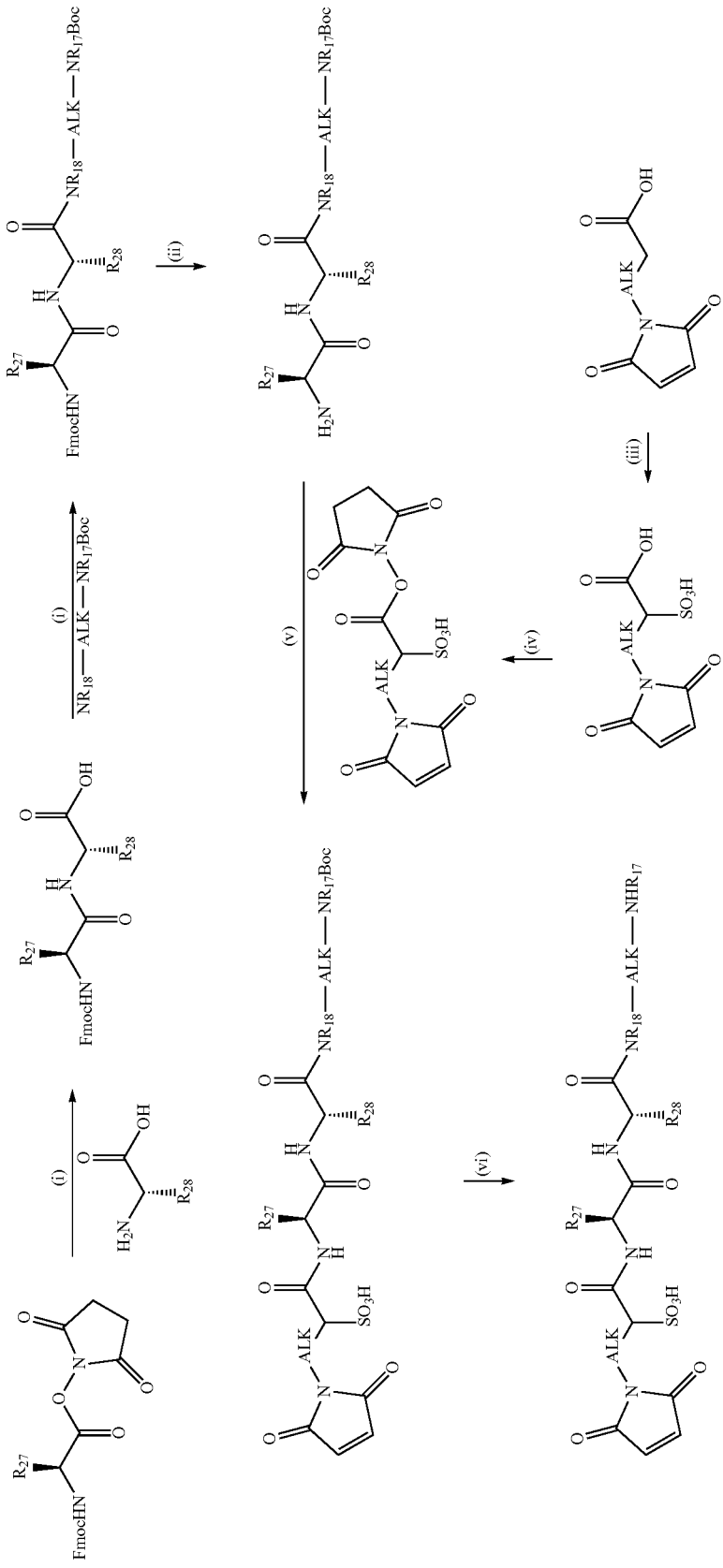

Step (i): peptide coupling; the reaction is performed in a polar solvent such as a DME/THF/H$_2$O mixture in the presence of a base such as sodium bicarbonate or in a polar solvent such as DCM in the presence of a coupling reagent such as propylphosphonic anhydride and a base such as, for example, TEA;

Step (ii): deprotection of the amine; the reaction is performed in a polar solvent such as a DCM/MeOH mixture in the presence of a base such as, for example, piperidine;

Step (iii): α-sulfonation of the carboxylic acid; the reaction is performed at 75° C. in a polar aprotic solvent like DCE by treatment with chlorosulfonic acid in the presence of a base such as, for example, DIEA;

Step (iv): activation of the carboxylic acid as a NHS ester; the reaction is performed in a polar aprotic solvent such as DCM by treatment with NHS in the presence of a coupling agent such as, for example, EDC;

Step (v): peptide coupling between the dipeptide and the NHS ester; the reaction is performed in a polar aprotic solvent such as a DCM/CH$_3$CN mixture;

Step (vi): deprotection using a solution of hydrochloric acid (for example solution in dioxane) or of trifluoroacetic acid.

NHS esters of Fmoc-L-amino acids are commercially available; the mono-protected diamines are commercially available for n=2 to 4 and R$_{17}$ and R$_{18}$=H or Me independently of each other; the maleimido acids are commercially available for n=1 to 12.

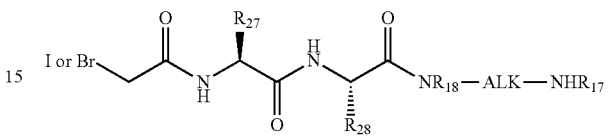

LP$_{25}$ prepared according to the scheme below:

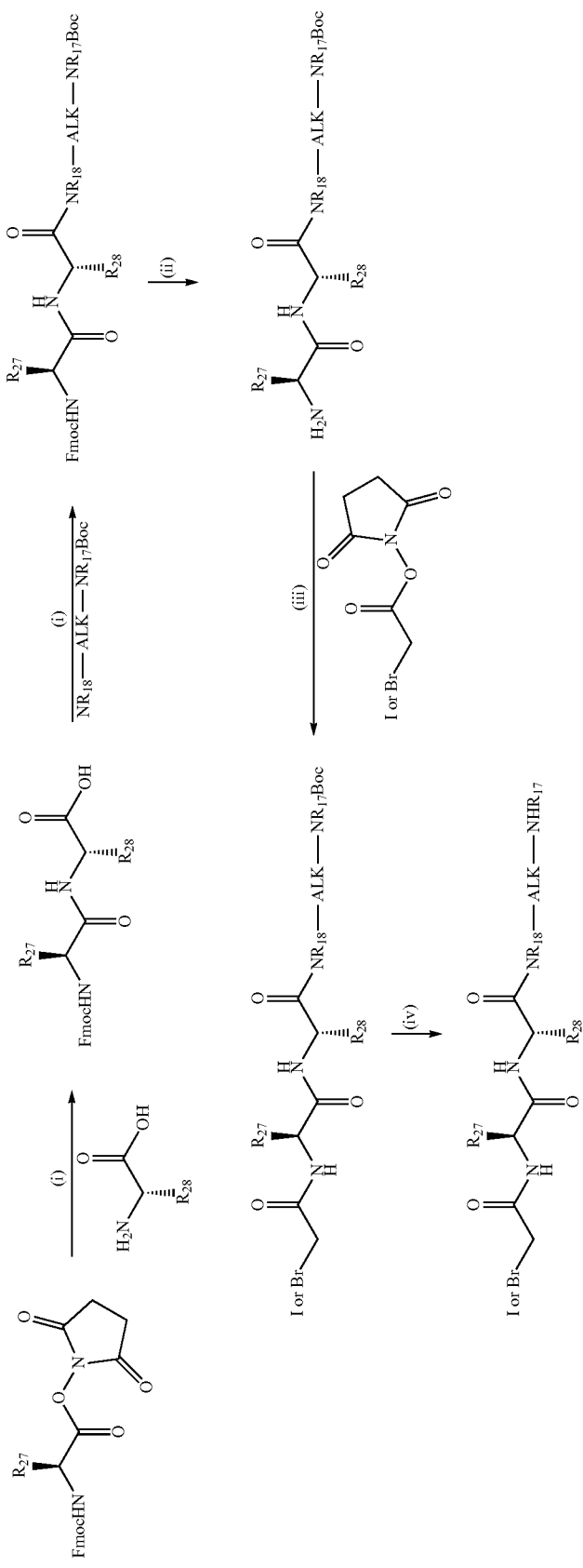

Step (i): peptide coupling; the reaction is performed in a polar solvent such as a DME/THF/H$_2$O mixture in the presence of a base such as sodium bicarbonate or in a polar solvent such as DCM in the presence of a coupling reagent such as propylphosphonic anhydride and a base such as, for example, TEA;

Step (ii): deprotection of the amine; the reaction is performed in a polar solvent such as a DCM/MeOH mixture in the presence of a base such as, for example, piperidine;

Step (iii): peptide coupling between the dipeptide and the NHS ester; the reaction is performed in a polar aprotic solvent such as a DCM/CH$_3$CN mixture;

Step (iv): deprotection using a solution of hydrochloric acid (for example solution in dioxane) or of trifluoroacetic acid.

NHS esters of Fmoc-L-amino acids are commercially available; the mono-protected diamines are commercially available for n=2 to 4 and R$_{17}$ and R$_{18}$=H or Me independently of each other; N-succinimidyl bromo- and iodo-acetates are commercially available.

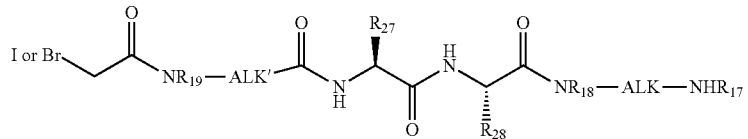

LP$_{26}$ prepared according to the scheme below:

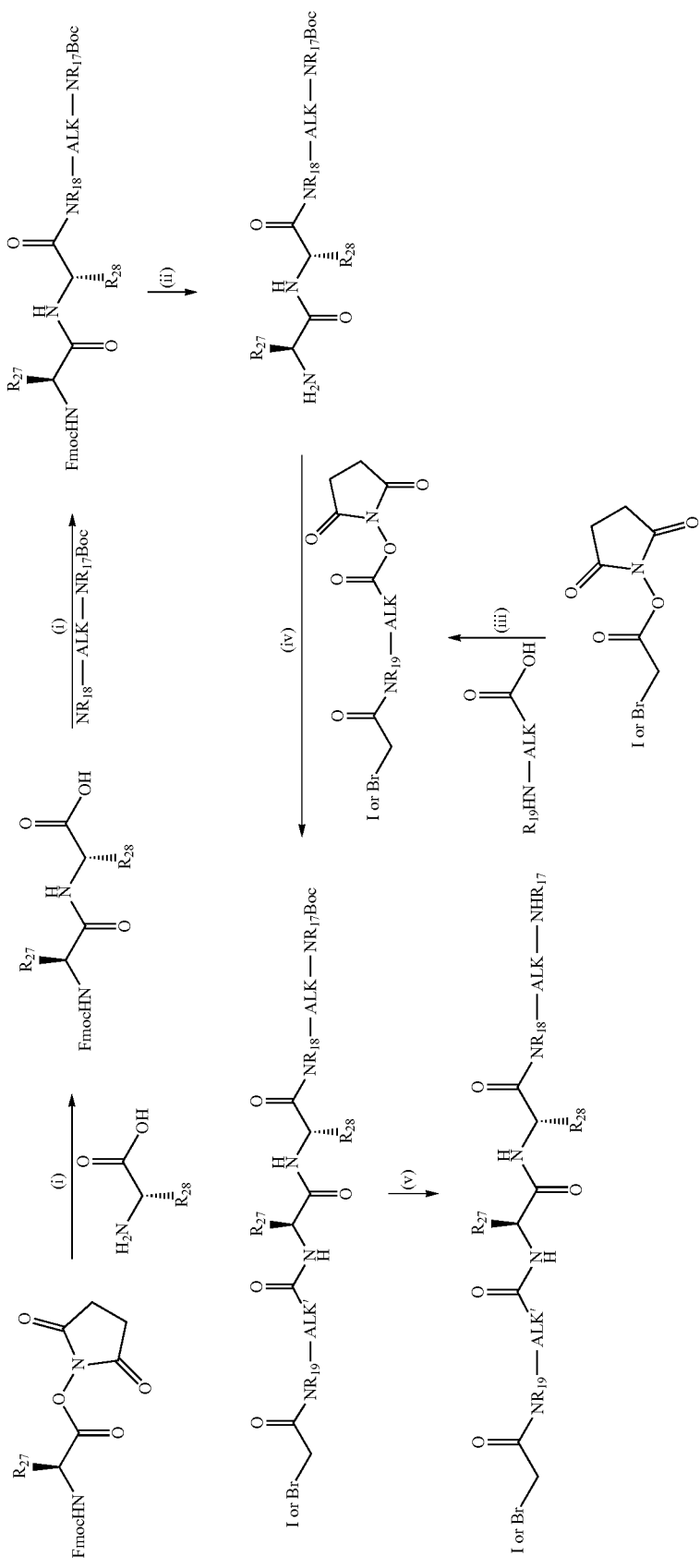

Step (i): peptide coupling; the reaction is performed in a polar solvent such as a DME/THF/$H_2O$ mixture in the presence of a base such as sodium bicarbonate or in a polar solvent such as DCM in the presence of a coupling reagent such as propylphosphonic anhydride and a base such as, for example, TEA;

Step (ii): deprotection of the amine; the reaction is performed in a polar solvent such as a DCM/MeOH mixture in the presence of a base such as, for example, piperidine;

Step (iii): coupling and activation of the carboxylic acid as a NHS ester; the coupling of N-succinimidyl bromo- and iodo-acetate with the amino carboxylic acid is performed in a polar aprotic solvent such as a DCM/DMF mixture followed by the addition of N,N'-disuccinimidyl carbonate and a base such as, for example, DIEA;

Step (iv): peptide coupling between the dipeptide and the NHS ester; the reaction is performed in a polar aprotic solvent such as a DCM/$CH_3CN$ mixture;

Step (v): deprotection using a solution of hydrochloric acid (for example solution in dioxane) or of trifluoroacetic acid.

NHS esters of Fmoc-L-amino acids are commercially available; the mono-protected diamines are commercially available for n=2 to 4 and $R_{17}$ and $R_{18}$=H or Me independently of each other; N-succinimidyl bromo- and iodo-acetates are commercially available; the amino carboxylic acids are commercially available for n=1 to 12 and the N-methylated amino carboxylic acids for n=1 to 7.

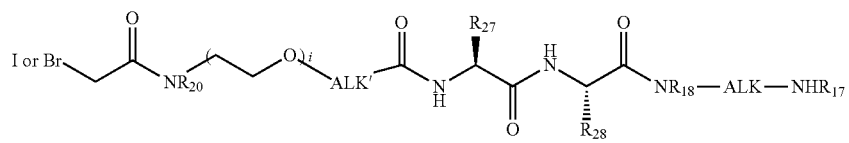

$LP_{27}$ prepared according to the scheme below:

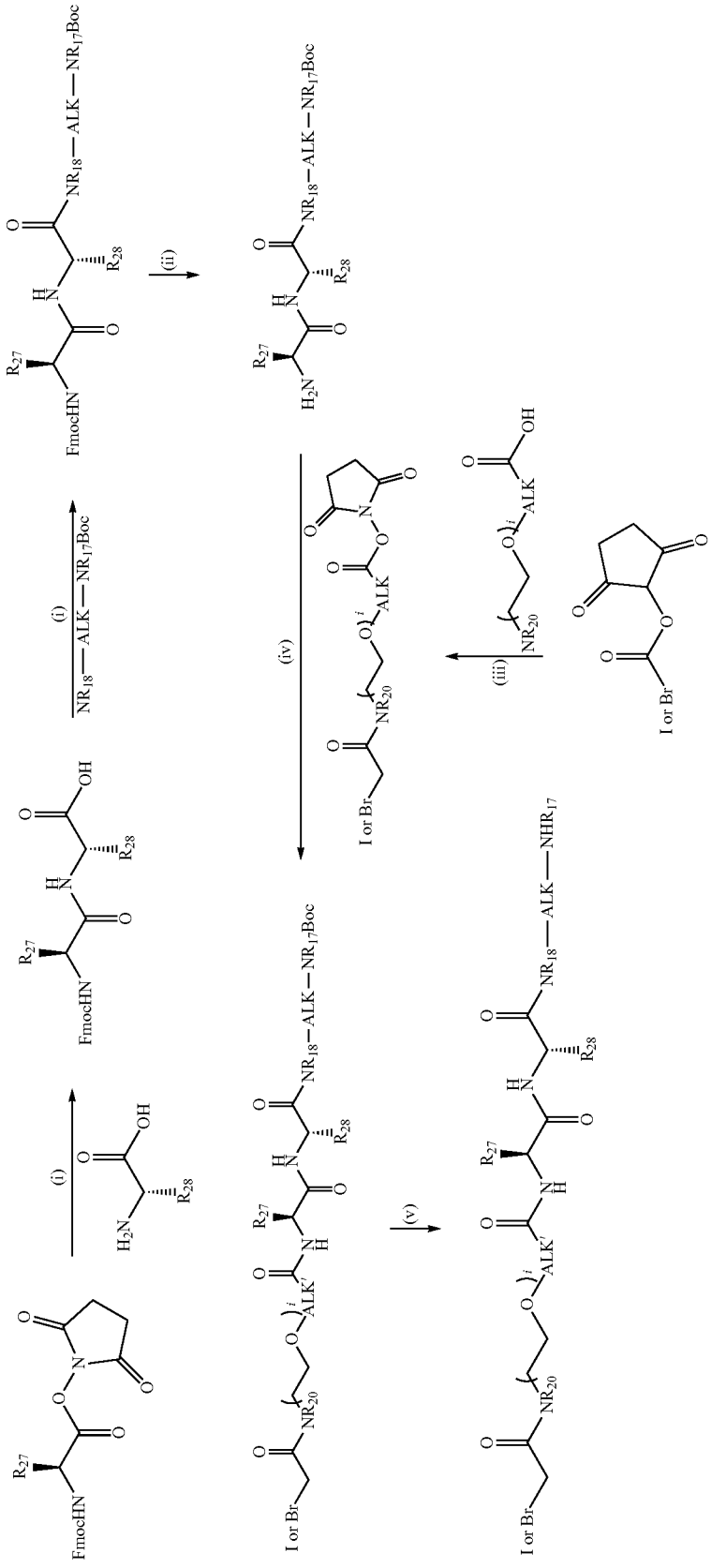

Step (i): peptide coupling; the reaction is performed in a polar solvent such as a DME/THF/H$_2$O mixture in the presence of a base such as sodium bicarbonate or in a polar solvent such as DCM in the presence of a coupling reagent such as propylphosphonic anhydride and a base such as, for example, TEA;

Step (ii): deprotection of the amine; the reaction is performed in a polar solvent such as a DCM/MeOH mixture in the presence of a base such as, for example, piperidine;

Step (iii): coupling and activation of the carboxylic acid as NHS ester; the coupling of N-succinimidyl bromo- and iodo-acetate with the amino carboxylic acid is performed in a polar aprotic solvent such as a DCM/DMF mixture followed by the addition of N,N'-disuccinimidyl carbonate and a base such as, for example, DIEA;

Step (iv): peptide coupling between the dipeptide and the NHS ester; the reaction is performed in a polar aprotic solvent such as a DCM/CH$_3$CN mixture;

Step (v): deprotection using a solution of hydrochloric acid (for example solution in dioxane) or of trifluoroacetic acid.

NHS esters of Fmoc-L-amino acids are commercially available; the mono-protected diamines are commercially available for n=2 to 4 and R$_{17}$ and R$_{18}$=H or Me independently of each other; N-succinimidyl bromo- and iodo-acetate are commercially available; in the case where ALK=CH$_2$CH$_2$ and R$_{20}$=H, the amino PEG carboxylic acids are commercially available for and i=1 to 6 and otherwise may be prepared from tert-butyl acrylate and the corresponding amino-PEG-alcohol; in the case where ALK≠CH$_2$CH$_2$, they may be prepared according to the schemes described for linker precursor LP$_{10}$.

LP$_{28}$

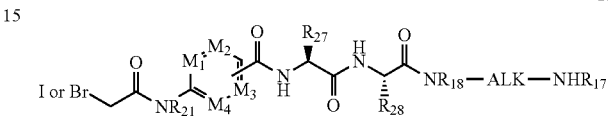

prepared according to the scheme below:

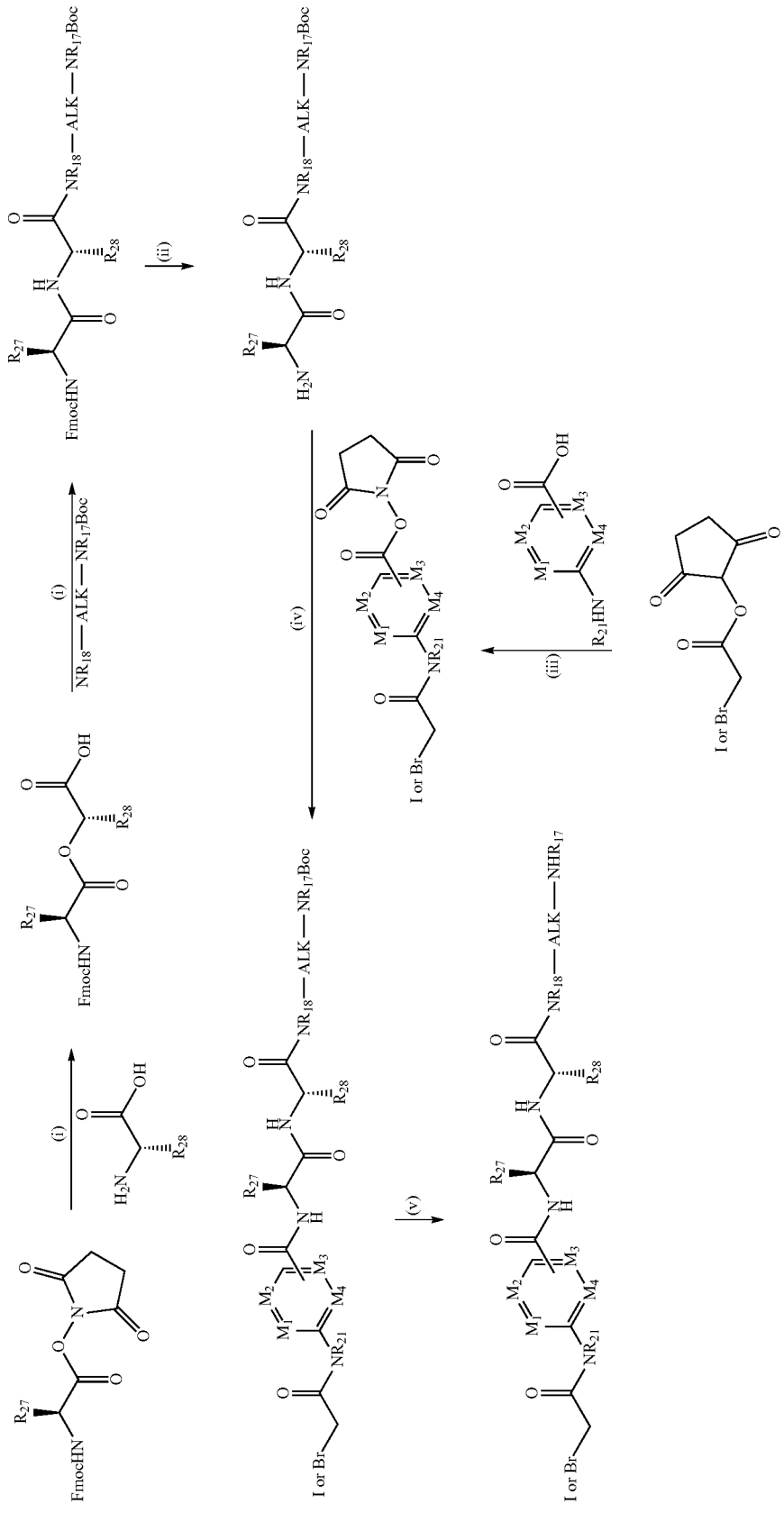

Step (i): peptide coupling; the reaction is performed in a polar solvent such as a DME/THF/H$_2$O mixture in the presence of a base such as sodium bicarbonate or in a polar solvent such as DCM in the presence of a coupling reagent such as propylphosphonic anhydride and a base such as, for example, TEA;

Step (ii): deprotection of the amine; the reaction is performed in a polar solvent such as a DCM/MeOH mixture in the presence of a base such as, for example, piperidine;

Step (iii): coupling and activation of the carboxylic acid as a NHS ester; the coupling of N-succinimidyl bromo- and iodo-acetate with the amino carboxylic acid is performed in a polar aprotic solvent such as a DCM/DMF mixture followed by the addition of N,N'-disuccinimidyl carbonate and a base such as, for example, DIEA;

Step (iv): peptide coupling between the dipeptide and the NHS ester; the reaction is performed in a polar aprotic solvent such as a DCM/CH$_3$CN mixture;

Step (v): deprotection using a solution of hydrochloric acid (for example solution in dioxane) or of trifluoroacetic acid.

NHS esters of Fmoc-L-amino acids are commercially available; the mono-protected diamines are commercially available for n=2 to 4 and R$_{17}$ and R$_{18}$=H or Me independently of each other; N-succinimidyl bromo- and iodo-acetate are commercially available; the amino-(hetero)aryl-carboxylic acids are commercially available, like for example 4-amino-2-benzoic acid, 6-amino-3-pyridine carboxylic acid, 5-amino-2-pyrazine carboxylic acid, 2-amino-5-pyrimidine carboxylic acid or 6-amino-1,2,4,5-tetrazine carboxylic acid.

LP$_{29}$

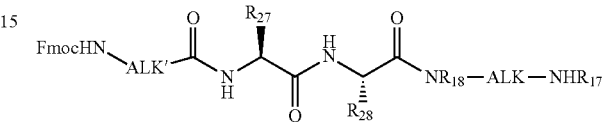

prepared according to the scheme below:

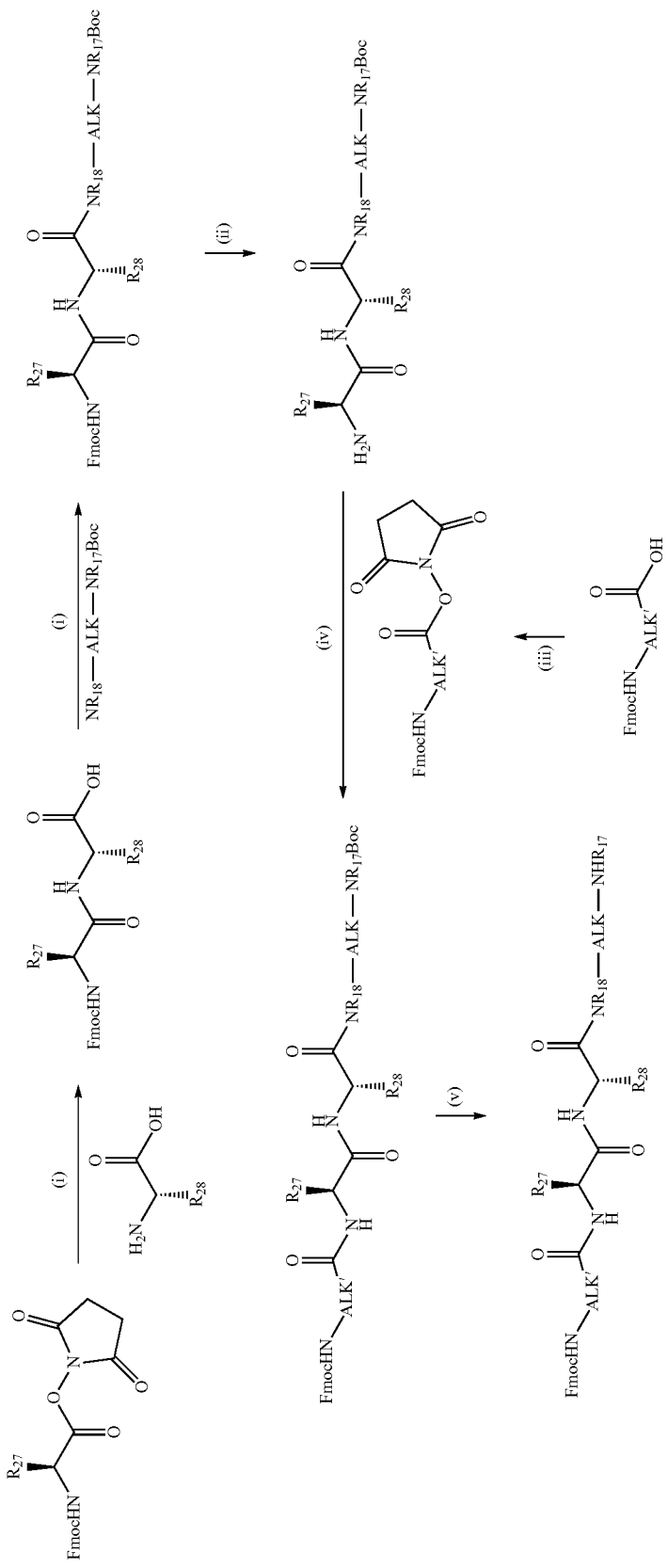

Step (i): peptide coupling; the reaction is performed in a polar solvent such as a DME/THF/H$_2$O mixture in the presence of a base such as sodium bicarbonate or in a polar solvent such as DCM in the presence of a coupling reagent such as propylphosphonic anhydride and a base such as, for example, TEA;

Step (ii): deprotection of the amine; the reaction is performed in a polar solvent such as a DCM/MeOH mixture in the presence of a base such as, for example, piperidine;

Step (iii): activation of the carboxylic acid as a NHS ester; the reaction is performed in a polar aprotic solvent such as DCM by treatment with NHS in the presence of a coupling agent such as, for example, EDC;

Step (iv): peptide coupling between the dipeptide and the NHS ester; the reaction is performed in a polar aprotic solvent such as a DCM/CH$_3$CN mixture;

Step (v): deprotection using a solution of hydrochloric acid (for example solution in dioxane) or of trifluoroacetic acid.

NHS esters of Fmoc-L-amino acids are commercially available; the mono-protected diamines are commercially available for n=2 to 4 and R$_{17}$ and R$_{18}$=H or Me independently of each other; the amino carboxylic acids are commercially available for n=1 to 12.

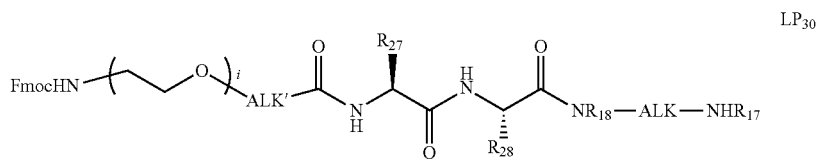

LP$_{30}$ prepared according to the scheme below:

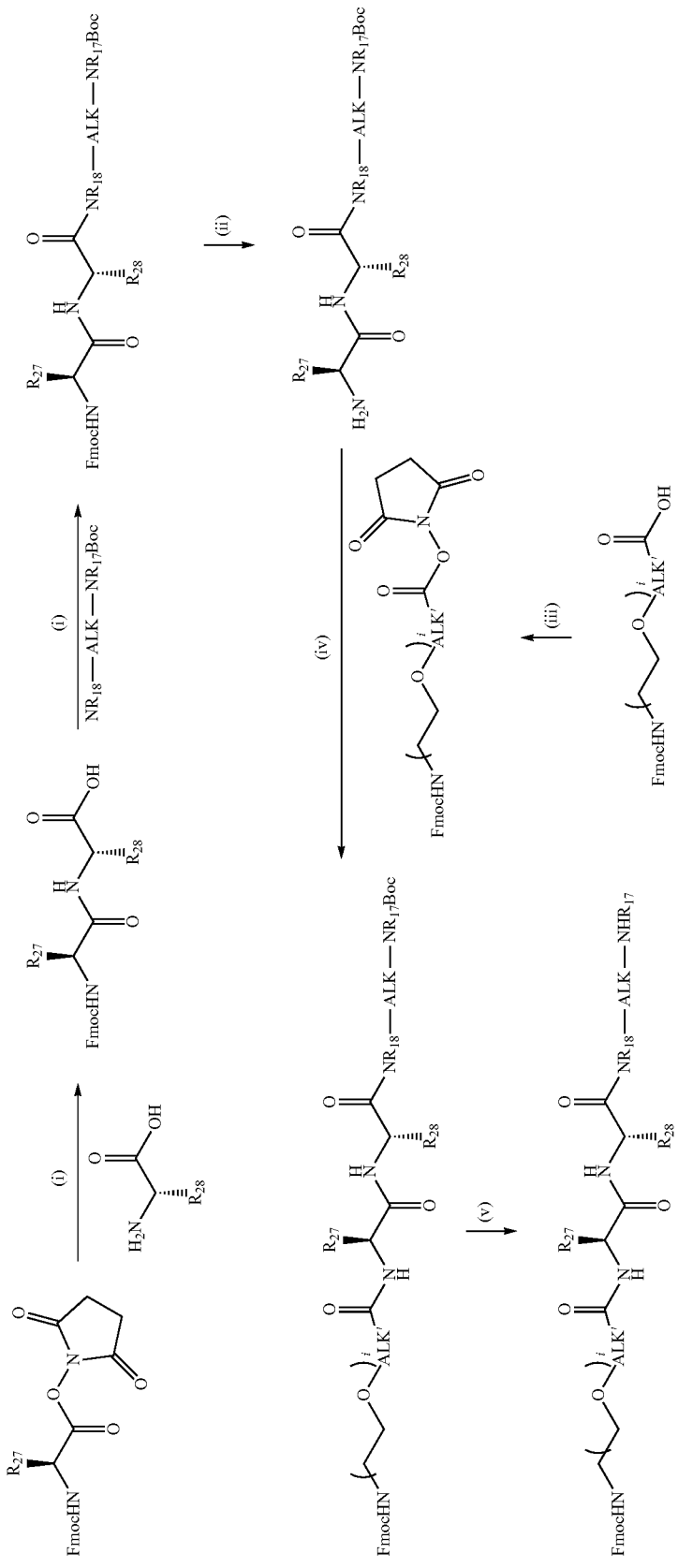

Step (i): peptide coupling; the reaction is performed in a polar solvent such as a DME/THF/H$_2$O mixture in the presence of a base such as sodium bicarbonate or in a polar solvent such as DCM in the presence of a coupling reagent such as propylphosphonic anhydride and a base such as, for example, TEA;

Step (ii): deprotection of the amine; the reaction is performed in a polar solvent such as a DCM/MeOH mixture in the presence of a base such as, for example, piperidine;

Step (iii): activation of the carboxylic acid as a NHS ester; the reaction is performed in a polar aprotic solvent such as DCM by treatment with NHS in the presence of a coupling agent such as, for example, supported DCC;

Step (iv): peptide coupling between the dipeptide and the NHS ester; the reaction is performed in a polar aprotic solvent such as a DCM/CH$_3$CN mixture;

Step (v): deprotection using a solution of hydrochloric acid (for example solution in dioxane) or of trifluoroacetic acid.

NHS esters of Fmoc-L-amino acids are commercially available; the mono-protected diamines are commercially available for n=2 to 4 and R$_{17}$ and R$_{18}$=H or Me independently of each other; Fmoc-protected amino PEG carboxylic acids are commercially available for and i=1 to 6 and otherwise may be prepared from tert-butyl acrylate and the corresponding amino-PEG-alcohol; in the case where ALK≠CH$_2$CH$_2$, they may be prepared according to the schemes for linker precursor LP$_{10}$. Protection of the amine function with a Fmoc group may be realized by treatment with FmocOSu (CAS number [82911-69-1]) in the presence of a base such as, for example, DIEA.

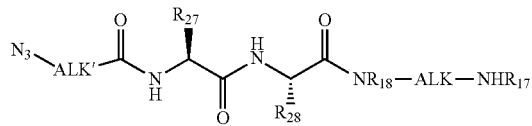

LP$_{31}$ prepared according to the scheme below:

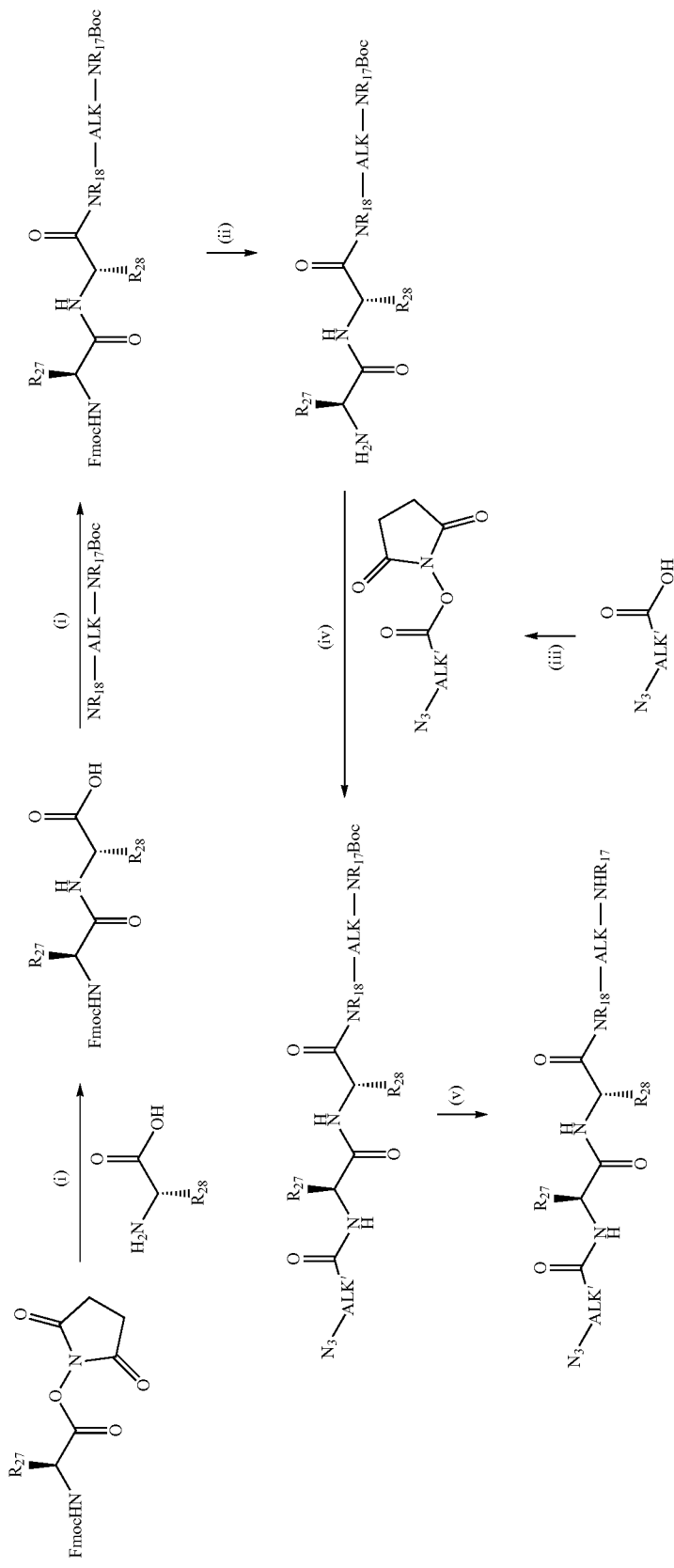

Step (i): peptide coupling; the reaction is performed in a polar solvent such as a DME/THF/H$_2$O mixture in the presence of a base such as sodium bicarbonate or in a polar solvent such as DCM in the presence of a coupling reagent such as propylphosphonic anhydride and a base such as, for example, TEA;

Step (ii): deprotection of the amine; the reaction is performed in a polar solvent such as a DCM/MeOH mixture in the presence of a base such as, for example, piperidine;

Step (iii): activation of the carboxylic acid as a NHS ester; the reaction is performed in a polar aprotic solvent such as DCM by treatment with NHS in the presence of a coupling agent such as, for example, EDC;

Step (iv): peptide coupling between the dipeptide and the NHS ester; the reaction is performed in a polar aprotic solvent such as a DCM/CH$_3$CN mixture;

Step (v): deprotection using a solution of hydrochloric acid (for example solution in dioxane) or of trifluoroacetic acid.

NHS esters of Fmoc-L-amino acids are commercially available; the mono-protected diamines are commercially available for n=2 to 4 and R$_{17}$ and R$_{18}$=H or Me independently of each other; the azido carboxylic acids may be prepared according to the schemes described for linker precursor LP$_{14}$.

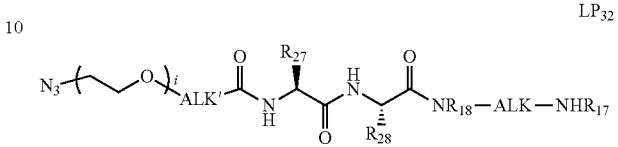

LP$_{32}$ prepared according to the scheme below:

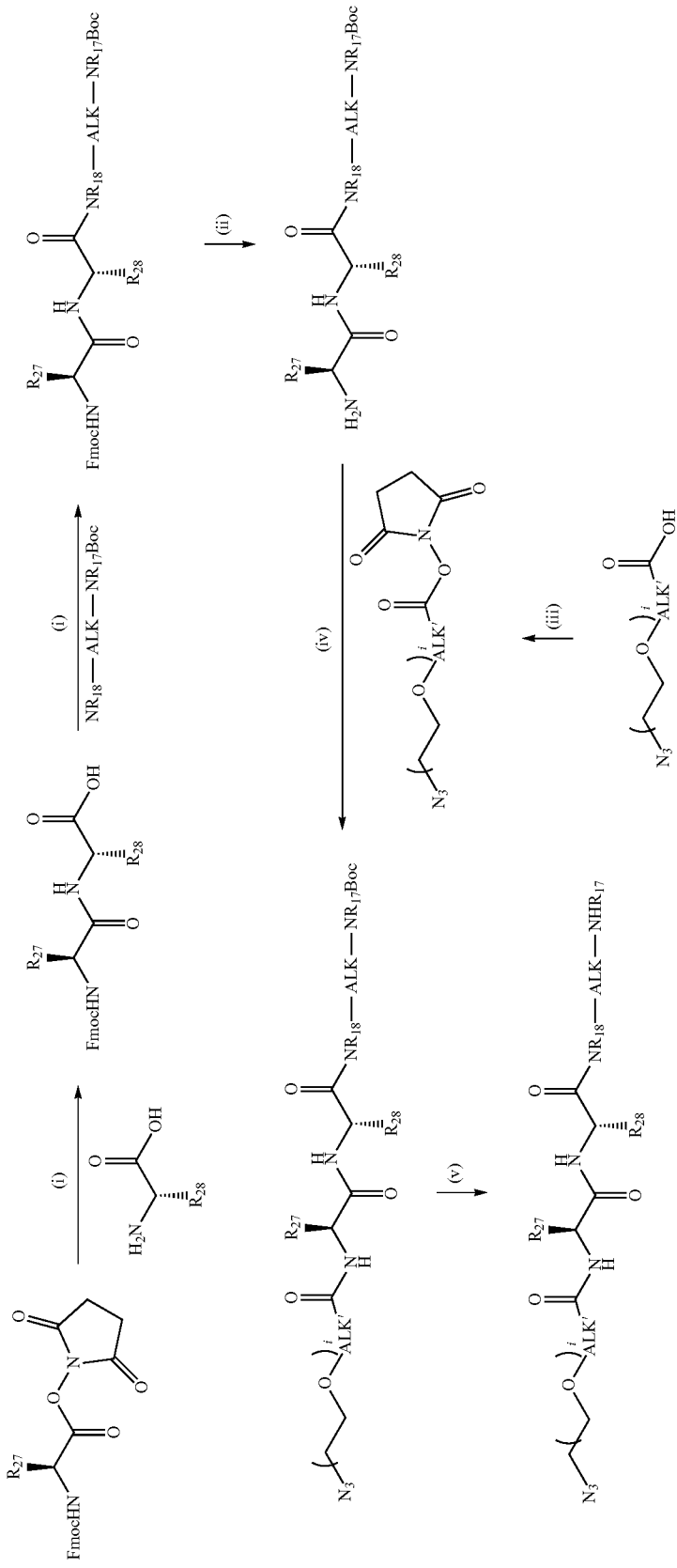

Step (i): peptide coupling; the reaction is performed in a polar solvent such as a DME/THF/H$_2$O mixture in the presence of a base such as sodium bicarbonate or in a polar solvent such as DCM in the presence of a coupling reagent such as propylphosphonic anhydride and a base such as, for example, TEA;

Step (ii): deprotection of the amine; the reaction is performed in a polar solvent such as a DCM/MeOH mixture in the presence of a base such as, for example, piperidine;

Step (iii): activation of the carboxylic acid as a NHS ester; the reaction is performed in a polar aprotic solvent such as DCM by treatment with NHS in the presence of a coupling agent such as, for example, supported DCC;

Step (iv): peptide coupling between the dipeptide and the NHS ester; the reaction is performed in a polar aprotic solvent such as a DCM/CH$_3$CN mixture;

Step (v): deprotection using a solution of hydrochloric acid (for example solution in dioxane) or of trifluoroacetic acid.

NHS esters of Fmoc-L-amino acids are commercially available; the mono-protected diamines are commercially available for n=2 to 4 and $R_{17}$ and $R_{18}$=H or Me independently of each other; azido PEG carboxylic acids may be prepared according to the schemes described for linker precursor $LP_{15}$.

LP$_{33}$

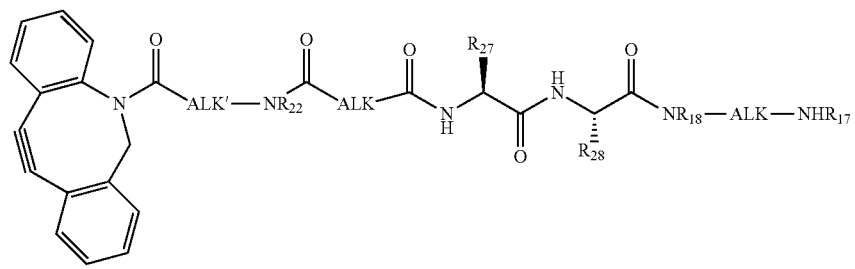

prepared according to the scheme below:

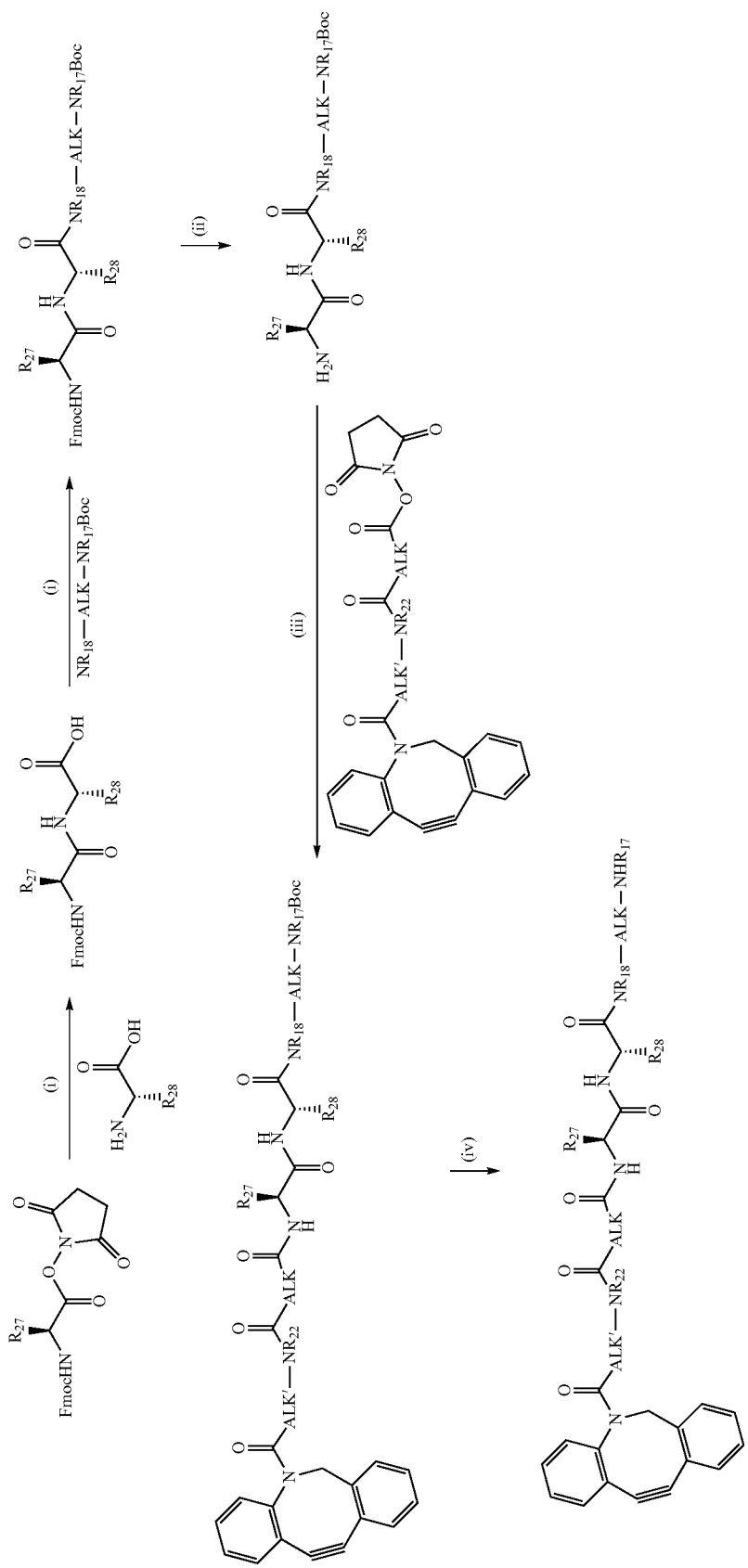

Step (i): peptide coupling; the reaction is performed in a polar solvent such as a DME/THF/H$_2$O mixture in the presence of a base such as sodium bicarbonate or in a polar solvent such as DCM in the presence of a coupling reagent such as propylphosphonic anhydride and a base such as, for example, TEA;

Step (ii): deprotection of the amine; the reaction is performed in a polar solvent such as a DCM/MeOH mixture in the presence of a base such as, for example, piperidine;

Step (iii): peptide coupling between the dipeptide and the NHS ester; the reaction is performed in a polar aprotic solvent such as a DCM/CH$_3$CN mixture;

Step (iv): deprotection using a solution of hydrochloric acid (for example solution in dioxane) or of trifluoroacetic acid.

NHS esters of Fmoc-L-amino acids are commercially available; the mono-protected diamines are commercially available for n=2 to 4 and R$_{17}$ and R$_{18}$=H or Me independently of each other; cyclooctyne linkers activated as NHS esters may be prepared according to the schemes described for linker precursor LP$_{16}$.

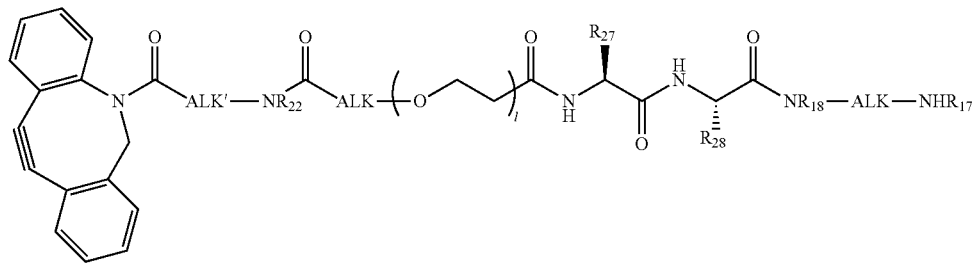

LP$_{34}$ prepared according to the scheme below:

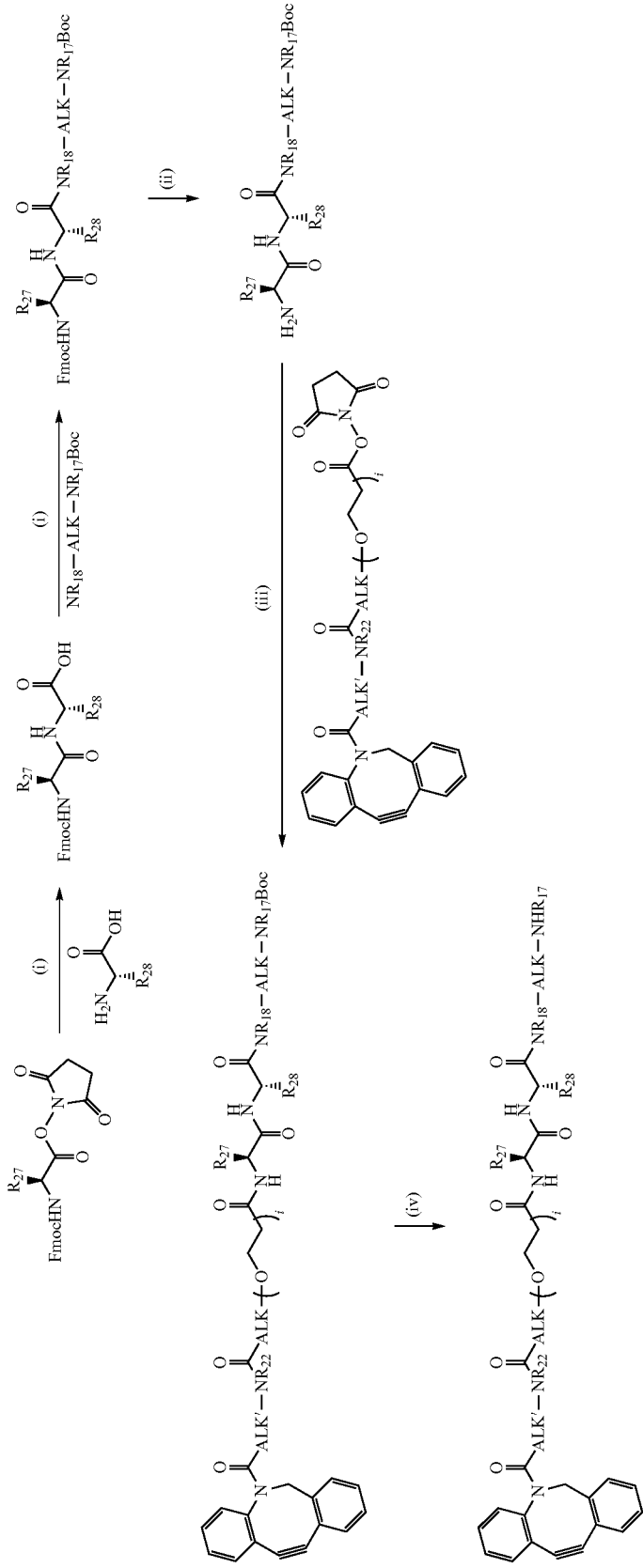

Step (i): peptide coupling; the reaction is performed in a polar solvent such as a DME/THF/H$_2$O mixture in the presence of a base such as sodium bicarbonate or in a polar solvent such as DCM in the presence of a coupling reagent such as propylphosphonic anhydride and a base such as, for example, TEA;

Step (ii): deprotection of the amine; the reaction is performed in a polar solvent such as a DCM/MeOH mixture in the presence of a base such as, for example, piperidine;

Step (iii): peptide coupling between the dipeptide and the NHS ester; the reaction is performed in a polar aprotic solvent such as a DCM/CH$_3$CN mixture;

Step (iv): deprotection using a solution of hydrochloric acid (for example solution in dioxane) or of trifluoroacetic acid.

NHS esters of Fmoc-L-amino acids are commercially available; the mono-protected diamines are commercially available for n=2 to 4 and R$_{17}$ and R$_{18}$=H or Me independently of each other; cyclooctyne linkers activated as NHS esters may be prepared according to the schemes described for linker precursor LP$_{17}$.

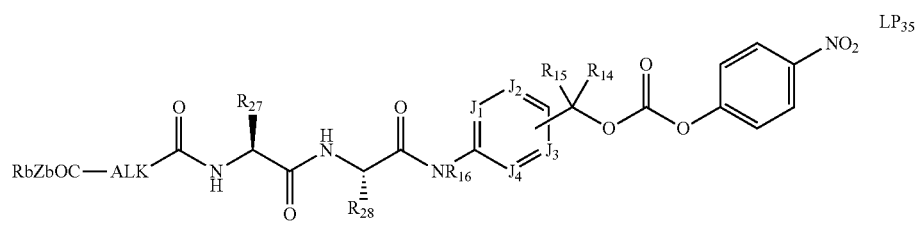

prepared according to the scheme below:

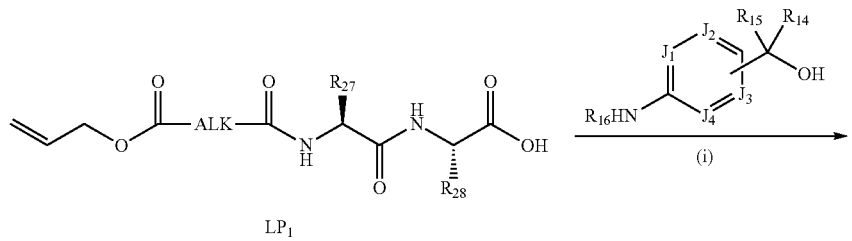

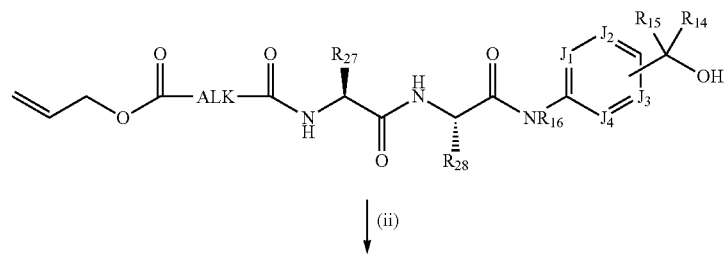

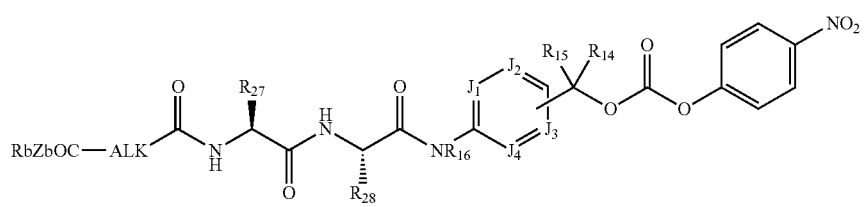

Step (i): peptide coupling between the linker precursor LP₁ and an aniline derivative; the reaction is performed in a polar solvent such as a DCM/MeOH mixture in the presence of a coupling agent such as, for example, EEDQ;

Step (ii): activation of the benzylic alcohol as a p-nitrophenyl-carbonate by treatment with p-nitrophenyl-chloroformate in the presence of a base such as, for example, DIEA.

Many aniline derivatives are commercially available such as, for example, 4-(hydroxymethyl)-aniline (CAS number [623-04-1]), 4-(1-hydroxyethyl)-aniline (racemic (CAS number [14572-89-5]) or enantiopure (R) (CAS number [210754-25-9]) or (S) (CAS number [500229-84-5])), 4-amino-α,α-dimethyl-benzene-methanol (CAS number [23243-04-1]), 4-amino-α-methoxy-α-methyl-benzenemethanol (CAS number [1379318-81-6]), 4-amino-α-methyl-α-trifluoromethyl-benzenemethanol (CAS number [851652-56-7]), 2-amino-benzenemethanol (CAS number [5344-90-1]), 2-amino-α-methyl-benzenemethanol (racemic (CAS number [10517-50-7]) or enantiopure (R) (CAS number [3205-21-8]) or (S) (CAS number [3205-21-8])), 6-amino-3-pyridinemethanol (CAS number [113293-71-3]), 6-amino-α-methyl-3-pyridinemethanol (CAS number [1335054-83-5]), 6-amino-α-ethyl-3-pyridinemethanol (CAS number [1355225-85-2]), 6-amino-α,α-dimethyl-3-pyridinemethanol (CAS number [843646-03-8]), 5-amino-3-pyridinemethanol (CAS number [873651-92-4]), 2-amino-3-pyridinemethanol (CAS number [23612-57-9]), 2-amino-α-methyl-3-pyridinemethanol (racemic (CAS number [869567-91-9]) or enantiopure (R) (CAS number [936718-01-3]) or (S) (CAS number [936718-00-2])), 2-amino-α-ethyl-3-pyridinemethanol (CAS number [914223-90-8]), 2-amino-α,α-dimethyl-3-pyridinemethanol (CAS number [213666-96-7]), 3-amino-4-pyridinemethanol (CAS number [152398-05-5]), 3-amino-α-methyl-4-pyridinemethanol (CAS number [1242470-88-7]), 3-amino-α,α-methyl-4-pyridinemethanol (CAS number [13357-81-8]), 4-amino-3-pyridinemethanol (CAS number [138116-34-4]), 4-amino-α-methyl-3-pyridinemethanol (CAS number [741223-49-4]), 4-amino-α,α-methyl-3-pyridinemethanol (CAS number [1339013-26-1]), 3-amino-2-pyridinemethanol (CAS number [52378-63-9]), 3-amino-α-methyl-2-pyridinemethanol (CAS number [954240-54-1]), 3-amino-α,α-methyl-2-pyridinemethanol (CAS number [899438-57-4]).

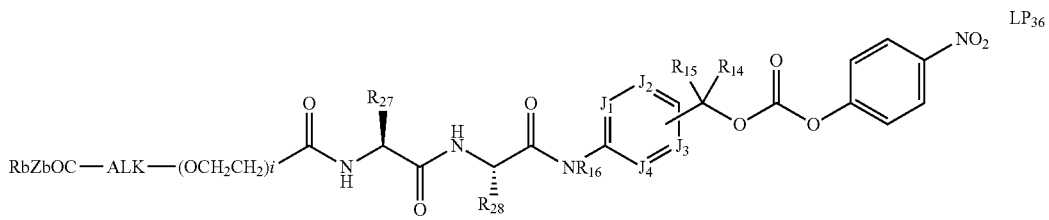

prepared according to the scheme below:

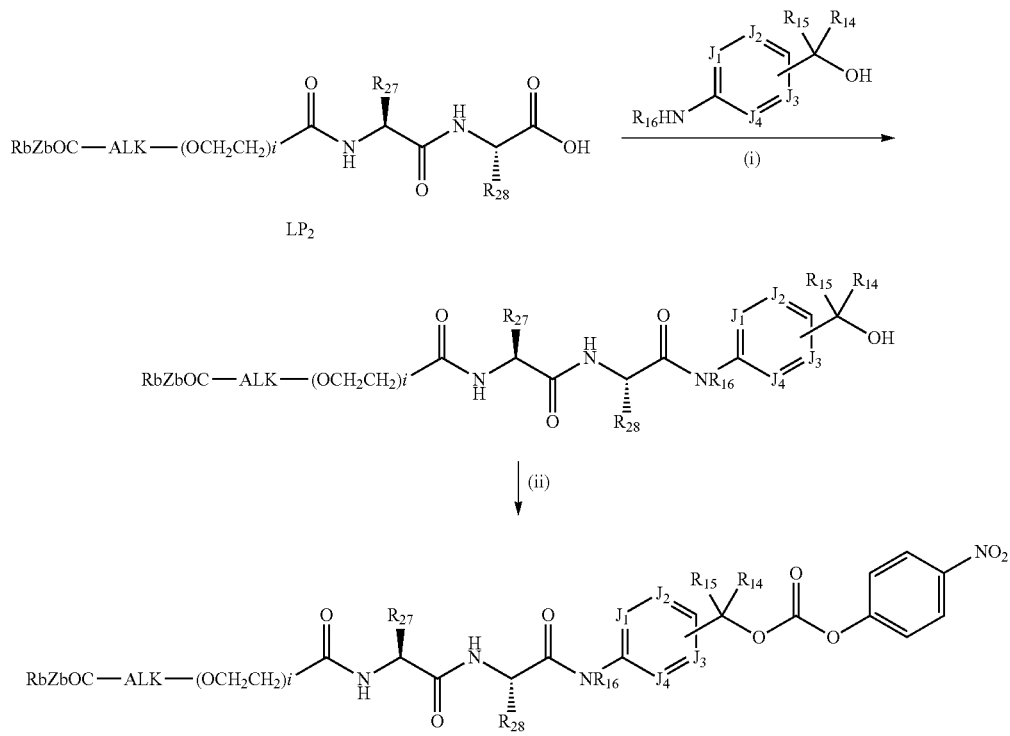

Step (i): peptide coupling between the linker precursor LP$_2$ and an aniline derivative; the reaction is performed in a polar solvent such as a DCM/MeOH mixture in the presence of a coupling agent such as, for example, EEDQ;

Step (ii): activation of the benzylic alcohol as a p-nitrophenyl-carbonate by treatment with p-nitrophenyl-chloroformate in the presence of a base such as, for example, DIEA.

Many aniline derivatives are commercially available such as, for example, those listed for LP$_{35}$.

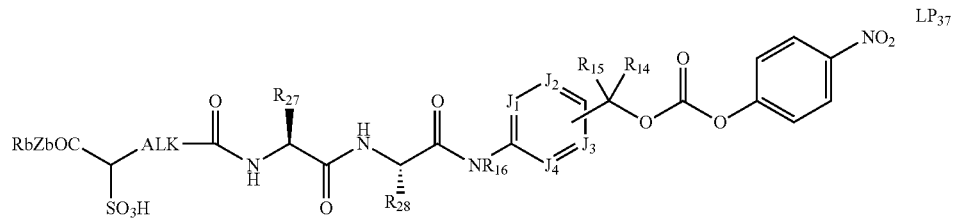

prepared according to the scheme below:

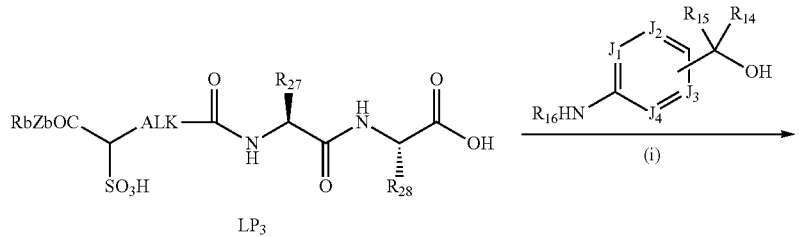

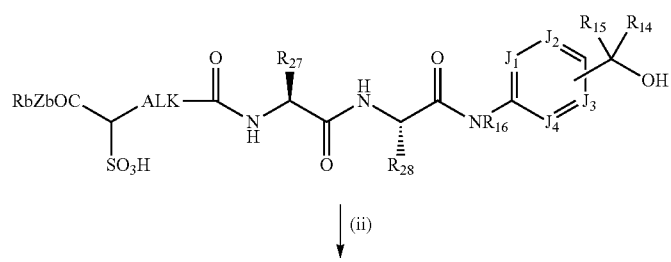

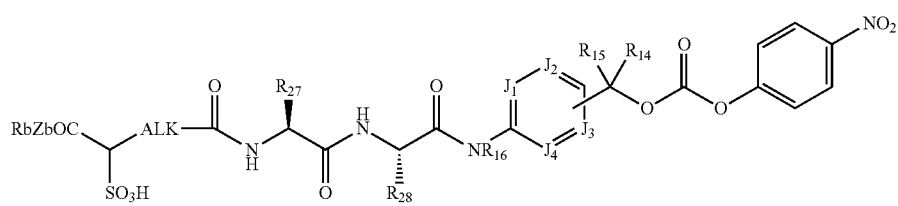

Step (i): peptide coupling between the linker precursor LP₃ and an aniline derivative; the reaction is performed in a polar solvent such as a DCM/MeOH mixture in the presence of a coupling agent such as, for example, EEDQ;

Step (ii): activation of the benzylic alcohol as a p-nitro-phenyl-carbonate by treatment with p-nitrophenyl-chloroformate in the presence of a base such as, for example, DIEA.

Many aniline derivatives are commercially available such as, for example, those listed for LP₃₅.

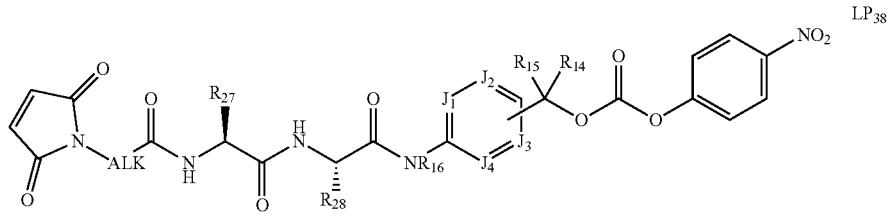

LP₃₈ prepared according to the scheme below:

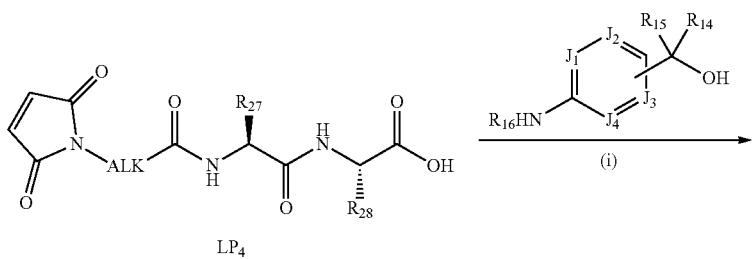

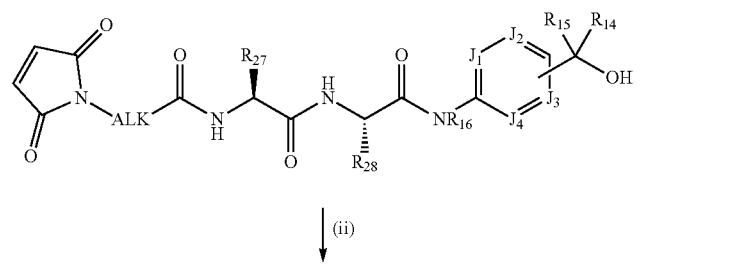

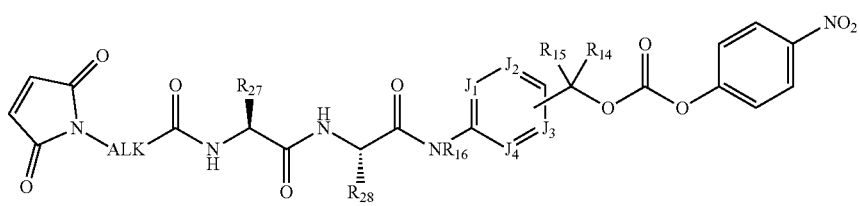

Step (i): peptide coupling between the linker precursor LP₄ and an aniline derivative; the reaction is performed in a polar solvent such as a DCM/MeOH mixture in the presence of a coupling agent such as, for example, EEDQ;

Step (ii): activation of the benzylic alcohol as a p-nitro-phenyl-carbonate by treatment with p-nitrophenyl-chloroformate in the presence of a base such as, for example, DIEA.

Many aniline derivatives are commercially available such as, for example, those listed for LP₃₅.

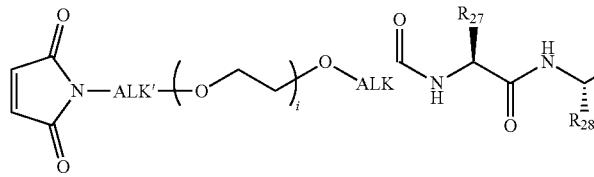
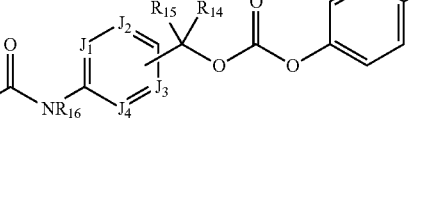

prepared according to the scheme below:

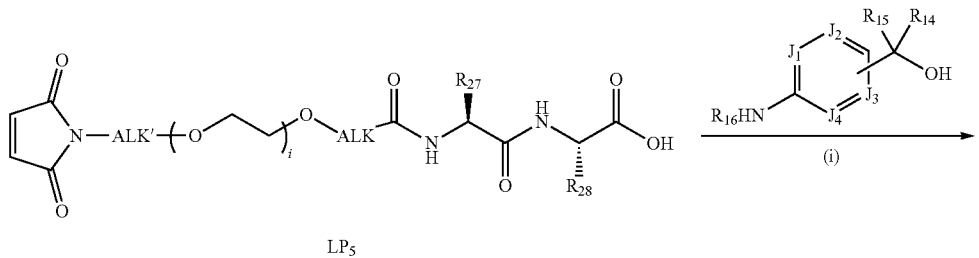

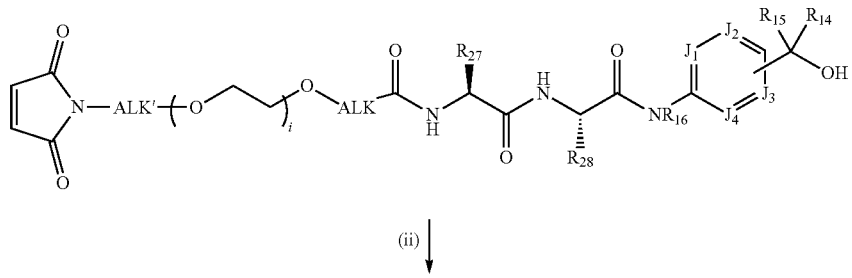

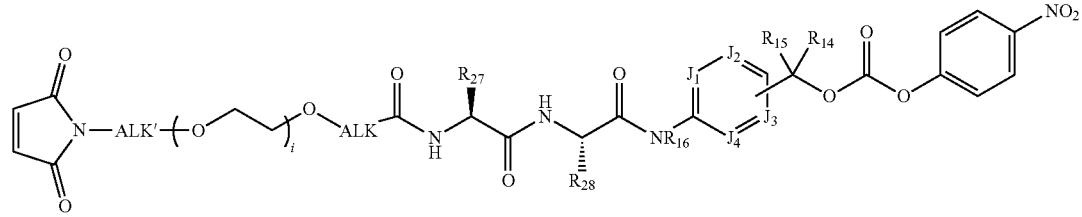

Step (i): peptide coupling between the linker precursor LP$_5$ and an aniline derivative; the reaction is performed in a polar solvent such as a DCM/MeOH mixture in the presence of a coupling agent such as, for example, EEDQ;

Step (ii): activation of the benzylic alcohol as a p-nitrophenyl-carbonate by treatment with p-nitrophenyl-chloroformate in the presence of a base such as, for example, DIEA.

Many aniline derivatives are commercially available such as, for example, those listed for LP$_{35}$.

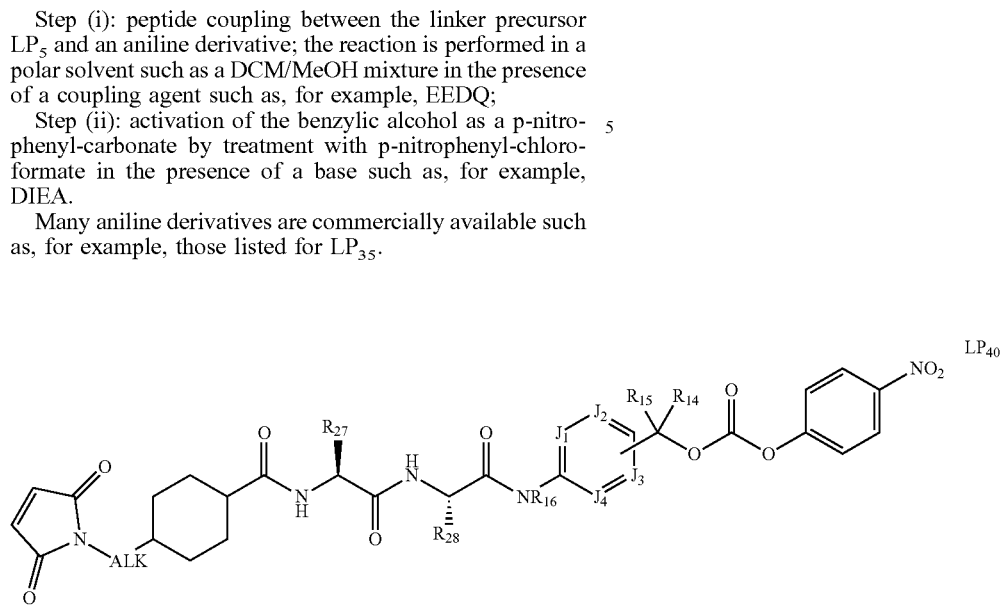

prepared according to the scheme below:

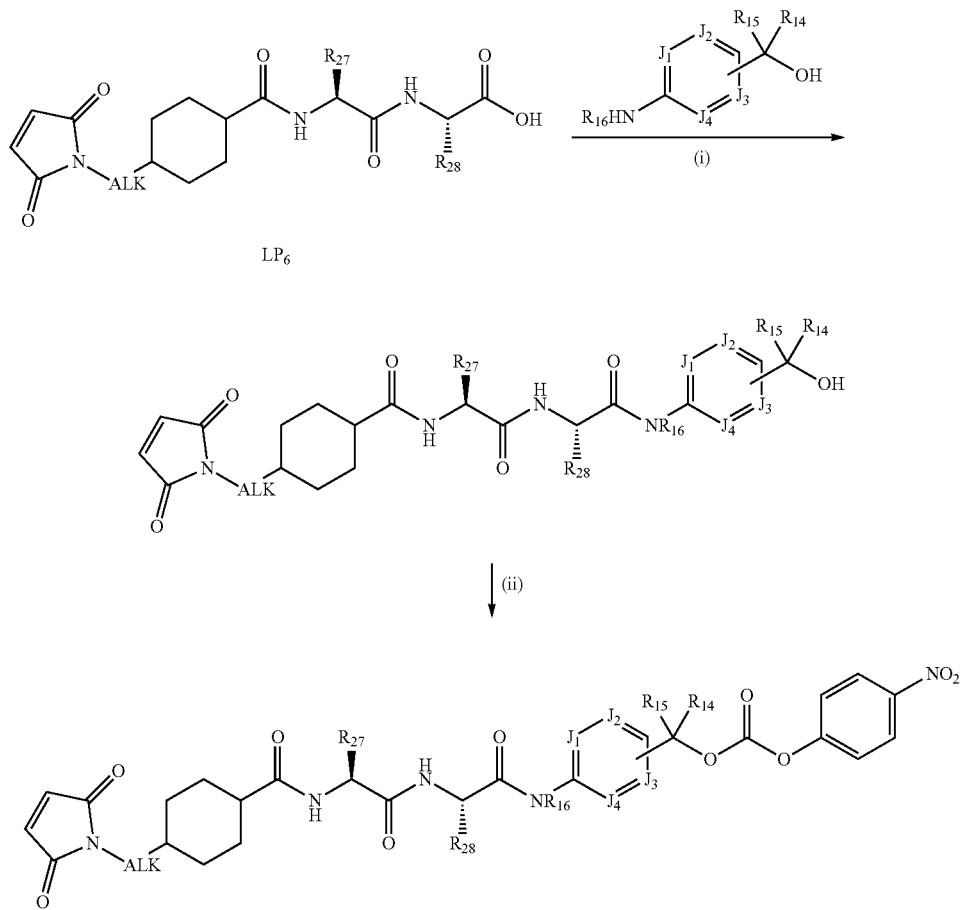

Step (i): peptide coupling between the linker precursor LP$_6$ and an aniline derivative; the reaction is performed in a polar solvent such as a DCM/MeOH mixture in the presence of a coupling agent such as, for example, EEDQ;

Step (ii): activation of the benzylic alcohol as a p-nitro-phenyl-carbonate by treatment with p-nitrophenyl-chloroformate in the presence of a base such as, for example, DIEA.

Many aniline derivatives are commercially available such as, for example, those listed for LP$_{35}$.

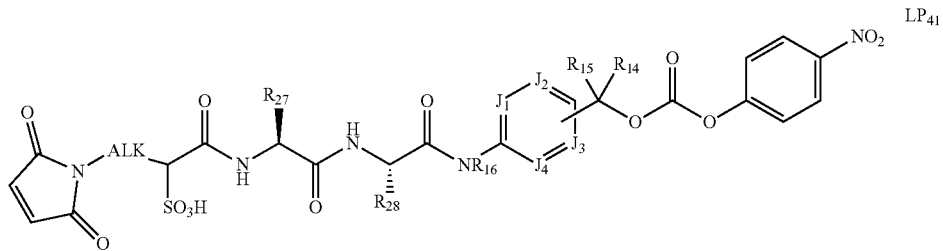

prepared according to the scheme below:

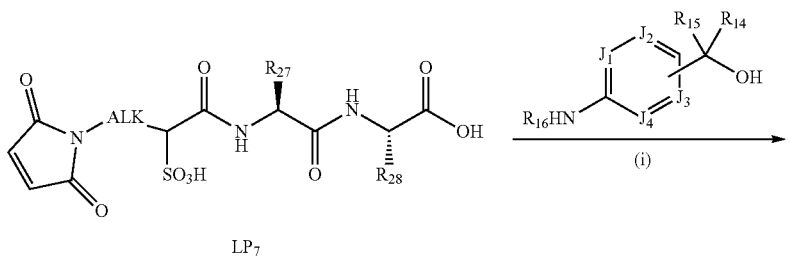

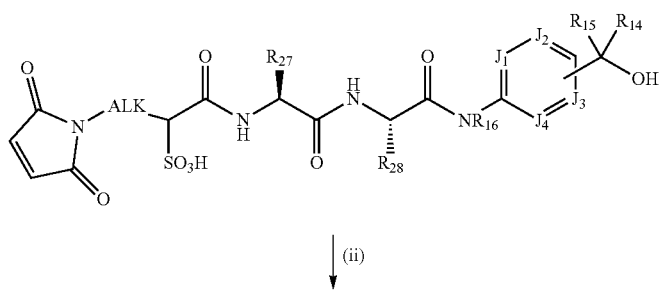

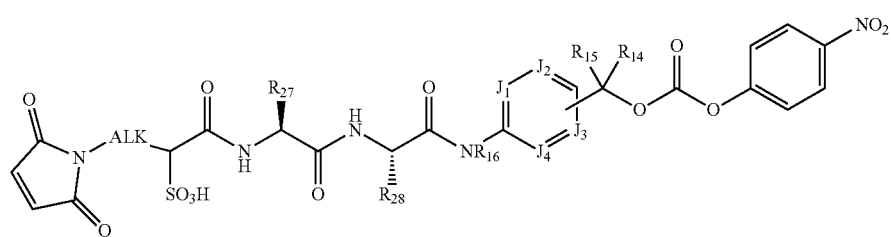

Step (i): peptide coupling between the linker precursor LP$_7$ and an aniline derivative; the reaction is performed in a polar solvent such as a DCM/MeOH mixture in the presence of a coupling agent such as, for example, EEDQ;

Step (ii): activation of the benzylic alcohol as a p-nitrophenyl-carbonate by treatment with p-nitrophenyl-chloroformate in the presence of a base such as, for example, DIEA.

Many aniline derivatives are commercially available such as, for example, those listed for LP$_{35}$.

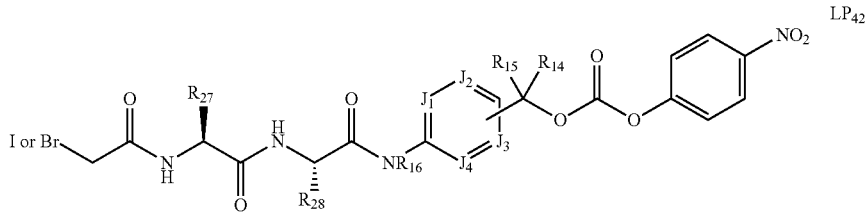

prepared according to the scheme below:

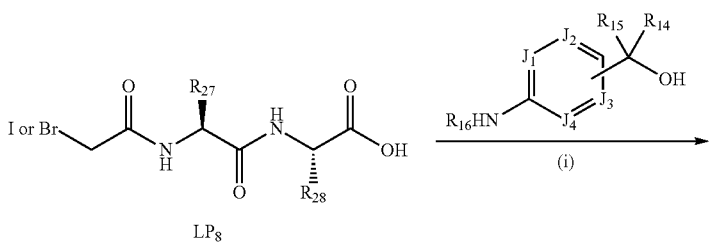

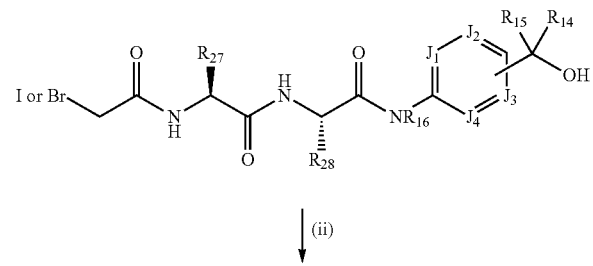

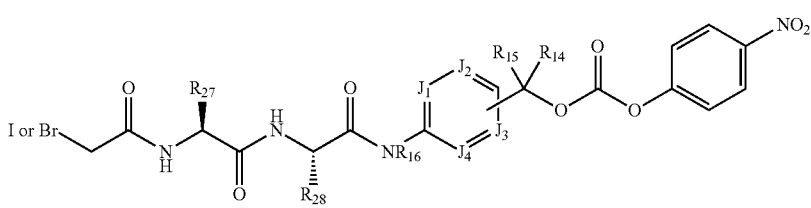

Step (i): peptide coupling between the linker precursor LP$_8$ and an aniline derivative; the reaction is performed in a polar solvent such as a DCM/MeOH mixture in the presence of a coupling agent such as, for example, EEDQ;

Step (ii): activation of the benzylic alcohol as a p-nitrophenyl-carbonate by treatment with p-nitrophenyl-chloroformate in the presence of a base such as, for example, DIEA.

Many aniline derivatives are commercially available such as, for example, those listed for LP$_{35}$.

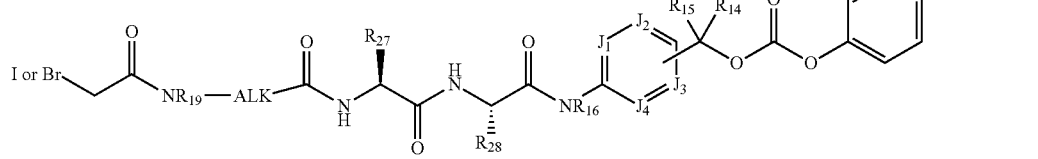

prepared according to the scheme below:

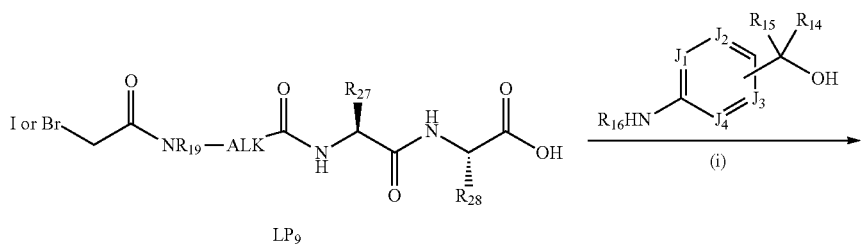

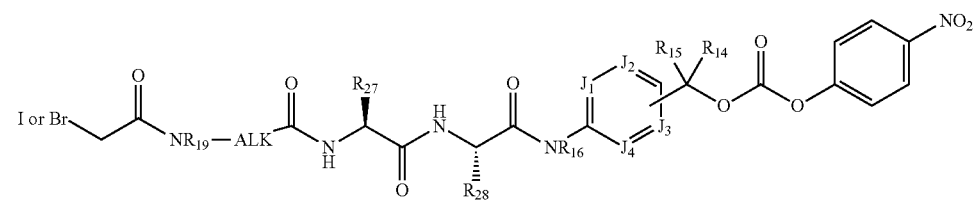

Step (i): peptide coupling between the linker precursor LP$_9$ and an aniline derivative; the reaction is performed in a polar solvent such as a DCM/MeOH mixture in the presence of a coupling agent such as, for example, EEDQ;

Step (ii): activation of the benzylic alcohol as a p-nitrophenyl-carbonate by treatment with p-nitrophenyl-chloroformate in the presence of a base such as, for example, DIEA.

Many aniline derivatives are commercially available such as, for example, those listed for LP$_{35}$.

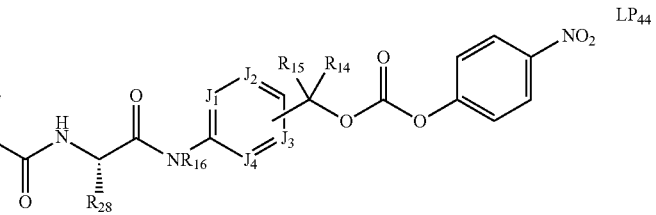

prepared according to the scheme below:

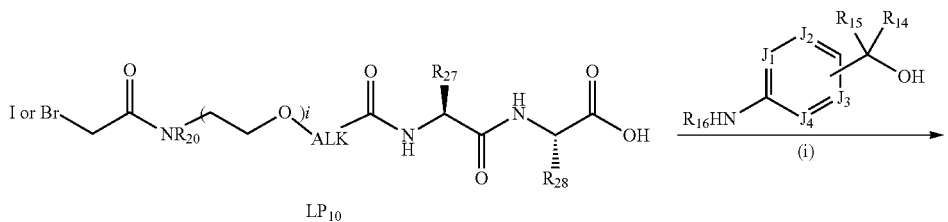

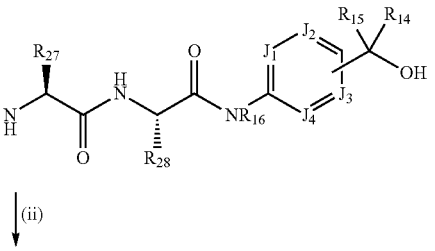

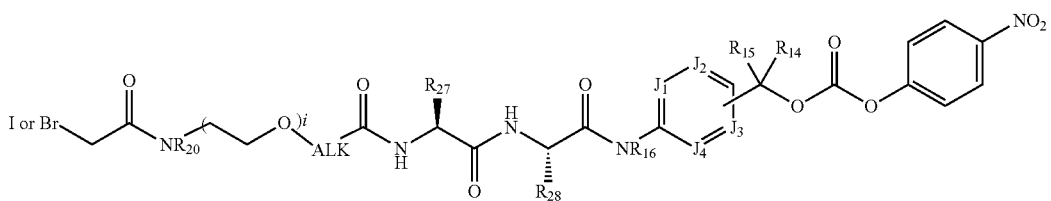

Step (i): peptide coupling between the linker precursor $LP_{10}$ and an aniline derivative; the reaction is performed in a polar solvent such as a DCM/MeOH mixture in the presence of a coupling agent such as, for example, EEDQ;

Step (ii): activation of the benzylic alcohol as a p-nitrophenyl-carbonate by treatment with p-nitrophenyl-chloroformate in the presence of a base such as, for example, DIEA.

Many aniline derivatives are commercially available such as, for example, those listed for $LP_{35}$.

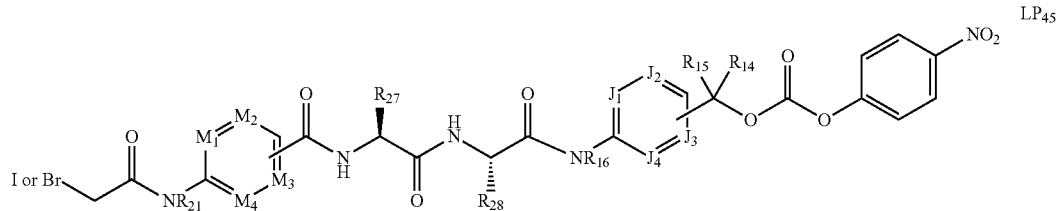

prepared according to the scheme below:

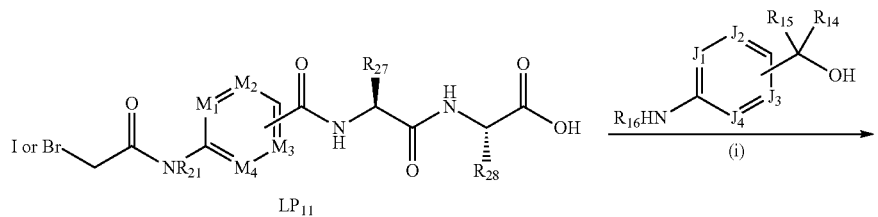

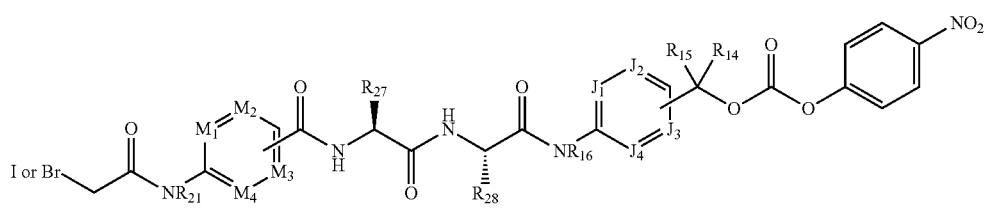

Step (i): peptide coupling between the linker precursor LP$_{11}$ and an aniline derivative; the reaction is performed in a polar solvent such as a DCM/MeOH mixture in the presence of a coupling agent such as, for example, EEDQ;

Step (ii): activation of the benzylic alcohol as a p-nitro-phenyl-carbonate by treatment with p-nitrophenyl-chloroformate in the presence of a base such as, for example, DIEA.

Many aniline derivatives are commercially available such as, for example, those listed for LP$_{35}$.

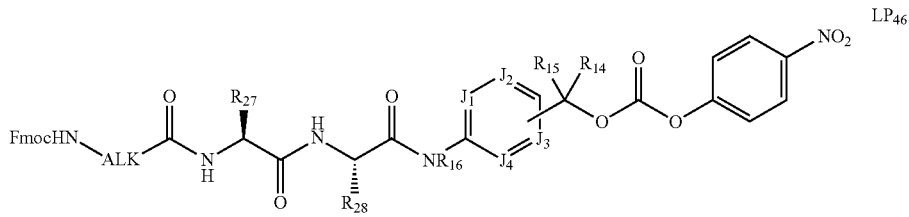

prepared according to the scheme below:

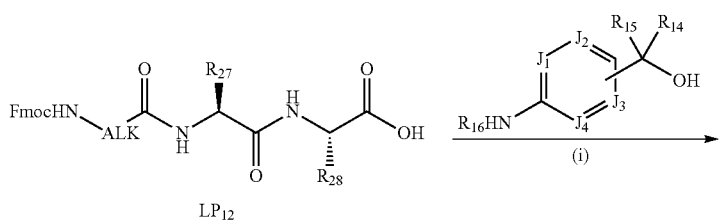

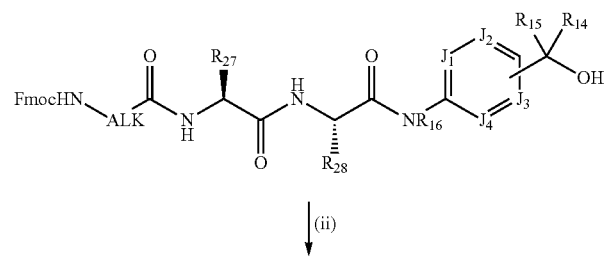

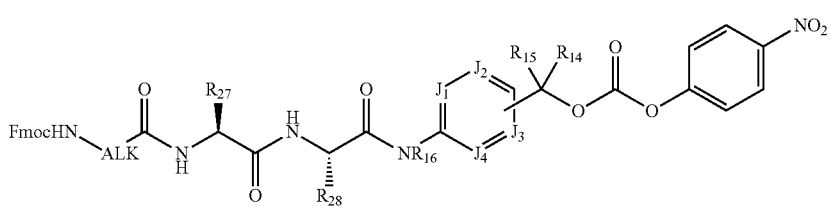

Step (i): peptide coupling between the linker precursor LP$_{12}$ and an aniline derivative; the reaction is performed in a polar solvent such as a DCM/MeOH mixture in the presence of a coupling agent such as, for example, EEDQ;

Step (ii): activation of the benzylic alcohol as a p-nitrophenyl-carbonate by treatment with p-nitrophenyl-chloroformate in the presence of a base such as, for example, DIEA.

Many aniline derivatives are commercially available such as, for example, those listed for LP$_{35}$.

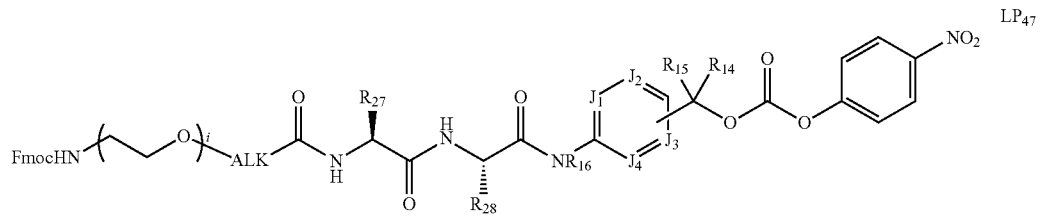

prepared according to the scheme below:

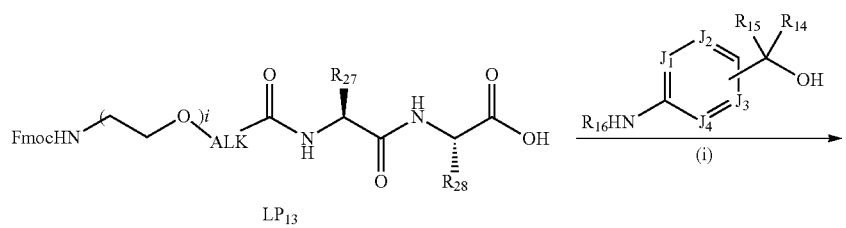

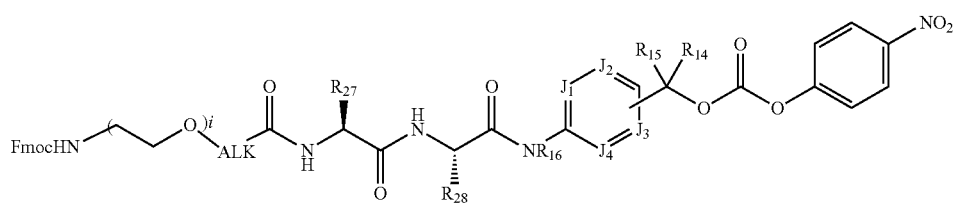

Step (i): peptide coupling between the linker precursor LP$_{13}$ and an aniline derivative; the reaction is performed in a polar solvent such as a DCM/MeOH mixture in the presence of a coupling agent such as, for example, EEDQ;

Step (ii): activation of the benzylic alcohol as a p-nitrophenyl-carbonate by treatment with p-nitrophenyl-chloroformate in the presence of a base such as, for example, DIEA.

Many aniline derivatives are commercially available such as, for example, those listed for LP$_{35}$.

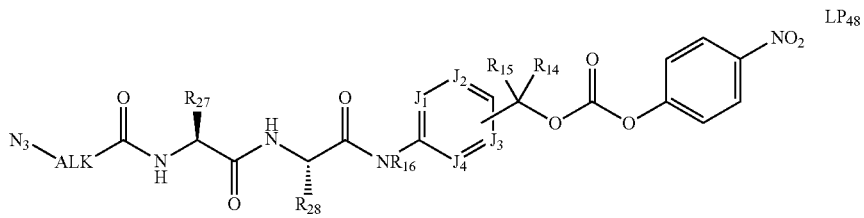

LP$_{48}$ prepared according to the scheme below:

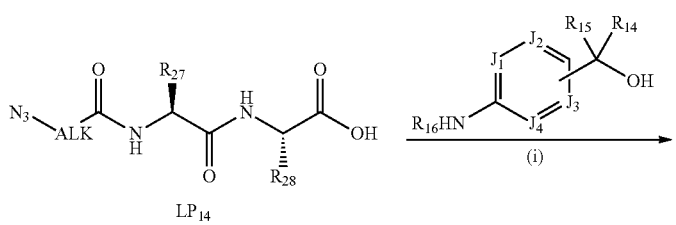

LP$_{14}$

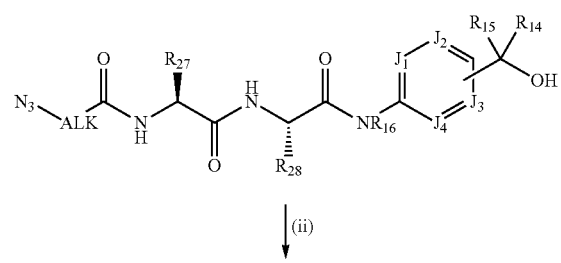

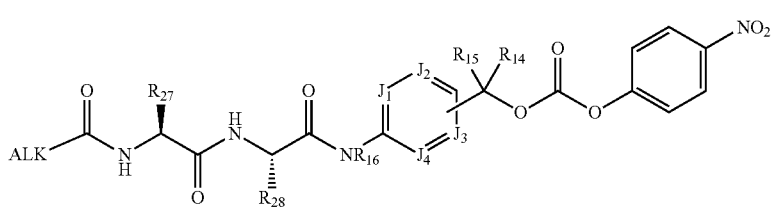

Step (i): peptide coupling between the linker precursor LP$_{14}$ and an aniline derivative; the reaction is performed in a polar solvent such as a DCM/MeOH mixture in the presence of a coupling agent such as, for example, EEDQ;

Step (ii): activation of the benzylic alcohol as a p-nitrophenyl-carbonate by treatment with p-nitrophenyl-chloroformate in the presence of a base such as, for example, DIEA.

Many aniline derivatives are commercially available such as, for example, those listed for LP$_{35}$.

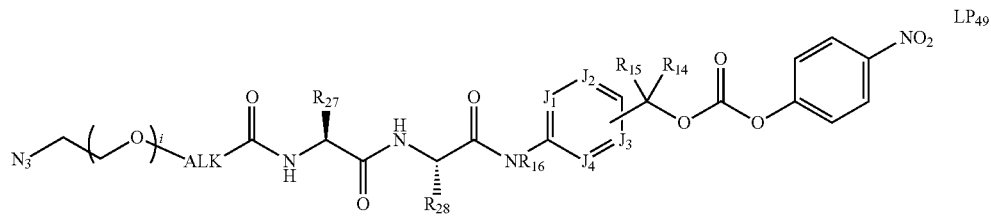

prepared according to the scheme below:

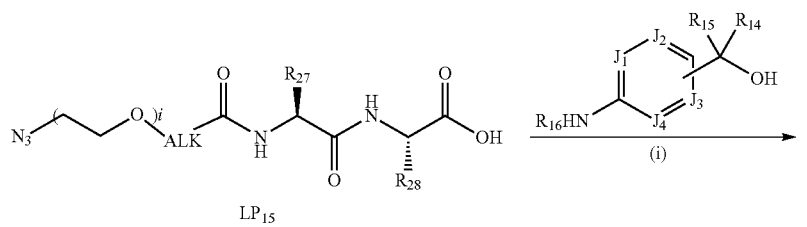

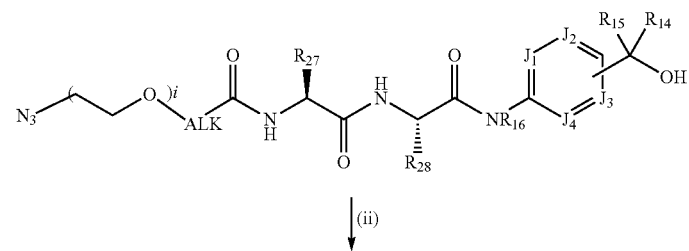

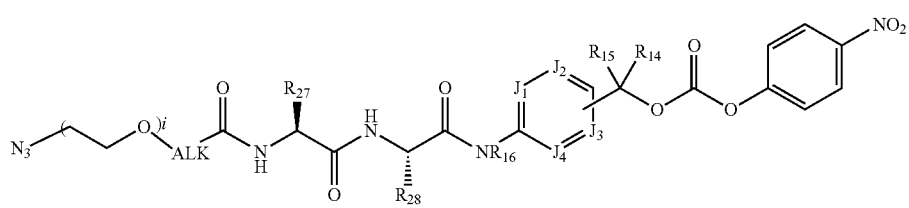

Step (i): peptide coupling between the linker precursor LP$_{15}$ and an aniline derivative; the reaction is performed in a polar solvent such as a DCM/MeOH mixture in the presence of a coupling agents such as, for example, EEDQ;

Step (ii): activation of the benzylic alcohol as a p-nitrophenyl-carbonate by treatment with p-nitrophenyl-chloroformate in the presence of a base such as, for example, DIEA.

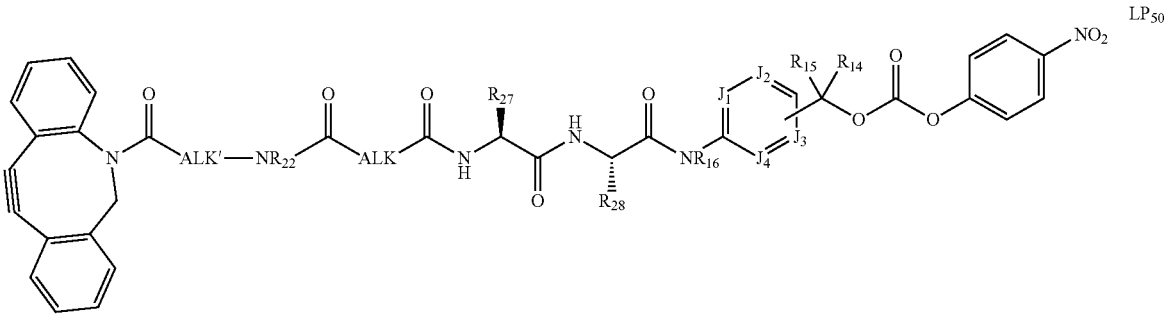

prepared according to the scheme below:

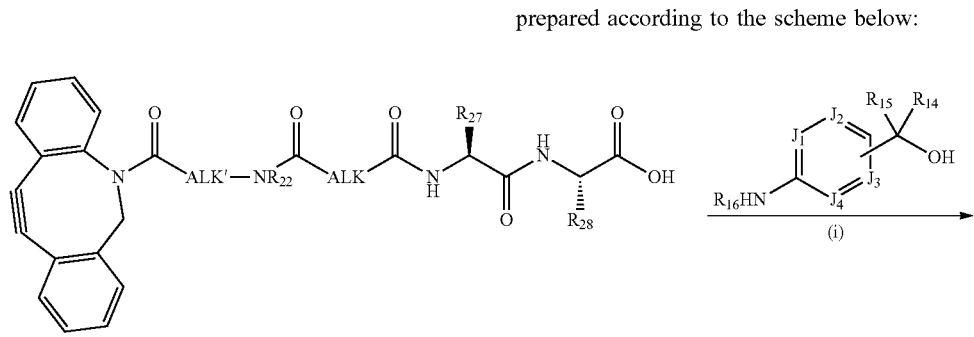

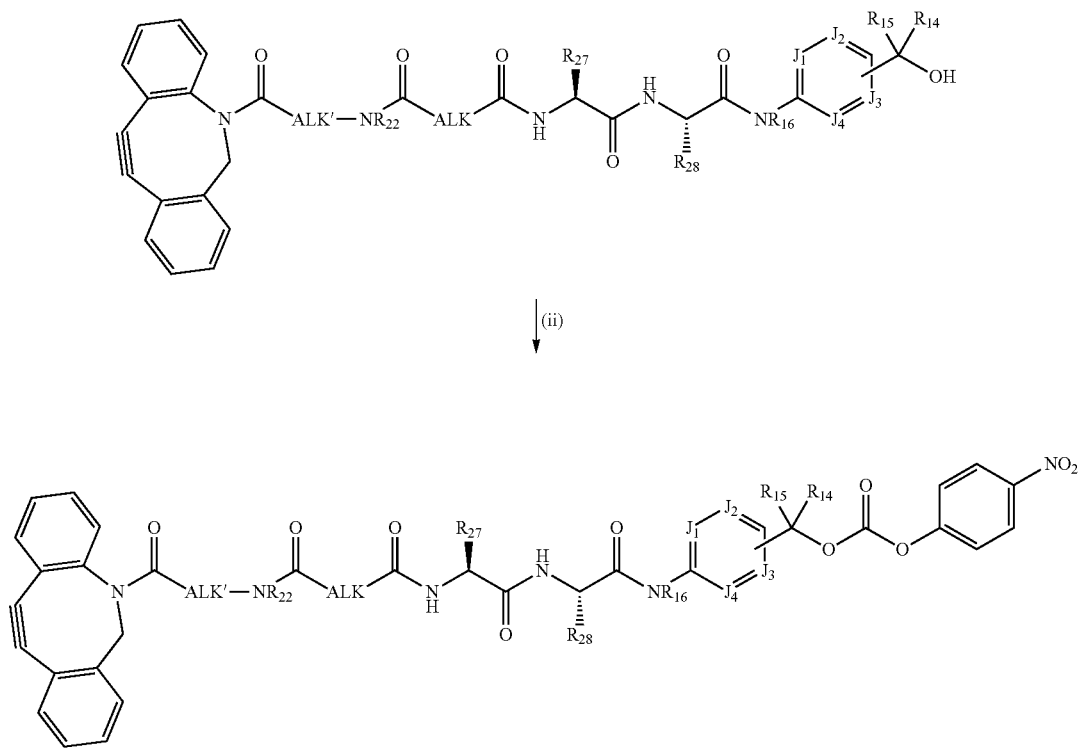

Step (i): peptide coupling between the linker precursor $LP_{16}$ and an aniline derivative; the reaction is performed in a polar solvent such as a DCM/MeOH mixture in the presence of a coupling agent such as, for example, EEDQ;

Step (ii): activation of the benzylic alcohol as a p-nitrophenyl-carbonate by treatment with p-nitrophenyl-chloroformate in the presence of a base such as, for example, DIEA.

Many aniline derivatives are commercially available such as, for example, those listed for $LP_{35}$.

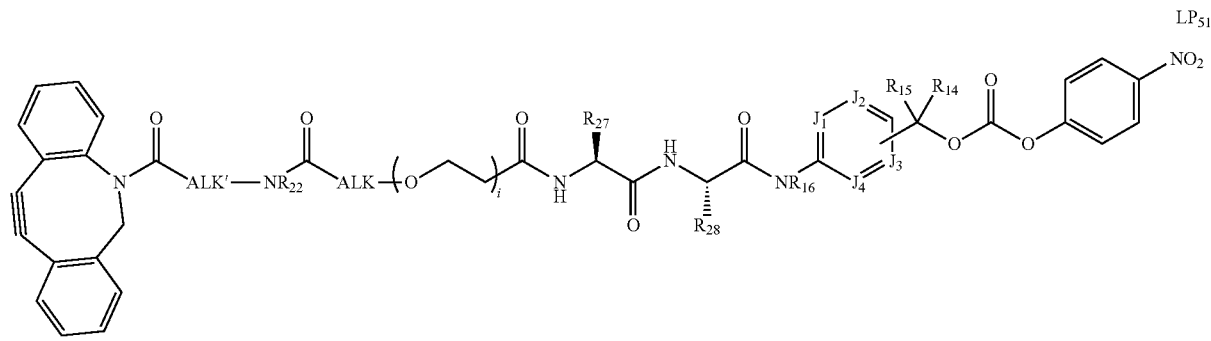

prepared according to the scheme below:

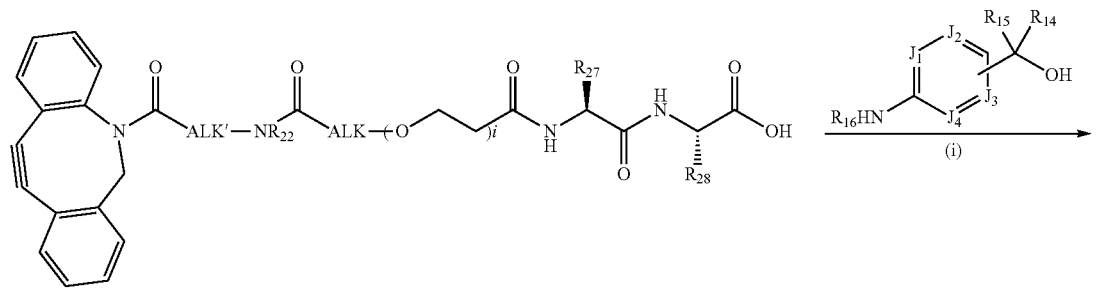

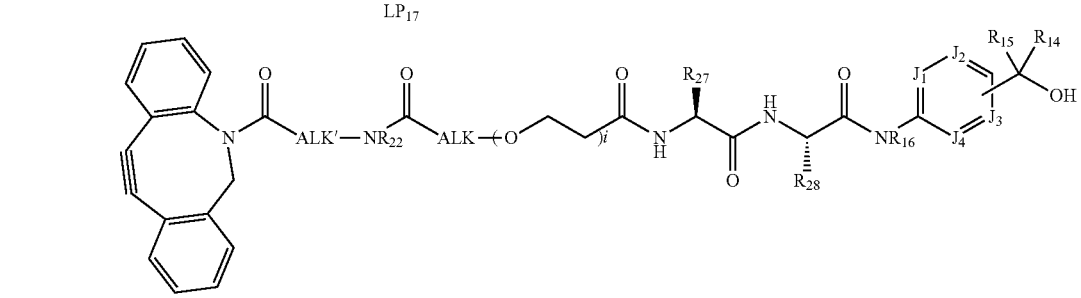

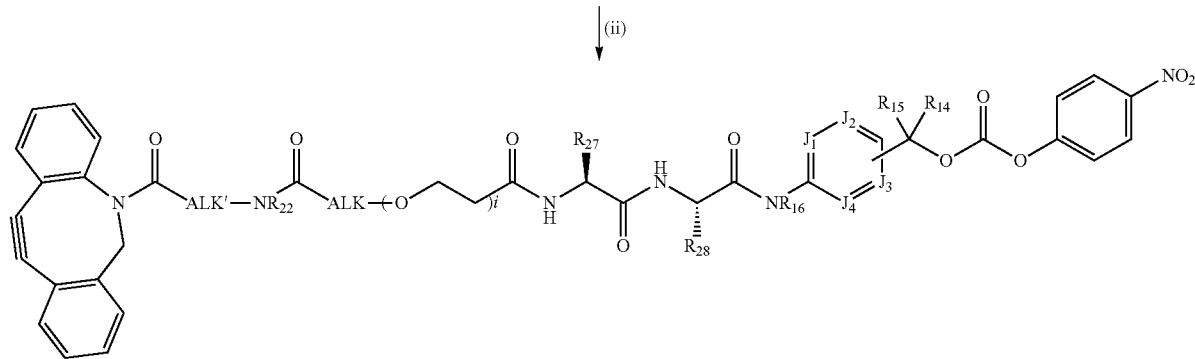

Step (i): peptide coupling between the linker precursor LP$_{17}$ and an aniline derivative; the reaction is performed in a polar solvent such as a DCM/MeOH mixture in the presence of a coupling agent such as, for example, EEDQ;

Step (ii): activation of the benzylic alcohol as a p-nitrophenyl-carbonate by treatment with p-nitrophenyl-chloroformate in the presence of a base such as, for example, DIEA.

Many aniline derivatives are commercially available such as, for example, those listed for LP$_{35}$.

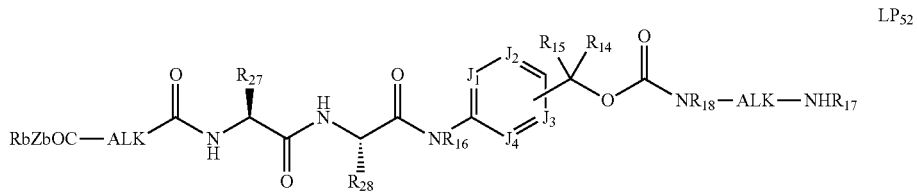

LP$_{52}$ prepared according to the scheme below:

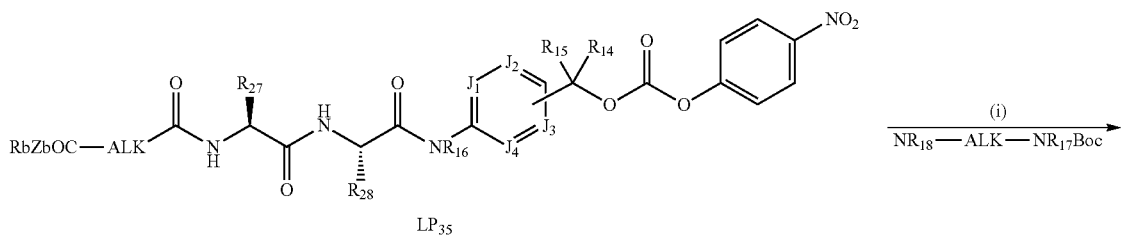

LP$_{35}$

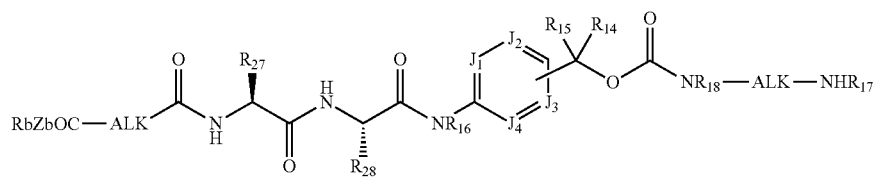

Step (i): formation of the carbamate between the linker precursor LP$_{35}$ and a monoprotected diamine; the reaction is performed in a polar solvent such as CH$_3$CN in the presence of a base such as, for example, DIEA; deprotection using a solution of hydrochloric acid (for example solution in dioxane) or of trifluoroacetic acid.

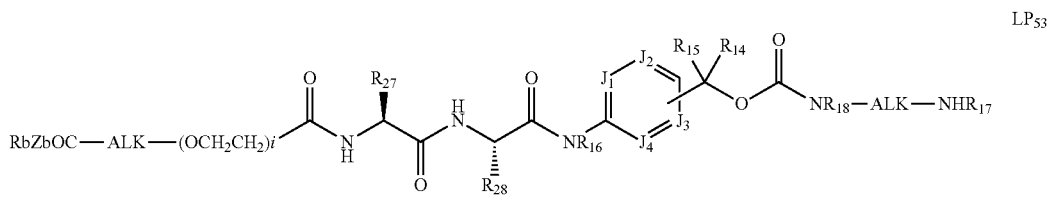

LP$_{53}$ prepared according to the scheme below:

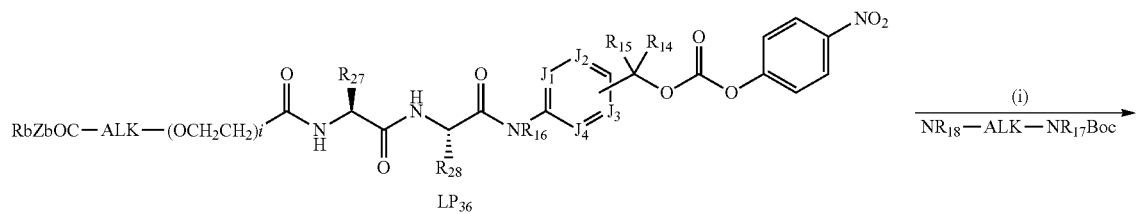

Step (i): formation of the carbamate between the linker precursor LP$_{36}$ and a monoprotected diamine; the reaction is performed in a polar solvent such as CH$_3$CN in the presence of a base such as, for example, DIEA; deprotection using a solution of hydrochloric acid (for example solution in dioxane) or of trifluoroacetic acid.

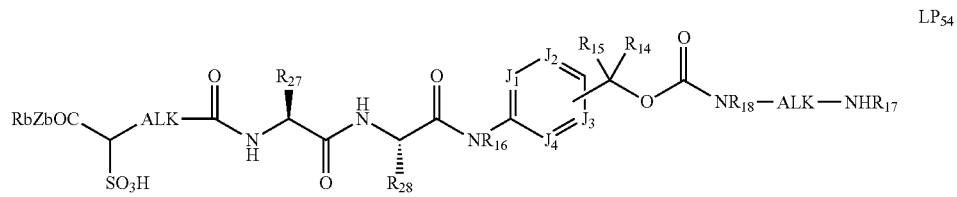

LP$_{54}$ prepared according to the scheme below:

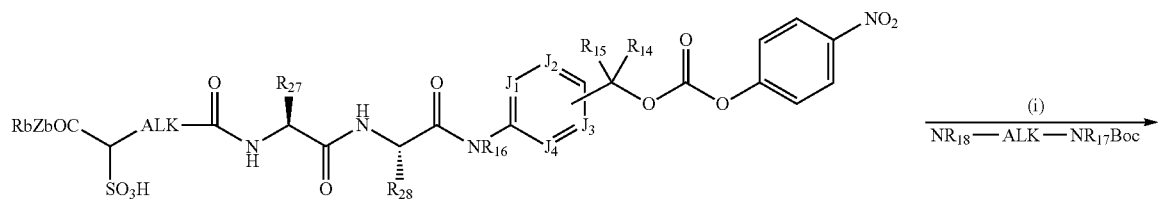

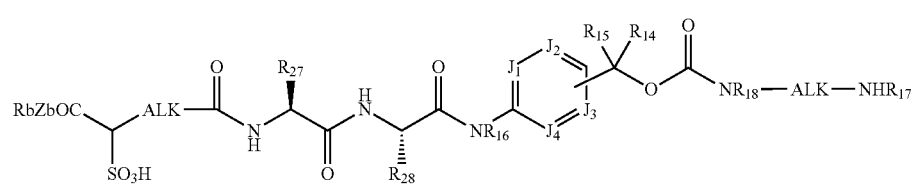

Step (i): formation of the carbamate between the linker precursor LP$_{37}$ and a monoprotected diamine; the reaction is performed in a polar solvent such as CH$_3$CN in the presence of a base such as, for example, DIEA; deprotection using a solution of hydrochloric acid (for example solution in dioxane) or of trifluoroacetic acid.

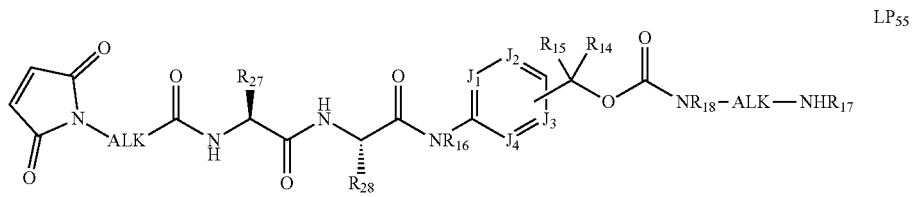

LP$_{55}$ prepared according to the scheme below:

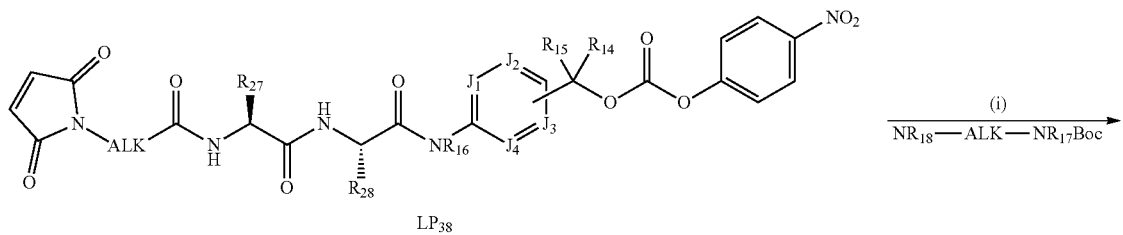

Step (i): formation of the carbamate between the linker precursor LP$_{38}$ and a monoprotected diamine; the reaction is performed in a polar solvent such as CH$_3$CN in the presence of a base such as, for example, DIEA; deprotection using a solution of hydrochloric acid (for example solution in dioxane) or of trifluoroacetic acid.

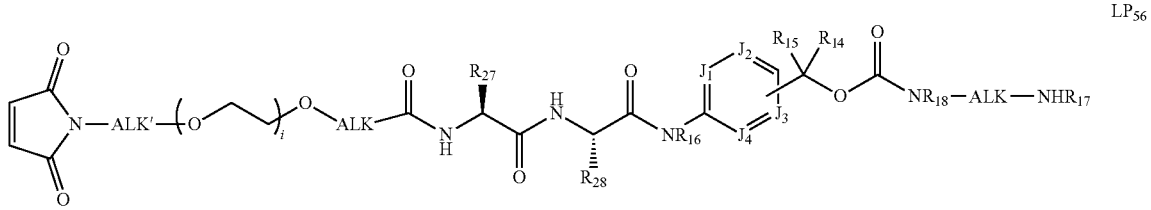

LP$_{56}$ prepared according to the scheme below:

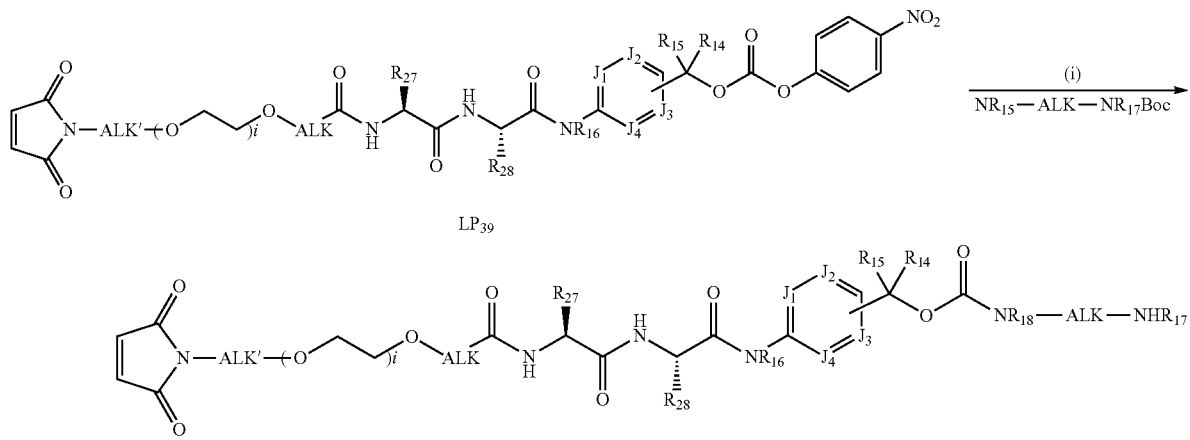

LP$_{39}$

Step (i): formation of the carbamate between the linker precursor LP$_{39}$ and a monoprotected diamine; the reaction is performed in a polar solvent such as CH$_3$CN in the presence of a base such as, for example, DIEA; deprotection using a solution of hydrochloric acid (for example solution in dioxane) or of trifluoroacetic acid.

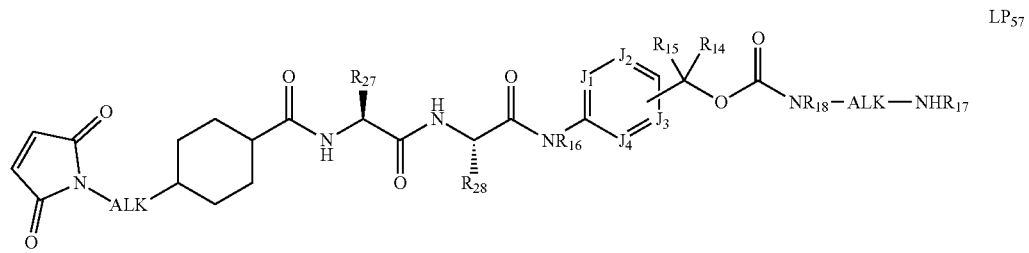

LP$_{57}$

40 prepared according to the scheme below:

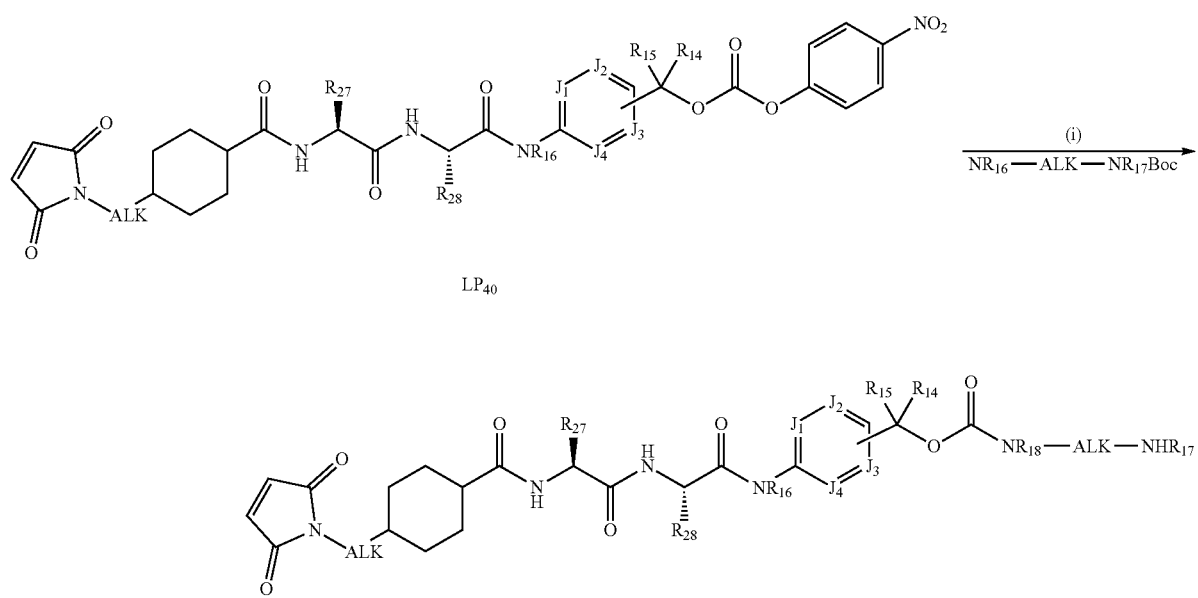

LP$_{40}$

Step (i): formation of the carbamate between the linker precursor LP$_{40}$ and a monoprotected diamine; the reaction is performed in a polar solvent such as CH$_3$CN in the presence of a base such as, for example, DIEA; deprotection using a solution of hydrochloric acid (for example solution in dioxane) or of trifluoroacetic acid.

LP$_{58}$

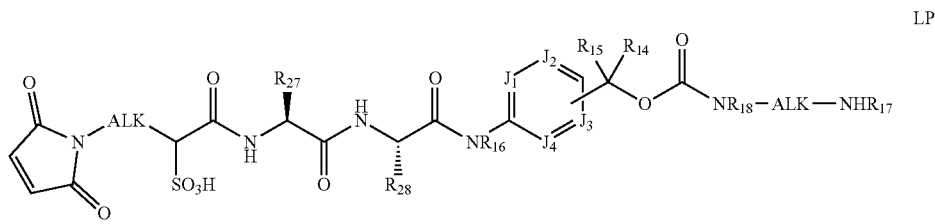

prepared according to the scheme below:

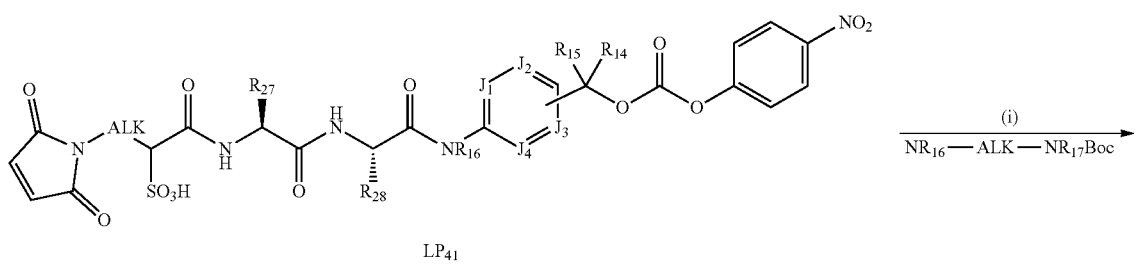

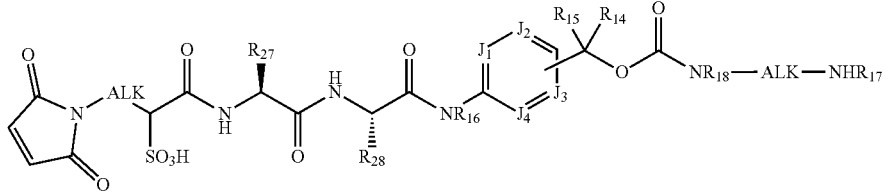

Step (i): formation of the carbamate between the linker precursor LP$_{41}$ and a monoprotected diamine; the reaction is performed in a polar solvent such as CH$_3$CN in the presence of a base such as, for example, DIEA; deprotection using a solution of hydrochloric acid (for example solution in dioxane) or of trifluoroacetic acid.

LP$_{59}$

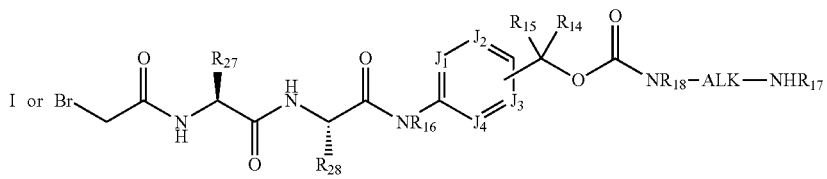

prepared according to the scheme below:

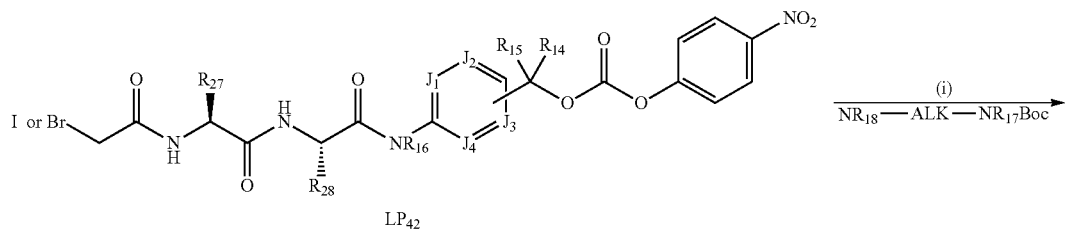

Step (i): formation of the carbamate between the linker precursor LP$_{42}$ and a monoprotected diamine; the reaction is performed in a polar solvent such as CH$_3$CN in the presence of a base such as, for example, DIEA; deprotection using a solution of hydrochloric acid (for example solution in dioxane) or of trifluoroacetic acid.

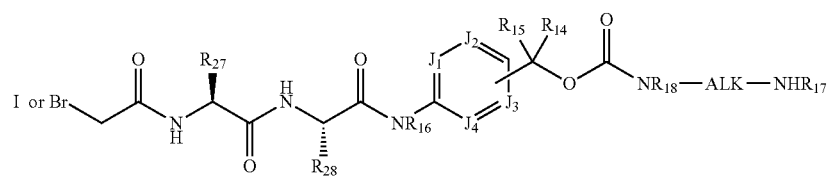

prepared according to the scheme below:

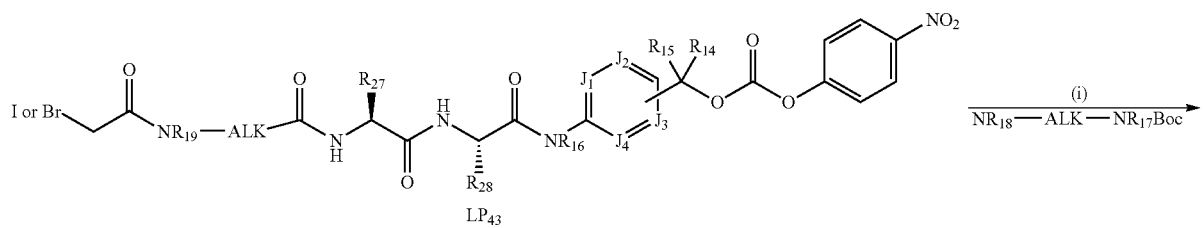

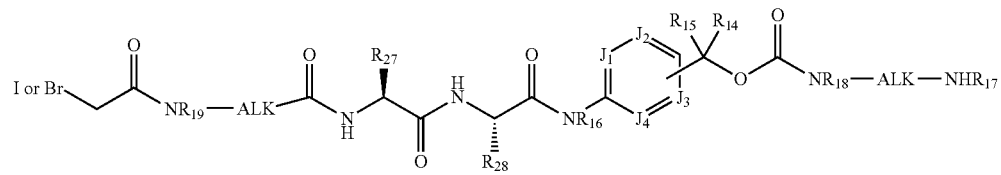

Step (i): formation of the carbamate between the linker precursor LP$_{43}$ and a monoprotected diamine; the reaction is performed in a polar solvent such as CH$_3$CN in the presence of a base such as, for example, DIEA; deprotection using a solution of hydrochloric acid (for example solution in dioxane) or of trifluoroacetic acid.

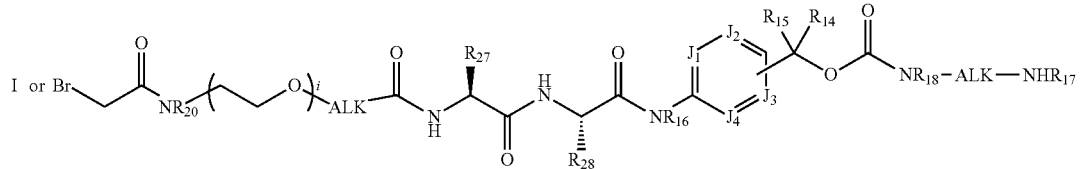

LP$_{61}$ prepared according to the scheme below:

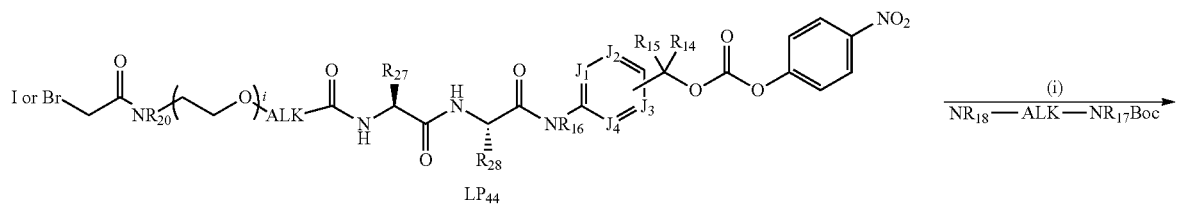

LP$_{44}$

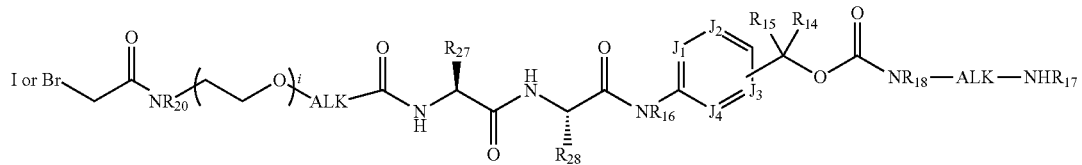

Step (i): formation of the carbamate between the linker precursor LP$_{44}$ and a monoprotected diamine; the reaction is performed in a polar solvent such as CH$_3$CN in the presence of a base such as, for example, DIEA; deprotection using a solution of hydrochloric acid (for example solution in dioxane) or of trifluoroacetic acid.

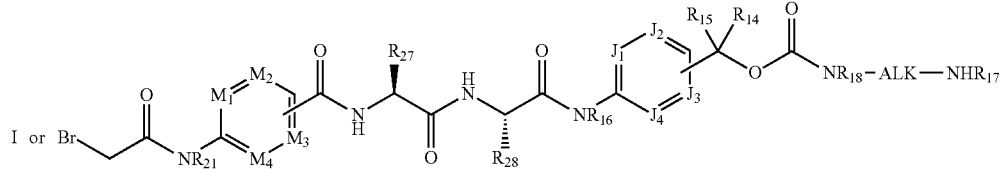

LP$_{62}$ prepared according to the scheme below:

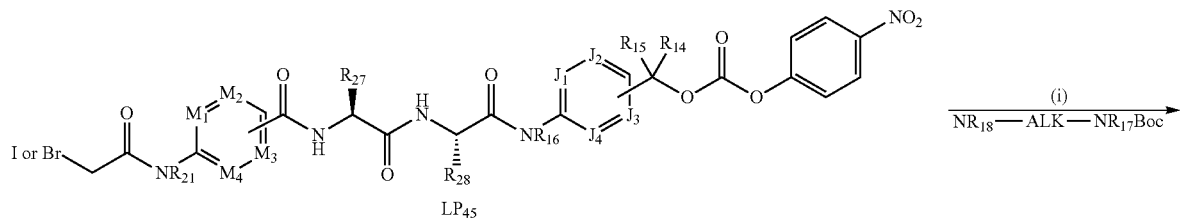

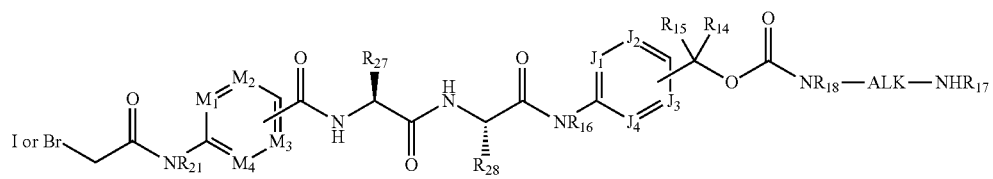

Step (i): formation of the carbamate between the linker precursor LP$_{45}$ and a monoprotected diamine; the reaction is performed in a polar solvent such as CH$_3$CN in the presence of a base such as, for example, DIEA; deprotection using a solution of hydrochloric acid (for example solution in dioxane) or of trifluoroacetic acid.

LP$_{63}$

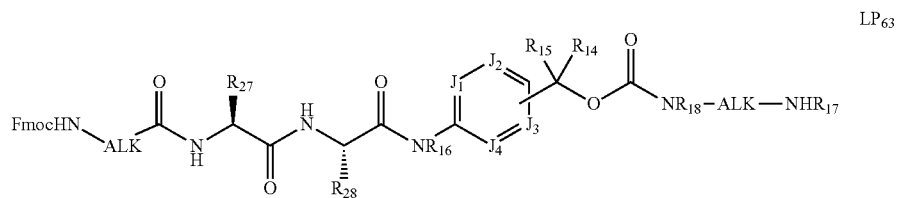

prepared according to the scheme below:

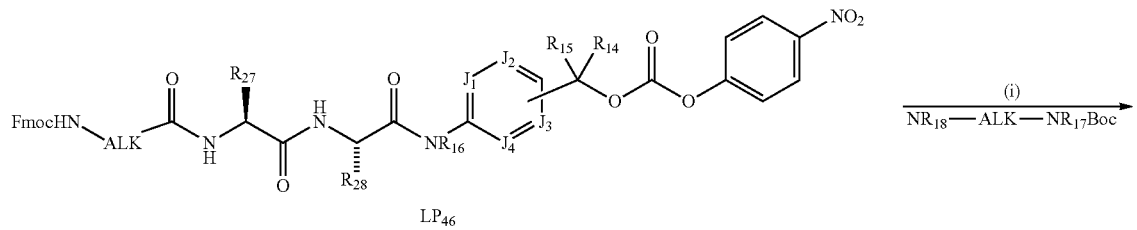

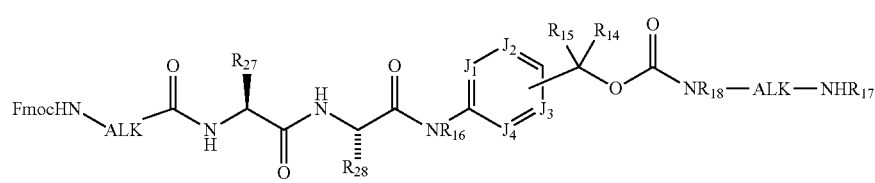

Step (i): formation of the carbamate between the linker precursor LP$_{46}$ and a monoprotected diamine; the reaction is performed in a polar solvent such as CH$_3$CN in the presence of a base such as, for example, DIEA; deprotection using a solution of hydrochloric acid (for example solution in dioxane) or of trifluoroacetic acid.

LP$_{64}$

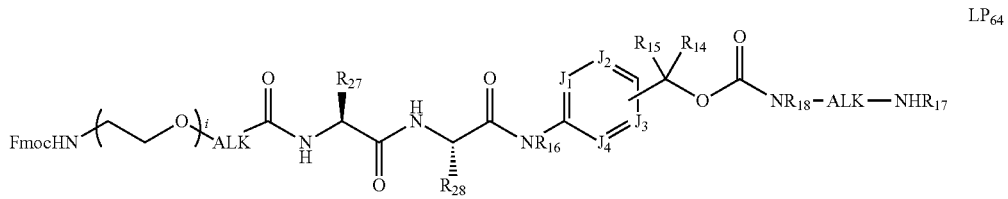

prepared according to the scheme below:

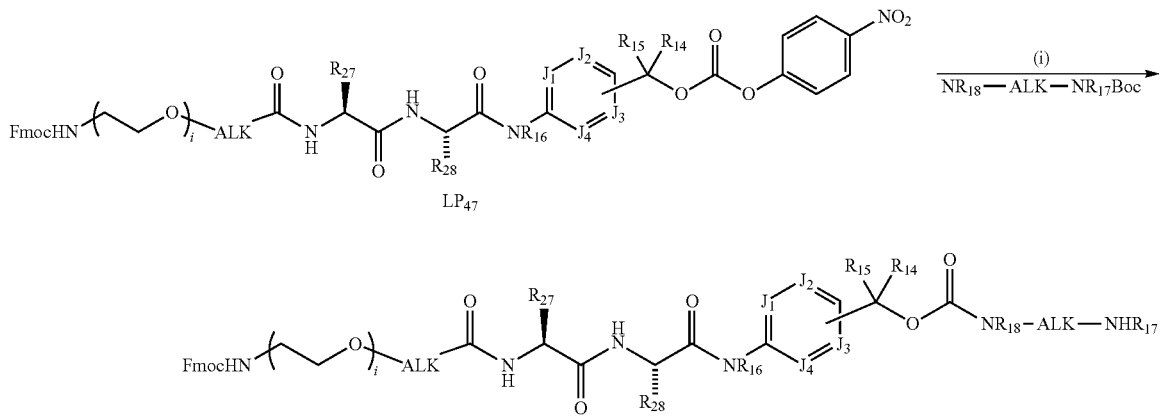

Step (i): formation of the carbamate between the linker precursor LP$_{47}$ and a monoprotected diamine; the reaction is performed in a polar solvent such as CH$_3$CN in the presence of a base such as, for example, DIEA; deprotection using a solution of hydrochloric acid (for example solution in dioxane) or of trifluoroacetic acid.

LP$_{65}$

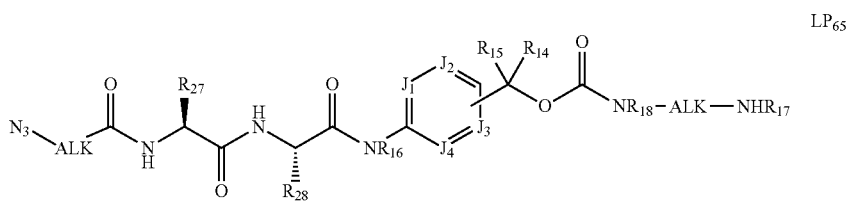

prepared according to the scheme below:

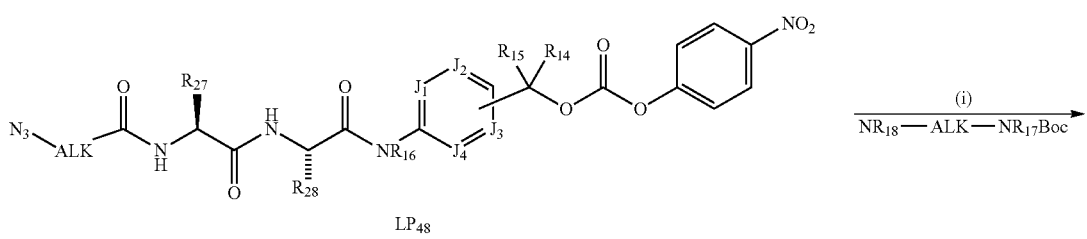

-continued

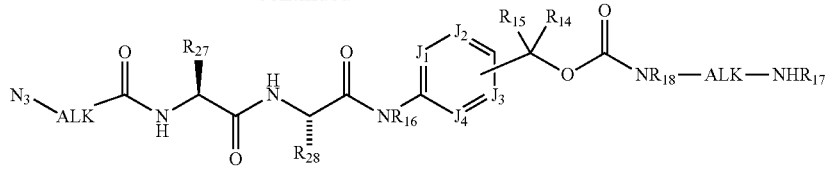

Step (i): formation of the carbamate between the linker precursor LP$_{48}$ and a monoprotected diamine; the reaction is performed in a polar solvent such as CH$_3$CN in the presence of a base such as, for example, DIEA; deprotection using a solution of hydrochloric acid (for example solution in dioxane) or of trifluoroacetic acid.

LP$_{66}$

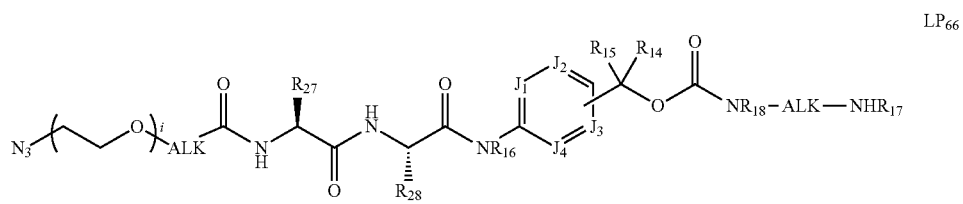

prepared according to the scheme below:

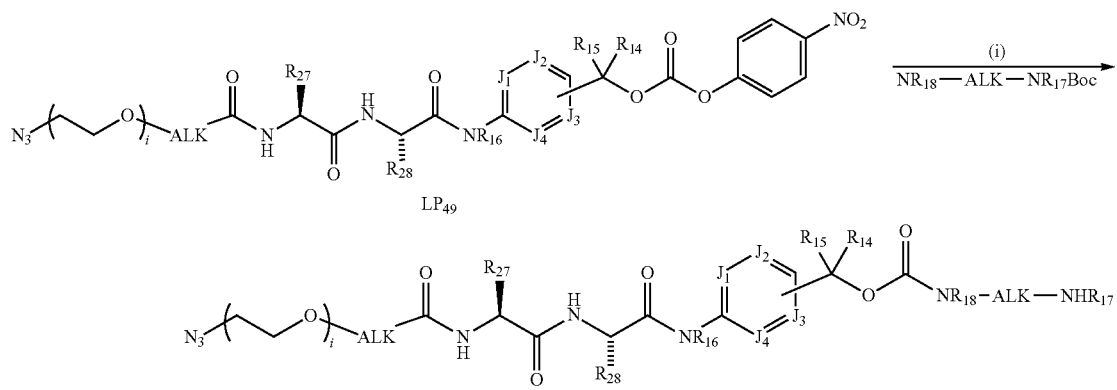

Step (i): formation of the carbamate between the linker precursor LP$_{49}$ and a monoprotected diamine; the reaction is performed in a polar solvent such as CH$_3$CN in the presence of a base such as, for example, DIEA; deprotection using a solution of hydrochloric acid (for example solution in dioxane) or of trifluoroacetic acid.

LP$_{67}$

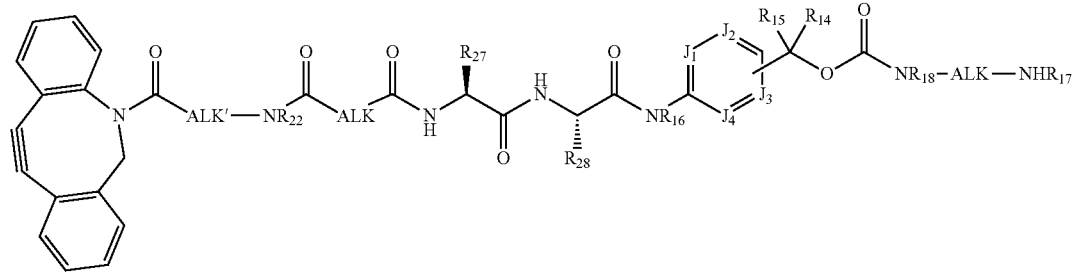

prepared according to the scheme below:

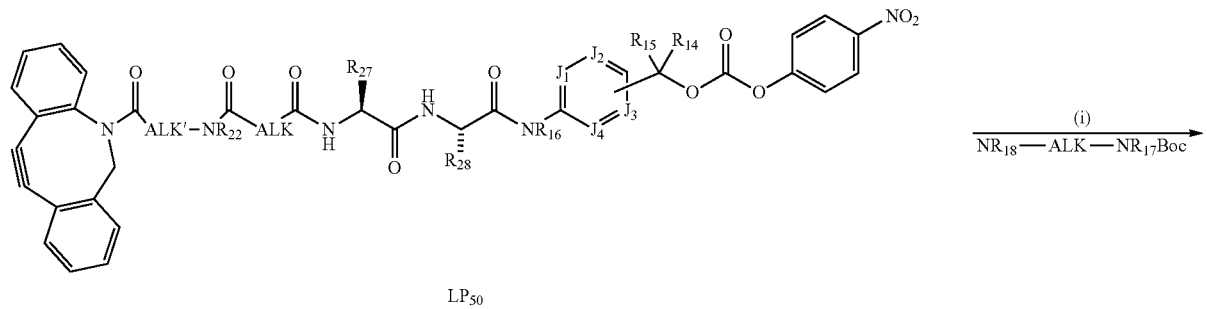

LP$_{50}$

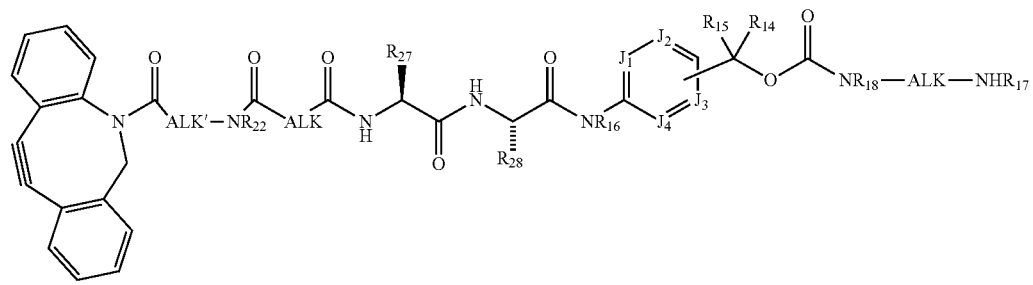

Step (i): formation of the carbamate between the linker precursor LP$_{50}$ and a monoprotected diamine; the reaction is performed in a polar solvent such as CH$_3$CN in the presence of a base such as, for example, DIEA; deprotection using a solution of hydrochloric acid (for example solution in dioxane) or of trifluoroacetic acid.

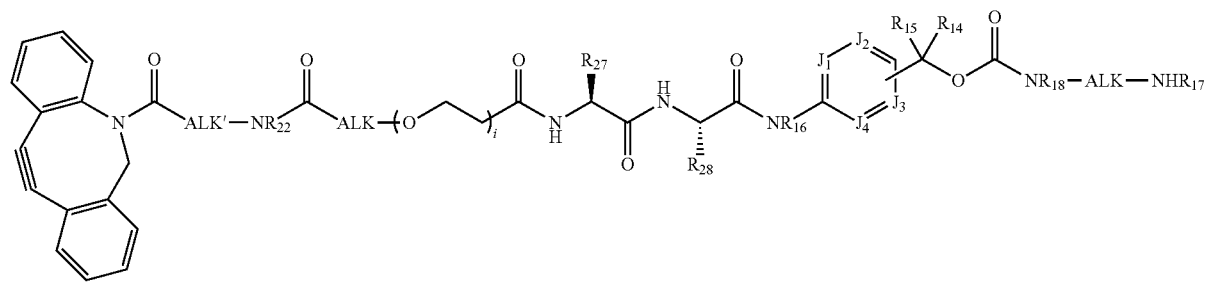

LP$_{68}$ prepared according to the scheme below:

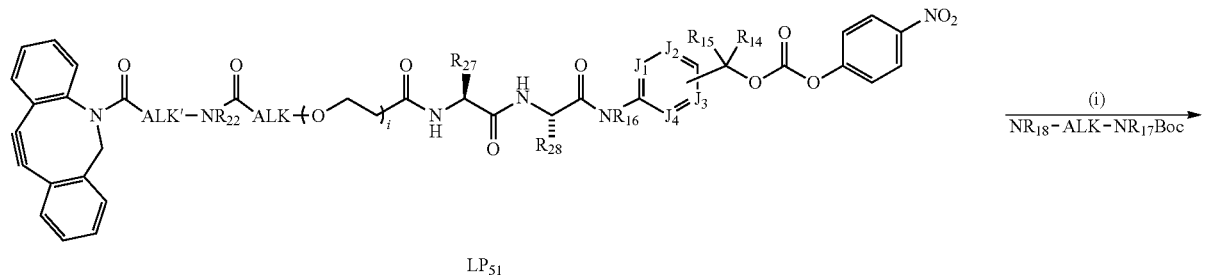

LP$_{51}$

-continued

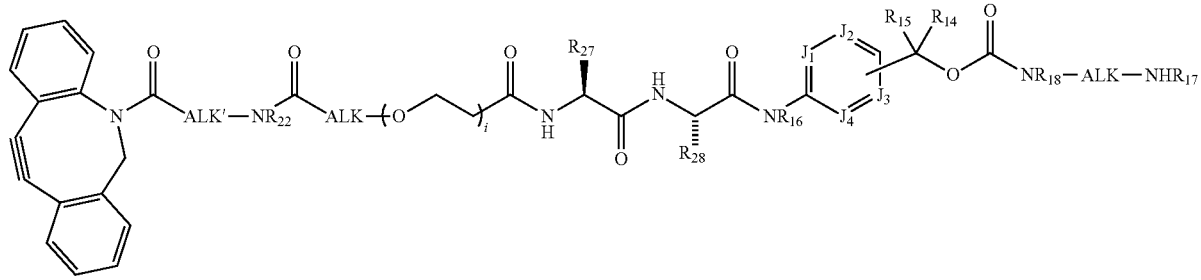

Step (i): formation of the carbamate; the reaction is performed in a polar solvent such as $CH_3CN$ in the presence of a base such as, for example, DIEA; deprotection using a solution of hydrochloric acid (for example solution in dioxane) or of trifluoroacetic acid.

$LP_{69}$

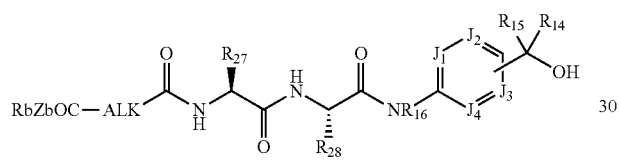

prepared according to the 1$^{st}$ step described for linker precursor $LP_{35}$.

$LP_{70}$

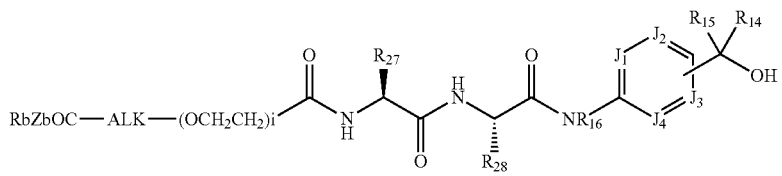

prepared according to the 1$^{st}$ step described for linker precursor $LP_{36}$.

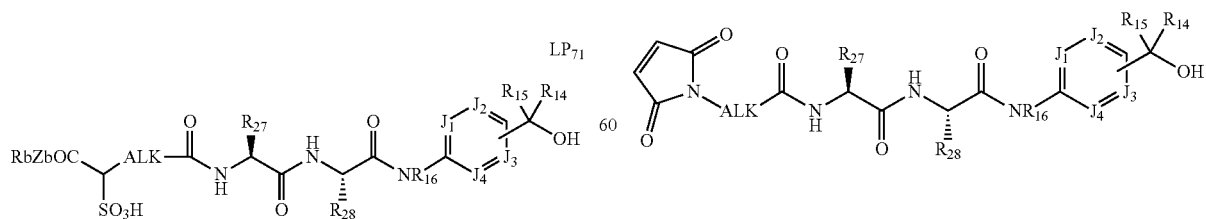

prepared according to the 1$^{st}$ step described for linker precursor $LP_{37}$.

prepared according to the 1$^{st}$ step described for linker precursor $LP_{38}$.

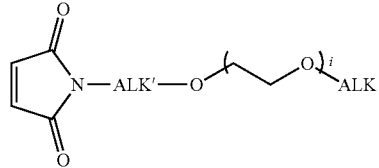

prepared according to the 1st step described for linker precursor LP₃₉.

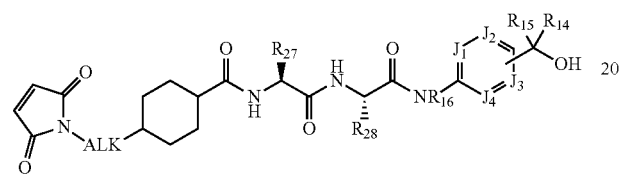

prepared according to the 1st step described for linker precursor LP₄₀.

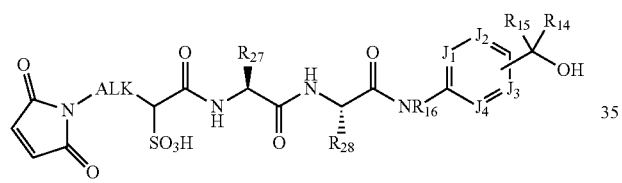

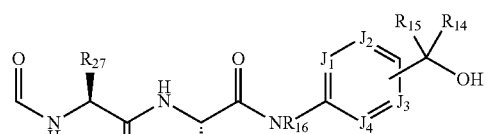

prepared according to the 1st step described for linker precursor LP₄₁.

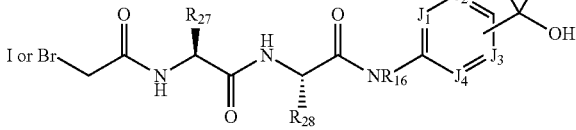

prepared according to the 1st step described for linker precursor LP₄₂.

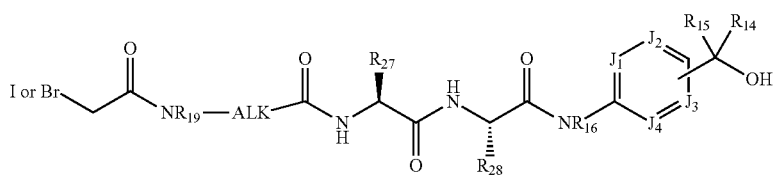

prepared according to the 1st step described for linker precursor LP₄₃.

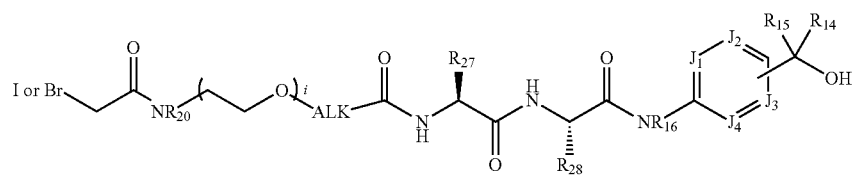

prepared according to the 1st step described for linker precursor LP₄₄.

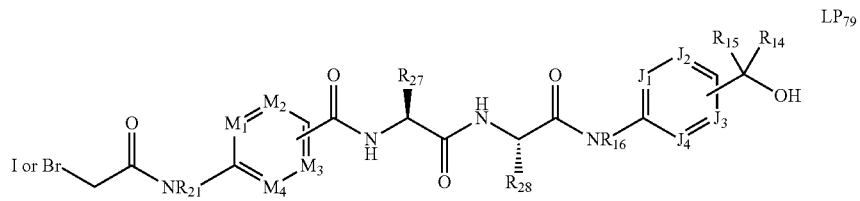
prepared according to the 1st step described for linker precursor LP$_{45}$.
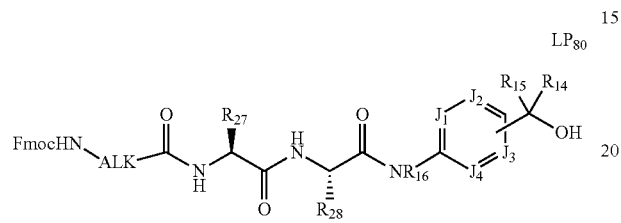
prepared according to the 1st step described for linker precursor LP$_{46}$.
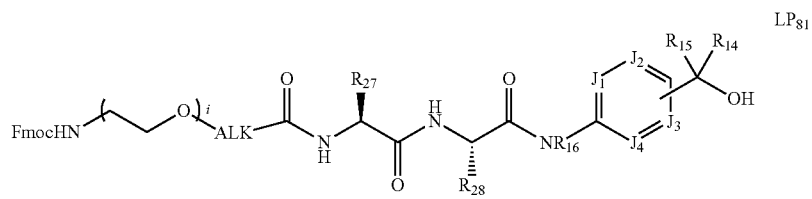
prepared according to the 1st step described for linker precursor LP$_{47}$.
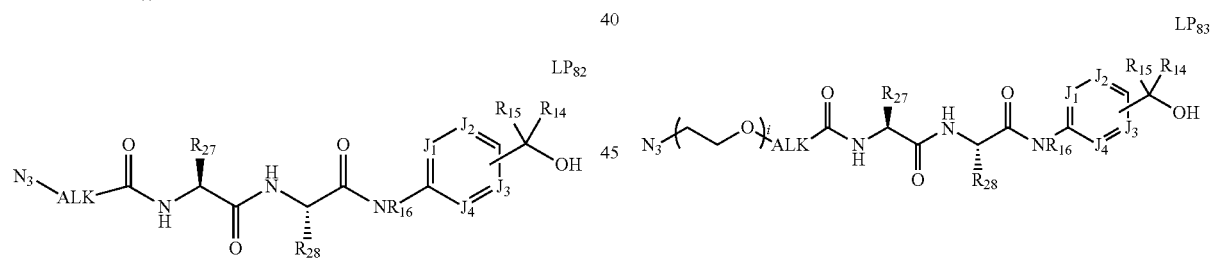
prepared according to the 1st step described for linker precursor LP$_{48}$.
prepared according to the 1st step described for linker precursor LP$_{49}$.
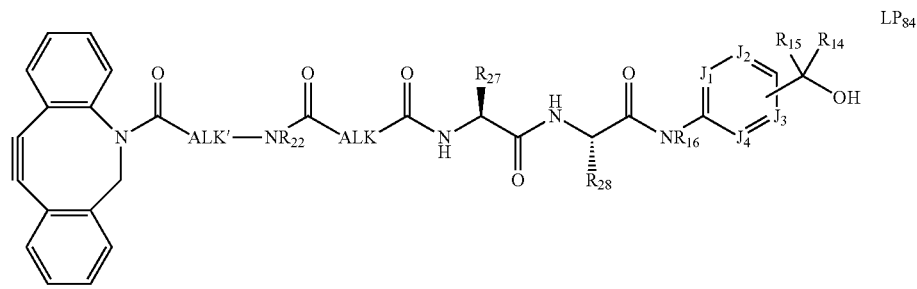

prepared according to the 1$^{st}$ step described for linker precursor LP$_{50}$.
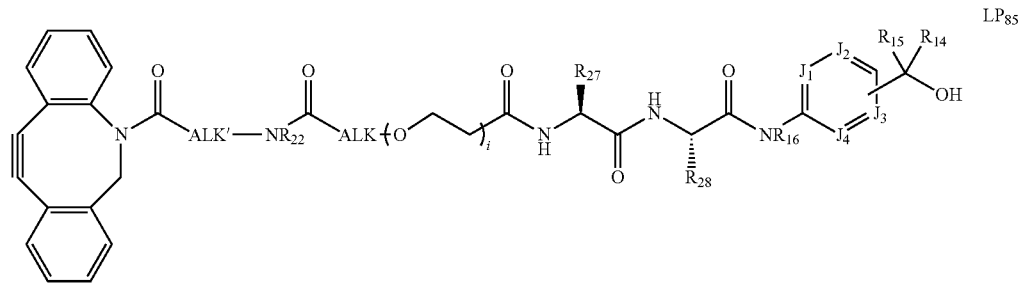
prepared according to the 1$^{st}$ step described for linker precursor LP$_{51}$.
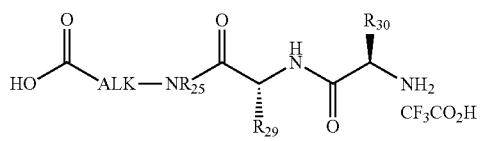
prepared according to the scheme below:
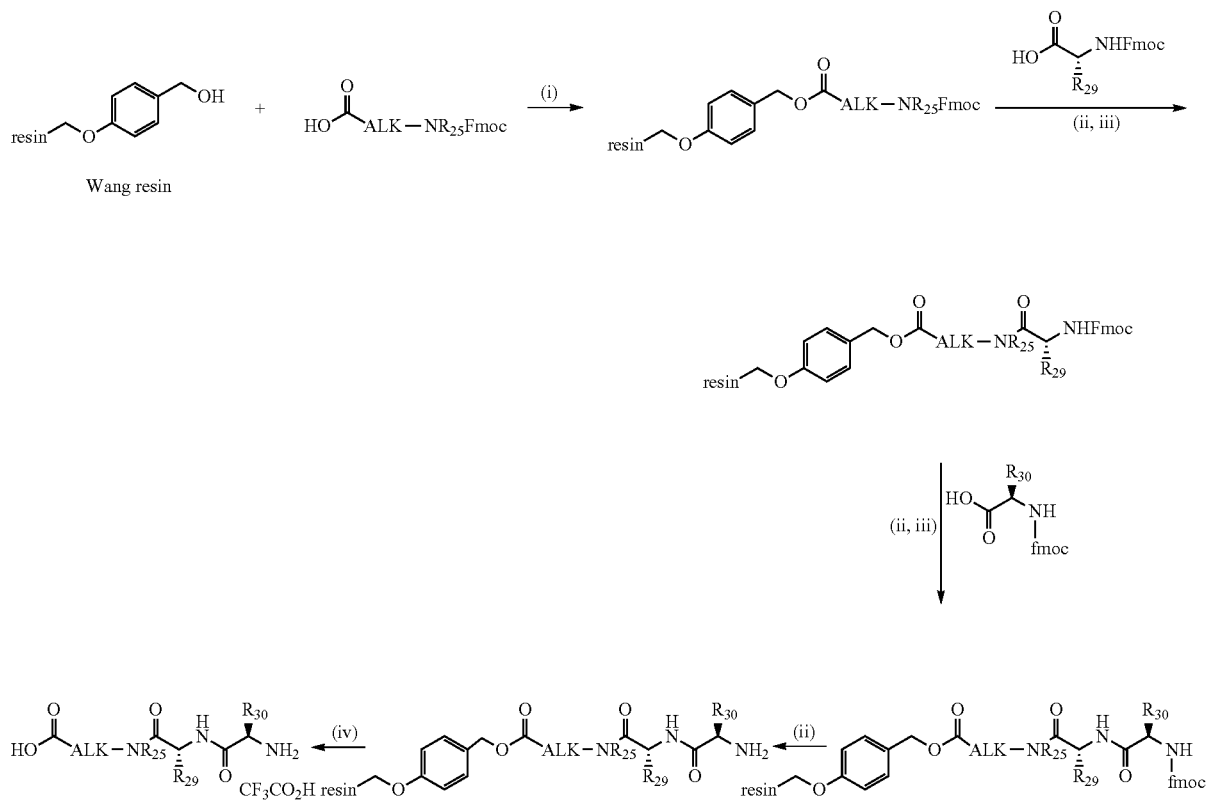

Step (i): coupling of the acid on Wang resin by esterification; the reaction is performed in a polar solvent such as DCM in the presence of a coupling reagent such as, for example, DIC and a base such as, for example, DMAP;

Step (ii): deprotection of the Fmoc group; the reaction is performed in a polar solvent such as DMF by treatment with a base such as, for example, piperidine;

Step (iii): peptidic coupling; the reaction is performed in a polar solvent such as DMF in the presence of coupling reagents such as, for example, HOBt and HATU and a base such as, for example, DIEA;

Step (iv): cleavage of the resin; the reaction is performed in a polar solvent such as a DCM/$H_2O$ mixture in the presence of an acid such as, for example, TFA.

Fmoc protected alkyl-amino acids are commercially available for n=1 to 9; Fmoc L-amino acids are commercially available.

$LP_{87}$

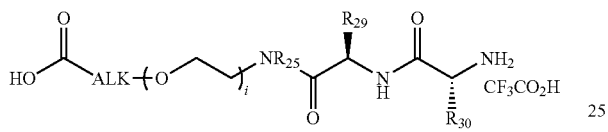

prepared according to the scheme below:

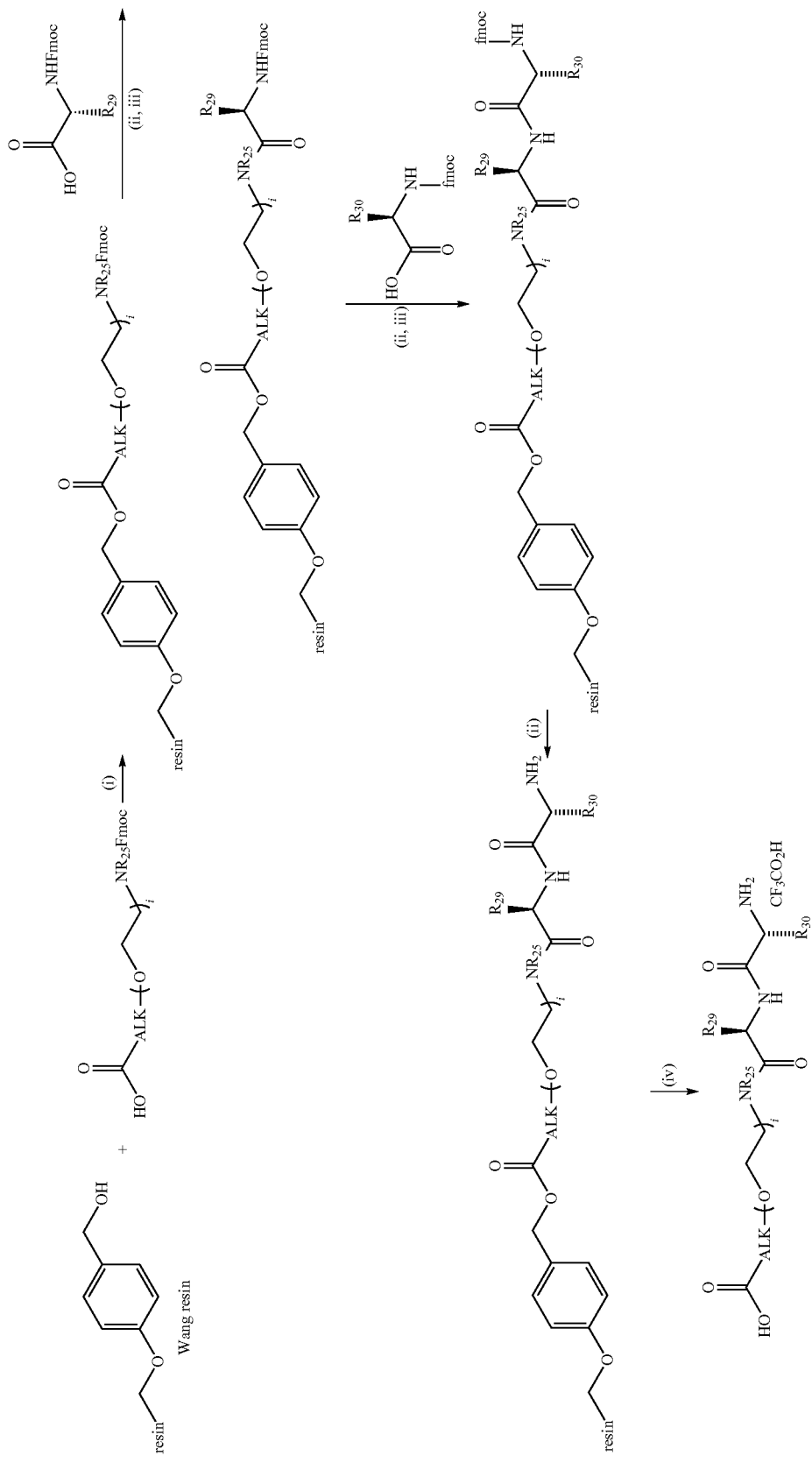

Step (i): coupling of the acid on Wang resin by esterification; the reaction is performed in a polar solvent such as DCM in the presence of a coupling reagent such as, for example, DIC and a base such as, for example, DMAP;

Step (ii): deprotection of the Fmoc group; the reaction is performed in a polar solvent such as DMF by treatment with a base such as, for example, piperidine;

Step (iii): peptidic coupling; the reaction is performed in a polar solvent such as DMF in the presence of coupling reagents such as, for example, HOBt and HATU and a base such as, for example, DIEA;

Step (iv): cleavage of the resin; the reaction is performed in a polar solvent such as a DCM/H$_2$O mixture in the presence of an acid such as, for example, TFA.

Fmoc-protected amino PEG carboxylic acids are commercially available for i=1 to 6 and otherwise may be prepared from tert-butyl acrylate and the corresponding amino-PEG-alcohol; in the case where ALK≠CH$_2$CH$_2$, they may be prepared according to the schemes described for linker precursor LP$_{10}$. Protection of the amine function with a Fmoc group may be realized by treatment with FmocOSu (CAS number [82911-69-1]) in the presence of a base such as, for example, DIEA; Fmoc L-amino acids are commercially available.

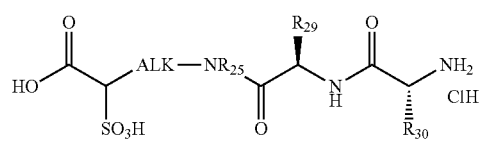

LP$_{88}$ prepared according to the scheme below:

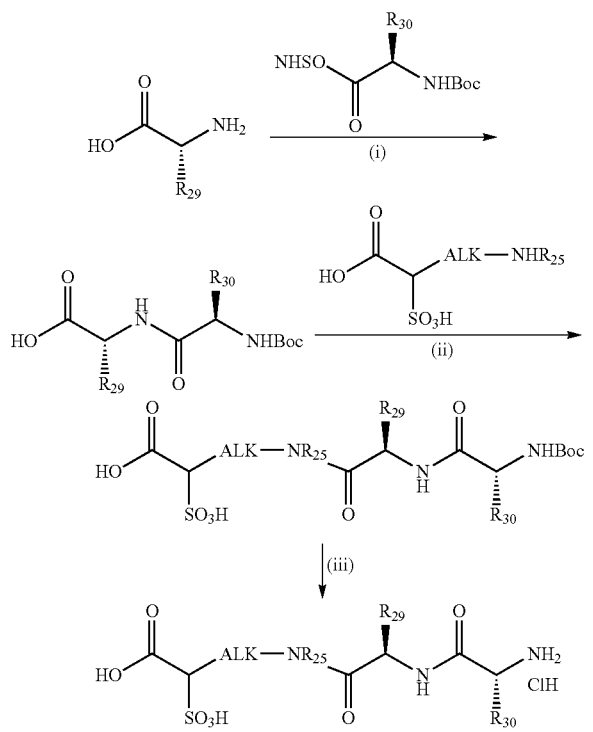

Step (i): peptidic coupling between Boc-L-amino acid-ONHS and L-amino acid; the reaction is performed in a polar solvent such as a DME/THF/H$_2$O mixture in the presence of a base such as, for example, sodium bicarbonate;

Step (ii): peptidic coupling with sulfo amino acids; the reaction is performed in a polar solvent such as CH$_3$CN in the presence of coupling reagents such as, for example, DCC and HOBt and a base such as, for example, DIEA;

Step (iii): deprotection of the Boc group using a solution of hydrochloric acid (for example solution in dioxane).

L-amino acids are commercially available; NHS esters of Boc-protected L-amino acids are commercially available; sulfo amino acids are commercially available for n=1 and 2 or otherwise may be prepared according to the scheme below:

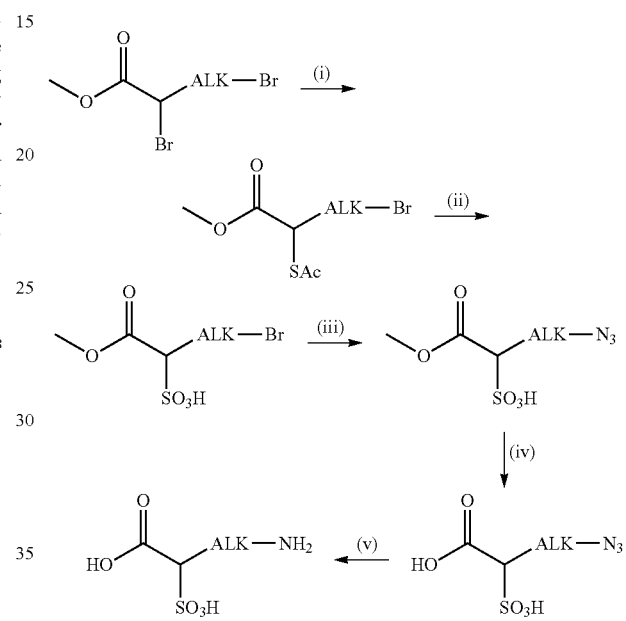

Step (i): substitution of the bromide by a thioacetyle; the reaction is performed in a polar aprotic solvent such as, for example, THF using thioacetic acid in the presence of a base such as, for example, DIEA;

Step (ii): formation of the sulfonic acid moiety; the reaction is performed by treatment with hydrogen peroxide and acetic acid;

Step (iii): substitution of the bromide by an azido; the reaction is performed in a polar solvent such as, for example, DMA by treatment with sodium azide;

Step (iv): methyl ester deprotection; the reaction is performed in acidic conditions such as, for example, a mixture of HCl and AcOH;

Step (v): reduction of the azido; the reaction is performed by hydrogenolysis in a polar solvent such as H$_2$O in the presence of a catalyst such as palladium on carbon.

Dibromo derivatives are commercially available for n=3, 4 and 9.

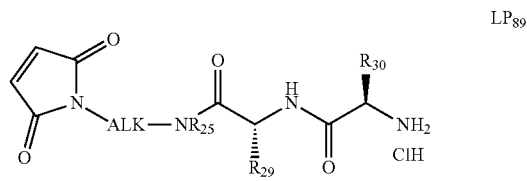

LP$_{89}$

315 prepared according to the scheme below:

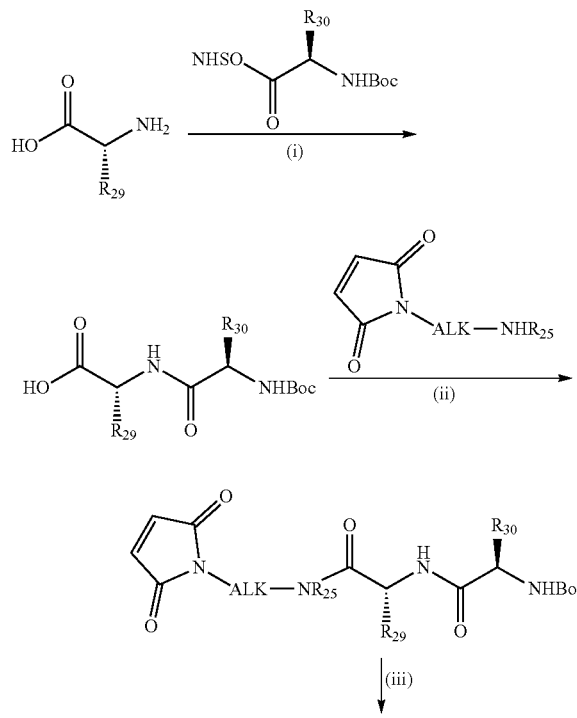

316

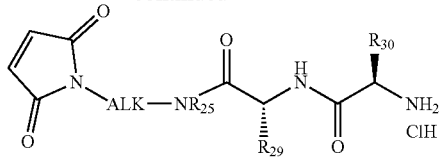

Step (i): peptidic coupling between Boc-L-amino acid-ONHS and L-amino acid; the reaction is performed in a polar solvent such as a DME/THF/H$_2$O mixture in the presence of a base such as, for example, sodium bicarbonate;

Step (ii): peptidic coupling with maleimido amines; the reaction is performed in a polar solvent such as CH$_3$CN in the presence of coupling reagents such as, for example, DCC and HOBt and a base such as, for example, DIEA;

Step (iii): deprotection of the Boc group using a solution of hydrochloric acid (for example solution in dioxane).

L-amino acids are commercially available; NHS esters of Boc-protected L-amino acids are commercially available; maleimido amines are commercially available for n=2 to 6.

LP$_{90}$

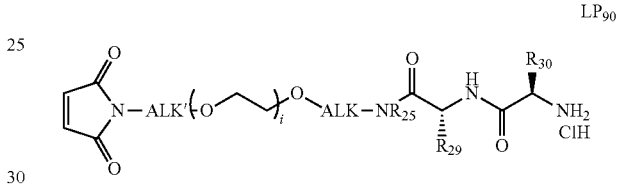

prepared according to the scheme below:

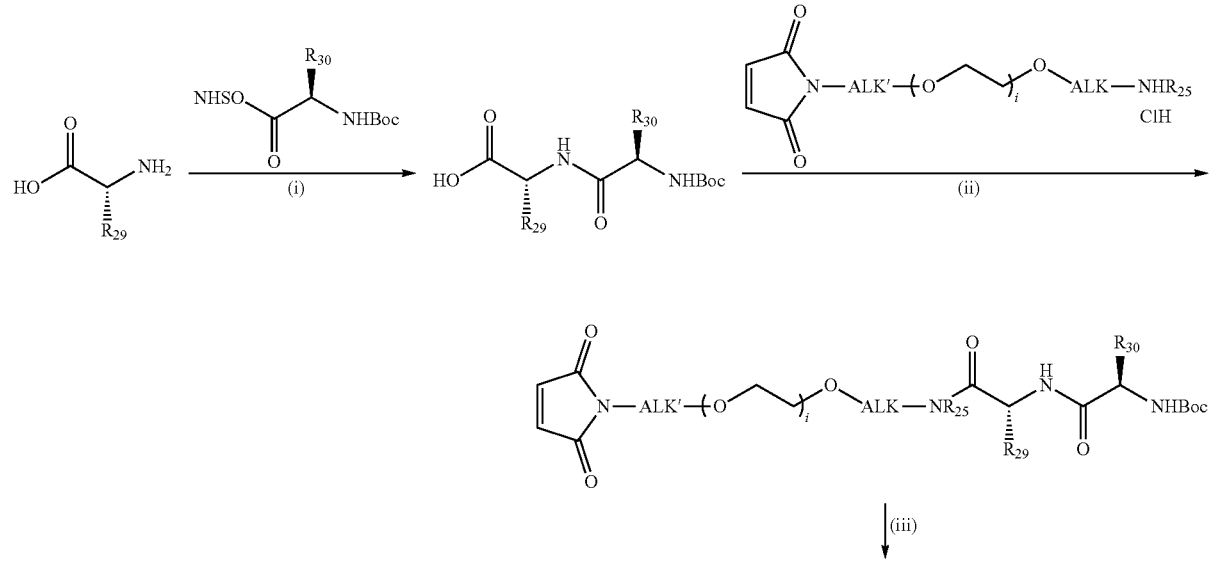

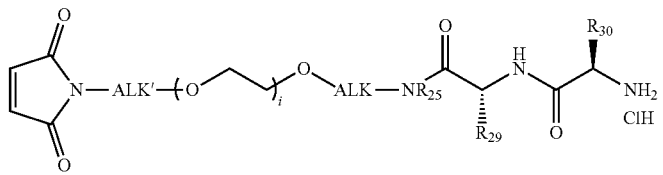

Step (i): peptidic coupling between Boc-L-amino acid-ONHS and L-amino acid; the reaction is performed in a polar solvent such as a DME/THF/H$_2$O mixture in the presence of a base such as, for example, sodium bicarbonate;

Step (ii): peptidic coupling with maleimido PEG amines; the reaction is performed in a polar solvent such as CH$_3$CN in the presence of coupling reagents such as, for example, DCC and HOBt and a base such as, for example, DIEA;

Step (iii): deprotection of the Boc group using a solution of hydrochloric acid (for example solution in dioxane).

L-amino acids are commercially available; NHS esters of Boc-protected L-amino acids are commercially available; maleimido PEG amines are commercially available for ALK=ALK'=CH$_2$CH$_2$ and i=0 and 1 or otherwise may be prepared according to the scheme below:

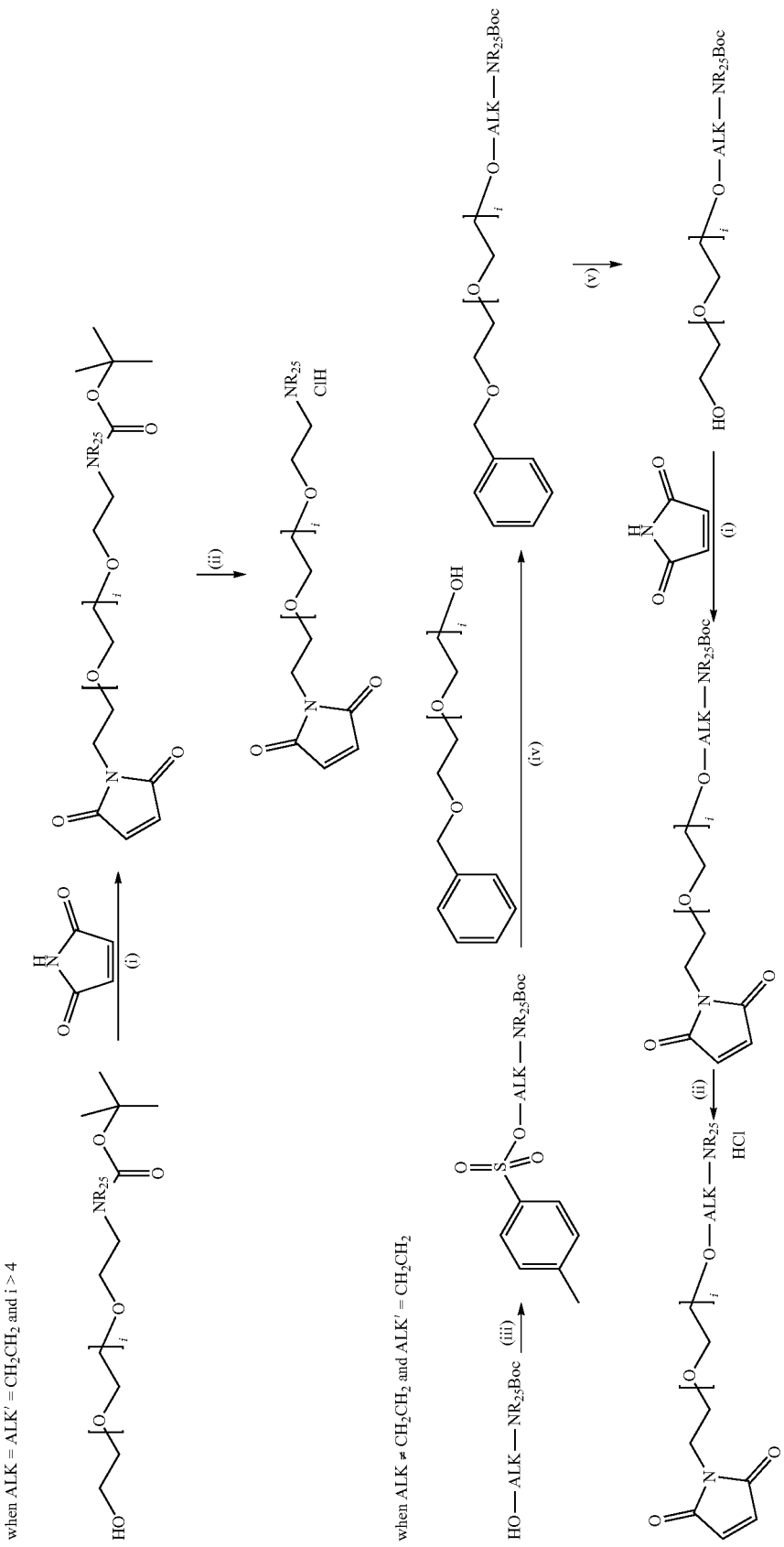

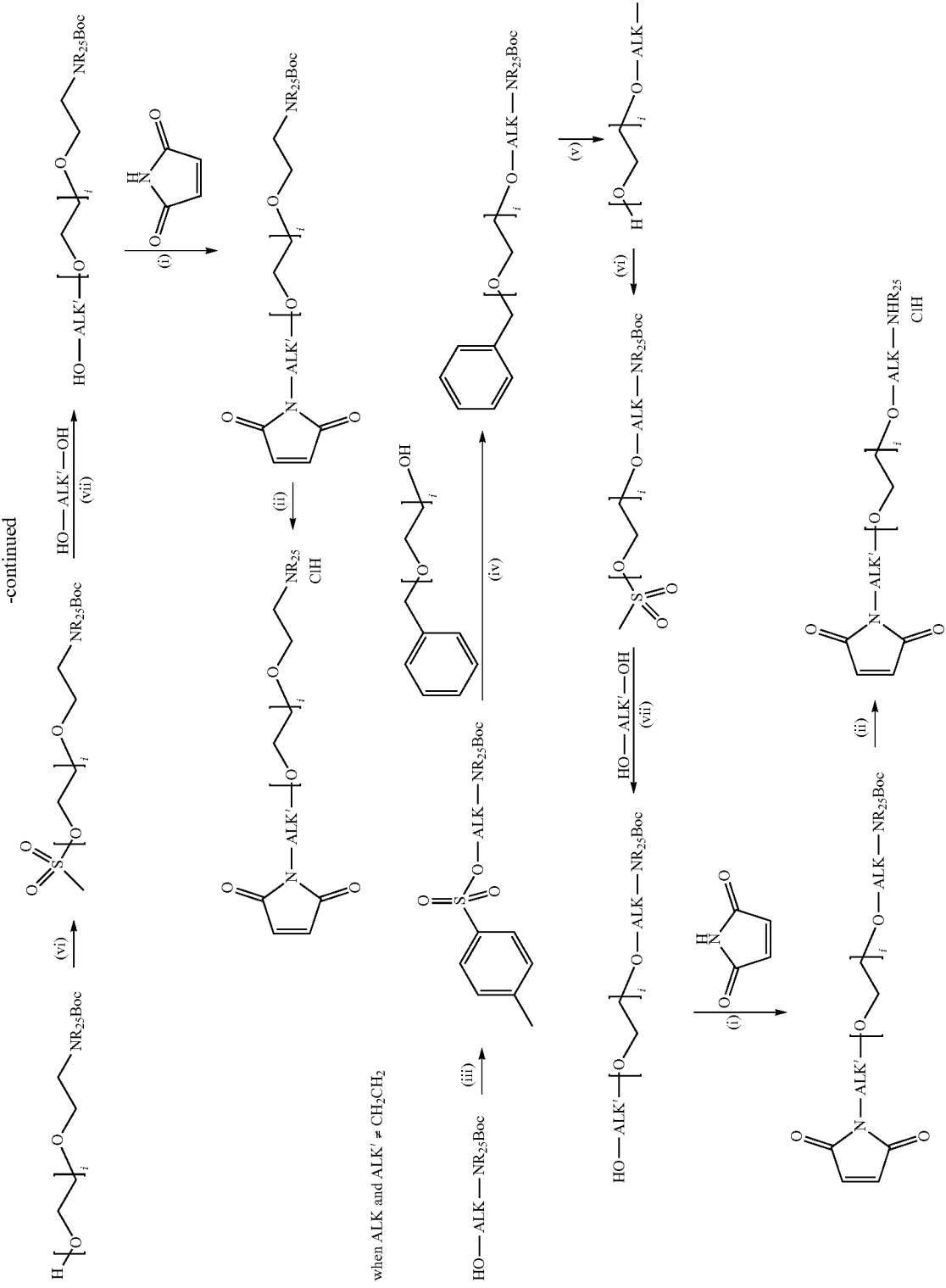

Step (i): Mitsunobu reaction on maleimide; the reaction is performed in a polar aprotic solvent such as, for example, THF by treatment of malemide by the PEG hydroxy acid in the presence of PPh$_3$ and DIAD;

Step (ii): deprotection using a solution of hydrochloric acid (for example solution in dioxane) or of trifluoroacetic acid;

Step (iii): activation of the alcohol as a tosylate; the reaction is performed in a polar aprotic solvent such as, for example, DCM by treatment with tosyl chloride in the presence of a base such as, for example, TEA;

Step (iv): substitution of the tosyl group; the reaction is performed in a polar aprotic solvent such as, for example, THF, in the presence of a base such as, for example, sodium hydride.

Step (v): deprotection of the benzyl group; the reaction is performed by hydrogenolysis in a polar solvent such as, for example, MeOH, in the presence of a catalytic amount of catalyst, such as, for example, palladium on carbon;

Step (vi): activation of the alcohol as a mesylate; the reaction is performed in a polar aprotic solvent such as, for example, DCM by treatment with methanesulfonyl chloride in the presence of a base such as, for example, TEA;

Step (vii): nucleophilic substitution; the reaction is performed in a polar aprotic solvent such as, for example, DMF in the presence of a base such as sodium hydride;

The starting Boc-protected PEG amino alcohols are commercially available for i=2 to 4 or can be prepared by treating commercially available PEG amino alcohols by Boc$_2$O for i=5 to 8; the starting ALK amino alcohols are commercially available for n=1 and 3 to 10; the starting PEG diols monoprotected with a benzyl group are commercially available for i=1 to 9; the starting ALK' diols are commercially available for n=1 to 12.

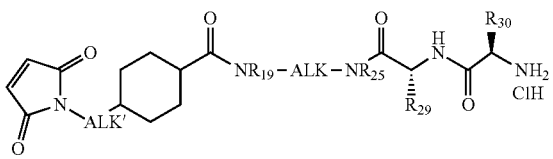

LP$_{91}$ prepared according to the scheme below:

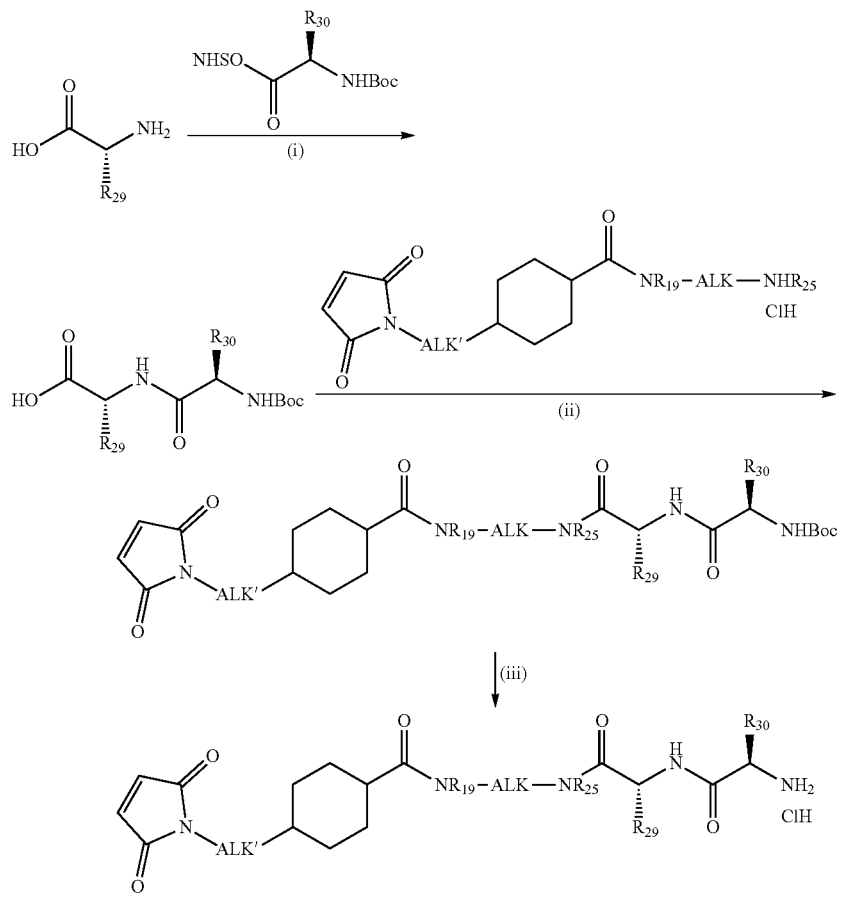

Step (i): peptidic coupling between Boc-L-amino acid-ONHS and L-amino acid; the reaction is performed in a polar solvent such as a DME/THF/H$_2$O mixture in the presence of a base such as, for example, sodium bicarbonate;

Step (ii): peptidic coupling with maleimido amines; the reaction is performed in a polar solvent such as CH$_3$CN in the presence of coupling reagents such as, for example, DCC and HOBt and a base such as, for example, DIEA;

Step (iii): deprotection of the Boc group using a solution of hydrochloric acid (for example solution in dioxane).

L-amino acids are commercially available; NHS esters of Boc-protected L-amino acids are commercially available; maleimido amines may be prepared according to the scheme below:

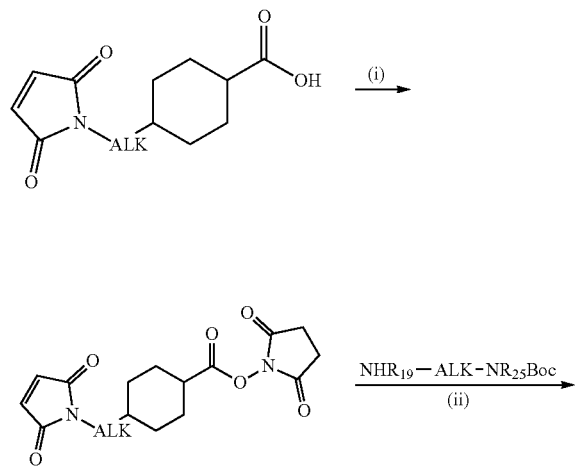

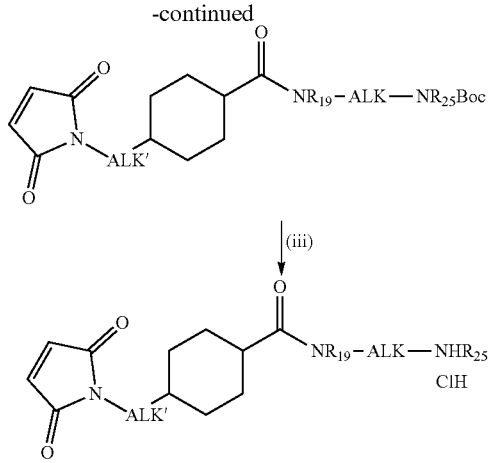

Step (i): activation of the carboxylic acid as a NHS ester; the reaction is performed in a polar solvent such as a mixture DMF/H$_2$O by treatment with N,N'-disuccinimidyl carbonate in the presence of a base such as, for example, DIEA;

Step (ii): peptide coupling; the reaction is performed in a polar aprotic solvent such as a DCM/CH$_3$CN mixture;

Step (iii): deprotection of the Boc group using a solution of hydrochloric acid (for example solution in dioxane).

The maleimido cyclohexanecarboxylic acid is commercially available for ALK=CH$_2$ or otherwise may be prepared according to the schemes described for LP$_6$; the diamines monoprotected with a Boc group are commercially available for n=1 to 10.

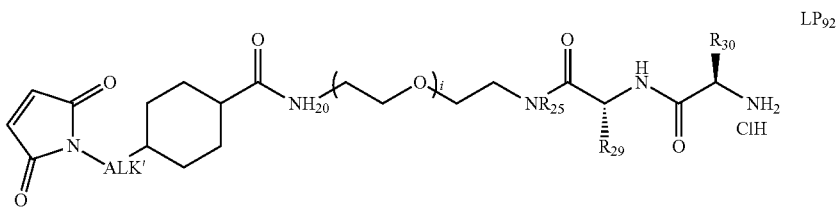

prepared according to the scheme below:

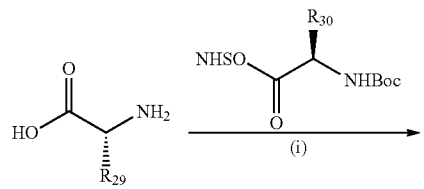

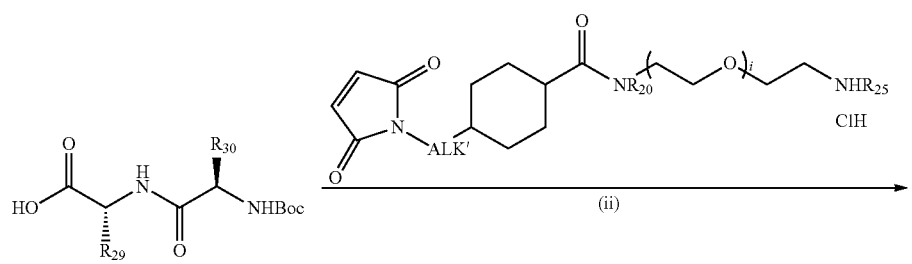

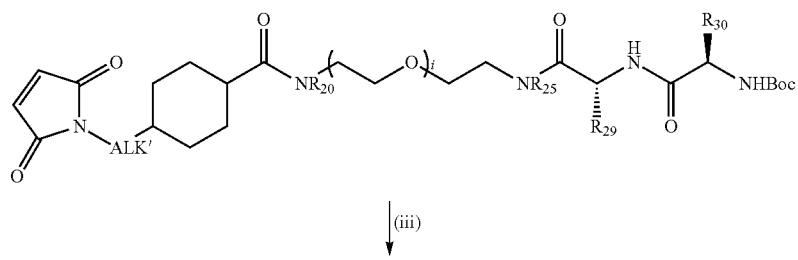

|(iii)

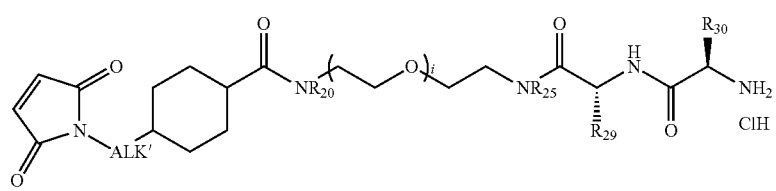

Step (i): peptidic coupling between Boc-L-amino acid-ONHS and L-amino acid; the reaction is performed in a polar solvent such as a DME/THF/H$_2$O mixture in the presence of a base such as, for example, sodium bicarbonate;

Step (ii): peptidic coupling with maleimido PEG amines; the reaction is performed in a polar solvent such as CH$_3$CN in the presence of coupling reagents such as, for example, DCC and HOBt and a base such as, for example, DIEA;

Step (iii): deprotection of the Boc group using a solution of hydrochloric acid (for example solution in dioxane).

L-amino acids are commercially available; NHS esters of Boc-protected L-amino acids are commercially available; maleimido PEG amines may be prepared according to the scheme below:

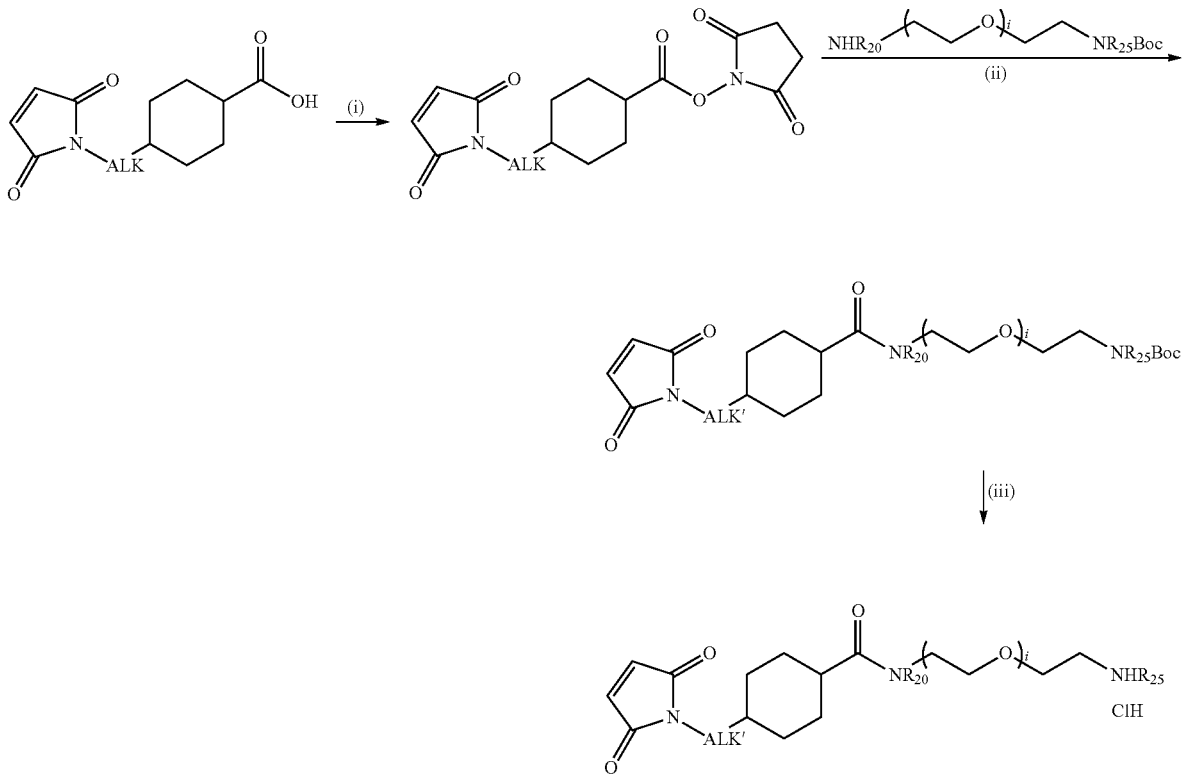

Step (i): activation of the carboxylic acid as a NHS ester; the reaction is performed in a polar solvent such as a mixture DMF/H₂O by treatment with N,N'-disuccinimidyl carbonate in the presence of a base such as, for example, DIEA;

Step (ii): peptide coupling; the reaction is performed in a polar aprotic solvent such as a DCM/CH₃CN mixture;

Step (iii): deprotection of the Boc group using a solution of hydrochloric acid (for example solution in dioxane).

The maleimido cyclohexanecarboxylic acid is commercially available for ALK=CH₂ or otherwise may be prepared according to the schemes described for LP₆; the PEG diamines monoprotected with a Boc group are commercially available for i=1 to 9.

LP₉₃

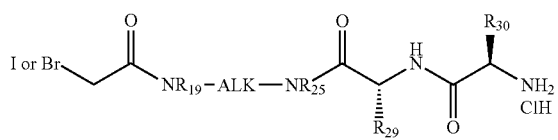

prepared according to the scheme below:

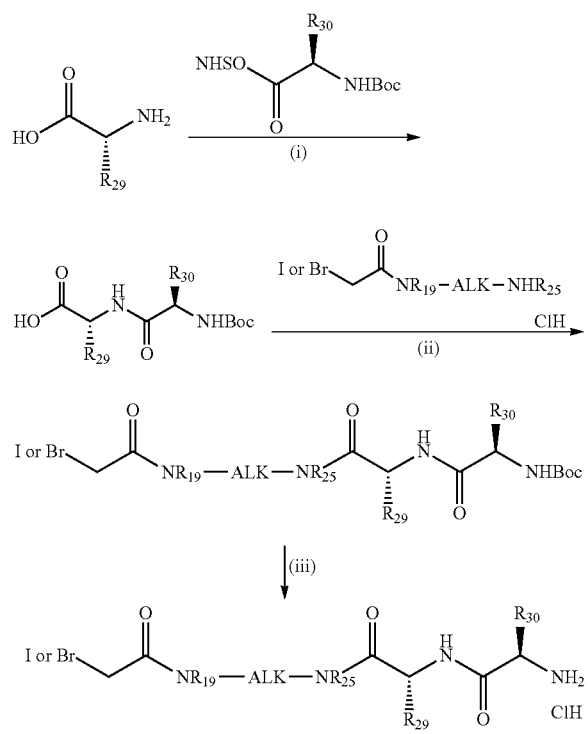

Step (i): peptidic coupling between Boc-L-amino acid-ONHS and L-amino acid; the reaction is performed in a polar solvent such as a DME/THF/H₂O mixture in the presence of a base such as, for example, sodium bicarbonate;

Step (ii): peptidic coupling with halogenoacetamido PEG amines; the reaction is performed in a polar solvent such as CH₃CN in the presence of coupling reagents such as, for example, DCC and HOBt and a base such as, for example, DIEA;

Step (iii): deprotection of the Boc group using a solution of hydrochloric acid (for example solution in dioxane).

L-amino acids are commercially available; NHS esters of Boc-protected L-amino acids are commercially available; halogenoacetamido amines are commercially available for n=2 to 4 and 8 or may be prepared according to the scheme below:

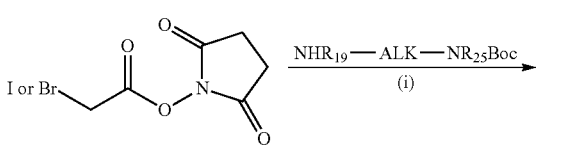

Step (ii): peptide coupling; the reaction is performed in a polar aprotic solvent such as a DCM/CH₃CN mixture;

Step (iii): deprotection of the Boc group using a solution of hydrochloric acid (for example solution in dioxane).

N-succinimidyl bromo- and iodo-acetates are commercially available; the diamines monoprotected with a Boc group are commercially available for n=1 to 10.

LP₉₄

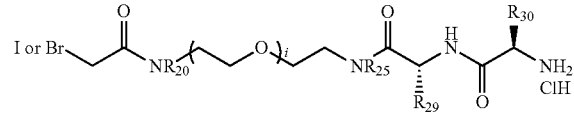

prepared according to the scheme below:

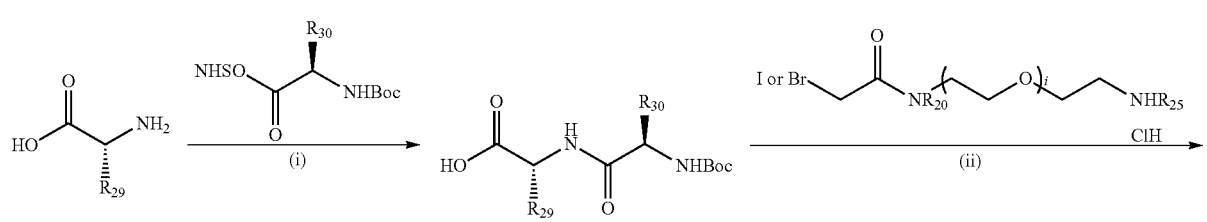

-continued

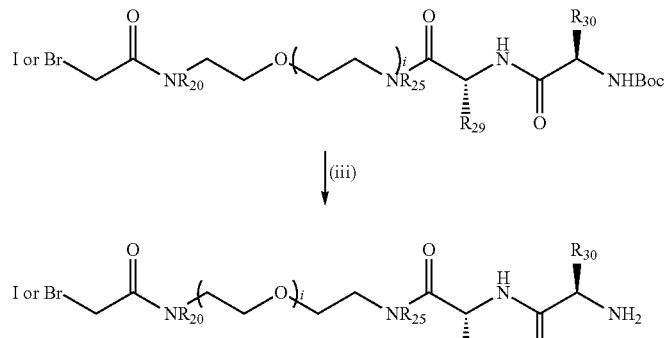

Step (i): peptidic coupling between Boc-L-amino acid-ONHS and L-amino acid; the reaction is performed in a polar solvent such as a DME/THF/H₂O mixture in the presence of a base such as, for example, sodium bicarbonate;

Step (ii): peptidic coupling with halogenoacetamido PEG amines; the reaction is performed in a polar solvent such as $CH_3CN$ in the presence of coupling reagents such as, for example, DCC and HOBt and a base such as, for example, DIEA;

Step (iii): deprotection of the Boc group using a solution of hydrochloric acid (for example solution in dioxane).

L-amino acids are commercially available; NHS esters of Boc-protected L-amino acids are commercially available; halogenoacetamido amines are commercially available for n=2 to 4 and 8 or may be prepared according to the scheme below:

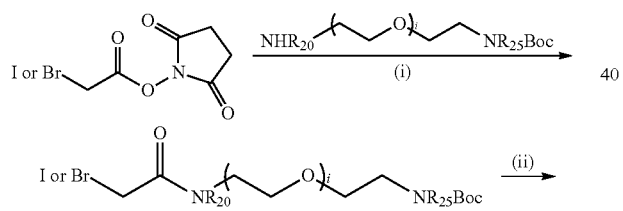

-continued

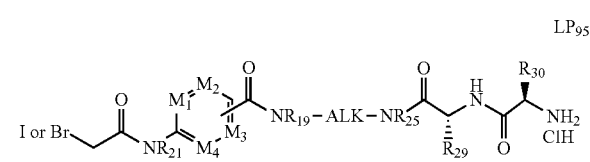

Step (ii): peptide coupling; the reaction is performed in a polar aprotic solvent such as a DCM/CH₃CN mixture;

Step (iii): deprotection of the Boc group using a solution of hydrochloric acid (for example solution in dioxane).

N-succinimidyl bromo- and iodo-acetates are commercially available; the PEG diamines monoprotected with a Boc group are commercially available for i=1 to 9.

LP95

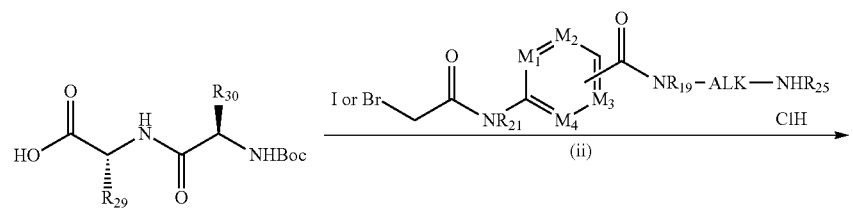

prepared according to the scheme below:

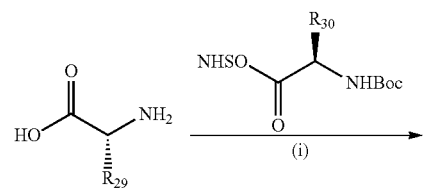

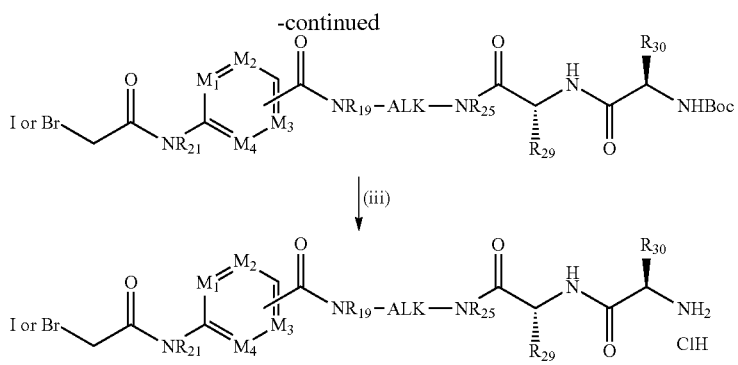

Step (i): peptidic coupling between Boc-L-amino acid-ONHS and L-amino acid; the reaction is performed in a polar solvent such as a DME/THF/H$_2$O mixture in the presence of a base such as, for example, sodium bicarbonate;

Step (ii): peptidic coupling with halogenoacetamido amines; the reaction is performed in a polar solvent such as CH$_3$CN in the presence of coupling reagents such as, for example, DCC and HOBt and a base such as, for example, DIEA;

Step (iii): deprotection of the Boc group using a solution of hydrochloric acid (for example solution in dioxane).

L-amino acids are commercially available; NHS esters of Boc-protected L-amino acids are commercially available; halogenoacetamido amines can be prepared according to the scheme below:

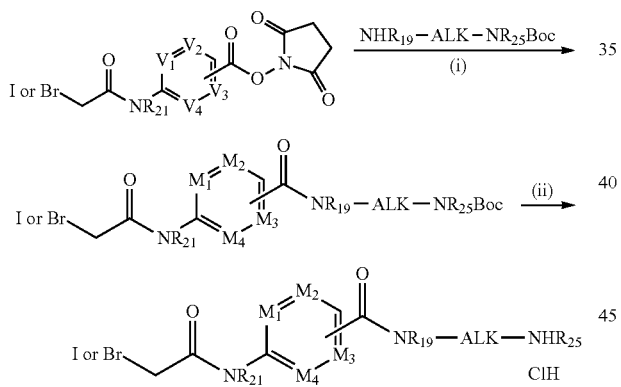

Step (ii): peptide coupling; the reaction is performed in a polar aprotic solvent such as a DCM/CH$_3$CN mixture;

Step (iii): deprotection of the Boc group using a solution of hydrochloric acid (for example solution in dioxane).

NHS esters of halogenoacetamides may be prepared as described for linker precursor LP$_{11}$; the diamines monoprotected with a Boc group are commercially available for n=1 to 10.

prepared according to the scheme below:

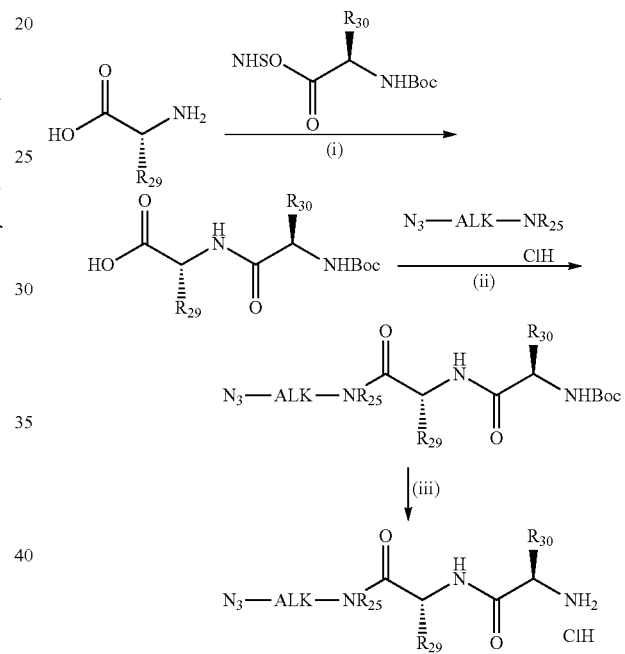

Step (i): peptidic coupling between Boc-L-amino acid-ONHS and L-amino acid; the reaction is performed in a polar solvent such as a DME/THF/H$_2$O mixture in the presence of a base such as, for example, sodium bicarbonate;

Step (ii): peptidic coupling with azido amines; the reaction is performed in a polar solvent such as CH$_3$CN in the presence of coupling reagents such as, for example, DCC and HOBt and a base such as, for example, DIEA;

Step (iii): deprotection of the Boc group using a solution of hydrochloric acid (for example solution in dioxane).

L-amino acids are commercially available; NHS esters of Boc-protected L-amino acids are commercially available; azido amines are commercially available for n=2 to 8 and 10.

LP$_{96}$ & LP$_{98}$

LP$_{97}$ & LP$_{99}$

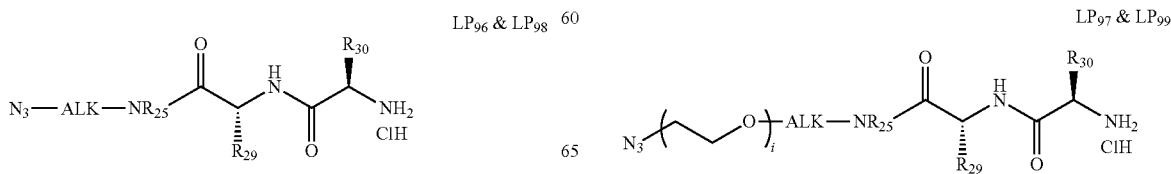

prepared according to the scheme below:

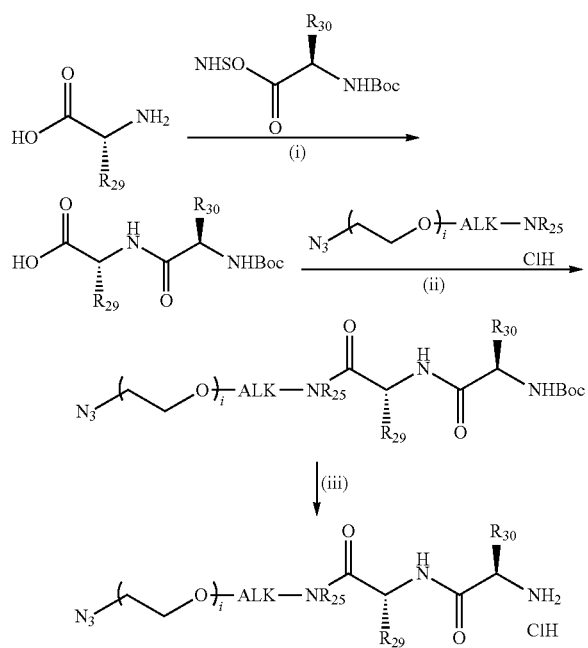

Step (i): peptidic coupling between Boc-L-amino acid-ONHS and L-amino acid; the reaction is performed in a polar solvent such as a DME/THF/H$_2$O mixture in the presence of a base such as, for example, sodium bicarbonate;

Step (ii): peptidic coupling with azido PEG amines; the reaction is performed in a polar solvent such as CH$_3$CN in the presence of coupling reagents such as, for example, DCC and HOBt and a base such as, for example, DIEA;

Step (iii): deprotection of the Boc group using a solution of hydrochloric acid (for example solution in dioxane).

L-amino acids are commercially available; NHS esters of Boc-protected L-amino acids are commercially available; for ALK=CH$_2$CH$_2$, azido PEG amines are commercially available for i=1 to 8 and 10, for ALK≠CH$_2$CH$_2$, azido PEG amines may be prepared according to the scheme below:

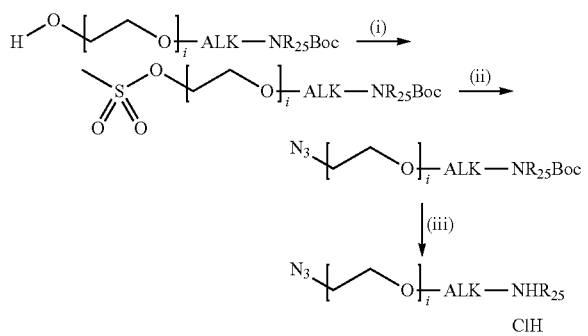

Step (i): activation of the alcohol as a mesylate; the reaction is performed in a polar aprotic solvent such as, for example, DCM by treatment with methanesulfonyl chloride in the presence of a base such as, for example, TEA;

Step (ii): substitution of the mesylate by an azido group; the reaction is performed in a polar solvent such as an acetone/H$_2$O mixture by treatment with sodium azide;

Step (iii): deprotection of the Boc group using a solution of hydrochloric acid (for example solution in dioxane). The starting PEG amino alcohols may be prepared as described for linker precursor LP$_{90}$.

LP$_{100}$

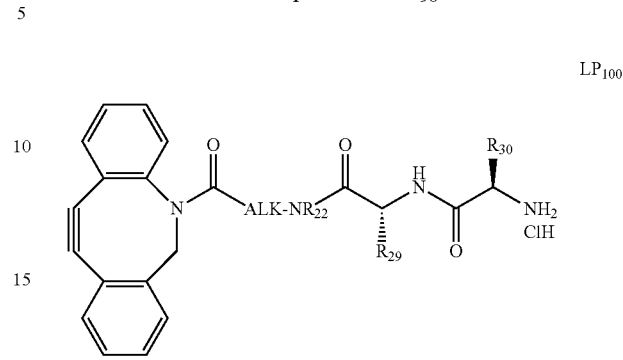

prepared according to the scheme below:

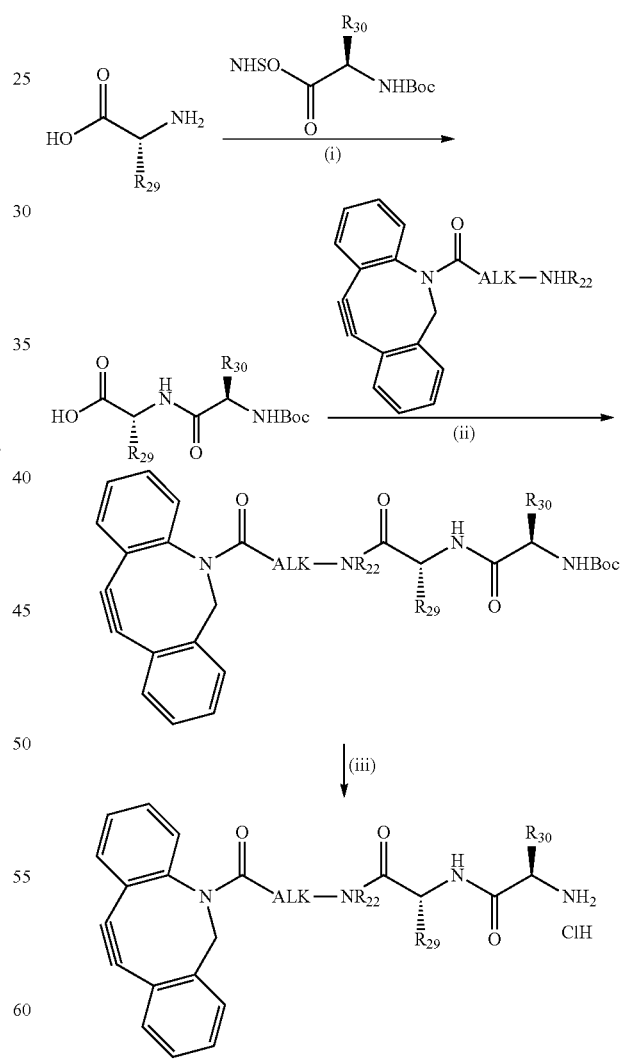

Step (i): peptidic coupling between Boc-L-amino acid-ONHS and L-amino acid; the reaction is performed in a polar solvent such as a DME/THF/H$_2$O mixture in the presence of a base such as, for example, sodium bicarbonate;

Step (ii): peptidic coupling with cyclooctyne amines; the reaction is performed in a polar solvent such as $CH_3CN$ in the presence of coupling reagents such as, for example, DCC and HOBt and a base such as, for example, DIEA;

Step (iii): deprotection of the Boc group using a solution of hydrochloric acid (for example solution in dioxane).

Cyclooctyne amines are commercially available for n=1, 2, 3 and 5.

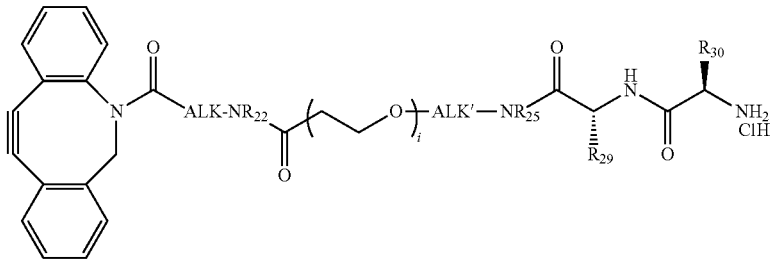

LP$_{101}$ prepared according to the scheme below:

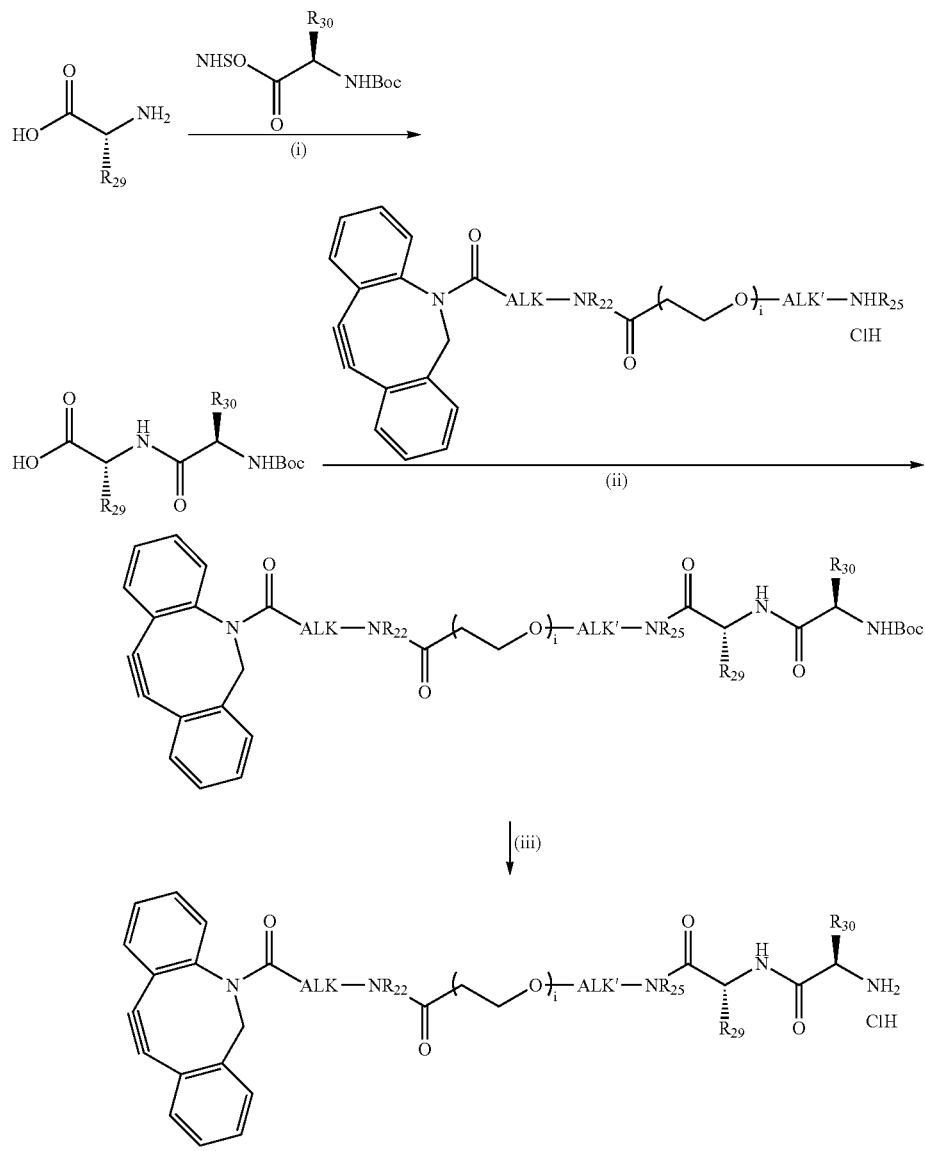

Step (i): peptidic coupling between Boc-L-amino acid-ONHS and L-amino acid; the reaction is performed in a polar solvent such as a DME/THF/H$_2$O mixture in the presence of a base such as, for example, sodium bicarbonate;

Step (ii): peptidic coupling with cyclooctyne PEG amines; the reaction is performed in a polar solvent such as CH$_3$CN in the presence of coupling reagents such as, for example, DCC and HOBt and a base such as, for example, DIEA;

Step (iii): deprotection of the Boc group using a solution of hydrochloric acid (for example solution in dioxane).

Cyclooctyne PEG amines may be prepared according to the scheme below:

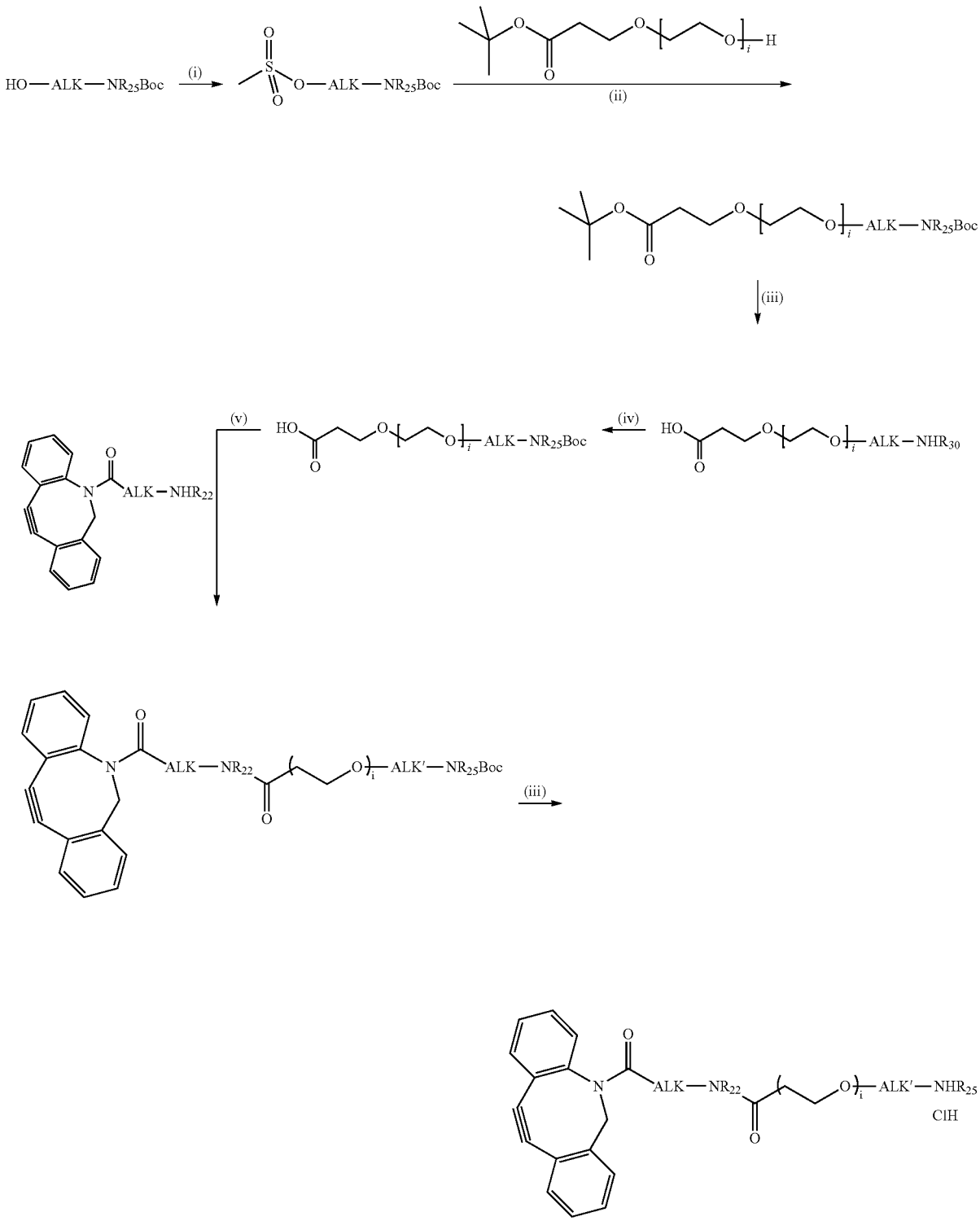

Step (i): activation of the alcohol as a mesylate; the reaction is performed in a polar aprotic solvent such as, for example, DCM by treatment with methanesulfonyl chloride in the presence of a base such as, for example, TEA;

Step (ii): nucleophilic substitution; the reaction is performed in a polar aprotic solvent such as, for example, DMF in the presence of a base such as sodium hydride;

Step (iii): deprotection using a solution of hydrochloric acid (for example solution in dioxane) or of trifluoroacetic acid;

Step (iv): protection of the amine with a Boc group; the reaction is performed in a polar solvent such as, for example, DCM, by treatment with $Boc_2O$ in the presence of a base such as, for example, TEA;

Step (v): peptidic coupling; the reaction is performed in a polar solvent such as, for example, DCM, in the presence of coupling reagents such as, for example, HOBt and EDC.

The starting ALK amino alcohols are commercially available for n=1 to 10; cyclooctynes are commercially available for n=1, 2, 3 and 5.

TABLE I

Cryptophycin payloads of formula (II)[1,2]

| LP | Linker precursor<br>Examples of LP | RCG1—L family derived from the precursor LP |
|---|---|---|
| $LP_1$ | (structure) | $L_1$ |
| $LP_2$ | (structure) | $L_2$ |
| $LP_3$ | (structure) | $L_3$ |
| $LP_4$ | (structure) | $L_4$ |

TABLE I-continued
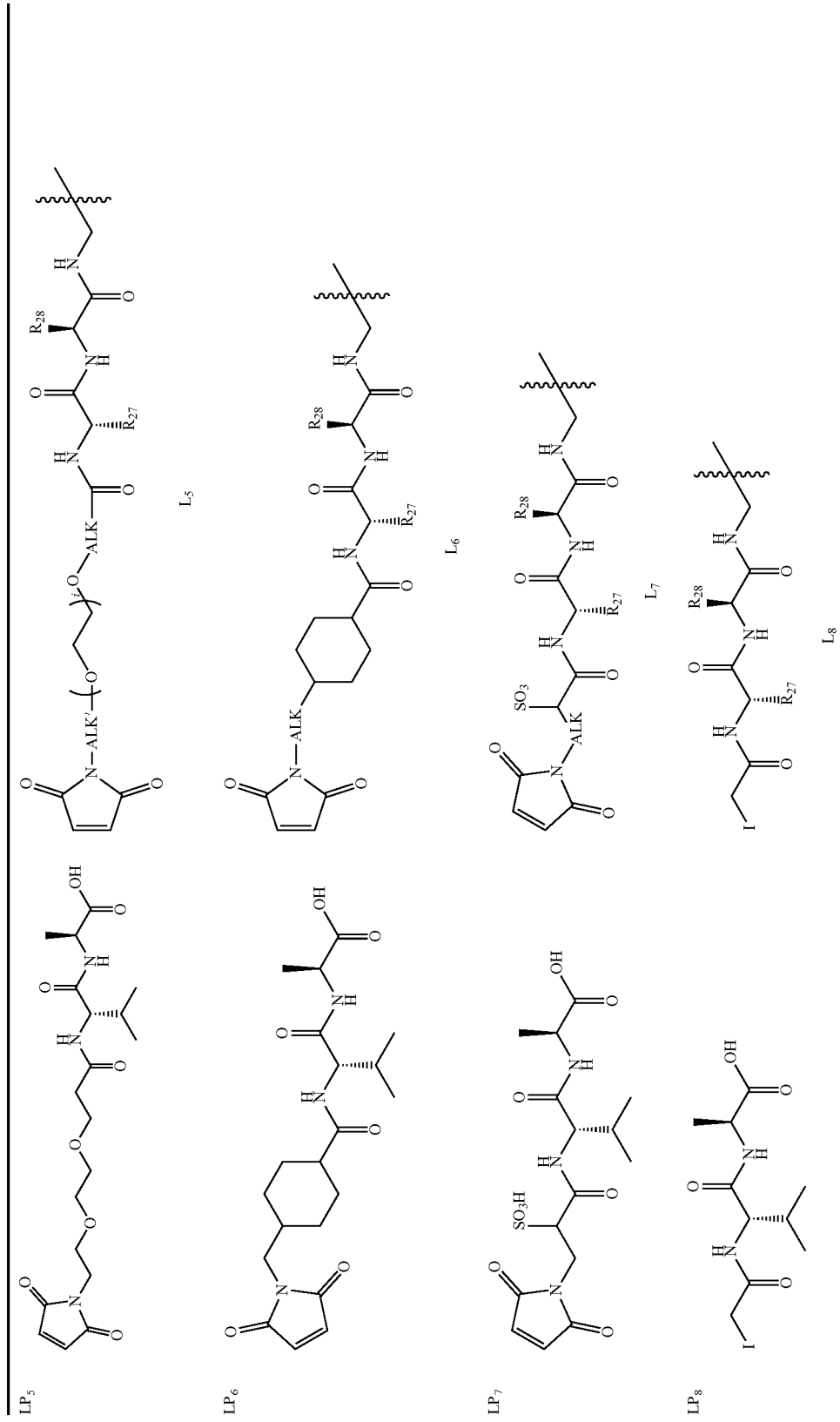

TABLE I-continued
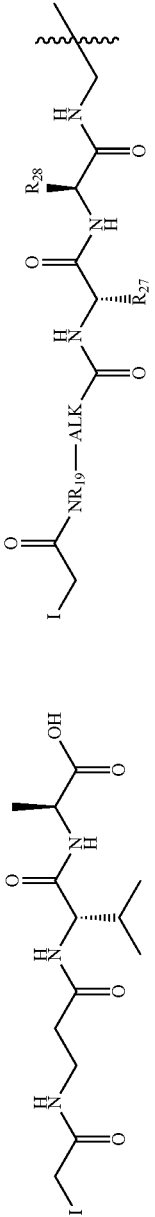

TABLE I-continued

TABLE I-continued

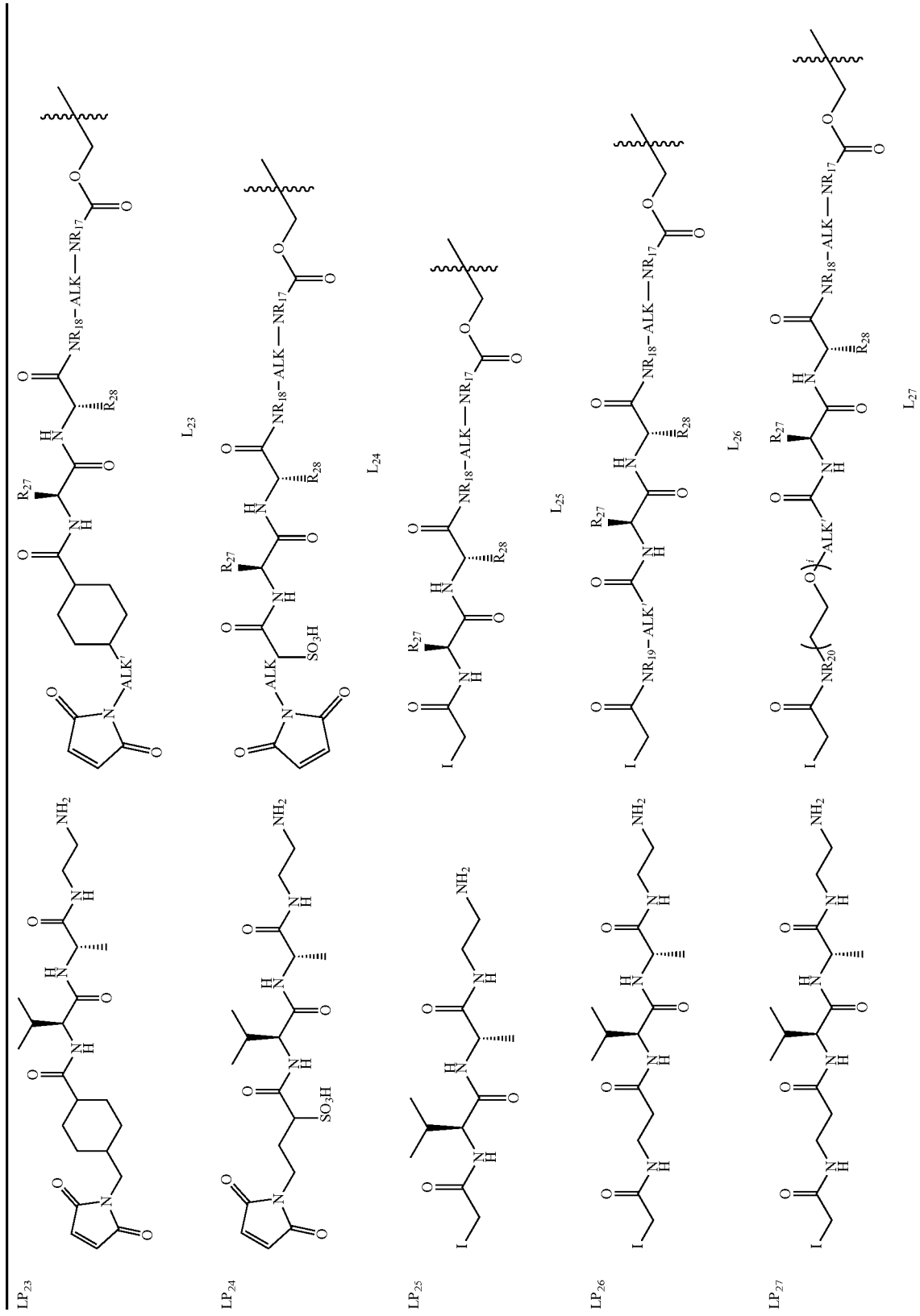

TABLE I-continued

| | |
|---|---|
| LP₂₈ | L₂₈ |
| LP₂₉ | L₂₉ |
| LP₃₀ | L₃₀ |
| LP₃₁ | L₃₁ |
| LP₃₂ | L₃₂ |

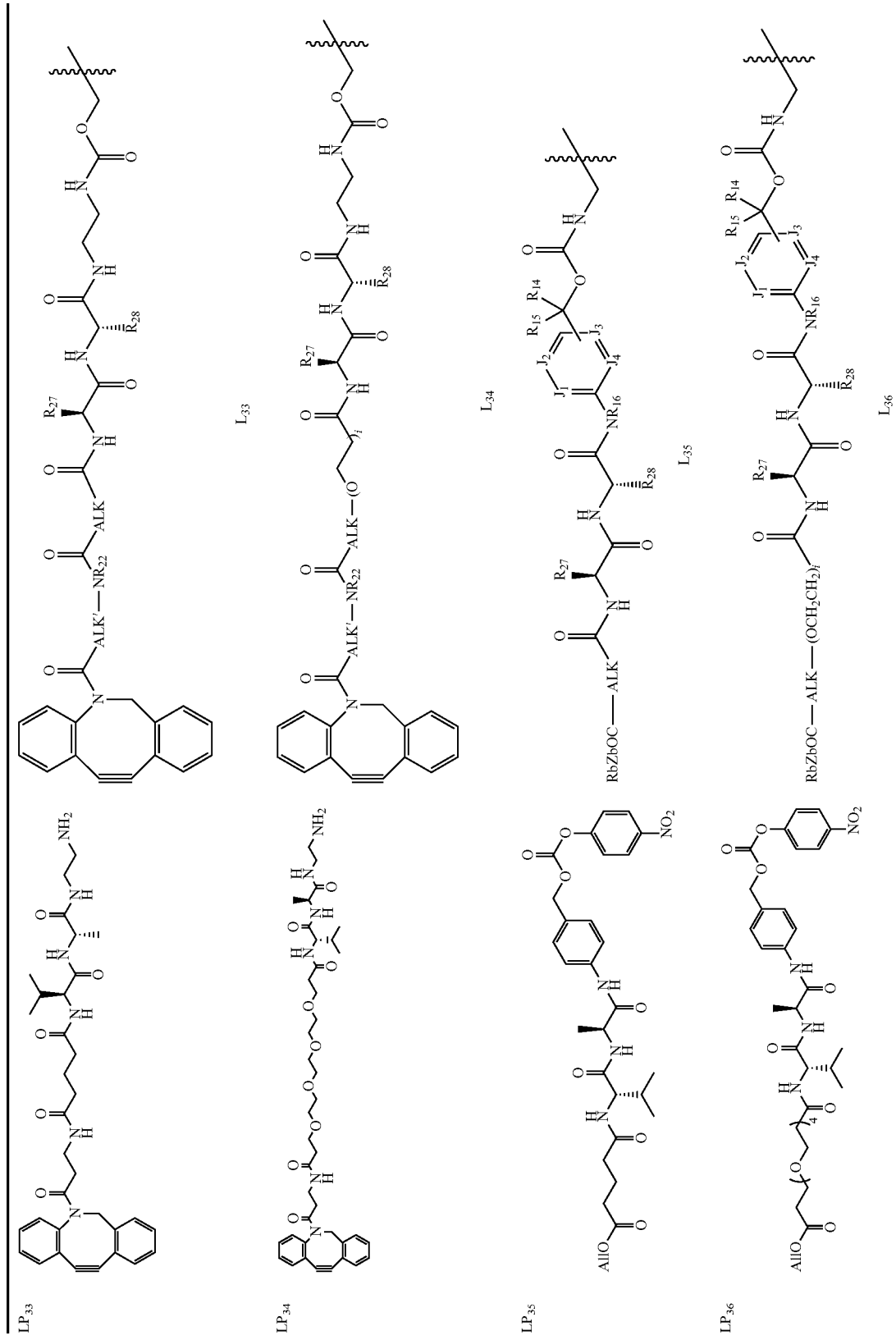

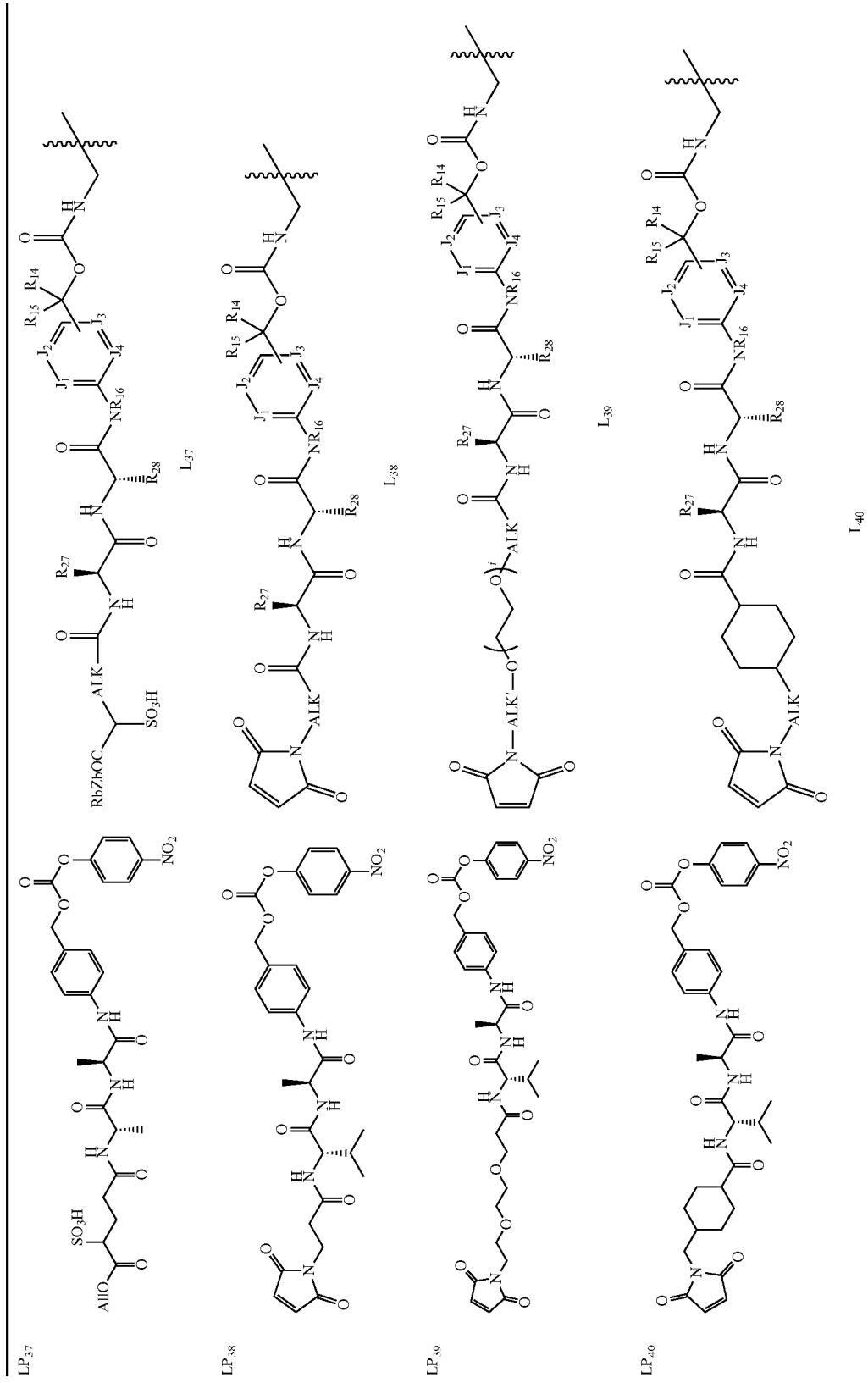

TABLE I-continued
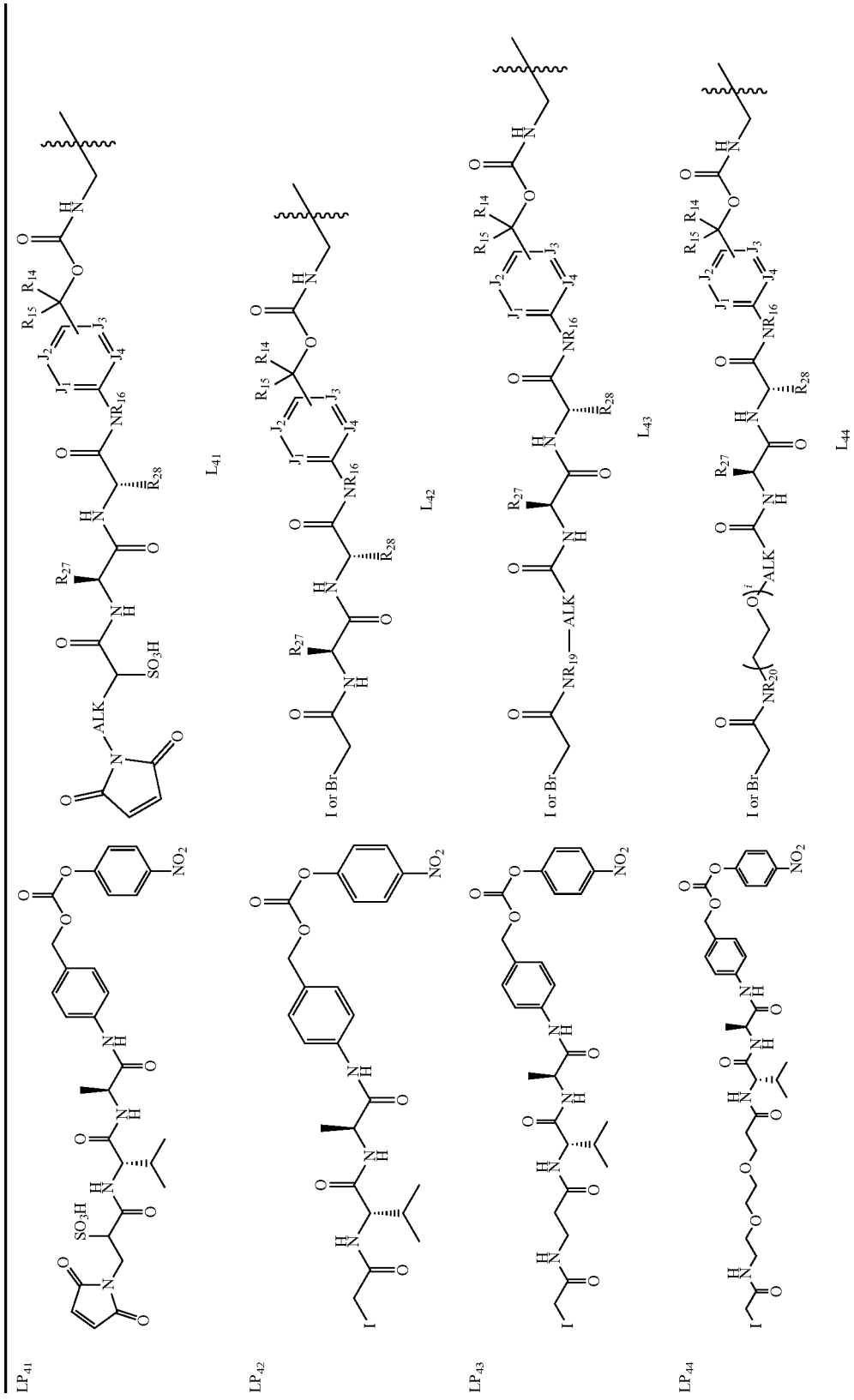

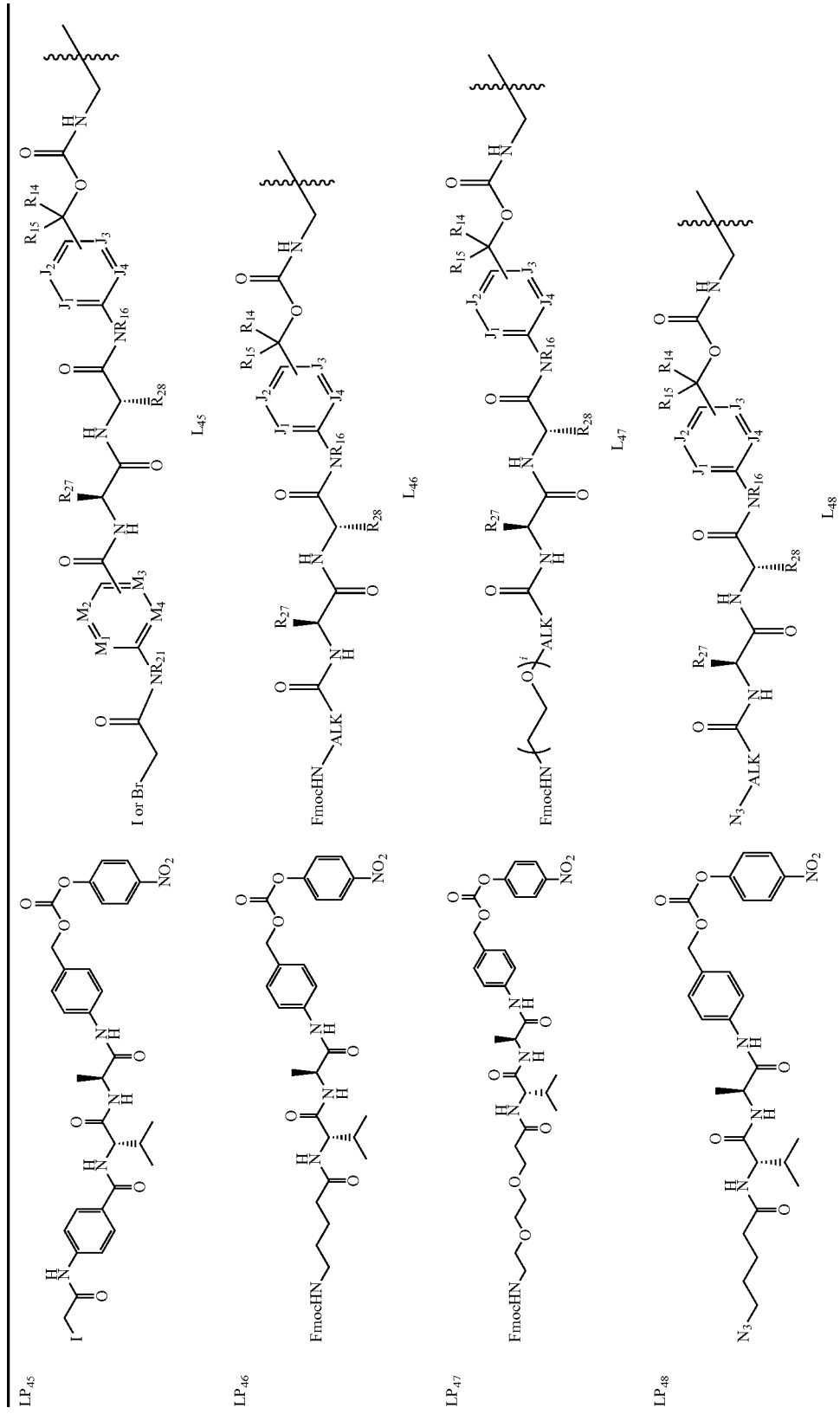

TABLE I-continued
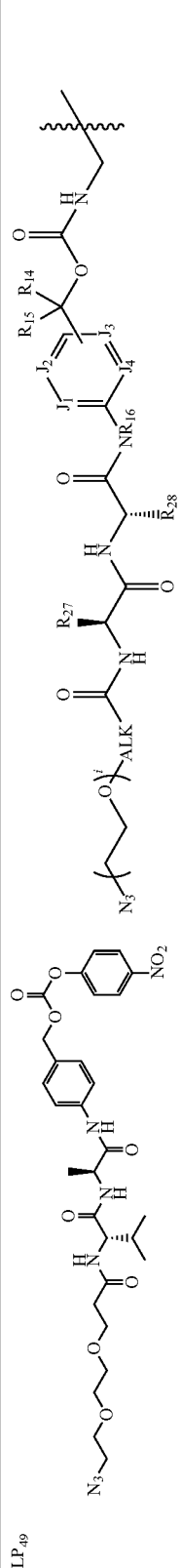

TABLE I-continued

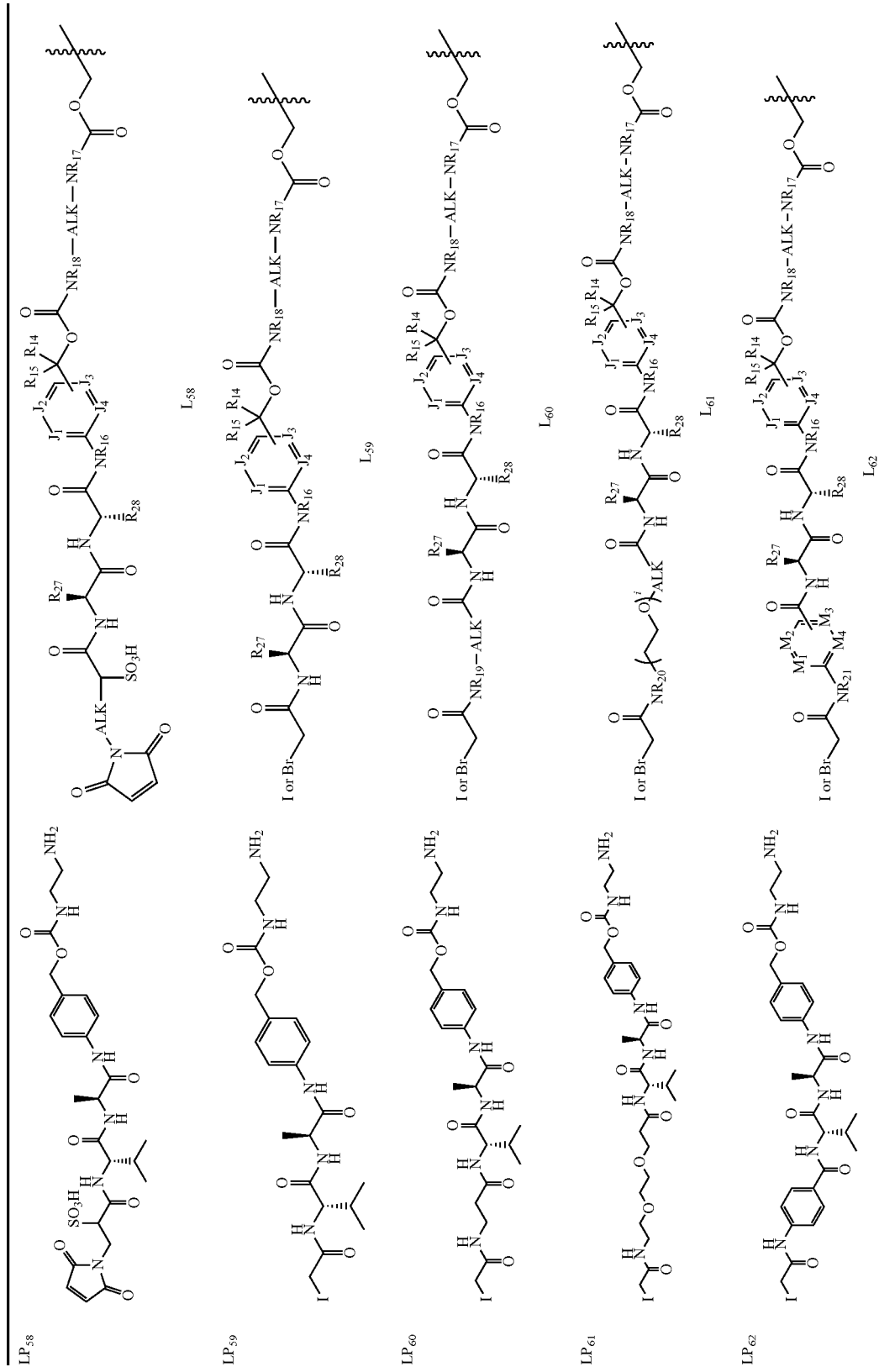

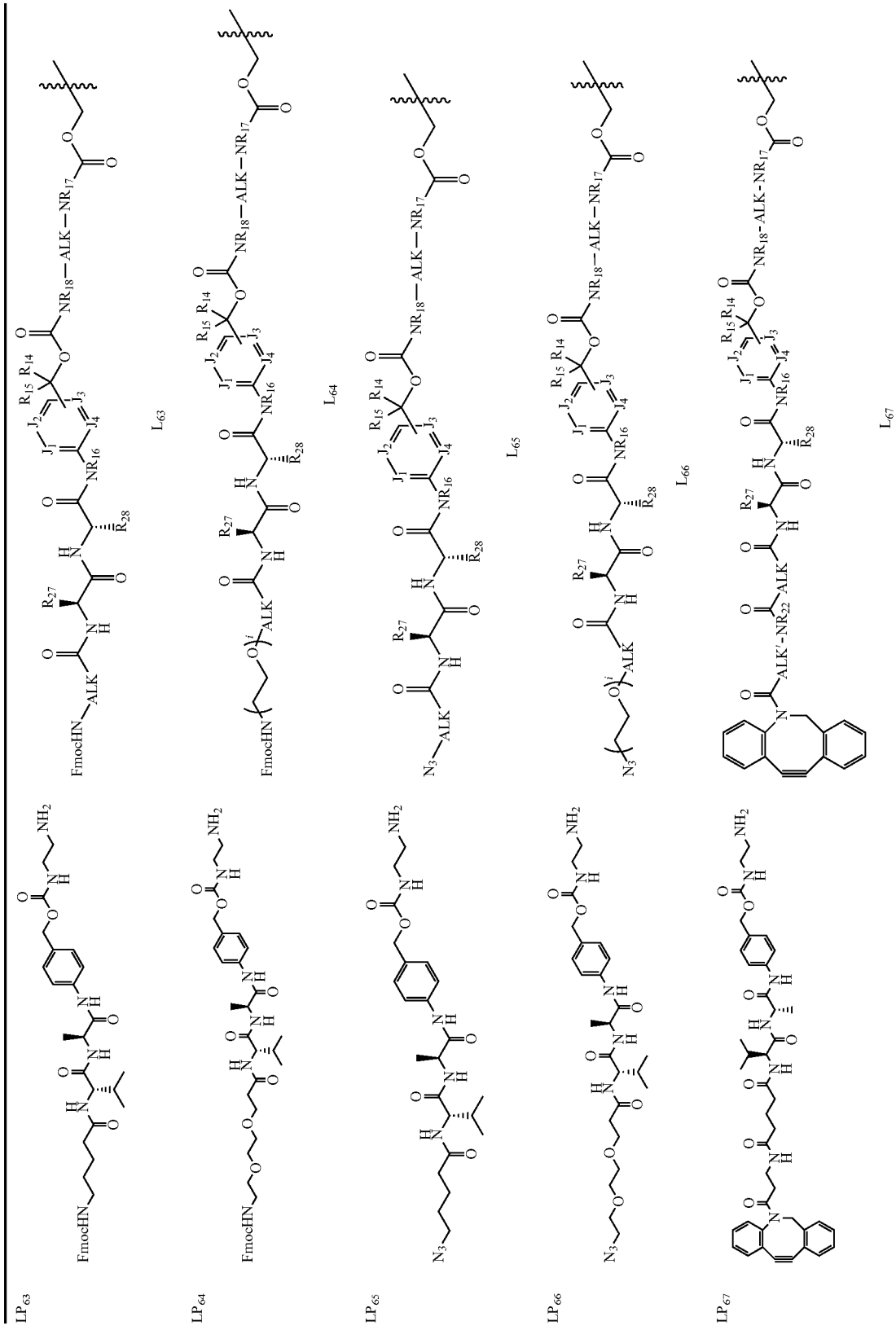

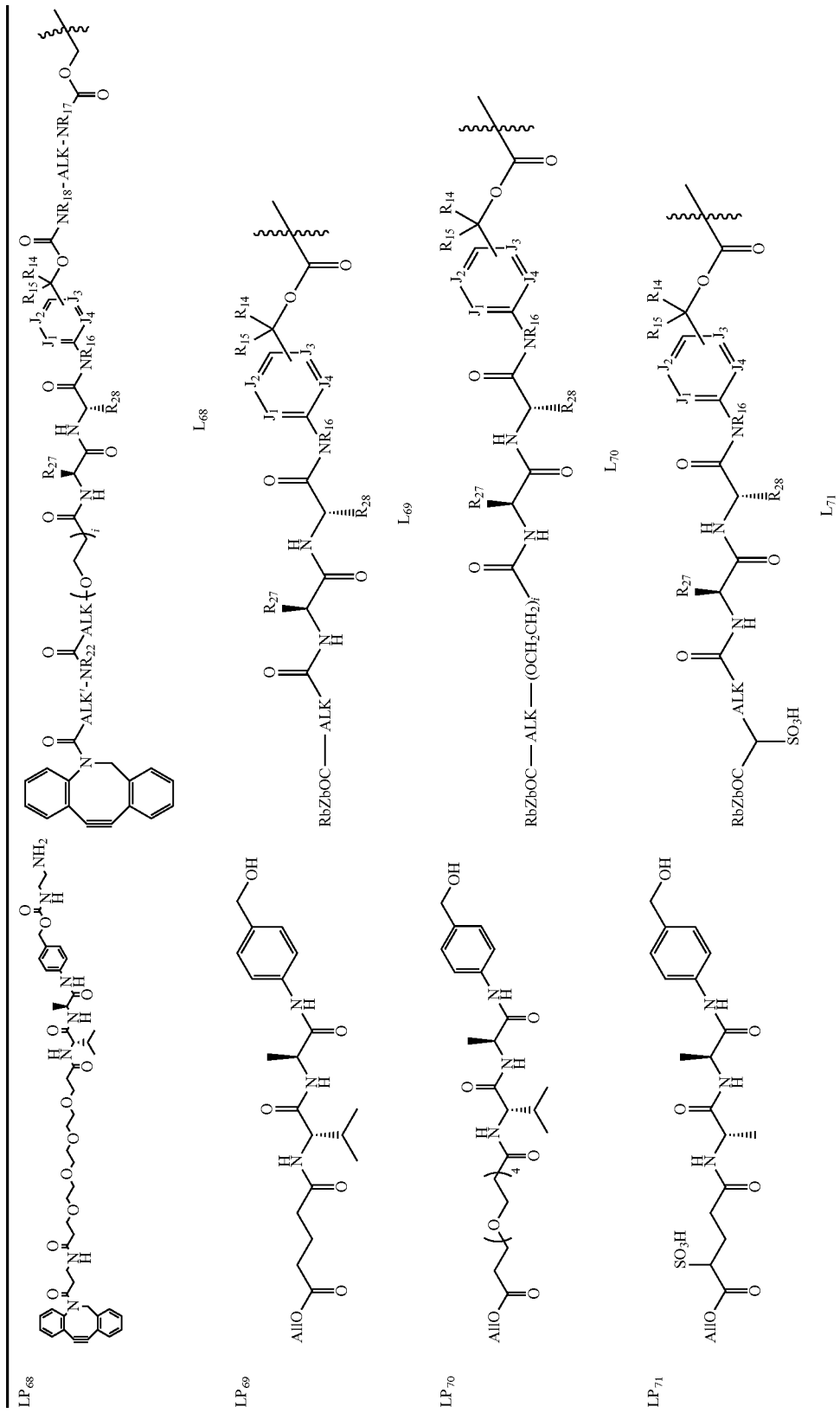

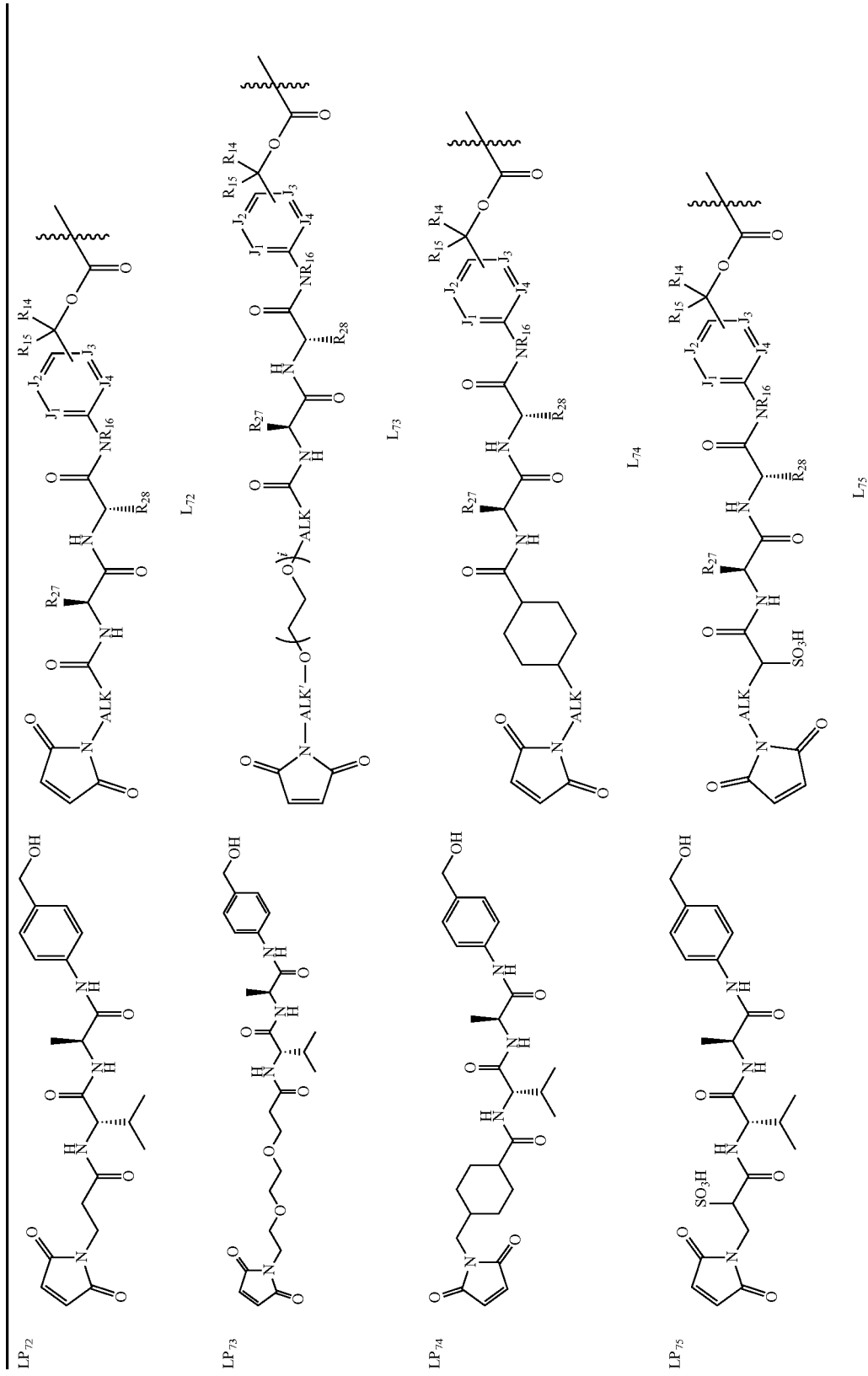

TABLE I-continued
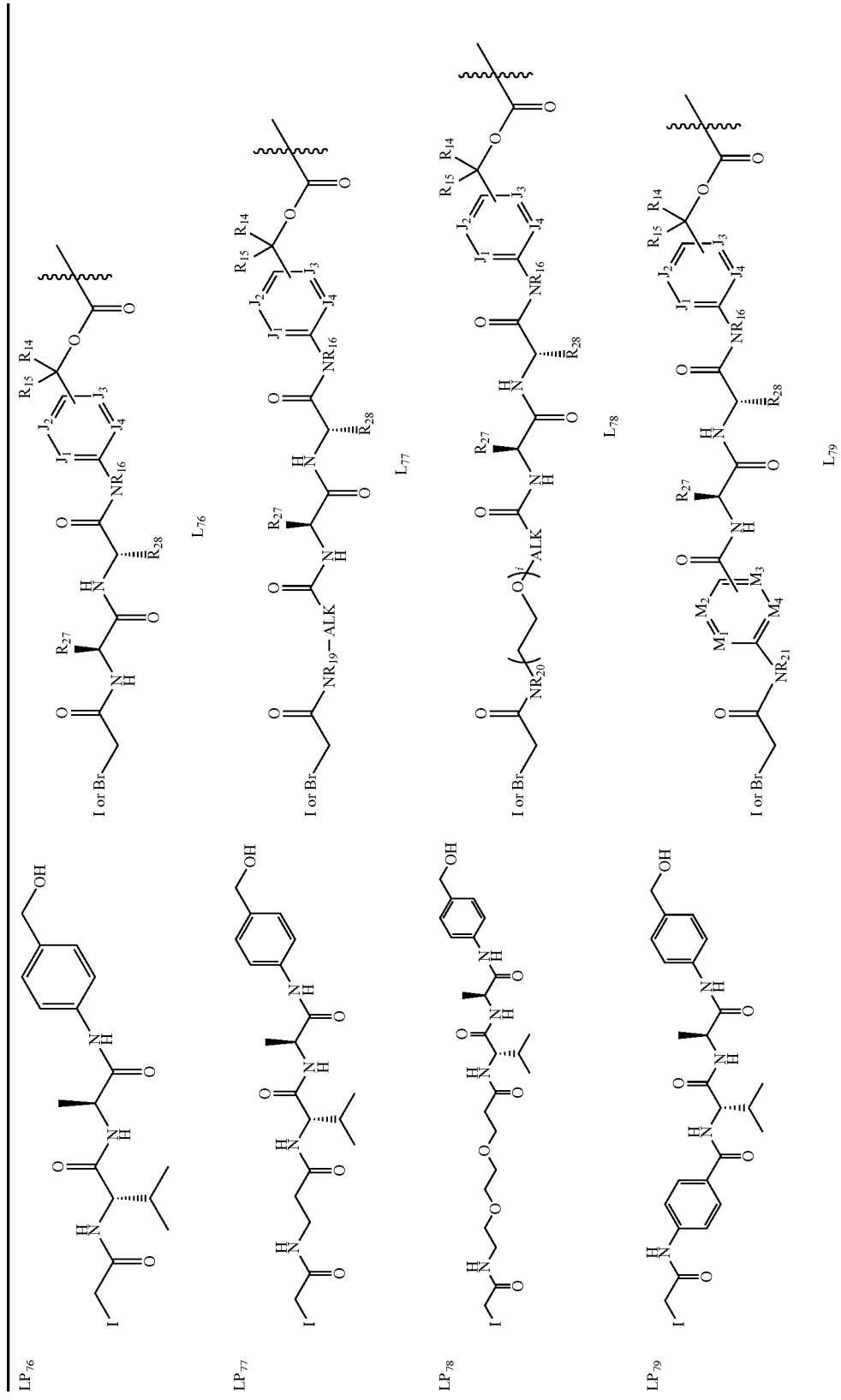

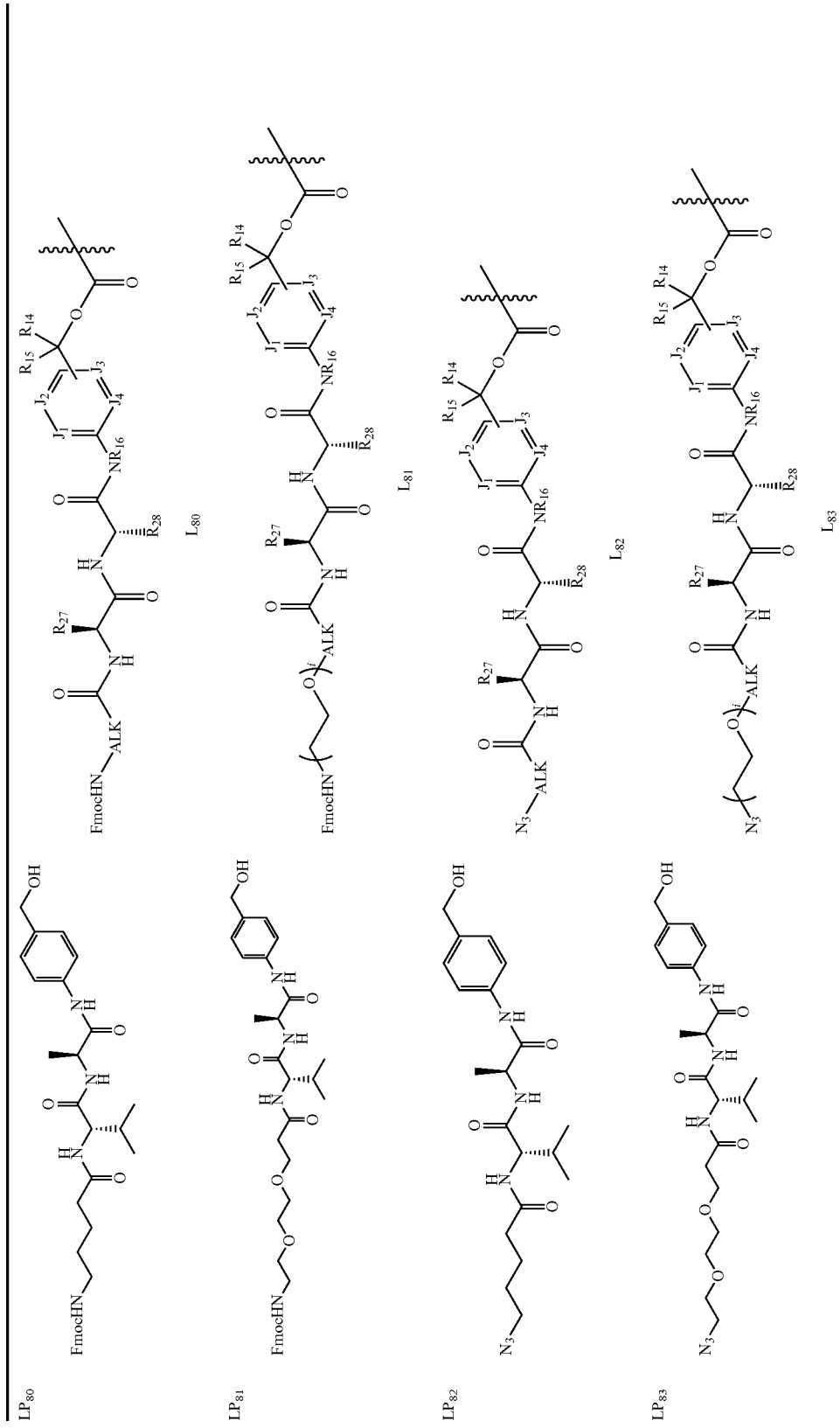

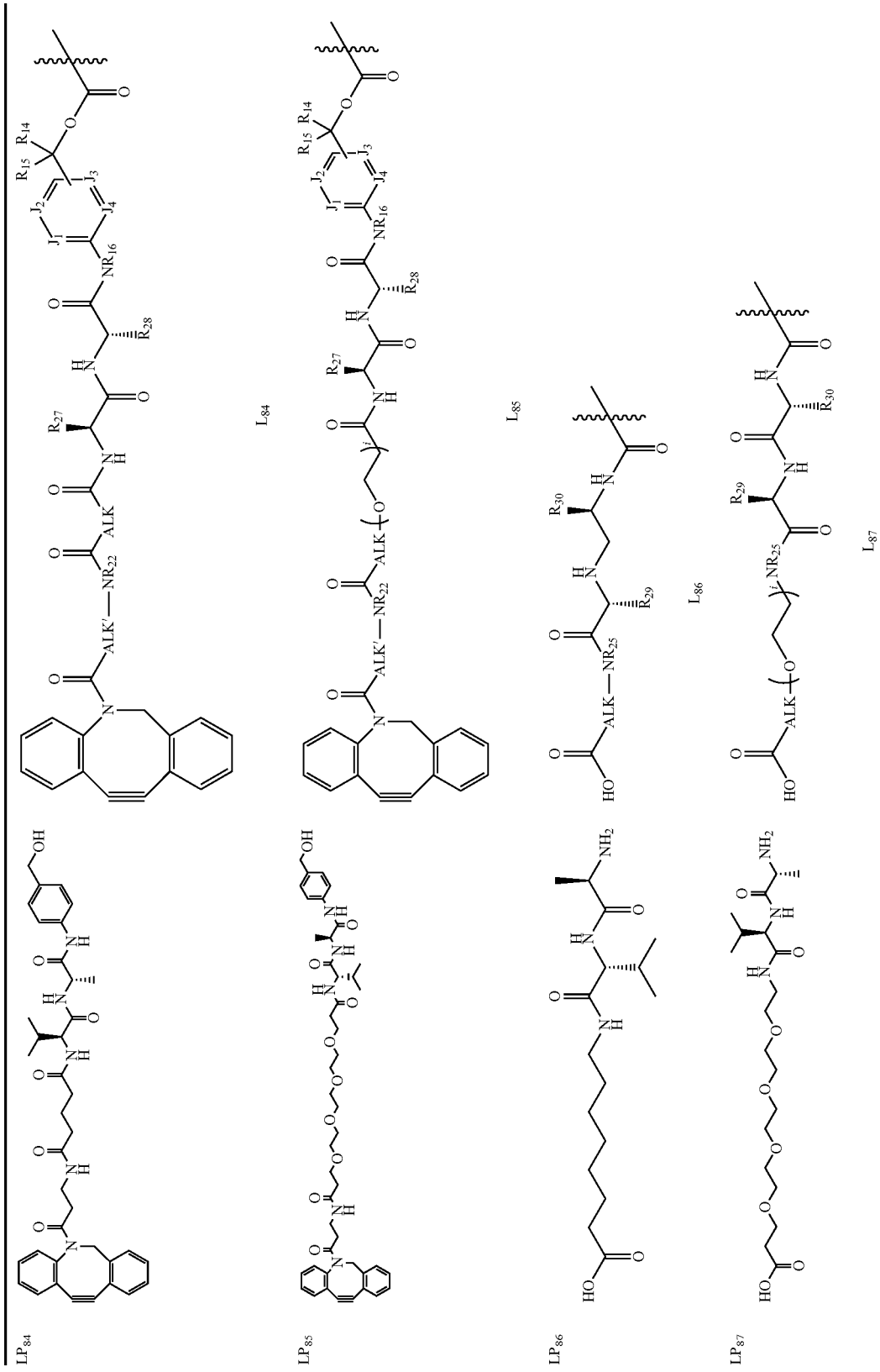

TABLE I-continued
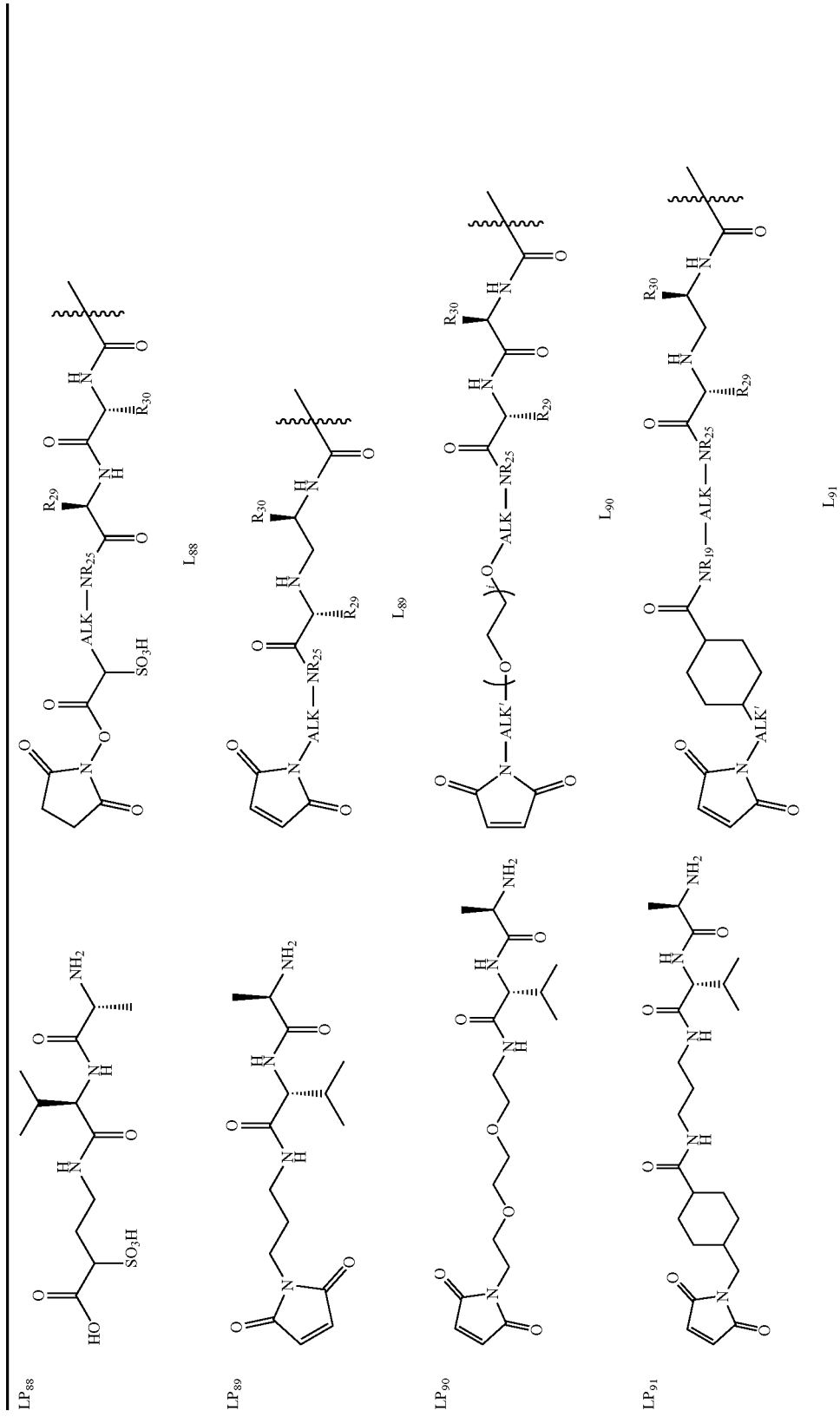

TABLE I-continued

TABLE I-continued
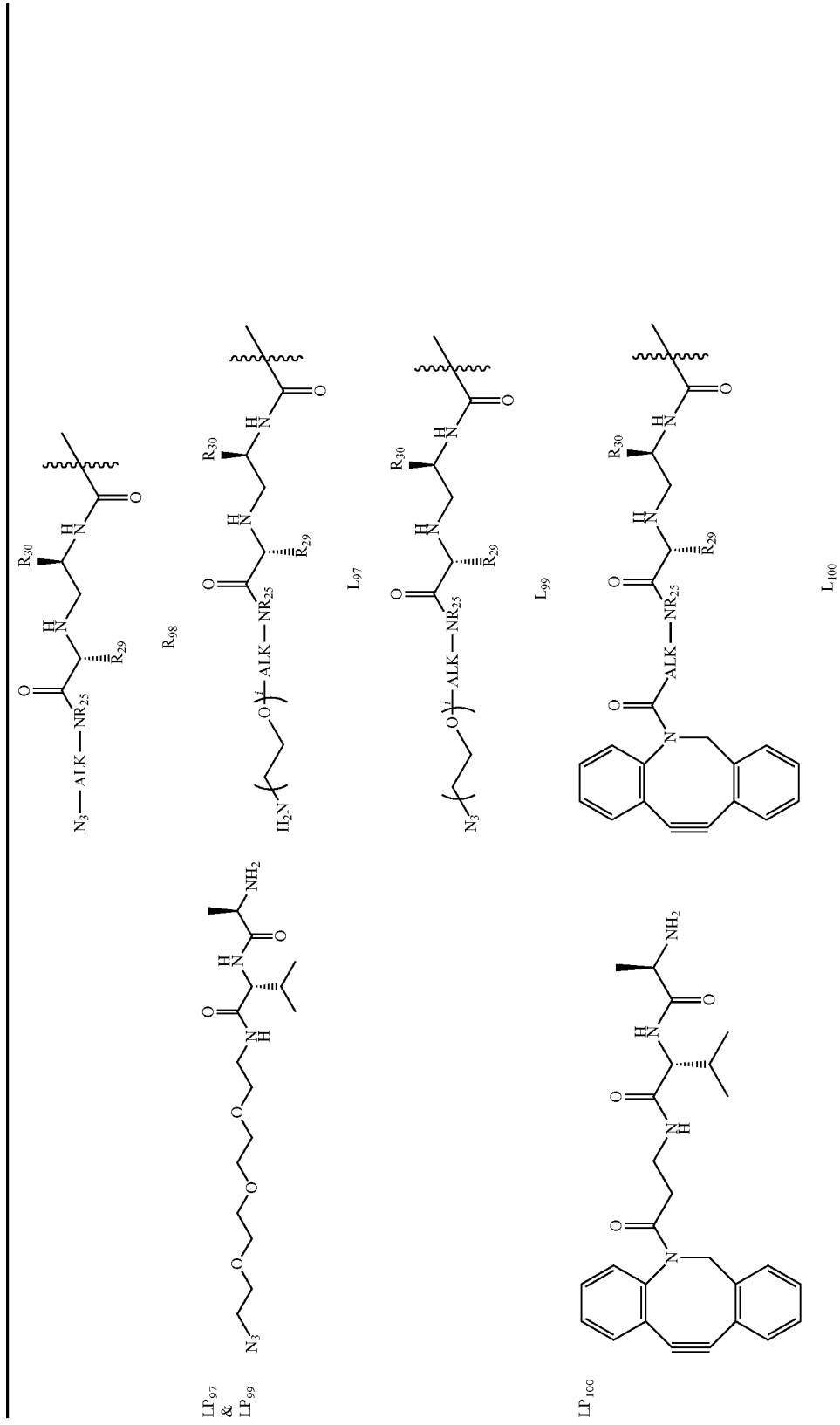

TABLE I-continued

TABLE I-continued
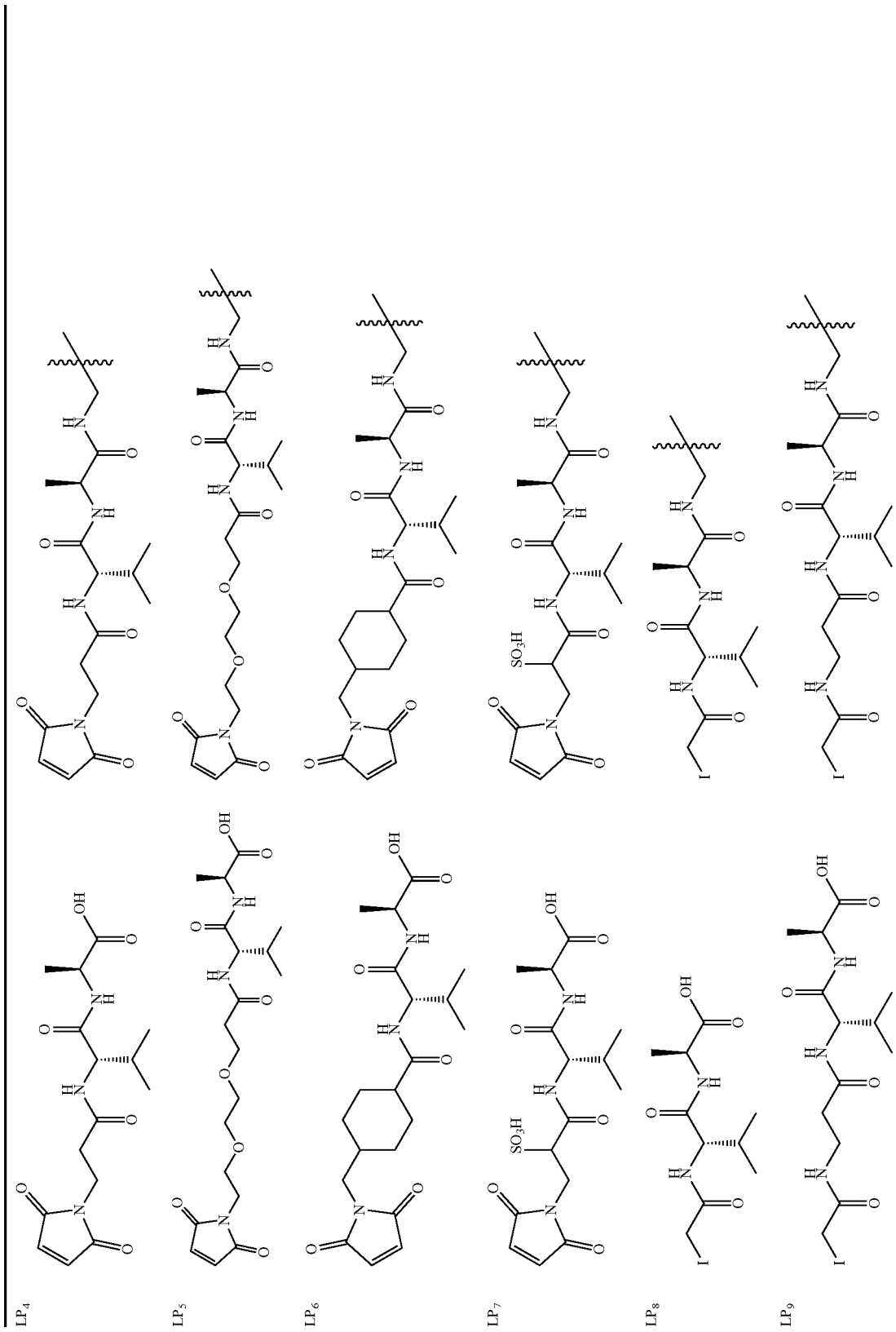

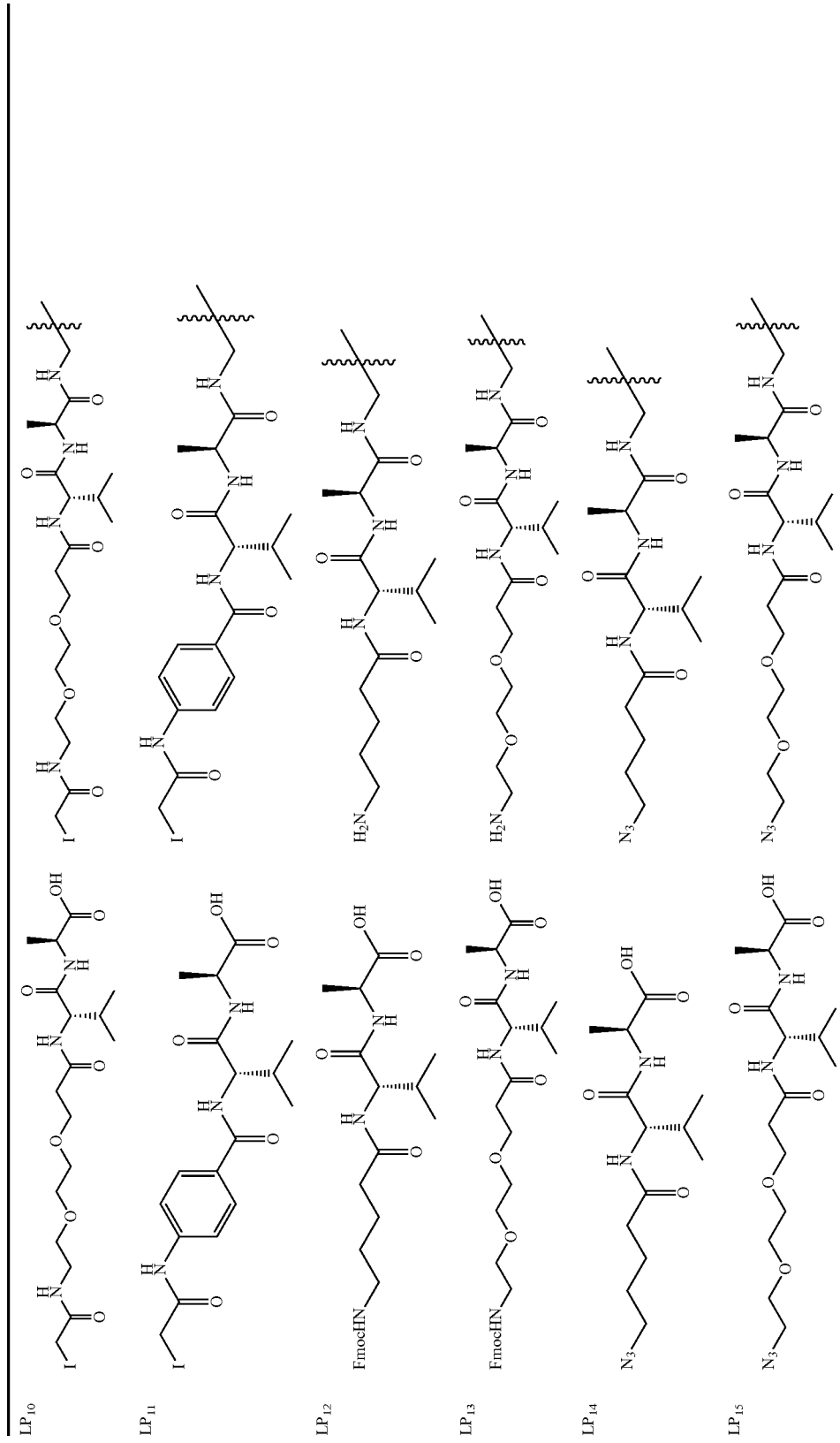

TABLE I-continued

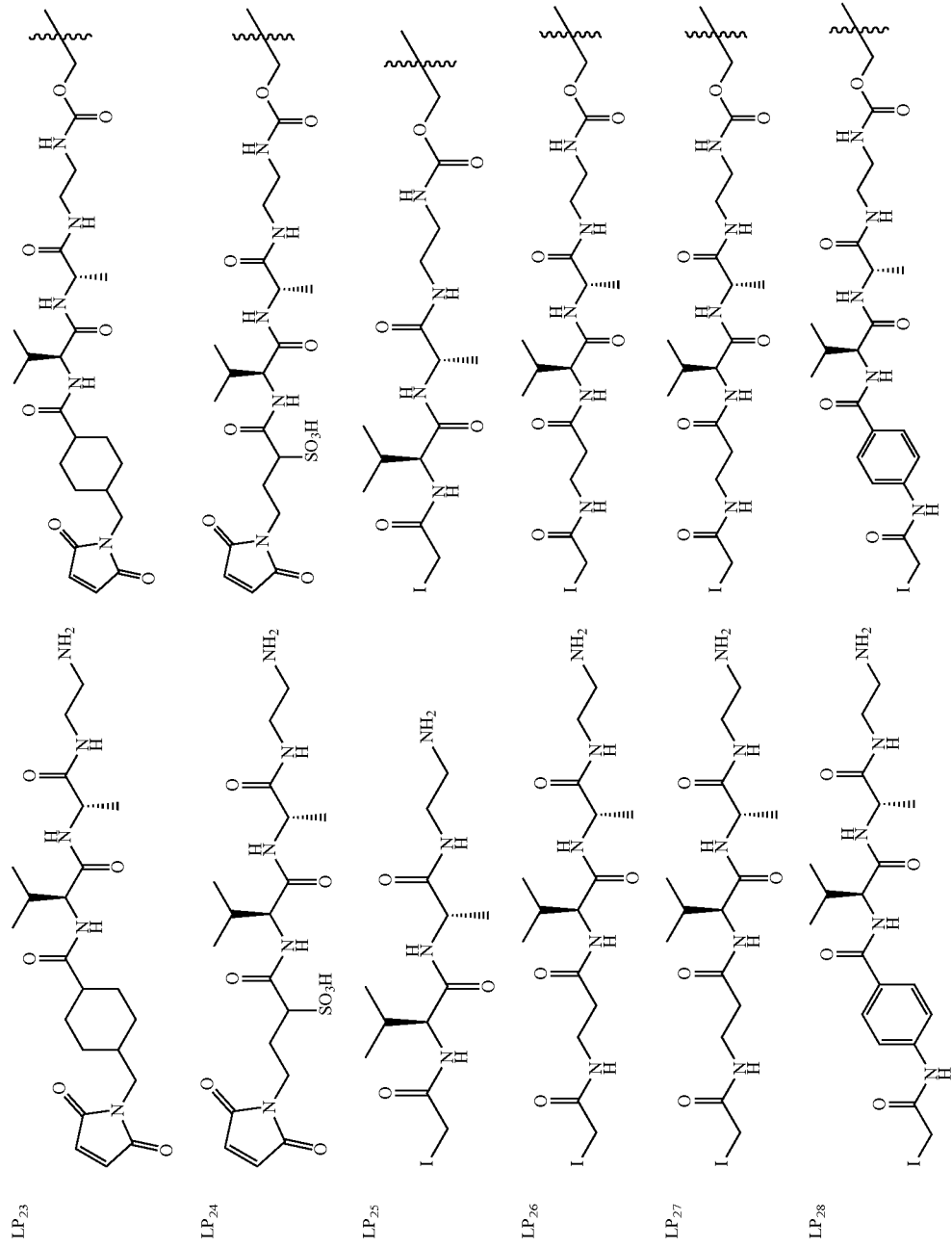

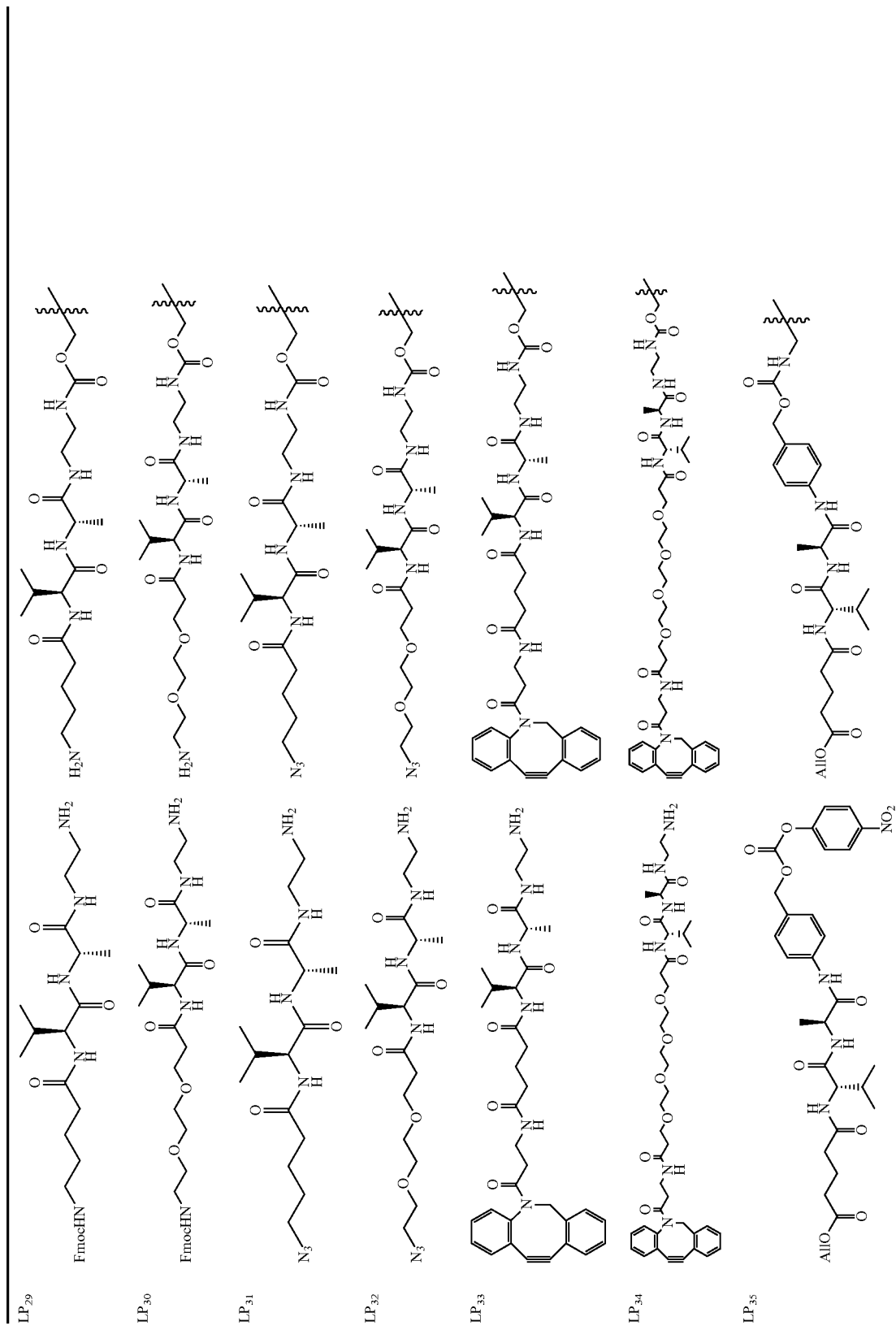

TABLE I-continued

| | |
|---|---|
| LP36 | |
| LP37 | |
| LP38 | |
| LP39 | |
| LP40 | |

TABLE I-continued
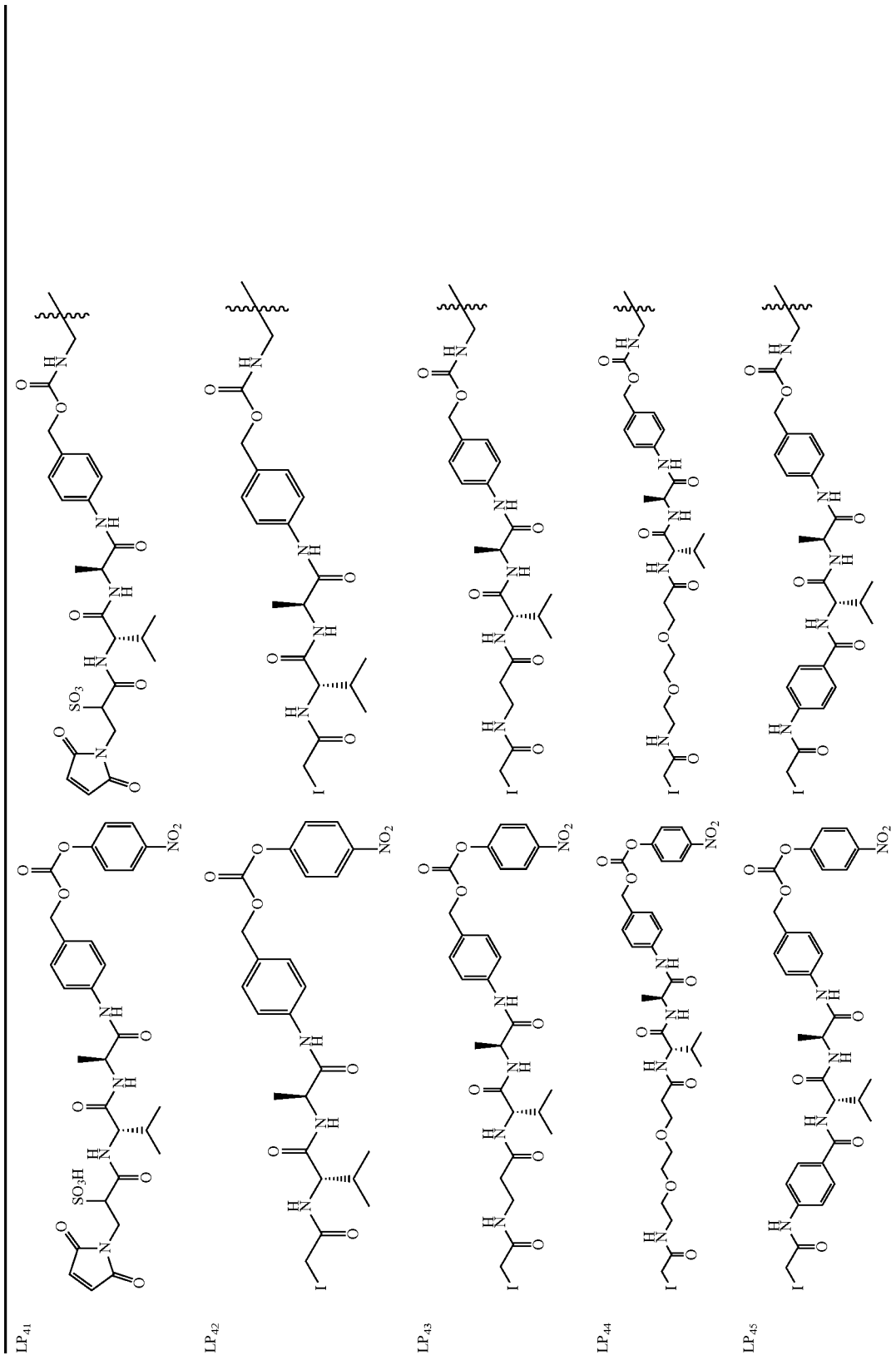

TABLE I-continued

| | |
|---|---|
| LP₄₆ | (structure) |
| LP₄₇ | (structure) |
| LP₄₈ | (structure) |
| LP₄₉ | (structure) |
| LP₅₀ | (structure) |
| LP₅₁ | (structure) |

TABLE I-continued
| | | |
|---|---|---|
| LP$_{52}$ | 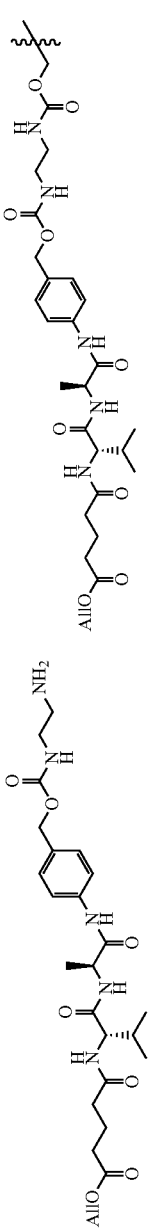 | 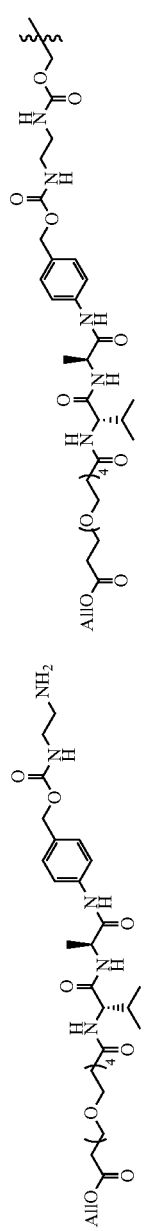 |
| LP$_{53}$ | 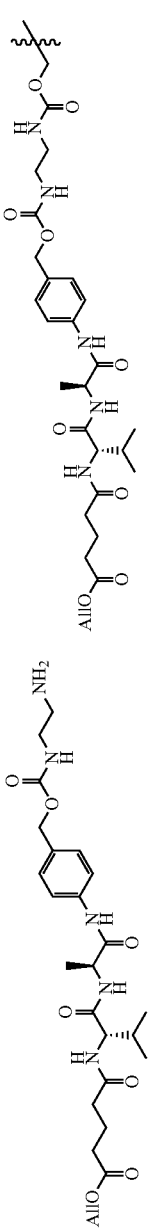 | 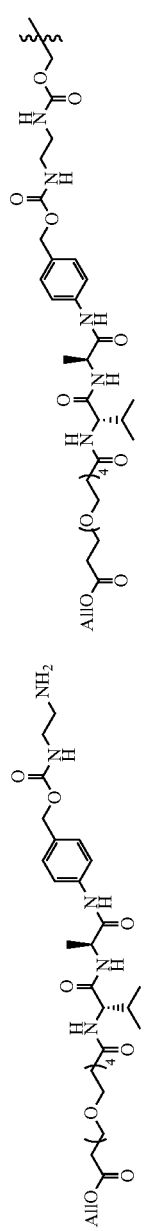 |
| LP$_{54}$ | 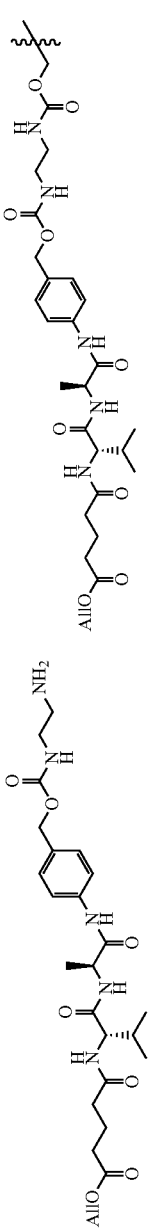 | 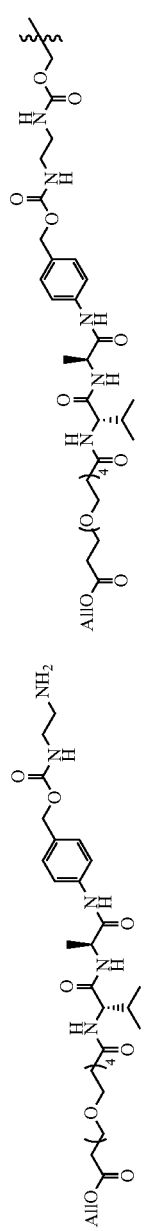 |
| LP$_{55}$ | 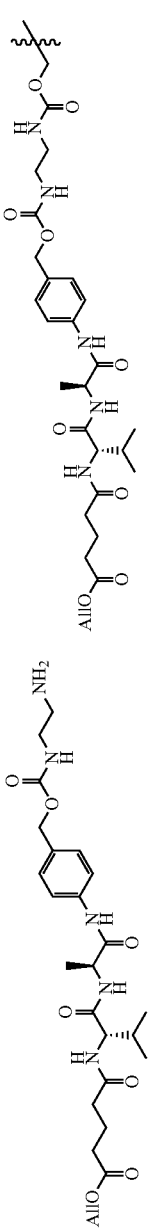 | 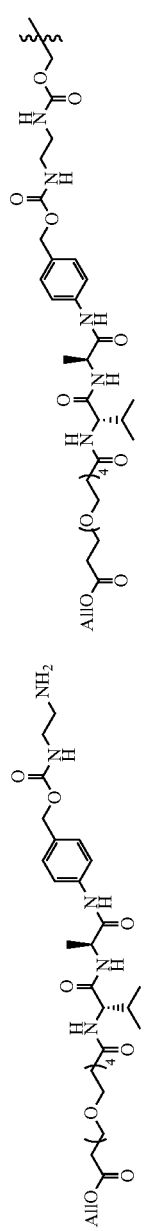 |
| LP$_{56}$ | 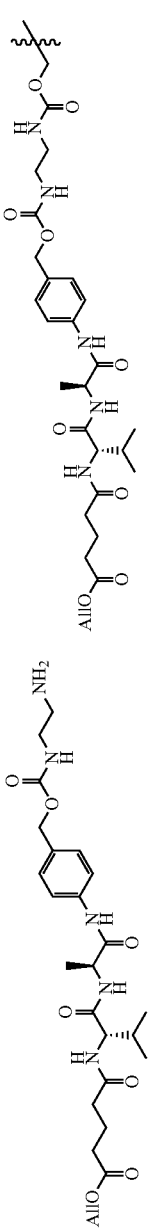 | 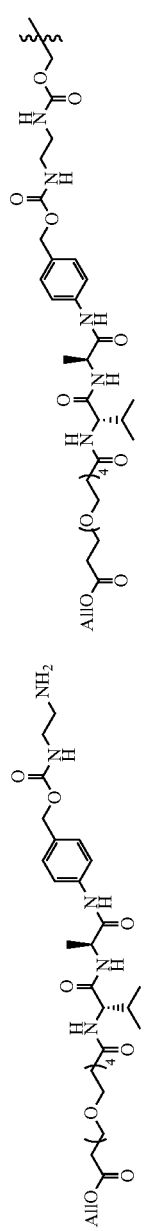 |
| LP$_{57}$ | 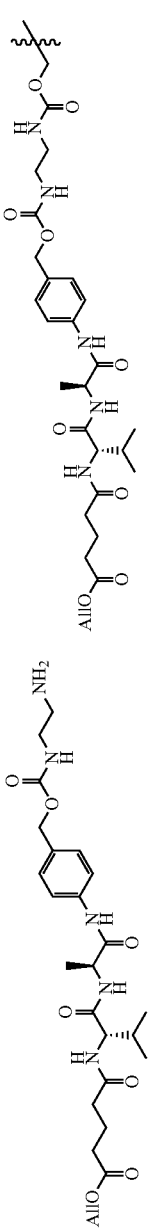 | |
| LP$_{58}$ | 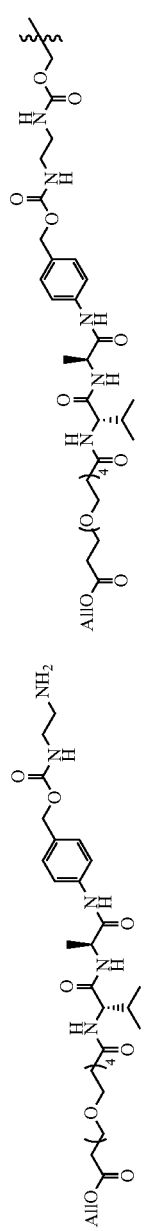 | |

TABLE I-continued

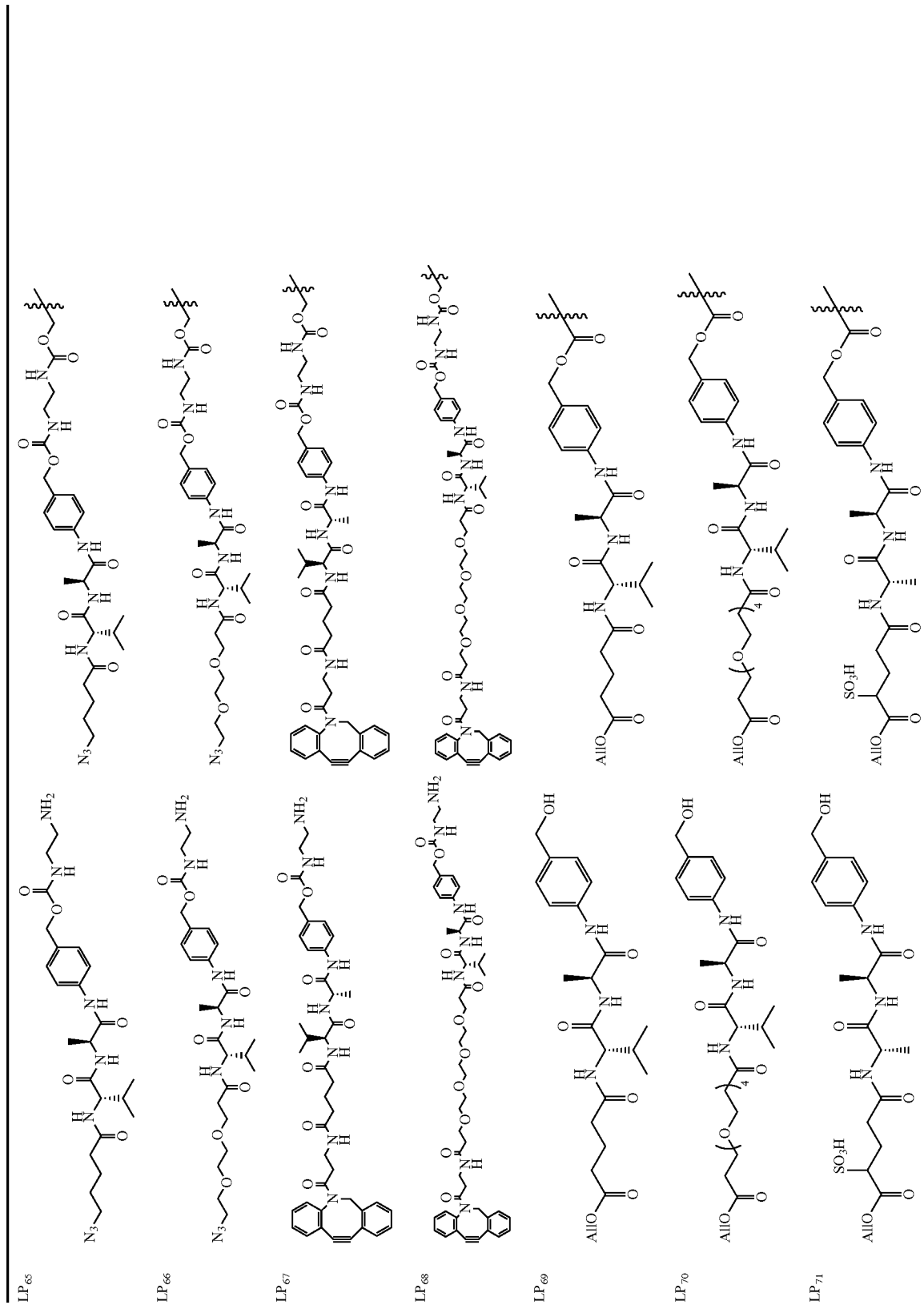

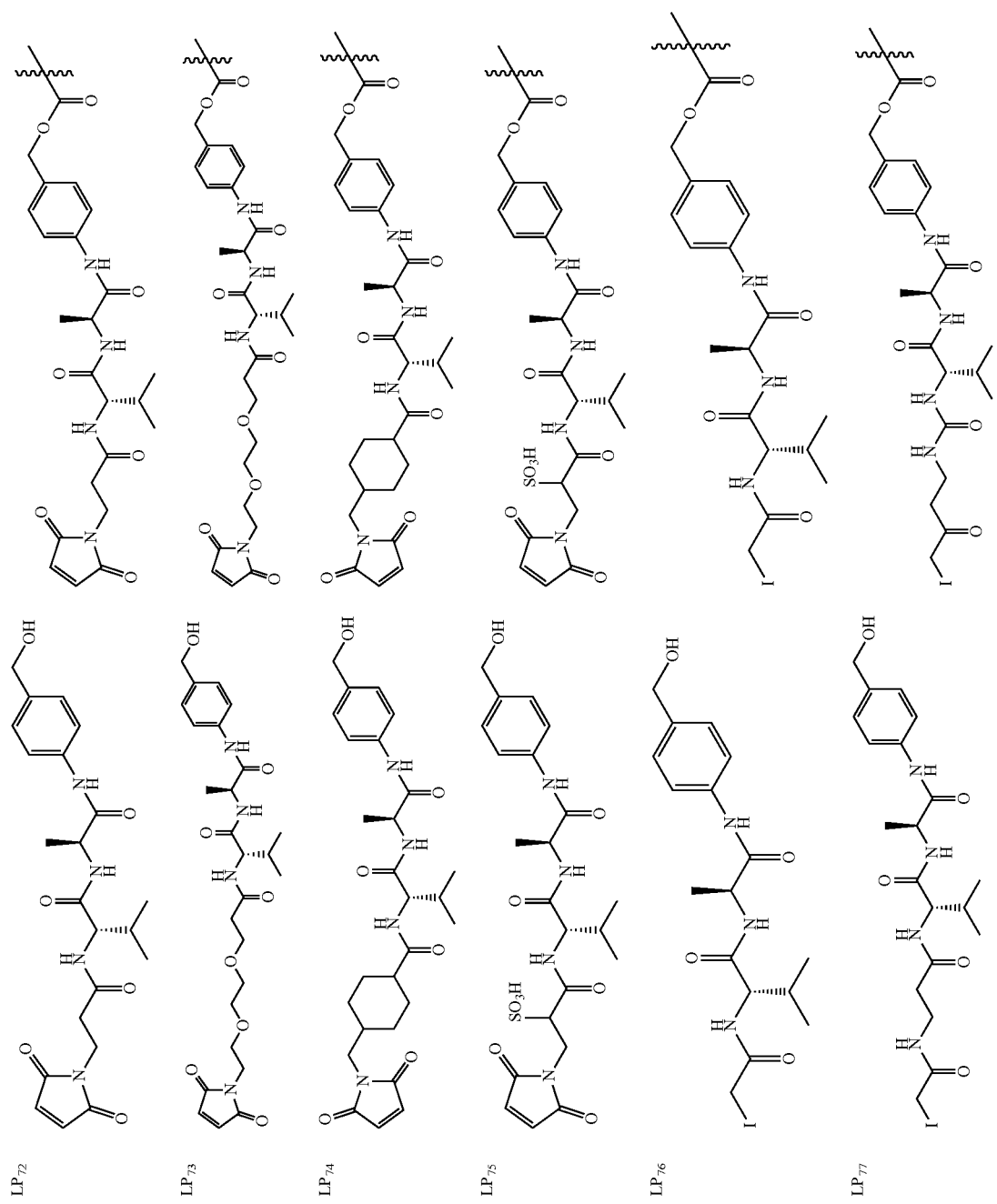

TABLE I-continued
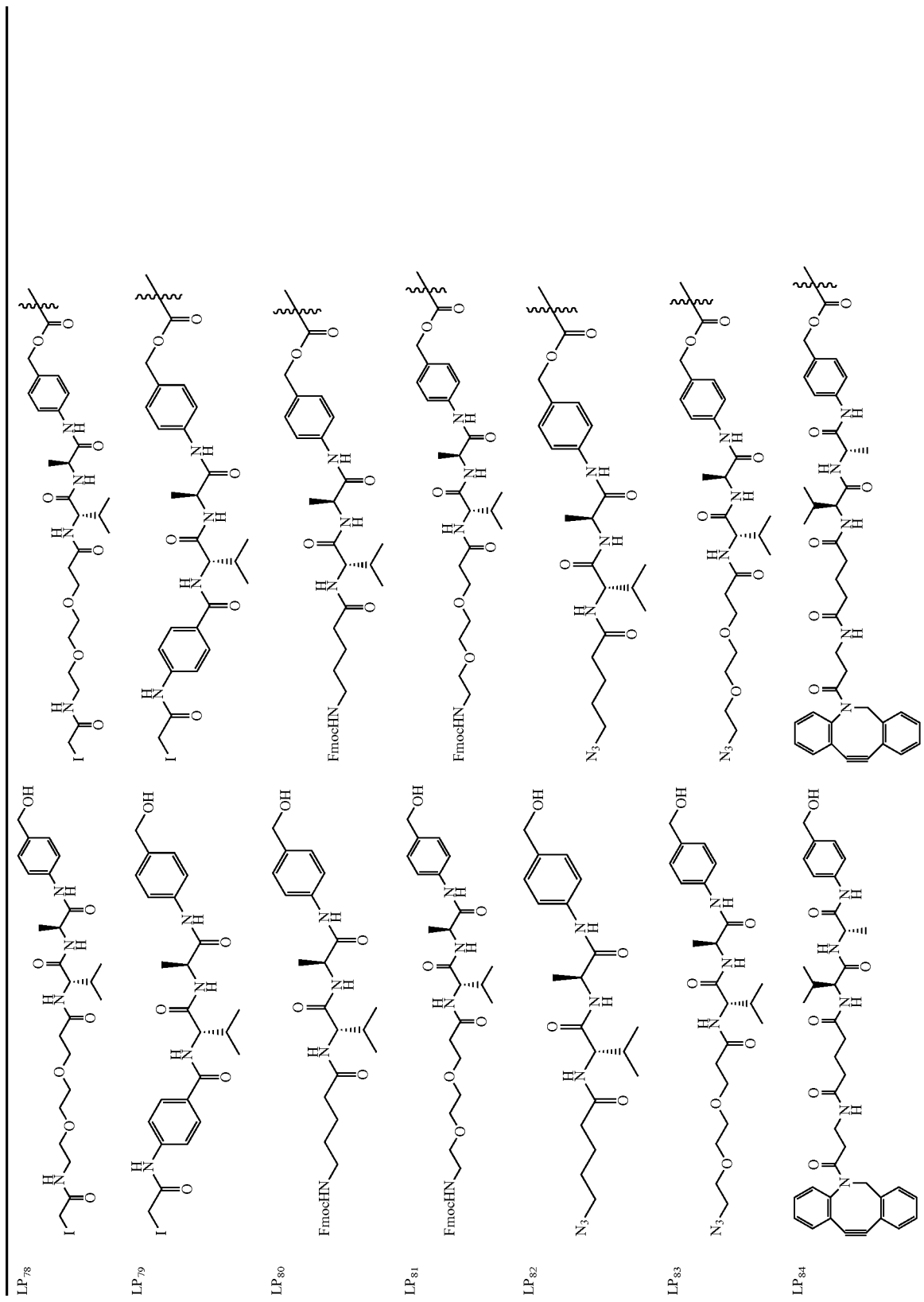

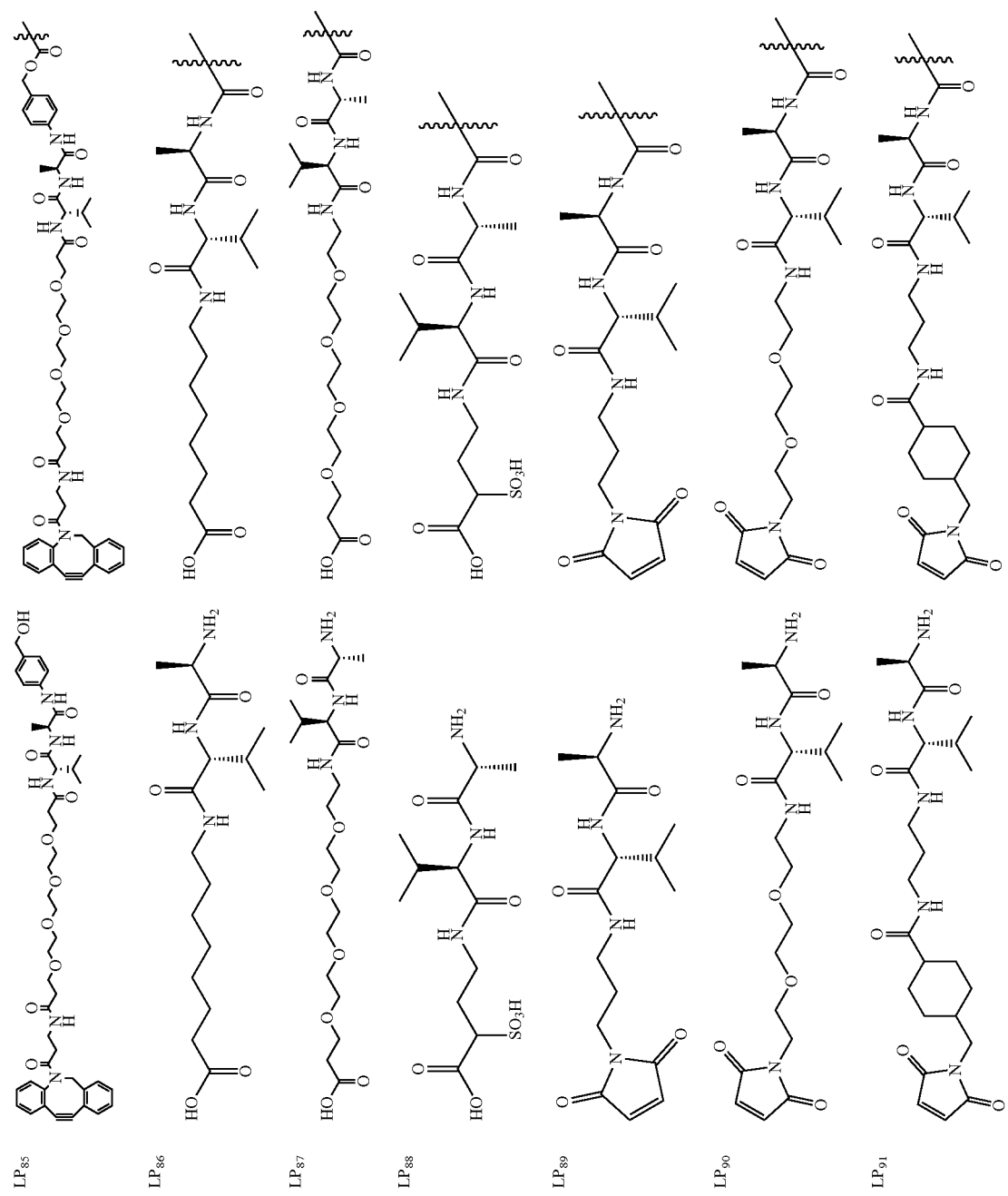

TABLE I-continued

TABLE I-continued
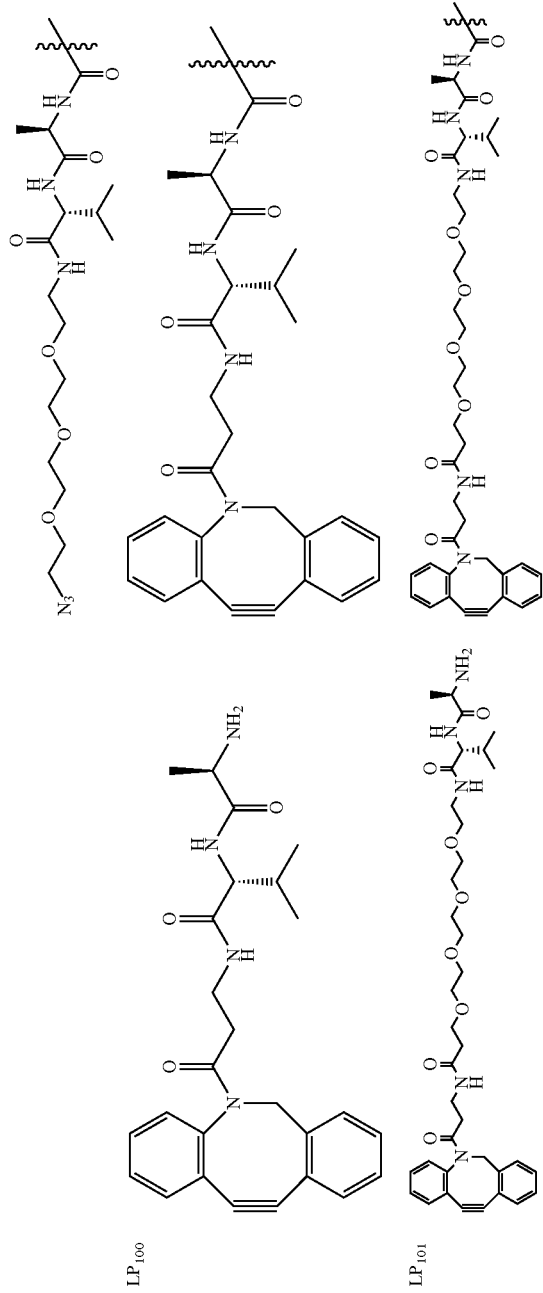
[1] the examples are given for a particular cryptophycin compound, but may apply to any cryptophycin compound of formula (I), especially $D_1$—$D_{19}$.
[2] in Table I, L is given here in the para position, but it is possible to obtain compounds in a similar manner with L in an ortho or meta position.

Process for Preparing the Conjugates of Formula (III)

The conjugates of the present invention can obtained via the process comprising the steps that consist in:
(i) placing in contact and leaving to react an optionally buffered aqueous solution of an antibody, optionally first modified by means of a modifying agent, and a solution of the cryptophycin payload of formula (II), the chemical group RCG1 of the compound of formula (II) being reactive towards the chemical groups RCG2 present on the antibody especially towards the amino groups present on antibodies, the said chemical groups RCG2 having been introduced, where appropriate, by the modifying agent, so as to attach the compound of formula (II) to the antibody by formation of a covalent bond;
(ii) and then in optionally separating the conjugate formed in step (i) from the cryptophycin payload and/or from the unreacted antibody and/or from any aggregates formed.

According to one variant and more particularly, in step (ii) the conjugate from step (i) is separated only from the unreacted cryptophycin payload and from any aggregates formed, and any unreacted antibody is left in the solution.

The function of the placing in contact is to react the chemical groups RCG1 and RCG2 in order to ensure attachment of the cryptophycin payload to the antibody by formation of a covalent bond; preferably, when RCG1 represents $C(=O)—Z_aR_a$, the reaction preferably takes place on the amino functions of the antibody, especially the ε-amino groups borne by the side chains of the lysine (Lys) residues of the antibody and the α-amino groups of N-terminal amino acids of antibody heavy and light chains. A conjugate of the following formula is obtained in this case: mAb-[NH—C(=O)-L*-Crypto]$_d$ with L*=fragment of a linker L comprising RCG1=—C(=O)— $Z_aR_a$ and such that L=-L*C(=O)— $Z_aR_a$ and d representing the drug-to-antibody ratio or DAR;

when RCG1 represents —$C_1$ or a maleimido or haloacetamido group, the antibody may comprise thiol chemical groups;

when RCG1 represents an azido group, the antibody may comprise a —C≡CH moiety or an activated triple bond such as a cyclooctyne;

when RCG1 represents —$NH_2$, the reaction may take place on amide function of the antibody using an enzymatic catalysis, especially the amide groups borne by the side chains of glutamine (Gln) residues of an antibody. A conjugate of the following formula is obtained in this case: mAb-[C(=O)—NH-L*-Crypto]$_d$ with L*=fragment of a linker L comprising RCG1=—$NH_2$ and such that L=-L*$NH_2$ and d representing the drug-to-antibody ratio or DAR;

when RCG1 represents —C≡CH or an activated C≡C such as a cyclooctyne moiety, the antibody may comprises azido groups.

The term "aggregates" means associations that may form between two or more antibodies, the antibodies possibly having been modified by conjugation. Aggregates are liable to form under the influence of a wide variety of parameters such as a high concentration of antibody in the solution, the pH of the solution, high shear forces, the number of grafted drugs and their hydrophobic nature, the temperature (see the references cited in the introduction of *J. Membrane Sci.* 2008, 318, 311-316), the influence of some of them, however, having not been clearly elucidated. In the case of proteins or antibodies, reference may be made to *AAPS Journal*, "Protein Aggregation and Bioprocessing" 2006, 8(3), E572-E579. The aggregate content may be determined via known techniques such as SEC (see in this respect *Analytical Biochemistry* 1993, 212 (2), 469-480).

The aqueous solution of the antibody may be buffered with buffers such as, for example, potassium phosphate or HEPES or a mixture of buffers such as buffer A described later. The buffer depends on the nature of the antibody. The cryptophycin payload is dissolved in a polar organic solvent such as, for example, DMSO or DMA.

The reaction takes place at a temperature generally of between 20° C. and 40° C. The reaction time may vary between 1 and 24 hours. The reaction between the antibody and the cryptophycin payload may be monitored by SEC with a refractometric and/or ultraviolet detector and/or HRMS in order to determine its degree of progress. If the degree of substitution is insufficient, the reaction can be left for longer and/or cryptophycin compound can be added. Reference may be made to the example section for further details regarding particular conditions. Particular embodiments are described in Examples 3, 7, 10, 14, 20 and 23.

A person skilled in the art has at his disposal various chromatographic techniques for the separation of step (ii): the conjugate may be purified, for example, by steric exclusion chromatography (SEC), by adsorption chromatography (for instance ion exchange, IEC), by hydrophobic interaction chromatography (HIC), by affinity chromatography, by chromatography on mixed supports such as ceramic hydroxyapatite, or by HPLC. Purification by dialysis or diafiltration may also be used.

After step (i) or (ii), the solution of the conjugate may undergo an ultrafiltration and/or diafiltration step (iii). After these steps, the conjugate in aqueous solution is thus obtained.

Antibody

The antibody can be a monoclonal antibody selected from the group consisting of a murine, chimeric, a humanized and a human antibody.

In one embodiment, the antibody is a monospecific antibody, i.e. an antibody specifically binding to one single target. Alternatively, it might be a multispecific antibody.

In one embodiment, the antibody is a IgG antibody, for instance an $IgG_1$, an $IgG_2$, an $IgG_3$ or an $IgG_4$ antibody.

The antibody according to the invention specifically binds to a target, thereby directing the biologically active compound as a cytotoxic compound towards said target. As used herein, "specifically binds" or "binds specifically to" or "binds to" or the like, means that an antibody or antigen-binding fragment thereof forms a complex with an antigen that is relatively stable under physiological conditions. Specific binding can be characterized by an equilibrium dissociation constant ($K_D$) of at least about $1\times10^{-8}$ M or less (e.g., a smaller $K_D$ denotes a tighter binding). Methods for determining whether two molecules specifically bind are well known in the art and include, for example, equilibrium dialysis, surface plasmon resonance, and the like. As described herein, antibodies have been characterized, for example, by their specific binding to target and/or target antigen using surface plasmon resonance, e.g., BIA-CORE™.

The target typically corresponds to a protein expressed at the cell surface, e.g. a protein expressed at the surface of tumour cells.

In one embodiment, the target is the EphA2 receptor. The EphA2 receptor is an Ephrin receptor, and is also referred to as "EPH receptor A2" or "Epithelial Cell Receptor Protein-Tyrosine kinase" (see e.g. OMIM Entry *176946, available at the omim.org/entry/176946 world wide web site, version updated on Jul. 21, 2016). The antibody specifically binding to the EphA2 receptor might for instance correspond to one of the antibodies described in WO2008/010101 or WO2011/039724.

In another embodiment, the target is CD19. CD19 is a cell surface molecule specifically expressed by B lymphocytes and follicular dendritic cells of the hematopoietic system, and is also referred to as "B-lymphocyte antigen CD19" (see e.g. OMIM Entry *107265, available at the omim.org/entry/107265 world wide web site, version last updated on May 11, 2015). The antibody specifically binding to CD19 might for instance correspond to Coltuximab, i.e. the antibody part (moiety) of Coltuximab Ravtansin.

The antibody may optionally be modified with a modifying agent so as to promote the attachment of the cryptophycin payload as previously described. The antibody may especially be monoclonal, polyclonal or multispecific. It may also be an antibody fragment. It may also be a murine, human, humanized or chimeric antibody. The antibody used in the examples of the present invention is hu2H11_R3574, an antagonist antibody against EphA2 receptor. The sequence of hu2H11_R3574 is described in WO2011/039724 (SEQ ID NO: 18 for the heavy chain and SEQ ID NO: 16 for the light chain).

Conjugate

A conjugate generally comprises from about 1 to 10 cryptophycin compounds covalently attached to the antibody (this is the degree of grafting or "drug-to-antibody ratio" or "DAR"). This number varies as a function of the nature of the antibody and of the cryptophycin compound, and also of the operating conditions used in the conjugation process (for example the number of equivalents of cryptophycin compound relative to the antibody, the reaction time, the nature of the solvent and of any cosolvent). Placing of the antibody and the cryptophycin compound in contact leads to a mixture comprising several conjugates that are individually distinguished from each other by different DARs; optionally the unreacted antibody; optionally aggregates. The DAR that is determined on the final solution thus corresponds to an average DAR. The DAR may be calculated from the deconvolution of the SEC-HRMS spectrum of the conjugate. The DAR (HRMS) is preferably greater than 0.5, more particularly between 1 and 10 and even more particularly between 2 and 7.

The conjugate may be used as an anticancer agent. Owing to the presence of the antibody, the conjugate is made highly selective towards tumor cells rather than healthy cells. This makes it possible to direct the cryptophycin compound in an environment similar thereto or directly therein; (in this respect, see the following publications that describe the use of monoclonal antibody conjugates in cancer treatment: "Antibody-drug conjugates for cancer therapy" Carter P. J., et al., Cancer J. 2008, 14, 154-169; "Targeted cancer therapy: conferring specificity to cytotoxic drugs" Chari R., Acc. Chem. Res. 2008, 41, 98-107). It is possible to treat solid or liquid cancers. The conjugate may be used alone or in combination with at least one other anticancer agent.

The conjugate is formulated in the form of a buffered aqueous solution at a concentration generally of between 1 and 10 mg/mL. This solution may be injected in perfusion form per se or may be rediluted to form a perfusion solution.

EXAMPLES

The examples which follow describe the preparation of certain compounds in accordance with the invention. These examples are not limitative, and merely illustrate the present invention.

Analytical Methods Used
High Pressure Liquid Chromatography Mass Spectrometry (LCMS)
Method A1

Spectra have been obtained on a Waters UPLC-SQD system in positive and/or negative electrospray mode (ES+/−) using ELSD and UV (210-400 nm) detection. Chromatographic conditions were the following:
column: ACQUITY BEH C18—1.7 µm—2.1×50 mm; solvents: A: $H_2O$ (0.1% formic acid), B: $CH_3CN$ (0.1% formic acid); column temperature: 50° C.; flow rate: 0.8 mL/min; gradient (2.5 min): from 5 to 100% of B in 1.8 min; 2.4 min: 100% of B; 2.45 min: from 100 to 5% of B in 0.05 min.

Method A2

Spectra have been obtained on a Waters XeVo-QTof system in positive electrospray mode (ES+) using ELSD and UV (210-400 nm) detection. Chromatographic conditions were the following:
column: ACQUITY BEH C18—1.7 µm—2.1×100 mm; solvents: A: $H_2O$ (0.1% formic acid), B: $CH_3CN$ (0.1% formic acid); column temperature: 70° C.; flow rate: 0.55 mL/min; gradient (11 min): from 5 to 97% of B in 8.3 min; 8.6 min: 97% of B; 9 min: from 97 to 5% of B in 0.7 min and 5% of B during 2 min.

Method A3

Spectra have been obtained on a Waters XeVo-QTof system in positive electrospray mode (ES+). Chromatographic conditions were the following:
column: ACQUITY BEH C18—1.7 µm—2.1×100 mm; solvents: A: $H_2O$ (0.1% formic acid), B: $CH_3CN$ (0.1% formic acid); column temperature: 45° C.; flow rate: 0.6 mL/min; gradient (5.3 min): 5% of B during 0.3 min; from 5 to 100% of B in 3.7 min; 4.6 min: 100% of B; 5.3 min 5% of B.

Method A4

Spectra have been obtained on a Waters UPLC-SQD system in positive and/or negative electrospray mode (ES+/−) using ELSD and UV (210-400 nm) detection. Chromatographic conditions were the following:
column: ACQUITY BEH C18—1.7 µm—2.1×50 mm; solvents: A: $H_2O$ (0.1% formic acid), B: $CH_3CN$ (0.1% formic acid); column temperature: 45° C.; flow rate: 0.8 mL/min; gradient (10 min): from 5 to 100% of B in 8.6 min; 9.6 min: 100% of B; 9.8 min: 5% of B.

Method A5

Spectra have been obtained on a Waters UPLC-SQD system in positive and/or negative electrospray mode (ES+/−) using ELSD and UV (210-400 nm) detection. Chromatographic conditions were the following:
column: ACQUITY CSH C18—1.7 µm—2.1×50 mm; solvents: A: $H_2O$ (0.1% formic acid), B: $CH_3CN$ (0.1% formic acid); column temperature: 40° C.; flow rate: 0.85 mL/min; gradient (2.5 min): from 5 to 100% of B in 1.8 min; 2.4 min: 100% of B; 2.45 min: from 100 to 5% of B in 0.05 min.

$^1$H Nuclear Magnetic Resonance (NMR)

The $^1$H NMR spectra were acquired on a Bruker Avance spectrometer, either of model DRX-300, DRX-400 or DRX-500. The chemical shifts (δ) are given in ppm.

Size Exclusion Chromatography-High Resolution Mass Spectrometry (SEC-HRMS)

The chromatographic analysis was performed on an Agilent HP1100 machine and a Waters BEH SEC 200 1.7 µm (2.1×150 mm) column at 30° C. with a flow rate of 0.5 mL/min and an isocratic elution of (A) 25 mM ammonium formate+1% formic acid/(B) $CH_3CN$+0.1% formic acid 70/30 for 15 minutes. The mass spectrometry was performed on a Waters QTOF-II machine with electrospray ionization in positive mode (ES+). The mass spectra were deconvoluted with the Waters MaxEnt1 software.

Analytical Size Exclusion Chromatography (SEC)

The analysis was performed on a Waters Alliance HPLC system or a Hitachi Lachrom system equipped with a photodiode array detector and a Tosoh Bioscience TSKgel G3000 SWXL 5 μm (7.8×300 mm) column with a flow rate of 0.5 mL/min and an isocratic elution of 30 minutes with a pH 7 buffer containing 0.2 M of KCl, 0.052 M of $KH_2PO_4$, 0.107 M of $K_2HPO_4$ and 20% by volume of isopropanol.

Buffers
- Buffer A (pH 6.5): NaCl (50 mM), potassium phosphate (50 mM), EDTA (2 mM)
- Buffer B (pH 6.5): NaCl (140 mM), potassium and sodium phosphate (9.6 mM)
- PBS (pH 7.4): $KH_2PO_4$ (1.06 mM), NaCl (155.17 mM), $Na_2HPO_4\cdot 7H_2O$ (2.97 mM)
- DPBS: KCl (2.67 mM), $KH_2PO_4$ (1.47 mM), NaCl (136.9 mM), $Na_2HPO_4$ (8.10 mM) adjusted at pH 6.5 with HCl 5N (1 mL per 1000 mL of buffer)

General Method Used for the Preparation of Antibody-Thud Conjugate (ADC)

A solution of antibody in an aqueous buffer composed of a 96:4 mixture of buffer A and 1 N HEPES was treated with an excess of a solution at approximately 10 mM of cryptophycin payload in DMA such that the final antibody concentration is 3 mg/mL and the percentage of DMA in the aqueous buffer is 20%. After stirring for 2 hours, the mixture was analysed by SEC-HRMS to determine the DAR on the population of monomeric antibodies. If the DAR was found insufficient, the mixture was treated with a further excess (1 to 5 equivalents) of cryptophycin solution in DMA for 2 additional hours at RT under stirring. The mixture was purified by gel filtration using a Superdex 200 pg matrix (HiLoad 16/60 or 26/60 desalting column, GEHealthcare) pre-equilibrated in aqueous buffer pH 6.5 (buffer B or DPBS) containing 10 to 20% of NMP. The fractions containing the monomeric conjugated antibody were pooled and concentrated on Amicon Ultra-15 (10 k or 50 k Ultracel membrane, Millipore) to a concentration of between 2 and 5 mg/mL. A buffer exchange or a dilution in the appropriate buffer was then performed to formulate the conjugate in the final buffer. In the case of a buffer exchange, it was realized by gel filtration using a Sephadex™ G25 matrix (NAP-5, NAP-10, NAP-25/PD-10 or Hiprep 26/10 desalting columns, GEHealthcare) pre-equilibrated with the final aqueous buffer whose composition and pH are suited to each conjugate. The conjugate was finally filtered through a Steriflip® filter unit (0.22 μm Durapore® PVDF membrane, Millipore). The final conjugate was assayed by UV spectrometry or SEC-HPLC so as to measure the conjugate concentration, by SEC-HPLC so as to determine the monomeric purity and by SEC-HRMS so as to determine the DAR from the deconvolution of the mass spectrum of the conjugate.

Synthesis of Fragment A: (2E,5S,6R,7E)-tert-butyl 8-(4-formylphenyl)-5-hydroxy-6-methylocta-2,7-dienoate

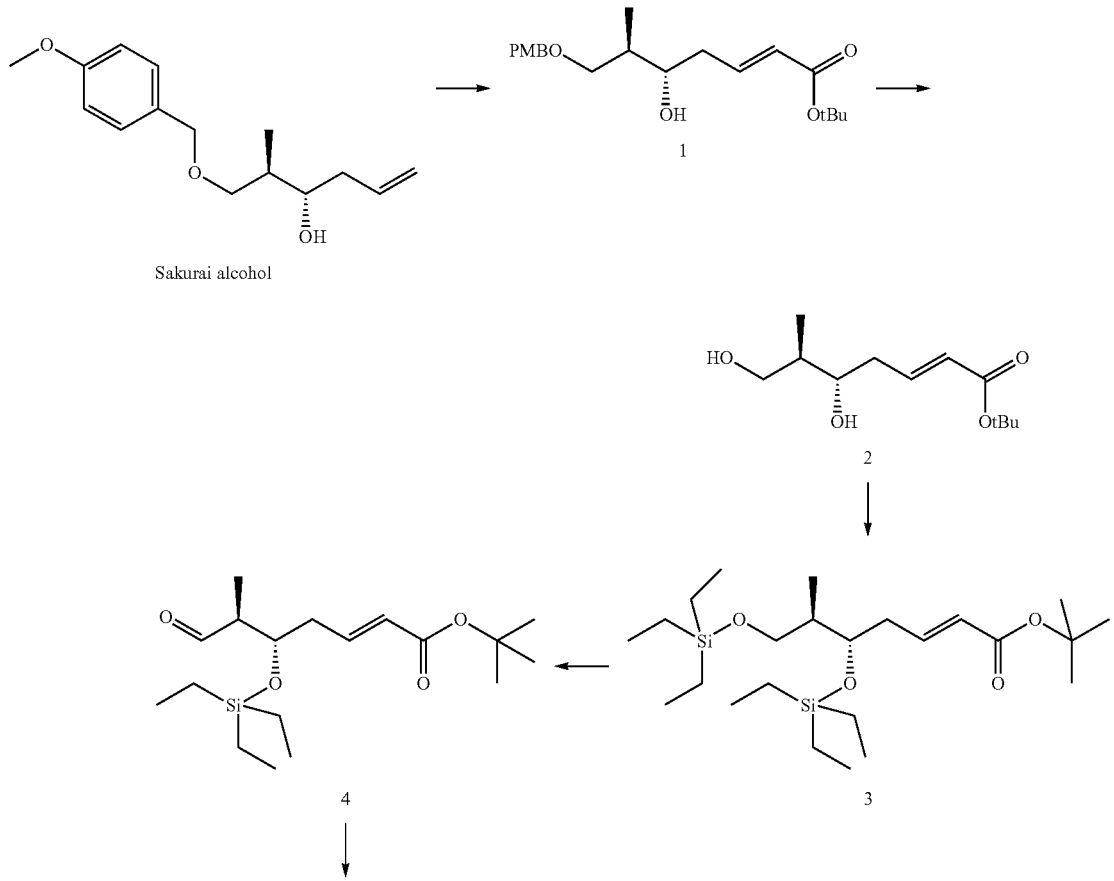

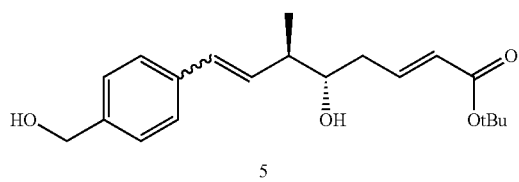

Compound 1: (2E,5S,6R)-tert-butyl 5-hydroxy-7-((4-methoxybenzyl)oxy)-6-methylhept-2-enoate Under argon, to a solution of (2R,3S)-1-[(4-methoxyphenyl)methoxy]-2-methyl-5-hexen-3-ol or Sakurai alcohol (CAS number [203926-55-0], 100 g, 399.5 mmol) in DCM (350 mL) were added tert-butyl acrylate (354.7 mL, 2.435 mol) and Grubbs catalyst (4.849 g, 2.435 mol). After stirring for 17 h at RT, the reaction mixture was filtered on 230 g of silica and eluted with a mixture of heptane/AcOEt (50/50, 6×300 mL). After concentration, the residue was purified by flash chromatography on 1.2 kg of silica gel (gradient elution heptane/EtOAc) to give 140.8 g of a brown oil. The oil was dissolved in anhydrous DCM (550 mL), 10 g of quadraPure™ TU resin was added to remove the excess of catalyst. The mixture was stirred for 3 h at 35° C. The resin was filtered and washed with DCM, the filtrate was concentrated and dried in vacuo to give 135.75 g of compound 1 as a brown oil (97%).

RMN $^1$H (500 MHz, δ in ppm, DMSO-d6): 0.85 (d, J=7.0 Hz, 3H); 1.42 (s, 9H); 1.72 (m, 1H); 2.18 (m, 1H); 2.30 (m, 1H); 3.24 (dd, J=7.0 and 9.3 Hz, 1H); 3.46 (dd, J=7.7 and 9.3 Hz, 1H); 3.49 (m, 1H); 3.73 (s, 3H); 4.35 (s, 2H); 4.65 (d, J=5.8 Hz, 1H); 5.76 (td, J=1.5 and 15.6 Hz, 1H); 6.83 (td, J=7.4 and 15.6 Hz, 1H); 6.90 (d, J=8.8 Hz, 2H); 7.23 (d, J=8.8 Hz, 2H).

Compound 2: (2E,5S,6R)-tert-butyl 5,7-dihydroxy-6-methylhept-2-enoate

To a solution of compound 1 in CH$_3$CN (910 mL), H$_2$O (90 mL) was added and the mixture was cooled at 12° C. before adding in 25 min a solution of CAN (196.7 g, 358.9 mmol) in H$_2$O (300 mL). Stirring was continued for 1 h at RT. Additional CAN (18.83 g, 34.36 mmol) dissolved in a mixture of CH$_3$CN (70 mL) and H$_2$O (30 mL) was added and stirred for 1 h at RT to complete the reaction. The mixture was quenched with NaCl until saturation of the aq. layer, then MTBE (400 mL) was added. After decantation, the aq. layer was extracted with MTBE (2×80 mL). The combined organic layers were washed with a 3:1 mixture of 5% NaHCO$_3$/H$_2$O (3×200 mL), sat. brine (2×130 mL), dried over MgSO$_4$, filtered and concentrated. The aq. layer was acidified with 2N HCl until pH 4, then saturated with NaCl and extracted with MTBE (2×150 mL). This second organic layer was washed with 5% NaHCO$_3$ (60 mL), sat. brine (60 mL), dried over MgSO$_4$, concentrated and combined with the first organic layer to give an brown orange oil.

The mixture was dissolved in MeTHF (300 mL), then were added 1,2-ethanedithiol (22 mL, 0.260 mol) and p-TsOH (1.651 g, 8.590 mmol). After stirring at 60° C. for 5 h, MTBE (200 mL) was added to the reaction mixture and it was washed with 5% NaHCO$_3$ (2×120 mL), sat. brine (120 mL), dried over MgSO$_4$, filtered, concentrated in vacuo and purified by flash chromatography on 520 g of silica gel (gradient elution DCM/MTBE) to give 29.48 g of compound 2 as a yellow oil (75%).

Compound 3: (2E,5S,6R)-tert-butyl 6-methyl-5,7-bis((triethylsilyl)oxy)hept-2-enoate Under argon to a solution of compound 2 (39.38 g, 0.171 mol) in anhydrous DCM (500 mL) was added imidazole (51.540 g, 0.749 mol). The yellow mixture was cooled at 0° C., then was added triethylchlorosilane (63.99 mL, 0.374 mol) and the solution was allowed to warm up to RT overnight. The reaction mixture was quenched with sat. NH$_4$Cl (400 mL), MTBE (300 mL) and ice. The pH was adjusted at 4 with 2M NaHSO$_4$, the layers were separated after vigorous stirring. The aq. layer was extracted with MTBE (200 mL). The combined organic layers were washed with half-sat. NH$_4$Cl (2×250 mL), phosphate buffer pH 7 (150 mL), sat. brine (150 mL), dried over MgSO$_4$, filtered, concentrated in vacuo and purified by flash chromatography on 490 g of silica gel (gradient elution heptane/Et$_2$O) to give 74.52 g of compound 3 as a pale yellow oil (95%).

Compound 4: (2E,5S,6S)-tert-butyl 6-methyl-7-oxo-5-((triethylsilyl)oxy)hept-2-enoate Under argon, to a solution of DMSO (102.400 mL, 1.427 mol) in DCM (300 mL) was dropwise added at −75° C. oxalyl chloride (63 mL, 0.719 mol) in 1 h and the stirring was continued for 15 min before adding, at −75° C., a solution of compound 3 in DCM (150 mL) while keeping the temperature below −70° C. The reaction mixture was allowed to warm up to −40° C. and the stirring continued for 2 h. The reaction mixture was cooled again at −75° C., then DIEA (425 mL, 2.432 mol) was added in 75 minutes while keeping the temperature below −65° C. The reaction mixture was allowed to warm up to RT and then quenched with MTBE (500 mL), ice, sat. NH$_4$Cl (200 mL) and 2M NaHSO$_4$ to reach pH 4. The layers were separated after vigorous stirring. The aq. layer was extracted with MTBE (200 mL). The combined organic layers were washed with NH$_4$C$_1$ (3×300 mL), phosphate buffer pH 7 (300 mL), sat. brine (300 mL), dried over MgSO$_4$, filtered, concentrated in vacuo and purified by flash chromatography on 1.25 kg of silica gel (gradient elution heptane/Et$_2$O) to give 51.74 g of compound 4 as an orange oil (93%).

Compound 5: (2E,5S,6R,7E)-tert-butyl 5-hydroxy-8-(4-(hydroxymethyl)phenyl)-6-methylocta-2,7-dienoate Under argon, to a suspension of phosphonium bromide (synthesis described in WO2011/001052, 147 g, 0.237 mol) in anhydrous THF (1.5 L) was added at −50° C. a 2.5 M solution of n-BuLi in hexane (90 mL, 0.225 mol). The temperature was allowed to warm up to −40° C. and the stirring was continued for 15 min. After warming to RT, the red mixture was stirred for 1 h. The reaction medium was cooled at −70° C. before adding a solution of compound 4 (51.63 g, 126.6 mmol) in THF (200 mL) while keeping the temperature below −65° C. When the addition was complete, the reaction mixture was allowed to warm up to RT and the stirring was continued overnight. The reaction mixture was filtered to remove the insoluble that was washed with MTBE (500 mL). The filtrate was partially concentrated at 42° C. (⅓), then quenched with ice, NH₄Cl (500 mL), MTBE (500 mL) and 2M NaHSO₄ to reach pH 4. The layers were separated and the aq. layer was extracted with MTBE (200 mL). The combined organic layers were washed with half-sat. NI-1₄C₁ (250 mL), phosphate buffer pH 7 (250 mL), sat. brine (250 mL), dried over MgSO₄, filtered and half-concentrated in vacuo until 250 mbar. The suspension was diluted with 50:50 heptane/MTBE (600 mL) cooled with an ice bath, filtered off and washed with 50:50 heptane/MTBE. The filtrate was concentrated in vacuo to give 100.05 g as a brown oil.

The crude compound was dissolved in anhydrous THF (320 mL), then was added TBAF trihydrate (90 g, 282.40 mmol) and the reaction mixture was stirred for 3 h. After concentration in vacuo, the crude was diluted with 10:1 MTBE/THF (770 mL), washed with a half-sat. NH₄Cl (3×200 mL), 1M NaHSO₄. (200 mL), phosphate buffer pH 7 (200 mL), sat. brine (200 mL), dried over MgSO₄, filtered and concentrated. The aq. layer was extracted with MTBE. After decantation, the organic layer was washed with phosphate buffer pH 7 (30 mL), sat. brine (30 mL), dried over MgSO₄ and filtered. After concentration, the combined organic layers were purified by flash chromatography on 1.25 kg of silica gel (gradient elution heptane/Et₂O) to give 36.91 g of compound 5 as a brown-red oil (88%).

Fragment A: (2E,5S,6R,7E)-tert-butyl 8-(4-formylphenyl)-5-hydroxy-6-methylocta-2,7-dienoate Under argon, to a solution of compound 5 (30.3 g, 91.7 mmol) in anhydrous DCM (600 mL) was added, at 10° C., manganese oxide (175 g, 3.013 mol) and the reaction mixture was stirred for 4 h at 35° C. The oxidant was filtered through a plug of celite and washed with warm aceton. The filtrate was concentrated to give 30.43 g of a red-orange oil.

Under argon, the oil was diluted with benzene (800 mL) and refluxing in the presence of AIBN (880 mg, 4.58 mmol), and thiophenol (2.81 mL, 27.51 mmol) for 1 h. Additional AIBN (530 mg, 0.03 eq) and thiophenol (1.03 mL, 10.087 mmol) were added and refluxing continued for an additional 1 h. Additional AIBN (530 mg, 0.03 eq) and thiophenol (1.03 mL, 10.087 mmol) were added and refluxing continued for 3 h. Additional AIBN (353 mg, 1.834 mmol) and thiophenol (468 µL, 4.58 mmol) were added and refluxing continued for 1 h. The conversion E/Z was 92/8, 352.6 mg of AIBN was added and refluxing continued for 1 h. The reaction mixture was cooled to RT and concentrated in vacuo to give 28.03 g of fragment A as an orange oil (92%) with a E/Z ratio superior to 98/2.

Synthesis of Fragment B: (R)-2-((tert-butoxycarbonyl)amino)-3-(3-chloro-4-methoxy-phenyl)propanoic Acid

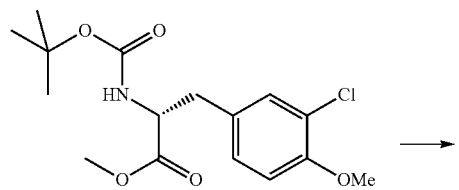

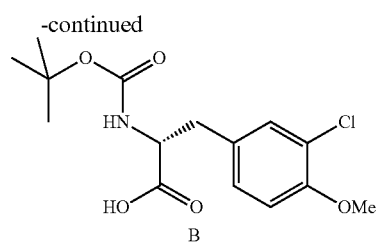

To a solution of methyl (R)-2-((tert-butoxycarbonyl)amino)-3-(3-chloro-4-methoxyphyl)-propanoate (CAS number [162465-44-3], 30 g, 87.26 mmol) in THF (225 mL), were added H₂O (30 mL) and LiOH monohydrate (4.4 g, 104.85 mmol). The reaction medium was stirred 2 h at RT. After this time, the reaction medium was diluted with H₂O (200 mL) then acidified at pH 2 with 5N HCl (20 mL) and extracted by EtOAc (2×250 mL). The combined organic phases were washed with H₂O (500 mL), dried over MgSO₄, filtered, concentrated in vacuo, diluted with Et₂O and concentrated in vacuo to give 26.9 g of fragment B as a white solid (94%).

RMN ¹H (300 MHz, δ in ppm, DMSO-d6): 1.21 to 1.37 (m, 9H); 2.74 (dd, J=11.0 and 14.3 Hz, 1H); 2.96 (dd, J=5.0 and 14.3 Hz, 1H); 3.81 (s, 3H); 4.04 (m, 1H); 6.99 to 7.09 (m, 2H); 7.18 (dd, J=2.3 and 8.7 Hz, 1H); 7.29 (d, J=2.3 Hz, 1H); 12.60 (broad m, 1H).

Synthesis of Fragment C1: methyl 3-amino-2,2-dimethylpropanoate hydrochloride

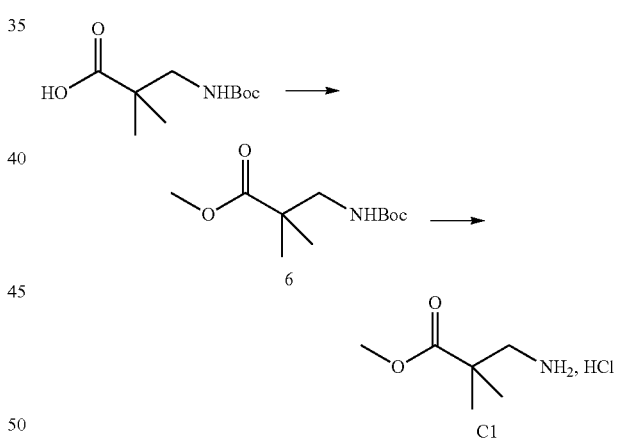

Compound 6: methyl 3-((tert-butoxycarbonyl)amino)-2,2-dimethylpropanoate

Under argon, to a solution of 3-([(tert-butoxy)carbonyl]amino)-2,2-dimethylpropanoic acid (CAS number [180181-02-6], 250 mg, 1.09 mmol) in DCM (6 mL) and MeOH (2 mL) was added, dropwise at 0° C., (trimethylsilyl)diazomethane (819.86 µL, 1.64 mmol) until yellow persistent color. Then AcOH was added until complete discoloration. The reaction mixture was concentrated in vacuo then diluted with H₂O and extracted with DCM twice. The combined organic phases were washed with sat. brine, dried over MgSO₄, filtered and concentrated in vacuo to give 260 mg of compound 6 as a colorless oil (quant.).

Fragment C1: methyl 3-amino-2,2-dimethylpropanoate hydrochloride

To a solution of compound 6 (260 mg, 1.12 mmol) in 1,4-dioxane (10 mL) was added 4N HCl in 1,4-dioxane (2.81 mL, 11.24 mmol). The reaction mixture was stirred at RT overnight then concentrated in vacuo to give 200 mg of fragment $C_1$ (quant.).

Synthesis of Fragment C2: methyl 3-amino-2,2-dimethylbutanoate hydrochloride

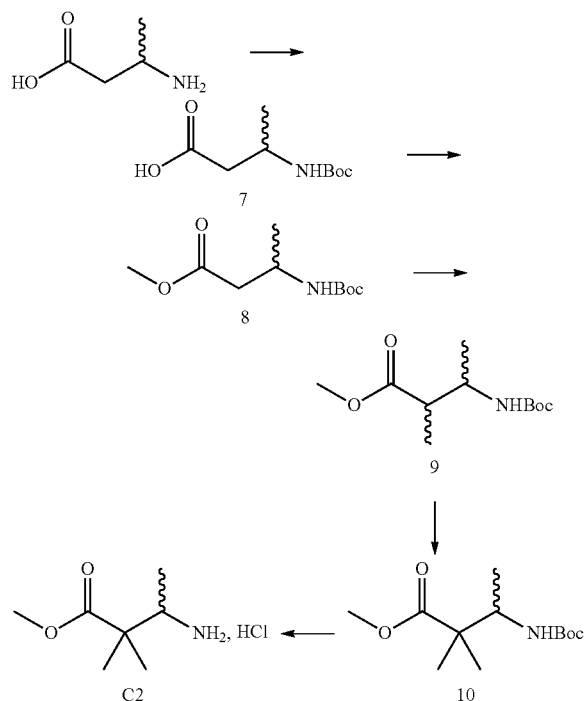

Compound 7: 3-((tert-butoxycarbonyl)amino)butanoic acid

To a solution of DL-3-aminobutyric acid (CAS number [541-48-02], 18.72 g, 176.09 mmol) in $H_2O$ (96 mL) were added di-tert-butyl dicarbonate (39.62 g, 176.09 mmol) and NaOH (8.03 g, 200.74 mmol) in $H_2O$ (76 mL) then tert-butyl alcohol (132 mL). The reaction mixture was stirred at RT overnight. After this time, the reaction medium was concentrated in vacuo then diluted with EtOAc (200 mL) and acidified at pH 3 with diluted HCl. After settling, the aq. phase was extracted with EtOAc (200 mL). The combined organic phases were dried over $MgSO_4$, filtered and concentrated in vacuo to give 34.5 g of compound 7 as a colorless oil (82%).

RMN $^1H$ (300 MHz, δ in ppm, $CDCl_3$-d1): 1.25 (d, J=7.0 Hz, 3H); 1.45 (s, 9H); 2.55 (m, 2H); 4.04 (m, 1H); 4.93 (broad m, 1H); 8.41 (broad m, 1H).

Compound 8: methyl 3-((tert-butoxycarbonyl)amino)butanoate

Under argon, a solution of compound 7 (10 g, 49.20 mmol) in toluene (350 mL) and MeOH (100 mL) was stirred at +5° C. Between +5° C. and +10° C., (trimethylsilyl)diazomethane (73.81 mL, 147.61 mmol) was added dropwise. The reaction mixture was stirred 3 h then evaporated in vacuo to give 10.8 g of compound 8 as a pale yellow oil (quant.).

RMN $^1H$ (300 MHz, δ in ppm, $CDCl_3$-d1): 1.20 (d, J=7.0 Hz, 3H); 1.45 (s, 9H); 2.50 (m, 2H); 3.69 (s, 3H); 4.03 (m, 1H); 4.90 (broad m, 1H).

Compound 9: methyl 3-((tert-butoxycarbonyl)amino)-2-methylbutanoate

Under argon, to a solution of LDA (2M in THF, 25.32 mL, 50.63 mmol) in THF (48 mL) at −70° C. was added dropwise a solution of compound 8 (5 g, 23.01 mmol) in THF (62 mL). The reaction mixture was stirred 1 h at −75° C. then iodomethane (5.79 mL, 92.05 mmol) was added dropwise at −70° C. The reaction mixture was stirred 3 h at −75° C. then at RT overnight. After this time, an aq. solution of 20% $NH_4Cl$ (100 mL) and $Et_2O$ (125 mL) were added. After settling, the organic phase was washed with sat. $NaHCO_3$ (80 mL) then sat. NaCl (80 mL). The combined aq. phases were extracted with $Et_2O$ (125 mL). The combined organic phases were dried over $MgSO_4$, filtered and concentrated in vacuo to give 5.49 g of crude oil. Crystallization with pentane (15 mL) gave 2.65 g of compound 9 after drying in vacuo. The pentane solution was concentrated in vacuo and purified by flash chromatography on 100 g of silica gel (gradient elution heptane/$Et_2O$) to give 1.98 g of compound 9. The two batches were pooled (87%) and used as such in the following step.

Compound 10: methyl 3-((tert-butoxycarbonyl)amino)-2-,2-dimethylbutanoate

Under argon, THF (46 mL) was cooled at −72° C. then were added LDA (2M in THF, 22 mL, 44.0 mmol) and dropwise at −72° C. (+/−2° C.) a solution of compound 9 (4.60 g, 19.89 mmol) in THF (64 mL). The reaction mixture was stirred 1 h 15 at −75° C. then iodomethane (5 mL, 79.55 mmol) was added dropwise at −72° C. (+/−2° C.). The reaction medium was stirred 3 h at −75° C. then overnight at RT. After this time, an aq. solution of 20% $NH_4Cl$ (50 mL) and $Et_2O$ (80 mL) were added. After settling, the organic phase was washed with sat. $NaHCO_3$ (50 mL) and sat. brine (50 mL). The combined aq. phases were extracted with $Et_2O$ (80 mL). The combined organic phases were dried over $MgSO_4$, filtered and concentrated in vacuo to give 6.5 g of crude oil that was purified by flash chromatography on 200 g of silica gel (gradient elution heptane/$iPr_2O$) to give 1.9 g of compound 10 as a colorless oil (39%).

RMN $^1H$ (400 MHz, δ in ppm, DMSO-d6): 0.92 (d, J=7.1 Hz, 3H); 1.02 (s, 3H); 1.04 (s, 3H); 1.48 (s, 9H); 3.58 (s, 3H); 3.88 (m, 1H); 6.62 (broad d, J=10.5 Hz, 1H). LCMS (A1): ES m/z=146, m/z=246 $[M+H]^+$; $t_R$=1.2 min.

Fragment C2: methyl 3-amino-2,2-dimethylbutanoate hydrochloride

In a round bottom flask, under magnetic stirring, compound 10 (0.3 g, 1.22 mmol) was introduced, followed by 1,4-dioxane (5 mL) and 4N HCl in 1,4-dioxane (5 mL). The reaction mixture was stirred at RT overnight then concentrated in vacuo. The crude solid obtained was precipitated in $iPr_2O$ (15 mL), filtered and dried to give 210 mg of fragment C2 as a white solid (95%).

LCMS (A1): ES m/z=146 $[M+H]^+$; $t_R$=0.8 min.

Synthesis of Fragment C3: ethyl 2-(1-aminocyclopropyl)-2,2-dimethylpropanoate

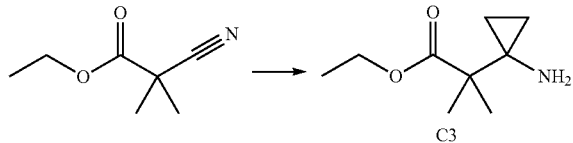

Under argon, to a solution of ethyl 2-cyano-2-methylpropionate (CAS number [1572-98-1], 2 g, 13.88 mmol) in Et₂O (48 mL) was added titanium (IV) isopropoxide (4.63 g, 15.97 mmol). The reaction mixture was stirred 10 min at RT then cooled at −5° C. A solution of ethylmagnesium bromide 3M in Et₂O (9.72 mL, 29.16 mmol) was added dropwise at −5° C.–0° C. in 25 min, the reaction mixture was then stirred 40 min without the cooling bath. At this time, a TLC showed than the reaction was complete. The reaction medium was cooled at 0° C. and boron trifluoride diethyl etherate (3M in Et₂O, 3.6 mL, 29.16 mmol) was added dropwise at 0° C. The reaction mixture was stirred 30 min without the cooling bath. After this time, 1N HCl was added at 0° C. until pH 1-2 (8 mL) then 2N NaOH until pH 8 (28 mL), the reaction mixture was extracted with EtOAc (3×150 mL). The combined organic phases were dried over MgSO₄, filtered and concentrated in vacuo to give 2.4 g of a crude yellow oil that was purified by flash chromatography on 70 g of silica gel (gradient elution DCM/MeOH) to give 915 mg of fragment C3 as a pale yellow oil (39%).

RMN ¹H (400 MHz, δ in ppm, CDCl₃-d/): 0.52 (m, 2H); 0.70 (m, 2H); 1.11 (s, 6H); 1.27 (t, J=7.2 Hz, 3H); 1.64 (broad s, 2H); 4.18 (q, J=7.2 Hz, 2H).

Synthesis of Fragment C4: methyl 3-amino-2-(hydroxymethyl)-2-methylpropanoate hydrochloride

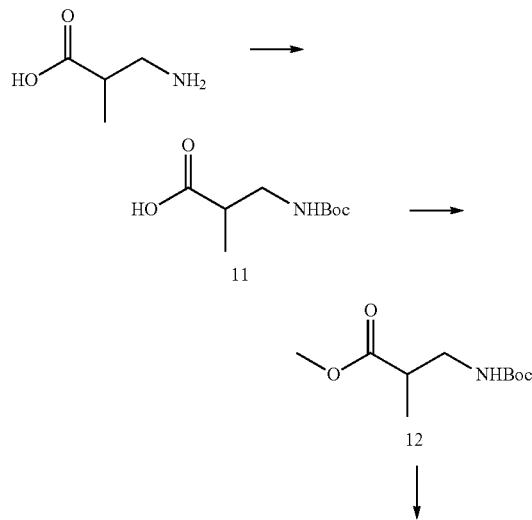

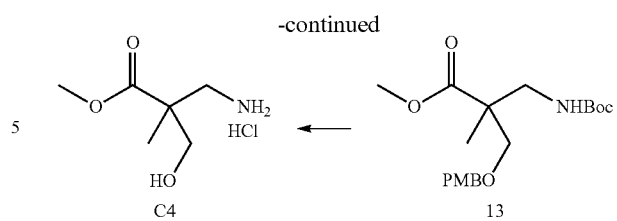

Compound 11: 3-((tert-butoxycarbonyl)amino)-2-methylpropanoic Acid

To a solution of DL-3-aminoisobutyric acid (CAS number [10569-72-9], 5 g, 47.52 mmol) in 2 N NaOH (24.7 mL) was added dropwise a solution of Boc₂O (11.73 g, 53.22 mmol) in THF (75 mL) while keeping the reaction medium temperature below 30° C. with a cold water bath. The reaction medium was stirred at RT for 18 h then concentrated in vacuo, diluted in H₂O (75 mL) and washed with MTBE (3×150 mL). The aqueous phase was acidified to pH 3 by addition of citric acid at 100 g/L (150 mL) and extracted with EtOAc (3×150 mL). The combined organic phases were washed with H₂O (3×45 mL), dried over MgSO₄, filtered and concentrated in vacuo to give 9.4 g of compound 11 as a colorless oil (97%).

RMN ¹H (400 MHz, δ in ppm, DMSO-d6): 1.01 (d, J=7.1 Hz, 3H); 1.38 (s, 9H); 2.48 (m, 1H); 2.91 (dt, J=6.1, 6.5 and 13.5 Hz, 1H); 3.15 (ddd, J=6.1, 7.4 and 13.5 Hz, 1H); 6.80 (t, J=6.1 Hz, 1H); 12.15 (broad s, 1H).

Compound 12: methyl 3-((tert-butoxycarbonyl)amino)-2-methylpropanoate

To a solution of compound 11 (9.4 g, 46.25 mmol) in acetone (300 mL) were added K₂CO₃ (16.14 g, 115.63 mmol) and CH₃I (13.26 g, 92.5 mmol). The reaction medium, a yellow suspension, was stirred at RT for 20 h then filtered over Clarcel. The cake thus obtained was washed with acetone, the filtrate concentrated in vacuo, diluted with DCM (100 mL), filtered over Clarcel, the cake thus obtained was washed with DCM and the filtrate concentrated in vacuo to give 9.4 g of compound 12 as a yellow liquid (93%).

RMN ¹H (400 MHz, δ in ppm, DMSO-d6): 1.01 (d, J=7.1 Hz, 3H); 1.37 (s, 9H); 2.54 (m, 1H); 2.91 (dt, J=6.2 and 13.5 Hz, 1H); 3.15 (ddd, J=6.2, 6.9 and 13.5 Hz, 1H); 3.59 (s, 3H); 6.90 (t, J=6.2 Hz, 1H).

Compound 13: methyl 3-((tert-butoxycarbonyl)amino)-2-(((4-methoxybenzyl)oxy)methyl)-2-methylpropanoate To a solution of DIEA (3.2 mL, 22.45 mmol) in THF (10 mL) cooled at −75° C. was added dropwise a solution of 1.6 M n-BuLi in THF (14 mL, 22.4 mmol). The reaction medium was stirred at −75° C. for 20 min; then was added dropwise at −75° C. a solution of compound 12 (2 g, 9.21 mmol) in THF (16 mL) and the reaction mixture was stirred at −75° C. for 10 min. A solution of 1-((chloromethoxy)methyl)-4-methoxybenzene (1.72 g, 9.21 mmol) in THF (16 mL) was then quickly added to the reaction mixture and the stirring carried on at −25° C. for 4 h. The reaction medium was diluted with DCM (100 mL) before the addition of a citric acid solution at 100 g/L (50 mL) while keeping the temperature below 5° C. The reaction medium was stirred at RT for 15 min. The organic phase was washed with a citric acid solution at 100 g/L (2×50 mL), H$_2$O (3×50 mL), dried over MgSO$_4$, filtered and concentrated in vacuo to give 4.08 g of a yellow-orange oil that was purified by flash chromatography on 150 g of silica gel (gradient elution heptane/EtOAc) to provide 2.05 g of compound 13 as a colorless oil (60%).

RMN $^1$H (400 MHz, δ in ppm, DMSO-d6): 1.03 (s, 3H); 1.37 (s, 9H); 3.14 (d, J=6.8 Hz, 2H); 3.31 (d, J=9.1 Hz, 1H); 3.48 (d, J=9.1 Hz, 1H); 3.58 (s, 3H); 3.73 (s, 3H); 4.38 (s, 2H); 6.76 (t, J=7.1 Hz, 1H); 6.90 (d, J=8.9 Hz, 2H); 7.20 (m, 2H).

Fragment C4: methyl 3-amino-2-(hydroxymethyl)-2-methylpropanoate hydrochloride

Compound 13 (1.5 g, 4.08 mmol) was treated with a 4 M HCl solution in dioxane (24 mL) at R.T. for 1 h. The reaction medium was then concentrated in vacuo and co-evaporated in the presence of toluene to give 794 mg of fragment C$_4$ as a viscous oil (quant.).

Synthesis of AD1: (2E,5S,6R,7E)-tert-butyl 5-(((S)-2-amino-4-methylpentanoyl)oxy)-8-(4-(azidomethyl)phenyl)-6-methylocta-2,7-dienoate

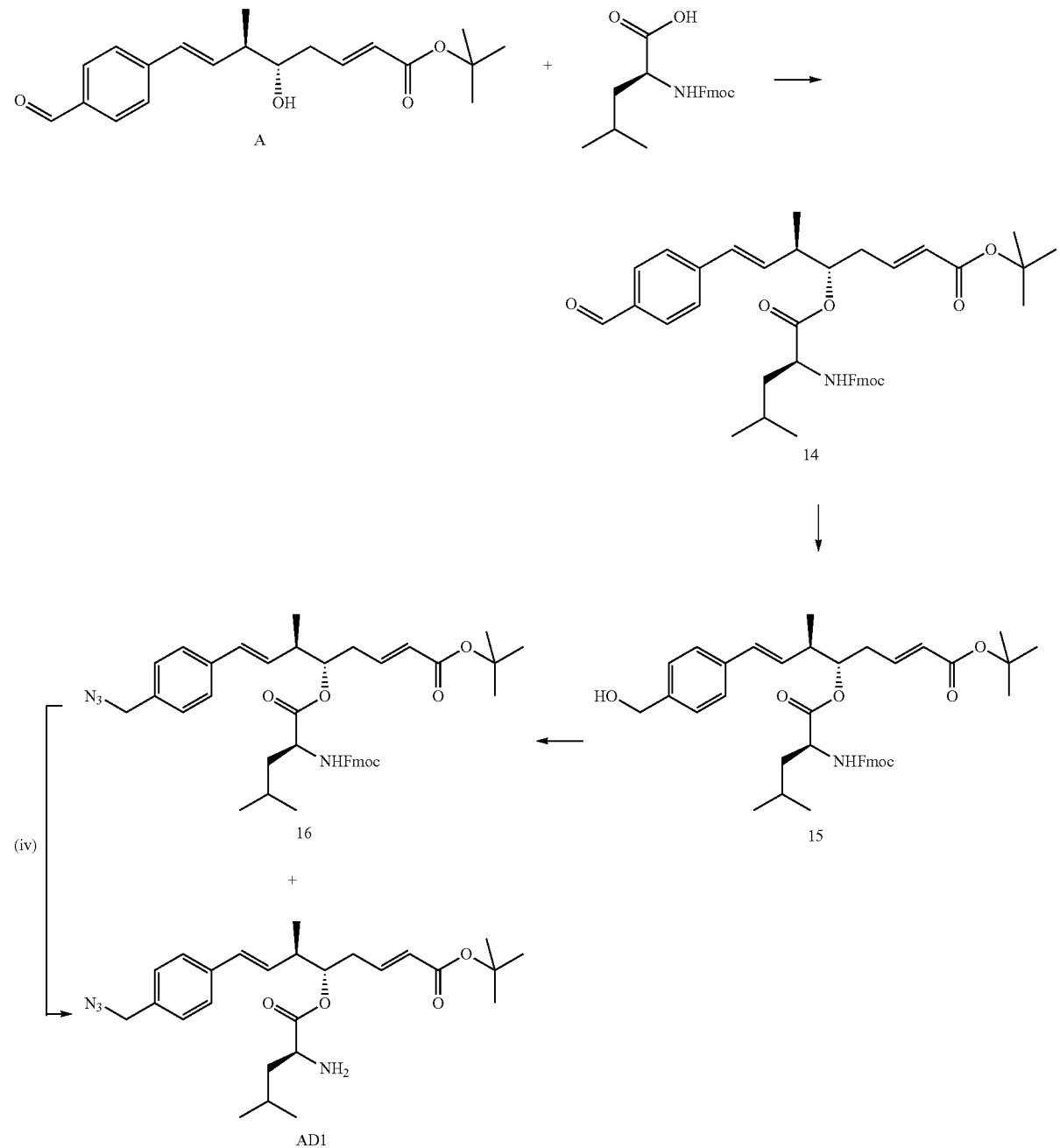

Compound 14: (2E,5S,6R,7E)-tert-butyl 5-(((S)-2-((((9H-fluoren-9-yl)methoxy)carbonyl)amino)-4-methylpentanoyl)oxy)-8-(4-formylphenyl)-6-methylocta-2,7-dienoate Under argon, in a round bottom flask under magnetic stirring, Fmoc-Leu-OH (4.9 g, 13.86 mmol) was introduced, followed by fragment A (3.5 g, 10.59 mmol) in DCM (100 mL) and DIEA (6.6 mL, 38.13 mmol). Then MNBA (5 g, 14.52 mmol) and DMAP (620 mg, 5.07 mmol) were added and the reaction mixture stirred overnight at RT. After this time, the reaction medium was washed with $H_2O$ (100 mL) and sat. brine (100 mL). The organic phase was dried over $MgSO_4$, filtered and concentrated in vacuo to give 9.1 g of crude orange oil that was purified by flash chromatography on 400 g of silica gel (gradient elution heptane/AcOEt) to give 5 g of compound 14 as a pale yellow oil (71%).

RMN $^1$H (400 MHz, δ in ppm, DMSO-d6): 0.77 (d, J=6.8 Hz, 6H); 1.05 (d, J=7.0 Hz, 3H); 1.33 to 1.64 (m, 4H); 1.38 (s, 9H); 2.39 to 2.63 (partially masked m, 2H); 4.01 (m, 1H); 4.13 to 4.31 (m, 3H); 4.95 (m, 1H); 5.81 (d, J=15.9 Hz, 1H); 6.37 (dd, J=8.8 and 16.2 Hz, 1H); 6.52 (d, J=16.2 Hz, 1H); 6.70 (td, J=7.3 and 15.9 Hz, 1H); 7.29 (t, J=7.9 Hz, 2H); 7.40 (t, J=7.9 Hz, 2H); 7.56 (d, J=8.4 Hz, 2H); 7.67 (dd, J=7.9 Hz, 2H); 7.74 to 7.82 (m, 3H); 7.87 (d, J=7.9 Hz, 2H); 9.93 (s, 1H). LCMS (A1): ES m/z=666 [M+H]+, m/z=689 [M+Na]$^+$; $t_R$=1.92 min.

Compound 15: (2E,5S,6R,7E)-tert-butyl 5-(((S)-2-((((9H-fluoren-9-yl)methoxy)carbonyl)amino)-4-methylpentanoyl)oxy)-8-(4-(hydroxymethyl)phenyl)-6-methylocta-2,7-dienoate Under argon, to a solution of compound 14 (5 g, 7.51 mmol) in MeTHF (60 mL), was added sodium trimethoxyborohydride (1.2 g, 8.91 mmol) portionwise. The reaction medium was stirred 5 h at RT. After this time, sat. $NH_4Cl$ (100 mL) and acetone (20 mL) were added. The reaction medium was stirred 1 h at RT. After settling, the organic phase was washed with $H_2O$ then with sat. brine (50 mL), dried over $MgSO_4$, filtered and concentrated in vacuo to give 5.3 g of crude yellow oil that was purified by flash chromatography on 300 g of silica gel (gradient elution heptane/AcOEt) to give 3.15 g of compound 15 as a white semi-solid (63%).

RMN $^1$H (400 MHz, δ in ppm, DMSO-d6): 0.80 (m, 6H); 1.02 (d, J=7.0 Hz, 3H); 1.35 to 1.66 (m, 4H); 1.38 (s, 9H); 2.35 to 2.56 (partially masked m, 2H); 4.02 (m, 1H); 4.15 to 4.32 (m, 3H); 4.43 (d, J=5.5 Hz, 2H); 4.92 (m, 1H); 5.12 (t, J=5.5 Hz, 1H); 5.80 (d, J=15.9 Hz, 1H); 6.10 (dd, J=8.8 et 16.2 Hz, 1H); 6.39 (d, J=16.2 Hz, 1H); 6.69 (m, 1H); 7.20 (d, J=8.4 Hz, 2H); 7.28 to 7.33 (m, 4H); 7.41 (t, J=7.9 Hz, 2H); 7.69 (t, J=7.9 Hz, 2H); 7.80 (d, J=8.2 Hz, 1H); 7.88 (d, J=7.9 Hz, 2H). LCMS (A1): ES m/z=668 [M+H]$^+$; m/z=690 [M+Na]+; m/z=712 [M–H+$HCO_2$H]$^-$; $t_R$=1.84 min.

Compound 16: (2E,5S,6R,7E)-tert-butyl 5-(((S)-2-((((9H-fluoren-9-yl)methoxy)carbonyl) amino)-4-methylpentanoyl)oxy)-8-(4-(azidomethyl)phenyl)-6-methylocta-2,7-dienoate Under argon, compound 15 (3.15 g, 4.72 mmol) and DCM (50 mL) were introduced in a round bottom flask. At 0° C., TEA (987 μL, 7.08 mmol) was added, followed by methanesulfonyl chloride (438 μL, 5.66 mmol), the reaction medium was stirred 1 h at 0° C. and 13 h at RT. After this time, DCM (50 mL) and water (50 mL) were added. After settling, the organic phase was washed with sat. brine (3×25 mL), dried over $MgSO_4$ and concentrated in vacuo. Under argon, the crude product thus obtained was dissolved in DMF (50 mL) and sodium azide (644 mg, 9.91 mmol) was added. The reaction medium was stirred overnight at RT. After this time, DMF was concentrated in vacuo and AcOEt was added. The mixture obtained was washed with 0.1N HCl (25 mL), with sat. $NaHCO_3$ (25 mL) and sat. brine (25 mL), dried over $MgSO_4$, filtered and concentrated in vacuo to give 3.3 g of crude that was purified by flash chromatography on 200 g of silica gel (gradient elution heptane/AcOEt) to give 1.8 g of compound 16 as a colorless gum (55%) and 740 mg of compound AD1 (33%).

LCMS (A2): ES m/z=715 [M+Na]+; $t_R$=8.95 min.

Compound AD1: (2E,5S,6R,7E)-tert-butyl 5-(((S)-2-amino-4-methylpentanoyl)oxy)-8-(4-(azidomethyl)phenyl)-6-methylocta-2,7-dienoate Under argon, in a round bottom flask under magnetic stirring, compound 16 (1.8 g, 2.6 mmol) and DCM (50 mL) were introduced, followed by piperidine (1.6 mL, 16.2 mmol). The reaction medium was stirred overnight at RT. After this time, it was washed with 1N HCl then with sat. $NaHCO_3$, sat. brine, dried over $MgSO_4$, filtered and concentrated in vacuo to give 2 g of crude that was purified by flash chromatography on 130 g of silica gel (gradient elution heptane/AcOEt) to give 1.48 g of compound AD1 as a pale yellow oil (quant.).

LCMS (A3): ES m/z=471 [M+H]$^+$; $t_R$=2.65 min.

Synthesis of AD2: (2E,5S,6R,7E)-tert-butyl 5-(((S)-2-amino-4,4-dimethylpentanoyl)oxy)-8-(4-(hydroxymethyl)phenyl)-6-methylocta-2,7-dienoate hydrochloride

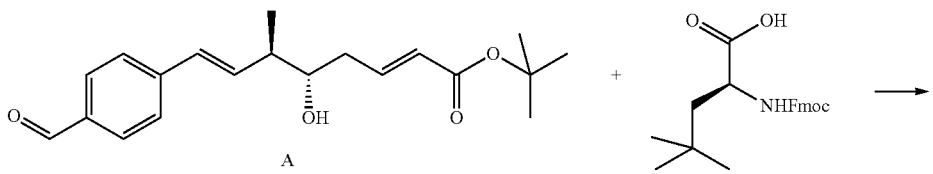

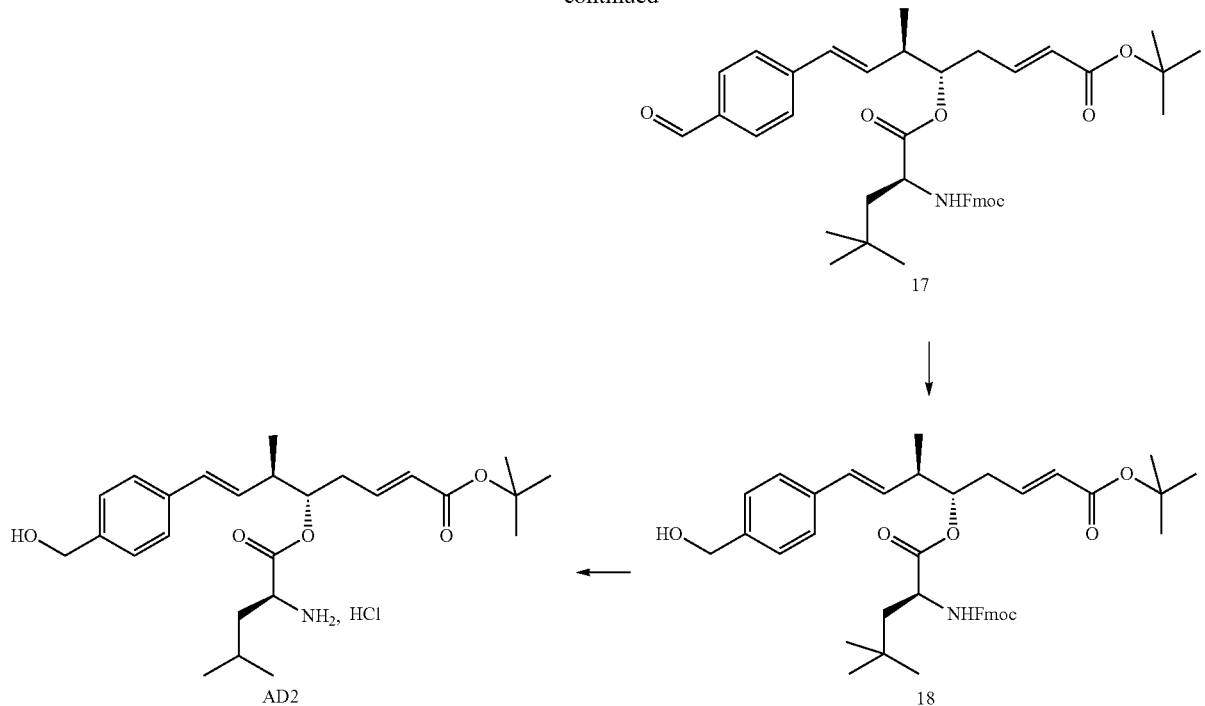

Compound 17: (2E,5S,6R,7E)-tert-butyl 5-(((S)-2-((((9H-fluoren-9-yl)methoxy)carbonyl)amino)-4,4-dimethylpentanoyl)oxy)-8-(4-formylphenyl)-6-methylocta-2,7-dienoate Under argon, in a round bottom flask to a solution of compound A (1.633 g, 4.94 mmol) in DCM (60 mL) were added L-Fmoc-tert-Leu-OH (1.82 g, 4.94 mmol), DIEA (2.57 mL, 14.83 mmol), MNBA (1.70 g, 4.94 mmol) and DMAP (241.51 mg, 1.98 mmol). After stirring for 2 h at RT, the reaction medium was diluted with $H_2O$ (50 mL) and extracted twice with DCM. The combined organic phases were washed with citric acid (2×50 mL), sat. $NaHCO_3$ (50 mL) and sat. brine (50 mL), dried over $MgSO_4$, filtered and concentrated in vacuo to give 3.24 g of crude compound 17 used directly in the subsequent reduction (96%).

Compound 18: (2E,5S,6R,7E)-tert-butyl 5-(((S)-2-((((9H-fluoren-9-yl)methoxy)carbonyl)amino)-4,4-dimethylpentanoyl)oxy)-8-(4-(hydroxymethyl)phenyl)-6-methylocta-2,7-dienoate Under argon, in a round bottom flask to a solution of compound 17 (3.24 g, 4.77 mmol) in MeTHF (60 mL) was added sodium trimethoxyborohydride (670.56 mg, 5.24 mmol) at 0° C. After stirring for 1 h at RT, additional sodium trimethoxyborohydride (304 mg, 2.38 mmol) was added and stirred for 2 h. Then the reaction medium was cooled at 0° C., diluted with acetone (18 mL) and sat. $NH_4C_1$ (36 mL) and extracted with AcOEt. The combined organic phases were washed with sat. brine, dried over $MgSO_4$, filtered, concentrated in vacuo and purified by flash chromatography on 100 g of silica gel (gradient Heptane/AcOEt) to give 2.61 g of compound 18 as a colorless amorphous solid (80%).

RMN $^1H$ (400 MHz, δ in ppm, DMSO-d6): 0.80 (s, 9H); 1.02 (d, J=7.0 Hz, 3H); 1.35 to 1.60 (m, 4H); 1.38 (s, 9H); 2.37 to 2.58 (partially masked m, 2H); 4.04 (m, 1H); 4.16 to 4.33 (m, 3H); 4.45 (d, J=5.7 Hz, 2H); 4.91 (m, 1H); 5.12 (t, J=5.7 Hz, 1H); 5.80 (d, J=16.0 Hz, 1H); 6.10 (dd, J=8.8 and 16.2 Hz, 1H); 6.39 (d, J=16.2 Hz, 1H); 6.69 (m, 1H); 7.21 (d, J=8.4 Hz, 2H); 7.25 to 7.33 (m, 4H); 7.40 (t, J=7.9 Hz, 2H); 7.68 (t, J=7.9 Hz, 2H); 7.78 (d, J=8.3 Hz, 1H); 7.88 (d, J=7.9 Hz, 2H). LCMS (A1): ES m/z=608; m/z=682 $[M+H]^+$; m/z=726 $[M-H+HCO_2H]^-$; $t_R$=1.85 min.

Compound AD2: (2E,5S,6R,7E)-tert-butyl 5-(((S)-2-amino-4,4-dimethylpentanoyl)oxy)-8-(4-(hydroxymethyl)phenyl)-6-methylocta-2,7-dienoate hydrochloride Under argon, in a round bottom flask, to a solution of compound 18 (2.61 g, 3.83 mmol) in DCM (40 mL) was added piperidine (7.60 mL, 76.56 mmol) and the reaction medium was stirred for 1 h at RT. Then it was concentrated and extracted with AcOEt. The combined organic layers were washed with 1N HCl, $H_2O$ and sat. brine, dried over $MgSO_4$, filtered and concentrated in vacuo. The residue was diluted with $iPr_2O$ (50 mL) and stirred for 40 h at RT. The crude product was filtered, washed with $iPr_2O$ and dried in vacuo 3 h at 40° C. to provide 1.706 g of compound AD2 as a colorless amorphous solid (90%).

RMN $^1H$ (400 MHz, δ in ppm, DMSO-d6): 0.88 (s, 9H); 1.10 (d, J=7.0 Hz, 3H); 1.39 to 1.49 (m, 1H); 1.42 (s, 9H); 1.75 (dd, J=6.1 and 15.1 Hz, 1H); 2.47 to 2.64 (partially masked m, 2H); 3.92 (t, J=5.5 Hz, 1H); 4.47 (d, J=5.7 Hz, 2H); 5.02 (m, 1H); 5.15 (t, J=5.7 Hz, 1H); 5.90 (d, J=15.9 Hz, 1H); 6.15 (dd, J=8.3 and 16.1 Hz, 1H); 6.44 (d, J=16.1 Hz, 1H); 6.77 (td, J=7.3 and 15.9 Hz, 1H); 7.26 (d, J=8.4 Hz, 2H); 7.34 (d, J=8.4 Hz, 2H); 8.10 (broad m, 3H). LCMS (A1): ES m/z=460 $[M+H]^+$; $t_R$=0.95 min.

Synthesis of AD3: (2R,3S)-1-((4-methoxybenzyl)oxy)-2-methylhex-5-en-3-yl (S)-2-amino-4,4-dimethylpentanoate

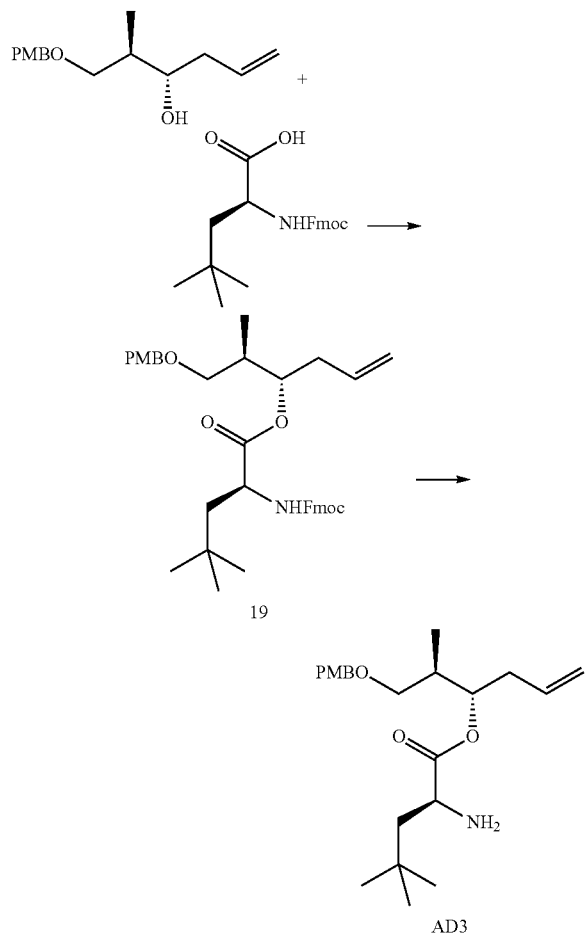

Compound 19: (2R,3S)-1-((4-methoxybenzyl)oxy)-2-methylhex-5-en-3-yl (S)-2-(((((9H-fluoren-9-yl)methoxy)carbonyl)amino)-4,4-dimethylpentanoate To a solution of Sakurai alcohol (1.02 g, 4.08 mmol) and (S)-2-((((9H-fluoren-9-yl)methoxy)carbonyl)amino)-4,4-dimethylpentanoic acid (1.5 g, 4.08 mmol) in THF (15 mL) were added 2,4,6-trichlorobenzoyl chloride (1.02 g, 4.08 mmol), dropwise TEA (1.14 mL, 8.16 mmol) and DMAP (126.0 mg, 1.02 mmol). The reaction medium was stirred at RT for 5 h, then cooled using an ice bath before the addition of 1N HCl (60 mL) while keeping the temperature below 10° C. The resulting medium was stirred at RT for 15 min and extracted with EtOAc (3×50 mL). The combined organic phases were washed with sat. NaHCO$_3$ (15 mL), sat. brine (3×15 mL), dried over MgSO$_4$, filtered, concentrated in vacuo and purified by three successive flash chromatographies on silica gel (150 g, gradient elution heptane/EtOAc; 150 g and 20 g, gradient elution DCM/MeOH) to give 1.78 g of compound 19 as a colorless oil (72%).

RMN $^1$H (400 MHz, δ in ppm, DMSO-d6): 0.85 (d, J=7.1 Hz, 3H); 0.89 (s, 9H); 1.51 (dd, J=2.8 and 14.3 Hz, 1H); 1.61 (dd, J=9.0 and 14.3 Hz, 1H); 1.95 (m, 1H); 2.21 (m, 1H); 2.31 (m, 1H); 3.20 (dd, J=6.5 and 9.6 Hz, 1H); 3.35 (m, 1H); 3.73 (s, 3H); 4.04 (m, 1H); 4.18 to 4.34 (m, 5H); 4.83 (m, 1H); 5.00 (dq, J=2.1 and 10.3 Hz, 1H); 5.05 (dq, J=2.1 and 7.3 Hz, 1H); 5.70 (m, 1H); 6.87 (d, J=8.7 Hz, 2H); 7.17 (d, J=8.7 Hz, 2H); 7.30 (m, 2H); 7.41 (t, J=7.8 Hz, 2H); 7.70 (d, J=7.8 Hz, 2H); 7.75 (d, J=8.3 Hz, 1H); 7.90 (d, J=7.8 Hz, 2H). LCMS (A5): ES m/z=600 [M+H]$^+$; m/z=617 [M+H+NH$_3$]+; m/z=644 [M−H+HCO$_2$H]$^−$; $t_R$=1.86 min.

Compound AD3: (2R,3S)-1-((4-methoxybenzyl)oxy)-2-methylhex-5-en-3-yl (S)-2-amino-4,4-dimethylpentanoate To a solution of compound 19 (1.78 g, 2.98 mmol) in DCM (63 mL) was added dropwise piperidine (1.77 mL, 17.9 mmol). The reaction medium was stirred at R.T. for 4 h, diluted with DCM (150 mL), washed with 1 N HCl (2×20 mL), sat. NaHCO$_3$ (20 mL), sat. brine (3×20 mL), dried over MgSO$_4$, filtered, concentrated in vacuo and purified by flash chromatography on 50 g of silica gel (gradient elution heptane/EtOAc) to give 644 mg of compound AD3 as a colorless oil (57%).

RMN $^1$H (400 MHz, δ in ppm, DMSO-d6): 0.88 (s, 9H); 0.89 (d, J=7.1 Hz, 3H); 1.21 (dd, J=6.9 and 13.9 Hz, 1H); 1.56 (dd, J=5.0 and 13.9 Hz, 1H); 1.66 (broad s, 2H); 2.00 (m, 1H); 2.24 (m, 1H); 2.33 (m, 1H); 3.26 (m, 2H); 3.38 (dd, J=5.5 and 9.4 Hz, 1H); 3.74 (s, 3H); 4.36 (s, 2H); 4.84 (m, 1H); 5.00 to 5.10 (m, 2H); 5.72 (m, 1H); 6.89 (d, J=8.8 Hz, 2H); 7.22 (d, J=8.8 Hz, 2H). LCMS (A5): ES m/z=378 [M+H]$^+$; $t_R$=0.88 min.

Synthesis of BC1: 3-((R)-2-((tert-butoxycarbonyl)amino)-3-(3-chloro-4-methoxyphenyl)-propanamido)-2,2-dimethylpropanoic Acid

Compound 20: methyl 3-((R)-2-((tert-butoxycarbonyl)amino)-3-(3-chloro-4-methoxyphenyl)-propanamido)-2,2-dimethylpropanoate Under argon, in a round bottom flask were introduced fragment C₁ (981.45 mg, 4.00 mmol) and DCM (50 mL), followed by DIEA (1.84 mL, 10.92 mmol), fragment B (1.2 g, 3.64 mmol), HOBt (563.40 mg, 4.00 mmol) and EDC (1.45 mL, 8.01 mmol). The reaction medium was stirred overnight at RT. After this time, the reaction medium was diluted with H₂O (30 mL) and extracted twice with DCM. The combined organic phases were washed with sat. brine, dried over MgSO₄, filtered and concentrated in vacuo to give 2.5 g of crude oil that was purified by flash chromatography on 110 g of silica gel (gradient elution heptane/AcOEt) to give 1.06 g of compound 20 as a white meringue (66%).

RMN ¹H (400 MHz, δ in ppm, DMSO-d6): 1.06 (s, 3H); 1.07 (s, 3H); 1.30 (s, 9H); 2.65 (dd, J=11.6 and 13.9 Hz, 1H); 2.82 (dd, J=4.0 and 13.9 Hz, 1H); 3.18 (dd, J=6.1 and 13.4 Hz, 1H); 3.29 (partially masked m, 1H); 3.60 (s, 3H); 3.81 (s, 3H); 4.11 (m, 1H); 6.90 (d, J=8.7 Hz, 1H); 7.04 (d, J=8.6 Hz, 1H); 7.19 (dd, J=2.3 and 8.6 Hz, 1H); 7.33 (broad s, 1H); 7.75 (large t, J=6.1 Hz, 1H).

Compound BC1: 3-((R)-2-((tert-butoxycarbonyl)amino)-3-(3-chloro-4-methoxyphenyl)-propanamido)-2,2-dimethylpropanoic Acid Under argon, in a round bottom flask were introduced compound 20 (1.06 g, 2.39 mmol) and THF (25 mL) followed by LiOH (70.18 mg, 2.87 mmol) and H₂O (1 mL). The reaction medium was stirred few hours before adding 70 mg of LiOH and stirred overnight at RT. After this time, Amberlit resin was added until pH 4, filtered then washed with THF and concentrated in vacuo to give 1 g of compound BC1 as a white solid (97%).

Synthesis of BC2: 3-((R)-2-((tert-butoxycarbonyl)amino)-3-(3-chloro-4-methoxyphenyl)-propanamido)-2,2-dimethylbutanoic acid

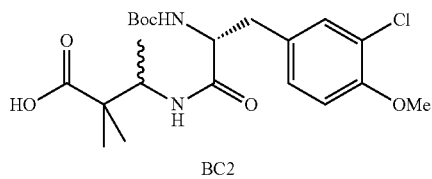

BC2

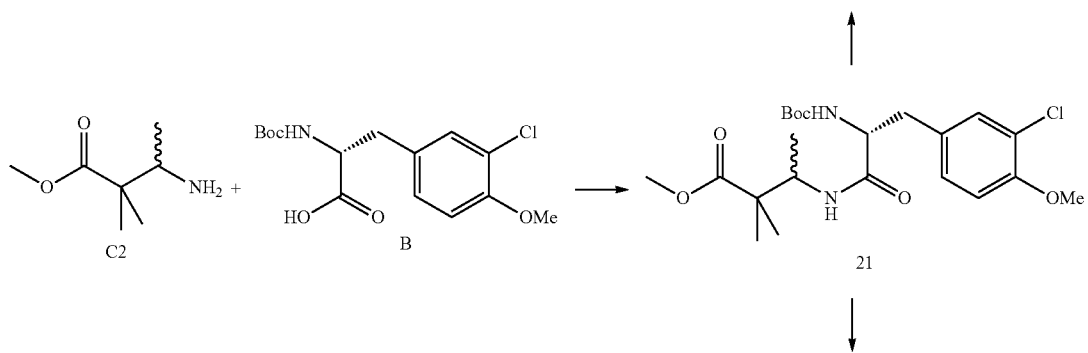

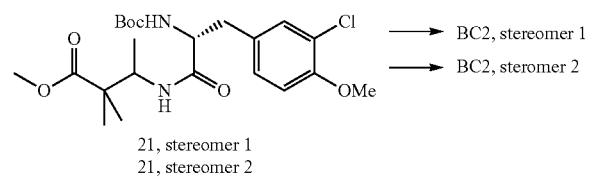

21, stereomer 1
21, stereomer 2

Compound 21: methyl 3-((R)-2-((tert-butoxycarbonyl)amino)-3-(3-chloro-4-methoxyphenyl)-propanamido)-2,2-dimethylbutanoate Under argon, in a round bottom flask were introduced fragment B (1.02 g, 2.78 mmol) and DCM (25 mL), followed by EDC (592 mg, 3.03 mmol) and HOBt (478 mg, 3.03 mmol). The reaction medium was stirred 15 min then fragment C2 (0.5 g, 2.75 mmol) and DIEA (1.7 mL, 9.73 mmol) were added. The reaction medium was stirred overnight at RT. After this time, the reaction medium was concentrated in vacuo then diluted with AcOEt. The organic layer was washed with sat. brine, dried over $MgSO_4$, filtered and concentrated in vacuo to give 1.45 g of crude oil that purified by flash chromatography on 100 g of silica gel (gradient elution heptane/AcOEt) to give 845 mg of compound 21 as a white foam (67%).

RMN $^1H$ (400 MHz, δ in ppm, DMSO-d6): diastereoisomer mixture 50:50; 0.87 (d, J=6.8 Hz, 1.5H); 0.97 (d, J=6.8 Hz, 1.5H); 1.01 (s, 1.5H); 1.03 (s, 1.5H); 1.07 (s, 3H); 1.31 (s, 9H); 2.58 to 2.87 (m, 2H); 3.59 (s, 1.5H); 3.60 (s, 1.5H); 3.81 (s, 3H); 3.99 to 4.20 (m, 2H); 6.90 (d, J=9.0 Hz, 0.5H); 6.97 (d, J=9.0 Hz, 0.5H); 7.05 (broad d, J=8.6 Hz, 1H); 7.19 (split dd, J=2.4 and 8.6 Hz, 1H); 7.32 (d, J=2.4 Hz, 0.5H); 7.34 (d, J=2.4 Hz, 0.5H); 7.54 (d, J=10.1 Hz, 0.5H); 7.62 (d, J=10.1 Hz, 0.5H). LCMS (A3): diastereoisomer mixture 50:50; ES m/z=457 [M+H]$^+$; m/z=479 [M+Na]$^+$; $t_R$=3.19-3.2 min.

Compound 21 stereomers 1 and 2: methyl 3-((R)-2-((tert-butoxycarbonyl)amino)-3-(3-chloro-4-methoxyphenyl)-propanamido)-2,2-dimethylbutanoate stereomers 1 and 2

Under argon, in a round bottom flask to a solution of fragment B (1.17 g, 3.55 mmol) in DCM (30 mL) were added EDC (741.75 mg, 3.87 mmol), HOBt (592.57 mg, 3.87 mmol). After stirring 15 min at RT, fragment C2 (639 mg, 3.52 mmol) and DIEA (2.17 mL, 12.31 mmol) were added. The reaction medium was stirred for 4 h, then concentrated and diluted with AcOEt (100 mL). The organic layers were washed with $H_2O$ (2×10 mL) and sat. brine (2×10 mL), dried over $MgSO_4$, filtered and concentrated in vacuo. The crude product was purified by flash chromatography on 50 g of silica gel (gradient elution heptane/AcOEt) to give 1.306 g of mixture of diastereoisomers (81%) that were separated by two successive flash chromatographies, the first one on 100 g of silica gel (gradient elution DCM/MeOH) to give 376 mg of compound 21 stereomer 1 (23%), the second one on 70 g of silica gel (gradient elution DCM/MeOH) to give 181 mg of compound 21 stereomer 1 (11%), 279 mg of compound 21 stereomer 2 (17%) and 476 mg of mixture of diasteroisomers.

Compound 21 Stereomer 1

RMN $^1H$ (400 MHz, δ in ppm, DMSO-d6): 0.85 (d, J=6.8 Hz, 3H); 1.07 (s, 6H); 1.31 (s, 9H); 2.57 (m, 1H); 2.80 (dd, J=5.2 and 13.8 Hz, 1H); 3.60 (s, 3H); 3.81 (s, 3H); 4.05 (m, 1H); 4.16 (m, 1H); 6.99 (d, J=8.7 Hz, 1H); 7.05 (d, J=8.6 Hz, 1H); 7.20 (dd, J=2.0 and 8.6 Hz, 1H); 7.34 (d, J=2.0 Hz, 1H); 7.57 (d, J=10.1 Hz, 1H). LCMS (A1): ES m/z=381; m/z=401; m/z=455 [M−H]$^-$; m/z=457 [M+H]$^+$; $t_R$=1.29 min.

Compound 21 Stereomer 2

RMN $^1H$ (400 MHz, δ in ppm, DMSO-d6): 0.95 (d, J=6.8 Hz, 3H); 1.00 (s, 3H); 1.03 (s, 3H); 1.31 (s, 9H); 2.55 (m, 1H); 2.80 (dd, J=5.0 and 14.3 Hz, 1H); 3.59 (s, 3H); 3.81 (s, 3H); 4.09 to 4.22 (m, 2H); 6.92 (d, J=8.8 Hz, 1H); 7.05 (d, J=8.6 Hz, 1H); 7.20 (dd, J=2.0 and 8.6 Hz, 1H); 7.34 (d, J=2.0 Hz, 1H); 7.64 (d, J=10.1 Hz, 1H). LCMS (A1): ES m/z=381; m/z=401; m/z=455 [M−H]$^-$; m/z=457 [M+H]$^+$; $t_R$=1.29 min.

Compound BC2: 3-((R)-2-((tert-butoxycarbonyl)amino)-3-(3-chloro-4-methoxyphenyl)-propanamido)-2,2-dimethylbutanoic acid Compound 21 (0.845 g, 1.85 mmol) and MeOH (20 mL) were introduced in a round bottom flask followed by 1.8 mL of 10M NaOH. The solution was stirred and heated at 50° C. overnight. The reaction medium was evaporated in vacuo then diluted with $H_2O$ (20 mL) and neutralized with 5N HCl. The solution was extracted twice with AcOEt. The combined organic layers were washed with sat. brine, dried avec $MgSO_4$, filtered and concentrated in vacuo to give 800 mg of compound BC2 as a white foam (97%).

RMN $^1H$ (400 MHz, δ in ppm, DMSO-d6): diastereoisomer mixture 50:50; 0.91 (d, J=6.8 Hz, 1.5H); 0.97 (d, J=6.8 Hz, 1.5H); 1.00 (s, 3H); 1.03 (s, 1.5H); 1.07 (s, 1.5H); 1.31 (s, 9H); 2.57 (m, 1H); 2.83 (m, 1H); 3.81 (s, 3H); 4.01 to 4.16 (m, 2H); 6.90 (d, J=9.0 Hz, 0.5H); 6.95 (d, J=9.0 Hz, 0.5H); 7.03 (d, J=8.6 Hz, 1H); 7.20 (broad, J=8.6 Hz, 1H); 7.31 (broad s, 1H); 7.49 (d, J=10.1 Hz, 0.5H); 7.54 (d, J=10.1 Hz, 0.5H); 11.94 (broad m, 1H). LCMS (A1): diastereoisomer mixture 50:50; ES m/z=387; m/z=443 [M+H]$^+$; $t_R$=1.20-1.21 min.

Compound BC2 Stereomer 1: 3-((R)-2-((tert-butoxycarbonyl)amino)-3-(3-chloro-4-methoxy phenyl)propanamido)-2,2-dimethylbutanoic acid stereomer 1

Compound 21 stereomer 1 (0.325 g, 1.85 mmol) and MeOH (8 mL) were introduced in a round bottom flask followed by 0.692 mL of 10M NaOH. The yellow solution was stirred and heated at 50° C. overnight. The reaction medium was evaporated in vacuo then diluted with $H_2O$ (20 mL) and extracted with AcOEt (3×5 mL). The aq. layers were acidified with 5N HCl and extracted with AcOEt (3×30 mL). The combined organic phases were washed with sat. brine (5 mL), dried over $MgSO_4$, filtered and concentrated in vacuo to give 303 mg of compound BC2 stereomer 1 as a white foam (96%) used directly in the subsequent reaction.

Compound BC2 Stereomer 2: 3-((R)-2-((tert-butoxycarbonyl)amino)-3-(3-chloro-4-methoxy phenyl)propanamido)-2,2-dimethylbutanoic acid stereomer 2

Compound 21 stereomer 2 (1.094 g, 2.39 mmol), THF (5 mL) and $H_2O$ (5 mL) were introduced in a round bottom flask followed by LiOH (301 mg, 7.18 mmol). The solution was stirred for 44 h at RT. The reaction was not complete, LiOH (301 mg) was added. The mixture was stirred for 48 h, then 301 mg of LiOH was added in THF (10 mL) and $H_2O$ (5 mL) and the reaction medium stirred 40 h at 60° C. The reaction medium was evaporated in vacuo. 1M citric acid was added until pH 2 and the mixture was extracted with AcOEt (2×20 mL). The combined organic layers were washed with $H_2O$, dried over $MgSO_4$, filtered and concentrated in vacuo to give 1.096 g of compound BC2 stereomer 2 as a white amorph solid (quant.) used directly in the subsequent reaction.

Synthesis of BC3: ethyl 2-((R)-1-(2-((tert-butoxycarbonyl)amino)-3-(3-chloro-4-methoxyphenyl)-propanamido)cyclopropyl)-2-methylpropanoic Acid

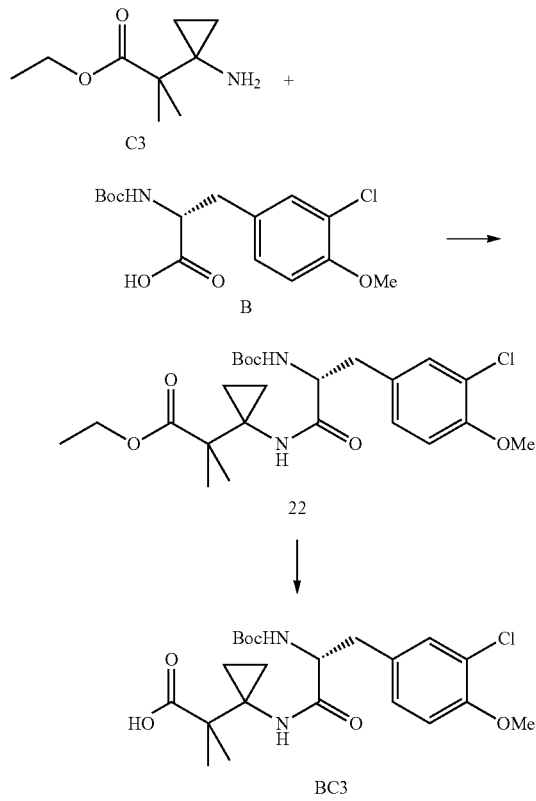

Compound 22: ethyl 2-((R)-1-(2-((tert-butoxycarbonyl)amino)-3-(3-chloro-4-methoxyphenyl)-propanamido)cyclopropyl)-2-methylpropanoate Under argon, in a round bottom flask were introduced fragment $C_3$ (1.2 g, 7.01 mmol) and THF (16.5 mL), followed by fragment B (2.54 g, 7.71 mmol), HOBt (1.77 g, 8.76 mmol), EDC (1.23 g, 8.06 mmol) and DIEA (1.35 mL, 7.71 mmol). The reaction medium was stirred for 2 h at RT. After this time, the reaction medium was diluted with $H_2O$ (25 mL) and extracted with AcOEt (250 mL). The organic layers were washed with $H_2O$ (2×25 mL), sat. brine (2×25 mL), dried over $MgSO_4$, filtered, concentrated and purified by flash chromatography, the first one on 200 g of silica gel (gradient elution heptane/AcOEt) to give 2.16 g of compound 22 as a colorless foam (64%) and 343 mg of mixture containing the expected compound that was further purified on 30 g of silica gel (gradient elution heptane/AcOEt) to give 160 mg of compound 22 as a colorless foam (4.7%).

RMN $^1$H (400 MHz, δ in ppm, DMSO-d6): 0.62 (m, 1H); 0.74 to 0.99 (m, 3H); 1.03 (s, 3H); 1.10 (s, 3H); 1.24 (t, J=7.2 Hz, 3H); 1.42 (s, 9H); 2.90 (m, 2H); 3.88 (s, 3H); 4.08 (m, 1H); 4.10 (q, J=7.2 Hz, 2H); 4.96 (m, 1H); 6.33 (broad s, 1H); 6.85 (d, J=8.5 Hz, 1H); 7.03 (dd, J=2.4 and 8.5 Hz, 1H); 7.17 (d, J=2.4 Hz, 1H).

Compound BC3: 2-((R)-1-(2-((tert-butoxycarbonyl)amino)-3-(3-chloro-4-methoxyphenyl)-propanamido)cyclopropyl)-2-methylpropanoic Acid Compound 22 (2.09 g, 4.33 mmol), THF (10 mL) and $H_2O$ (8 mL) were introduced in a round bottom flask followed by LiOH (726.33 mg, 17.31 mmol). The solution was stirred and heated at 65° C. After 16 h, the reaction was not completed, 726.33 mg of LiOH in 10 mL $H_2O$ were added. The mixture was stirred for 48 h at 65° C. After cooling, the reaction medium was diluted with $H_2O$ (20 mL) then extracted with AcOEt (3×40 mL). The organic layers were washed with $H_2O$ (2×10 mL), dried over $MgSO_4$, filtered and concentrated in vacuo to give 1.29 g of mixture ester/acid. The aq. layer was acidified with 5N HCl until pH 3, then extracted with AcOEt (3×50 mL). The organic layers were washed with $H_2O$ (2×10 mL), dried over $MgSO_4$, filtered and concentrated in vacuo to give 787 mg of compound BC3 as a beige foam (40%).

RMN $^1$H (400 MHz, δ in ppm, DMSO-d6): 0.50 to 0.90 (m, 4H); 1.03 (s, 6H); 1.30 (s, 9H); 2.60 (dd, J=10.5 and 14.1 Hz, 1H); 2.78 (dd, J=5.0 and 14.1 Hz, 1H); 3.81 (s, 3H); 3.97 (m, 1H); 6.80 (d, J=8.7 Hz, 1H); 7.03 (d, J=8.5 Hz, 1H); 7.18 (dd, J=2.0 and 8.5 Hz, 1H); 7.31 (d, J=2.0 Hz, 1H); 7.86 (s, 1H); 12.11 (broad m, 1H).

Synthesis of BC4: (S)-3-((R)-2-acrylamido-3-(3-chloro-4-methoxyphenyl)propanamido)-2,2-dimethylbutanoic acid

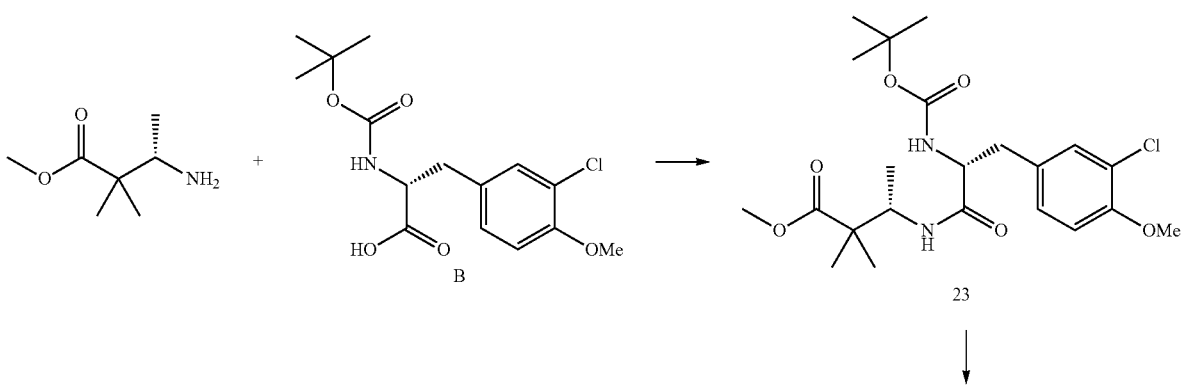

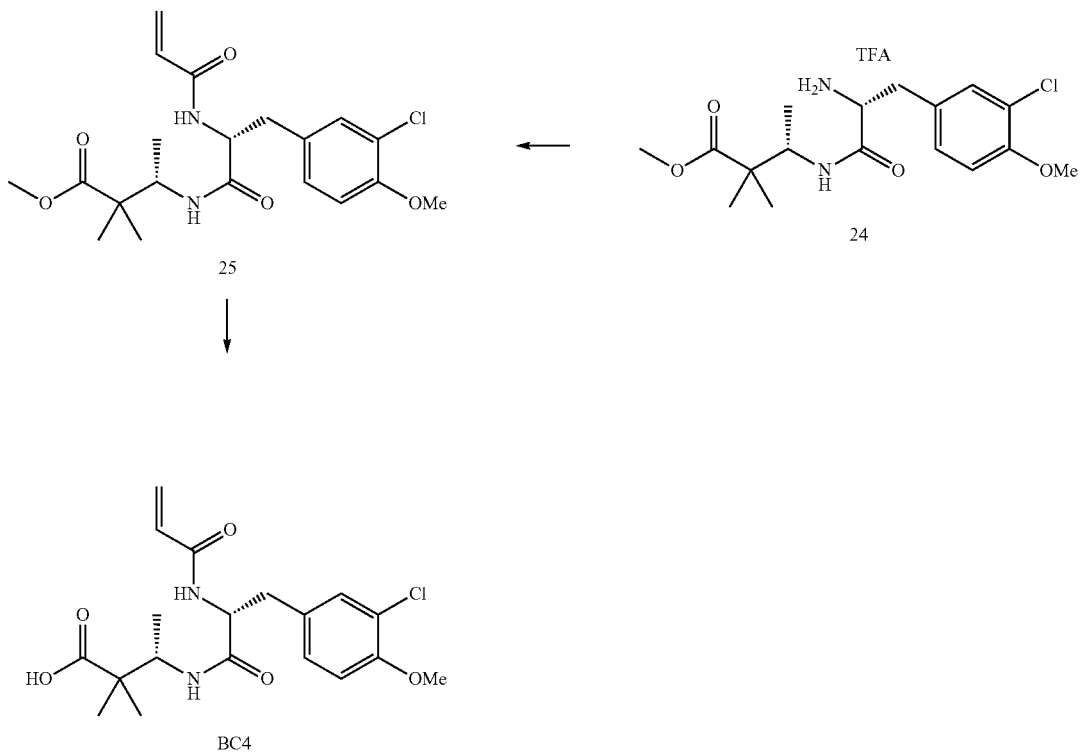

Compound 23: methyl (S)-3-((R)-2-((tert-butoxycarbonyl)amino)-3-(3-chloro-4-methoxyphenyl)-propanamido)-2,2-dimethylbutanoate To a solution of fragment B (2 g, 6.06 mmol) in DCM (60 mL) were added EDC (1.13 mL, 7.06 mmol) and HOBt (948 mg, 6.67 mmol). The reaction medium was stirred at RT for 15 min then were added methyl (S)-3-amino-2,2-dimethylbutanoate (881 mg, 6.06 mmol) and DIEA (1.53 mL, 9.10 mmol). The reaction medium was stirred at RT for 4 h, concentrated in vacuo and diluted with EtOAc (100 mL) and H₂O (20 mL). The aqueous phase was extracted with EtOAc (20 mL); the combined organic phases were washed with sat. brine (2×20 mL), dried over MgSO₄, filtered, concentrated in vacuo and purified by flash chromatography on 150 g of silica gel (gradient elution heptane/EtOAc) to give 2.21 g of compound 23 as a colorless lacquer (79%).

RMN ¹H (400 MHz, δ in ppm, DMSO-d6): 0.88 (d, J=7.0 Hz, 3H); 1.08 (s, 6H); 1.32 (s, 9H); 2.67 (dd, J=9.9 and 13.6 Hz, 1H); 2.82 (dd, J=5.2 and 13.6 Hz, 1H); 3.62 (s, 3H); 3.83 (s, 3H); 4.06 (m, 1H); 4.77 (m, 1H) 6.97 (d, J=8.6 Hz, 1H); 7.05 (d, J=8.6 Hz, 1H); 7.20 (dd, J=2.4 and 8.6 Hz, 1H); 7.33 (d, J=2.4 Hz, 1H); 7.55 (d, J=9.8 Hz, 1H).

Compound 24: methyl (S)-3-((R)-2-amino-3-(3-chloro-4-methoxyphenyl)propanamido)-2,2-dimethylbutanoate 2,2,2-trifluoroacetate To a solution of compound 23 (2.2 g, 4.81 mmol) in DCM (25 mL) was added TFA (3.6 mL, 48.1 mmol). The reaction medium was stirred at RT overnight, concentrated in vacuo and co-evaporated in the presence of toluene to provide 2.0 g of compound 24 as a diastereoisomer mixture (88%).

RMN ¹H (400 MHz, δ in ppm, DMSO-d6): 0.80 (d, J=6.9 Hz, 3H); 1.04 (s, 3H); 1.10 (s, 3H); 2.95 (d, J=7.0 Hz, 2H); 3.62 (s, 3H); 3.84 (s, 3H); 4.00 (m, 1H); 4.15 (m, 1H); 7.10 to 7.30 (m, 3H); 8.00 (d, J=9.5 Hz, 1H); 8.22 (broad s, 3H).

Compound 25: methyl (S)-3-((R)-2-acrylamido-3-(3-chloro-4-methoxyphenyl)propanamido)-2,2-dimethylbutanoate To a solution of compound 24 (2.0 g, 4.25 mmol) in DCM (20 mL) were added acryloyl chloride (536 µL, 6.37 mmol) and DIEA (2.5 mL, 12.74 mmol). The reaction medium was stirred at RT for 2 h then diluted with H₂O (20 mL). The aqueous phase was extracted with DCM (2×20 mL), the combined organic phases were washed with sat. brine (2×20 mL), dried over MgSO₄, filtered, concentrated in vacuo and purified by flash chromatography on 100 g of silica gel (gradient elution heptane/EtOAc) to give 850 mg of compound 25 as a 85:15 diastereoisomer mixture (68%).

RMN ¹H (400 MHz, δ in ppm, DMSO-d6): 0.85 (d, J=6.9 Hz, 3H); 1.03 (s, 3H); 1.04 (s, 3H); 2.72 (dd, J=9.7 and 13.9 Hz, 1H); 2.86 (dd, J=5.8 and 13.9 Hz, 1H); 3.58 (s, 3H); 3.80 (s, 3H); 4.15 (m, 1H); 4.56 (m, 1H); 5.56 (dd, J=2.3 and 10.2 Hz, 1H); 6.03 (dd, J=2.3 and 17.2 Hz, 1H); 6.28 (dd, J=10.2 and 17.2 Hz, 1H); 7.02 (d, J=8.5 Hz, 1H); 7.17 (dd, J=2.2 and 8.5 Hz, 1H); 7.31 (d, J=2.2 Hz, 1H); 7.72 (d, J=9.8 Hz, 1H); 8.36 (d, J=8.6 Hz, 1H).

Compound BC4: (S)-3-((R)-2-acrylamido-3-(3-chloro-4-methoxyphenyl)propanamido)-2,2-dimethylbutanoic Acid To a solution of tBuOK (1.11 g, 9.86 mmol) in THF (4 mL) cooled at 0° C. were added $H_2O$ (47 μL) and compound 25 (450 mg, 1.10 mmol). The reaction medium was stirred at RT for 3 h, then acidified with 1N HCl (5 mL). The aqueous phase was extracted with DCM (2×20 mL); the combined organic phases were washed with $H_2O$ (30 mL), sat. brine (20 mL), dried over $MgSO_4$, filtered and concentrated in vacuo. The two diastereoisomers were separated by supercritical fluid chromatography on a Chiralpak AS 10 μm column (isocratic elution at 85/15 $CO_2$/[MeOH+0.1% TEA] to give 385 mg of compound BC4 as an amorphous solid (89%).

RMN $^1H$ (400 MHz, δ in ppm, DMSO-d6): 0.88 (d, J=6.9 Hz, 3H); 0.99 (s, 3H); 1.00 (s, 3H); 2.71 (dd, J=9.4 and 13.7 Hz, 1H); 2.88 (dd, J=5.3 and 13.7 Hz, 1H); 3.80 (s, 3H); 4.10 (m, 1H); 4.54 (m, 1H); 5.55 (dd, J=2.3 and 10.2 Hz, 1H); 6.01 (dd, J=2.3 and 17.1 Hz, 1H); 6.28 (dd, J=10.2 and 17.1 Hz, 1H); 7.02 (d, J=8.7 Hz, 1H); 7.17 (dd, J=2.4 and 8.7 Hz, 1H); 7.32 (d, J=2.4 Hz, 1H); 7.80 (d, J=9.8 Hz, 1H); 8.39 (d, J=8.8 Hz, 1H); 12.00 (broad s, 1H). LCMS (A5): ES m/z=395 [M−H]$^-$; m/z=397 [M+H]$^+$; $t_R$=0.92 min.

Synthesis of BC5: (S)-3-((R)-2-((tert-butoxycarbonyl)amino)-3-(3-chloro-4-methoxyphenyl)-propanamido)-2,2-dimethylbutanoic acid

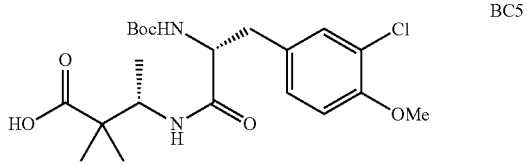 [SMILES: COc1ccc(C[C@@H](NC(=O)OC(C)(C)C)C(=O)N[C@@H](C)C(C)(C)C(=O)O)cc1Cl]

Compound BC5 was prepared starting from methyl (3S)-3-amino-2,2-dimethylbutanoate (MFCD09256689) and following general synthesis of building block BC depicted in Scheme 32 and described for compounds BC1 and BC2.

RMN $^1H$ (400 MHz, δ in ppm, DMSO-d6): 0.89 (d, J=7.0 Hz, 3H); 1.02 (s, 3H); 1.04 (s, 3H); 1.30 (s, 9H); 2.68 (dd, J=13.6 and 10.2 Hz, 1H); 2.82 (dd, J=5.2 and 13.6 Hz, 1H); 3.80 (s, 3H); 4.05 (m, 1H); 4.12 (m, 1H); 7.00 (d, J=8.7 Hz, 1H); 7.05 (d, J=8.7 Hz, 1H); 7.20 (dd, J=2.2 and 8.7 Hz, 1H); 7.32 (d, J=2.2 Hz, 1H); 7.52 (d, J=9.9 Hz, 1H); 12.35 (broad s, 1H). LCMS (A1): ES m/z=441 [M−H]$^-$; m/z=443 [M−H]$^+$; m/z=883 [2M−H]$^-$; $t_R$=1.16 min.

Synthesis of BC6: 3-((R)-2-acrylamido-3-(3-chloro-4-methoxyphenyl)propanamido)-2-(hydroxymethyl)-2-methylpropanoic Acid

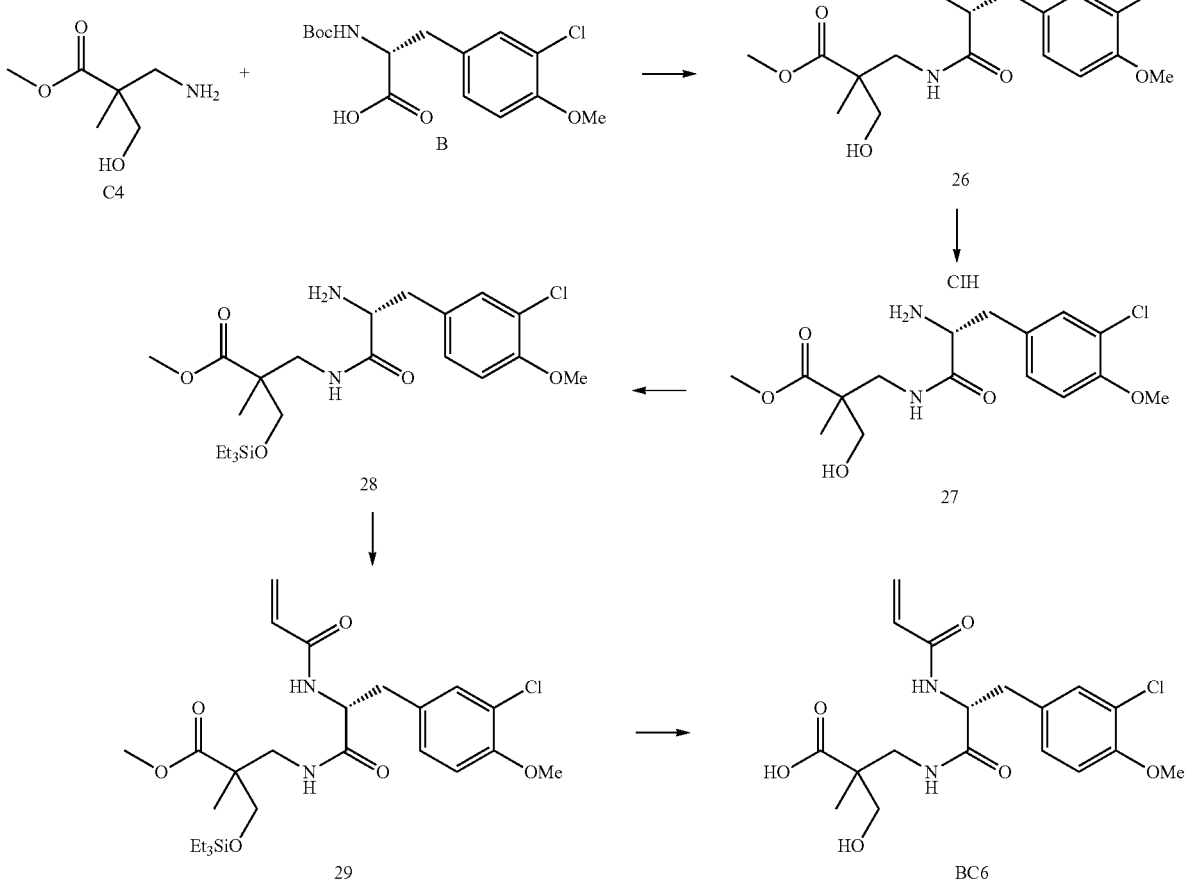

Compound 26: methyl 3-((R)-2-((tert-butoxycarbonyl)amino)-3-(3-chloro-4-methoxyphenyl)-propanamido)-2-(hydroxymethyl)-2-methylpropanoate To a solution of fragment C₄ (1.059 g, 5.77 mmol) in THF (60 mL) were added DIEA (2.06 mL, 11.76 mmol), fragment B (1.90 g, 5.77 mmol), HOBt (935 mg, 6.92 mmol) and EDC (1.23 mL, 6.92 mmol). The reaction medium was stirred at RT for 48 h, concentrated in vacuo and purified by flash chromatography on 200 g of silica gel (isocratic elution heptane/EtOAc) to give 1.05 g of compound 26 as a colorless oil (39%).

RMN ¹H (400 MHz, δ in ppm, DMSO-d6): 0.98 (s, 3H); 1.30 (s, 9H); 2.63 (m, 1H); 2.83 (m, 1H); 3.18 to 3.48 (m, 4H); 3.60 (s, 3H); 3.80 (s, 3H); 4.10 (m, 1H); 4.81 (m, 1H); 6.98 (d, J=8.9 Hz, 1H); 7.04 (d, J=8.7 Hz, 1H); 7.20 (dd, J=2.1 and 8.7 Hz, 1H); 7.35 (d, J=2.1 Hz, 1H); 7.83 (m, 1H). LCMS (A5): ES m/z=457 [M−H]⁻; m/z=459 [M−H]⁺; m/z=503 [M−H+HCO₂H]⁻; $t_R$=1.1 min.

Compound 27: methyl 3-((R)-2-amino-3-(3-chloro-4-methoxyphenyl)propanamido)-2-(hydroxymethyl)-2-methylpropanoate hydrochloride Compound 26 (1.05 g, 2.29 mmol) was treated with HCl 4M in dioxane (16 mL, 64 mmol) for 1 h at RT. The reaction medium was concentrated in vacuo and co-evaporated twice in the presence of toluene. The crude product was triturated with iPr₂O (10 mL), filtered and washed twice with iPr₂O (5 mL). The cake was then dissolved in DCM, filtered and concentrated in vacuo to give 809 mg of compound 27 as a white foam (90%) that was used without further purification.

RMN ¹H (400 MHz, δ in ppm, DMSO-d6): 0.92 (s, 1.5H); 0.97 (s, 1.5H); 2.88 (m, 1H); 3.00 (m, 1H); 3.19 to 3.47 (m, 4H); 3.60 (s, 3H); 3.85 (s, 3H); 4.05 (m, 1H); 4.89 (m, 1H); 7.11 (split d, J=8.6 Hz, 1H); 7.19 (split dd, J=2.0 and 8.6 Hz, 1H); 7.38 (split d, J=2.0 Hz, 1H); 8.15 (broad s, 3H); 8.39 (m, 1H).

Compound 28: methyl 3-((R)-2-amino-3-(3-chloro-4-methoxyphenyl)propanamido)-2-methyl-2-(((triethylsilyl)oxy)methyl)propanoate To a solution of compound 27 (809 mg, 2.05 mmol) in DCM (4 mL) cooled with an ice bath were added TEA (1.43 mL, 10.23 mmol) and chlorotriethylsilane (1.37 mL, 8.19 mmol) while keeping the temperature below 4° C. Stirring at 4° C. was carried on for 10 min then the reaction medium was stirred at RT for 20 h. Sat. brine (20 mL) and DCM were added to the medium that was stirred for 10 min. The organic phase was washed with sat. brine (3×10 mL), dried over MgSO₄, filtered, concentrated in vacuo and purified by flash chromatography on 70 g of silica gel (gradient elution DCM/MeOH) to give 706 mg of compound 28 as a pale yellow oil (73%).

RMN ¹H (400 MHz, δ in ppm, DMSO-d6): 0.52 (q, J=8.0 Hz, 6H); 0.89 (t, J=8.0 Hz, 9H); 0.98 (s, 3H); 1.70 (broad s, 2H); 2.54 (m, 1H); 2.82 (m, 1H); 3.18 to 3.45 (m, 3H); 3.58 (m, 2H); 3.60 (s, 3H); 3.80 (s, 3H); 7.03 (d, J=8.7 Hz, 1H); 7.14 (dd, J=2.3 and 8.7 Hz, 1H); 7.28 (split d, J=2.3 Hz, 1H); 7.78 (m, 1H). LCMS (A5): ES m/z=471 [M−H]⁻; m/z=473 [M+H]⁺; m/z=517 [M−H+HCO₂H]⁻; $t_R$=0.97 min.

Compound 29: methyl 3-((R)-2-acrylamido-3-(3-chloro-4-methoxyphenyl)propanamido)-2-methyl-2-(((triethylsilyl)oxy)methyl)propanoate To a solution of compound 28 (704 mg, 1.49 mmol) in DCM (19 mL) cooled with an ice/acetone bath were added DIEA (780 μL, 4.46 mmol) and dropwise acryloyl chloride (181 μL, 2.23 mmol). The reaction medium was stirred at 0-5° C. for 1 h then EtOAc was added (38 mL) and the medium washed with 1N HCl (5 mL), sat. NaHCO₃ (5 mL), sat. brine (3×15 mL), dried over MgSO₄, filtered, concentrated in vacuo and purified by flash chromatography on 30 g of silica gel (gradient elution DCM/MeOH) to give 742 mg of compound 29 as a colorless oil (94%).

RMN ¹H (400 MHz, δ in ppm, DMSO-d6): 0.52 (split q, J=8.0 Hz, 6H); 0.89 (split t, J=8.0 Hz, 9H); 0.99 (s, 1.5H); 1.01 (s, 1.5H); 2.69 (m, 1H); 2.87 (m, 1H); 3.20 (m, 1H); 3.28 (m, 1H); 3.50 (dd, J=3.1 and 9.9 Hz, 1H); 3.58 (s, 3H); 3.68 (d, J=9.9 Hz, 1H); 3.80 (s, 3H); 4.59 (m, 1H); 5.55 (d, J=10.3 Hz, 1H); 6.00 (d, J=17.3 Hz, 1H); 6.25 (split dd, J=10.3 and 17.3 Hz, 1H); 7.02 (d, J=8.5 Hz, 1H); 7.18 (split dd, J=2.0 and 8.5 Hz, 1H); 7.31 (split d, J=2.0 Hz, 1H); 7.96 (m, 1H); 8.39 (d, J=8.9 Hz, 1H). LCMS (A5): ES m/z=525 [M−H]⁻; m/z=527 [M+H]⁺; m/z=571 [M−H+HCO₂H]⁻; $t_R$=1.54 min.

Compound BC6: 3-((R)-2-acrylamido-3-(3-chloro-4-methoxyphenyl)propanamido)-2-(hydroxymethyl)-2-methylpropanoic Acid To a suspension of tBuOK (1.42 g, 12.65 mmol) in THF (7 mL) cooled with an ice/acetone bath was added H₂O (50 μL), the medium was stirred for 10 min before the addition of a solution of compound 29 (741 mg, 1.41 mmol) in THF (7 mL). Stirring was carried on at 0° C. for 10 min then at RT for 1 h. The reaction medium was cooled with an ice bath before the addition of 1N HCl (16.9 mL). After 15 min of stirring, the reaction medium was extracted with DCM (3×25 mL). The combined organic phases were washed with sat. brine (2×15 mL), H₂O (15 mL), dried over MgSO₄, filtered and concentrated in vacuo to give 656 mg of compound BC6 as a yellow foam (quant.).

RMN ¹H (400 MHz, δ in ppm, DMSO-d6): 0.91 (s, 3H); 2.69 (m, 1H); 2.90 (dd, J=4.8 and 13.6 Hz, 1H); 3.18 to 3.42 (m, 4H); 3.80 (s, 3H); 4.59 (m, 1H); 4.73 (broad, 1H); 5.55 (d, J=2.3 and 10.3 Hz, 1H); 6.00 (dd, J=2.3 and 17.2 Hz, 1H); 6.24 (dd, J=10.3 and 17.2 Hz, 1H); 7.03 (d, J=8.7 Hz, 1H); 7.19 (dd, J=2.0 and 8.7 Hz, 1H); 7.35 (d, J=2.0 Hz, 1H); 8.00 (m, 1H); 8.39 (d, J=8.8 Hz, 1H); 12.30 (broad s, 1H). LCMS (A5): ES m/z=397 [M−H]⁻; m/z=399 [M+H]⁺; $t_R$=0.77 min.

Synthesis of Examples 1 to 3: benzylic amine of aza-C52, NHS ester of glutaryl-Val-Ala-aza-C52 benzylic amine and Corresponding ADC
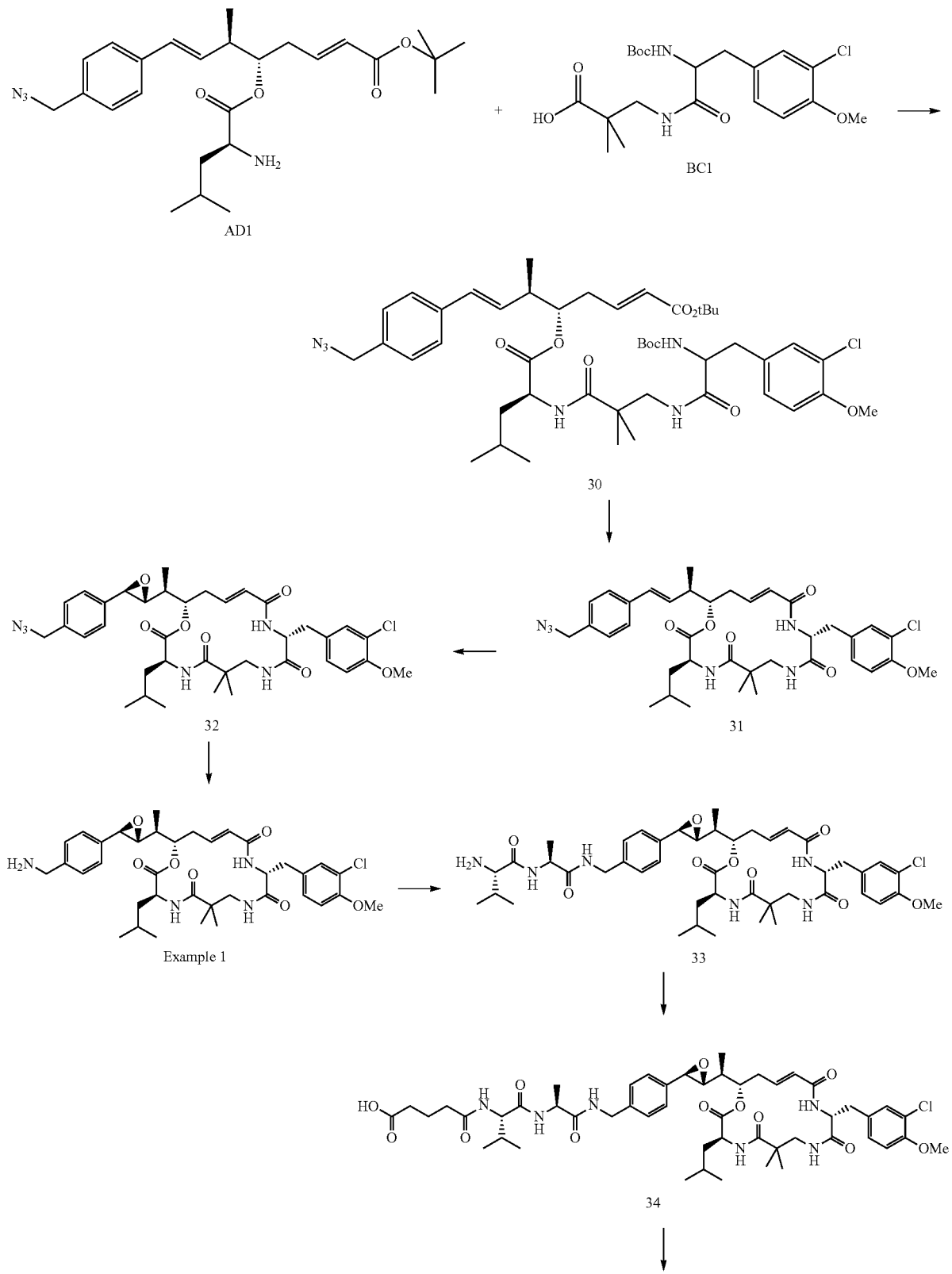

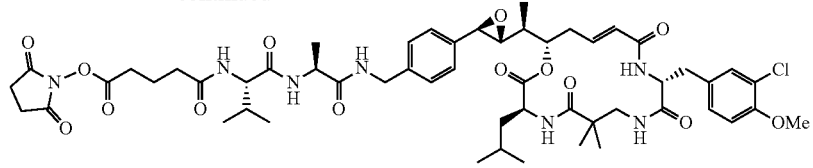

Example 2

↓

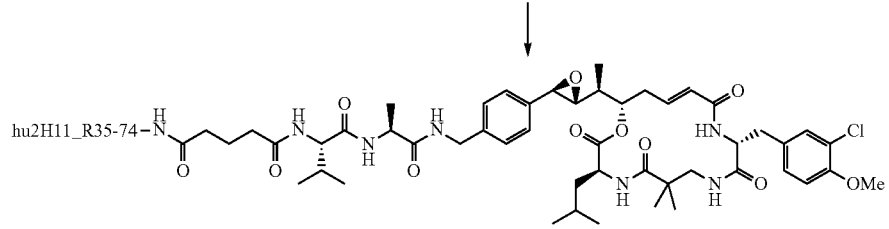

Example 2

Compound 30: (6R,13S)-(1E,3R,4S,6E)-1-(4-(az-idomethyl)phenyl)-8-(tert-butoxy)-3-methyl-8-oxoocta-1,6-dien-4-yl 6-(3-chloro-4-methoxybenzyl)-13-isobutyl-2,2,10,10-tetramethyl-4,7,11-trioxo-3-oxa-5,8,12-triazatetradecan-14-oate Under argon, in a round bottom flask were introduced compound BC1 (899.55 mg, 2.10 mmol) in DMF (25 mL), HATU (861 mg, 2.20 mmol) and HOAt (302 mg, 2.20 mmol). The mixture was stirred for 30 minutes at RT. After that, compound AD1 (940 mg, 2 mmol) and DIEA (1.05 mL, 5.99 mmol) were added. The reaction medium was stirred for 4 h at RT. After this time, the reaction medium was diluted with $H_2O$ (50 mL) and extracted with AcOEt (2×40 mL). The organic layers were washed with sat. brine (25 mL), dried over $MgSO_4$, filtered, concentrated and purified by flash chromatography on 80 g of silica gel (gradient elution heptane/AcOEt) to give 1.011 g of compound 30 as a yellow semi-solid (57%).

RMN $^1$H (400 MHz, δ in ppm, DMSO-d6): 0.76 (d, J=6.7 Hz, 3H); 0.78 (d, J=6.7 Hz, 3H); 1.03 (d, J=7.0 Hz, 3H); 1.07 (s, 6H); 1.39 (s, 9H); 1.37 to 1.63 (m, 3H); 1.41 (s, 9H); 2.36 to 2.60 (partially masked m, 3H); 2.64 (dd, J=9.5 and 14.1 Hz, 1H); 2.86 (dd, J=5.6 and 14.1 Hz, 1H); 3.18 (dd, J=6.1 and 13.5 Hz, 1H); 3.25 (dd, J=6.9 and 13.5 Hz, 1H); 3.79 (s, 3H); 4.09 (m, 1H); 4.26 (m, 1H); 4.40 (s, 2H); 4.92 (m, 1H); 5.81 (d, J=15.9 Hz, 1H); 6.17 (dd, J=8.4 and 16.1 Hz, 1H); 6.44 (d, J=15.9 Hz, 1H); 6.70 (m, 1H); 6.94 (d, J=8.9 Hz, 1H); 7.02 (d, J=8.7 Hz, 1H); 7.18 (dd, J=2.3 and 8.9 Hz, 1H); 7.31 (m, 3H); 7.42 (d, J=8.5 Hz, 2H); 7.59 (t, J=6.3 Hz, 1H); 7.77 (d, J=7.9 Hz, 1H). LCMS (A1): ES m/z=879 [M−H]$^-$; m/z=881 [M+H]$^+$; m/z=925 [M−H+HCO$_2$H]$^-$; $t_R$=1.89 min.

Compound 31: (3S,10R,16S,E)-16-((R,E)-4-(4-(az-idomethyl)phenyl)but-3-en-2-yl)-10-(3-chloro-4-methoxybenzyl)-3-isobutyl-6,6-dimethyl-1-oxa-4,8,11-triazacyclohexadec-13-ene-2,5,9,12-tetraone Compound 31 was prepared in two steps.

Step 1: in a round bottom flask were introduced compound 30 (1.011 g, 1.15 mmol) in DCM (10 mL). After cooling to 0° C., TFA (1.72 mL, 22.94 mmol) and 100 µL of $H_2O$ were added. The reaction medium was stirred for 72 h at RT. Upon completion, toluene was added to the medium and it was concentrated in vacuo to give 900 mg of amino/acid intermediate (quant.).

RMN $^1$H (400 MHz, δ in ppm, DMSO-d6): 0.76 (d, J=6.7 Hz, 3H); 0.78 (d, J=6.7 Hz, 3H); 1.03 (d, J=7.0 Hz, 3H); 1.07 (s, 3H); 1.08 (s, 3H); 1.38 to 1.62 (m, 3H); 2.35 to 2.58 (partially masked m, 3H); 2.79 (dd, J=11.0 and 13.8 Hz, 1H); 3.00 (dd, J=4.1 and 13.8 Hz, 1H); 3.16 (dd, J=5.9 and 13.5 Hz, 1H); 3.28 to 3.39 (masked m, 1H); 3.81 (s, 3H); 4.03 (m, 1H); 4.26 (m, 1H); 4.40 (s, 2H); 4.92 (m, 1H); 5.82 (d, J=16.1 Hz, 1H); 6.16 (dd, J=8.8 and 16.4 Hz, 1H); 6.42 (d, J=16.4 Hz, 1H); 6.73 (m, 1H); 7.09 (d, J=8.6 Hz, 1H); 7.18 (dd, J=2.0 and 8.6 Hz, 1H); 7.32 (d, J=8.6 Hz, 2H); 7.37 (d, J=2.0 Hz, 1H); 7.41 (d, J=8.6 Hz, 2H); 7.84 (d, J=7.9 Hz, 1H); 8.01 (broad s large, 3H); 8.10 (t, J=6.4 Hz, 1H); 12.2 (broad s, 1H). LCMS (A1): ES m/z=723 [M−H]$^-$; m/z=725 [M+H]$^+$; $t_R$=1.09 min.

Step 2: in a round bottom flask, to a solution of amino/acid intermediate (840 mg, 1.16 mmol) in 200 mL of $CH_3CN$ were added DIEA (1.95 mL, 11.58 mmol), HOAt (159.23 mg, 1.16 mmol) and HATU (499.40 mg, 1.27 mmol). The reaction medium was stirred for 3 h at RT. After concentration in vacuo, the crude was diluted with AcOEt (200 mL), neutralized with 0.5M citric acid (12 mL) and 1N HCl (6 mL). The organic layer was separated, washed with sat. NaHSO$_3$, sat. NaHCO$_3$, sat. brine, dried over MgSO$_4$, filtered, concentrated and purified by flash chromatography on 40 g of silica gel (gradient elution DCM/MeOH) to give 558 mg of compound 31 as a white solid (68%).

RMN $^1$H (400 MHz, δ in ppm, DMSO-d6): 0.60 (d, J=6.7 Hz, 3H); 0.61 (d, J=6.7 Hz, 3H); 0.97 (s, 3H); 1.07 (s, 3H); 1.09 (d, J=7.0 Hz, 3H); 1.15 (m, 1H); 1.33 to 1.48 (m, 2H); 2.24 (m, 1H); 2.53 to 2.70 (m, 2H); 2.88 (large d, J=13.6 Hz, 1H); 3.01 (dd, J=3.5 and 14.5 Hz, 1H); 3.23 to 3.32 (masked m, 1H); 3.80 (s, 3H); 4.18 (m, 1H); 4.35 (m, 1H); 4.40 (s, 2H); 4.95 (m, 1H); 5.86 (dd, J=1.7 and 15.8 Hz, 1H); 6.13 (dd, J=8.8 and 16.1 Hz, 1H); 6.40 (m, 1H); 6.47 (d, J=16.1 Hz, 1H); 7.04 (d, J=8.6 Hz, 1H); 7.18 (dd, J=2.0 and 8.6 Hz, 1H); 7.29 (d, J=2.0 Hz, 1H); 7.32 (d, J=8.6 Hz, 2H); 7.41 (broad d, J=8.6 Hz, 3H); 7.89 (d, J=8.9 Hz, 1H); 8.1 (d, J=8.2 Hz, 1H). LCMS (A1): ES m/z=705 [M−H]$^-$; m/z=707 [M+H]$^+$; $t_R$=1.58 min.

Compound 32: (3S,10R,16S, E)-16-((S)-1-((2R,3R)-3-(4-(azidomethyl)phenyl)oxiran-2-yl)ethyl)-10-(3-chloro-4-methoxybenzyl)-3-isobutyl-6,6-dimethyl-1-oxa-4,8,11-triazacyclohexadec-13-ene-2,5,9,12-tetraone In a round bottom flask, to a solution of compound 31 (410 mg, 0.579 mmol) in DCM (50 mL) was added, at 0° C., m-CPBA (259 mg, 1.16 mmol). After stirring for 16 h at RT, m-CPBA (130 mg) was added twice in 24 h. Once the reaction completed, the crude mixture was stirred for 1 h with sat. NaHCO$_3$ (15 mL) and sat. Na$_2$S$_2$O$_3$ (15 mL) then extracted with DCM (3×15 mL). The organic layers were washed with sat. brine (15 mL), dried over MgSO$_4$, filtered and concentrated to give 440 mg of a mixture of alpha and beta epoxides as a yellow semi-solid. Alpha and beta epoxides were separated by chiral liquid chromatography that was carried out on a 76×350 mm column packed with 1.1 kg of 10 μm Chiralpak AD (amylose tris-3,5-dimethylphenyl-carbamate coated on a silica gel support, Chiral Technologies Europe) using isocratic elution with 80:20 heptane/EtOH. After concentration, 185 mg of compound 32 were obtained as a white solid (44%) and 118 mg of the alpha epoxide were obtained as a white solid (28%).

RMN $^1$H (400 MHz, δ in ppm, DMSO-d6): 0.72 (d, J=6.7 Hz, 3H); 0.74 (d, J=6.7 Hz, 3H); 0.96 (s, 3H); 1.04 (d, J=7.0 Hz, 3H); 1.08 (s, 3H); 1.11 (m, 1H); 1.40 to 1.55 (m, 2H); 1.79 (m, 1H); 2.26 (m, 1H); 2.64 (m, 2H); 2.85 (broad d, J=13.2 Hz, 1H); 3.00 (m, 2H); 3.25 (dd, J=10.2 and 13.2 Hz, 1H); 3.80 (s, 3H); 3.90 (d, J=2.0 Hz, 1H); 4.17 (m, 1H); 4.35 (m, 1H); 4.46 (s, 2H); 5.12 (m, 1H); 5.80 (dd, J=1.7 and 16.0 Hz, 1H); 6.39 (ddd, J=3.8, 11.6 and 16.0 Hz, 1H); 7.04 (d, J=8.6 Hz, 1H); 7.18 (dd, J=2.0 and 8.6 Hz, 1H); 7.29 (d, J=2.0 Hz, 1H); 7.31 to 7.40 (m, 5H); 7.94 (d, J=9.1 Hz, 1H); 8.40 (d, J=8.1 Hz, 1H). LCMS (A1): ES m/z=723 [M+H]$^+$; t$_R$=1.48 min.

Example 1: (3S,10R,16S,E)-16-((S)-1-((2R,3R)-3-(4-(aminomethyl)phenyl)oxiran-2-yl)ethyl)-10-(3-chloro-4-methoxybenzyl)-3-isobutyl-6,6-dimethyl-1-oxa-4,8,11-triazacyclohexadec-13-ene-2,5,9,12-tetraone In a round bottom flask, to a solution of compound 32 (185 mg, 255.79 μmol) in DCM (6 mL), MeOH (6 mL) and H$_2$O (0.8 mL), was added TCEP (81.47 mg, 281.37 μmol). The solution was stirred 16 h at RT. Once the reaction complete, the crude mixture was diluted with sat. NaHCO$_3$ (15 mL) and extracted with DCM (2×30 mL). The organic layers were washed with sat. brine, dried over MgSO$_4$, filtered, concentrated and purified by two successive flash chromatographies, on 15 g of silica gel (gradient elution DCM/MeOH) to give 90 mg of example 1 as a white solid (51%).

RMN $^1$H (400 MHz, δ in ppm, DMSO-d6): 0.72 (d, J=6.6 Hz, 3H); 0.75 (d, J=6.6 Hz, 3H); 0.97 (s, 3H); 1.03 (d, J=7.1 Hz, 3H); 1.07 (s, 3H); 1.14 (m, 1H); 1.42 to 1.57 (m, 2H); 1.77 (m, 1H); 1.92 (broad m, 2H); 2.26 (m, 1H); 2.64 (m, 2H); 2.86 (broad d, J=13.0 Hz, 1H); 2.94 (dd, J=2.0 and 8.0 Hz, 1H); 3.00 (dd, J=3.6 and 14.4 Hz, 1H); 3.27 (dd, J=10.2 and 13.0 Hz, 1H); 3.70 (s, 2H); 3.80 (s, 3H); 3.84 (d, J=2.0 Hz, 1H); 4.18 (m, 1H); 4.34 (m, 1H); 5.11 (m, 1H); 5.79 (dd, J=1.7 and 15.6 Hz, 1H); 6.38 (ddd, J=4.1, 11.6 and 15.6 Hz, 1H); 7.05 (d, J=8.6 Hz, 1H); 7.16 (dd, J=2.0 and 8.6 Hz, 1H); 7.22 (d, J=8.5 Hz, 2H); 7.28 (d, J=2.0 Hz, 1H); 7.31 (d, J=8.5 Hz, 2H); 7.35 (d, J=10.2 Hz, 1H); 7.91 (d, J=9.0 Hz, 1H); 8.38 (d, J=8.0 Hz, 1H). LCMS (A1): ES m/z=695 [M–H]$^-$; m/z=697 [M+H]$^+$; t$_R$=0.83 min.

Compound 33: (S)-2-amino-N—((S)-1-((4-((2R,3R)-3-((S)-1-((3S,10R,16S,E)-10-(3-chloro-4-methoxybenzyl)-3-isobutyl-6,6-dimethyl-2,5,9,12-tetraoxo-1-oxa-4,8,11-triazacyclohexadec-13-en-16-yl)ethyl)oxiran-2-yl)benzyl)amino)-1-oxopropan-2-yl)-3-methylbutanamide Under argon, in a round bottom flask to a solution of example 1 (90 mg, 129.01 μmol) in DCM (20 mL), were added (S)-2-((S)-2-((((9H-fluoren-9-yl)methoxy)carbonyl)amino)-3-methylbutan-amido)propanoic acid or FmocVa-lAla (CAS number [150114-97-9], 79.47 mg, 193.61 μmol), EDC (34.27 μL, 193.61 μmol) and HOBt (20.93 mg, 154.9 μmol). The reaction medium was stirred overnight at RT. After this time, piperidine (129 μL, 1.29 mmol) was added and stirred for 2 h. The solvent was removed and the crude residue was purified by flash chromatography on 15 g of silica gel (gradient elution DCM/MeOH) to give 50 mg of compound 33 (45%) as a white solid.

RMN $^1$H (400 MHz, δ in ppm, DMSO-d6): 0.75 (m, 9H); 0.88 (d, J=7.1 Hz, 3H); 0.96 (s, 3H); 1.03 (d, J=7.1 Hz, 3H); 1.08 (s, 3H); 1.18 (m, 1H); 1.23 (d, J=7.0 Hz, 3H); 1.42 to 1.57 (m, 2H); 1.70 (broad m, 2H); 1.79 (m, 1H); 1.92 (m, 1H); 2.26 (m, 1H); 2.63 (m, 2H); 2.86 (broad d, J=13.0 Hz, 1H); 2.99 (m, 3H); 3.22 to 3.33 (partially masked m, 1H); 3.80 (s, 3H); 3.86 (d, J=2.0 Hz, 1H); 4.18 (m, 1H); 4.28 (d, J=6.3 Hz, 2H); 4.33 (m, 2H); 5.11 (m, 1H); 5.79 (dd, J=1.7 and 15.6 Hz, 1H); 6.39 (ddd, J=4.1, 11.6 and 15.6 Hz, 1H); 7.03 (d, J=8.6 Hz, 1H); 7.16 (dd, J=2.0 and 8.6 Hz, 1H); 7.24 (s, 4H); 7.28 (d, J=2.0 Hz, 1H); 7.37 (d, J=10.2 Hz, 1H); 7.92 (d, J=9.1 Hz, 1H); 8.07 (broad d, J=8.3 Hz, 1H); 8.38 (d, J=8.1 Hz, 1H); 8.42 (t, J=6.3 Hz, 1H). LCMS (A1): ES m/z=434 [M+2H]$^{2+}$; m/z=865 [M–H]$^-$; m/z=867 [M+H]$^+$; m/z=911 [M–H+HCO$_2$H]$^-$; t$_R$=0.88 min.

Compound 34: 5-(((S)-1-(((S)-1-((4-((2R,3R)-3-((S)-1-((3S,10R,16S,E)-10-(3-chloro-4-methoxybenzyl)-3-isobutyl-6,6-dimethyl-2,5,9,12-tetraoxo-1-oxa-4,8,11-triazacyclohexadec-13-en-16-yl)ethyl)oxiran-2-yl)benzyl)amino)-1-oxopropan-2-yl)amino)-3-methyl-1-oxobutan-2-yl)amino)-5-oxopentanoic acid Under argon, in a round bottom flask, to a solution of compound 33 (54 mg, 57.64 μmol) in DMF (5 mL) was added glutaric anhydride (8 mg, 69.17 μmol). The reaction medium was stirred for 3.5 h at RT. After this time, the solvent was removed and the crude residue was purified by flash chromatography on 1.8 g of silica gel (gradient elution DCM/MeOH) to give 51 mg of compound 34 as a white solid (90%).

RMN $^1$H (500 MHz, δ in ppm, DMSO-d6): 0.73 (d, J=6.7 Hz, 3H); 0.76 (d, J=6.7 Hz, 3H); 0.81 (d, J=7.0 Hz, 3H); 0.84 (d, J=7.0 Hz, 3H); 0.97 (s, 3H); 1.03 (d, J=7.2 Hz, 3H); 1.05 (s, 3H); 1.15 (m, 1H); 1.22 (d, J=7.2 Hz, 3H); 1.43 to 1.52 (m, 2H); 1.70 (m, 2H); 1.77 (m, 1H); 1.97 (m, 1H); 2.17 (m, 2H); 2.24 (m, 1H); 2.55 to 2.68 (m, 2H); 2.85 (broad d, J=12.7 Hz, 1H); 2.96 (dd, J=1.8 and 7.7 Hz, 1H); 2.99 (dd, J=3.0 and 14.6 Hz, 1H); 3.23 to 3.40 (partially masked m, 1H); 3.80 (s, 3H); 3.85 (d, J=1.8 Hz, 1H); 4.22 to 4.38 (m, 4H); 5.11 (m, 1H); 5.79 (d, J=14.9 Hz, 1H); 6.37 (ddd, J=4.1, 11.3 and 14.9 Hz, 1H); 7.04 (d, J=8.7 Hz, 1H); 7.15 (dd, J=2.0 et 8.7 Hz, 1H); 7.23 (broad s, 4H); 7.28 (d, J=2.0 Hz, 1H); 7.37 (broad d, J=10.7 Hz, 1H); 7.87 (d, J=8.7 Hz, 1H); 7.93 (d, J=9.2 Hz, 1H); 8.06 (m large, 1H); 8.37 (broad m, 1H); 8.41 (broad m, 1H); 12.03 (broad m, 1H). LCMS (A1): ES m/z=979 [M−H]⁻; m/z=981 [M+H]⁺; t$_R$=1.17 min.

Example 2: 2,5-dioxopyrrolidin-1-yl 5-(((S)-1-(((S)-1-((4-((2R,3R)-3-((S)-1-((3S,10R,16S,E)-10-(3-chloro-4-methoxybenzyl)-3-isobutyl-6,6-dimethyl-2,5,9,12-tetraoxo-1-oxa-4,8,11-triazacyclohexadec-13-en-16-yl)ethyl)oxiran-2-yl)benzyl)amino)-1-oxopropan-2-yl)amino)-3-methyl-1-oxobutan-2-yl) amino)-5-oxopentanoate Under argon, in a round bottom flask, to a solution of compound 34 (30 mg, 30.56 μmol) in THF (5 mL) were added DIEA (5.34 μL, 30.56 μmol) and DSC (16.31 mg, 61.13 μmol). The reaction medium was stirred for 2 h at RT. After this time, the solvent was removed and the crude residue was purified by flash chromatography on 1.3 g of silica gel (gradient elution DCM/iPrOH) to give 9 mg of example 2 as a white solid. A second batch containing the expected compound as well as an impurity was diluted with MeTHF, washed twice with H$_2$O, sat. brine, dried over MgSO4, filtered and concentrated to give 15 mg of example 2 as a white solid (global yield of 73%).

RMN ¹H (500 MHz, δ in ppm, DMSO-d6): 0.73 (d, J=6.7 Hz, 3H); 0.77 (d, J=6.7 Hz, 3H); 0.82 (d, J=7.0 Hz, 3H); 0.84 (d, J=7.0 Hz, 3H); 0.96 (s, 3H); 1.03 (d, J=7.2 Hz, 3H); 1.07 (s, 3H); 1.15 (m, 1H); 1.23 (d, J=7.2 Hz, 3H); 1.43 to 1.56 (m, 2H); 1.78 (m, 1H); 1.81 (m, 1H); 1.97 (m, 1H); 2.20 to 2.33 (m, 3H); 2.58 to 2.69 (m, 4H); 2.80 (s, 4H); 2.85 (broad d, J=12.7 Hz, 1H); 2.98 (dd, J=2.1 and 7.9 Hz, 1H); 3.00 (dd, J=3.2 and 14.7 Hz, 1H); 3.22 to 3.34 (partially masked m, 1H); 3.80 (s, 3H); 3.85 (d, J=2.1 Hz, 1H); 4.15 (m, 2H); 4.22 to 4.38 (m, 4H); 5.11 (m, 1H); 5.79 (d, J=15.1 Hz, 1H); 6.38 (ddd, J=3.9, 11.2 and 15.1 Hz, 1H); 7.04 (d, J=8.7 Hz, 1H); 7.15 (dd, J=2.2 and 8.7 Hz, 1H); 7.22 (broad s, 4H); 7.29 (d, J=2.2 Hz, 1H); 7.36 (broad d, J=10.3 Hz, 1H); 7.89 (d, J=8.7 Hz, 1H); 7.92 (d, J=8.9 Hz, 1H); 8.04 (d, J=7.4 Hz, 1H); 8.32 (t, J=6.1 Hz, 1H); 8.39 (d, J=8.0 Hz, 1H). LCMS (A1): ES m/z=540; m/z=1076 [M−H]⁻; m/z=1078 [M+H]⁺; m/z=1122 [M−H+HCO$_2$H]⁻; t$_R$=1.23 min.

Example 3: mAb-Ex2

The general method described previously was used for the preparation of example 3. 60 mg of hu2H11_R35-74 were reacted with 161 μL of a 9.96 mM solution of example 2 in DMA (1.733 mg, 4 eq.) for 2 h. At that time, 121 μL of the solution of example 2 (3 eq.) were added and the medium stirred for 2 h. At that time, 121 μL of the solution of example 2 (3 eq.) were added and stirred for 2 h. After purification on Superdex 200 pg in DPBS pH 6.5+20% NMP, concentration on Amicon Ultra-15, buffer exchange on PD-10 in buffer B pH 6.5+5% NMP and filtration on Steriflip, 39.9 mg of example 3 were obtained as a colorless limpid solution at a concentration of 2.28 mg/mL with a DAR of 4.6 (HRMS), a monomeric purity of 99% and a global yield of 66%.

SEC-HRMS: spectrum for intact ADC in FIG. 1; m/z=150346 (D1); m/z=151307 (D2); m/z=152274 (D3); m/z=153240 (D4); m/z=154200 (D5); m/z=155165 (D6); m/z=156133 (D7); m/z=157095 (D8).

Synthesis of Examples 4 to 7: benzylic amine of (S)-3-neopentyle-aza-C52, NHS ester of glutaryl-Val-Ala-(S)-3-neopentyle-aza-C52 benzylic amine and Corresponding ADC

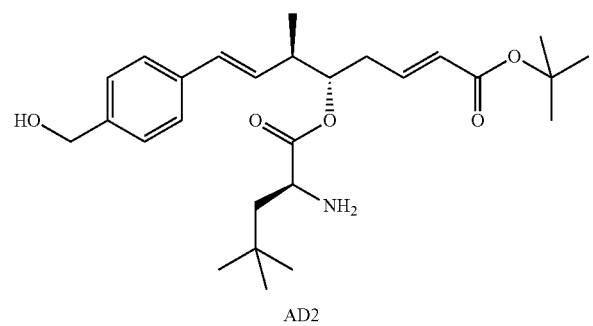

AD2

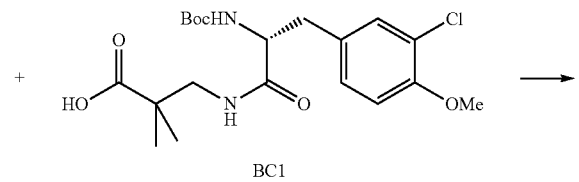

BC1

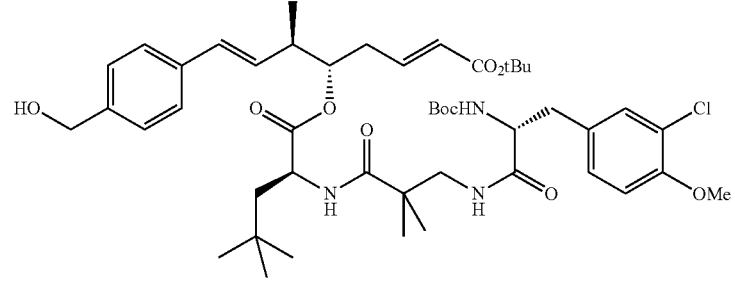

35

↓

465
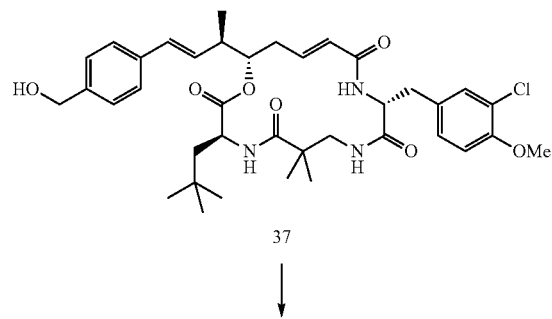
37
↓
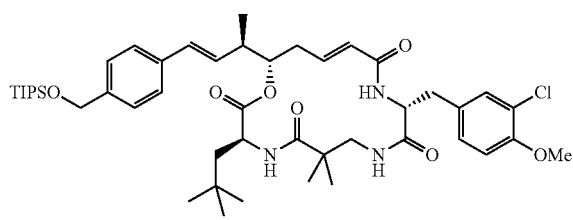
38
466
-continued
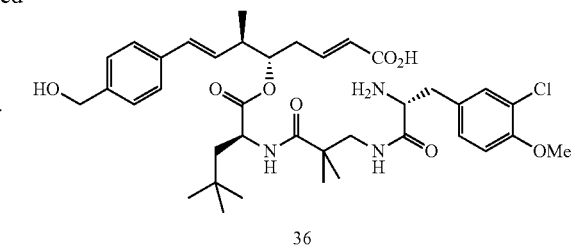
36
Example 4
↓
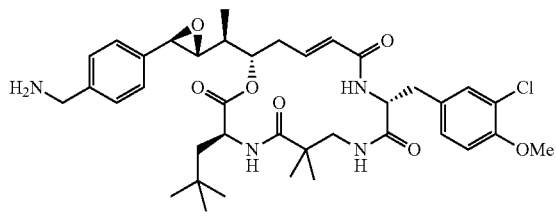
Example 5    39
Example 5
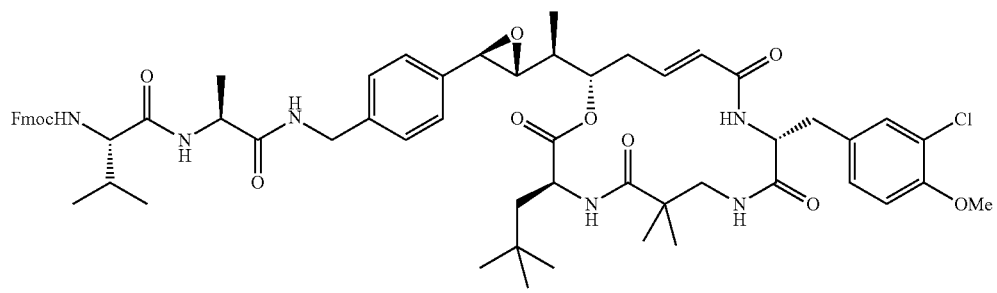
40

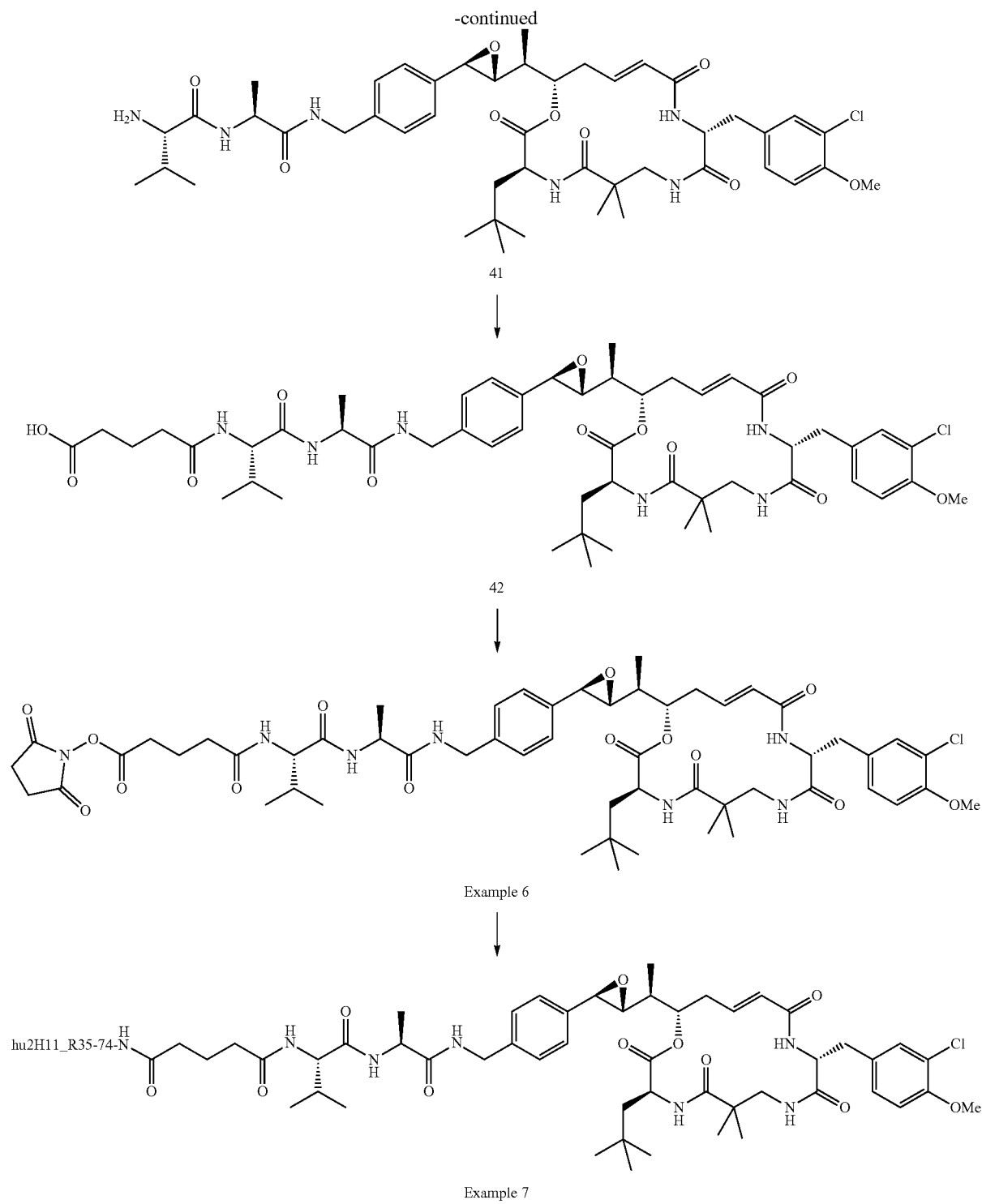

Example 6

Example 7

Compound 35: (6R,13S)-(1E,3R,4S,6E)-8-(tert-butoxy)-1-(4-(hydroxymethyl)phenyl)-3-methyl-8-oxoocta-1,6-dien-4-yl 6-(3-chloro-4-methoxybenzyl)-2,2,10,10-tetramethyl-13-neopentyl-4,7,11-trioxo-3-oxa-5,8,12-triazatetradecan-14-oate Under argon, in a round bottom flask, to a solution of fragment BC1 (1.32 g, 3.08 mmol) in DCM (60 mL) were added DIEA (1.53 mL, 9.25 mmol), HOAt (503.75 mg, 3.70 mmol) and HATU (1.41 g, 3.70 mmol). The yellow suspension was stirred for 30 min at RT, then fragment AD2 (1.7 g, 3.08 mmol) was added. The reaction medium was stirred for 2 h at RT. After this time, 1.53 mL of DIEA were added and stirred for 1 h. The mixture was neutralized with 1M citric acid (50 mL) and extracted with AcOEt (2×80 mL). The organic layers were washed with 1M NaHSO$_4$, H$_2$O, dried over MgSO$_4$, filtered, concentrated and purified by flash chromatography on 100 g of silica gel (gradient elution heptane/AcOEt) to give 1.475 g of compound 35 as a colorless solid (57%).

Compound 36: (2E,5S,6R,7E)-5-(((S)-2-(3-((R)-2-amino-3-(3-chloro-4-methoxyphenyl)-propanamido)-2,2-dimethylpropanamido)-4,4-dimethylpentanoyl)oxy)-8-(4-(hydroxymethyl)-phenyl)-6-methylocta-2,7-dienoic acid In a round bottom flask, to a solution of compound 35 (1.475 g, 1.69 mmol) in DCM (20 mL), were added TFA (8 mL, 52.27 mmol) and H₂O (2 mL). The reaction medium was stirred for 5 h at RT. The solvent was removed. The residue was diluted with H₂O (20 mL) and AcOEt (20 mL) and treated with 2M NaOH (2 mL) for 2 h at RT. The organic layer was separated and the aq. layer was extracted with AcOEt (2×10 mL), dried over MgSO₄, filtered and concentrated to give 1.24 g of a colorless solid. The solid was dissolved in AcOEt (10 mL) and H₂O (10 mL) and treated with 2M NaOH (400 µL) for 2 h at RT. The organic layer was separated, the aq. layers were extracted with AcOEt (2×10 mL), dried over MgSO₄, filtered, concentrated and purified by flash chromatography on 100 g of silica gel (gradient elution heptane/AcOEt) to give 990 mg of compound 36 as a white solid (82%).

RMN ¹H (400 MHz, δ in ppm, DMSO-d6): 0.80 (s, 9H); 0.99 (s, 3H); 1.02 (d, J=7.0 Hz, 3H); 1.05 (s, 3H); 1.52 (dd, J=2.0 and 14.8 Hz, 1H); 1.69 (dd, J=9.9 and 14.8 Hz, 1H); 2.36 to 2.61 (partially masked m, 4H); 2.84 (dd, J=5.0 and 13.9 Hz, 1H); 3.18 (d, J=7.5 Hz, 2H); 3.40 (dd, J=5.1 and 8.1 Hz, 1H); 3.80 (s, 3H); 4.29 (m, 1H); 4.45 (s, 2H); 4.90 (m, 1H); 5.12 (broad m, 1H); 5.81 (d, J=15.5 Hz, 1H); 6.10 (dd, J=8.4 and 15.9 Hz, 1H); 6.40 (d, J=15.9 Hz, 1H); 6.70 (td, J=7.5 and 15.5 Hz, 1H); 7.01 (d, J=8.7 Hz, 1H); 7.11 (dd, J=2.4 and 8.7 Hz, 1H); 7.25 (m, 3H); 7.32 (d, J=8.2 Hz, 2H); 7.72 (t, J=6.5 Hz, 1H); 7.79 (d, J=7.8 Hz, 1H). LCMS (A1): ES m/z=712 [M−H]⁻; m/z=714 [M+H]⁺; $t_R$=0.94 min.

Compound 37: (3S,10R,16S, E)-10-(3-chloro-4-methoxybenzyl)-16-((R,E)-4-(4-(hydroxymethyl)-phenyl)but-3-en-2-yl)-6,6-dimethyl-3-neopentyl-1-oxa-4,8,11-triazacyclohexadec-13-ene-2,5,9,12-tetraone Under argon, in a round bottom flask, were introduced compound 36 (990 mg, 1.39 mmol) and CH₃CN (150 mL), heated with a water bath at 50° C. until complete solubilization and stirred for 10 min. After that, DIEA (687.20 µL, 4.16 mmol), HOAt (207.51 mg, 1.52 mmol) and HATU (579.7 mg, 1.52 mmol) were added and stirred for 30 min at RT. The reaction medium was neutralized with 1M citric acid (30 mL). The solvent was removed and the aq. layer was extracted with AcOEt (2×40 mL). The organic layers were washed with 1M NaHSO₄, H₂O, dried over MgSO₄, filtered and concentrated. The crude solid was diluted with H₂O (200 mL) and stirred for 1 h. The solid was filtered then diluted with AcOEt, dried over MgSO₄, filtered and concentrated to give a mixture of compound 37 and HATU. The solid was stirred with MeTHF (50 mL) and H₂O (50 mL). The organic layer was separated, washed with H₂O (4×20 mL), dried over MgSO₄, filtered, concentrated and purified by flash chromatography on 10 g of silica gel (gradient elution heptane/AcOEt) to give 680 mg of compound 37 as a colorless solid (70%).

RMN ¹H (400 MHz, δ in ppm, DMSO-d6): 0.68 (s, 9H); 0.98 (s, 3H); 1.03 (s, 3H); 1.09 (d, J=6.9 Hz, 3H); 1.19 (broad d, J=14.5 Hz, 1H); 1.58 (dd, J=10.3 and 14.5 Hz, 1H); 2.23 (m, 1H); 2.52 to 2.70 (m, 3H); 2.86 (broad d, J=12.7 Hz, 1H); 3.00 (dd, J=3.3 and 14.8 Hz, 1H); 3.22 to 3.33 (partially masked m, 1H); 3.80 (s, 3H); 4.18 (m, 1H); 4.42 (m, 1H); 4.46 (d, J=6.0 Hz, 2H); 4.91 (m, 1H); 5.13 (t, J=6.0 Hz, 1H); 5.85 (broad d, J=15.0 Hz, 1H); 6.05 (dd, J=8.4 and 15.9 Hz, 1H); 6.40 (m, 2H); 7.03 (d, J=8.7 Hz, 1H); 7.18 (dd, J=2.2 and 8.7 Hz, 1H); 7.25 (d, J=8.5 Hz, 2H); 7.29 (d, J=2.2 Hz, 1H), 7.31 (d, J=8.5 Hz, 2H); 7.42 (d, J=10.6 Hz, 1H); 7.94 (d, J=9.1 Hz, 1H); 8.41 (d, J=8.2 Hz, 1H). LCMS (A1): ES m/z=694 [M−H]⁻; m/z=696 [M+H]⁺; $t_R$=1.36 min.

Compound 38: (3S,10R,16S,E)-10-(3-chloro-4-methoxybenzyl)-6,6-dimethyl-3-neopentyl-16-((R,E)-4-(4-(((triisopropylsilyl)oxy)methyl)phenyl)but-3-en-2-yl)-1-oxa-4,8,11-triazacyclohexadec-13-ene-2,5,9,12-tetraone Under argon, at 0° C. in a round bottom flask, to a solution of compound 37 (680 mg, 0.976 mmol) in CHCl₃ (10 mL) were added 1H-imidazole (305.84 mg, 4.49 mmol) and chlorotriisopropylsilane (480.13 µl, 2.25 mmol). The reaction medium was stirred for 5 h at RT then diluted with sat. NH₄Cl and MTBE (30 mL). The organic layer was washed with 1M NaHSO₄, sat. NaHCO₃, sat. brine, dried over MgSO₄, filtered and concentrated to give 970 mg of compound 38 as an orange amorphous solid (quant.).

RMN ¹H (500 MHz, δ in ppm, DMSO-d6): 0.63 (s, 9H); 0.87 á 1.17 (m, 31H); 1.53 (dd, J=10.9 and 14.3 Hz, 1H); 2.22 (m, 1H); 2.51 to 2.70 (m, 3H); 2.86 (broad d, J=13.0 Hz, 1H); 3.00 (dd, J=3.2 and 14.9 Hz, 1H); 3.24 to 3.35 (partially masked m, 1H); 3.80 (s, 3H); 4.18 (m, 1H); 4.41 (m, 1H); 4.76 (s, 2H); 4.91 (m, 1H); 5.87 (broad d, J=15.4 Hz, 1H); 6.06 (dd, J=8.9 and 15.9 Hz, 1H); 6.40 (m, 2H); 7.03 (d, J=8.5 Hz, 1H); 7.18 (broad d, J=8.5 Hz, 1H); 7.25 (d, J=8.3 Hz, 2H); 7.28 (d, J=8.3 Hz, 2H); 7.30 (broad s, 1H); 7.42 (d, J=10.5 Hz, 1H); 7.93 (d, J=9.2 Hz, 1H); 8.42 (d, J=8.1 Hz, 1H). LCMS (A1): ES m/z=850 [M−H]⁻; m/z=852 [M+H]⁺; m/z=896 [M−H+HCO₂H]⁻; $t_R$=2.15 min.

Example 4: (3S,10R,16S,E)-10-(3-chloro-4-methoxybenzyl)-16-((S)-1-((2R,3R)-3-(4-(hydroxymethyl)phenyl)oxiran-2-yl)ethyl)-6,6-dimethyl-3-neopentyl-1-oxa-4,8,11-triazacyclohexadec-13-ene-2,5,9,12-tetraone Example 4 was prepared in 2 steps.
Step 1: under argon, in a round bottom flask, to a solution of compound 38 (832 mg, 0.976 mmol) in DCM (10 mL) was added, in three times, m-CPBA (339.15 mg, 1.51 mmol). The reaction mixture was stirred for 50 h at RT then diluted with DCM (10 mL) and stirred for 15 min with sat. NaHCO₃ (30 mL) and Na₂S₂O₃ (30 mL). The organic layer was separated, washed with sat. brine, dried over MgSO₄, filtered and concentrated to give 1.1 g of mixture of alpha and beta epoxides as a colorless foam (quant.).
Step 2: the mixture of alpha and beta epoxides was diluted in THF (30 mL) and 1M TBAF (952.32 µL) was added. After stirring for 2 h, 952 µL of TBAF were added. After stirring for 1 h, the mixture was diluted with H₂O (50 mL) and extracted with AcOEt (3×50 mL). The organic layers were washed with sat. brine, dried over MgSO₄, filtered and concentrated to give 770 mg of a mixture of alpha and beta epoxides as a yellow solid (quant.). Alpha and beta epoxides were separated by chiral liquid chromatography that was carried out on a 76×350 mm column packed with 1.1 kg of 10 μm Chiralpak AD (amylose tris-3,5-dimethylphenylcarbamate coated on a silica gel support, Chiral Technologies Europe) using isocratic elution with 75:25 heptane/EtOH. After concentration, 190 mg of example 4 were obtained as a white solid (31%) and 125 mg of the alpha epoxide were obtained as a white solid (20%).

RMN $^1$H (500 MHz, δ in ppm, DMSO-d6): 0.81 (s, 9H); 0.98 (s, 3H); 1.03 (d, J=7.0 Hz, 3H); 1.05 (s, 3H); 1.26 (m, 1H); 1.71 (dd, J=10.4 and 14.5 Hz, 1H); 1.82 (m, 1H); 2.26 (m, 1H); 2.52 (m, 2H); 2.84 (d, J=12.8 Hz, 1H); 2.92 (dd, J=2.1 and 7.8 Hz, 1H); 3.00 (dd, J=3.1 and 14.5 Hz, 1H); 3.24 to 3.36 (partially masked m, 1H); 3.81 (s, 3H); 3.90 (d, J=2.1 Hz, 1H); 4.17 (ddd, J=3.4, 8.0 and 11.7 Hz, 1H); 4.42 (m, 1H); 4.50 (d, J=6.0 Hz, 2H); 5.10 (m, 1H); 5.20 (t, J=6.0 Hz, 1H); 5.79 (dd, J=1.8 and 15.4 Hz, 1H); 6.39 (ddd, J=3.8, 11.5 and 15.4 Hz, 1H); 7.05 (d, J=8.6 Hz, 1H); 7.16 (dd, J=2.1 and 8.6 Hz, 1H); 7.26 (d, J=8.3 Hz, 2H); 7.29 (d, J=2.1 Hz, 1H); 7.32 (d, J=8.3 Hz, 2H); 7.41 (d, J=10.3 Hz, 1H); 8.02 (d, J=9.2 Hz, 1H); 8.38 (d, J=8.2 Hz, 1H). LCMS (A1): ES m/z=710 [M−H]$^-$; m/z=712 [M+H]$^+$; $t_R$=1.28 min.

Compound 39: (3S,10R,16S,E)-16-((S)-1-((2R,3R)-3-(4-(azidomethyl)phenyl)oxiran-2-yl)ethyl)-10-(3-chloro-4-methoxybenzyl)-6,6-dimethyl-3-neopentyl-1-oxa-4,8,11-triazacyclohexadec-13-ene-2,5,9,12-tetraone Under argon, in a round bottom flask, to a solution of example 4 (100 mg, 140 μmol) in THF (5 mL) were added DPPA (156.82 μl, 701.98 μmol) and DBU (110.22 μl, 701.98 μmol). The solution was stirred for 6 h at RT then diluted with H$_2$O and extracted with AcOEt (3×30 mL). The organic layer was separated, washed with sat. brine, dried over MgSO$_4$, filtered, concentrated and purified on 15 g of silica gel (gradient elution DCM/iPrOH) to give 100 mg of compound 39 as a white solid (40%).

RMN $^1$H (400 MHz, δ in ppm, DMSO-d6): 0.80 (s, 9H); 0.97 (s, 3H); 1.03 (d, J=7.0 Hz, 3H); 1.04 (s, 3H); 1.28 (d, J=14.5 Hz, 1H); 1.69 (dd, J=10.7 and 14.5 Hz, 1H); 1.84 (m, 1H); 2.28 (m, 1H); 2.62 (m, 2H); 2.84 (d, J=12.8 Hz, 1H); 2.93 to 3.03 (m, 2H); 3.22 to 3.34 (partially masked m, 1H); 3.80 (s, 3H); 3.92 (broad s, 1H); 4.17 (m, 1H); 4.40 to 4.49 (m, 3H); 5.10 (m, 1H); 5.80 (d, J=15.8 Hz, 1H); 6.39 (ddd, J=3.8, 11.7 and 15.8 Hz, 1H); 7.03 (d, J=8.7 Hz, 1H); 7.16 (dd, J=2.2 and 8.7 Hz, 1H); 7.28 (d, J=2.1 Hz, 1H); 7.32 (d, J=8.3 Hz, 2H); 7.39 (d, J=8.3 Hz, 2H); 7.41 (m, 1H); 8.00 (d, J=9.1 Hz, 1H); 8.36 (d, J=8.2 Hz, 1H). LCMS (A1): ES m/z=735 [M−H]$^-$; m/z=737 [M+H]$^+$; $t_R$=1.54 min.

Example 5: (3S,10R,16S,E)-16-((S)-1-((2R,3R)-3-(4-(aminomethyl)phenyl)oxiran-2-yl)ethyl)-10-(3-chloro-4-methoxybenzyl)-6,6-dimethyl-3-neopentyl-1-oxa-4,8,11-triazacyclohexadec-13-ene-2,5,9,12-tetraone In a round bottom flask, to a solution of compound 39 (100 mg, 122.07 μmol) in DCM (2.5 mL) and MeOH (2.5 mL) was added dropwise a solution of TCEP (38.88 mg, 134.28 μmol) in H$_2$O (500 μL). The reaction medium was stirred for 24 h at RT. The reaction mixture was diluted with H$_2$O and sat. NaHCO$_3$, extracted with DCM (3×10 mL). The organic layer was separated, washed with sat. brine, dried over MgSO$_4$, filtered and concentrated to give 73 mg of example 5 as a white solid (84%) used without further purification in the next step.

RMN $^1$H (500 MHz, δ in ppm, DMSO-d6): 0.82 (s, 9H); 0.97 (s, 3H); 1.03 (d, J=7.0 Hz, 3H); 1.04 (s, 3H); 1.29 (d, J=14.4 Hz, 1H); 1.70 (dd, J=10.2 and 14.4 Hz, 1H); 1.80 (m, 1H); 2.02 (broad m, 2H); 2.25 (m, 1H); 2.62 (m, 2H); 2.83 (d, J=13.0 Hz, 1H); 2.93 (dd, J=2.2 and 7.8 Hz, 1H); 2.99 (dd, J=3.4 and 14.5 Hz, 1H); 3.23 to 3.35 (partially masked m, 1H); 3.71 (s, 2H); 3.80 (s, 3H); 3.88 (d, J=2.2 Hz, 1H); 4.17 (ddd, J=3.5, 8.5 and 11.5 Hz, 1H); 4.41 (m, 1H); 5.09 (m, 1H); 5.79 (d, J=15.7 Hz, 1H); 6.39 (ddd, J=3.7, 11.4 and 15.7 Hz, 1H); 7.05 (d, J=8.7 Hz, 1H); 7.16 (dd, J=2.3 and 8.7 Hz, 1H); 7.22 (d, J=8.4 Hz, 2H); 7.28 (d, J=2.3 Hz, 1H); 7.34 (d, J=8.4 Hz, 2H); 7.40 (d, J=10.3 Hz, 1H); 8.02 (d, J=8.9 Hz, 1H); 8.38 (d, J=8.2 Hz, 1H). LCMS (A1): ES m/z=709 [M−H]$^-$; m/z=711 [M+H]$^+$; $t_R$=0.86 min.

Compound 40: (9H-fluoren-9-yl)methyl ((S)-1-(((S)-1-((4-((2R,3R)-3-((S)-1-((3S,10R,16S, E)-10-(3-chloro-4-methoxybenzyl)-6,6-dimethyl-3-neopentyl-2,5,9,12-tetraoxo-1-oxa-4,8,11-triazacyclohexadec-13-en-16-yl)ethyl)oxiran-2-yl)benzyl)amino)-1-oxopropan-2-yl)amino)-3-methyl-1-oxobutan-2-yl)carbamate Under argon, in a round bottom flask were introduced example 5 (73 mg, 82.10 μmol) and DMF (1 mL), followed by FmocValAla (50.55 mg, 123.16 μmol), HOBt (17.75 mg, 131.37 μmol), DCM (10 mL) and EDC (14.53 μl, 82.10 μmol). The solution was stirred for 4 h at RT then diluted with H$_2$O (10 mL) and extracted with DCM (3×20 mL). The organic layer was separated, washed with H$_2$O, dried over MgSO$_4$, filtered, concentrated and purified on 15 g of silica gel (gradient elution DCM/iPrOH) to give 90 mg of compound 40 as a colorless solid (99%).

RMN $^1$H (500 MHz, δ in ppm, DMSO-d6): 0.80 (s, 9H); 0.84 (d, J=7.1 Hz, 3H); 0.86 (d, J=7.1 Hz, 3H); 0.93 (s, 3H); 1.02 (d, J=7.1 Hz, 3H); 1.04 (s, 3H); 1.24 (d, J=7.3 Hz, 3H); 1.29 (d, J=14.5 Hz, 1H); 1.70 (dd, J=10.5 and 14.5 Hz, 1H); 1.81 (m, 1H); 1.99 (m, 1H); 2.25 (m, 1H); 2.60 (m, 2H); 2.82 (d, J=13.0 Hz, 1H); 2.91 (dd, J=1.9 and 7.6 Hz, 1H); 2.99 (dd, J=3.4 and 14.5 Hz, 1H); 3.29 (m, 1H); 3.80 (s, 3H); 3.88 (d, J=1.9 Hz, 1H); 3.90 (m, 1H); 4.16 (ddd, J=3.4, 8.0 and 11.8 Hz, 1H); 4.20 to 4.35 (m, 6H); 4.41 (m, 1H); 5.09 (m, 1H); 5.79 (d, J=15.7 Hz, 1H); 6.39 (ddd, J=3.7, 11.6 and 15.7 Hz, 1H); 7.05 (d, J=8.6 Hz, 1H); 7.15 (dd, J=2.5 and 8.6 Hz, 1H); 7.21 (d, J=8.5 Hz, 2H); 7.24 (d, J=8.5 Hz, 2H); 7.28 (d, J=2.5 Hz, 1H); 7.32 (d, J=7.9 Hz, 2H); 7.38 to 7.47 (m, 4H); 7.73 (t, J=7.9 Hz, 2H); 7.89 (d, J=7.9 Hz, 2H); 8.03 (d, J=9.1 Hz, 1H); 8.05 (d, J=7.9 Hz, 1H); 8.39 (m, 2H). LCMS (A1): ES m/z=1103 [M+H]$^+$; m/z=1147 [M−H+HCO$_2$H]$^-$; $t_R$=1.71 min.

Compound 41: (S)-2-amino-N—((S)-1-((4-((2R,3R)-3-((S)-1-((3S,10R,16S,E)-10-(3-chloro-4-methoxybenzyl)-6,6-dimethyl-3-neopentyl-2,5,9,12-tetraoxo-1-oxa-4,8,11-triazacyclohexadec-13-en-16-yl)ethyl)oxiran-2-yl)benzyl)amino)-1-oxopropan-2-yl)-3-methylbutanamide Under argon, in a round bottom flask, were introduced compound 40 (104 mg, 76.65 μmol) in DCM (5 mL) followed by piperidine (138.87 μl, 1.40 mmol). The solution was stirred for 5 h at RT then concentrated and purified on 10 g of silica gel (gradient elution DCM/MeOH/H$_2$O) to give 50 mg of compound 41 as a colorless solid (60%).

RMN $^1$H (500 MHz, δ in ppm, DMSO-d6): 0.76 (d, J=7.0 Hz, 3H); 0.81 (s, 9H); 0.88 (d, J=7.0 Hz, 3H); 0.97 (s, 3H); 1.02 (d, J=7.1 Hz, 3H); 1.04 (s, 3H); 1.22 (d, J=7.3 Hz, 3H);

1.29 (d, J=14.6 Hz, 1H); 1.66 (broad m, 2H); 1.70 (dd, J=10.6 and 14.6 Hz, 1H); 1.81 (m, 1H); 1.92 (m, 1H); 2.25 (m, 1H); 2.60 (m, 2H); 2.83 (d, J=13.0 Hz, 1H); 2.93 (dd, J=1.9 and 7.4 Hz, 1H); 2.99 (m, 2H); 3.28 (dd, J=10.4 and 13.0 Hz, 1H); 3.80 (s, 3H); 3.89 (d, J=1.9 Hz, 1H); 4.16 (ddd, J=3.2 and 8.2 et 11.8 Hz, 1H); 4.29 (d, J=6.0 Hz, 2H); 4.34 (m, 1H); 4.41 (m, 1H); 5.09 (m, 1H); 5.79 (dd, J=1.7 and 15.5 Hz, 1H); 6.38 (ddd, J=3.8, 11.3 and 15.5 Hz, 1H); 7.04 (d, J=8.7 Hz, 1H); 7.16 (dd, J=2.2 and 8.7 Hz, 1H); 7.25 (m, 4H); 7.29 (d, J=2.2 Hz, 1H); 7.40 (d, J=10.4 Hz, 1H); 8.02 (d, J=9.1 Hz, 1H); 8.08 (d large, J=7.7 Hz, 1H); 8.39 (d, J=8.2 Hz, 1H); 8.45 (t, J=6.0 Hz, 1H). LCMS (A1): ES m/z=441 [M+2H]$^{2+}$; m/z=879 [M−H]$^-$; m/z=881 [M+H]$^+$; m/z=925 [M−H+HCO$_2$H]$^-$; $t_R$=0.99 min.

Compound 42: 5-(((S)-1-(((S)-1-((4-((2R,3R)-3-((S)-1-((3S,10R,16S,E)-10-(3-chloro-4-methoxy-benzyl)-6,6-dimethyl-3-neopentyl-2,5,9,12-tetraoxo-1-oxa-4,8,11-triazacyclohexadec-13-en-16-yl)ethyl)oxiran-2-yl)benzyl)amino)-1-oxopropan-2-yl)amino)-3-methyl-1-oxobutan-2-yl)amino)-5-oxopentanoic acid Under argon, in a round bottom flask, were introduced compound 41 (50 mg, 51.05 µmol) in DCM (10 mL) followed by glutaric anhydride (10.48 mg, 91.89 µmol). The reaction medium was stirred for 2 h at RT, concentrated and purified on 10 g of silica gel (gradient elution DCM/MeOH/H$_2$O) to give 42 mg of compound 42 as a colorless solid (82%).

RMN $^1$H (500 MHz, δ in ppm, DMSO-d6): 0.80 (s, 9H); 0.82 (d, J=7.0 Hz, 3H); 0.85 (d, J=7.0 Hz, 3H); 0.97 (s, 3H); 1.02 (d, J=7.0 Hz, 3H); 1.04 (s, 3H); 1.23 (d, J=7.2 Hz, 3H); 1.29 (d, J=14.2 Hz, 1H); 1.70 (m, 3H); 1.81 (m, 1H); 1.96 (m, 1H); 2.18 to 2.25 (m, 5H); 2.61 (m, 2H); 2.83 (d, J=13.0 Hz, 1H); 2.93 (dd, J=2.0 and 7.4 Hz, 1H); 3.00 (dd, J=3.1 and 14.5 Hz, 1H); 3.29 (dd, J=10.4 and 13.0 Hz, 1H); 3.80 (s, 3H); 3.89 (d, J=2.0 Hz, 1H); 4.16 (m, 2H); 4.25 to 4.31 (m, 3H); 4.42 (m, 1H); 5.09 (m, 1H); 5.79 (dd, J=1.9 and 15.5 Hz, 1H); 6.39 (ddd, J=3.8, 11.6 et 15.5 Hz, 1H); 7.05 (d, J=8.7 Hz, 1H); 7.15 (dd, J=2.1 and 8.7 Hz, 1H); 7.23 (m, 4H); 7.28 (d, J=2.1 Hz, 1H); 7.40 (d, J=10.4 Hz, 1H); 7.83 (d, J=8.7 Hz, 1H); 8.02 (m, 2H); 8.35 (t, J=6.1 Hz, 1H); 8.39 (d, J=8.0 Hz, 1H); 12.04 (broad m, 1H). LCMS (A1): ES m/z=498 [M+2H]$^{2+}$; m/z=993 [M−H]$^-$; m/z=995 [M+H]$^+$; $t_R$=1.27 min.

Example 6: 2,5-dioxopyrrolidin-1-yl 5-(((S)-1-(((S)-1-((4-((2R,3R)-3-((S)-1-((3S,10R,16S,E)-10-(3-chloro-4-methoxybenzyl)-6,6-dimethyl-3-neopentyl-2,5,9,12-tetraoxo-1-oxa-4,8,11-triazacyclohexadec-13-en-16-yl)ethyl)oxiran-2-yl)benzyl)amino)-1-oxopropan-2-yl)amino)-3-methyl-1-oxobutan-2-yl)amino)-5-oxopentanoate Under argon, in a round bottom flask, were introduced compound 42 (23 mg, 23.10 µmol) in DCM (5 mL), followed by DSC (8.29 mg, 32.34 µmol) and DIEA (5.63 µL, 32.34 µmol). The reaction medium was stirred for 2 h at RT. After this time, 2 mg of DSC, 1 µL of DIEA and DCM (2 mL) were added and stirred for 1 h at RT. The solvent was removed and the crude residue was purified by flash chromatography on 10 g of silica gel (gradient elution DCM/iPrOH) to give 20 mg of example 6 as a colorless solid (79%).

RMN $^1$H (500 MHz, δ in ppm, DMSO-d6): 0.80 (s, 9H); 0.82 (d, J=7.0 Hz, 3H); 0.85 (d, J=7.0 Hz, 3H); 0.97 (s, 3H); 1.02 (d, J=7.0 Hz, 3H); 1.04 (s, 3H); 1.23 (d, J=7.2 Hz, 3H); 1.30 (d, J=14.2 Hz, 1H); 1.70 (dd, J=10.7 and 14.7 Hz, 1H); 1.81 (m, 3H); 1.97 (m, 1H); 2.21 to 2.32 (m, 3H); 2.61 (m, 2H); 2.68 (t, J=7.8 Hz, 2H); 2.80 (broad s, 4H); 2.83 (d, J=13.0 Hz, 1H); 2.94 (dd, J=2.0 et 7.6 Hz, 1H); 3.00 (dd, J=3.4 and 14.9 Hz, 1H); 3.28 (dd, J=10.5 and 13.0 Hz, 1H); 3.80 (s, 3H); 3.88 (d, J=2.0 Hz, 1H); 4.16 (m, 2H); 4.23 to 4.31 (m, 3H); 4.42 (m, 1H); 5.10 (m, 1H); 5.79 (dd, J=1.9 and 15.3 Hz, 1H); 6.39 (ddd, J=3.8, 11.4 and 15.3 Hz, 1H); 7.05 (d, J=8.8 Hz, 1H); 7.16 (dd, J=2.2 and 8.8 Hz, 1H); 7.23 (m, 4H); 7.28 (d, J=2.2 Hz, 1H); 7.40 (d, J=10.5 Hz, 1H); 7.89 (d, J=8.7 Hz, 1H); 8.02 (d, J=9.1 Hz, 1H); 8.06 (d, J=7.5 Hz, 1H); 8.34 (t, J=6.1 Hz, 1H); 8.39 (d, J=8.1 Hz, 1H). LCMS (A1): ES m/z=546.5 [M+2H]$^{2+}$; m/z=1090 [M−H]$^-$; m/z=1092 [M+H]$^+$; m/z=1136 [M−H+HCO$_2$H]$^-$; $t_R$=1.34 min.

Example 7: mAb-Ex6

The general method described previously was used for the preparation of example 7. 60 mg of hu2H11_R35-74 were reacted with 233 µL of a 10.6 mM solution of example 6 in DMA (5 eq.) for 2 h. After purification on Superdex 200 pg in DPBS pH 6.5+20% NMP, concentration on Amicon Ultra-15, buffer exchange on NAP-25 in buffer B pH 6.5+5% NMP and filtration on Steriflip, 39 mg of example 7 were obtained as a colorless limpid solution at a concentration of 1.98 mg/mL with a DAR of 4.1 (HRMS), a monomeric purity of 100% and a global yield of 66%. SEC-HRMS: spectrum for intact ADC in FIG. 2; m/z=149370 (naked mAb); m/z=150357 (D1); m/z=151330 (D2); m/z=152307 (D3); m/z=153285 (D4); m/z=154262 (D5); m/z=155238 (D6); m/z=156222 (D7).

Synthesis of Examples 8 to 10: benzylic amine of 7-Me-aza-C52 Stereomer 1, NHS ester of benzylic amine Stereomer 1 and Corresponding ADC

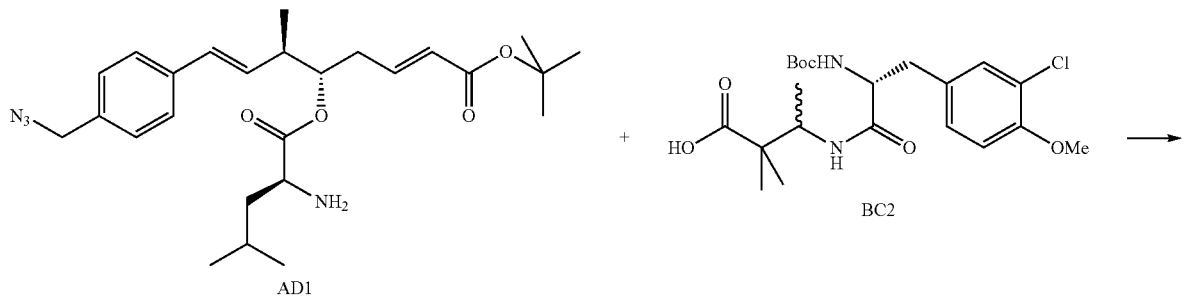

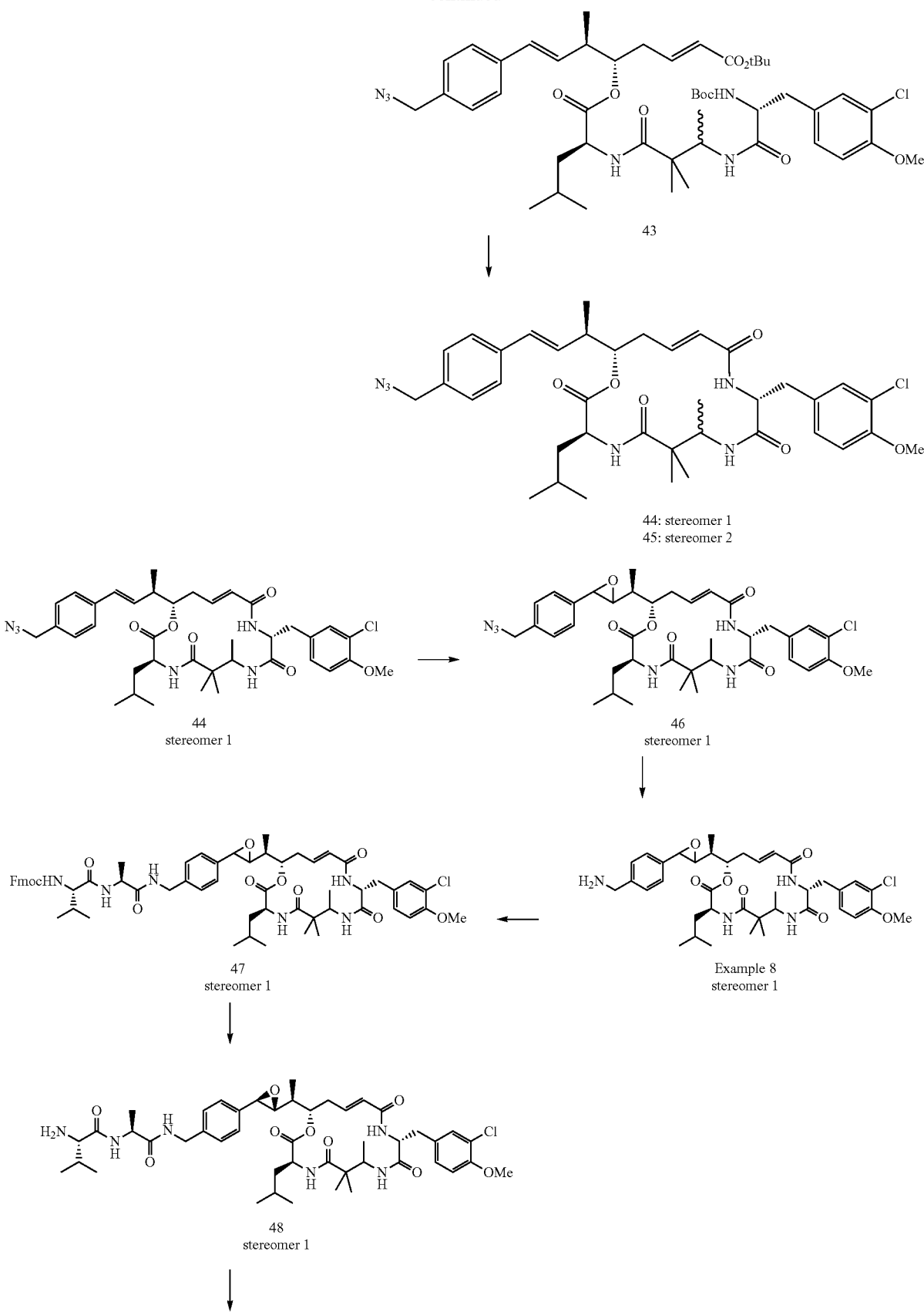

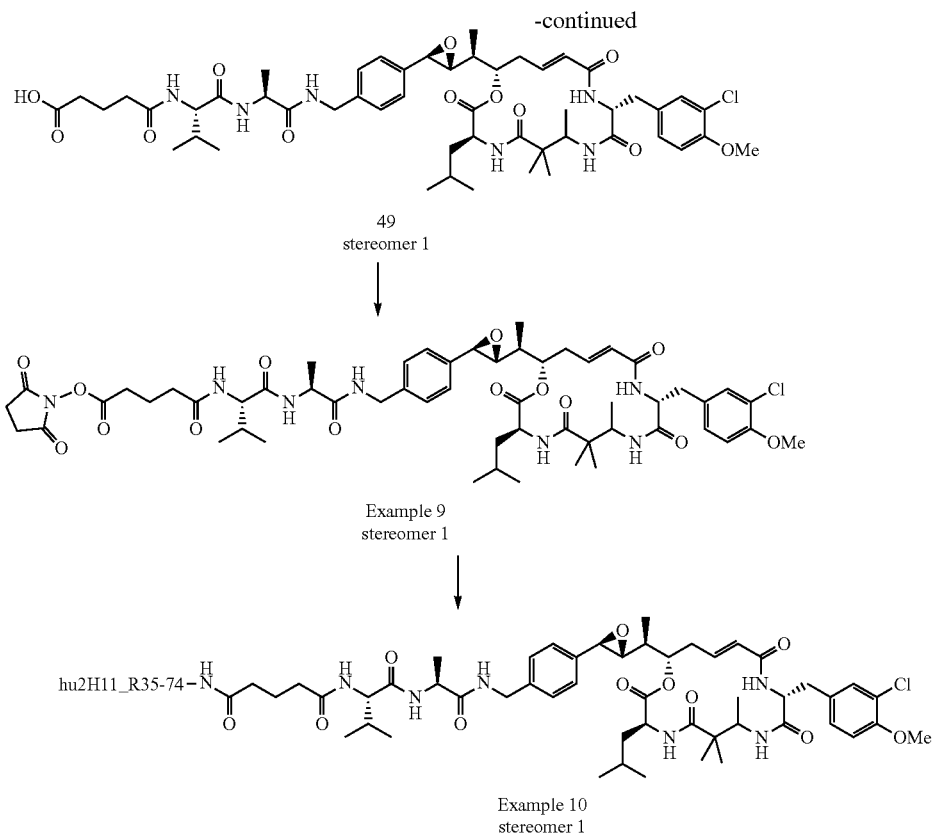

49
stereomer 1

Example 9
stereomer 1

Example 10
stereomer 1

Compound 43: (6R,13S)-(1E,3R,4S,6E)-1-(4-(az-idomethyl)phenyl)-8-(tert-butoxy)-3-methyl-8-oxoocta-1,6-dien-4-yl 6-(3-chloro-4-methoxybenzyl)-13-isobutyl-2,2,9,10,10-pentamethyl-4,7,11-trioxo-3-oxa-5,8,12-triazatetradecan-14-oate Under argon, in a round bottom flask, were introduced fragment BC2 (1.10 g, 2.48 mmol) in DMF (5 mL), followed by HATU (950 mg, 2.5 mmol) and HOAt (340 mg, 2.5 mmol). The mixture was stirred for 30 min at RT, then fragment AD1 (1.24 g, 2.18 mmol) and DIEA (1.2 mL, 6.87 mmol) were added. The yellow solution was stirred for 16 h at RT, quenched with $H_2O$ and extracted with AcOEt (3×30 mL). The organic layers were washed with $H_2O$, sat. brine, dried over $MgSO_4$, filtered, concentrated and purified on 200 g of silica gel (gradient elution heptane/AcOEt) to give 1.55 g of compound 43 as a white meringue (77%).

RMN $^1$H (400 MHz, δ in ppm, DMSO-d6): 55/45 diastereoisomer mixture; 0.82 to 0.89 (m, 6H); 0.85 (d, J=7.0 Hz, 1.65H); 0.91 (d, J=7.0 Hz, 1.35H); 0.99 to 1.09 (m, 9H); 1.30 (s, 9H); 1.40 (s, 10H); 1.50 to 1.70 (m, 2H); 2.38 to 2.59 (partially masked m, 3H); 2.68 (m, 1H); 2.84 (m, 1H); 3.79 (s, 1.35H); 3.81 (s, 1.65H); 4.00 to 4.18 (m, 2H); 4.30 (m, 1H); 4.40 (broad s, 2H); 4.92 (m, 1H); 5.81 (d, J=15.7 Hz, 1H); 6.18 (dd, J=8.3 and 16.1 Hz, 1H); 6.45 (d, J=16.1 Hz, 1H); 6.71 (td, J=7.3 and 15.7 Hz, 1H); 6.94 (d, J=8.1 Hz, 0.45H); 6.96 (d, J=8.1 Hz, 0.55H); 7.04 (split d, J=8.7 Hz, 1H); 7.19 (broad d, J=8.7 Hz, 1H); 7.30 (d, J=7.8 Hz, 2H); 7.32 (broad s, 1H); 7.41 (d, J=8.7 Hz, 2H); 7.52 (d, J=10.1 Hz, 0.45H); 7.59 (d, J=10.1 Hz, 0.55H); 7.74 (m, 1H). LCMS (A1): 55/45 diastereoisomer mixture; ES m/z=895 [M+H]$^+$; m/z=917 [M+Na]+; $t_R$=6.94-6.98 min.

Compounds 44 & 45: (3S,10R,16S, E)-16-((R,E)-4-(4-(azidomethyl)phenyl)but-3-en-2-yl)-10-(3-chloro-4-methoxybenzyl)-3-isobutyl-6,6,7-trimethyl-1-oxa-4,8,11-triazacyclohexadec-13-ene-2,5,9,12-tetraone Compounds 44 & 45 were obtained in two steps.

Step 1: at 0° C., in a round bottom flask, to a solution of compound 43 (1.50 g, 1.67 mmol) in 11 mL of DCM were added TFA (2.6 mL, 34.65 mmol) and 100 µL of $H_2O$. The mixture was stirred for 15 min at 0° C. and at RT for 6.5 h. The reaction medium was then evaporated in vacuo and co-evaporated in the presence of toluene to give 1.7 g of deprotected intermediate as an orange solid.

RMN $^1$H (500 MHz, δ in ppm, DMSO-d6): 55/45 diastereoisomer mixture; 0.70 to 0.80 (m, 7.65H); 0.90 (s, 1.35H); 0.95 (m, 3H); 1.01 to 1.09 (m, 6H); 1.38 to 1.68 (m, 3H); 2.40 to 2.60 (partially masked m, 3H); 2.80 to 3.02 (m, 2H); 3.81 (s, 1.35H); 3.82 (s, 1.65H); 3.96 to 4.08 (m, 1H); 4.18 (m, 1H); 4.28 (m, 1H); 4.41 (s, 2H); 4.91 (m, 1H); 5.83 (d, J=15.7 Hz, 0.45H); 5.85 (d, J=15.7 Hz, 0.55H); 6.18 (m, 1H); 6.43 (d, J=16.1 Hz, 0.45H); 6.46 (d, J=16.1 Hz, 0.55H); 6.74 (m, 1H); 7.08 to 7.20 (m, 2H); 7.30 (masked m, 0.45H); 7.32 (d, J=7.8 Hz, 2H); 7.37 (d, J=2.0 Hz, 0.55H); 7.42 (m, 2H); 7.76 (d, J=8.00 Hz, 0.45H); 7.79 (d, J=8.00 Hz, 0.55H); 7.86 (d, J=10.1 Hz, 0.55H); 8.00 (d, J=10.1 Hz, 0.45H); 8.11 (broad m, 3H); 12.22 (broad m, 1H). LCMS (A1): 55/45 diastereoisomer mixture; ES m/z=737 [M−H]$^-$; m/z=739 [M+H]$^+$; $t_R$=1.07-1.09 min.

Step 2: in a round bottom flask, to a solution of deprotected intermediate (1.43 g, 1.68 mmol) in 25 mL of $CH_3CN$ were added DIEA (3 mL, 16.23 mmol), HOAt (250.91 mg, 1.84 mmol) and HATU (700.91 mg, 1.84 mmol). The mixture was stirred for 1 h at RT. Then the solvent was removed, the medium diluted with AcOEt (200 mL), neutralized with 0.5 M citric acid and HCl.

The organic layer was separated, washed with sat. NaHSO$_3$, sat. NaHCO$_3$, sat. brine, dried over MgSO$_4$, filtered, concentrated and purified on 100 g of silica gel (gradient elution DCM/MeOH) to give 640 mg of compounds 44 & 45 as a yellow solid (53%).

Diastereoisomers at C$_7$ were separated by chiral liquid chromatography that was carried out on a 76.5×350 mm column packed with 1.1 kg of 10 μm Whelk 01 SS (4-(3, 5-dinitrobenzamido) tetrahydrophenanthrene, Regis Technologies) using isocratic elution with 50:50 heptane/EtOH. After concentration, 210 mg of compound 44 (stereomer 1) were obtained as a white solid (17%) and 236 mg of compound 45 (stereomer 2) were obtained as a white solid (19%).

Compound 44 (stereomer 1)

RMN $^1$H (500 MHz, δ in ppm, DMSO-d6): 0.60 (d, J=6.7 Hz, 3H); 0.62 (d, J=6.7 Hz, 3H); 0.98 (s, 3H); 1.05 (d, J=7.0 Hz, 3H); 1.10 (d, J=7.0 Hz, 3H); 1.14 (s, 3H); 1.18 (m, 1H); 1.40 to 1.54 (m, 2H); 2.24 (m, 1H); 2.48 to 2.61 (partially masked m, 2H); 2.65 (dd, J=11.8 and 14.5 Hz, 1H); 3.04 (dd, J=3.2 and 14.5 Hz, 1H); 3.55 (m, 1H); 3.81 (s, 3H); 4.19 (m, 2H); 4.40 (s, 2H); 4.96 (m, 1H); 5.91 (dd, J=1.4 and 15.5 Hz, 1H); 6.13 (dd, J=8.9 and 16.1 Hz, 1H); 6.40 (ddd, J=3.9, 11.3 and 15.5 Hz, 1H); 6.46 (d, J=16.1 Hz, 1H); 7.03 (d, J=8.7 Hz, 1H); 7.19 (dd, J=2.1 and 8.7 Hz, 1H); 7.30 (d, J=2.1 Hz, 1H); 7.32 (d, J=8.4 Hz, 2H); 7.41 (d, J=8.4 Hz, 2H); 7.87 (d, J=8.9 Hz, 1H); 8.36 (d, J=9.9 Hz, 1H); 8.40 (d, J=8.0 Hz, 1H). LCMS (A1): ES m/z=719 [M−H]$^-$; m/z=721 [M+H]$^+$; t$_R$=1.61 min Compound 45 (stereomer 2)

RMN $^1$H (δ in ppm, DMSO-d6): 0.59 (d, J=6.7 Hz, 3H); 0.67 (d, J=6.7 Hz, 3H); 0.88 (d, J=6.7 Hz, 3H); 1.03 (s, 3H); 1.10 (d, J=7.0 Hz, 3H); 1.19 (s, 3H); 1.21 (m, 1H); 1.49 to 1.60 (m, 2H); 2.23 (m, 1H); 2.46 to 2.61 (partially masked m, 2H); 2.71 (dd, J=11.3 and 14.5 Hz, 1H); 2.98 (dd, J=3.7 and 14.5 Hz, 1H); 3.48 (m, 1H); 3.80 (s, 3H); 4.05 (m, 1H); 4.11 (ddd, J=3.7, 7.6 and 11.3 Hz, 1H); 4.40 (s, 2H); 4.90 (m, 1H); 5.93 (d, J=15.7 Hz, 1H); 6.14 (dd, J=8.7 and 16.1 Hz, 1H); 6.47 (d, J=16.1 Hz, 1H); 6.51 (ddd, J=5.2, 10.3 and 15.5 Hz, 1H); 7.02 (d, J=8.7 Hz, 1H); 7.21 (dd, J=2.4 and 8.7 Hz, 1H); 7.31 (d, J=8.4 Hz, 2H); 7.37 (d, J=2.4 Hz, 2H); 7.41 (d, J=8.4 Hz, 2H); 7.87 (d, J=6.9 Hz, 1H); 7.89 (d, J=9.0 Hz, 1H); 8.51 (d, J=7.6 Hz, 1H). LCMS (A1): ES m/z=719 [M−H]$^-$; m/z=721 [M+H]$^+$; t$_R$=1.61 min.

Compound 46: (3S,10R,16S,E)-16-((S)-1-(3-(4-(azidomethyl)phenyl)oxiran-2-yl)ethyl)-10-(3-chloro-4-methoxybenzyl)-3-isobutyl-6,6,7-trimethyl-1-oxa-4,8,11-triazacyclohexadec-13-ene-2,5,9,12-tetraone At 0° C., under argon, in a round bottom flask to a solution of compound 44 (154 mg, 213.51 μmol) in DCM (10 mL) was added m-CPBA (80 mg, 324.51 μmol). The reaction medium was stirred at RT for 5 d. The reaction mixture was diluted with DCM (15 mL) and stirred 15 min with sat. NaHCO$_3$ (6 mL) and Na$_2$S$_2$O$_3$ (6 mL). The organic layer was separated, washed with sat. brine (2×3 mL), dried over MgSO$_4$, filtered and concentrated to give 150 mg of compound 46 as a white solid (quant.).

RMN $^1$H (500 MHz, δ in ppm, DMSO-d6): 60/40 diastereoisomer mixture; 0.75 (d, J=6.8 Hz, 1.8H); 0.79 (d, J=6.8 Hz, 3H); 0.85 (d, J=6.8 Hz, 1.2H); 0.95 to 0.99 (m, 4.2H); 1.02 to 1.09 (m, 4.8H); 1.15 (s, 1.8H); 1.18 (s, 1.2H); 1.20 (m, 0.6H); 1.38 (m, 0.4H); 1.59 to 1.62 (m, 2H); 1.80 (m, 0.6H); 1.89 (m, 0.4H); 2.25 (m, 0.6H); 2.40 to 2.71 (partially masked m, 2.4H); 2.96 to 3.08 (m, 2H); 3.54 (m, 1H); 3.80 (s, 3H); 3.82 (d, J=1.9 Hz, 0.4H); 3.92 (d, J=1.9 Hz, 0.6H); 4.14 to 4.29 (m, 2H); 4.40 to 4.50 (m, 2H); 5.11 (m, 1H); 5.85 (dd, J=2.0 and 15.5 Hz, 0.6H); 5.95 (dd, J=2.0 and 15.5 Hz, 0.4H); 6.38 (m, 1H); 7.04 (split d, J=8.8 Hz, 1H); 7.16 (dd, J=2.2 and 8.8 Hz, 0.6H); 7.19 (dd, J=2.2 and 8.8 Hz, 0.4H); 7.28 (d, J=2.2 Hz, 0.6H); 7.30 (d, J=2.2 Hz, 0.4H); 7.30 to 7.40 (m, 4H); 7.89 (d, J=8.1 Hz, 0.6H); 7.92 (d, J=8.1 Hz, 0.4H); 8.29 (d, J=10.0 Hz, 0.6H); 8.32 (d, J=8.1 Hz, 0.6H); 8.35 (d, J=10.0 Hz, 0.4H); 8.40 (d, J=8.1 Hz, 0.4H). LCMS (A1): ES m/z=735 [M−H]$^-$; m/z=737 [M+H]$^+$; t$_R$=1.52 min.

Example 8: (3S,10R,16S,E)-16-((S)-1-(3-(4-(aminomethyl)phenyl)oxiran-2-yl)ethyl)-10-(3-chloro-4-methoxybenzyl)-3-isobutyl-6,6,7-trimethyl-1-oxa-4,8,11-triazacyclohexadec-13-ene-2,5,9,12-tetraone At 0° C., in a round bottom flask, to a solution of compound 46 (60 mg, 81.38 μmol) in DCM (3 mL) and MeOH (3 mL) was dropwise added a solution of TCEP (38.9 mg, 134.3 μmol) in 1 mL of H$_2$O. The reaction mixture was stirred at RT for 35 h, then diluted with DCM (15 mL) and sat. NaHCO$_3$. After stirring for 10 min, the organic layer was separated, washed with sat. brine, dried over MgSO$_4$, filtered, concentrated in vacuo and purified on 5 g of silica gel (gradient elution DCM/MeOH) to give 23 mg of example 8 as a white solid (40%).

RMN $^1$H (500 MHz, δ in ppm, DMSO-d6): 60/40 diastereoisomer mixture; 0.77 (d, J=7.0 Hz, 1.8H); 0.81 (split d, J=7.0 Hz, 3H); 0.88 (d, J=7.0 Hz, 1.4H); 0.95 (d, J=7.0 Hz, 1.2H); 0.98 (s, 1.8H); 1.00 (s, 1.2H); 1.02 to 1.09 (m, 4.8H); 1.17 (s, 1.8H); 1.19 (s, 1.2H); 1.22 (m, 0.6H); 1.40 (m, 0.4H); 1.51 to 1.64 (m, 2H); 1.78 (m, 0.6H); 1.89 (m, 0.4H); 2.28 (m, 0.6H); 2.40 to 2.71 (partially masked m, 2.4H); 2.96 (dd, J=2.2 and 7.5 Hz, 0.6H); 2.99 (dd, J=2.2 and 7.5 Hz, 0.4H); 3.03 (m, 1H); 3.55 (m, 1H); 3.70 (s, 1.2H); 3.72 (s, 1.8H); 3.78 (d, J=2.2 Hz, 0.4H); 3.81 (s, 3H); 3.88 (d, J=2.2 Hz, 0.6H); 4.12 to 4.30 (m, 2H); 5.12 (m, 1H); 5.84 (dd, J=1.8 and 15.6 Hz, 0.6H); 5.96 (dd, J=1.8 and 15.6 Hz, 0.4H); 6.39 (m, 1H); 7.05 (d, J=8.7 Hz, 1H); 7.16 to 7.38 (m, 6H); 7.90 (d, J=8.1 Hz, 0.6H); 7.93 (d, J=8.1 Hz, 0.4H); 8.28 (d, J=10.0 Hz, 0.6H); 8.32 (d, J=8.1 Hz, 0.6H); 8.37 (d, J=10.0 Hz, 0.4H); 8.41 (d, J=8.1 Hz, 0.4H). LCMS (A1): ES m/z=709 [M−H]$^-$; m/z=711 [M+H]$^+$; t$_R$=0.86 min.

Compound 47: (9H-fluoren-9-yl)methyl ((S)-1-(((S)-1-((4-(3-((S)-1-((3S,10R,16S, E)-10-(3-chloro-4-methoxybenzyl)-3-isobutyl-6,6,7-trimethyl-2,5,9,12-tetraoxo-1-oxa-4,8,11-triazacyclohexadec-13-en-16-yl)ethyl)oxiran-2-yl)benzyl)amino)-1-oxopropan-2-yl)amino)-3-methyl-1-oxobutan-2-yl)carbamate Under argon, in a round bottom flask were introduced example 8 (110 mg, 154.65 μmol) and DMF (2 mL), followed by FmocValAla (90 mg, 219 μmol), HOBt (30 mg, 222 μmol), DCM (10 mL) and EDC (35 μl, 197.52 μmol). The solution was stirred at RT for 3 h 30 then quenched with H$_2$O (10 mL) and extracted by DCM (3×10 mL). The organic layer was separated, washed with sat. NaHCO$_3$, sat. brine, dried over MgSO$_4$, filtered, concentrated in the presence of toluene and purified on 15 g of silica gel (gradient elution DCM/MeOH) to give 49 mg of compound 47 as a white solid (46%).

RMN $^1$H (500 MHz, δ in ppm, DMSO-d6): 60/40 diastereoisomer mixture; 0.76 (d, J=7.0 Hz, 1.8H); 0.80 (m, 3H); 0.82 to 0.89 (m, 6.4H); 0.95 (d, J=7.0 Hz, 1.2H); 0.98 (s, 1.8H); 1.00 (s, 1.2H); 1.02 to 1.09 (m, 4.8H); 1.17 (s, 1.8H); 1.19 (s, 1.2H); 1.20 to 1.32 (m, 3.6H); 1.40 (m, 0.4H); 1.51 to 1.63 (m, 2H); 1.78 (m, 0.6H); 1.85 (m, 0.4H); 2.00 (m, 1H); 2.27 (m, 0.6H); 2.40 to 2.72 (partially masked m, 2.4H); 2.96 (m, 1H); 3.04 (m, 1H); 3.55 (m, 1H); 3.77 (d, J=2.2 Hz, 0.4H); 3.81 (s, 3H); 3.88 (d, J=2.2 Hz, 0.6H); 3.90 (m, 1H); 4.15 to 4.38 (m, 6H); 5.12 (m, 1H); 5.85 (dd, J=1.8 and 15.6 Hz, 0.6H); 5.95 (dd, J=1.8 and 15.6 Hz, 0.4H); 6.39 (m, 1H); 7.05 (split d, J=8.7 Hz, 1H); 7.15 to 7.48 (m, 19H); 7.73 (t, J=8.1 Hz, 2H); 7.90 (d, J=8.1 Hz, 2.6H); 7.92 (d, J=8.1 Hz, 0.4H); 8.05 (d, J=8.1 Hz, 1H); 8.25 to 8.45 (m, 3H). LCMS (A1): ES m/z=552 [M+2H]$^{2+}$; m/z=1103 [M+H]$^+$; m/z=1147 [M−H+HCO$_2$H]$^−$; $t_R$=1.55-1.57 min.

Compound 48: (25)-2-amino-N-((25)-1-((4-((2R,3R)-3-((1 S)-1-((3S,10R,16S,E)-10-(3-chloro-4-methoxybenzyl)-3-isobutyl-6,6,7-trimethyl-2,5,9,12-tetraoxo-1-oxa-4,8,11-triazacyclohexadec-13-en-16-yl)ethyl)oxiran-2-yl)benzyl)amino)-1-oxopropan-2-yl)-3-methylbutanamide In a round bottom flask, piperidine (60 μL, 600.6 μmol) was added to a solution of compound 47 (50 mg, 45.30 μmol) in DCM (5 mL). The resulting mixture was stirred for 24 h at RT, concentrated in vacuo and purified on 5 g of silica gel (gradient elution DCM/MeOH) to give 70 mg of alpha and beta epoxides.

RMN $^1$H (500 MHz, δ in ppm, DMSO-d6): 60/40 diastereoisomer mixture; 0.75 (d, J=7.0 Hz, 1.8H); 0.80 (m, 3H); 0.82 to 0.92 (m, 6.4H); 0.96 (d, J=7.0 Hz, 1.2H); 0.98 (s, 1.8H); 1.00 (s, 1.2H); 1.02 to 1.09 (m, 4.8H); 1.15 (s, 1.8H); 1.19 (s, 1.2H); 1.20 to 1.42 (m, 4H); 1.50 to 1.70 (masked m, 2H); 1.78 (m, 0.6H); 1.85 (m, 0.4H); 2.00 (m, 1H); 2.25 (m, 0.6H); 2.40 to 2.72 (partially masked m, 2.4H); 2.92 to 3.08 (m, 3H); 3.54 (m, 1H); 3.79 (d, J=2.1 Hz, 0.4H); 3.81 (s, 3H); 3.88 (d, J=2.1 Hz, 0.6H); 4.13 to 4.41 (m, 6H); 5.12 (m, 1H); 5.85 (d, J=15.4 Hz, 0.6H); 5.93 (d, J=15.4 Hz, 0.4H); 6.38 (m, 1H); 7.05 (d, J=8.7 Hz, 1H); 7.15 to 7.32 (m, 6H); 7.90 (d, J=8.3 Hz, 0.6H); 7.93 (d, J=8.3 Hz, 0.4H); 8.10 to 8.55 (m, 7H). LCMS (A1): ES m/z=441 [M+2H]$^{2+}$; m/z=879 [M−H]$^−$; m/z=881 [M+H]$^+$; m/z=925 [M−H+HCO$_2$H]$^−$; $t_R$=0.92 min.

Alpha and beta epoxides were separated by chiral liquid chromatography that was carried out on a 76×350 mm column packed with 1.1 kg of 10 μm Chiralpak AD (amylose tris-3,5-dimethylphenylcarbamate coated on a silica gel support, Chiral Technologies Europe) using isocratic elution with 70:30 heptane/EtOH. After concentration, 28 mg of compound 48 were obtained as a white solid (70%) and 19 mg of the alpha epoxide were obtained as a white solid.

RMN $^1$H (500 MHz, δ in ppm, DMSO-d6): 0.75 (d, J=7.0 Hz, 6H); 0.80 (d, J=7.0 Hz, 3H); 0.88 (d, J=7.0 Hz, 3H); 0.98 (s, 3H); 1.03 (d, J=7.0 Hz, 6H); 1.17 (s, 3H); 1.23 (d, J=7.0 Hz, 3H); 1.35 (m, 1H); 1.50 to 1.68 (m, 2H); 1.78 (m, 1H); 1.91 (m, 1H); 2.26 (m, 1H); 2.58 to 2.70 (m, 2H); 2.96 (dd, J=1.9 and 7.7 Hz, 1H); 2.99 (d, J=4.8 Hz, 1H); 3.02 (dd, J=3.3 and 14.8 Hz, 1H); 3.53 (m, 1H); 3.80 (s, 3H); 3.89 (d, J=1.9 Hz, 1H); 4.10 to 4.23 (m, 3H); 4.28 (d, J=6.1 Hz, 2H); 4.35 (m, 1H); 5.11 (m, 1H); 5.83 (dd, J=1.9 and 15.2 Hz, 1H); 6.37 (ddd, J=4.0, 11.2 and 15.2 Hz, 1H); 7.03 (d, J=8.8 Hz, 1H); 7.18 (dd, J=2.4 and 8.8 Hz, 1H); 7.26 (s, 4H); 7.29 (d, J=2.4 Hz, 1H); 7.90 (d, J=8.2 Hz, 1H); 8.08 (broad d, J=7.7 Hz, 1H); 8.29 (d, J=10.1 Hz, 1H); 8.33 (d, J=8.2 Hz, 1H); 8.46 (t, J=6.7 Hz, 1H). LCMS (A1): ES m/z=441 [M+2H]$^{2+}$; m/z=879 [M−H]$^−$; m/z=881 [M+H]$^+$; m/z=925 [M−H+HCO$_2$H]$^−$; $t_R$=0.92 min.

Compound 49: 5-(((S)-1-(((S)-1-((4-((2R,3R)-3-((S)-1-((3S,10R,16S,E)-10-(3-chloro-4-methoxybenzyl)-3-isobutyl-6,6,7-trimethyl-2,5,9,12-tetraoxo-1-oxa-4,8,11-triazacyclohexadec-13-en-16-yl)ethyl)oxiran-2-yl)benzyl)amino)-1-oxopropan-2-yl)amino)-3-methyl-1-oxobutan-2-yl)amino)-5-oxopentanoic acid Under argon, in a round bottom flask, a solution of glutaric anhydride (3.78 mg, 32.44 μmol) in DCM (4 mL) was added to a solution of compound 48 (26 mg, 29.5 μmol) in DCM (9 mL). The resulting mixture was stirred 2 h at RT, concentrated in vacuo and purified on 2.5 g of silica gel (gradient elution DCM/MeOH/H$_2$O) to give 18 mg of compound 49 as a white solid (61%).

RMN $^1$H (500 MHz, δ in ppm, DMSO-d6): 0.78 (d, J=7.0 Hz, 3H); 0.80 (d, J=7.0 Hz, 3H); 0.82 (d, J=7.0 Hz, 3H); 0.84 (d, J=7.0 Hz, 3H); 0.97 (s, 3H); 1.03 (d, J=7.0 Hz, 6H); 1.15 (s, 3H); 1.23 (broad d, J=7.0 Hz, 4H); 1.49 to 1.61 (m, 2H); 1.70 (m, 2H); 1.78 (m, 1H); 1.97 (m, 1H); 2.20 (m, 4H); 2.25 (m, 1H); 2.62 (m, 2H); 2.95 (m, 1H); 3.02 (m, 1H); 3.53 (m, 1H); 3.80 (s, 3H); 3.88 (s, 1H); 4.10 to 4.22 (m, 3H); 4.24 to 4.31 (m, 3H); 5.11 (m, 1H); 5.83 (d, J=15.7 Hz, 1H); 6.36 (m, 1H); 7.03 (d, J=8.7 Hz, 1H); 7.19 (broad d, J=8.7 Hz, 1H); 7.23 (m, 4H); 7.29 (broad s, 1H); 7.87 (d, J=8.9 Hz, 1H); 7.90 (d, J=8.1 Hz, 1H); 8.06 (d large, J=7.3 Hz, 1H); 8.29 (d, J=10.1 Hz, 1H); 8.37 (m, 2H); 12.0 (broad m, 1H). LCMS (A1): ES m/z=993 [M−H]$^−$; m/z=995 [M+H]$^+$; $t_R$=1.21 min.

Example 9: 2,5-dioxopyrrolidin-1-yl 5-(((S)-1-(((S)-1-((4-((2R,3R)-3-((S)-1-((3S,10R,16S,E)-10-(3-chloro-4-methoxybenzyl)-3-isobutyl-6,6,7-trimethyl-2,5,9,12-tetraoxo-1-oxa-4,8,11-triazacyclohexadec-13-en-16-yl)ethyl)oxiran-2-yl)benzyl)amino)-1-oxopropan-2-yl)amino)-3-methyl-1-oxobutan-2-yl)amino)-5-oxopentanoate Under argon, in a round bottom flask, to a solution of compound 49 (15 mg, 15.07 μmol) in DCM (5 mL) were added DSC (5.63 mg, 21.09 μmol) and DIEA (3.56 μL, 21.09 μmol). The resulting mixture was stirred for 1 h at RT, concentrated in vacuo and purified on 2.5 g of silica gel (gradient elution DCM/MeOH) to give 7.7 mg of example 9 as a white solid (47%).

RMN $^1$H (500 MHz, δ in ppm, DMSO-d6): 0.78 (d, J=6.7 Hz, 3H); 0.80 (d, J=6.7 Hz, 3H); 0.82 (d, J=7.0 Hz, 3H); 0.85 (d, J=7.0 Hz, 3H); 0.99 (s, 3H); 1.04 (d, J=7.2 Hz, 6H); 1.18 (s, 3H); 1.26 (m, 4H); 1.57 (m, 2H); 1.79 (m, 1H); 1.83 (m, 2H); 1.99 (m, 1H); 2.22 to 2.33 (m, 3H); 2.60 á 2.71 (m, 4H); 2.82 (s, 4H); 2.97 (dd, J=2.1 and 7.7 Hz, 1H); 3.04 (dd, J=3.4 and 14.7 Hz, 1H); 3.55 (m, 1H); 3.81 (s, 3H); 3.89 (d, J=2.1 Hz, 1H); 4.19 (m, 3H); 4.26 to 4.34 (m, 3H); 5.12 (m, 1H); 5.86 (dd, J=2.0 and 15.7 Hz, 1H); 6.38 (ddd, J=3.8, 11.2 and 15.7 Hz, 1H); 7.05 (d, J=8.7 Hz, 1H); 7.19 (dd, J=2.2 and 8.7 Hz, 1H); 7.26 (m, 4H); 7.29 (d, J=2.2 Hz, 1H); 7.91 (m, 2H); 8.09 (m, 1H); 8.29 (d, J=9.9 Hz, 1H); 8.35 (m, 2H). LCMS (A1): ES m/z=1092 [M+H]$^+$; m/z=1136 [M−H+HCO$_2$H]$^−$; $t_R$=1.26 min.

Example 10: mAb-Ex9

The general method described previously was used for the preparation of example 10. 60 mg of hu2H11_R35-74 were reacted with 198 μL of a 10.78 mM solution of example 9 in DMA (5 eq.) for 2 h. At that time, 120 μL of the solution of example 9 (3 eq.) were added and the medium stirred for 2 h. After purification on Superdex 200 pg in DPBS pH 6.5+20% NMP, concentration on Amicon Ultra-15, buffer exchange on PD-10 in buffer B pH 6.5+5% NMP and filtration on Steriflip, 46 mg of example 10 were obtained as a colorless limpid solution at a concentration of 2.23 mg/mL with a DAR of 4.7 (HRMS), a monomeric purity of 99.2% and a global yield of 78%. SEC-HRMS: spectrum for intact ADC in FIG. 3; m/z=150345 (D1); m/z=151319 (D2); m/z=152297 (D3); m/z=153274 (D4); m/z=154251 (D5); m/z=155222 (D6); m/z=156202 (D7); m/z=157183 (D8).

Synthesis of Examples 11 to 14: benzylic amine of 3-(S)-neopentyl-7-Me-aza-C52 Stereomer 1, NHS ester of glutaryl-Val-Ala-3-(S)-neopentyl-7-Me-aza-C52 benzylic amine Stereomer 1 and Corresponding ADC

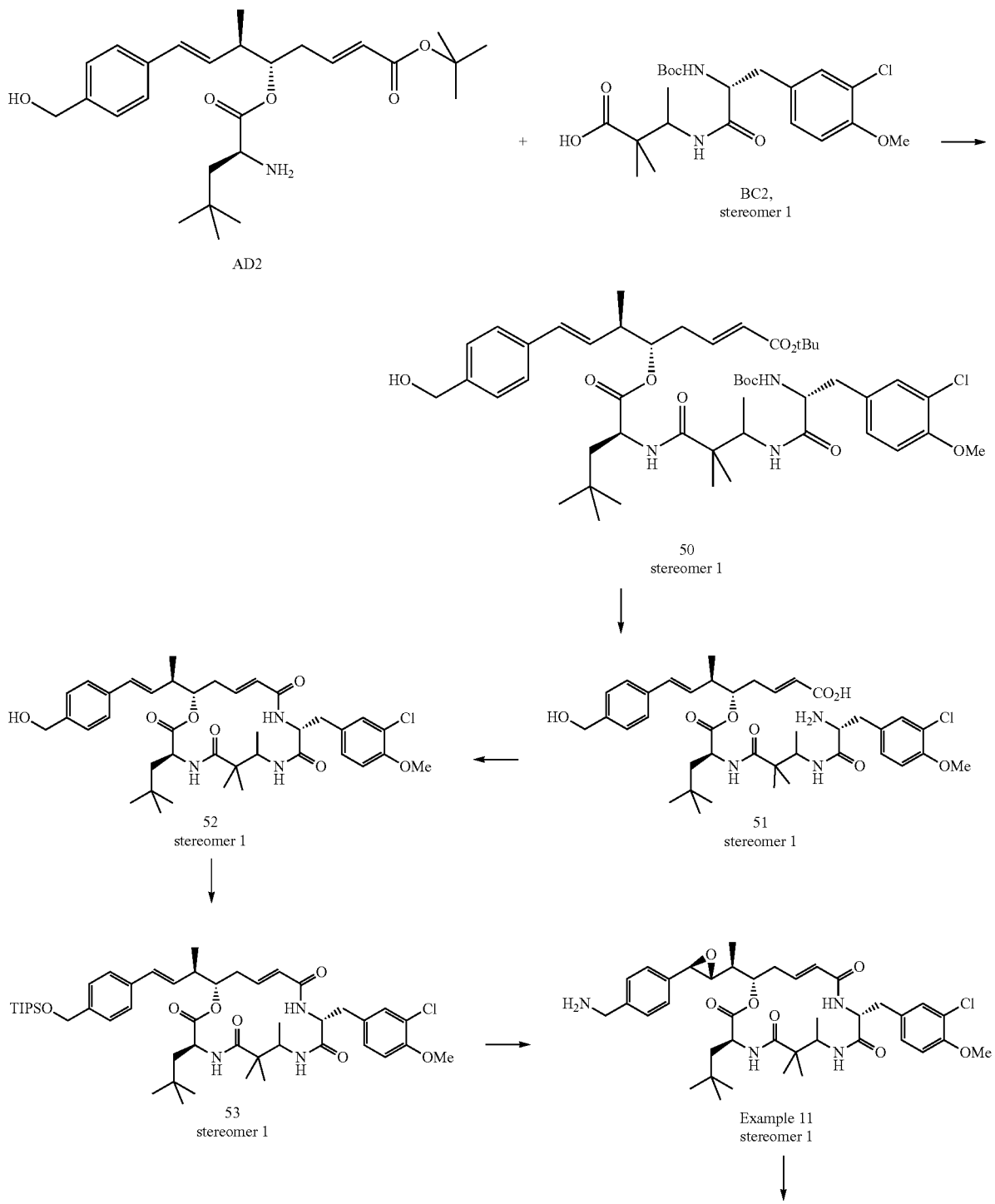

485 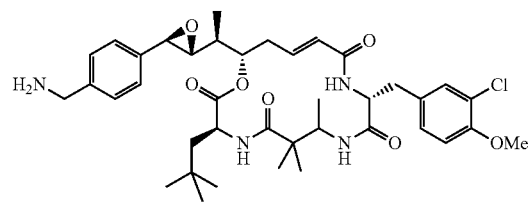
Example 12
stereomer 1
486 -continued 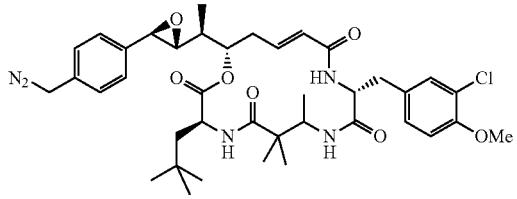
54
stereomer 1
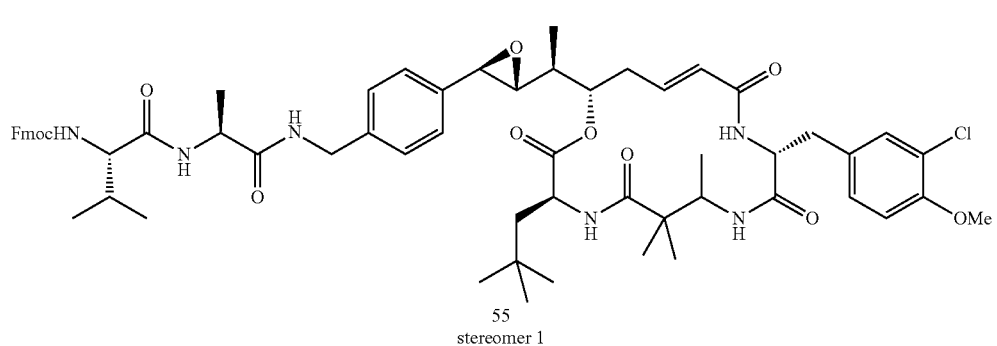
55
stereomer 1
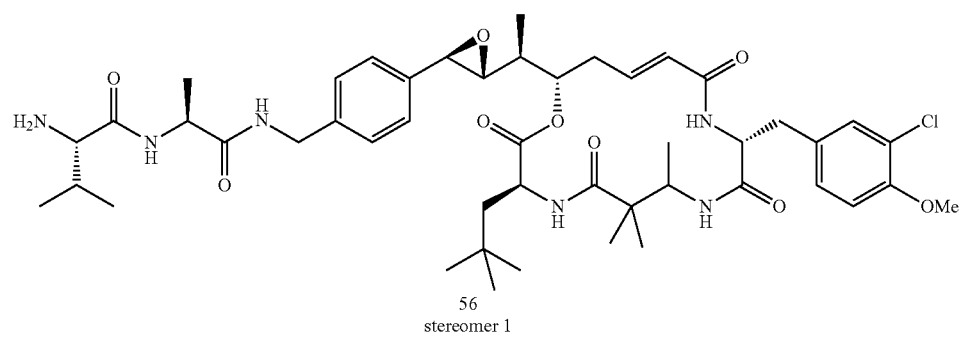
56
stereomer 1
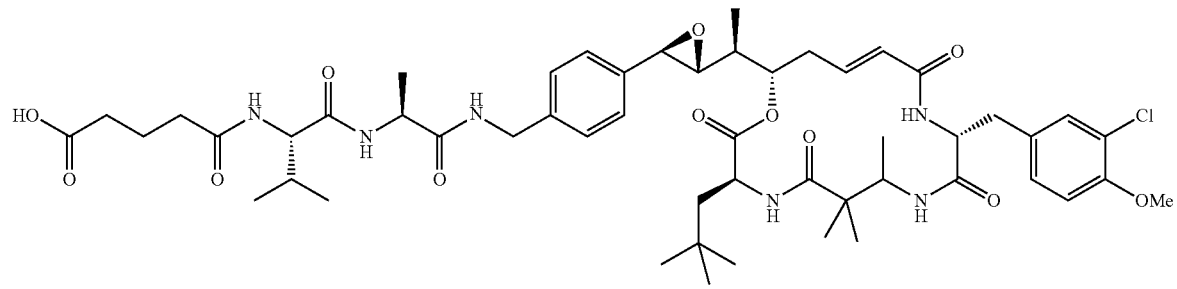
57
stereomer 1

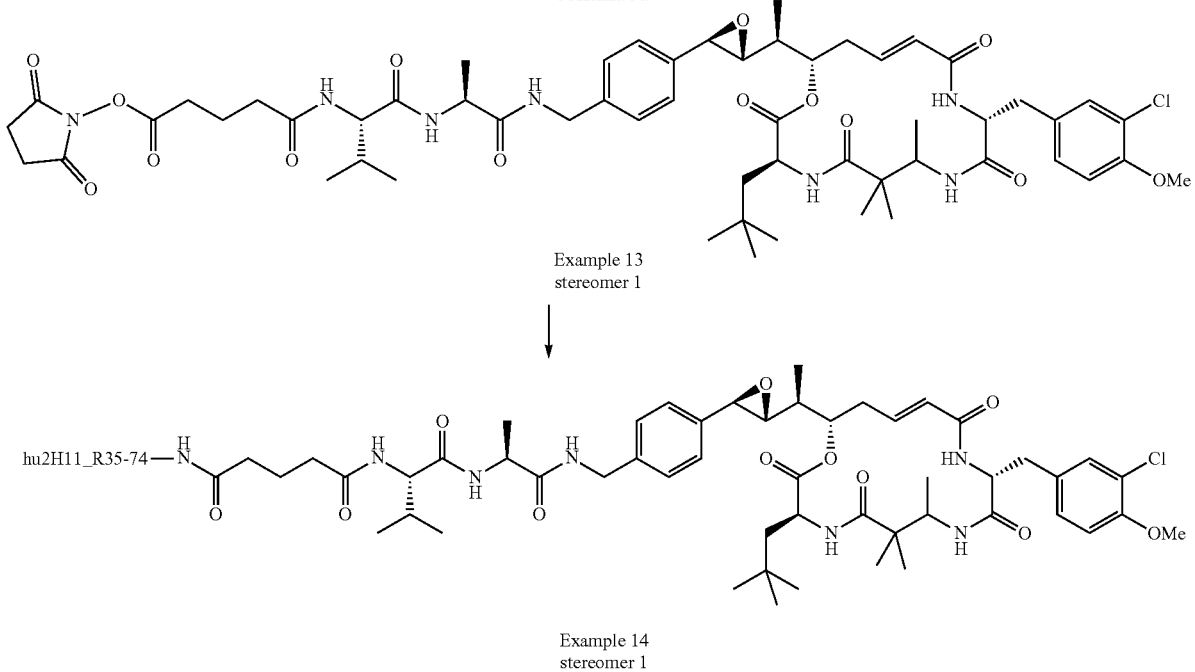

Example 13
stereomer 1

↓

Example 14
stereomer 1

Compound 50: (6R,13S)-(1E,3R,4S,6E)-8-(tert-butoxy)-1-(4-(hydroxymethyl)phenyl)-3-methyl-8-oxoocta-1,6-dien-4-yl 6-(3-chloro-4-methoxybenzyl)-2,2,9,10,10-pentamethyl-13-neopentyl-4,7,11-trioxo-3-oxa-5,8,12-triazatetradecan-14-oate Under argon, in a round bottom flask, to a solution of fragment BC2 (742 mg, 1.68 mmol) in DMF (20 mL) were added HATU (716 mg, 1.83 mmol) and HOAt (251 mg, 1.83 mmol). The mixture was stirred 30 min at RT. Then a solution of fragment AD1 (730 mg, 1.59 mmol) in DMF (10 mL) and DIEA (981 µL, 5.56 mmol) were added. The reaction medium was stirred for 24 h at RT. After this time, the reaction medium was diluted with ice (200 g), extracted with AcOEt (4×200 mL). The organic layers were washed with $H_2O$ (80 mL), sat. brine (2×80 mL), dried over $MgSO_4$, filtered, concentrated and purified by two successive flash chromatographies, the first one on 300 g of silica gel (gradient elution DCM/MeOH) and the second one on 70 g of silica gel (gradient elution DCM/MeOH) to give 428 mg of compound 50 as a colorless foam (30%).

Compound 51: (2E,5S,6R,7E)-5-(((2S)-2-(3-((R)-2-amino-3-(3-chloro-4-methoxyphenyl)-propanamido)-2,2-dimethylbutanamido)-4,4-dimethylpentanoyl)oxy)-8-(4-(hydroxymethyl)phenyl)-6-methylocta-2,7-dienoic acid In a round bottom flask, were introduced compound 50 (428 mg, 483.87 µmol) and DCM (27 mL). The solution was cooled at 0° C. then TFA (8 mL, 106.62 mmol) was added. The mixture was stirred for 1.5 h at RT. The solvent was removed and co-evaporated under reduced pressure with toluene (3×100 mL). The crude oil was diluted with 1:1 AcOEt/$H_2O$ (75 mL) and neutralized with 2M NaOH (250 µL) until pH 6-7. The mixture was stirred for 6 h at RT. The layers were separated. The aq. layer was extracted with AcOEt (3×50 mL). The organic layers were washed with sat. brine (2×15 mL), dried over $MgSO_4$, filtered and concentrated to give 374 mg of compound 51 as a colorless foam (quant.).

Compound 52: (3S,10R,16S, E)-10-(3-chloro-4-methoxybenzyl)-16-((R,E)-4-(4-(hydroxymethyl)-phenyl)but-3-en-2-yl)-6,6,7-trimethyl-3-neopentyl-1-oxa-4,8,11-triazacyclohexadec-13-ene-2,5,9,12-tetraone Under argon, in a round bottom flask, to a solution of compound 51 (352 mg, 483.31 µmol) in $CH_3CN$ (60 mL) were added HATU (208 mg, 531.64 mmol), HOAt (73.09 mg, 531.64 µmol) and DIEA (244.52 µL, 1.45 mmol). The reaction medium was stirred for 45 min at RT. After this time, the reaction medium was neutralized with 0.5 N citric acid until pH 4, concentrated partially in vacuo and extracted with AcOEt (150 mL). The organic layer was washed with sat. $NaHCO_3$ (10 mL), sat. brine (3×10 mL), dried over $MgSO_4$, filtered, concentrated and purified by flash chromatography on 15 g of silica gel (gradient elution DCM/MeOH) to give 188 mg of compound 52 as a colorless foam (54%).

Compound 53: (3S,10R,16S,E)-10-(3-chloro-4-methoxybenzyl)-6,6,7-trimethyl-3-neopentyl-16-((R, E)-4-(4-(((triisopropylsilyl)oxy)methyl)phenyl)but-3-en-2-yl)-1-oxa-4,8,11-triazacyclohexadec-13-ene-2,5,9,12-tetraone At 0° C., under argon, in a round bottom flask, to a solution of compound 52 (188 mg, 264.68 µmol) in DCM (7 mL), were added 1H-imidazole (83.72 mg, 1.2 mmol) and 1M chlorotriisopropylsilane (134.15 µl). The reaction medium was stirred for 5 h at RT, then quenched with sat. $NH_4Cl$ and stirred for 15 min. The layers were separated. The aq. layer was extracted with DCM (3×25 mL). The organic layers were washed with 1M $NaHSO_4$ (10 mL), sat.

NaHCO₃ (10 mL), sat. brine, dried over MgSO₄, filtered, concentrated and purified by flash chromatography on 10 g of silica gel (gradient elution DCM/MeOH) to give 137 mg of compound 53 as a colorless foam (59%).

Example 11: (3S,10R,16S,E)-10-(3-chloro-4-methoxybenzyl)-16-((S)-1-((2R,3R)-3-(4-(hydroxymethyl)phenyl)oxiran-2-yl)ethyl)-6,6,7-trimethyl-3-neopentyl-1-oxa-4,8,11-triazacyclohexadec-13-ene-2,5,9,12-tetraone Example 11 was prepared in two steps.

Step 1: at 0° C. under argon, in a round bottom flask, to a solution of compound 53 (137 mg, 158.08 μmol) in DCM (5.5 mL) was added a solution of m-CPBA (50.66 mg, 205.51 μmol) in DCM (2 mL) and the reaction medium was stirred for 2 h. Then 39 mg of m-CPBA were added twice after 2 h of stirring. After 16 h of stirring, the mixture was quenched with sat. NaHCO₃ (30 mL) and Na₂S₂O₃ (30 mL), stirred for 15 min and diluted with DCM (40 mL). The layers were separated. The aq. layer was extracted with DCM (2×20 mL). The organic layers were washed with sat. brine (2×8 mL), dried over MgSO₄, filtered and concentrated to give 160 mg of alpha and beta epoxides as a colorless solid (quant.).

RMN ¹H (500 MHz, δ in ppm, DMSO-d6): 60/40 diastereoisomer mixture; 0.80 to 0.91 (m, 12H); 0.97 to 1.09 (m, 24H); 1.12 to 1.21 (m, 6H); 1.32 (d, J=14.7 Hz, 0.6H); 1.40 (d, J=14.7 Hz, 0.4H); 1.70 to 1.87 (m, 1H); 1.90 (dd, J=10.1 and 14.7 Hz, 0.4H); 1.97 (dd, J=10.1 and 14.7 Hz, 0.6H); 2.28 (m, 0.6H); 2.40 (m, 0.4H); 2.55 to 2.79 (m, 2H); 2.90 to 3.00 (m, 2H); 3.44 (m, 1H); 3.79 (d, J=2.1 Hz, 0.4H); 3.80 (s, 3H); 3.90 (d, J=2.1 Hz, 0.6H); 4.03 to 4.22 (m, 2H); 4.78 (s, 0.8H); 4.80 (s, 1.2H); 5.03 (m, 1H); 5.90 (dd, J=1.5 and 15.5 Hz, 0.6H); 5.99 (dd, J=1.5 and 15.5 Hz, 0.4H); 6.40 to 6.55 (m, 1H); 7.02 to 7.07 (m, 1H); 7.13 to 7.38 (m, 6H); 7.85 to 7.93 (m, 2H); 8.40 (d, J=7.3 Hz, 0.6H); 8.51 (d, J=7.3 Hz, 0.4H). LCMS (A1): ES m/z=880 [M−H]⁻; m/z=882 [M+H]⁺; m/z=926 [M−H+HCO₂H]⁻; t_R=2.05-2.06 min.

Step 2: at 0° C. under argon, in a round bottom flask, to a solution of alpha and beta epoxides (177 mg, 200.53 μmol) in THF (7.5 mL) was dropwise added 1M TBAF (221 μL, 221 μmol). After stirring for 2 h at RT, 50 μL of TBAF were added and stirred for 3.5 h. The reaction medium was diluted with H₂O (9 mL), stirred for 10 min and extracted with DCM (3×25 mL). The combined organic layers were washed with sat. brine (3×8 mL), dried over MgSO₄, filtered and concentrated to give 210 mg of alpha and beta epoxides as a colorless solid (quant.).

RMN ¹H (500 MHz, δ in ppm, DMSO-d6): 60/40 diastereoisomer mixture; 0.82 to 1.25 (m, 21H); 1.32 (d, J=14.5 Hz, 0.6H); 1.42 (d, J=14.5 Hz, 0.4H); 1.80 (m, 1H); 1.91 (dd, J=10.0 and 14.5 Hz, 0.4H); 1.98 (dd, J=10.0 and 14.5 Hz, 0.6H); 2.22 to 2.48 (m, 1H); 2.55 to 2.78 (m, 2H); 2.89 to 3.03 (m, 2H); 3.44 (m, 1H); 3.79 (d, J=2.2 Hz, 0.4H); 3.80 (s, 3H); 3.90 (d, J=2.2 Hz, 0.6H); 4.04 to 4.22 (m, 2H); 4.48 (d, J=5.8 Hz, 0.8H); 4.50 (d, J=5.8 Hz, 1.2H); 5.03 (m, 1H); 5.16 (t, J=5.8 Hz, 0.4H); 5.19 (t, J=5.8 Hz, 0.6H); 5.89 (dd, J=1.9 and 15.6 Hz, 0.6H); 5.99 (dd, J=1.9 and 15.6 Hz, 0.4H); 6.40 to 6.52 (m, 1H); 7.02 (d, J=8.7 Hz, 0.6H); 7.04 (d, J=8.7 Hz, 0.4H); 7.16 to 7.37 (m, 6H); 7.83 to 7.94 (m, 2H); 8.39 (d, J=7.4 Hz, 0.6H); 8.50 (d, J=7.4 Hz, 0.4H). LCMS (A1): ES m/z=724 [M−H]⁻; m/z=726 [M+H]⁺; t_R=1.29 min.

Alpha and beta epoxides were separated by chiral liquid chromatography that was carried out on a 76×350 mm column packed with 1.1 kg of 10 μm Chiralpak AD (amylose tris-3,5-dimethylphenylcarbamate coated on a silica gel support, Chiral Technologies Europe) using isocratic elution with 75:25 heptane/EtOH. After concentration, 66 mg of example 11 were obtained as a white solid (45%) and 45 mg of the alpha epoxide were obtained as a white solid (31%).

RMN ¹H (500 MHz, δ in ppm, DMSO-d6): 0.82 to 0.89 (m, 12H); 0.99 (s, 3H); 1.03 (d, J=6.9 Hz, 3H); 1.19 (s, 3H); 1.34 (d, J=14.6 Hz, 1H); 1.80 (m, 1H); 1.98 (dd, J=10.1 and 14.6 Hz, 1H); 2.26 (m, 1H); 2.61 (m, 1H); 2.69 (dd, J=11.1 and 14.6 Hz, 1H); 2.91 (dd, J=2.1 and 7.8 Hz, 1H); 2.94 (dd, J=3.7 and 14.6 Hz, 1H); 3.42 (m, 1H); 3.80 (s, 3H); 3.91 (d, J=2.1 Hz, 1H); 4.03 to 4.14 (m, 2H); 4.50 (d, J=5.8 Hz, 2H); 5.03 (m, 1H); 5.19 (t, J=5.8 Hz, 1H); 5.89 (dd, J=2.1 and 15.5 Hz, 1H); 6.43 (ddd, J=4.7, 10.9 and 15.5 Hz, 1H); 7.03 (d, J=8.7 Hz, 1H); 7.20 (dd, J=2.3 and 8.7 Hz, 1H); 7.23 (d, J=8.4 Hz, 2H); 7.30 (d, J=2.3 Hz, 1H); 7.33 (d, J=8.4 Hz, 2H); 7.86 (d, J=8.4 Hz, 1H); 7.92 (d, J=7.1 Hz, 1H); 8.39 (d, J=9.1 Hz, 1H). LCMS (A1): ES m/z=724 [M−H]⁻; m/z=726 [M+H]⁺; t_R=1.29 min.

Compound 54: (3S,10R,16S,E)-16-((S)-1-((2R,3R)-3-(4-(azidomethyl)phenyl)oxiran-2-yl)ethyl)-10-(3-chloro-4-methoxybenzyl)-6,6,7-trimethyl-3-neopentyl-1-oxa-4,8,11-triazacyclohexadec-13-ene-2,5,9,12-tetraone Under argon, in a round bottom flask, to a solution of example 11 (66 mg, 90.87 μmol) in THF (5 mL) were added, at 0° C., DPPA (100.23 μl, 454.36 μmol) and DBU (69.27 μl, 454.36 μmol). The solution was stirred for 5 h at RT then diluted with H₂O and extracted with AcOEt (2×15 mL). The organic layer was separated, washed with sat. brine (2×5 mL), dried over MgSO₄, filtered, concentrated and purified on 15 g of silica gel (gradient elution DCM/iPrOH) to give 64 mg of compound 54 as a colorless solid (94%).

Example 12: (3S,10R,16S,E)-16-((S)-1-((2R,3R)-3-(4-(aminomethyl)phenyl)oxiran-2-yl)ethyl)-10-(3-chloro-4-methoxybenzyl)-6,6,7-trimethyl-3-neopentyl-1-oxa-4,8,11-triazacyclohexadec-13-ene-2,5,9,12-tetraone In a round bottom flask, to a solution of compound 54 (64 mg, 85.18 μmol) in DCM (3 mL), MeOH (3 mL) and H₂O (400 μL) was added TCEP (26.86 mg, 93.70 μmol). The reaction medium was stirred for 24 h at RT. The reaction mixture was diluted with DCM (15 mL) and sat. NaHCO₃, stirred for 10 min and extracted with DCM (3×15 mL). The combined organic layers were washed with sat. brine, dried over MgSO₄, filtered, concentrated and purified by flash chromatography on 4.5 g of amino-propyl modified silica gel (gradient elution DCM/MeOH) to give 42 mg of example 12 as a white solid (68%).

Compound 55: (9H-fluoren-9-yl)methyl ((2S)-1-(((2S)-1-((4-((2R,3R)-3-((1S)-1-((3S,10R,16S,E)-10-(3-chloro-4-methoxybenzyl)-6,6,7-trimethyl-3-neopentyl-2,5,9,12-tetraoxo-1-oxa-4,8,11-triazacyclohexadec-13-en-16-yl)ethyl)oxiran-2-yl)benzyl)amino)-1-oxopropan-2-yl)amino)-3-methyl-1-oxobutan-2-yl)carbamate Under argon, in a round bottom flask, were introduced example 12 (42 mg, 57.91 μmol) and DMF (1 mL), followed by FmocValAla (34.44 mg, 86.86 μmol), HOBt (13.20 mg, 93.81 µmol), DCM (10 mL) and EDC (10.36 µl, 57.91 µmol). The reaction medium was stirred for 3 h at RT and then diluted with H₂O (15 mL), stirred for 10 min at RT and extracted with DCM (3×20 mL). The combined organic layers were dried over MgSO₄, filtered and concentrated to give 83 mg of compound 55 as a white solid (quant.).

Compound 56: (2S)-2-amino-N-((2S)-1-((4-((2R,3R)-3-((1S)-1-((3S,10R,16S, E)-10-(3-chloro-4-methoxybenzyl)-6,6,7-trimethyl-3-neopentyl-2,5,9,12-tetraoxo-1-oxa-4,8,11-triazacyclohexadec-13-en-16-yl)ethyl)oxiran-2-yl)benzyl)amino)-1-oxopropan-2-yl)-3-methylbutanamide In a round bottom flask, piperidine (57.8 µL, 579.10 µmol) was added to a solution of compound 55 (64.73 mg, 57.91 µmol) in DCM (10 mL). After stirring 5 h, 57.8 µL of piperidine were added and the medium was stirred overnight at RT. The reaction medium was concentrated in vacuo and purified on 15 g of silica gel (gradient DCM/MeOH/H₂O) to give 30 mg of compound 56 as a colorless solid (58%).

RMN ¹H (500 MHz, δ in ppm, DMSO-d6): 0.86 (d, J=7.0 Hz, 3H); 0.82 to 0.90 (m, 15H); 1.00 (s, 3H); 1.03 (d, J=7.0 Hz, 3H); 1.19 (s, 3H); 1.24 (d, J=7.0 Hz, 3H); 1.34 (d, J=14.6 Hz, 1H); 1.66 (broad m, 2H); 1.80 (m, 1H); 1.91 (m, 1H); 1.98 (dd, J=10.2 and 14.6 Hz, 1H); 2.27 (m, 1H); 2.60 (m, 1H); 2.69 (dd, J=11.1 and 14.6 Hz, 1H); 2.91 (dd, J=2.0 and 7.7 Hz, 1H); 2.94 (dd, J=3.7 and 14.6 Hz, 1H); 2.99 (d, J=4.9 Hz, 1H); 3.43 (m, 1H); 3.80 (s, 3H); 3.91 (d, J=2.0 Hz, 1H); 4.03 to 4.12 (m, 2H); 4.29 (d, J=6.2 Hz, 2H); 4.34 (m, 1H); 5.03 (m, 1H); 5.89 (dd, J=1.8 and 15.6 Hz, 1H); 6.43 (ddd, J=4.8, 10.9 and 15.6 Hz, 1H); 7.02 (d, J=8.6 Hz, 1H); 7.20 (dd, J=2.2 and 8.6 Hz, 1H); 7.22 (d, J=8.4 Hz, 2H); 7.26 (d, J=8.4 Hz, 2H); 7.32 (d, J=2.2 Hz, 1H); 7.86 (d, J=8.4 Hz, 1H); 7.92 (d, J=7.2 Hz, 1H); 8.07 (broad d, J=7.9 Hz, 1H); 8.40 (d, J=7.3 Hz, 1H); 8.45 (t, J=6.2 Hz, 1H). LCMS (A1): ES m/z=448 [M+2H]²⁺; m/z=893 [M−H]⁻; m/z=895 [M+H]⁺; m/z=939 [M−H+HCO₂H]⁻; t$_R$=1.29 min.

Compound 57: 5-(((2S)-1-(((2S)-1-((4-((2R,3R)-3-((1S)-1-((3S,10R,16S,E)-10-(3-chloro-4-methoxybenzyl)-6,6,7-trimethyl-3-neopentyl-2,5,9,12-tetraoxo-1-oxa-4,8,11-triazacyclohexadec-13-en-16-yl)ethyl)oxiran-2-yl)benzyl)amino)-1-oxopropan-2-yl)amino)-3-methyl-1-oxobutan-2-yl)amino)-5-oxopentanoic acid Under argon, in a round bottom flask, a solution of glutaric anhydride (4.29 mg, 36.85 µmol) in DCM (2 mL) was added to a solution of compound 56 (30 mg, 33.5 µmol) in DCM (6 mL). The reaction medium was stirred for 2 h at RT, concentrated partially in vacuo and purified on 2.5 g of silica gel (gradient elution DCM/MeOH/H₂O) to give 34 mg of compound 57 as a colorless lacquer (quant.).

RMN ¹H (500 MHz, δ in ppm, DMSO-d6): 0.80 to 0.89 (m, 18H); 0.99 (s, 3H); 1.03 (d, J=7.0 Hz, 3H); 1.19 (s, 3H); 1.24 (d, J=7.0 Hz, 3H); 1.34 (d, J=14.6 Hz, 1H); 1.70 (m, 2H); 1.80 (m, 1H); 1.97 (m, 2H); 2.19 (m, 4H); 2.26 (m, 1H); 2.60 (m, 1H); 2.70 (dd, J=11.2 and 14.6 Hz, 1H); 2.90 (dd, J=2.2 and 7.8 Hz, 1H); 2.95 (dd, J=3.7 and 14.6 Hz, 1H); 3.43 (m, 1H); 3.80 (s, 3H); 3.91 (d, J=2.2 Hz, 1H); 4.03 to 4.18 (m, 3H); 4.22 to 4.33 (m, 3H); 5.03 (m, 1H); 5.90 (d, J=15.5 Hz, 1H); 6.43 (ddd, J=4.9, 11.0 and 15.5 Hz, 1H); 7.02 (d, J=8.6 Hz, 1H); 7.19 to 7.28 (m, 5H); 7.32 (d, J=2.2 Hz, 1H); 7.85 (broad d, J=8.9 Hz, 2H); 7.91 (d, J=7.2 Hz, 1H); 8.06 (broad d, J=7.5 Hz, 1H); 8.36 (broad t, J=6.6 Hz, 1H); 8.42 (d, J=7.8 Hz, 1H); 12.10 (broad m, 1H). LCMS (A1): ES m/z=1007 [M−H]⁻; m/z=1009 [M+H]⁺; t$_R$=1.21 min.

Example 13: 2,5-dioxopyrrolidin-1-yl 5-(((2S)-1-(((2S)-1-((4-((2R,3R)-3-((1S)-1-((3S,10R,16S,E)-10-(3-chloro-4-methoxybenzyl)-6,6,7-trimethyl-3-neopentyl-2,5,9,12-tetraoxo-1-oxa-4,8,11-triazacyclohexadec-13-en-16-yl)ethyl)oxiran-2-yl)benzyl)amino)-1-oxopropan-2-yl)amino)-3-methyl-1-oxobutan-2-yl)amino)-5-oxopentanoate Under argon, in a round bottom flask, to a solution of compound 57 (33 mg, 32.69 µmol) in DCM (8 mL) were added DSC (11.72 mg, 45.76 µmol) and DIEA (7.7 µL, 45.76 µmol). The reaction medium was stirred for 1 h at RT, concentrated in vacuo and purified by two successive flash chromatographies on 2.5 g of silica gel (gradient elution DCM/iPrOH) to give 17.9 mg of example 13 as a colorless solid (49%).

RMN ¹H (500 MHz, δ in ppm, DMSO-d6): 0.80 to 0.90 (m, 18H); 1.00 (s, 3H); 1.04 (d, J=7.0 Hz, 3H); 1.19 (s, 3H); 1.24 (d, J=7.0 Hz, 3H); 1.34 (d, J=14.6 Hz, 1H); 1.80 (m, 1H); 1.83 (m, 2H); 1.98 (m, 2H); 2.26 (m, 1H); 2.29 (m, 2H); 2.60 (m, 1H); 2.68 (t, J=7.5 Hz, 2H); 2.70 (dd, J=11.2 and 14.6 Hz, 1H); 2.80 (s, 4H); 2.91 (dd, J=2.2 and 7.6 Hz, 1H); 2.95 (dd, J=3.7 and 14.6 Hz, 1H); 3.43 (m, 1H); 3.80 (s, 3H); 3.90 (d, J=2.2 Hz, 1H); 4.06 to 4.15 (m, 2H); 4.18 (dd, J=6.9 and 8.7 Hz, 1H); 4.21 to 4.33 (m, 3H); 5.03 (m, 1H); 5.89 (d, J=15.5 Hz, 1H); 6.43 (ddd, J=4.9, 10.9 and 15.5 Hz, 1H); 7.02 (d, J=8.7 Hz, 1H); 7.20 (dd, J=2.3 and 8.7 Hz, 1H); 7.23 (d, J=8.4 Hz, 2H); 7.25 (d, J=8.4 Hz, 2H); 7.31 (d, J=2.3 Hz, 1H); 7.84 (d, J=8.6 Hz, 1H); 7.89 (m, 2H); 8.04 (d, J=7.5 Hz, 1H); 8.33 (t, J=6.5 Hz, 1H); 8.39 (d, J=7.6 Hz, 1H). LCMS (A1): ES m/z=796; m/z=1104 [M−H]⁻; m/z=1106 [M+H]⁺; m/z=1150 [M−H+HCO₂H]⁻; t$_R$=1.26 min.

Example 14: mAb-Ex13

The general method described previously was used for the preparation of example 14. 60 mg of hu2H11_R35-74 were reacted with 200 µL of a 10.05 mM solution of example 13 in DMA (5 eq.) for 2 h. At that time, 180 µL of the solution of example 13 (4.5 eq.) were added and the medium stirred for 2 h. After purification on Superdex 200 pg in buffer B pH 6.5+10% NMP, concentration on Amicon Ultra-15, buffer exchange on PD-10 in buffer B pH 6.5+5% NMP and filtration on Steriflip, 46 mg of example 14 were obtained as a colorless limpid solution at a concentration of 2 mg/mL with a DAR of 3.5 (HRMS), a monomeric purity of 99.7% and a global yield of 77%.

SEC-HRMS: spectrum for intact ADC in FIG. 4; m/z=149336 (naked mAb); m/z=150328 (D1); m/z=151319 (D2); m/z=152311 (D3); m/z=153302 (D4); m/z=154295 (D5); m/z=155290 (D6); m/z=156282 (D7).

Example 15: (3S,10R,16S,E)-10-(3-chloro-4-methoxybenzyl)-16-((S)-1-(3-(4-(hydroxy-methyl)phenyl)oxiran-2-yl)ethyl)-3,6,6-trimethyl-1-oxa-4,8,11-triazacyclohexadec-13-ene-2,5,9,12-tetraone

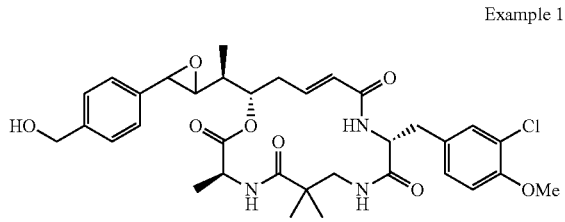

Example 15

Example 15 was prepared following general route B depicted in Scheme 2 and described for examples 4 and 11.

RMN $^1$H (500 MHz, δ in ppm, DMSO-d6): 65/35 diastereoisomer mixture; 0.93 to 1.26 (m, 12H); 1.75 (m, 0.65H); 1.83 (m, 0.35H); 2.22 (m, 0.65H); 2.41 (m, 0.35H); 2.55 to 2.70 (m, 2H); 2.81 (d, J=13.7 Hz, 0.65H); 2.88 (d, J=13.7 Hz, 0.35H); 2.93 (dd, J=2.1 and 8.2 Hz, 0.65H); 3.00 (m, 1.35H); 3.22 to 3.35 (partially masked m, 1H); 3.77 (d, J=2.1 Hz, 0.35H); 3.81 (s, 3H); 3.88 (d, J=2.1 Hz, 0.65H); 4.25 to 4.39 (m, 1.65H); 4.34 (m, 0.35H); 4.48 (d, J=6.0 Hz, 0.7H); 4.50 (d, J=6.0 Hz, 1.3H); 5.08 (m, 1H); 5.17 (t, J=6.0 Hz, 0.35H); 5.20 (t, J=6.0 Hz, 0.65H); 5.78 (dd, J=1.9 and 15.5 Hz, 0.65H); 5.89 (dd, J=1.9 and 15.5 Hz, 0.35H); 6.40 (m, 1H); 7.04 (d, J=8.7 Hz, 1H); 7.16 (dd, J=2.2 and 8.7 Hz, 0.65H); 7.19 (dd, J=2.2 and 8.7 Hz, 0.35H); 7.20 to 7.34 (m, 5H); 7.58 (broad d, J=10.2 Hz, 0.65H); 7.64 (broad d, J=10.2 Hz, 0.35H); 8.00 (d, J=8.4 Hz, 0.65H); 8.07 (d, J=8.4 Hz, 0.35H); 8.35 (d, J=8.3 Hz, 0.65H); 8.44 (d, J=8.3 Hz, 0.35H). LCMS (A1): ES m/z=654 [M−H]$^−$; m/z=656 [M+H]$^+$; $t_R$=1.06 min.

Example 16: (3S,10R,16S,E)-10-(3-chloro-4-methoxybenzyl)-16-((S)-1-(3-(4-(hydroxy-methyl)phenyl)oxiran-2-yl)ethyl)-6,6-dimethyl-3-isopropyl-1-oxa-4,8,11-triazacyclohexadec-13-ene-2,5,9,12-tetraone

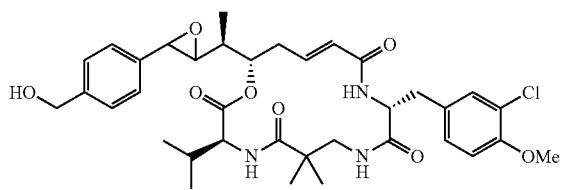

Example 16

Example 16 was prepared following general route B depicted in Scheme 2 and described for examples 4 and 11.

RMN $^1$H (500 MHz, δ in ppm, DMSO-d6): 60/40 diastereoisomer mixture; 0.72 (d, J=7.0 Hz, 1.8H); 0.82 (d, J=7.0 Hz, 1.2H); 0.84 (d, J=7.0 Hz, 1.8H); 0.87 (d, J=7.0 Hz, 1.2H); 0.98 (s, 1.8H); 0.99 (d, J=7.0 Hz, 1.8H); 1.01 (s, 1.2H); 1.05 (d, J=7.0 Hz, 1.2H); 1.09 (s, 1.8H); 1.11 (s, 1.2H); 1.82 (m, 1H); 1.91 (m, 0.6H); 2.01 (m, 0.4H); 2.30 (m, 1H); 2.52 to 2.72 (m, 2H); 2.88 to 3.04 (m, 3H); 3.25 to 3.35 (masked m, 1H); 3.79 (d, J=2.2 Hz, 0.4H); 3.80 (s, 3H); 3.88 (d, J=2.2 Hz, 0.6H); 4.09 to 4.21 (m, 2H); 4.48 (d, J=5.8 Hz, 0.8H); 4.50 (d, J=5.8 Hz, 1.2H); 5.14 to 5.29 (m, 2H); 5.79 (dd, J=1.7 and 15.4 Hz, 0.6H); 5.90 (dd, J=1.7 and 15.4 Hz, 0.4H); 6.40 to 6.52 (m, 1H); 7.05 (d, J=8.7 Hz, 1H); 7.10 (dd, J=2.0 and 10.2 Hz, 1H); 7.17 (m, 1H); 7.21 to 7.35 (m, 5H); 7.70 (d, J=9.3 Hz, 0.6H); 7.80 (d, J=9.3 Hz, 0.4H); 8.39 (d, J=8.0 Hz, 0.6H); 8.44 (d, J=8.0 Hz, 0.4H). LCMS (A1): ES m/z=682 [M−H]$^−$; m/z=684 [M+H]$^+$; $t_R$=1.16 min.

Example 17: (3S,10R,16S,E)-10-(3-chloro-4-methoxybenzyl)-16-((S)-1-(3-(4-(hydroxy-methyl)phenyl)oxiran-2-yl)ethyl)-3-tert-butyl-6,6-dimethyl-1-oxa-4,8,11-triazacyclohexadec-13-ene-2,5,9,12-tetraone

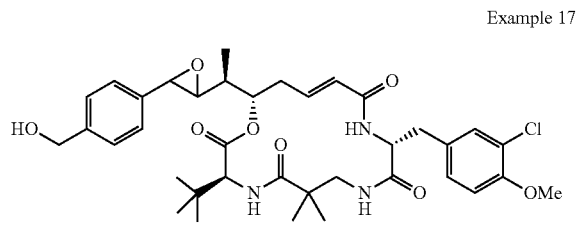 [SMILES: COc1ccc(C[C@H]2NC(=O)/C=C/C[C@@H]([C@H](C)C3OC3c3ccc(CO)cc3)OC(=O)[C@H](C(C)(C)C)NC(=O)C(C)(C)CNC2=O)cc1Cl]

Example 17

Example 17 was prepared following general route B depicted in Scheme 2 and described for examples 4 and 11.

RMN $^1$H (400 MHz, δ in ppm, DMSO-d6): 50/50 diastereoisomer mixture; 0.90 (s, 4.5H); 0.91 (s, 4.5H); 1.00 (d, J=7.0 Hz, 1.5H); 1.03 (s, 1.5H); 1.05 (s, 1.5H); 1.06 (d, J=7.0 Hz, 1.5H); 1.10 (s, 1.5H); 1.12 (s, 1.5H); 1.85 (m, 1H); 2.32 (m, 1H); 2.55 to 2.72 (m, 2H); 2.90 to 3.03 (m, 3H); 3.25 to 3.35 (masked m, 1H); 3.81 (s, 3H); 3.90 (d, J=2.2 Hz, 1H); 4.15 (m, 1H); 4.36 (d, J=10.0 Hz, 0.5H); 4.43 (d, J=10.0 Hz, 0.5H); 4.49 (d, J=5.9 Hz, 1H); 4.51 (d, J=5.9 Hz, 1H); 5.15 (t, J=5.9 Hz, 0.5H); 5.18 (t, J=5.9 Hz, 0.5H); 5.29 (m, 1H); 5.79 (dd, J=2.0 and 15.4 Hz, 0.5H); 5.90 (d, J=15.4 Hz, 0.5H); 6.39 (m, 1H); 6.91 (dd, J=2.5 and 10.4 Hz, 0.5H); 6.98 (dd, J=2.5 and 10.4 Hz, 0.5H); 7.05 (split d, J=8.7 Hz, 1H); 7.15 (split dd, J=2.4 and 8.7 Hz, 1H); 7.20 to 7.39 (m, 6H); 8.32 (d, J=7.9 Hz, 0.5H); 8.40 (d, J=7.9 Hz, 0.5H). LCMS (A4): ES m/z=696 [M−H]$^−$; m/z=698 [M+H]$^+$; $t_R$=4.13-4.16 min.

Example 18: (3S,10R,16S,E)-16-((S)-1-((2R,3R)-3-(4-(aminomethyl)phenyl)oxiran-2-yl)ethyl)-10-(3-chloro-4-methoxybenzyl)-3-isobutyl-6,6,7-trimethyl-1-oxa-4,8,11-triazacyclohexadec-13-ene-2,5,9,12-tetraone Example 18

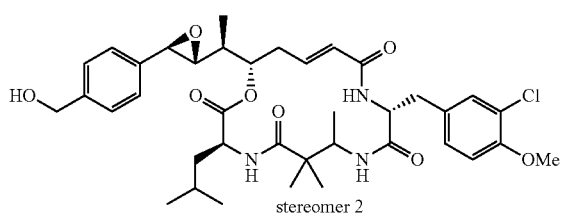

stereomer 2

Example 18 was prepared following general route A depicted in Scheme 1 and described for example 8.

RMN $^1$H (500 MHz, δ in ppm, DMSO-d6): 0.78 (d, J=7.0 Hz, 3H); 0.84 (d, J=7.0 Hz, 3H); 0.87 (d, J=7.0 Hz, 3H); 1.00 (s, 3H); 1.03 (d, J=7.0 Hz, 3H); 1.19 (s, 3H); 1.30 (m, 1H); 1.50 to 1.90 (m, 5H); 2.28 (m, 1H); 2.55 to 2.76 (m, 2H); 2.90 to 3.00 (m, 2H); 3.48 (m, 1H); 3.70 (s, 2H); 3.80 (s, 3H); 3.89 (s, 1H); 4.02 to 4.15 (m, 2H); 5.06 (m, 1H); 5.88 (d, J=15.5 Hz, 1H); 6.47 (m, 1H); 7.03 (d, J=8.7 Hz, 1H); 7.20 (m, 3H); 7.31 (m, 3H); 7.80 (d, J=8.7 Hz, 1H); 7.89 (d, J=7.3 Hz, 1H); 8.41 (d, J=8.2 Hz, 1H).

Example 19: 2,5-dioxopyrrolidin-1-yl 5-(((S)-1-(((S)-1-((4-((2R,3R)-3-((S)-1-((3S,10R,16S,E)-10-(3-chloro-4-methoxybenzyl)-3-isobutyl-6,6,7-trimethyl-2,5,9,12-tetraoxo-1-oxa-4,8,11-triazacyclohexadec-13-en-16-yl)ethyl)oxiran-2-yl)benzyl)amino)-1-oxopropan-2-yl)amino)-3-methyl-1-oxobutan-2-yl)amino)-5-oxopentanoate Example 19

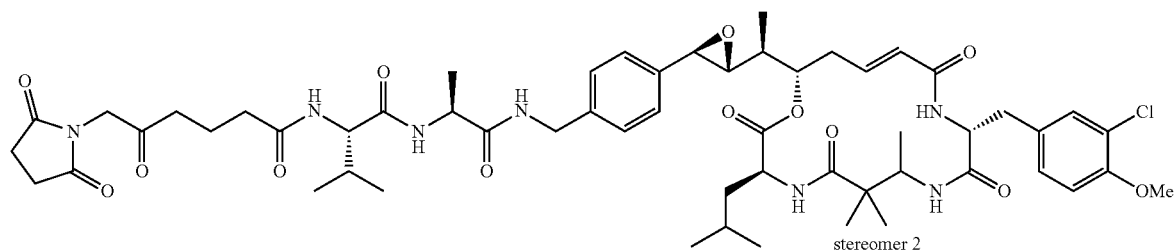

stereomer 2

Example 19 was prepared as depicted in Scheme 3 and described for examples 2, 6, 9 and 13.

RMN $^1$H (500 MHz, δ in ppm, DMSO-d6): 0.79 (d, J=7.0 Hz, 3H); 0.81 to 0.89 (m, 18H); 1.01 (s, 3H); 1.03 (d, J=7.0 Hz, 3H); 1.20 (s, 3H); 1.24 (d, J=7.0 Hz, 3H); 1.31 (m, 1H); 1.60 to 1.74 (m, 2H); 1.78 to 1.86 (m, 3H); 1.96 (m, 1H); 2.21 to 2.31 (m, 3H); 2.55 to 2.72 (m, 4H); 2.80 (s, 4H); 2.96 (m, 2H); 3.47 (m, 1H); 3.80 (s, 3H); 3.89 (d, J=2.2 Hz, 1H); 4.03 to 4.14 (m, 2H); 4.17 (dd, J=6.8 and 8.6 Hz, 1H); 4.21 to 4.33 (m, 3H); 5.06 (m, 1H); 5.89 (d, J=15.5 Hz, 1H); 6.47 (ddd, J=5.2, 10.5 and 15.5 Hz, 1H); 7.02 (d, J=8.7 Hz, 1H); 7.20 (dd, J=2.3 and 8.7 Hz, 1H); 7.23 (m, 4H); 7.32 (d, J=2.3 Hz, 1H); 7.80 (d, J=8.3 Hz, 1H); 7.89 (m, 2H); 8.04 (d, J=7.6 Hz, 1H); 8.32 (t, J=6.3 Hz, 1H); 8.42 (d, J=7.6 Hz, 1H). LCMS (A1): ES m/z=1092 [M+H]$^+$; m/z=1136 [M−H+HCO$_2$H]$^-$; t$_R$=1.23 min.

Example 20: mAb-Ex19

Example 20

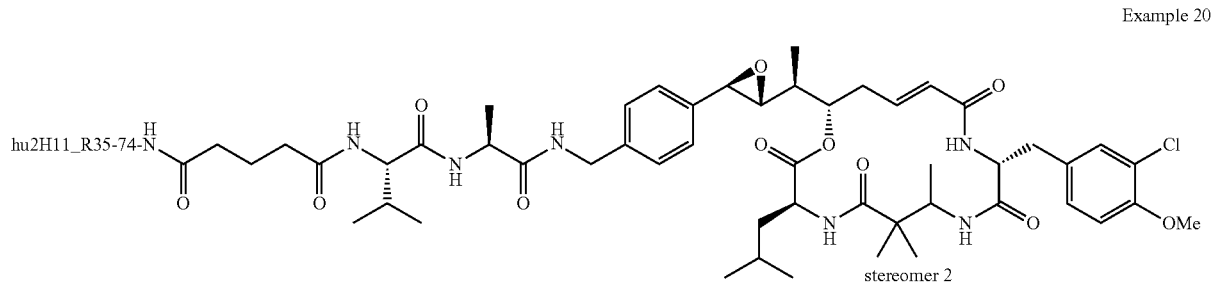

stereomer 2

Example 20 was prepared in a similar way to examples 3, 7, 10 and 14. 45 mg of example 20 were obtained as a colorless limpid solution at a concentration of 2.55 mg/mL with a DAR of 4.4 (HRMS), a monomeric purity of 99.1% and a global yield of 78%.

SEC-HRMS: spectrum for intact ADC in FIG. 5; m/z=150368 (D1); m/z=151350 (D2); m/z=152327 (D3); m/z=153304 (D4); m/z=154281 (D5); m/z=155255 (D6); m/z=156237(D7); m/z=157217 (D8).

Example 21: (3S,10R,16S,E)-16-((S)-1-(3-(4-(aminomethyl)phenyl)oxiran-2-yl)ethyl)-10-(3-chloro-4-methoxybenzyl)-7-cyclopropyl-3-isobutyl-6,6-dimethyl-1-oxa-4,8,11-triazacyclo-hexadec-13-ene-2,5,9,12-tetraone Example 21
Example 22

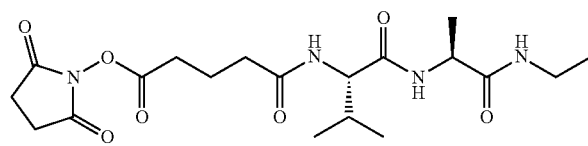

Example 21 was prepared following general route A depicted in Scheme 1 and described for examples 1 and 8.

Example 22: 2,5-dioxopyrrolidin-1-yl 5-(((S)-1-(((S)-1-((4-((2R,3R)-3-((3S,10R,16S,E)-10-(3-chloro-4-methoxybenzyl)-7-cyclopropyl-3-isobutyl-6,6-dimethyl-1,2,5,9,12-pentaoxo-1-oxa-4,8,11-triazacyclohexadec-13-en-16-yl)-2-methyloxiran-2-yl)benzyl)amino)-1-oxopropan-2-yl)amino)-3-methyl-1-oxobutan-2-yl)amino)-5-oxopentanoate Example 22 was prepared as depicted in Scheme 3 and described for example 16.

RMN 1H (500 MHz, δ in ppm, DMSO-d6): 0.34 (m, 1H); 0.66 (m, 1H); 0.74 (d, J=7.0 Hz, 3H); 0.76 (d, J=6.7 Hz, 3H); 0.78 (s, 3H); 0.80 (m, 1H); 0.82 (d, J=7.0 Hz, 3H); 0.85 (d, J=7.0 Hz, 3H); 0.96 (d, J=7.0 Hz, 3H); 1.06 (s, 3H); 1.11 (m, 1H); 1.20 (m, 1H); 1.23 (d, J=7.0 Hz, 3H); 1.43 to 1.54 (m, 2H); 1.78 (m, 1H); 1.82 (m, 2H); 1.98 (m, 1H); 2.22 (m, 1H); 2.28 (m, 2H); 2.65 (m, 3H); 2.79 (m, 1H); 2.81 (s, 4H); 2.97 (dd, J=2.2 and 7.9 Hz, 1H); 3.80 (s, 3H); 3.89 (d, J=2.2 Hz, 1H); 4.02 (m, 1H); 4.17 (dd, J=6.7 and 8.7 Hz, 1H); 4.27 (d, J=6.3 Hz, 2H); 4.30 (m, 1H); 4.37 (m, 1H); 5.10 (m, 1H); 5.79 (dd, J=1.8 and 15.5 Hz, 1H); 6.39 (ddd, J=4.0, 11.6 and 15.5 Hz, 1H); 7.02 (d, J=8.7 Hz, 1H); 7.11 (dd, J=2.3 and 8.7 Hz, 1H); 7.20 (d, J=2.3 Hz, 1H); 7.22 (m, 4H); 7.46 (s, 1H); 7.77 (d, J=9.0 Hz, 1H); 7.89 (d, J=8.6 Hz, 1H); 8.05 (d, J=7.5 Hz, 1H); 8.29 (d, J=7.6 Hz, 1H); 8.32 (t, J=6.3 Hz, 1H).

Example 23: mAb-Ex22

Example 23

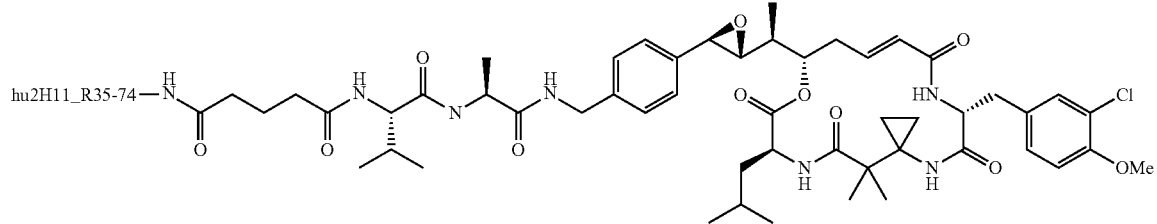

Example 23 was prepared in a similar way to examples 3, 7, 10 and 14. 45 mg of example 23 were obtained as a colorless limpid solution at a concentration of 2.14 mg/mL with a DAR of 3.6 (HRMS), a monomeric purity of 100% and a global yield of 75%.

SEC-HRMS: spectrum for intact ADC in FIG. 6; m/z=150341 (D1); m/z=151329 (D2); m/z=152317 (D3); m/z=153308 (D4); m/z=154296 (D5); m/z=155287 (D6); m/z=156279 (D7); m/z=157267 (D8).

Example 24: (3S,7S,10R,16S,E)-16-((S)-1-((2R, 3R)-3-(4-(azidomethyl)phenyl)oxiran-2-yl)-ethyl)-10-(3-chloro-4-methoxybenzyl)-6,6,7-trimethyl-3-neopentyl-1-oxa-4,8,11-triazacyclohexadec-13-ene-2,5,9,12-tetraone Example 25: (3S,7S,10R,16S,E)-16-((S)-1-((2R, 3R)-3-(4-(aminomethyl)phenyl)oxiran-2-yl)ethyl)-10-(3-chloro-4-methoxybenzyl)-6,6,7-trimethyl-3-neopentyl-1-oxa-4,8,11-triazacyclohexadec-13-ene-2,5,9,12-tetraone

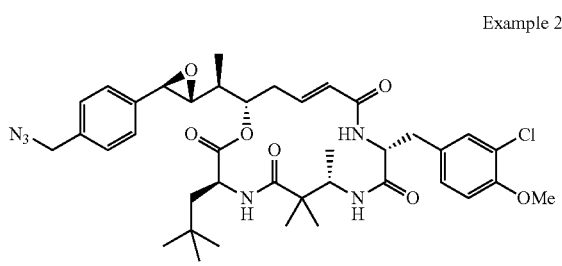

Example 24

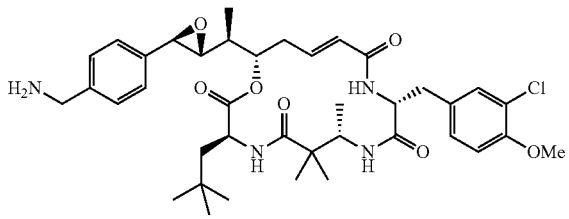

Example 25

Example 24 was prepared following general route C depicted in Scheme 3 and described for example 32.

RMN ¹H (500 MHz, δ in ppm, DMSO-d6): 0.83 (s, 9H); 0.88 (d, J=6.8 Hz, 3H); 1.00 (s, 3H); 1.03 (d, J=7.1 Hz, 3H); 1.19 (s, 3H); 1.33 (d, J=14.5 Hz, 1H); 1.84 (m, 1H); 1.97 (dd, J=9.8 and 14.5 Hz, 1H); 2.27 (dd, J=11.1 and 14.5 Hz, 1H); 2.61 (m, 1H); 2.69 (dd, J=11.1 and 14.2 Hz, 1H); 2.92 (dd, J=2.1 and 7.7 Hz, 1H); 2.96 (dd, J=3.6 and 14.2 Hz, 1H); 3.43 (m, 1H); 3.80 (s, 3H); 3.96 (d, J=2.1 Hz, 1H); 4.08 (ddd, J=3.6, 7.1 and 11.1 Hz, 1H); 4.12 (m, 1H); 4.46 (s, 2H); 5.05 (ddd, J=1.3, 3.9 and 11.3 Hz, 1H); 5.90 (dd, J=1.3 and 15.3 Hz, 1H); 6.45 (ddd, J=4.7, 10.7 and 15.3 Hz, 1H); 7.02 (d, J=8.7 Hz, 1H); 7.20 (dd, J=2.4 and 8.7 Hz, 1H); 7.32 (m, 3H); 7.40 (d, J=8.4 Hz, 2H); 7.88 (d, J=8.4 Hz, 1H); 7.92 (d, J=7.1 Hz, 1H); 8.40 (d, J=7.4 Hz, 1H). LCMS (A5): ES m/z=749 [M–H]⁻; m/z=751 [M–H]⁺; m/z=795 [M–H+HCO₂H]⁻; $t_R$=1.52 min.

Example 25 was prepared as described for examples 1, 5, 8 and 11.

RMN ¹H (400 MHz, δ in ppm, DMSO-d6): 0.86 (s, 9H); 0.88 (d, J=6.9 Hz, 3H); 0.98 (s, 3H); 1.02 (d, J=7.1 Hz, 3H); 1.18 (s, 3H); 1.34 (d, J=14.5 Hz, 1H); 1.80 (m, 1H); 1.98 (dd, J=9.8 and 14.5 Hz, 1H); 2.27 (dd, J=11.1 and 14.5 Hz, 1H); 2.40 (broad m, 2H); 2.62 (m, 1H); 2.68 (dd, J=11.1 and 14.2 Hz, 1H); 2.90 (dd, J=2.1 and 7.7 Hz, 1H); 2.96 (dd, J=3.6 and 14.2 Hz, 1H); 3.43 (m, 1H); 3.76 (s, 2H); 3.80 (s, 3H); 3.91 (d, J=2.1 Hz, 1H); 4.02 to 4.15 (m, 2H); 5.04 (ddd, J=1.3, 3.9 and 11.3 Hz, 1H); 5.88 (dd, J=1.3 and 15.4 Hz, 1H); 6.45 (ddd, J=4.7, 10.7 and 15.3 Hz, 1H); 7.03 (d, J=8.5 Hz, 1H); 7.20 (dd, J=2.2 and 8.5 Hz, 1H); 7.23 (d, J=8.3 Hz, 2H); 7.32 (d, J=2.2 Hz, 2H); 7.36 (d, J=8.3 Hz, 2H); 7.86 (d, J=8.3 Hz, 1H); 7.93 (d, J=6.9 Hz, 1H); 8.40 (d, J=7.1 Hz, 1H). LCMS (A5): ES m/z=723 [M–H]⁻; m/z=725 [M–H]+; m/z=769 [M–H+HCO₂H]⁻; $t_R$=0.87 min.

Synthesis of Examples 26 to 28: 3-(S)-neopentyl-7-(S)-Me-aza-C52 benzylic Alcohol, NHS ester of glutaryl-Val-Ala-EDA-3-(S)-neopentyl-7-(S)-Me-aza-C52 benzylic Alcohol and Corresponding ADC

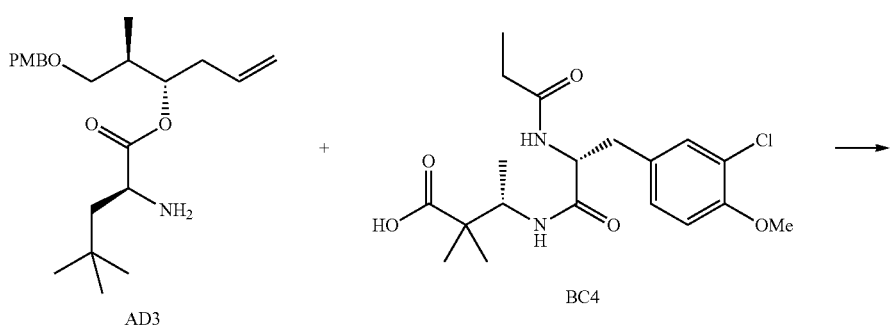

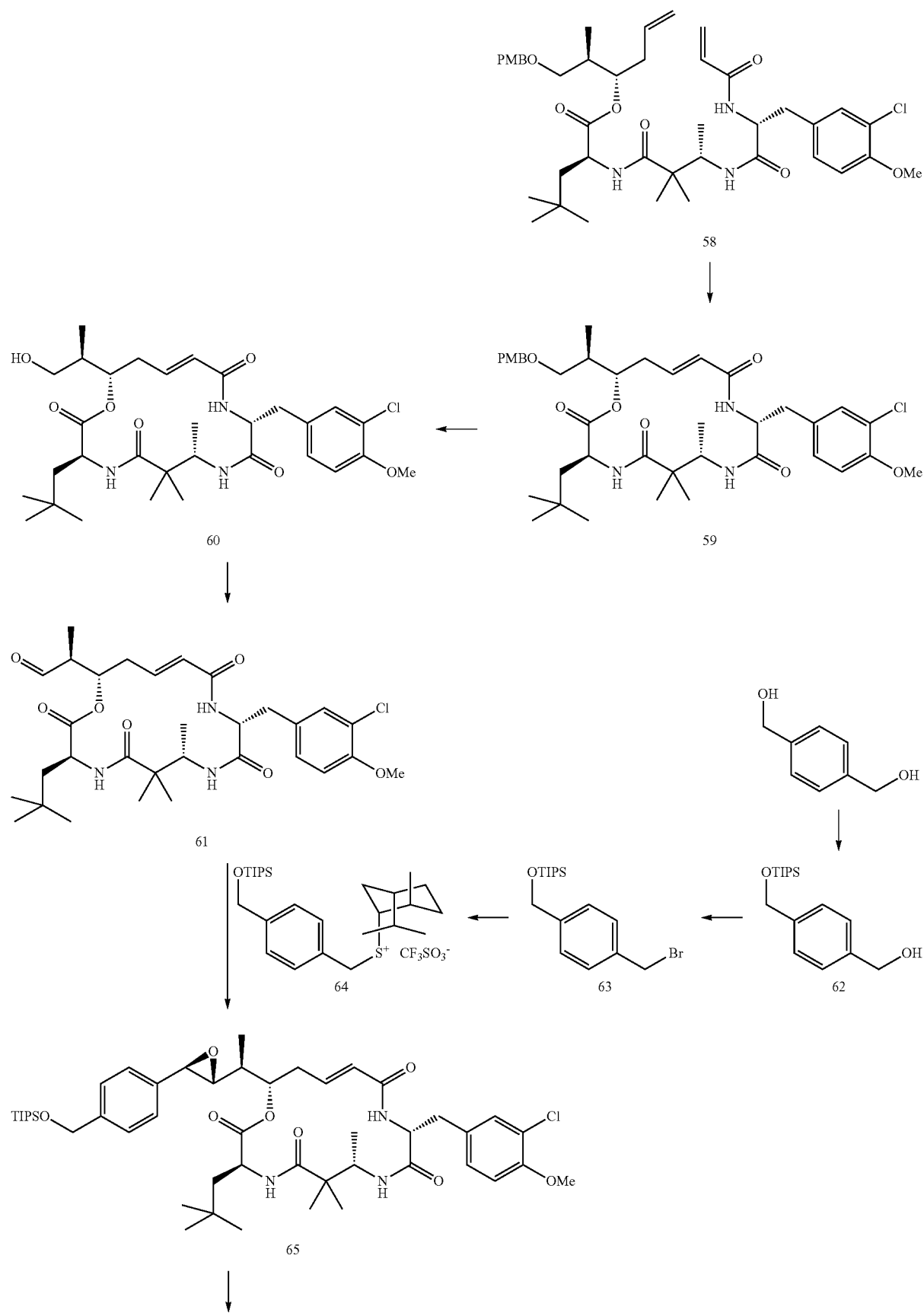

-continued
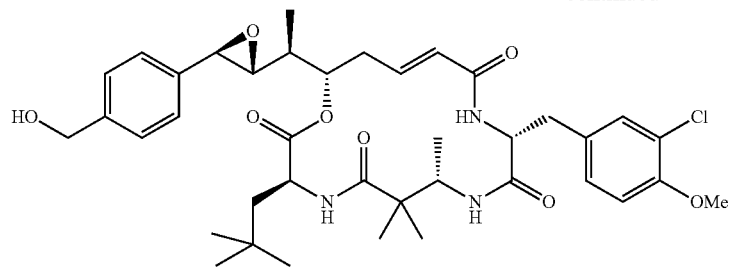
Example 26
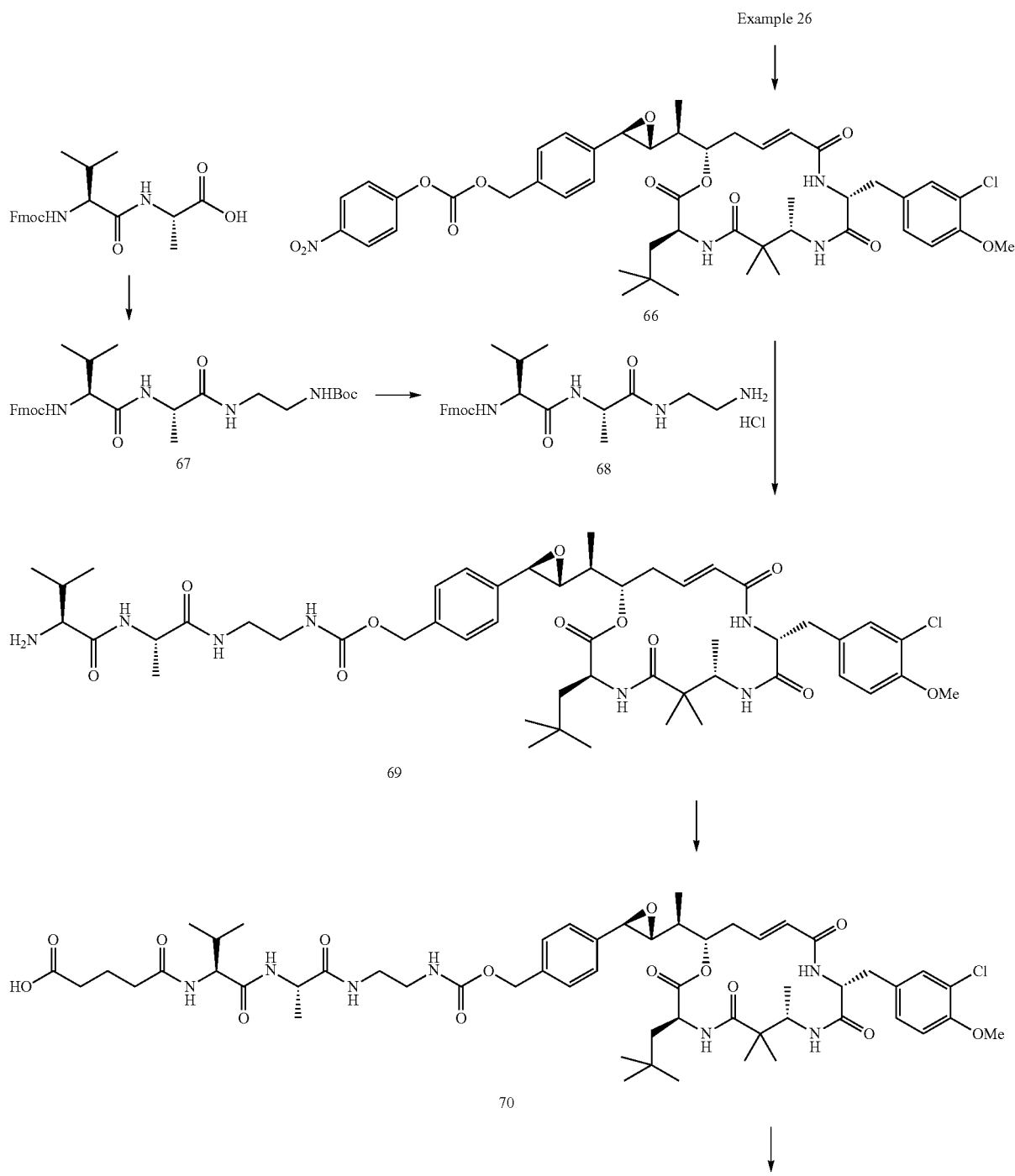

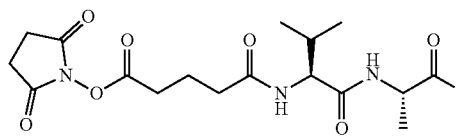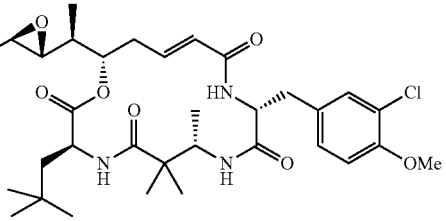

Example 27

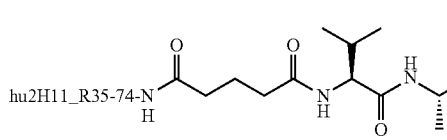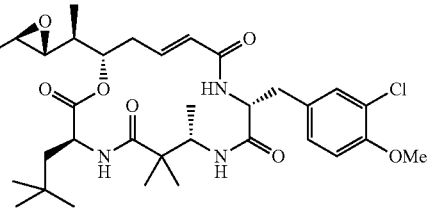

Example 28

Compound 58: (2R,3S)-1-((4-methoxybenzyl)oxy)-2-methylhex-5-en-3-yl (S)-2-((S)-3-((R)-2-acrylamido-3-(3-chloro-4-methoxyphenyl)propanamido)-2,2-dimethylbutanamido)-4,4-dimethylpentanoate To a solution of compound BC4 (365 mg, 919.7 µmol) in DMF (12 mL) were added HATU (402 mg, 1.06 mmol) and HOAt (144 mg, 1.06 mmol), the reaction medium was stirred at RT for 30 min then were added a solution of compound AD3 (365 mg, 965.7 µmol) in DMF (5 mL) and DIEA (562 µL, 3.22 mmol). The reaction medium was stirred at RT for 4 h, then diluted with H₂O (50 mL) and extracted with EtOAc (3×50 mL). The combined organic phases were washed with H₂O (15 mL), sat. brine (3×15 mL), dried over MgSO₄, filtered, concentrated in vacuo and purified by two successive flash chromatographies on 30 g of silica gel (gradient elution DCM/MeOH and heptane/EtOAc) to give 564 mg of compound 58 as a colorless foam (81%).

RMN ¹H (400 MHz, δ in ppm, DMSO-d6): 0.83 (d, J=6.9 Hz, 3H); 0.85 (s, 9H); 0.87 (d, J=6.9 Hz, 3H); 1.00 (s, 3H); 1.03 (s, 3H); 1.55 (dd, J=2.4 and 14.5 Hz, 1H); 1.78 (dd, J=9.5 and 14.5 Hz, 1H); 1.96 (m, 1H); 2.20 (m, 1H); 2.30 (m, 1H); 2.72 (dd, J=9.6 and 13.9 Hz, 1H); 2.87 (dd, J=5.3 and 13.9 Hz, 1H); 3.20 (dd, J=6.5 and 9.5 Hz, 1H); 3.37 (dd, J=5.4 and 9.5 Hz, 1H); 3.76 (s, 3H); 3.80 (s, 3H); 4.19 (m, 1H); 4.28 (m, 1H); 4.34 (s, 2H); 4.55 (m, 1H); 4.82 (m, 1H); 5.00 (d, J=10.2 Hz, 1H); 5.07 (d, J=17.4 Hz, 1H); 5.55 (dd, J=2.3 and 10.2 Hz, 1H); 5.71 (m, 1H); 6.01 (dd, J=2.3 and 17.1 Hz, 1H); 6.28 (dd, J=10.2 and 17.1 Hz, 1H); 6.90 (d, J=8.7 Hz, 2H); 7.02 (d, J=8.6 Hz, 1H); 7.17 (dd, J=2.3 and 8.6 Hz, 1H); 7.22 (d, J=8.7 Hz, 2H); 7.32 (d, J=2.3 Hz, 1H); 7.65 (d, J=9.5 Hz, 1H); 7.70 (d, J=7.9 Hz, 1H); 8.35 (d, J=8.4 Hz, 1H). LCMS (A5): ES m/z=754 [M−H]⁻; m/z=756 [M−H]+; m/z=800 [M−H+HCO₂H]⁻; $t_R$=1.62 min.

Compound 59: (3S,7S,10R,16S, E)-10-(3-chloro-4-methoxybenzyl)-16-((R)-1-((4-methoxy-benzyl)oxy)propan-2-yl)-6,6,7-trimethyl-3-neopentyl-1-oxa-4,8,11-triazacyclohexadec-13-ene-2,5,9,12-tetraone To a solution of compound 58 (560 mg, 740.4 µmol) in DCM (56 mL) was added under Ar Grubbs I catalyst (31.0 mg, 37.02 µmol). The reaction medium was stirred at RT for 1 h 30 before the addition of 31.0 mg of catalyst. Stirring was carried on at RT for 1 h 30 before the addition of 31.0 mg of catalyst. Stirring was carried on at RT for 1 h 30 before the addition of 31.0 mg of catalyst and the reaction medium was stirred at RT for 1 h 30. It was the concentrated in vacuo and purified by flash chromatography on 25 g of silica gel (gradient elution DCM/MeOH) to give 330 mg of compound 59 (61%) and 220 mg that were further purified by flash chromatography on 15 g of silica gel (gradient elution DCM/MeOH) to give 204 mg of compound 59 (37%) as a mixture with tricyclohexylphosphine oxide.

RMN ¹H (400 MHz, δ in ppm, DMSO-d6): 0.85 (s, 9H); 0.88 (d, J=6.9 Hz, 3H); 0.91 (d, J=7.1 Hz, 3H); 1.04 (s, 3H); 1.20 (s, 3H); 1.29 (d, J=14.5 Hz, 1H); 1.95 (dd, J=9.8 and 14.5 Hz, 1H); 1.99 (m, 1H); 2.26 (m, 1H); 2.43 (m, 1H); 2.72 (dd, J=10.1 and 14.3 Hz, 1H); 2.97 (dd, J=3.6 and 14.3 Hz, 1H); 3.27 (dd, J=6.1 and 9.3 Hz, 1H); 3.40 (dd, J=5.8 and 9.3 Hz, 1H); 3.46 (m, 1H); 3.72 (s, 3H); 3.80 (s, 3H); 4.10 (m, 1H); 4.13 (m, 1H); 4.38 (s, 2H); 4.97 (m, 1H); 5.93 (d, J=15.4 Hz, 1H); 6.43 (ddd, J=4.8, 10.7 and 15.4 Hz, 1H); 6.90 (d, J=8.7 Hz, 2H); 7.02 (d, J=8.6 Hz, 1H); 7.17 (d, J=8.6 Hz, 3H); 7.36 (d, J=2.3 Hz, 1H); 7.88 (m, 2H); 8.48 (d, J=7.5

Hz, 1H). LCMS (A5): ES m/z=726 [M−H]⁻; m/z=728 [M+H]⁺; m/z=772 [M−H+HCO₂H]⁻; t_R=1.54 min.

Compound 60: (3S,7S,10R,16S,E)-10-(3-chloro-4-methoxybenzyl)-16-((R)-1-hydroxypropan-2-yl)-6,6,7-trimethyl-3-neopentyl-1-oxa-4,8,11-triazacyclo-hexadec-13-ene-2,5,9,12-tetraone Compound 59 (532 mg, 730.4 µmol) was treated with a solution of TFA (3.93 mL) in DCM (36 mL) at RT for 30 min. The reaction medium was poured on 9% aq. NaHCO₃ (130 mL) under magnetic stirring. Stirring was carried on for 30 min then the aqueous phase was extracted with DCM (2×70 mL). The combined organic phases were washed with H₂O (3×20 mL), dried over MgSO₄, filtered, concentrated in vacuo and purified by flash chromatography on 30 g of silica gel (gradient elution DCM/MeOH) to give 299 mg of compound 60 as a white foam (67%).

RMN ¹H (400 MHz, δ in ppm, DMSO-d6): 0.88 (d, J=6.9 Hz, 3H); 0.89 (s, 9H); 0.90 (d, J=7.0 Hz, 3H) 1.03 (s, 3H); 1.20 (s, 3H); 1.36 (dd, J=1.8 and 14.5 Hz, 1H); 1.80 (m, 1H); 1.96 (dd, J=9.6 and 14.5 Hz, 1H); 2.25 (m, 1H); 2.43 (m, 1H); 2.72 (dd, J=11.1 and 14.3 Hz, 1H); 2.97 (dd, J=3.8 and 14.3 Hz, 1H); 3.25 (m, 1H); 3.45 (m, 2H); 3.80 (s, 3H); 4.10 (m, 1H); 4.16 (m, 1H); 4.57 (t, J=5.3 Hz, 1H); 4.98 (m, 1H); 5.93 (dd, J=1.3 and 15.3 Hz, 1H); 6.45 (ddd, J=4.9, 10.7 and 15.3 Hz, 1H); 7.02 (d, J=8.6 Hz, 1H); 7.22 (dd, J=2.3 and 8.6 Hz, 1H); 7.36 (d, J=2.3 Hz, 1H); 7.89 (m, 2H); 8.48 (d, J=7.3 Hz, 1H). LCMS (A5): ES m/z=606 [M−H]⁻; m/z=608 [M+H]⁺; t_R=1.2 min.

Compound 61: (S)-2-((3S,7S,10R,16S, E)-10-(3-chloro-4-methoxybenzyl)-6,6,7-trimethyl-3-neopentyl-2,5,9,12-tetraoxo-1-oxa-4,8,11-triazacyclohexadec-13-en-16-yl)propanal To a solution of compound 60 (297 mg, 488.4 µmol) in DCM (6 mL) cooled with an ice/acetone bath were added at 0° C. a solution of KBr (58.11 mg, 488.4 µmol) in H₂O (1.18 mL), TEMPO (1.57 mg, 9.8 µmol) and dropwise an aqueous solution of 1.56M sodium hypochlorite pH 9.5 (467.6 µL, 732.52 µmol). Stirring was carried on at 0° C. for 15 min then was added at 0° C. sat. Na₂S₂O₃ (3.56 mL), the ice bath was removed and the reaction medium stirred for 10 min. It was then extracted with DCM (3×25 mL), the combined organic phases were washed with H₂O (2×10 mL), dried over MgSO₄, filtered, concentrated in vacuo and purified by flash chromatography on 15 g of silica gel (gradient elution DCM/MeOH) to give 139 mg of compound 61 as a white lacquer (47%).

RMN ¹H (400 MHz, δ in ppm, DMSO-d6): 0.85 (s, 9H); 0.90 (d, J=7.0 Hz, 3H); 1.03 (s, 3H); 1.04 (d, J=6.9 Hz, 3H); 1.20 (s, 3H); 1.26 (d, J=15.3 Hz, 1H); 1.95 (m, 1H); 2.44 (m, 1H); 2.57 (m, 1H); 2.72 (dd, J=11.2 and 14.4 Hz, 1H); 2.80 (m, 1H); 2.98 (dd, J=3.1 and 14.4 Hz, 1H); 3.80 (s, 3H); 4.10 (m, 3H); 5.22 (m, 1H); 5.98 (d, J=15.3 Hz, 1H); 6.47 (ddd, J=4.9, 10.8 and 15.3 Hz, 1H); 7.04 (d, J=8.7 Hz, 1H); 7.22 (dd, J=2.3 and 8.7 Hz, 1H); 7.37 (s, 1H); 7.90 (m, 1H); 7.92 (d, J=8.2 Hz, 1H); 8.53 (d, J=7.6 Hz, 1H); 9.68 (s, 1H). LCMS (A5): ES m/z=604 [M−H]⁻; m/z=606 [M−H]+; m/z=650 [M−H+HCO₂H]⁻; t_R=1.28 min.

Compound 62: (4-(((triisopropylsilyl)oxy)methyl)phenyl)methanol

To a solution of 1,4-benzenedimethanol (2 g, 14.33 mmol) in THF (100 mL) was added imidazole (1.13 g, 16.48 mmol). The reaction medium was stirred at RT for 15 min then was added triisopropylsilyl chloride (3.14 mL, 14.33 mmol) and stirring was carried on at RT overnight. Et₂O (50 mL) was added to the reaction mixture and the organic phase was washed twice with sat. brine (100 mL), filtered over MgSO₄, concentrated in vacuo, dissolved in DCM, filtered, concentrated in vacuo and purified by flash chromatography on 200 g of silica gel (isocratic elution 8:2 heptane/EtOAc) to give 1.9 g of compound 62 as a colorless oil (45%).

RMN ¹H (400 MHz, δ in ppm, DMSO-d6): 1.04 (d, J=6.7 Hz, 18H); 1.15 (m, 3H); 4.48 (d, J=5.7 Hz, 2H); 4.78 (s, 2H); 5.13 (t, J=5.7 Hz, 1H); 7.29 (s, 4H).

Compound 63: ((4-(bromomethyl)benzyl)oxy)triisopropylsilane

To a suspension of N-bromosuccinimide (1.29 g, 7.16 mmol) in DCM (65 mL) cooled at 0° C. was added dropwise dimethyl sulfide (953 µL, 12.9 mmol). Stirring was carried on at 0° C. for 10 min then the reaction medium was cooled at −20° C. and stirred at −20° C. for 10 min. A solution of compound 62 (1.9 g, 6.45 mmol) in DCM (30 mL) cooled at −20° C. was then added dropwise. Stirring was carried on at −20° C. for 15 min then at 0° C. for 15 min and at RT overnight. The reaction medium was washed twice with sat. brine (100 mL), dried over MgSO₄, filtered, concentrated in vacuo and purified by two successive flash chromatographies on 40 g of silica gel (gradient elution heptane/EtOAc). The fractions containing the expected compound were combined, concentrated in vacuo and dissolved in heptane (8 mL). The suspension was filtered, the filtrate concentrated in vacuo, dissolved in Et₂O (5 mL), cooled at −20° C., filtered, concentrated in vacuo to give 1.18 g of compound 63 as a pale yellow oil (51%).

RMN ¹H (400 MHz, δ in ppm, DMSO-d6): 1.04 (d, J=6.8 Hz, 18H); 1.15 (m, 3H); 4.70 (s, 2H); 4.81 (s, 2H); 7.29 (d, J=8.4 Hz, 2H); 7.41 (d, J=8.4 Hz, 2H). LCMS (A5): ES m/z=104; m/z=356 [M]+; t_R=1.99 min.

Compound 64: (1R,4S,5R,6S)-4,7,7-trimethyl-6-(4-(((triisopropylsilyl)oxy)methyl)benzyl)-6-thiabicyclo[3.2.1]octan-6-ium trifluoromethanesulfonate To (1R,4R,5R)-4,7,7-trimethyl-6-thiabicyclo[3.2.1]octane (CAS number [5718-75-2], 562.3 mg, 3.3 mmol) was added a solution of compound 63 (1.18 g, 3.3 mmol) in DCM (3.4 mL). A solution of lithium trifluoromethanesulfonate (2.63 g, 16.51 mmol) in H₂O (3 mL) was then added dropwise and the reaction medium was stirred at RT overnight. H₂O (15 mL) and DCM (15 mL) were then added to the reaction medium and stirring carried on at RT for 10 min. The aqueous phase was extracted with DCM (3×20 mL), the combined organic phases were washed with sat. brine (3×8 mL), dried over MgSO₄, filtered and concentrated in vacuo. The pale yellow oil was triturated in iPr₂O (5 mL), the solid thus obtained was filtered, washed with iPr₂O (2×5 mL) and dried under vacuum to give 1.125 g of compound 64 as a white solid (57%).

RMN ¹H (400 MHz, δ in ppm, DMSO-d6): 1.04 (m, 21H); 1.15 (m, 3H); 1.45 (m, 1H); 1.60 (m, 2H); 1.68 (s, 3H); 1.71 (m, 1H); 1.74 (s, 3H); 1.98 (m, 1H); 2.40 (d, J=14.6 Hz, 1H); 2.45 (m, 1H); 2.58 (broad d, J=14.6 Hz, 1H); 3.85 (m, 1H); 4.56 (d, J=12.6 Hz, 1H); 4.83 (s, 2H); 4.90 (d, J=12.6 Hz, 1H); 7.44 (d, J=8.4 Hz, 2H); 7.57 (d, J=8.4 Hz, 2H).

Compound 65: (3S,7S,10R,16S,E)-10-(3-chloro-4-methoxybenzyl)-6,6,7-trimethyl-3-neopentyl-16-((S)-1-((2R,3R)-3-(4-(((triisopropylsilyl)oxy)methyl)phenyl)oxiran-2-yl)ethyl)-1-oxa-4,8,11-triazacyclohexadec-13-ene-2,5,9,12-tetraone To a solution of compounds 61 (138 mg, 227.7 μmol) and 64 (149.5 mg, 250.4 μmol) in DCM (4 mL) cooled at −70° C. was added dropwise BEMP (CAS number [98015-45-3], 90.2 μL, 296.0 μmol). The reaction mixture was stirred at −70° C. for 2 h, sat. brine (7 mL) was added to the reaction mixture, the bath removed and stirring carried on vigorously up to RT. The aqueous phase was extracted with DCM (3×20 mL), the combined organic phases were dried over MgSO₄, filtered, concentrated in vacuo and purified by flash chromatography on 10 g of silica gel (gradient elution DCM/MeOH) to give 163 mg of compound 65 as a colorless oil (30%) and 60 mg of compound 61 (43%).

RMN ¹H (500 MHz, δ in ppm, DMSO-d6): 0.84 (s, 9H); 0.88 (d, J=6.9 Hz, 3H); 1.00 (s, 3H); 1.04 (d, J=7.1 Hz, 3H); 1.05 (d, J=7.3 Hz, 18H); 1.15 (m, 3H); 1.19 (s, 3H); 1.32 (d, J=14.8 Hz, 1H); 1.82 (m, 1H); 1.97 (dd, J=9.9 and 14.8 Hz, 1H); 2.28 (dt, J=11.1 and 14.9 Hz, 1H); 2.61 (m, 1H); 2.69 (dd, J=11.2 and 14.3 Hz, 1H); 2.91 (dd, J=2.2 and 7.6 Hz, 1H); 2.95 (dd, J=3.8 and 14.3 Hz, 1H); 3.43 (m, 1H); 3.80 (s, 3H); 3.91 (d, J=2.2 Hz, 1H); 4.08 (ddd, J=3.8, 7.4 and 11.2 Hz, 1H); 4.12 (m, 1H); 4.81 (s, 2H); 5.04 (ddd, J=1.5, 4.5 and 11.1 Hz, 1H); 5.89 (dd, J=1.5 and 15.2 Hz, 1H); 6.44 (ddd, J=4.5, 10.6 and 15.2 (d, J=2.3 Hz, 1H); 7.36 (d, J=8.4 Hz, 2H); 7.88 (d, J=8.4 Hz, 1H); 7.91 (d, J=7.1 Hz, 1H); 8.39 (d, J=7.4 Hz, 1H). LCMS (A4): ES m/z=120; m/z=882 [M+H]⁺; t$_R$=7.65 min.

Example 26: (3S,7S,10R,16S,E)-10-(3-chloro-4-methoxybenzyl)-164(S)-1-((2R,3R)-3-(4-(hydroxymethyl)phenyl)oxiran-2-yl)ethyl)-6,6,7-trimethyl-3-neopentyl-1-oxa-4,8,11-triazacyclohexadec-13-ene-2,5,9,12-tetraone To a solution of compound 65 in THF cooled at 0° C. was added TBAF. The reaction medium was stirred at 0° C. for 1 h 30 then H₂O (5 mL) was added and stirring carried on for 20 min. The reaction medium was extracted with DCM (3×20 mL), the combined organic phase were washed with sat. brine (3×5 mL), dried over MgSO₄, filtered, concentrated in vacuo and purified by flash chromatography on 15 g of silica gel (gradient elution EtOAc/MeOH/H₂O) to give 69 mg of example 26 as a white lacquer (91%).

RMN ¹H (400 MHz, δ in ppm, DMSO-d6): 0.85 (s, 9H); 0.89 (d, J=6.9 Hz, 3H); 1.00 (s, 3H); 1.04 (d, J=7.1 Hz, 3H); 1.19 (s, 3H); 1.35 (d, J=14.8 Hz, 1H); 1.80 (m, 1H); 1.99 (dd, J=9.9 and 14.8 Hz, 1H); 2.27 (dt, J=11.1 and 14.9 Hz, 1H); 2.61 (m, 1H); 2.69 (dd, J=11.2 and 14.3 Hz, 1H); 2.90 (dd, J=2.2 and 7.6 Hz, 1H); 2.95 (dd, J=3.8 and 14.3 Hz, 1H); 3.43 (m, 1H); 3.80 (s, 3H); 3.91 (d, J=2.2 Hz, 1H); 4.06 to 4.15 (m, 2H); 4.50 (d, J=5.9 Hz, 2H); 5.03 (dd, J=1.5, 3.7 and 11.5 Hz, 1H); 5.20 (t, J=5.9 Hz, 1H); 5.89 (dd, J=1.5 and 15.3 Hz, 1H); 6.43 (ddd, J=4.6, 10.7 and 15.3 Hz, 1H); 7.02 (d, J=8.6 Hz, 1H); 7.20 (dd, J=2.2 and 8.6 Hz, 1H); 7.23 (d, J=8.3 Hz, 2H); 7.32 (m, 3H); 7.87 (d, J=8.3 Hz, 1H); 7.92 (d, J=7.0 Hz, 1H); 8.40 (d, J=7.4 Hz, 1H). LCMS (A5): ES m/z=724 [M−H]⁻; m/z=726 [M−H]+; m/z=770 [M−H+HCO₂H]⁻; t$_R$=1.29 min.

Compound 66: 4-((2R,3R)-3-((S)-1-((3S,7S,10R,16S,E)-10-(3-chloro-4-methoxybenzyl)-6,6,7-trimethyl-3-neopentyl-2,5,9,12-tetraoxo-1-oxa-4,8,11-triazacyclohexadec-13-en-16-yl)ethyl)oxiran-2-yl)benzyl (4-nitrophenyl) carbonate To a solution of example 26 (68 mg, 93.6 μmol) in DCM (5 mL) were added bis (4-nitrophenyl)carbonate (118.7 mg, 374.5 μmol) and dropwise DIEA (49 μL, 281.0 μmol). The reaction medium was stirred at RT for 6 d then sat. brine was added and it was extracted with DCM (3×10 mL). The combined organic phases were dried over MgSO₄, filtered, concentrated in vacuo and purified by flash chromatography on 5 g of silica gel (gradient elution DCM/MeOH) to give 79 mg of compound 66 as a white lacquer (94%).

RMN ¹H (400 MHz, δ in ppm, DMSO-d6): 0.85 (s, 9H); 0.89 (d, J=6.9 Hz, 3H); 1.00 (s, 3H); 1.05 (d, J=7.1 Hz, 3H); 1.19 (s, 3H); 1.34 (d, J=14.6 Hz, 1H); 1.83 (m, 1H); 1.97 (dd, J=9.9 and 14.6 Hz, 1H); 2.28 (dt, J=11.1 and 14.9 Hz, 1H); 2.61 (m, 1H); 2.69 (dd, J=11.2 and 14.3 Hz, 1H); 2.93 (m, 2H); 3.42 (m, 1H); 3.79 (s, 3H); 3.99 (d, J=2.2 Hz, 1H); 4.09 (m, 2H); 5.05 (dd, J=1.3, 4.0 and 11.1 Hz, 1H); 5.31 (s, 2H); 5.89 (dd, J=1.3 and 15.3 Hz, 1H); 6.47 (ddd, J=4.8, 10.8 and 15.3 Hz, 1H); 7.01 (d, J=8.6 Hz, 1H); 7.21 (dd, J=2.2 and 8.6 Hz, 1H); 7.31 (d, J=2.2 Hz, 1H); 7.36 (d, J=8.5 Hz, 2H); 7.50 (d, J=8.5 Hz, 2H); 7.59 (d, J=9.3 Hz, 2H); 7.87 (d, J=8.3 Hz, 1H); 7.92 (d, J=7.0 Hz, 1H); 8.32 (d, J=9.3 Hz, 2H); 8.39 (d, J=7.4 Hz, 1H). LCMS (A5): ES m/z=889 [M−H]⁻; m/z=891 [M+H]⁺; m/z=935 [M−H+HCO₂H]⁻; t$_R$=1.55 min.

Compound 67: (9H-fluoren-9-yl)methyl ((S)-1-(((S)-1-((2-NBoc-aminoethyl)amino)-1-oxopropan-2-yl)amino)-3-methyl-1-oxobutan-2-yl)carbamate hydrochloride To a suspension of Fmoc-Val-Ala-OH (3.5 g, 8.53 mmol) in DCM (100 mL) were added TEA (3.6 mL, 25.58 mL) leading to complete dissolution of starting material, N-Boc-EDA (1.62 mL, 10.23 mmol) and a solution of propylphosphonic anhydride (6.51 g, 10.23 mmol) 50% in DCM. The reaction medium was stirred at RT for 3 h then 1N NaOH (50 mL) was added and the suspension filtered, washed with H₂O and DCM. The organic phase of the filtrate was washed with H₂O. The cake and the organic phase were combined, partially concentrated in vacuo, filtered, washed with DCM and dried to give 3.952 g of compound 67 as a white powder (84%).

RMN ¹H (400 MHz, δ in ppm, DMSO-d6): 0.84 (d, J=7.0 Hz, 3H); 0.86 (d, J=7.0 Hz, 3H); 1.19 (d, J=7.1 Hz, 3H); 1.37 (s, 9H); 1.99 (m, 1H); 2.92 to 3.14 (m, 4H); 3.88 (dd, J=6.9 and 9.1 Hz, 1H); 4.19 to 4.35 (m, 4H); 6.71 (m, 1H); 7.32 (m, 2H); 7.38 (m, 1H); 7.42 (m, 2H); 7.73 (m, 2H); 7.84 (t, J=6.8 Hz, 1H); 7.89 (d, J=7.8 Hz, 2H); 7.92 (d, J=7.8 Hz, 1H).

Compound 68: (9H-fluoren-9-yl)methyl ((S)-1-(((S)-1-((2-aminoethyl)amino)-1-oxopropan-2-yl)amino)-3-methyl-1-oxobutan-2-yl)carbamate hydrochloride To as suspension of compound 67 (100 mg, 159.5 µmol) in dioxane (3 mL) was added HCl 4N in dioxane (905 µL, 3.62 mmol). The reaction medium was stirred at RT for 20 h then concentrated in vacuo. The crude product was resuspended in iPr$_2$O (3 mL), immersed in an ultrasonic bath and filtered. The cake thus obtained was washed with iPr$_2$O (2×3 mL) and dried under vacuum to give 78 mg of compound 68 as a white solid (88%).

RMN $^1$H (400 MHz, δ in ppm, DMSO-d6): 0.85 (d, J=6.9 Hz, 3H); 0.87 (d, J=6.9 Hz, 3H); 1.23 (d, J=7.1 Hz, 3H); 1.99 (m, 1H); 2.83 (m, 2H); 3.29 (m, 2H); 3.89 (dd, J=6.9 and 8.9 Hz, 1H); 4.19 to 4.38 (m, 4H); 7.33 (m, 2H); 7.42 (m, 3H); 7.75 (m, 2H); 7.88 (broad s, 3H); 7.90 (d, J=7.6 Hz, 2H); 8.08 (d, J=7.3 Hz, 1H); 8.14 (d, J=5.9 Hz, 1H).

Compound 69: 4-((2R,3R)-3-((S)-1-((3S,7S,10R,16S,E)-10-(3-chloro-4-methoxybenzyl)-6,6,7-trimethyl-3-neopentyl-2,5,9,12-tetraoxo-1-oxa-4,8,11-triazacyclohexadec-13-en-16yl)ethyl)oxiran 2-yl)benzyl (2-((S)-2-((S)-2-amino-3-methylbutanamido)propanamido)ethyl)carbamate To a suspension of compounds 66 (78 mg, 87.5 µmol) and 68 (51.4 mg, 105.0 µmol) in DCM was added DIEA (44.0 µL, 262.5 µmol). The reaction medium is stirred at RT overnight then were added compound 68 (24 mg, 49 µmol) and DIEA (15 µL) and stirring was carried on at RT for 1 d. Piperidine (87.0 µL, 875.0 µmol) was added and stirring carried on at RT overnight. The reaction medium was concentrated in vacuo and purified by two successive flash chromatographies on 5 g of silica gel (gradient elution EtOAc/MeOH/H2O) to give 57 mg of compound 69 as a white lacquer (66%).

RMN $^1$H (500 MHz, δ in ppm, DMSO-d6): 0.75 (d, J=7.0 Hz, 3H); 0.85 (s, 9H); 0.86 (d, J=7.0 Hz, 3H); 0.87 (d, J=6.7 Hz, 3H); 0.99 (s, 3H); 1.04 (d, J=7.0 Hz, 3H); 1.18 (m, 6H); 1.33 (d, J=14.5 Hz, 1H); 1.75 (broad s, 2H); 1.81 (m, 1H); 1.92 (m, 1H); 1.98 (dd, J=10.0 and 14.5 Hz, 1H); 2.28 (m, 1H); 2.61 (m, 1H); 2.69 (dd, J=11.3 and 14.7 Hz, 1H); 2.90 (dd, J=2.0 and 7.5 Hz, 1H); 2.96 (m, 1H); 2.98 (d, J=4.7 Hz, 1H); 3.05 (m, 2H); 3.12 (m, 2H); 3.43 (m, 1H); 3.81 (s, 3H); 3.93 (d, J=2.0 Hz, 1H); 4.09 (m, 2H); 4.26 (m, 1H); 5.01 (s, 2H); 5.04 (m, 1H); 5.89 (dd, J=1.5 and 15.2 Hz, 1H); 6.45 (ddd, J=4.5, 10.4 and 15.2 Hz, 1H); 7.02 (d, J=8.8 Hz, 1H); 7.20 (dd, J=2.4 and 8.8 Hz, 1H); 7.26 (t, J=6.0 Hz, 1H); 7.29 (d, J=8.4 Hz, 2H); 7.32 (d, J=2.5 Hz, 1H); 7.37 (d, J=8.4 Hz, 2H); 7.88 (d, J=8.4 Hz, 1H); 7.93 (d, J=7.1 Hz, 1H); 8.00 (t, J=6.0 Hz, 1H); 8.03 (d, J=8.1 Hz, 1H); 8.41 (d, J=7.2 Hz, 1H). LCMS (A5): ES m/z=492 [M+2H]$^{2+}$; m/z=980 [M−H]$^−$; m/z=982 [M+H]$^+$; m/z=1026 [M−H+HCO$_2$H]$^−$; t$_R$=0.91 min.

Compound 70: (9S,12S)-1-(4-((2R,3R)-3-((S)-1-((3S,7S,10R,16S, E)-10-(3-chloro-4-methoxy-benzyl)-6,6,7-trimethyl-3-neopentyl-2,5,9,12-tetraoxo-1-oxa-4,8,11-triazacyclohexadec-13-en-16-yl)ethyl)oxiran-2-yl)phenyl)-12-isopropyl-9-methyl-3,8,11,14-tetraoxo-2-oxa-4,7,10,13-tetraazaoctadecan-18-oic acid To a solution of compound 69 (56.0 mg, 56.8 µL) in DCM (8 mL) was added a solution of glutaric anhydride (7.27 mg, 62.5 µmol) in DCM (4 mL). The reaction medium was stirred at RT for 2 h, concentrated in vacuo and purified by flash chromatography on 5 g of silica gel (gradient elution DCM/MeOH/H$_2$O) to give 35.5 mg of compound 70 as a white lacquer (56%).

RMN $^1$H (500 MHz, δ in ppm, DMSO-d6): 0.81 (d, J=7.0 Hz, 3H); 0.83 (d, J=7.0 Hz, 3H); 0.85 (s, 9H); 0.87 (d, J=6.5 Hz, 3H); 0.99 (s, 3H); 1.04 (d, J=7.1 Hz, 3H); 1.19 (m, 6H); 1.32 (d, J=14.3 Hz, 1H); 1.70 (m, 2H); 1.81 (m, 1H); 1.92 (m, 1H); 1.98 (m, 2H); 2.15 (m, 2H); 2.19 (t, J=7.5 Hz, 2H); 2.27 (m, 1H); 2.61 (m, 1H); 2.69 (dd, J=11.1 and 14.1 Hz, 1H); 2.91 (d, J=7.6 Hz, 1H); 2.95 (m, 1H); 3.04 (m, 2H); 3.10 (m, 2H); 3.41 (m, 1H); 3.80 (s, 3H); 3.93 (s, 1H); 4.03 to 4.16 (m, 3H); 4.19 (m, 1H); 5.01 (s, 2H); 5.04 (m, 1H); 5.89 (d, J=15.6 Hz, 1H); 6.43 (ddd, J=5.3, 11.0 and 15.6 Hz, 1H); 7.02 (d, J=8.7 Hz, 1H); 7.20 (dd, J=2.3 and 8.7 Hz, 1H); 7.28 (d, J=8.4 Hz, 2H); 7.30 (m, 1H); 7.32 (d, J=2.3 Hz, 1H); 7.36 (d, J=8.4 Hz, 2H); 7.88 (m, 2H); 7.93 (d, J=7.4 Hz, 1H); 7.98 (broad s, 1H); 8.06 (broad s, 1H); 8.42 (d, J=7.4 Hz, 1H). LCMS (A5): ES m/z=549 [M+2H]$^{2+}$; m/z=1094 [M−H]$^−$; m/z=1096 [M−H]+; t$_R$=1.21 min.

Example 27: 2,5-dioxopyrrolidin-1-yl (9S,12S)-1-(4-((2R,3R)-3-((S)-1-((3S,7S,10R,16S,E)-10-(3-chloro-4-methoxybenzyl)-6,6,7-trimethyl-3-neopentyl-2,5,9,12-tetraoxo-1-oxa-4,8,11-triazacyclohexadec-13-en-16-yl)ethyl)oxiran-2-yl)phenyl)-12-isopropyl-9-methyl-3,8,11,14-tetraoxo-2-oxa-4,7,10,13-tetraazaoctadecan-18-oate To a solution of compound 70 (14.6 mg, 13.3 µmol) in DCM (5 mL) under Ar were added DSC (4.3 mg, 16.0 µmol) and DIEA (2.8 µL, 16.0 µmol). The reaction medium was stirred at RT for 3 h then were added DSC (1.5 mg, 5.6 µmol) and DIEA (1 µL, 5.7 µmol) and stirring was carried on at RT for 1 h. The reaction medium was concentrated in vacuo and purified by flash chromatography on 16.4 g of diol-modified silica gel (gradient elution DCM/iPrOH) to give 11.4 mg of example 27 as a white lacquer (72%).

RMN $^1$H (500 MHz, δ in ppm, DMSO-d6): 0.81 (d, J=7.0 Hz, 3H); 0.83 (d, J=7.0 Hz, 3H); 0.85 (s, 9H); 0.88 (d, J=6.5 Hz, 3H); 0.99 (s, 3H); 1.04 (d, J=7.1 Hz, 3H); 1.19 (m, 6H); 1.34 (d, J=14.4 Hz, 1H); 1.83 (m, 3H); 1.98 (m, 2H); 2.26 (m, 1H); 2.29 (m, 2H); 2.60 (m, 1H); 2.68 (t, J=7.6 Hz, 2H); 2.70 (dd, J=11.2 and 14.3 Hz, 1H); 2.80 (s, 4H); 2.91 (dd, J=2.3 and 7.6 Hz, 1H); 2.95 (dd, J=3.7 and 14.3 Hz, 1H); 2.99 to 3.20 (m, 4H); 3.43 (m, 1H); 3.80 (s, 3H); 3.93 (d, J=2.2 Hz, 1H); 4.05 to 4.25 (m, 4H); 5.01 (s, 2H); 5.03 (m, 1H); 5.89 (dd, J=1.6 and 15.4 Hz, 1H); 6.44 (ddd, J=4.6, 10.9 and 15.4 Hz, 1H); 7.02 (d, J=8.5 Hz, 1H); 7.20 (m, 2H); 7.28 (d, J=8.5 Hz, 2H); 7.31 (d, J=2.3 Hz, 1H); 7.37 (d, J=8.5 Hz, 2H); 7.86 (m, 3H); 7.91 (d, J=7.1 Hz, 1H); 7.95 (d, J=7.6 Hz, 1H); 8.39 (d, J=7.3 Hz, 1H). LCMS (A5): ES m/z=311; m/z=1191 [M−H]$^−$; m/z=1193 [M+H]$^+$; m/z=1237 [M−H+HCO$_2$H]$^−$; t$_R$=1.26 min.

Example 28: mAb-Ex27

Example 28 was prepared in a similar way to examples 3, 7, 10 and 14. 1.56 mg of example 28 were obtained as a colorless limpid solution at a concentration of 0.78 mg/mL with a DAR of 4 (HRMS), a monomeric purity of 100% and a global yield of 13%.

SEC-HRMS: m/z=149405 (naked mAb); m/z=150486 (D1); m/z=151568 (D2); m/z=152645 (D3); m/z=153725 (D4); m/z=154802 (D5); m/z=155882 (D6); m/z=156961 (D7); m/z=158039 (D8).

Synthesis of Example 29: maleimido-mc-vc-PABA-3-(S)-neopentyl-7-(S)-Me-aza-C52 benzylic amine

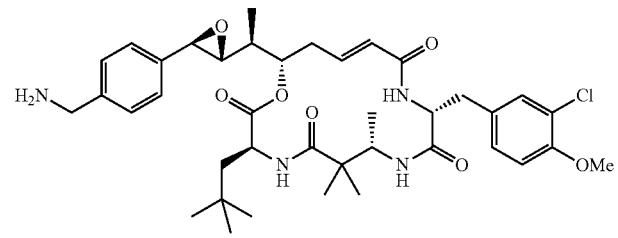

example 25

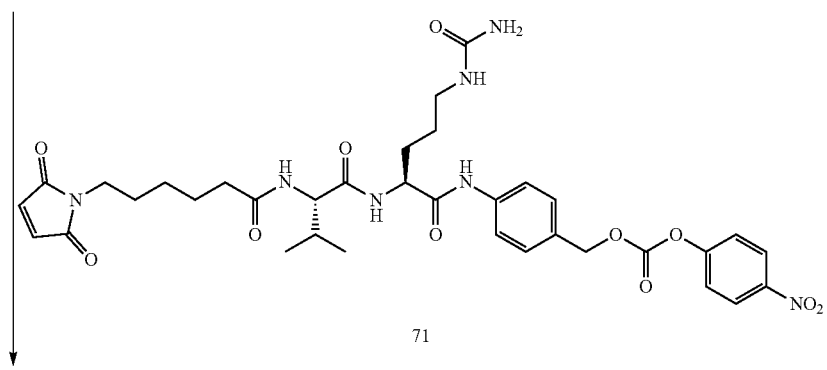

71

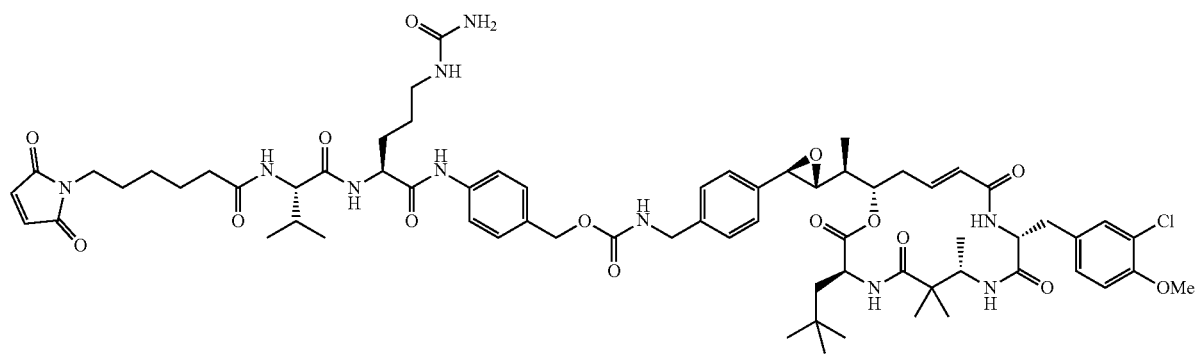

example 29

Compound 71: 4-((S)-2-((S)-2-(6-(2,5-dioxo-2,5-dihydro-1H-pyrrol-1-yl)hexanamido)-3-methylbutanamido)-5-ureidopentanamido)benzyl (4-nitrophenyl) Carbonate Compound 72 was prepared as described by Verma V. A., et al., in *Bioorg Med Chem Lett* 2015, 25, 864-868.

RMN $^1$H (400 MHz, δ in ppm, DMSO-d6): 0.83 (d, J=7.0 Hz, 3H); 0.87 (d, J=7.0 Hz, 3H); 1.18 (m, 2H); 1.31 to 1.75 (m, 8H); 1.96 (m, 1H); 2.10 (m, 1H); 2.18 (m, 1H); 2.96 (m, 1H); 3.01 (m, 1H); 3.37 (t, J=7.2 Hz, 2H); 4.19 (dd, J=7.0 and 8.6 Hz, 1H); 4.38 (m, 1H); 5.24 (s, 2H); 5.42 (s, 2H); 5.98 (t, J=6.0 Hz, 1H); 7.00 (s, 2H); 7.40 (d, J=8.7 Hz, 2H); 7.57 (d, J=9.2 Hz, 2H); 7.66 (d, J=8.7 Hz, 2H); 7.81 (d, J=8.6 Hz, 1H); 8.12 (d, J=7.9 Hz, 1H); 8.31 (d, J=9.2 Hz, 2H); 10.08 (s, 1H). LCMS (A5): ES m/z=738 [M+H]$^+$; m/z=782 [M−H+HCO$_2$H]$^-$; $t_R$=1.1 min.

Example 29: 4-((S)-2-((S)-2-(6-(2,5-dioxo-2,5-dihydro-1H-pyrrol-1-yl)hexanamido)-3-methyl-butanamido)-5-ureidopentanamido)benzyl (4-((2R,3R)-3-((S)-1-((3S,7S,10R,16S,E)-10-(3-chloro-4-methoxybenzyl)-6,6,7-trimethyl-3-neopentyl-2,5,9,12-tetraoxo-1-oxa-4,8,11-triazacyclohexadec-13-en-16-yl)ethyl)oxiran-2-yl)benzyl)carbamate To compound 71 (16.0 mg, 21.7 μmol) were added a solution of example 25 (14.3 mg, 19.7 μmol) in DCM (2.5 mL) and DIEA (3.4 μL, 19.7 μmol). The reaction medium was stirred at RT overnight then was added DMF (1 mL) and stirring was carried on at RT for 1 d. H$_2$O (8 mL) was added to the reaction medium, stirring carried on for 15 min then the aqueous phase was extracted with DCM (3×10 mL). The combined organic phases were dried over MgSO$_4$, filtered, concentrated in vacuo, co-evaporated twice with toluene and purified by flash chromatography on 5 g on silica gel (gradient elution DCM/MeOH) to give 15.8 mg of example 29 as a white solid (60%).

RMN $^1$H (400 MHz, δ in ppm, DMSO-d6): 0.81 (d, J=7.0 Hz, 3H); 0.85 (d, J=7.0 Hz, 3H); 0.86 (s, 9H); 0.89 (d, J=6.8 Hz, 3H); 0.99 (s, 3H); 1.04 (d, J=7.0 Hz, 3H); 1.18 (s, 3H); 1.19 (m, 2H); 1.31 to 1.75 (m, 9H); 1.80 (m, 1H); 1.96 (m, 2H) 2.10 (m, 1H); 2.18 (m, 1H); 2.27 (m, 1H); 2.61 (m, 1H); 2.69 (dd, J=10.8 and 14.3 Hz, 1H); 2.90 (dd, J=2.1 and 7.6 Hz, 1H); 2.96 (m, 2H); 3.01 (m, 1H); 3.37 (t, J=7.2 Hz, 2H); 3.42 (m, 1H); 3.80 (s, 3H); 3.90 (d, J=2.1 Hz, 1H); 4.08 (m, 1H); 4.11 (m, 1H); 4.20 (m, 3H); 4.39 (m, 1H); 4.97 (s, 2H); 5.04 (m, 1H); 5.40 (s, 2H); 5.89 (dd, J=1.7 and 15.5 Hz, 1H); 5.97 (t, J=6.2 Hz, 1H); 6.45 (ddd, J=4.8, 10.7 and 15.5 Hz, 1H); 6.99 (s, 2H); 7.01 (d, J=8.7 Hz, 1H); 7.20 (dd, J=2.2 and 8.7 Hz, 1H); 7.21 to 7.30 (m, 6H); 7.31 (d, J=2.2 Hz, 1H); 7.59 (d, J=8.7 Hz, 2H); 7.78 (m, 2H); 7.85 (d, J=8.5 Hz, 1H); 7.90 (d, J=6.9 Hz, 1H); 8.07 (d, J=7.8 Hz, 1H); 8.39 (d, J=7.3 Hz, 1H); 9.97 (s, 1H). LCMS (A5): ES m/z=662 [M+2H]$^{2+}$; m/z=1322 [M−H]$^−$; m/z=1324 [M−H]$^+$; m/z=1368 [M−H+HCO$_2$H]$^−$; t$_R$=1.3 min.

Synthesis of Examples 30 & 31: NHS ester of non-cleavable triazole-3-(S)-neopentyl-7-(S)-Me-aza-C52 and Corresponding ADC

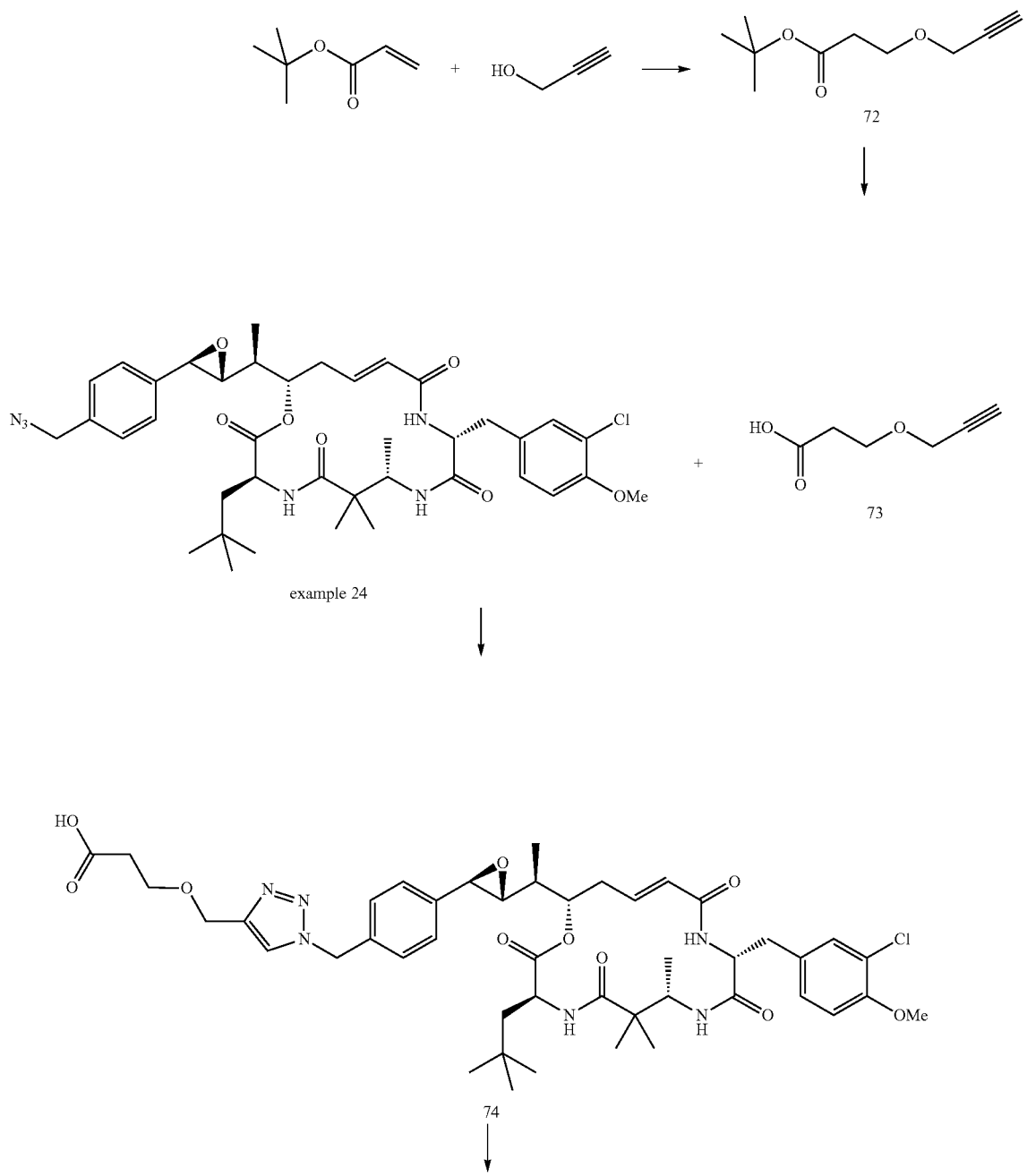

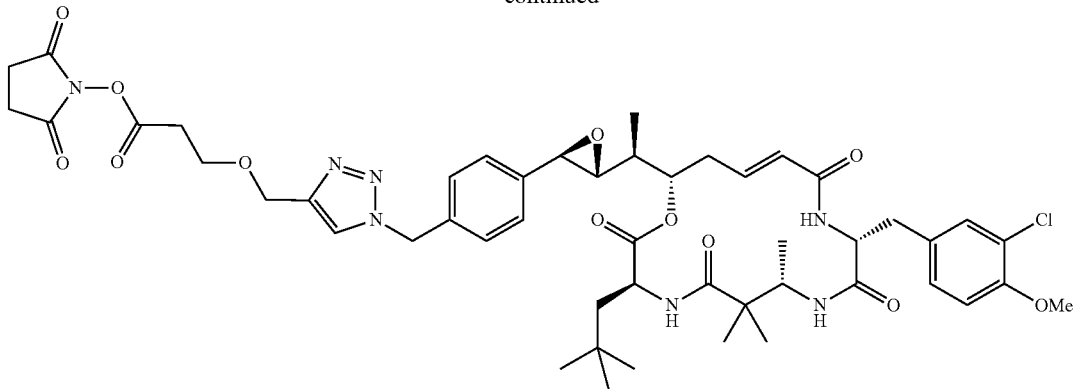

example 30

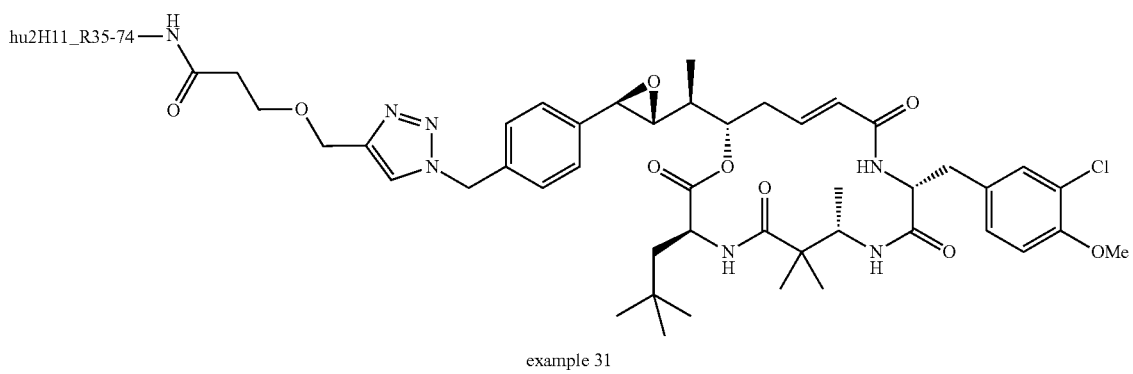

example 31

Compound 72: tert-butyl 3-(prop-2-yn-1-yloxy)propanoate

To a solution of propargyl alcohol (1.362 mL, 23.4 mmol) in THF (23 mL) was added sodium (20.08 mg, 0.874 mmol), the reaction medium was heated at 60° C. until complete solubilization of sodium then cooled down at RT before the addition of tert-butyl acrylate (2.286 mL, 15.6 mmol). The reaction medium was stirred at RT overnight then H$_2$O (25 mL) was added and the aqueous phase was extracted with EtOAc (3×25 mL). The combined organic phase were dried over Na$_2$SO$_4$, filtered and concentrated in vacuo to give 2 g of compound 72 as a colorless oil (70%).

Compound 73: 3-(prop-2-yn-1-yloxy)propanoic Acid

To a solution of compound 72 (2.0 g, 10.86 mmol) in DCM (50 mL) was added TFA (8.065 mL, 108.6 mmol). The reaction medium was stirred at RT overnight, concentrated in vacuo, co-evaporated with toluene and purified by flash chromatography on 80 g of silica gel (gradient elution DCM/MeOH) to give 1.1 g of compound 73 as an oil (80%).

RMN $^1$H (400 MHz, δ in ppm, DMSO-d6): 2.46 (t, J=6.4 Hz, 2H); 3.43 (t, J=2.4 Hz, 1H); 3.63 (t, J=6.4 Hz, 2H); 4.11 (d, J=2.4 Hz, 2H); 12.20 (broad, 1H).

Compound 74: 3-((1-(4-(((2R,3R)-3-((S)-1-((3S,7S, 10R,16S, E)-10-(3-chloro-4-methoxybenzyl)-6,6,7-trimethyl-3-neopentyl-2,5,9,12-tetraoxo-1-oxa-4,8, 11-triazacyclohexadec-13-en-16-yl)ethyl)oxiran-2-yl)benzyl)-1H-1,2,3-triazol-4-yl)methoxy)propanoic Acid To a solution of example 24 (50 mg, 66.6 μmol) in THF (0.5 mL) were added compound 73 (17.05 mg, 113.1 μmol), 0.1M aq. copper (II) sulfate (266 μL, 26.6 μmol) and 0.2M aq. sodium ascorbate (266 μL, 53.2 μmol). The reaction medium was stirred at RT for 1 d then H$_2$O (1 mL) was added and the aqueous phase was extracted with EtOAc (3×1 mL). The combined organic phases were washed with sat. brine, dried over MgSO$_4$, filtered, concentrated in vacuo and purified by filtration on Sephadex LH20 (elution DCM) to give 40 mg of an oil that was further purified by flash chromatography on 5 g of silica gel (gradient elution DCM/MeOH) to give 20 mg of compound 74 (35%).

RMN $^1$H (500 MHz, δ in ppm, DMSO-d6): 0.82 (s, 9H); 0.88 (d, J=6.7 Hz, 3H); 1.00 (s, 3H); 1.04 (d, J=7.1 Hz, 3H); 1.18 (s, 3H); 1.31 (d, J=14.6 Hz, 1H); 1.80 (m, 1H); 1.97 (dd, J=10.0 and 14.6 Hz, 1H); 2.25 (m, 1H); 2.42 (t, J=6.6 Hz, 2H); 2.60 (m, 1H); 2.70 (dd, J=10.9 and 14.4 Hz, 1H); 2.90 (dd, J=2.2 and 7.6 Hz, 1H); 2.95 (dd, J=3.6 and 14.4 Hz, 1H); 3.44 (m, 1H); 3.62 (t, J=6.6 2H); 3.80 (s, 3H); 3.94 (d, J=2.2 Hz, 1H); 4.08 (m, 2H); 4.49 (s, 2H); 5.03 (m, 1H); 5.59 (s, 2H); 5.89 (dd, J=1.7 and 15.3 Hz, 1H); 6.43 (ddd, J=4.8, 10.8 and 15.3 Hz, 1H); 7.02 (d, J=8.7 Hz, 1H); 7.20 (dd, J=2.4 and 8.7 Hz, 1H); 7.29 (d, J=8.4 Hz, 2H); 7.32 (d, J=2.4 Hz, 1H); 7.35 (d, J=8.4 Hz, 2H); 7.85 (d, J=8.4 Hz, 1H); 7.90 (d, J=7.0 Hz, 1H); 8.13 (s, 1H); 8.46 (m, 1H); 12.20 (broad, 1H). LCMS (A5): ES m/z=440 [M+2H]$^{2+}$; m/z=877 [M−H]$^{-}$; m/z=879 [M+H]$^{+}$; $t_R$=1.24 min.

Example 30: 2,5-dioxopyrrolidin-1-yl 3-((1-(4-((2R,3R)-3-((S)-1-((3S,7S,10R,16S,E)-10-(3-chloro-4-methoxybenzyl)-6,6,7-trimethyl-3-neopentyl-2,5,9,12-tetraoxo-1-oxa-4,8,11-triaza-cyclohexadec-13-en-16-yl)ethyl)oxiran-2-yl)benzyl)-1H-1,2,3-triazol-4-yl)methoxy)propanoate To a solution of compound 74 (20 mg, 22.7 µmol) in DCM (5 mL) were added DIEA (5.0 µL, 28.5 µmol) and DSC (6.34 mg, 23.8 µmol). The reaction medium was stirred at RT for 3 h then were added DSC (3 mg, 11.3 µmol) and DIEA (5 µL, 28.5 µmol) and stirring was carried on at RT for 2 h. The reaction medium was then concentrated in vacuo and purified by two successive flash chromatographies on 1.5 g of diol-modified silica gel (gradient elution DCM/iPrOH) to give 11.5 mg of example 30 (50%).
RMN $^1$H (500 MHz, δ in ppm, DMSO-d6): 0.83 (s, 9H); 0.87 (d, J=6.6 Hz, 3H); 0.99 (s, 3H); 1.03 (d, J=7.1 Hz, 3H); 1.04 (d, J=6.6 Hz, 3H); 1.19 (s, 3H); 1.32 (d, J=14.5 Hz, 1H); 1.81 (m, 1H); 1.96 (dd, J=10.2 and 14.5 Hz, 1H); 2.25 (m, 1H); 2.60 (m, 1H); 2.70 (dd, J=11.2 and 14.5 Hz, 1H); 2.80 (s, 4H); 2.90 (dd, J=2.0 and 7.4 Hz, 1H); 2.94 (t, J=6.1 Hz, 2H); 2.97 (dd, J=3.6 and 14.1 Hz, 1H); 3.42 (m, 1H); 3.74 (t, J=6.1 Hz, 2H); 3.80 (s, 3H); 3.92 (d, J=2.0 Hz, 1H); 4.09 (m, 2H); 4.55 (s, 2H); 5.03 (m, 1H); 5.59 (s, 2H); 5.89 (dd, J=1.6 and 15.2 Hz, 1H); 6.44 (ddd, J=4.7, 10.6 and 15.2 Hz, 1H); 7.02 (d, J=8.6 Hz, 1H); 7.20 (dd, J=2.4 and 8.6 Hz, 1H); 7.29 (d, J=8.3 Hz, 2H); 7.32 (m, 3H); 7.86 (d, J=8.4 Hz, 1H); 7.90 (d, J=6.9 Hz, 1H); 8.14 (s, 1H); 8.39 (d, J=7.5 Hz, 1H). LCMS (A5): ES m/z=120; m/z=974 [M−H]$^{-}$; m/z=976 [M−H]$^{+}$; m/z=1020 [M−H+HCO$_2$H]$^{-}$; $t_R$=1.29 min.

Example 31: mAb-Ex. 30

Example 31 was prepared in a similar way to examples 3, 7, 10 and 14. 5.4 mg of example 31 were obtained as a colorless limpid solution at a concentration of 1.8 mg/mL with a DAR of 4 (HRMS), a monomeric purity of 98.1% and a global yield of 45%.
SEC-HRMS: m/z=149399 (naked mAb); m/z=150245 (D1); m/z=151101 (D2); m/z=151965 (D3); m/z=152831 (D4); m/z=153679 (D5); m/z=154546 (D6); m/z=155408 (D7); m/z=156273 (D8); m/z=157284(D9).

Synthesis of Example 32:
3-(S)-neopentyl-6-Me-6-CH$_2$OH-aza-C52 benzylic amine

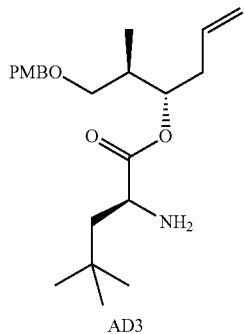

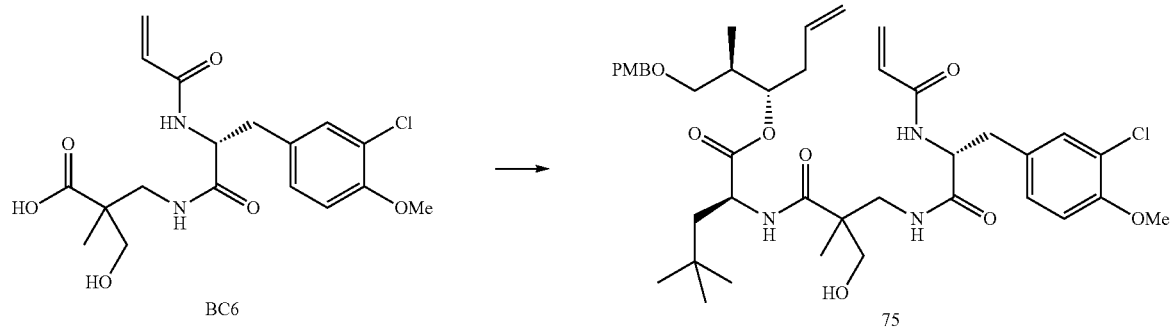

-continued

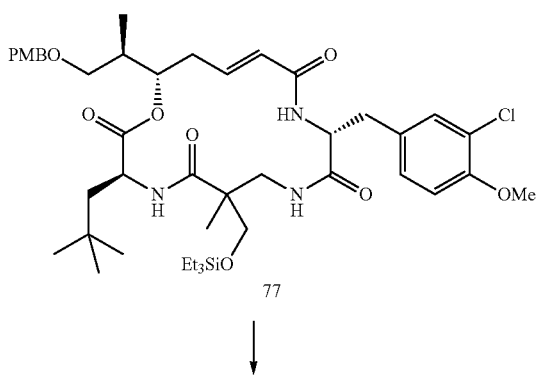
77

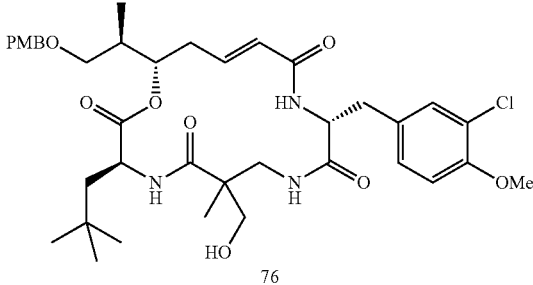
76

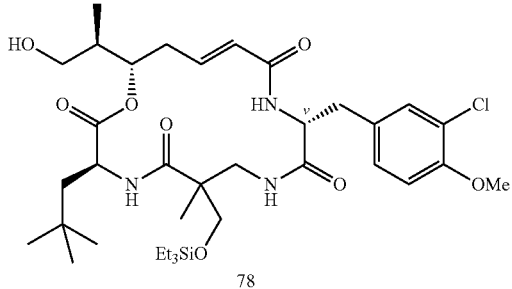
78

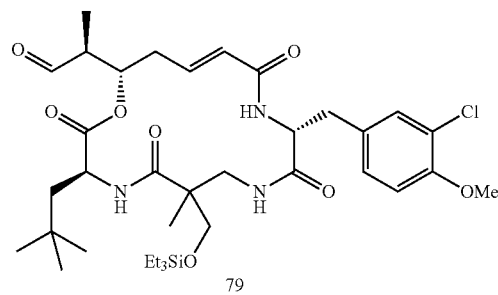
79

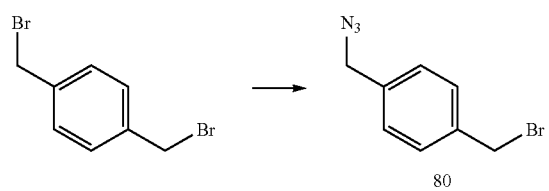
80

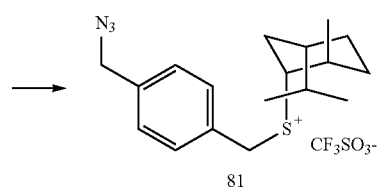
81

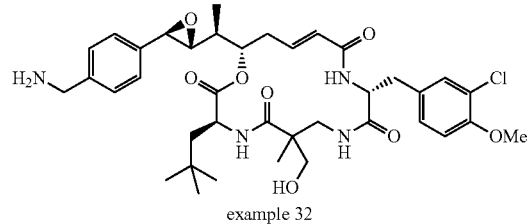
example 32

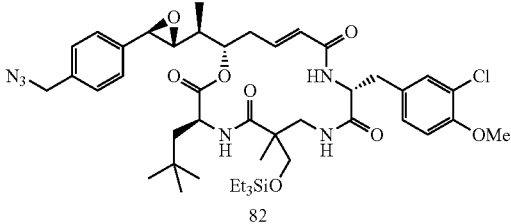
82

Compound 75: (2R,3S)-1-((4-methoxybenzyl)oxy)-2-methylhex-5-en-3-yl (2S)-2-((4-((R)-2-acrylamido-3-(3-chloro-4-methoxyphenyl)propanamido)-3-(hydroxymethyl)-3-methyl-2-oxobutyl)amino)-4,4-dimethylpentanoate To a solution of compound BC6 (385.6 mg, 773.5 µmol) in DMF (12 mL) were added HATU (348.7 mg, 889.5 µmol) and HOAt (122.3 mg, 889.5 µmol). The reaction medium was stirred at RT for 30 min then were added a solution of compound AD3 (292 mg, 773.5 µmol) in DMF (5 mL) and DIEA (475.2 µL, 2.71 mmol) and stirring was carried on at RT for 4 h. H$_2$O (50 mL) was added and the aqueous phase was extracted with EtOAc (3×50 mL). The combined organic phases were washed with H$_2$O (15 mL), sat. brine (3×15 mL), dried over MgSO$_4$, filtered, concentrated in vacuo and purified by flash chromatography on 30 g of silica gel (gradient elution DCM/MeOH) to give 383 mg of compound 75 as a yellow oil (65%).

RMN $^1$H (500 MHz, δ in ppm, DMSO-d6): 55/45 diastereoisomer mixture; 0.85 to 0.88 (m, 12H); 0.91 (s, 1.65H); 0.92 (s, 1.35H); 1.56 (m, 1H); 1.60 (m, 1H); 1.98 (m, 1H); 2.21 (m, 1H); 2.30 (m, 1H); 2.71 (m, 1H); 2.92 (m, 1H); 3.19 to 3.45 (m, 6H); 3.73 (s, 3H); 3.80 (s, 3H); 4.29 (m, 1H); 4.33 (m, 2H); 4.58 (m, 1H); 4.82 (m, 1H); 4.95 to 5.09 (m, 3H); 5.55 (dd, J=2.2 and 10.2 Hz, 1H); 5.71 (m, 1H); 6.01 (dd, J=2.2 and 17.2 Hz, 1H); 6.23 (dd, J=10.2 and 17.2 Hz, 1H); 6.89 (m, 2H); 7.01 (d, J=8.6 Hz, 1H); 7.17 (dd, J=2.2 and 8.6 Hz, 1H); 7.21 (m, 2H); 7.34 (d, J=2.2 Hz, 1H); 7.82 (d, J=8.0 Hz, 0.45H); 7.84 (d, J=8.0 Hz, 0.55H); 7.98 (t, J=6.5 Hz, 0.45H); 8.00 (t, J=6.5 Hz, 0.55H); 8.39 (d, J=8.6 Hz, 1H). LCMS (A5): ES m/z=756 [M–H]$^-$; m/z=758 [M–H]+; m/z=802 [M–H+HCO$_2$H]$^-$; t$_R$=1.54-1.56 min.

Compound 76: (3S,10R,16S,E)-10-(3-chloro-4-methoxybenzyl)-6-(hydroxymethyl)-16-((R)-1-((4-methoxybenzyl)oxy)propan-2-yl)-6-methyl-3-neopentyl-1-oxa-4,8,11-triazacyclohexadec-13-ene-2,5,9,12-tetraone To a solution of compound 75 (380 mg, 501.1 µmol) in DCM (38 mL) under Ar was added Grubbs I catalyst (20.97 mg, 25.05 µmol). The reaction medium was stirred under Ar at RT for 4 h then was added Grubbs I catalyst (20.97 mg, 25.05 µmol). Stirring was carried on at RT for 3 h then was added Grubbs I catalyst (20.97 mg, 25.05 µmol) and stirring carried on at RT. After 24 h of reaction, Grubbs I catalyst (20.97 mg, 25.05 µmol) was added and stirring carried on for 4 h. The reaction medium was concentrated in vacuo and purified by flash chromatography on 20 g of silica gel (isocratic elution heptane/EtOAc) to give 170 mg of compound 76 stereomer 1 (56%) and 138 mg of compound 76 stereomer 2 (37%).

Compound 76 Stereomer 1

RMN $^1$H (400 MHz, δ in ppm, DMSO-d6): 0.83 (s, 9H); 0.91 (d, J=7.1 Hz, 3H); 1.02 (s, 3H); 1.30 (dd, J=2.4 and 14.6 Hz, 1H); 1.53 (dd, J=9.9 and 14.6 Hz, 1H); 1.99 (m, 1H); 2.28 (m, 1H); 2.45 (m, 1H); 2.67 (m, 1H); 2.91 (dd, J=3.0 and 13.7 Hz, 1H); 2.97 (dd, J=4.0 and 14.5 Hz, 1H); 3.17 to 3.49 (m, 5H); 3.72 (s, 3H); 3.80 (s, 3H); 4.18 (m, 1H); 4.37 (m, 2H); 4.50 (td, J=2.4 and 9.6 Hz, 1H); 5.00 (m, 3H); 5.82 (dd, J=1.9 and 15.4 Hz, 1H); 6.39 (ddd, J=4.2, 11.6 and 15.4 Hz, 1H); 6.90 (d, J=8.7 Hz, 2H); 7.04 (d, J=8.6 Hz, 1H); 7.12 (m, 1H); 7.15 (dd, J=2.3 and 8.6 Hz, 1H); 7.21 (d, J=8.7 Hz, 2H); 7.28 (d, J=2.3 Hz, 1H); 8.09 (d, J=9.6 Hz, 1H); 8.38 (d, J=8.0 Hz, 1H). LCMS (A4): ES m/z=728 [M−H]$^-$; m/z=730 [M−H]+; m/z=774; $t_R$=5.15 min.

Compound 76 Stereomer 2

RMN $^1$H (400 MHz, δ in ppm, DMSO-d6): 0.83 (s, 9H); 0.88 (s, 3H); 0.91 (d, J=7.1 Hz, 3H); 1.28 (dd, J=2.4 and 14.6 Hz, 1H); 1.67 (dd, J=9.9 and 14.6 Hz, 1H); 1.99 (m, 1H); 2.28 (m, 1H); 2.45 (m, 1H); 2.67 (m, 1H); 3.02 (dd, J=3.3 and 14.2 Hz, 1H); 3.08 (dd, J=1.9 and 13.5 Hz, 1H); 3.25 to 3.42 (m, 4H); 3.55 (dd, J=5.1 and 11.0 Hz, 1H); 3.73 (s, 3H); 3.81 (s, 3H); 4.17 (m, 1H); 4.37 (m, 2H); 4.44 (td, J=2.1 and 9.3 Hz, 1H); 4.80 (t, J=5.1 Hz, 1H); 5.00 (m, 2H); 5.86 (dd, J=1.6 and 15.1 Hz, 1H); 6.38 (ddd, J=4.0, 11.4 and 15.3 Hz, 1H); 6.90 (d, J=8.8 Hz, 2H); 7.04 (d, J=8.7 Hz, 1H); 7.19 (dd, J=2.2 and 8.7 Hz, 1H); 7.22 (d, J=8.8 Hz, 2H); 7.30 (d, J=2.2 Hz, 1H); 7.42 (d, J=10.4 Hz, 1H); 7.92 (d, J=8.9 Hz, 1H); 8.45 (d, J=8.0 Hz, 1H). LCMS (A4): ES m/z=728 [M−H]$^-$; m/z=730 [M+H]$^+$; m/z=774; $t_R$=4.79 min.

Compound 77: (3S,10R,16S,E)-10-(3-chloro-4-methoxybenzyl)-16-((R)-1-((4-methoxy-benzyl)oxy) propan-2-yl)-6-methyl-3-neopentyl-6-(((triethylsilyl) oxy)methyl)-1-oxa-4,8,11-triaza-cyclohexadec-13-ene-2,5,9,12-tetraone To a solution of compound 76 stereomer 1 (170 mg, 232.8 µmol) in DCM (3 mL) cooled with an ice bath were added at 4° C. chlorotriethylsilane (159.3 µL, 931.1 µmol) and dropwise TEA (131.1 µL, 931.1 µmol). The reaction medium was stirred at 4° C. for 30 min then at RT for 20 h. The reaction medium was diluted with DCM (50 mL) and brine (10 mL) and stirring was carried on for 10 min. The organic phase was washed with sat. brine (2×10 mL), dried over MgSO$_4$, filtered and concentrated in vacuo. The other diastereoisomer of compound 76 (138 mg, 189.0 µmol) was similarly protected, both batches were pooled and purified by flash chromatography on 20 g of silica gel (isocratic elution heptane/EtOAc) to give 139 mg of compound 77 stereomer 1 as a colorless foam (39%) and 107 mg of compound 77 stereomer 2 as a colorless foam (30%).

Compound 77 Stereomer 1

RMN $^1$H (400 MHz, δ in ppm, DMSO-d6): 0.62 (q, J=8.1 Hz, 6H); 0.83 (s, 9H); 0.91 (d, J=7.1 Hz, 3H); 0.96 (t, J=8.1 Hz, 9H); 1.04 (s, 3H); 1.66 (dd, J=3.4 and 14.4 Hz, 1H); 1.43 (dd, J=9.3 and 14.4 Hz, 1H); 1.99 (m, 1H); 2.28 (m, 1H); 2.47 (m, 1H); 2.68 (m, 1H); 2.92 (dd, J=3.0 and 13.5 Hz, 1H); 2.99 (dd, J=4.0 and 14.8 Hz, 1H); 3.21 to 3.40 (m, 3H); 3.48 (m, 1H); 3.63 (d, J=10.3 Hz, 1H); 3.73 (s, 3H); 3.81 (s, 3H); 4.17 (m, 1H); 4.36 (m, 2H); 4.51 (td, J=2.9 and 9.4 Hz, 1H); 5.02 (m, 1H); 5.82 (dd, J=1.8 and 15.4 Hz, 1H); 6.39 (ddd, J=4.3, 11.6 and 15.4 Hz, 1H); 6.89 (d, J=8.7 Hz, 2H); 7.02 (m, 1H); 7.04 (d, J=8.7 Hz, 1H); 7.15 (dd, J=2.3 and 8.7 Hz, 1H); 7.21 (d, J=8.7 Hz, 2H); 7.29 (d, J=2.3 Hz, 1H); 7.96 (d, J=9.4 Hz, 1H); 8.31 (d, J=8.0 Hz, 1H). LCMS (A4): ES m/z=842 [M−H]$^-$; m/z=844 [M−H]$^+$; m/z=888 [M−H+HCO$_2$H]$^-$; $t_R$=7.08 min.

Compound 77 Stereomer 2

RMN $^1$H (400 MHz, δ in ppm, DMSO-d6): 0.52 (q, J=8.1 Hz, 6H) 0.84 (s, 9H); 0.88 to 0.93 (m, 15H); 1.29 (dd, J=2.6 and 14.5 Hz, 1H); 1.68 (dd, J=10.1 and 14.5 Hz, 1H); 1.99 (m, 1H); 2.28 (m, 1H); 2.47 (m, 1H); 2.68 (m, 1H); 3.01 (dd, J=3.4 and 14.5 Hz, 1H); 3.15 (d, J=12.8 Hz, 1H); 3.33 (m, 1H); 3.48 (d, J=10.4 Hz, 1H); 3.73 (s, 3H); 3.81 (s, 3H); 3.83 (d, J=10.4 Hz, 1H); 4.17 (m, 1H); 4.36 (m, 2H); 4.45 (td, J=2.4 and 9.2 Hz, 1H); 5.01 (m, 1H); 5.84 (dd, J=1.8 and 15.3 Hz, 1H); 6.39 (ddd, J=3.9, 11.4 and 15.3 Hz, 1H); 6.90 (d, J=8.8 Hz, 2H); 7.05 (d, J=8.6 Hz, 1H); 7.19 (dd, J=2.2 and 8.6 Hz, 1H); 7.22 (d, J=8.8 Hz, 2H); 7.30 (d, J=2.2 Hz, 1H); 7.47 (d, J=10.4 Hz, 1H); 8.01 (d, J=9.2 Hz, 1H); 8.41 (d, J=8.0 Hz, 1H). LCMS (A4): ES m/z=842 [M−H]$^-$; m/z=844 [M+H]$^+$; m/z=888 [M−H+HCO$_2$H]$^-$; $t_R$=6.88 min.

Compound 78: 3S,10R,16S,E)-10-(3-chloro-4-methoxybenzyl)-16-((R)-1-hydroxypropan-2-yl)-6-methyl-3-neopentyl-6-(((triethylsilyl)oxy)methyl)-1-oxa-4,8,11-triazacyclohexadec-13-ene-2,5,9,12-tetraone To a solution of both diastereoisomers of compound 77 (245 mg, 290.1 µmol) in DCM (10 mL) and H$_2$O (2.5 mL) cooled with an ice/acetone bath were added DDQ (339.4 mg, 1.45 mmol) and 2,6-di-tert-butylpyridine (171.7 mg, 870.3 µmol). The reaction medium was stirred at 0° C. for 2 h then was diluted with aq. NaHCO$_3$ (10 mL) and DCM (10 mL) and stirring was carried on for 10 min. The aqueous phase was extracted with DCM (3×20 mL), the combined organic phases were washed with sat. brine (3×5 mL), dried over MgSO$_4$, filtered, concentrated in vacuo and purified by flash chromatography on 20 g of silica gel (gradient elution DCM/MeOH) to give 155 mg of compound 78 as a white foam (74%).

RMN $^1$H (400 MHz, δ in ppm, DMSO-d6): 0.49 to 0.65 (m, 6H); 0.80 to 1.07 (m, 24H); 1.35 to 1.71 (m, 2H); 1.83 (m, 1H); 2.28 (m, 1H); 2.47 (m, 1H; 2.68 (m, 1H); 2.90 to 3.50 (m, 5.96H); 3.65 (d, J=10.6 Hz, 0.52H); 3.80 (s, 3H); 3.82 (d, J=10.6 Hz, 0.52H); 4.18 (m, 1H); 4.29 to 4.70 (m, 2H); 5.02 (m, 1H); 5.80 to 5.89 (m, 1H); 6.05 (m, 0.11H); 6.39 (m, 0.89H); 6.98 to 7.31 (m, 3.48H); 7.47 (d, J=10.6 Hz, 0.52H); 7.87 (d, J=9.4 Hz, 0.11H); 7.96 (d, J=9.4 Hz, 0.52H); 8.00 (d, J=9.4 Hz, 0.37H); 8.31 (d, J=8.0 Hz, 0.63H); 8.42 (d, J=8.4 Hz, 0.37H). LCMS (A4): ES m/z=722 [M−H]$^-$; m/z=724 [M−H]$^+$; m/z=768 [M−H+HCO$_2$H]$^-$; $t_R$=5.68-5.78 min.

Compound 79: 2S)-2-((3S,10R,16S, E)-10-(3-chloro-4-methoxybenzyl)-6-methyl-3-neopentyl-2,5,9,12-tetraoxo-6-(((triethylsilyl)oxy)methyl)-1-oxa-4,8,11-triazacyclohexadec-13-en-16-yl)propanal To a solution of compound 78 (154 mg, 212.6 µmol) in DCM (1.5 mL) cooled with an ice/acetone bath were added at 0° C. a solution of KBr (25.6 mg, 212.6 µmol) in $H_2O$ (612 µL), a solution of TEMPO at 5 mg/mL in DCM (137 µL, 4.25 µmol) and dropwise an aqueous solution of 1.56M sodium hypochlorite pH 9.5 (204 µL, 318.9 µmol). Stirring was carried on at 0° C. for 15 min then was added at 0° C. sat. $Na_2S_2O_3$ (1.9 mL), the ice bath was removed and the reaction medium stirred for 10 min. It was then extracted with DCM (3×20 mL), the combined organic phases were washed with $H_2O$ (2×10 mL), dried over $MgSO_4$, filtered, concentrated in vacuo and purified by flash chromatography on 15 g of silica gel (gradient elution DCM/MeOH) to give 36 mg of compound 61 (23%).

RMN $^1$H (400 MHz, δ in ppm, DMSO-d6): 72/28 diastereoisomer mixture: 0.49 to 0.65 (m, 6H); 0.80 to 1.08 (m, 24H); 1.32 to 1.69 (m, 2H); 2.40 (m, 1H); 2.68 (m, 2H); 2.79 (m, 1H); 2.89 to 3.70 (m, 5H); 3.80 (s, 3H); 4.10 to 4.53 (m, 2H); 5.02 (m, 0.28H); 5.28 (m, 0.72H); 5.78 to 5.91 (m, 1H); 6.07 (m, 0.28H); 6.40 (m, 0.72H); 7.00 to 7.51 (m, 4H); 7.90 (d, J=9.4 Hz, 0.28H); 7.98 (d, J=9.4 Hz, 0.72H); 8.34 (m, 1H); 9.59 (d, J=2.5 Hz, 0.28H); 9.63 (d, J=1.8 Hz, 0.72H). LCMS (A5): m/z=722 [M+H]$^+$; $t_R$=1.71 min.

Compound 80: 1-(azidomethyl)-4-(bromomethyl)benzene

To a solution of p-xylene dibromide (2.0 g, 7.2 mmol) in DMF (20 mL) was added in 20 min a solution of sodium azide (584.9 mg, 8.64 mmol) in DMF (20 mL). The reaction medium was stirred at RT for 20 h then poured on ice (100 g) and extracted with EtOAc (3×50 mL). The combined organic phase were washed with sat. brine (3×15 mL), dried over $MgSO_4$, filtered, concentrated in vacuo, co-evaporated with toluene and purified by flash chromatography on 70 g of silica gel (elution $Et_2O$) to give to give 773 mg of compound 80 as a colorless oil (47%).

RMN $^1$H (400 MHz, δ in ppm, DMSO-d6): 4.45 (s, 2H); 4.71 (s, 2H); 7.35 (d, J=8.5 Hz, 2H); 7.47 (d, J=8.5 Hz, 2H).

Compound 81: (1R,4S,5R,6S)-6-(4-(azidomethyl)benzyl)-4,7,7-trimethyl-6-thiabicyclo[3.2.1]octan-6-ium trifluoromethanesulfonate To (1R,4R,5R)-4,7,7-trimethyl-6-thiabicyclo[3.2.1]octane (CAS number [5718-75-2], 580.1 mg, 3.41 mmol) was added a solution of compound 80 (770 mg, 3.41 mmol) in DCM (2.2 mL). A solution of lithium trifluoromethanesulfonate (2.71 g, 17.03 mmol) in $H_2O$ 2 mL) was then added dropwise and the reaction medium was stirred at RT for 2 d. $H_2O$ (15 mL) and DCM (15 mL) were then added to the reaction medium and stirring carried on at RT for 10 min. The aqueous phase was extracted with DCM (3×15 mL), the combined organic phases were washed with sat. brine (3×8 mL), dried over $MgSO_4$, filtered and concentrated in vacuo. The pale yellow oil was triturated in $iPr_2O$ (5 mL), the solid thus obtained was filtered, washed with $iPr_2O$ (2×5 mL) and dried under vacuum to give 1.266 g of compound 81 as a white solid (79%).

RMN $^1$H (400 MHz, δ in ppm, DMSO-d6): 1.08 (d, J=7.2 Hz, 3H); 1.45 (m, 1H); 1.55 to 1.80 (m, 3H); 1.69 (s, 3H); 1.75 (s, 3H); 1.99 (m, 1H); 2.40 (d, J=13.8 Hz, 1H); 2.45 (m, 1H); 2.59 (dm, J=13.8 Hz, 1H); 3.88 (t, J=4.6 Hz, 1H); 4.52 (s, 2H); 4.60 (d, J=12.8 Hz, 1H); 4.90 (d, J=12.8 Hz, 1H); 7.47 (d, J=8.5 Hz, 2H); 7.61 (d, J=8.5 Hz, 2H).

Compound 82: (3S,10R,16S,E)-16-((S)-1-((2R,3R)-3-(4-(azidomethyl)phenyl)oxiran-2-yl)ethyl)-10-(3-chloro-4-methoxybenzyl)-6-methyl-3-neopentyl-6-(((triethylsilyl)oxy)methyl)-1-oxa-4,8,11-triazacyclohexadec-13-ene-2,5,9,12-tetraone To a solution of compounds 79 (35 mg, 48.5 µmol) and 81 (24.8 mg, 53.3 µmol) in DCM (1.5 mL) cooled at −70° C. was added dropwise BEMP (CAS number [98015-45-3], 18.6 µL, 63.0 µmol). The reaction mixture was stirred at −70° C. for 2 h 30, sat. brine (1.5 mL) was added to the reaction mixture, the bath removed and stirring carried on vigorously up to RT. The aqueous phase was extracted with DCM (3×10 mL), the combined organic phases were dried over $MgSO_4$, filtered, concentrated in vacuo and purified by flash chromatography on 5 g of silica gel (gradient elution DCM/MeOH) to give 10.2 mg of compound 82 as a colorless lacquer (24%).

RMN $^1$H (500 MHz, δ in ppm, DMSO-d6): 0.61 (q, J=8.1 Hz, 6H); 0.80 (s, 9H); 0.98 (t, J=8.1 Hz, 9H); 1.02 (s, 3H); 1.03 (d, J=7.1 Hz, 3H); 1.34 (dd, J=2.5 and 14.4 Hz, 1H); 1.44 (dd, J=10.0 and 14.4 Hz, 1H); 1.85 (m, 1H); 2.27 (m, 1H); 2.62 (m, 2H); 2.88 (dd, J=2.6 and 13.5 Hz, 1H); 2.97 (dd, J=3.7 and 14.2 Hz, 1H); 3.00 (dd, J=2.3 and 7.3 Hz, 1H); 3.35 (m, 1H); 3.48 (dd, J=9.5 and 14.2 Hz, 1H); 3.61 (d, J=10.3 Hz, 1H); 3.81 (s, 3H); 3.92 (d, J=2.3 Hz, 1H); 4.15 (m, 1H); 4.46 (s, 2H); 4.48 (td, J=2.5 and 9.7 Hz, 1H); 5.10 (m, 1H); 5.78 (dd, J=2.2 and 15.3 Hz, 1H); 6.40 (ddd, J=4.3, 11.6 and 15.3 Hz, 1H); 7.04 (m, 2H); 7.14 (dd, J=2.3 and 8.6 Hz, 1H); 7.28 (d, J=2.3 Hz, 1H); 7.33 (d, J=8.4 Hz, 2H); 7.39 (d, J=8.4 Hz, 2H); 7.96 (d, J=9.7 Hz, 1H); 8.28 (d, J=8.0 Hz, 1H). LCMS (A5): ES m/z=120; m/z=865 [M−H]$^−$; m/z=867 [M+H]$^+$; m/z=911 [M−H+HCO$_2$H]$^−$; $t_R$=1.87 min.

Example 32: (3S,10R,16S,E)-16-((S)-1-((2R,3R)-3-(4-(aminomethyl)phenyl)oxiran-2-yl)ethyl)-10-(3-chloro-4-methoxybenzyl)-6-methyl-3-neopentyl-6-(((triethylsilyl)oxy)methyl)-1-oxa-4, 8,11-triazacyclohexadec-13-ene-2,5,9,12-tetraone To a solution of compound 82 (9.4 mg, 10.84 µmol) in DCM (1.3 mL) and MeOH (0.7 mL) was added a solution of TCEP (3.45 mg, 11.9 µmol) in $H_2O$ (0.7 mL). The reaction medium was stirred at RT overnight then was added aq. $NaHCO_3$ (2.5 mL) and stirring carried on for 10 min. The aqueous phase was extracted with DCM (3×10 mL), the combined organic phases were dried over $MgSO_4$, filtered, concentrated in vacuo and purified by flash chromatography on 5 g of silica gel (gradient elution DCM/MeOH/$H_2O$) to give 4.55 mg of example 32 as a white lacquer (57%).

RMN $^1$H (500 MHz, δ in ppm, DMSO-d6): 0.82 (s, 9H); 1.01 (s, 3H); 1.03 (d, J=7.1 Hz, 3H); 1.33 (dd, J=2.3 and 14.5 Hz, 1H); 1.56 (dd, J=10.1 and 14.5 Hz, 1H); 1.82 (m, 1H); 2.27 (m, 1H); 2.64 (m, 2H); 2.88 (dd, J=2.6 and 13.5 Hz, 1H); 2.92 (dd, J=2.2 and 7.3 Hz, 1H); 2.96 (dd, J=4.0 and 11.2 Hz, 1H); 3.19 (dd, J=4.3 and 10.9 Hz, 1H); 3.41 (m, 2H); 3.74 (s, 2H); 3.81 (s, 3H); 3.88 (d, J=2.2 Hz, 1H); 4.18 (m, 1H); 4.47 (td, J=2.1 and 9.4 Hz, 1H); 4.91 (dd, J=4.2 and 6.2 Hz, 1H); 5.08 (m, 1H); 5.76 (dd, J=2.3 and 15.5 Hz, 1H); 6.40 (ddd, J=3.7, 11.5 and 15.5 Hz, 1H); 7.05 (d, J=8.8 Hz, 1H); 7.11 (m, 1H); 7.14 (dd, J=2.4 and 8.8 Hz, 1H); 7.22 (d, J=8.3 Hz, 2H); 7.25 (d, J=2.4 Hz, 1H); 7.35 (d, J=8.3 Hz, 2H); 8.08 (d, J=9.4 Hz, 1H); 8.31 (d, J=8.0 Hz, 1H). LCMS (A5): ES m/z=725 [M−H]⁻; m/z=727 [M−H]⁺; $t_R$=0.79 min.

Pharmacological Results

The compounds of the invention were subjected to pharmacological tests for determining their antitumoral effect. The ADC of formula (III) were also assessed in terms of plasmatic stability. For illustrative purposes, two conjugates, ADC1 and ADC2 depicted below, derived from WO2011/001052 were also tested.

The inhibitory activity is given by the concentration which inhibits 50% of the activity.

TABLE II

| | Structural comment[1] | IC$_{50}$ (pM) HCT116 | IC$_{50}$ (pM) MDA-MD-231 |
|---|---|---|---|
| C52 | β epoxide | 76 | 90 |
| Ex. 1 | β epoxide | 163 | 250 |

ADC 1

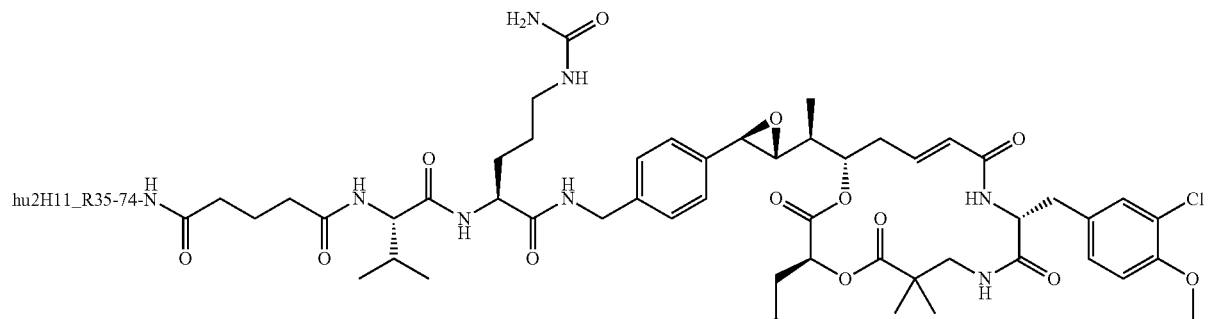

ADC 2

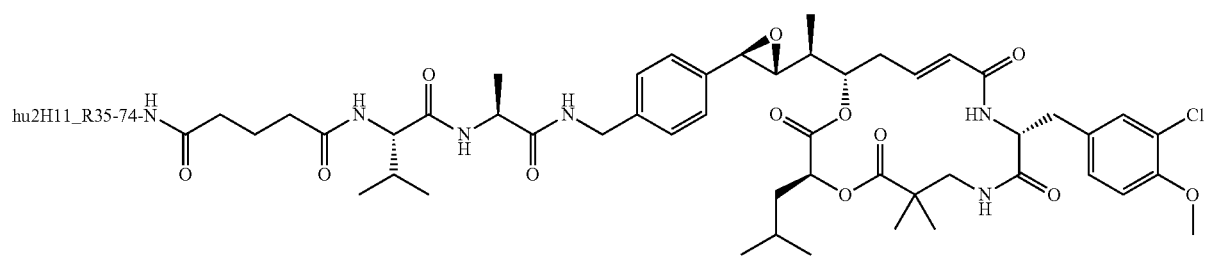

Evaluation of the Inhibition of Proliferation of the HCT116 and MDA-MB-231 Cell Lines by the Cryptophycin Compounds of Formula (I)

HCT116 and MDA-MB-231 cells in their exponential growth phase were trypsinized and resuspended in their respective culture medium (DMEM/F12 Gibco #21331, 10% FCS Gibco #10500-056, 2 nM glutamine Gibco #25030 for the MDA-MB-231 cells; DMEM Gibco #11960, 10% FCS Gibco #10500-056, 2 mM glutamine Gibco #25030 for the HCT116 cells). The cell suspension was seeded in Cytostar 96-well culture plates (GE Healthcare Europe, # RPNQ0163) in the whole culture medium containing serum at a density of 5000 cells/well. After incubation for 4 h, successive dilutions of the cryptophycin compounds were added to the wells at concentrations decreasing from $10^{-7}$ to $10^{-12}$ M (in triplicate for each concentration). The cells were cultured at 37° C. in an atmosphere containing 5% CO₂ in the presence of the cryptophycin compounds for 3 d. On the 4th day, 10 μl of a ¹⁴C-thymidine solution (0.1 μCi/well, Perkin Elmer # NEC56825000) were added to each well. The incorporation of ¹⁴C-thymidine was measured 96 h after the start of the experiment with a microbeta radioactivity counter (Perkin Elmer). The data were expressed in the form of a percentage of survival by determining the ratio between the reduced count obtained with the cells treated with the cryptophycin compound and the count obtained with the cells of the control wells (treated with the culture medium alone).

TABLE II-continued

| | Structural comment[1] | IC$_{50}$ (pM) HCT116 | IC$_{50}$ (pM) MDA-MD-231 |
|---|---|---|---|
| Ex. 4 | β epoxide | 51 | 82 |
| Ex. 8 | α/β epoxide 3:7 | 518 | 564 |
| Ex. 11 | β epoxide | n.t. | 102 |
| Ex. 15 | α/β epoxide 35:65 | n.t. | 511 |
| Ex. 16 | α/β epoxide 4:6 | n.t. | 2815 |
| Ex. 17 | α/β epoxide 5:5 | n.t. | 856 |
| Ex. 18 | β epoxide | 179 | 228 |
| Ex. 21 | α/β epoxide 3:7 | n.t. | 456 |
| Ex. 32 | β epoxide | n.t. | 1777 |

[1]Cryptophycin compounds of formula (I) were tested either as pure β epoxides or as a mixture of α and β epoxides as specified in the column entitled "structural comment". It is known from the literature that the β epoxides are usually 50 to 100 times more potent than the α epoxide (see for example, Al-Awar R.S., etal., J Med Chem 2003, 46, 2985-3007).

Cryptophycin compounds of formula (I) were found to inhibit the proliferation of HCT116 and MDA-MB-231 cell lines with IC$_{50}$ ranging from 50 μM to 2.815 nM.

Evaluation of the Inhibition of Proliferation of the MDA-MB-231 Cell Line by the ADC of Formula (III)

MDA-MB-231 cells in their exponential growth phase were trypsinized and resuspended in their culture medium (DMEM/F12 Gibco #21331, 10% FCS Gibco #10500-056, 2 nM glutamine Gibco #25030). The cell suspension was seeded in Cytostar 96-well culture plates (GE Healthcare Europe, # RPNQ0163) in the whole culture medium containing serum at a density of 5000 cells/well. After incubation for 4 h, successive dilutions of the ADC are added to the wells at concentrations decreasing from $10^{-7}$ to $10^{-12}$ M (in triplicate for each concentration). The cells were cultured at 37° C. in an atmosphere containing 5% $CO_2$ in the presence of the ADC for 3 d. On the $4^{th}$ day, 10 µl of a $^{14}C$-thymidine solution (0.1 ρCi/well, Perkin Elmer # NEC56825000) were added to each well. The incorporation of $^{14}C$-thymidine was measured 96 h after the start of the experiment with a microbeta radioactivity counter (Perkin Elmer). The data were expressed in the form of a percentage of survival by determining the ratio between the reduced count obtained with the cells treated with the ADC and the count obtained with the cells of the control wells (treated with the culture medium alone). In certain experiments, the naked antibody was added to the wells at a concentration of 1 µM at the start of the experiment and the inhibition of proliferation was measured as described previously.

TABLE III

| | $IC_{50}$ (pM), MDA-MB-231 | |
|---|---|---|
| | ADC alone | in the presence of naked antibody |
| ADC1 | 42 | 4571 |
| ADC2 | 46 | 9377 |
| Ex. 3 | 20 | 3738 |
| Ex. 7 | 38 | 18042 |
| Ex. 10 | 35 | 10367 |
| Ex. 14 | 53 | 25887 |
| Ex. 20 | 43 | 11871 |
| Ex. 23 | 129 | 64270 |
| Ex. 31 | 72 | 31784 |

Cryptophycin ADC of formula (III), as well as ADC1 and ADC2, were found to inhibit the proliferation of MDA-MB-231 cell line with $IC_{50}$ ranging from 20 µM to 130 µM and selectivity ratio ADC alone vs ADC+naked antibody between 185 and 500.

Determination of the MTD of the ADC of Formula (III) Following Single i.v. Administration in SCID Mice MTD was determined as the maximal dose that does not induce 15% body weight loss during 3 consecutive days for an individual mouse or 20% body weight loss during 1 day or mortality. It was evaluated after a single intravenous (i.v.) bolus injection in 3 female SCID mice and during a period of 28 days post-treatment.

TABLE IV

| | MTD (mg/kg) |
|---|---|
| Ex. 3 | 20 |
| Ex. 7 | 30 |
| Ex. 10 | 40 |
| Ex. 14 | ≥50 |
| Ex. 20 | 20 |
| Ex. 23 | ≥40 |

Cryptophycin ADC of formula (III) displayed MTD in SCID mice ranging from 20 mg/kg to 50 mg/kg.

Evaluation of the In Vivo Antitumor Activity of ADC of Formula (III) Against MDA-MB-231 in SCID Mice Following Single i.v. Administration In vivo antitumor activity was evaluated at 3 dose-levels against measurable breast MDA-MB-231 xenografts implanted s.c. in female SCID mice. Control groups were left untreated. Conjugates were administered by a single i.v. bolus injection, the day of the treatment was indicated on each graph by an arrow (▼).

For the evaluation of antitumor activity of conjugates, animals were weighed twice weekly and tumors were measured twice weekly by caliper. Animal body weights included the tumor weights. Tumor volume were calculated using the formula mass $(mm^3)$=[length (mm)×width $(mm)^2$]/2. The primary efficacy end points were ΔT/ΔC, percent median regression, partial and complete regressions (PR and CR). Changes in tumor volume for each treated (T) and control (C) were calculated for each tumor by subtracting the tumor volume on the day of first treatment (staging day) from the tumor volume on the specified observation day. The median ΔT was calculated for the treated group and the median ΔC was calculated for the control group. Then the ratio ΔT/ΔC was calculated and expressed as a percentage: ΔT/ΔC=(delta T/delta C)×100.

The percentage of tumor regression was defined as the % of tumor volume decrease in the treated group at a specified observation day (t) compared to its volume on the first day of first treatment (t0). At a specific time point and for each animal, % regression was calculated. The median % regression was then calculated for the group. % regression (at t)=(($Volume_{t0}$–$Volume_{t}$)/$Volume_{t0}$)×100. Regressions were defined as partial (PR) if the tumor volume decreased to 50% of the tumor volume at the start of treatment and complete (CR) when tumor volume cannot be measured (0 $mm^3$). Tumor free survivor (TFS) was defined as the animals with undetectable tumors at the end of the study (>100 days post last treatment).

Evaluation of the In Vivo Antitumor Activity of Ex. 3 Against MDA-MB-231 in SCID Mice Following Single i.v. Administration

TABLE V

| | Dose | Median ΔT/ΔC | Median % of | Regressions | | |
|---|---|---|---|---|---|---|
| | (mg/kg) | in % (day) | regression | PR | CR | TFS |
| Control | — | — | — | — | — | — |
| ADC2 | 2.5 | <0 (d53) | 90% | 4/6 | 3/6 | 0/6 |
| | 1.25 | 18 (d49) | — | 0/6 | 0/6 | 0/6 |
| Ex. 3 | 2.5 | <0 (d53) | 100% | 6/6 | 5/6 | 0/6 |
| | 1.25 | 9 (d53) | — | 2/6 | 0/6 | 0/6 |
| | 0.625 | 44 (d42) | — | 0/6 | 0/6 | 0/6 |

Evaluation of the In Vivo Antitumor Activity of Ex. 7 Against MDA-MB-231 in SCID Mice Following Single i.v. Administration

TABLE V

| Dose (mg/kg) | Median ΔT/ΔC in % (day) | Median % of regression | Regressions PR | CR | TFS |
|---|---|---|---|---|---|
| Control | — | — | — | — | — |
| ADC2 2.5 | <0 (d53) | 90% | 4/6 | 3/6 | 0/6 |
| 1.25 | 18 (d49) | — | 0/6 | 0/6 | 0/6 |
| Ex. 7 2.5 | <0 (d53) | 100% | 6/6 | 6/6 | 1/6 |
| 1.25 | <0 (d53) | 64% | 5/6 | 1/6 | 0/6 |
| 0.625 | 42 (d42) | — | 0/6 | 0/6 | 0/6 |

Evaluation of the In Vivo Antitumor Activity of Ex. 10 Against MDA-MB-231 in SCID Mice Following Single i.v. Administration

TABLE VI

| Dose (mg/kg) | Median ΔT/ΔC in % (day) | Median % of regression | Regressions PR | CR | TFS |
|---|---|---|---|---|---|
| Control | — | — | — | — | — |
| ADC2 2.5 | <0 (d42) | 14% | 0/6 | 0/6 | 0/6 |
| 1.25 | 6 (d42) | — | 0/6 | 0/6 | 0/6 |
| Ex. 10 2.5 | <0 (d59) | 95% | 6/6 | 3/6 | 0/6 |
| 1.25 | <0 (d46) | 32% | 0/6 | 0/6 | 0/6 |
| 0.625 | 16 (d42) | — | 0/6 | 0/6 | 0/6 |

Evaluation of the In Vivo Antitumor Activity of Ex. 14 Against MDA-MB-231 in SCID Mice Following Single i.v. Administration

TABLE VII

| Dose (mg/kg) | Median ΔT/ΔC in % (d34) | Median % of regression | Regressions PR | CR | TFS |
|---|---|---|---|---|---|
| Control | — | — | — | — | — |
| ADC2 2.5 | 21 | — | 0/6 | 0/6 | 0/6 |
| 1.25 | 48 | — | 0/6 | 0/6 | 0/6 |
| Ex. 14 5 | <0 | 100% | 6/6 | 6/6 | 1/6 |
| 2.5 | <0 | 11% | 1/6 | 0/6 | 0/6 |
| 1.25 | 39 | — | 0/6 | 0/6 | 0/6 |

Evaluation of the In Vivo Antitumor Activity of Ex. 20 Against MDA-MB-231 in SCID Mice Following Single i.v. Administration

TABLE VIII

| Dose (mg/kg) | Median ΔT/ΔC in % (day 40) | Median % of regression | Regressions PR | CR | TFS |
|---|---|---|---|---|---|
| Control | — | — | — | — | — |
| ADC2 2.5 | <0 | 49% | 4/6 | 0/6 | 0/6 |
| 1.25 | 14 | — | 0/6 | 0/6 | 0/6 |
| Ex. 20 5 | <0 | 100% | 6/6 | 6/6 | 6/6 |
| 2.5 | <0 | 100% | 6/6 | 4/6 | 1/6 |
| 1.25 | <0 | 3% | 3/6 | 1/6 | 0/6 |

Evaluation of the In Vivo Antitumor Activity of Ex. 23 Against MDA-MB-231 in SCID Mice Following Single i.v. Administration

TABLE VIII

| Dose (mg/kg) | Median ΔT/ΔC in % (day 40) | Median % of regression | Regressions PR | CR | TFS |
|---|---|---|---|---|---|
| Control | — | — | — | — | — |
| ADC2 2.5 | <0 | 49% | 4/6 | 0/6 | 0/6 |
| 1.25 | 14 | — | 0/6 | 0/6 | 0/6 |
| Ex. 23 5 | <0 | 81% | 6/6 | 3/6 | 0/6 |
| 2.5 | 16 | — | 1/6 | 0/6 | 0/6 |
| 1.25 | 36 | — | 0/6 | 0/6 | 0/6 |

These results showed that all the tested examples of the invention, as well as $ADC_2$, displayed antitumor activity at doses ranging from 0.625 mg/kg to 5 mg/kg.

Determination of PK Parameters of Ex. 3 and Ex. 7 Following a Single i.v. Administration in SCID Mice (5 mg/kg)

In vivo pharmacokinetics of ADC and total antibody were evaluated in female SCID mice following administration of the conjugate by a single i.v. bolus injection. Female SCID mice (5-6 weeks of age, weight on average 20-25 g) were housed in a sterile room, under aseptic conditions in a laminar hood and were fed ad libitum. The ADC was administered (non-serial design, n=3/sampling time) as an i.v. bolus at one dose level (10 mL/kg). For each animal and at each selected time point (i.e. 0.083, 0.25, 24, 72, 96, 168, 240, 336 h), 600 µL of blood were collected via cardiac puncture and blood samples were then centrifuged (15 min at 4° C. and 3500 tr/min). Quantification of ADC and total antibody in plasma samples was performed using immunoassays. Plasma concentration versus time profiles and PK parameters of conjugate and total antibody in mouse were characterized using non-compartmental analysis (Phoenix, WinNonLin version 6.3) and are depicted in FIGS. 15 and 16. The area under the concentration-time curve, AUC (µg·day/mL) was estimated by the trapezoidal rule. Concentration at t=0 $C_0$ (µg/mL), Clearance CL (L/(day·kg)), and terminal elimination half-life $t_{1/2}$ (day) were derived and calculated from the curve.

TABLE IX

| Analytes | $C_0$ (µg/mL) | $AUC_{last}$ (µg · day/mL) | $t_{last}$ (day) | AUC (µg · day/mL) | CL (L/(day · kg)) | $V_{ss}$ (L/kg) | $t_{1/2z}$ (day) |
|---|---|---|---|---|---|---|---|
| Ex. 3 ADC | 62.8 | 191 | 14 | 217 | 0.023 | 0.14 | 4.8 |
| total | 74.9 | 455 | 14 | 791[a] | 0.0063[a] | 0.10[a] | 11[a] |
| Ex. 7 ADC | 81.8 | 235 | 14 | 266 | 0.019 | 0.12 | 4.8 |
| total | 77.4 | 368 | 14 | 741[b] | 0.0067[b] | 0.14[b] | 16[b] |

[a]informative data only as $AUC_{ext}$ >> 30% (i.e. 42%);
[b]informative data only as $AUC_{ext}$ >> 30% (i.e. 50%).

Evaluation by HRMS of Plasmatic Stability of Cryptophycin ADC of Formula (III) Following Single i.v. Administration in SCID Mice at 5 mg/kg Plasma samples from the PK study were also analyzed by LC-HRMS. The chromatographic analysis was performed on a Waters Acquity I Class and a Waters Mass Prep Micro Desalting 20 μm (2.1×5 mm) column at 80° C. with a gradient elution of (A) water+0.1% formic acid/(B) $CH_3CN$+0.1% formic acid described below.

| Time (min) | % B | Flow (ml/min) |
|---|---|---|
| 0.00 | 5 | 0.5 |
| 0.50 | 5 | 0.5 |
| 0.51 | 5 | 0.2 |
| 2.00 | 90 | 0.2 |
| 2.10 | 5 | 0.5 |
| 2.70 | 90 | 0.5 |
| 2.80 | 5 | 0.5 |
| 3.40 | 90 | 0.5 |
| 3.50 | 5 | 0.5 |
| 4.00 | 5 | 0.5 |

The mass spectrometry was performed on a Waters QTOF Synapt G2-S machine with electrospray ionization in positive mode (ES+). The mass spectra were deconvoluted with the Waters Biopharmalynx software. HRMS spectra were obtained for all tested examples and are depicted in FIGS. 20 to 25.

These results showed that all tested examples of the invention didn't display the metabolization observed with reference ADC, ADC1 and ADC2.

It is therefore apparent that the compounds of the invention have an anticancer activity and that the conjugates of the invention display an improved stability in mice plasma.

Accordingly, in another of its aspects, the invention also relates to the use of cryptophycin compounds of formula (I) or of the conjugates of formula (III) as anticancer agents.

The present invention, according to another of its aspects, also provides medicaments which comprise a conjugate of formula (III).

These medicaments are employed therapeutically, especially in the treatment of cancer.

According to another of its aspects, the present invention relates to pharmaceutical compositions comprising as active principle a conjugate of formula (III) according to the invention. These pharmaceutical compositions comprise an effective dose of at least one conjugate of formula (III) according to the invention and also at least one pharmaceutically acceptable excipient.

The said excipients are selected, in accordance with the pharmaceutical form and method of administration desired, from the customary excipients, which are known to a person skilled in the art.

The present invention, according to another of its aspects, also provides a method of treating the pathologies indicated above, which comprises administering to a patient an effective dose of a conjugate of formula (III) according to the invention.

The invention claimed is:

1. A compound of formula (I):

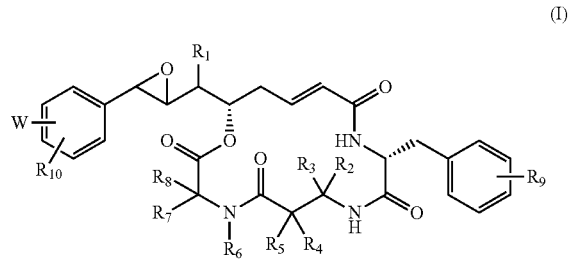

(I)

wherein:

$R_1$ represents a -($C_1$-$C_6$)alkyl group;

$R_2$ and $R_3$ represent, independently of each other, a hydrogen atom or a -($C_1$-$C_6$)alkyl group, or alternatively $R_2$ and $R_3$ form together with the carbon atom to which they are attached a -($C_3$-$C_6$)cycloalkyl group or a -($C_3$-$C_6$)heterocycloalkyl group;

$R_4$ and $R_5$ represent, independently of each other, a hydrogen atom, a -($C_1$-$C_6$)alkyl group, a -($C_1$-$C_6$)alkyl-NH($R_{12}$) group, a -($C_1$-$C_6$)alkyl-OH group, a -($C_1$-$C_6$)alkyl-SH group, or a -($C_1$-$C_6$)alkyl-$CO_2$H group, or alternatively $R_4$ and $R_5$ form together with the carbon atom to which they are attached a -($C_3$-$C_6$)cycloalkyl group or a -($C_3$-$C_6$)heterocycloalkyl group;

$R_6$ represents a hydrogen atom or a -($C_1$-$C_6$)alkyl group;

$R_7$ and $R_8$ represent, independently of each other, a hydrogen atom, a -($C_1$-$C_6$)alkyl group, a -($C_1$-$C_6$)alkyl-$CO_2$H group, or a -($C_1$-$C_6$)alkyl-N($C_1$-$C_6$)alkyl$_2$ group, or alternatively $R_7$ and $R_8$ form together with the carbon atom to which they are attached a -($C_3$-$C_6$) cycloalkyl group or a -($C_3$-$C_6$)heterocycloalkyl group;

$R_9$ represents one or more substituents chosen, independently of each other, from: a hydrogen atom, -OH, a -($C_1$-$C_4$)alkoxy group, a halogen atom, -$NH_2$, a -NH ($C_1$-$C_6$)alkyl group, a -N($C_1$-$C_6$)alkyl$_2$ group, a -NH ($C_1$-$C_6$)cycloalkyl group, and a -($C_3$-$C_6$)heterocycloalkyl group;

$R_{10}$ represents at least one substituent chosen from a hydrogen atom and a -($C_1$-$C_4$)alkyl group;

W represents

-$C_1$-$C_6$)alkyl-NH($R_{11}$),

-($C_1$-$C_6$)alkyl-OH,

-($C_1$-$C_6$)alkyl-SH,

-$CO_2$H,

-C(=O)$NH_2$,

-($C_1$-$C_6$)alkyl-$CO_2$H,

-($C_1$-$C_6$)alkyl-C(=O)$NH_2$, or

-($C_1$-$C_6$)alkyl-$N_3$; and $R_{11}$ and $R_{12}$ represent, independently of each other, a hydrogen atom or a -($C_1$-$C_6$)alkyl group.

2. The compound of formula (I) according to claim 1, having the following structure:

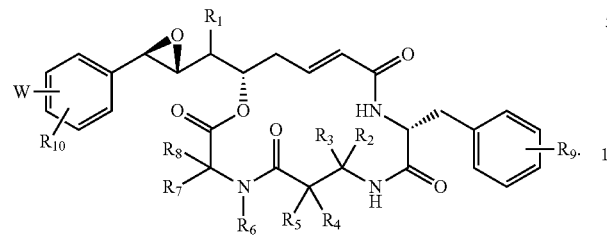

3. The compound of formula (I) according to claim 1, wherein $R_1$ represents a methyl group.

4. The compound of formula (I) according to claim 1, wherein:
  each of $R_2$ and $R_3$ represents a hydrogen atom, or
  one of $R_2$ and $R_3$ represents a methyl group and the other one represents a hydrogen atom, or
  $R_2$ and $R_3$ form together with the carbon atom to which they are attached a cyclopropyl group.

5. The compound of formula (I) according to claim 1, wherein each of $R_4$ and $R_5$ represents a methyl group.

6. The compound of formula (I) according to claim 1, wherein $R_6$ represents a hydrogen atom.

7. The compound of formula (I) according to claim 1, wherein $R_7$ and $R_8$ represent, independently of each other, a hydrogen atom or a -($C_1$-$C_6$)alkyl group.

8. The compound of formula (I) according to claim 1, wherein $R_9$ represents two substituents independently of each other selected from a methoxy group and a chlorine atom.

9. The compound of formula (I) according to claim 1, wherein $R_{10}$ represents a hydrogen atom.

10. The compound of formula (I) according to claim 1, wherein:
  $R_1$ represents a ($C_1$-$C_6$)alkyl group;
  each of $R_2$ and $R_3$ represents a hydrogen atom;
  $R_6$ represents a hydrogen atom;
  $R_9$ represents two substituents independently of each other selected from a methoxy group and a chlorine atom; and
  $R_{10}$ represents a hydrogen atom.

11. The compound of formula (I) according to claim 1, wherein:
  $R_1$ represents a -($C_1$-$C_6$)alkyl group;
  one of $R_2$ and $R_3$ represents a -($C_1$-$C_6$)alkyl group, and the other one represents a hydrogen atom;
  $R_6$ represents a hydrogen atom;
  $R_9$ represents two substituents independently of each other selected from a methoxy group and a chlorine atom; and
  $R_{10}$ represents a hydrogen atom.

12. The compound of formula (I) according to claim 1, wherein W is selected from the group consisting of -($C_1$-$C_6$)alkyl-$NHR_{11}$, -($C_1$-$C_6$)alkyl-OH, -($C_1$-$C_6$)alkyl-SH and -($C_1$-$C_6$)alkyl-$CO_2$H.

13. The compound of formula (I) according to claim 1, wherein W represents a -$CH_2$—$NH_2$ group or a -$CH_2$—OH group.

14. The compound of formula (I) according to claim 1, wherein the compound is selected from the group consisting of:

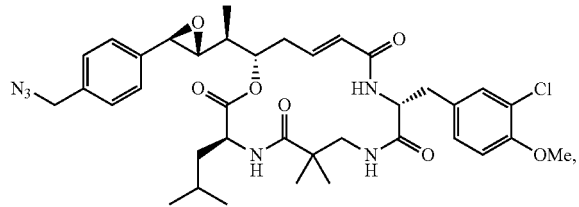

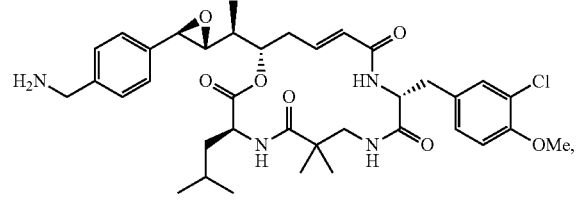

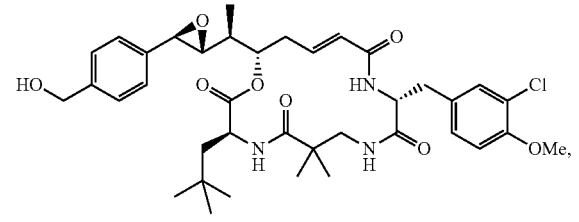

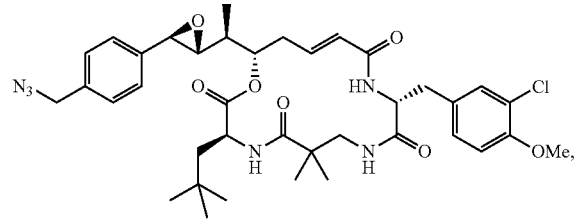

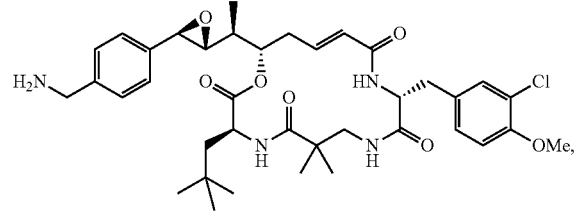

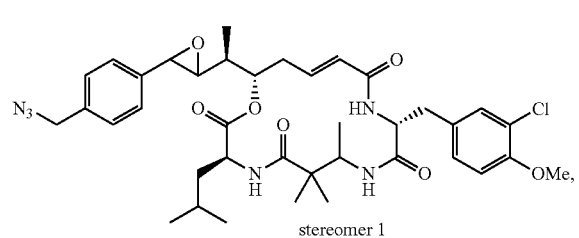

stereomer 1

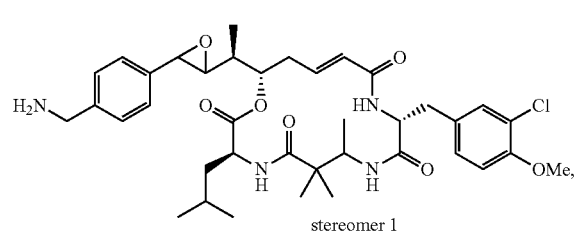

stereomer 1

537
-continued

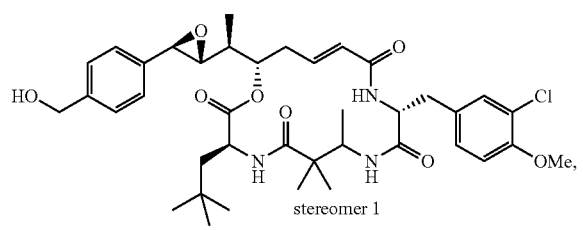
stereomer 1

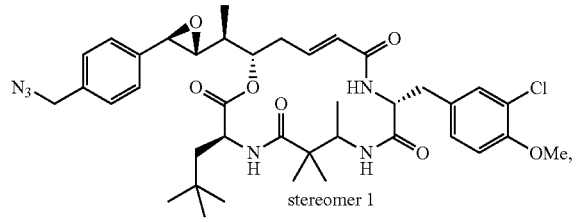
stereomer 1

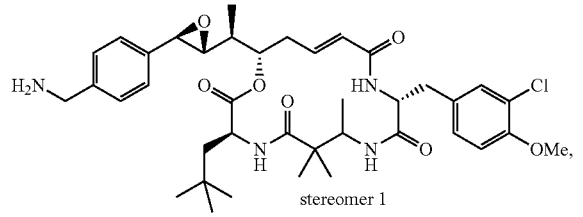
stereomer 1

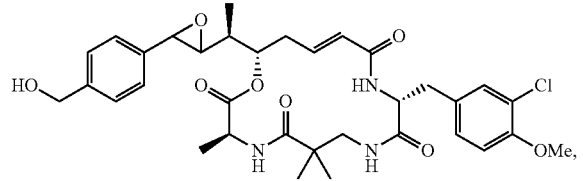

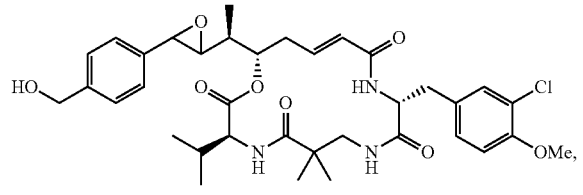

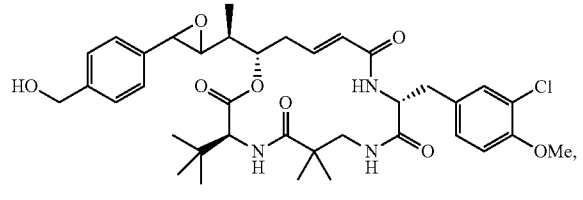

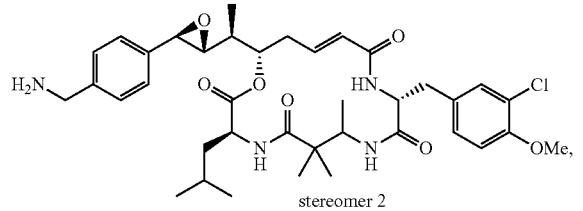
stereomer 2

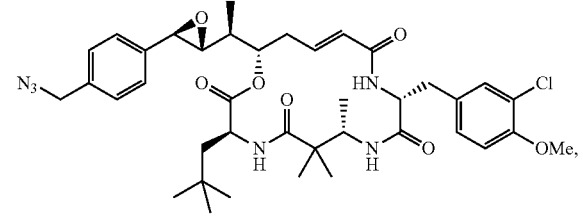

538
-continued

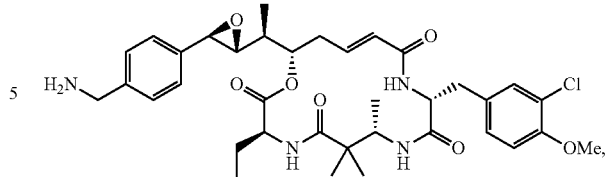

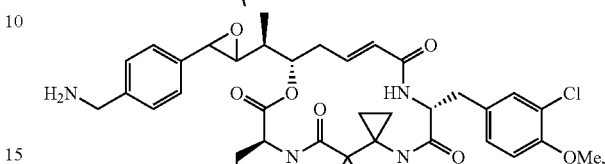

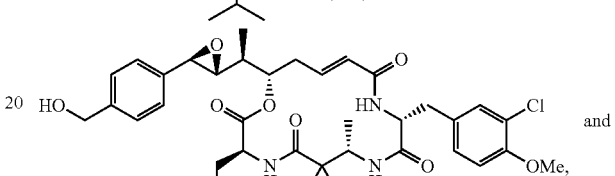
and

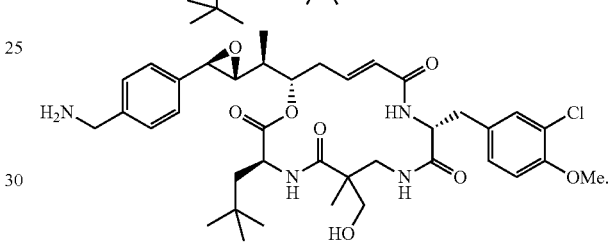

15. A compound of formula (II):

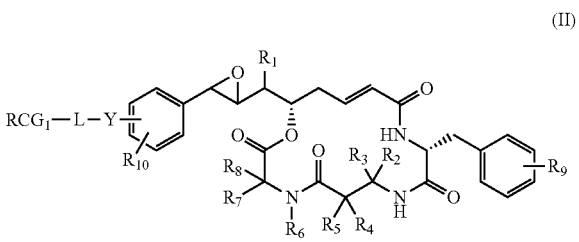

(II)

wherein
$R_1$ represents a -($C_1$-$C_6$)alkyl group;
$R_2$ and $R_3$ represents, independently of each other, a hydrogen atom or a -$C_1$-$C_6$ alkyl group, or alternatively $R_2$ and $R_3$ form together with the carbon atom to which they are attached a -($C_3$-$C_6$) cycloalkyl group or a -($C_3$-$C_6$)heterocycloalkyl group;
$R_4$ and $R_5$ represent; independently of each other; a hydrogen atom; a -($C_1$-$C_6$)alkyl group; a -($C_1$-$C_6$)alkyl-NH($R_{12}$) group, a -($C_1$-$C_6$)alkyl-OH group a -($C_1$-$C_6$) alkyl-SH group or a -($C_1$-$C_6$)alkyl-$CO_2$H group; or alternatively $R_4$ and $R_5$ form together with the carbon atom to which they are attached a -($C_3$-$C_6$)cycloalkyl group or a -($C_3$-$C_6$)heterocycloalkyl group;
$R_6$ represents a hydrogen atom or a -($C_1$-$C_6$)alkyl group;
$R_7$ and $R_8$ represent; independently of each other; a hydrogen atom; a -($C_1$-$C_6$)alkyl-$CO_2$H group, or a -($C_1$-$C_6$)alkyl-N($C_1$-$C_6$) group, or alternatively $R_7$ and $R_8$ form together with the carbon atom to which they are attached a-($C_3$-$C_6$)cycloalkyl group or a -($C_3$-$C_6$) heterocycloalkyl group;

R$_9$ represents one or more sustitutes chosen, independently of each other, from: a hydrogen atom, -OH, a -(C$_1$-C$_4$)alkxoxy group, a halogen atome, -NH$_2$, a -NH(C$_1$-C$_6$)cycloalkyl group or a a -N(C$_1$-C$_6$)alkyl$_2$ group, a -NH(C$_1$-C$_6$)cycloalkyl group, and a -(C$_3$-C$_6$) cycloalkyl group;

R$_{10}$ represents at least one substitute chosen from a hydrogen atom and a -(C$_1$-C$_4$)alkyl group;

Y is selected from the group consisting of -(C$_1$-C$_6$)alkyl-NR$_{11}$-,-(C$_1$-C$_6$)-O-, -(C$_1$-C$_6$)alkyl-S-, -C(=O)O-, -O(=O)NH-, -(C$_1$-C$_6$)alkyl-C(=O)O-, and -(C$_1$-C$_6$)alkyl-C(=O)NH-;

R$_{11}$ represents a hydrogen atom or a -(C$_1$-C$_6$)alkyl group;

L represents a linker; and

RCGi represents a reactive chemical group present at the end of the linker, the linker L being of formula (IV):

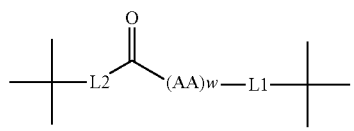

(IV)

wherein:

L1 represents a single bond or a -NR$_{16}$(hetero)aryl-CR$_{15}$R$_{14}$-O-C(=O)- group if Y is -(C$_1$-C$_6$)alkyl-N(R$_{11}$)-, a -NR$_{18}$-(C$_2$-C$_6$)alkyl-NR$_{17}$-C(=O)- group or a -NR$_{16}$(hetero)aryl-CR$_{15}$R$_{14}$-O-C(=O)-NR$_{18}$-($_2$-C$_6$)alkyl-NR$_{17}$-C(=O) - group if Y is -(C$_1$-C$_6$)alkyl- -O- or -(C$_1$-C$_6$)alkyl- S-, or a -NR$_{16}$(hetero)aryl-CR$_{15}$R$_{14}$- group if Y is -C(=O)O-, -(=O)NH-, -(C$_1$-C$_6$)alkyl-C(=O)O- or -(C$_1$-C$_6$)alkyl-C(=O)NH-;

L$_1$ is covalently bound to Y;

R$_{14}$, R$_{15}$, R$_{16}$, R$_{17}$ and R$_{18}$ each represent, independently of each other, a hydrogen atom or a -(C$_1$-C$_6$)alkyl group;

(AA)$_w$, represents a sequence of w amino acids AA connected together via peptide bonds;

w represents an integer ranging from 1 to 12;

L$_2$ represents a single bond, a -(C$_1$-C$_6$)alkyl- group, a -(C$_1$-C$_6$)alkyl-(OCH$_2$CH$_2$)- group, a -(C$_1$-C$_6$)alkyl-(OCH$_2$CH$_2$)$_i$-O(C$_1$-C$_6$)alkyl- group, a -(CH$_2$CH$_2$O)$_i$(C$_1$-C$_6$)alkyl- group, a -CH(SO$_3$H)-(C$_1$-C$_6$)alkyl- group, a -(C$_1$-C$_6$)alkyl-CH(SO$_3$H)- group, a -(C$_1$-C$_6$)alkyl-cyclohexyl- group, a -NR$_{19}$-(C$_1$-C$_6$)alkyl- group, a -NR$_{20}$-(CH$_2$CH$_2$O)$_i$(C$_1$-C$_6$)alkyl- group, a -NR$_{21}$-aryl- group, a -NR$_{21}$-heteroaryl- group, a -(C$_1$-C$_6$)alkyl-NR$_{22}$C(=O)-(C$_1$-alkyl- group or a (C$_1$-C$_6$)alkyl-NR$_{22}$C(=O)-(C$_1$-C$_6$)alkyl-(OCH$_2$CH$_2$)$_i$- group;

R$_{19}$, R$_{20}$, R$_{21}$ and R$_{22}$ each represent, independently of each other, a hydrogen atom or a (Ci- C6)alkyl group;

L2 is covalently bound to RCG1;

i represents an integer between 1 and 50; and each amino acid AA denotes a natural or unnatural amino acid, of configuration D or L.

16. The compound of formula (II) according to claim 15, having the following structure:

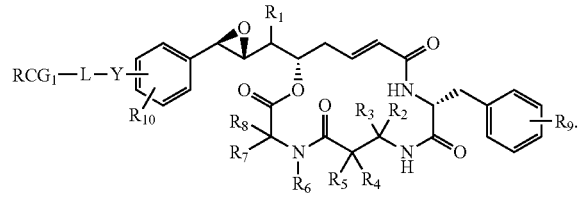

17. The compound of formula (II) according to claim 15, wherein Y represents a -(C$_1$-C$_6$)alkyl-NR$_{11}$-group.

18. The compound of formula (II) according to claim 15, wherein Y represents a -CH$_2$—NH- group.

19. The compound of formula (II) according to claim 15, wherein the sequence (AA), has the formula:

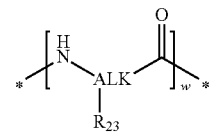

in which R$_{23}$ represents the side chain of AA.

20. The compound of formula (II) according to claim 15, wherein each amino acid AA is independently selected from the group consisting of alanine (Ala), citrulline (Cit), glutamine (Gln), glycine (Gly), ε-acetyl-lysine (AcLys), and valine (Val).

21. The compound of formula (II) according to claim 15, wherein RCG1 is chosen from:

-C(=O)—Z$_a$ R$_a$ group, wherein

Z$_a$ represents a single bond, -O- or -NH-; and

R$_a$ represents a hydrogen atom, a -(C$_1$-C$_6$)alkyl group, a -(C$_3$-C$_7$)cycloalkyl group, a -(C$_5$-C$_{10}$)aryl group, a -(C$_5$-C$_{10}$)heteroaryl group, a -(C$_3$-C$_7$)heterocycloalkyl group or a succinimidyl group; or

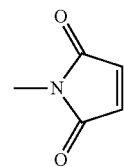

541

$R_a$ is selected from one of the following reactive groups:
the maleimido group,

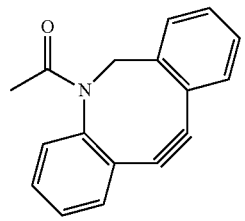 [SMILES: CC(=O)N1Cc2ccccc2C#Cc2ccccc21]

542

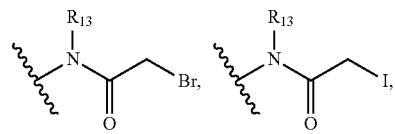

-Cl, -N₃, -OH, -SH, -NH2, -C≡CH, a group or a -O-(C₁-C₆)alkyl hydroxylamine group, wherein $R_{13}$ represents a hydrogen atom or a -(C₁-C₆)alkyl group.

22. The compound of formula (II) according to claim 15, wherein L2 represents a -(C₁-C₆)alkyl-group, a-(C₁-C₆)alkyl-(OCH₂CH₂)- group or a -CH(SO₃H)-(C₁-C₆)alkyl-group.

23. The compound of formula (II) according to claim 15, wherein the compounds is selected from the group consisting of:

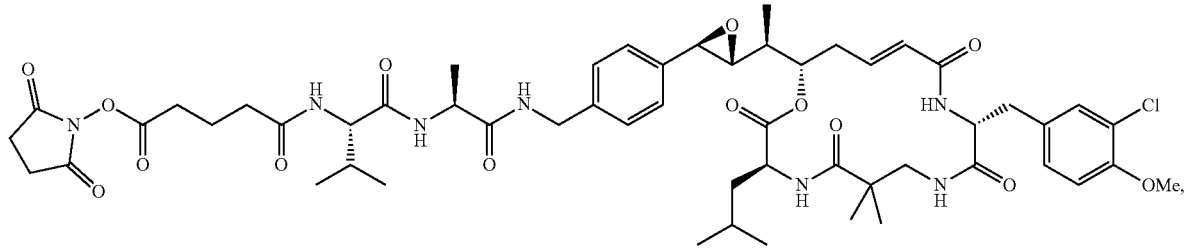

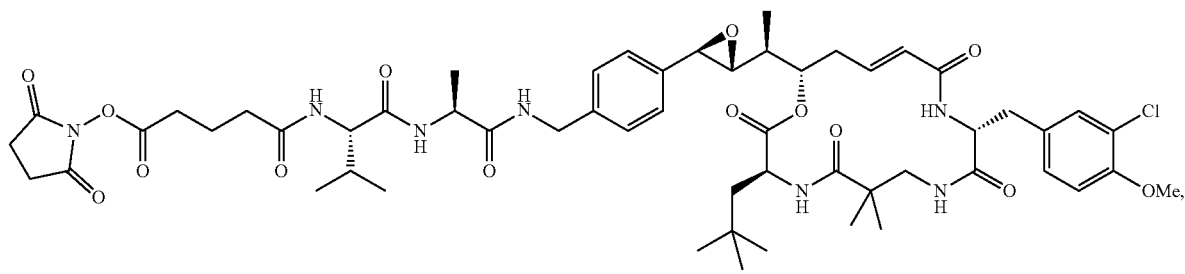

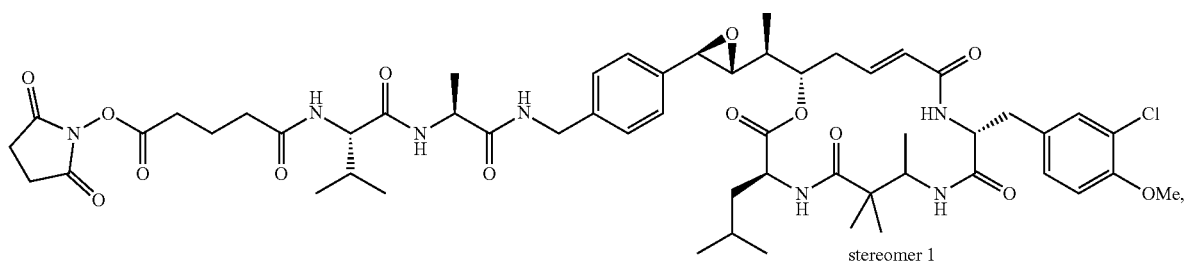

stereomer 1

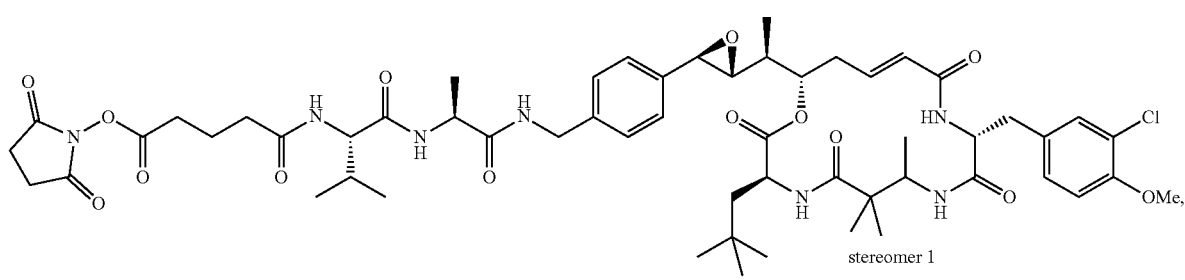

stereomer 1

-continued

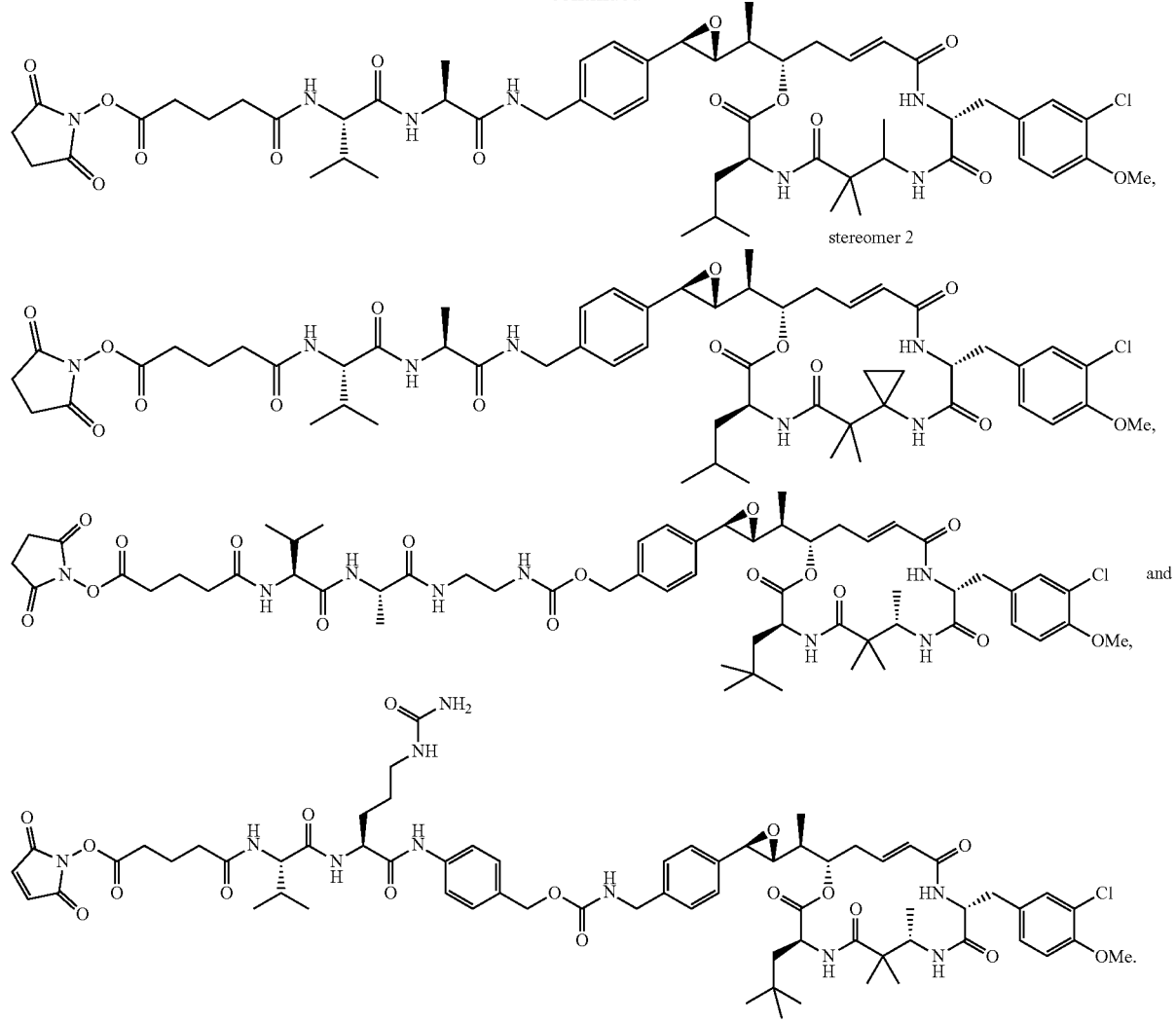

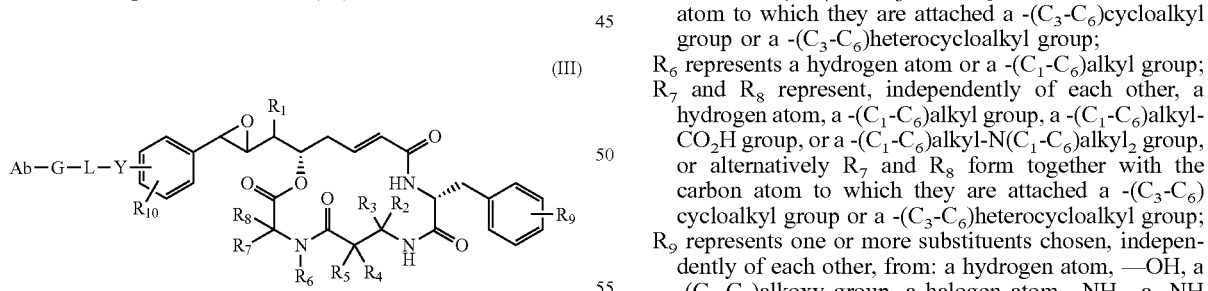

24. A compound of formula (III):

(III)

Ab—G—L—Y—[structure with R1, R10, R8, R7, R6, R5, R4, R3, R2, R9]

wherein $R_1$ represents a -($C_1$-$C_6$)alkyl group;

$R_2$ and $R_3$ represent, independently of each other, a hydrogen atom or a -($C_1$-$C_6$)alkyl group, or alternatively $R_2$ and $R_3$ form together with the carbon atom to which they are attached a -($C_3$-$C_6$)cycloalkyl group or a -($C_3$-$C_6$)heterocycloalkyl group;

$R_4$ and $R_5$ represent, independently of each other, a hydrogen atom, a -($C_1$-$C_6$)alkyl group, a -($C_1$-$C_6$)alkyl-NH($R_{12}$) group, a -($C_1$-$C_6$)alkyl-OH group, a -($C_1$-$C_6$)alkyl-SH group, or a -($C_1$-$C_6$)alkyl-$CO_2$H group, or alternatively $R_4$ and $R_5$ form together with the carbon atom to which they are attached a -($C_3$-$C_6$)cycloalkyl group or a -($C_3$-$C_6$)heterocycloalkyl group;

$R_6$ represents a hydrogen atom or a -($C_1$-$C_6$)alkyl group;

$R_7$ and $R_8$ represent, independently of each other, a hydrogen atom, a -($C_1$-$C_6$)alkyl group, a -($C_1$-$C_6$)alkyl-$CO_2$H group, or a -($C_1$-$C_6$)alkyl-N($C_1$-$C_6$)alkyl$_2$ group, or alternatively $R_7$ and $R_8$ form together with the carbon atom to which they are attached a -($C_3$-$C_6$)cycloalkyl group or a -($C_3$-$C_6$)heterocycloalkyl group;

$R_9$ represents one or more substituents chosen, independently of each other, from: a hydrogen atom, —OH, a -($C_1$-$C_4$)alkoxy group, a halogen atom, -$NH_2$, a -NH($C_1$-$C_6$)alkyl group, a -N($C_1$-$C_6$)alkyl$_2$ group, a -NH($C_1$-$C_6$)cycloalkyl group, and a ($C_3$-$C_6$)heterocycloalkyl group;

$R_{10}$ represents at least one substituent chosen from a hydrogen atom and a -($C_1$-$C_4$)alkyl group;

Y is selected from the group consisting of -($C_1$-$C_6$)alkyl-$NR_{11}$-, -($C_1$-$C_6$)alkyl-O-, -$C_1$-$C_6$)alkyl-S-, -C(=O)O-, -C(=O)NH-, -($C_1$-$C_6$)alkyl-C(=O)O-, and -($C_1$-$C_6$)alkyl-C(=O)NH-;

L represents a linker; and $RCG_1$ represents a reactive chemical group present at the end of the linker, the linker L being of formula (IV);

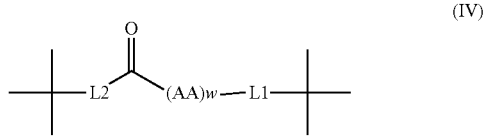

(IV)

wherein;
L1 represents
a single bond or a -NR$_{16}$(hetero)aryl-CR$_{15}$R$_{14}$-O-C(=O)- group if Y is -(C$_1$-C$_6$)alkyl-N(R$_{11}$)-,
a -NR$_{18}$-(C$_2$-C$_6$)alkyl-NR$_{17}$-C(=O)- group or a -NR$_{16}$(hetero)aryl-CR$_{15}$R$_{14}$-O-C(=O)-NR$_{18}$-(C$_2$-C$_6$)alkyl-NR$_{17}$-C(=O)- group if Y is -(c$_1$-c$_6$)alkyl-O- or -(C$_1$-C$_6$)alkyl-S-, or
a -NR$_{16}$(hetero)aryl-CR$_{15}$R$_{14}$- group if Y is -C(=O)O-, -C(=O)NH-, -(C$_1$-C$_6$) alkyl-C(=O)O- or -(C$_1$-C$_6$)alkyl-C(=O)NH-;
L1 is covalently bound to Y;
R$_{14}$, R$_{15}$, R$_{16}$, R$_{17}$ and R$_{18}$ each represent, independently of each other, a hydrogen atom or a -(C$_1$-C$_6$) alkyl group;
(AA)$_w$ represents a sequence of W amino acids AA connected together via peptide bonds;
w represents an integer ranging from 1 to 12;
L2 represents a single bond, a -(C$_1$-C$_6$)alkyl group, a -(C$_1$-C$_6$)alkyl-(OCH$_2$CH$_2$)$_i$- group, a -(C$_1$-C$_6$)alkyl-(OCH$_2$CH$_2$)$_i$-O(C$_1$-C$_6$)alkyl- group, a -(CH$_2$CH$_2$O)$_i$(c$_1$-C$_6$)alkyl- group, a -CH(SO$_3$H)-(C$_1$-C$_6$)alkyl- group, a -(C$_1$-C$_6$)alkyl-CH(SO$_3$H)- group, a -(C$_1$-C$_6$) alkyl-cyclohexyl- group, a -NR$_{19}$-(C$_1$-C$_6$)alkyl- group, a -NR$_{20}$-(CH$_2$CH$_2$O)$_i$(C$_1$-C$_6$)alkyl- group, a -NR$_{21}$-aryl- group, a -NR$_{21}$-heteroaryl- group, a -(C$_1$-C$_6$)alkyl-NR$_{22}$C(=O)-(C$_1$-C$_6$)alkyl- group or a -(C$_1$-C$_6$)alkyl-NR$_{22}$C(=O)-(C$_1$-C$_6$)alkyl-(OCH$_2$CH$_2$)$_i$- group;
R$_{19}$, R$_{20}$, R$_{21}$ and R$_{22}$ each represent, independently of each other, a hydrogen atom or a (c$_1$-C$_6$)alkyl group;
L2 is covalently bound to RCG1;
i represents an integer between 1 and 50; and
each amino acid AA denotes a natural or unnatura amino acid, of configuration D or L,
G represents the product of reaction RCG1, a reactive group present at the end of the linker and RCG2, an orthogonal reactive group present on Ab; and
Ab represents an antibody.

25. The compound of formula (III) according to claim 24 having the following structure:

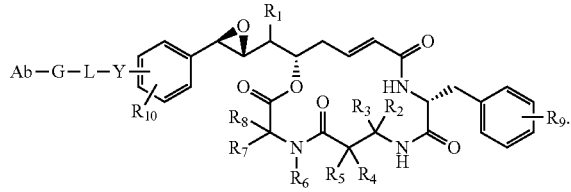

26. The compound of formula (III) according to claim 24, wherein RCG2 is selected from the group consisting of:
(i) one or more ε-amino groups borne by side chains of lysine residues that are present at the surface of the antibody,
(ii) one or more α-amino groups of N-terminal amino acids of heavy and light chains of the antibody,
(iii) one or more saccharide groups of the hinge region of the antibody,
(iv) one or more thiols of cysteines generated by reducing intra-chain disulfide bonds of the antibody or the thiols of engineered cysteines of the antibody,
(v) one or more amide groups borne by side chains of glutamine residues that are present at the surface of an antibody, and
(v) one or more aldehyde groups introduced into the antibody using a formylglycine generating enzyme.

27. The compound of formula (III) according to claim 24, wherein:
when RCG1 represents a N-hydroxysuccinimidyl ester, RCG2 represents a -NH$_2$ group, or
when RCG1 represents a maleimido or a haloacetamido function or a —Cl group, RCG2 represents a —SH group, or
when RCG1 represents a —N$_3$ group, RCG2 represents a —C≡CH group or an activated C≡C or
when RCG1 represents a -OH or -NH$_2$ group, RCG2 represents a carboxylic acid or amide function, or
when RCG1 represents a —SH group, RCG2 represents a maleimido or a haloacetamido function, or
when RCG1 represents a —C≡CH function or an activated C≡C, RCG2 represents a -N$_3$ group, or
when RCG1 represents a O-alkyl hydroxylamine function or a Pictet-Spengler reaction substrate, RCG2 represents an aldehyde or a ketone function.

28. The compound of formula (III) according to claim 24, wherein G is selected from:

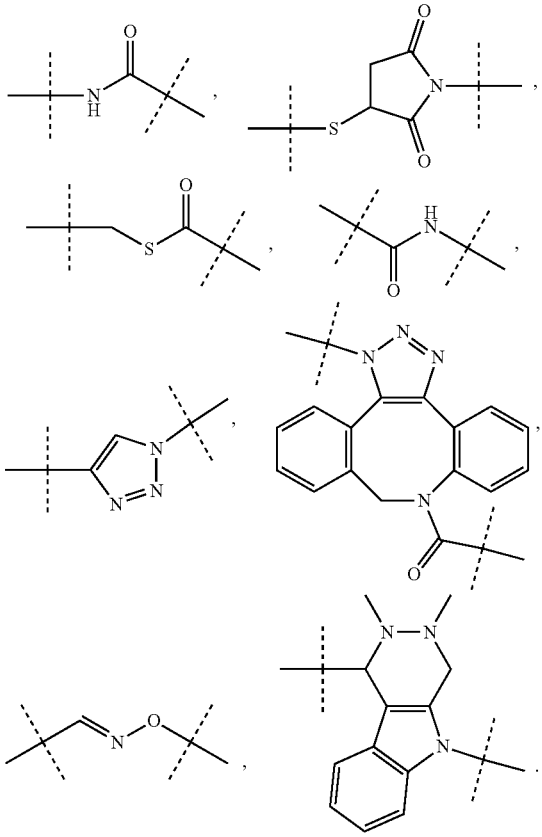

29. A method for preparing the compound compound of formula (I) according to claim 1, the method comprising the following steps:

(a) performing a peptide coupling by contacting AD3;

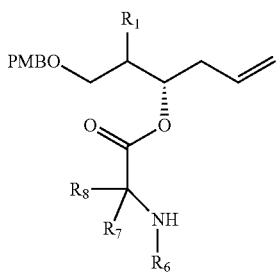

with BC:

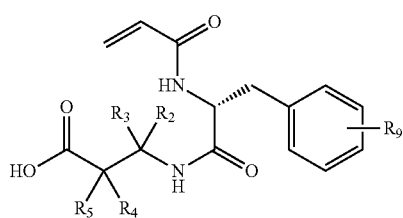

in the presense of coupling reagents to form;

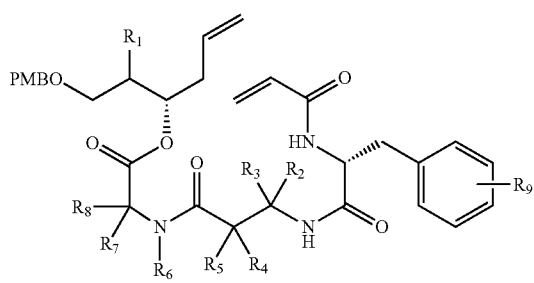

(b) subjecting the product of step (a) to a ring closing metathesis in the presence of a catalyst to form;

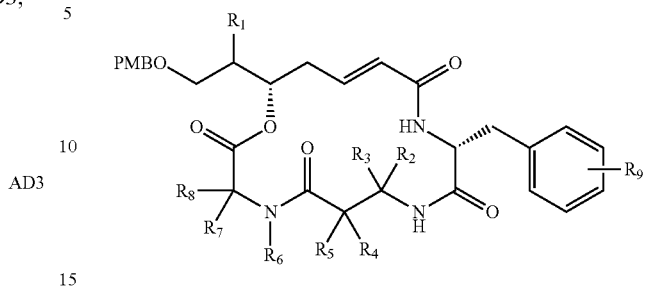

(c) deprotecting the product of step (b) under acidic conditions and oxidizing the unprotected alcohol using an oxidizing agent to form;

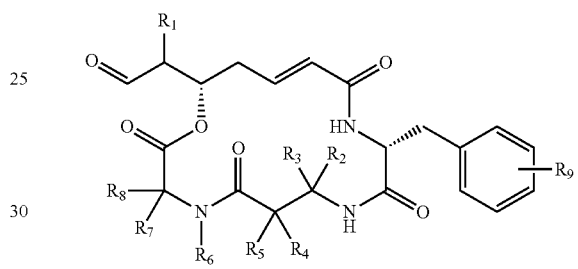

(d) subjecting the product of step (c) to epoxidation by asymmetric Corey-Chaykovsky reaction using appropriately sobstituted isothiocineole-derived chiral sulfonium in the presence of a base to form:

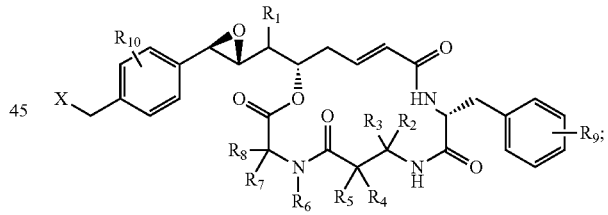

$X = N_3, P_2$
$X = OH, P_4$ and (e) optionally reducing an azido group to form:

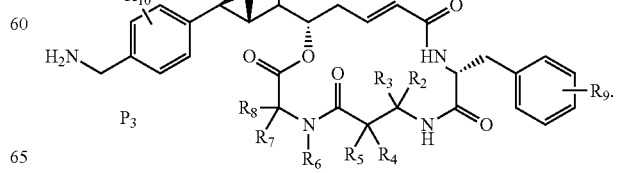

30. A compound for preparing a compound of formula (III)

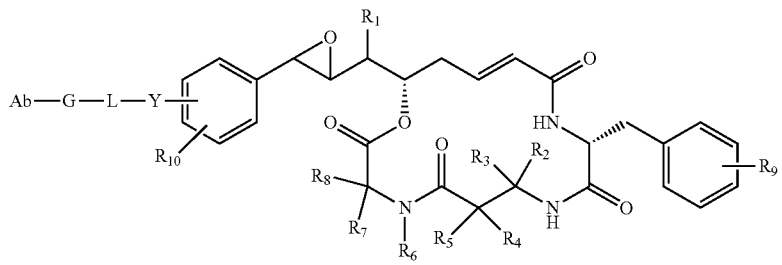

wherein
- $R_1$ represents a $-(C_1-C_6)$alkyl group;
- $R_2$ and $R_3$ represent, independently of each other, a hydrogen atom or a $-(C_1-C_6)$alkyl group, or alternatively $R_2$ and $R_3$ form together with the carbon atom to which they are attached a $-(C_3-C_6)$cycloalkyl group or a $-(C_3-C_6)$heterocycloalkyl group;
- $R_4$ and $R_5$ represent, independently of each other, a hydrogen atom, a $-(C_1-C_6)$alkyl group, a $-(C_1-C_6)$alkyl-$NH(R_{12})$ group, a $-(C_1-C_6)$alkyl-OH group, a $-(C_1-C_6)$alkyl-SH group, or a $-(C_1-C_6)$alkyl-$CO_2H$ group, or alternatively $R_4$ and $R_5$ form together with the carbon atom to which they are attached a $-(C_3-C_6)$cycloalkyl group or a $-(C_3-C_6)$heterocycloalkyl group;
- $R_6$ represents a hydrogen atom or a $-(C_1-C_6)$alkyl group;
- $R_7$ and $R_8$ represent, independently of each other, a hydrogen atom, a $-(C_1-C_6)$alkyl group, a $-(C_1-C_6)$alkyl-$CO_2H$ group, or a $-(C_1-C_6)$alkyl-$N(C_1-C_6)$alkyl$_2$ group, or alternatively $R_7$ and $R_8$ form together with the carbon atom to which they are attached a $-(C_3-C_6)$cycloalkyl group or a $-(C_3-C_6)$heterocycloalkyl group;
- $R_9$ represents one or more substituents chosen, independently of each other, from: a hydrogen atom, —OH, a $-(C_1-C_4)$alkoxy group, a halogen atom, -$NH_2$, a -NH$(C_1-C_6)$alkyl group, a -N$(C_1-C_6)$alkyl$_2$ group, a -NH$(C_1-C_6)$cycloalkyl group, and a $(C_3-C_6)$heterocycloalkyl group;
- $R_{10}$ represents at least one substituent chosen from a hydrogen atom and a $-(C_1-C_4)$alkyl group;
- Y is selected from the group consisting of $-(C_1-C_6)$alkyl-$NR_{11}$-, $-(C_1-C_6)$alkyl-O-, $-C_1-C_6$)alkyl-S-, -C(=O)O-, -C(=O)NH-, $-(C_1-C_6)$alkyl-C(=O)O-, and $-(C_1-C_6)$alkyl-C(=O)NH-;
- L represents a linker; and
- $RCG_1$ represents a reactive chemical group present at the end of the linker, the linker L being of formula (IV);

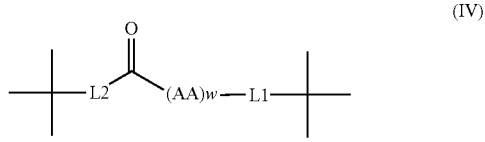

wherein;
L1 represents
a single bond or a -$NR_{16}$(hetero)aryl-$CR_{15}R_{14}$-O-C(=O)- group if Y is $-(C_1-C_6)$alkyl-$N(R_{11})$-, a -$NR_{18}$-$(C_2-C_6)$alkyl-$NR_{17}$-C(=O)- group or a -$NR_{16}$(hetero)aryl-$CR_{15}R_{14}$-O-C(=O)-$NR_{18}$-$(c_2$-$C_6)$alkyl-$NR_{17}$-C(=O)- group if Y is -$(c_1$-$c_6)$alkyl-O- or $-(C_1-C_6)$alkyl-S-, or
a -$NR_{16}$(hetero)aryl-$CR_{15}R_{14}$- group if Y is -C(=O) O-, -C(=O)NH-, $-(C_1-C_6)$ alkyl-C(=O)O- or $-(C_1-C_6)$alkyl-C(=O)NH-;
L1 is covalently bound to Y;
$R_{14}$, $R_{15}$, $R_{16}$, $R_{17}$ and $R_{18}$ each represent, independently of each other, a hydrogen atom or a $-(C_1-C_6)$ alkyl group;
$(AA)_w$ represents a sequence of W amino acids AA connected together via peptide bonds;
w represents an integer ranging from 1 to 12;
L2 represents a single bond, a $-(C_1-C_6)$alkyl group, a $-(C_1-C_6)$alkyl-$(OCH_2CH_2)_i$- group, a $-(C_1-C_6)$alkyl-$(OCH_2CH_2)_i$-O$(C_1-C_6)$alkyl- group, a $-(CH_2CH_2O)_i(c_1$-$C_6)$alkyl- group, a -CH$(SO_3H)$-$(C_1-C_6)$alkyl- group, a $-(C_1-C_6)$alkyl-CH$(SO_3H)$- group, a $-(C_1-C_6)$ alkyl-cyclohexyl- group, a -$NR_{19}$-$(C_1-C_6)$ alkyl- group, a -$NR_{20}$-$(CH_2CH_2O)_i(C_1-C_6)$alkyl- group, a -$NR_{21}$-aryl- group, a -$NR_{21}$-heteroaryl- group, a $-(C_1-C_6)$alkyl-$NR_{22}$C(=O)-$(C_1-C_6)$alkyl- group or a $-(C_1-C_6)$alkyl-$NR_{22}$C(=O)-$(C_1-C_6)$alkyl-$(OCH_2CH_2)_i$- group;
$R_{19}$, $R_{20}$, $R_{21}$ and $R_{22}$ each represent, independently of each other, a hydrogen atom or a $(c_1$-$C_6)$alkyl group;
L2 is covalently bound to RCG1;
i represents an integer between 1 and 50; and
each amino acid AA denotes a natural or unnatural amino acid, of configuration D or L,
G represents the product of reaction between RCG1, a reactive group present at the end of the linker and RCG2, an orthogonal reactive group present on Ab; and
Ab represents an antibody, comprising the steps of:
(i) placing in contact and leaving to react:
an optionally buffered aqueous solution of an antibody, optionally modified by means of a modifying agent, and
a solution of a compound of formula (II) as defined in claim 15, wherein the chemical group RCG1 of the compound of formula (II) is reactive towards the chemical group RCG2 present on the antibody especially towards the amino groups present on antibodies, the said chemical groups RCG2 having been introduced, where appropriate, by the modifying agent, so as to attach the compound of formula (II) to the antibody by formation of a covalent bond; and
(ii) optionally separating the conjugate formed in step (i) from the compound of formula (II) and/or from the unreacted antibody and/or from any aggregates that may have formed.

31. A medicament, wherein the medicament comprises a conjugate of formula (III)

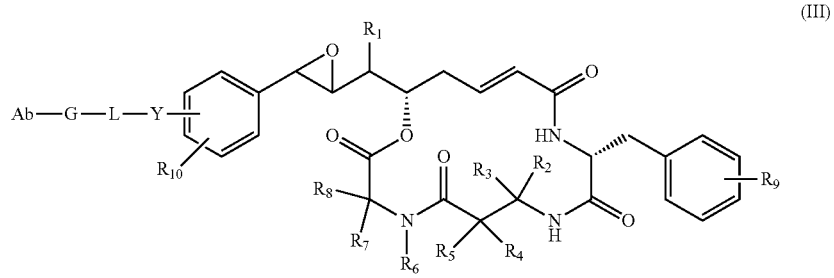

(III)

wherein $R_1$ represents a -($C_1$-$C_6$)alkyl group;

$R_2$ and $R_3$ represent, independently of each other, a hydrogen atom or a -($C_1$-$C_6$)alkyl group, or alternatively $R_2$ and $R_3$ form together with the carbon atom to which they are attached a -($C_3$-$C_6$)cycloalkyl group or a -($C_3$-$C_6$)heterocycloalkyl group;

$R_4$ and $R_5$ represent, independently of each other, a hydrogen atom, a -($C_1$-$C_6$)alkyl group, a -($C_1$-$C_6$)alkyl-NH($R_{12}$) group, a -($C_1$-$C_6$)alkyl-OH group, a -($C_1$-$C_6$)alkyl-SH group, or a -($C_1$-$C_6$)alkyl-$CO_2$H group, or alternatively $R_4$ and $R_5$ form together with the carbon atom to which they are attached a -($C_3$-$C_6$)cycloalkyl group or a -($C_3$-$C_6$)heterocycloalkyl group;

$R_6$ represents a hydrogen atom or a -($C_1$-$C_6$)alkyl group;

$R_7$ and $R_8$ represent, independently of each other, a hydrogen atom, a -($C_1$-$C_6$)alkyl group, a -($C_1$-$C_6$)alkyl-$CO_2$H group, or a -($C_1$-$C_6$)alkyl-N($C_1$-$C_6$)alkyl$_2$ group, or alternatively $R_7$ and $R_8$ form together with the carbon atom to which they are attached a -($C_3$-$C_6$)cycloalkyl group or a -($C_3$-$C_6$)heterocycloalkyl group;

$R_9$ represents one or more substituents chosen, independently of each other, from: a hydrogen atom, —OH, a -($C_1$-$C_4$)alkoxy group, a halogen atom, -$NH_2$, a -NH($C_1$-$C_6$)alkyl group, a -N($C_1$-$C_6$)alkyl$_2$ group, a -NH($C_1$-$C_6$)cycloalkyl group, and a ($C_3$-$C_6$)heterocycloalkyl group;

$R_{10}$ represents at least one substituent chosen from a hydrogen atom and a -($C_1$-$C_4$)alkyl group;

Y is selected from the group consisting of -($C_1$-$C_6$)alkyl-$NR_{11}$-, -($C_1$-$C_6$)alkyl-O-, -($C_1$-$C_6$)alkyl-S-, -C(=O)O-, -C(=O)NH-, -($C_1$-$C_6$)alkyl-C(=O)O-, and -($C_1$-$C_6$)alkyl-C(=O)NH-;

L represents a linker; and $RCG_1$ represents a reactive chemical group present at the end of the linker, the linker L being of formula (IV);

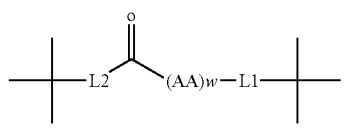

(IV)

wherein;

L1 represents a single bond or a -$NR_{16}$(hetero)aryl-$CR_{15}R_{14}$-O-C(=O)- group if Y is -($C_1$-$C_6$)alkyl-N($R_{11}$)-, a -$NR_{18}$-($C_2$-$C_6$)alkyl-$NR_{17}$-C(=O)- group or a -$NR_{16}$(hetero)aryl-$CR_{15}R_{14}$-O-C(=O)-$NR_{18}$-($C_2$-$C_6$)alkyl-$NR_{17}$-C(=O)- group if Y is -($C_1$-$C_6$)alkyl-O- or -($C_1$-$C_6$)alkyl-S-, or a -$NR_{16}$(hetero)aryl-$CR_{15}R_{14}$- group if Y is -C(=O)O-, -C(=O)NH-, -($C_1$-$C_6$) alkyl-C(=O)O- or -($C_1$-$C_6$)alkyl-C(=O)NH-;

L1 is covalently bound to Y;

$R_{14}$, $R_{15}$, $R_{16}$, $R_{17}$ and $R_{18}$ each represent, independently of each other, a hydrogen atom or a -($C_1$-$C_6$) alkyl group;

$(AA)_w$ represents a sequence of W amino acids AA connected together via peptide bonds;

w represents an integer ranging from 1 to 12;

L2 represents a single bond, a -($C_1$-$C_6$)alkyl group, a -($C_1$-$C_6$)alkyl-($OCH_2CH_2$)$_i$- group, a -($C_1$-$C_6$)alkyl-($OCH_2CH_2$)$_i$-O($C_1$-$C_6$)alkyl- group, a -($CH_2CH_2O$)$_i$($C_1$-$C_6$)alkyl- group, a -CH($SO_3H$)-($C_1$-$C_6$)alkyl- group, a -($C_1$-$C_6$)alkyl-CH($SO_3H$)- group, a -($C_1$-$C_6$) alkyl-cyclohexyl- group, a -$NR_{19}$-($C_1$-$C_6$) alkyl- group, a -$NR_{20}$-($CH_2CH_2O$)$_i$($C_1$-$C_6$)alkyl- group, a -$NR_{21}$-aryl- group, a -$NR_{21}$-heteroaryl- group, a -($C_1$-$C_6$)alkyl-$NR_{22}$C(=O)-($C_1$-$C_6$)alkyl- group or a -($C_1$-$C_6$)alkyl-$NR_{22}$C(=O)-($C_1$-$C_6$)alkyl-($OCH_2CH_2$)$_i$- group;

$R_{19}$, $R_{20}$, $R_{21}$ and $R_{22}$ each represent, independently of each other, a hydrogen atom or a ($C_1$-$C_6$)alkyl group;

L2 is covalently bound to RCG1;

i represents an integer between 1 and 50; and each amino acid AA denotes a natural or unnatural amino acid, of configuration D or L, G represents the product of reaction between RCG1, a reactive group present at the end of the linker and RCG2, an orthogonal reactive group present on Ab; and Ab represents an antibody.

32. A pharmaceutical composition, wherein the composition comprises a conjugate of formula (III)

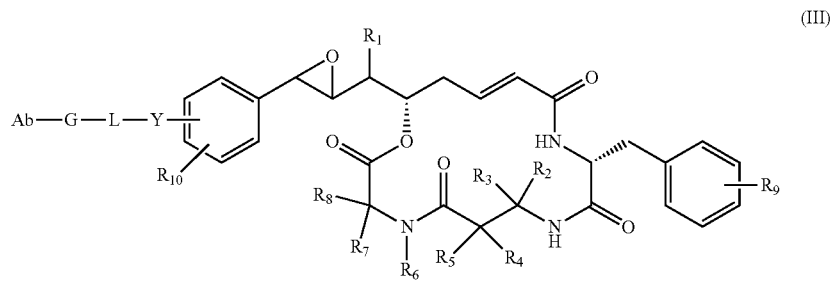

(III)

wherein $R_1$ represents a -($c_1$-$C_6$)alkyl group;

$R_2$ and $R_3$ represent, independently of each other, a hydrogen atom or a -($C_1$-$C_6$)alkyl group, or alternatively $R_2$ and $R_3$ form together with the carbon atom to which they are attached a -($C_3$-$C_6$)cycloalkyl group or a -($C_3$-$C_6$)heterocycloalkyl group;

$R_4$ and $R_5$ represent, independently of each other, a hydrogen atom, a -($C_1$-$C_6$)alkyl group, a -($C_1$-$C_6$)alkyl-NH($R_{12}$) group, a -($C_1$-$C_6$)alkyl-OH group, a -($C_1$-$C_6$) alkyl-SH group, or a -($C_1$-$C_6$)alkyl-$CO_2$H group, or alternatively $R_4$ and $R_5$ form together with the carbon atom to which they are attached a -($C_3$-$C_6$)cycloalkyl group or a -($C_3$-$C_6$)heterocycloalkyl group;

$R_6$ represents a hydrogen atom or a -($C_1$-$C_6$)alkyl group;

$R_7$ and $R_8$ represent, independently of each other, a hydrogen atom, a -($C_1$-$C_6$)alkyl group, a -($C_1$-$C_6$)alkyl-$CO_2$H group, or a -($C_1$-$C_6$)alkyl-N($C_1$-$C_6$)alkyl$_2$ group, or alternatively $R_7$ and $R_8$ form together with the carbon atom to which they are attached a -($C_3$-$C_6$) cycloalkyl group or a -($C_3$-$C_6$)heterocycloalkyl group;

$R_9$ represents one or more substituents chosen, independently of each other, from: a hydrogen atom, —OH, a -($C_1$-$C_4$)alkoxy group, a halogen atom, -$NH_2$, a -NH($C_1$-$C_6$)alkyl group, a -N($C_1$-$C_6$)alkyl$_2$ group , a -NH($C_1$-$C_6$)cycloalkyl group, and a ($C_3$-$C_6$)heterocycloalkyl group;

$R_{10}$ represents at least one substituent chosen from a hydrogen atom and a -($C_1$-$C_4$)alkyl group;

Y is selected from the group consisting of -($C_1$-$C_6$)alkyl-$NR_{11}$-, -($C_1$-$C_6$)alkyl-O-, -$C_1$-$C_6$)alkyl-S-, -C(=O)O-, -C(=O)NH-, -($C_1$-$C_6$)alkyl-C(=O)O-, and -($C_1$-$C_6$)alkyl-C(=O)NH-;

L represents a linker; and $RCG_1$ represents a reactive chemical group present at the end of the linker, the linker L being of formula (IV);

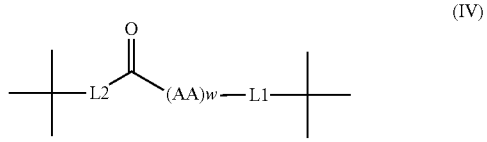

(IV)

wherein;

L1 represents a single bond or a -$NR_{16}$(hetero)aryl-$CR_{15}R_{14}$-O-C(=O)- group if Y is -($C_1$-$C_6$)alkyl-N($R_{11}$)-;

a -$NR_{18}$-($C_2$-$C_6$)alkyl-$NR_{17}$-C(=O)- group or a -$NR_{16}$(hetero)aryl-$CR_{15}R_{14}$-O-C(=O)-$NR_{18}$-($c_2$-$C_6$)alkyl-$NR_{17}$-C(=O)- group if Y is -($c_1$-$c_6$)alkyl-O- or -($C_1$-$C_6$)alkyl-S-, or a -$NR_{16}$(hetero)aryl-$CR_{15}R_{14}$- group if Y is -C(=O) O-, -C(=O)NH-, -($C_1$-$C_6$) alkyl-C(=O)O- or -($C_1$-$C_6$)alkyl-C(=O)NH-;

L1 is covalently bound to Y;

$R_{14}$, $R_{15}$, $R_{16}$, $R_{17}$ and $R_{18}$ each represent, independently of each other, a hydrogen atom or a -($C_1$-$C_6$) alkyl group;

$(AA)_w$ represents a sequence of W amino acids AA connected together via peptide bonds;

w represents an integer ranging from 1 to 12;

L2 represents a single bond, a -($C_1$-$C_6$)alkyl group, a -($C_1$-$C_6$)alkyl-($OCH_2CH_2$)$_i$- group, a -($C_1$-$C_6$)alkyl-($OCH_2CH_2$)$_i$-O($C_1$-$C_6$)alkyl- group, a -($CH_2CH_2O$)$_i$($c_1$-$C_6$)alkyl- group, a -CH($SO_3$H)-($C_1$-$C_6$) alkyl- group, a -($C_1$-$C_6$)alkyl-CH($SO_3$H)- group, a -($C_1$-$C_6$) alkyl-cyclohexyl- group, a -$NR_{19}$-($C_1$-$C_6$) alkyl- group, a -$NR_{20}$-($CH_2CH_2O$)$_i$($C_1$-$C_6$)alkyl-group, a -$NR_{21}$-aryl- group, a -$NR_{21}$-heteroaryl-group, a -($C_1$-$C_6$)alkyl-$NR_{22}$C(=O)-($C_1$-$C_6$)alkyl-group or a -($C_1$-$C_6$)alkyl-$NR_{22}$C(=O)-($C_1$-$C_6$)alkyl-($OCH_2CH_2$)$_i$- group;

$R_{19}$, $R_{20}$, $R_{21}$ and $R_{22}$ each represent, independently of each other, a hydrogen atom or a ($c_1$-$C_6$)alkyl group;

L2 is covalently bound to RCG1;

i represents an integer between 1 and 50; and each amino acid AA denotes a natural or unnatura amino acid, of configuration D or L, G represents the product of reaction between RCG1, a reactive group present at the end of the linker and RCG2, an orthogonal reactive group present on Ab; and Ab represents an antibody.

33. The compound of formula (I) according to claim 1, wherein:

$R_1$ represents a methyl group;

one of $R_2$ and $R_3$ represents a methyl group and the other one represents a hydrogen atom ;

each of $R_4$ and $R_5$ represents a methyl group;

$R_6$ represents a hydrogen atom;

$R_7$ and $R_5$ represent, independently of each other, a hydrogen atom or a -($C_1$-$C_6$)alkyl group;

$R_9$ represents two sub stituents independently of each other selected from a methoxy group and a chlorine atom;

W represents a -$CH_2$-$NH_2$ group or a -$CH_2$-OH group; and $R_{10}$ represents a hydrogen atom.

34. The compound of formula (II) according to claim 15, wherein $R_1$ represents a methyl group.

35. The compound of formula (II) according to claim 15, wherein:
   each of $R_2$ and $R_3$ represents a hydrogen atom, or
   one of $R_2$ and $R_3$ represents a methyl group and the other one represents a hydrogen atom, or
   $R_2$ and $R_3$ form together with the carbon atom to which they are attached a cyclopropyl group.

36. The compound of formula (II) according to claim 15, wherein each of $R_4$ and $R_5$ represents a methyl group.

37. The compound of formula (II) according to claim 15, wherein $R_6$ represents a hydrogen atom.

38. The compound of formula (II) according to claim 15, wherein $R_7$ and $R_5$ represent, independently of each other, a hydrogen atom or a -$(C_1-C_6)$alkyl group.

39. The compound of formula (II) according to claim 15, wherein $R_9$ represents two sub stituents independently of each other selected from a methoxy group and a chlorine atom.

40. The compound of formula (II) according to claim 15, wherein $R_{10}$ represents a hydrogen atom.

41. The compound of formula (II) according to claim 15, wherein:
   $R_1$ represents a -$(C_1-C_6)$alkyl group;
   each of $R_2$ and $R_3$ represents a hydrogen atom;
   $R_6$ represents a hydrogen atom;
   $R_9$ represents two substituents independently selected from a methoxy group and a chlorine atom; and
   $R_{10}$ represents a hydrogen atom.

42. The compound of formula (II) according to claim 15, wherein:
   $R_1$ represents a -$(C_1-C_6)$alkyl group;
   one of $R_2$ and $R_3$ represents a -$(C_1-C_6)$alkyl group, and the other one represents a hydrogen atom;
   $R_6$ represents a hydrogen atom;
   $R_9$ represents two sub stituents independently of each other selected from a methoxy group and a chlorine atom; and
   $R_{10}$ represents a hydrogen atom.

43. The compound of formula (II) according to claim 15, wherein:
   $R_1$ represents a methyl group;
   one of $R_2$ and $R_3$ represents a methyl group and the other one represents a hydrogen atom;
   each of $R_4$ and $R_5$ represents a methyl group;
   $R_6$ represents a hydrogen atom;
   $R_7$ and $R_5$ represent, independently of each other, a hydrogen atom or a -$(C_1-C_6)$alkyl group;
   $R_9$ represents two sub stituents independently of each other selected from a methoxy group and a chlorine atom;
   Y represents a -$CH_2$-$NH_2$ or a -$CH_2$-OH group; and
   $R_{10}$ represents a hydrogen atom.

44. The compound of formula (III) according to claim 24, wherein $R_1$ represents a methyl group.

45. The compound of formula (III) according to claim 24, wherein: each of $R_2$ and $R_3$ represents a hydrogen atom, or one of $R_2$ and $R_3$ represents a methyl group and the other one represents a hydrogen atom, or $R_2$ and $R_3$ form together with the carbon atom to which they are attached a cyclopropyl group.

46. The compound of formula (III) according to claim 24, wherein each of $R_4$ and $R_5$ represents a methyl group.

47. The compound of formula (III) according to claim 24, wherein $R_6$ represents a hydrogen atom.

48. The compound of formula (III) according to claim 24, wherein $R_7$ and $R_5$ represent, independently of each other, a hydrogen atom or a -$(C_1-C_6)$alkyl group.

49. The compound of formula (III) according to claim 24, wherein $R_9$ represents two sub stituents independently of each other selected from a methoxy group and a chlorine atom.

50. The compound of formula (III) according to claim 24, wherein $R_{10}$ represents a hydrogen atom.

51. The compound of formula (III) according to claim 24, wherein:
   $R_1$ represents a -$(C_1-C_6)$alkyl group;
   each of $R_2$ and $R_3$ represents a hydrogen atom;
   $R_6$ represents a hydrogen atom;
   $R_9$ represents two sub stituents independently of each other selected from a methoxy group and a chlorine atom; and
   $R_{10}$ represents a hydrogen atom.

52. The compound of formula (III) according to claim 24, wherein:
   $R_1$ represents a -$(C_1-C_6)$alkyl group;
   one of $R_2$ and $R_3$ represents a -$(C_1-C_6)$alkyl group, and the other one represents a hydrogen atom;
   $R_6$ represents a hydrogen atom;
   $R_9$ represents two sub stituents independently of each other selected from a methoxy group and a chlorine atom; and
   $R_{10}$ represents a hydrogen atom.

53. The compound of formula (III) according to claim 24, wherein:
   $R_1$ represents a methyl group;
   one of $R_2$ and $R_3$ represents a methyl group and the other one represents a hydrogen atom;
   each of $R_4$ and $R_5$ represents a methyl group;
   $R_6$ represents a hydrogen atom;
   $R_7$ and $R_5$ represent, independently of each other, a hydrogen atom or a -$(C_1-C_6)$alkyl group;
   $R_9$ represents two sub stituents independently of each other selected from a methoxy group and a chlorine atom;
   Y represents a -$CH_2$-$NH_2$ or a -$CH_2$-OH group; and
   $R_{10}$ represents a hydrogen atom.

* * * * *

UNITED STATES PATENT AND TRADEMARK OFFICE
CERTIFICATE OF CORRECTION

PATENT NO. : 10,941,139 B2  
APPLICATION NO. : 15/768792  
DATED : March 9, 2021  
INVENTOR(S) : Antony Bigot et al.

Page 1 of 3

It is certified that error appears in the above-identified patent and that said Letters Patent is hereby corrected as shown below:

In the Claims

Column 534, Claim 1, Line 55, cancel "-$C_1$-$C_6$)alkyl-NH($R_{11}$)" and insert -- -($C_1$-$C_6$)alkyl-NH($R_{11}$) --.

Column 539, Claim 15, Line 34-36, cancel "a -$NR_{16}$(hetero)aryl-$CR_{15}R_{14}$-O-C(=O)-$NR_{18}$-($_2$-$C_6$)alkyl-$NR_{17}$-C(=O)- group" and insert -- a -$NR_{16}$(hetero)aryl-$CR_{15}R_{14}$-O-C(=O)-$NR_{18}$-($C_2$-$C_6$)alkyl-NR17-C(=O)- group --;  
Line 37, cancel "-($C_1$-$C_6$)alkyl- -O-" and insert -- -($C_1$-$C_6$)alkyl- O- --;  
Line 41, cancel "$L_1$" and insert -- L1 --; and  
Line 62, cancel "a (Ci-C6)alkyl group;" and insert -- a ($C_1$-$C_6$)alkyl group; --.

Column 541, Claim 21, Lines 5-15 cancel: 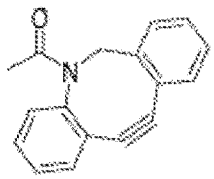 .

Column 542, Claim 21, Line 8, cancel "-$C_1$" and insert -- -CI --;

Line 8, cancel "a group" and insert -- a 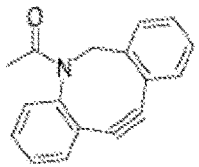 group --;  
Claim 22, Line 13, cancel "alkyl-($OCH_2CH_2$)- group," and insert -- alkyl-($OCH_2CH2$)$_1$- group, --.

Column 543, Claim 24, Line 58, cancel "-($c_1$-$C_6$)alkyl" and insert -- -($C_1$-$C_6$)alkyl --.

Column 544, Claim 24, Line 62, cancel "-$C_1$-$C_6$)alkyl-S-" and insert -- -($C_1$-$C_6$)alkyl-S- --.

Signed and Sealed this  
Twenty-eighth Day of November, 2023

*Katherine Kelly Vidal*

Katherine Kelly Vidal  
*Director of the United States Patent and Trademark Office*

CERTIFICATE OF CORRECTION (continued)
U.S. Pat. No. 10,941,139 B2

Column 545, Claim 24, Line 14, cancel "-NR$_{16}$(hetero)aryl-CR$_{15}$R$_{14}$-O-C(=O)-NR$_{18}$-(c$_2$-"
and insert -- -NR$_{16}$(hetero)aryl-CR$_{15}$R$_{14}$-O-C(=O)-NR$_{18}$-(C$_2$- --;
Line 15, cancel "-(c$_1$-c$_6$)alkyl-" and insert -- -(C$_1$-C$_6$)alkyl- --;
Lines 30-31, cancel "a -(CH$_2$CH$_2$O)$_i$(c$_1$-C$_6$)alkyl- group," and insert -- a -(CH$_2$CH$_2$O)$_i$(C$_1$-C$_6$)alkyl- group, --;
Line 33, cancel "a -NR$_{20}$-(CH$_2$CH$_2$O)$_i$(C$_1$-C$_6$)alkyl- group," and insert -- a -NR$_{20}$-(CH$_2$CH$_2$O)$_i$(C$_1$-C$_6$)alkyl- group, --;
Line 39, cancel "a (c$_1$-C$_6$)alkyl group" and insert -- a (C$_1$-C$_6$)alkyl group --; and
Line 42, "unnatura" should read "unnatural".

Column 546, Claim 27, Line 20, after "C=C" add -- , --.

Column 547, Claim 29, Line 5, the ";" in "AD3;" should be ":".

Column 549, Claim 30, Line 1, cancel "A compound for" and insert -- A method for --;
Line 18, cancel "a -(c$_1$-C$_6$)alkyl group" and insert -- a -(C$_1$-C$_6$)alkyl group --; and
Line 49, cancel "-C$_1$-C$_6$)alkyl-S-" and insert -- -(C$_1$-C$_6$)alkyl-S- --.

Column 550, Claim 30, Line 18, cancel "-NR$_{16}$(hetero)aryl-CR$_{15}$R$_{14}$-O-C(=O)-NR$_{18}$-(c$_2$-"
and insert -- -NR$_{16}$(hetero)aryl-CR$_{15}$R$_{14}$-O-C(=O)-NR$_{18}$-(C$_2$- --;
Line 19, cancel "-(c$_1$-c$_6$)alkyl-" and insert -- -(C$_1$-C$_6$)alkyl- --;
Line 33, cancel "a -(CH$_2$CH$_2$O)$_i$(c$_1$-C$_6$)alkyl- group" and insert -- a -(CH$_2$CH$_2$O)$_i$(C$_1$-C$_6$)alkyl- group --;
Line 37, cancel "a -NR$_{20}$-(CH$_2$CH$_2$O)$_i$(C$_1$-C$_6$)alkyl- group" and insert -- a -NR$_{20}$-(CH$_2$CH$_2$O)$_i$(C$_1$-C$_6$)alkyl- group --;
Line 45, cancel "unnatura" and insert -- unnatural --; and
Line 64, cancel "conjugate" and insert -- compound --.

Column 551, Claim 31, Line 1, cancel the text from "medicament" to "conjugate" and insert -- method of treating cancer in a patient in need thereof, comprising administering a therapeutically effective amount of a compound --;
Line 21, cancel "a -(c$_1$-C$_6$)alkyl group" and insert -- a -(C$_1$-C$_6$)alkyl group --; and
Line 53, cancel "-C$_1$-C$_6$)alkyl-S-" and insert -- -(C$_1$-C$_6$)alkyl-S- --.

Column 552, Claim 31, Lines 25-27, cancel "a -NR$_{16}$(hetero)aryl-CR$_{15}$R$_{14}$-O-C(=O)-NR$_{18}$-(c$_2$-C$_6$)alkyl-NR$_{17}$-C(=O)- group" and insert -- a -NR$_{16}$(hetero)aryl-CR$_{15}$R$_{14}$-O-C(=O)-NR$_{18}$-(C$_2$-C$_6$)alkyl-NR$_{17}$-C(=O)- group --
Lines 27-28, cancel "-(c$_1$-c$_6$)alkyl-O-" and insert -- -(C$_1$-C$_6$)alkyl-O --;
Line 46, cancel "a -(CH$_2$CH$_2$O)$_i$(c$_1$-C$_6$)alkyl- group" and insert -- a -(CH$_2$CH$_2$O)$_i$(C$_1$-C$_6$)alkyl- group --;
Line 50, cancel "a -NR$_{20}$-(CH$_2$CH$_2$O)$_i$(C$_1$-C$_6$)alkyl- group" and insert -- a -NR$_{20}$-(CH$_2$CH$_2$O)$_i$(C$_1$-C$_6$)alkyl- group --;
Line 56, cancel "a -(c$_1$-C$_6$)alkyl group" and insert -- a -(C$_1$-C$_6$)alkyl group --; and
Line 61, cancel "unnatura" and insert -- unnatural --.

CERTIFICATE OF CORRECTION (continued)
U.S. Pat. No. 10,941,139 B2

Column 553, Claim 32, Line 2, cancel "conjugate" and insert -- compound --;
Line 18, cancel "a -($c_1$-$C_6$)alkyl group" and insert -- a -($C_1$-$C_6$)alkyl group --; and
Line 49, cancel "-$C_1$-$C_6$)alkyl-S-" and insert -- -($C_1$-$C_6$)alkyl-S- --.

Column 554, Claim 32, Line 35, cancel "a -($CH_2CH_2O)_i(c_1$-$C_6$)alkyl- group" and insert
-- a -$(CH_2CH_2O)_i(C_1$-$C_6$)alkyl- group --;
Line 38, cancel "a -$NR_{20}$-$(CH_2CH_2O)_i(C_1$-$C_6$)alkyl- group" and insert -- a -$NR_{20}$-$(CH_2CH_2O)_i(C_1$-$C_6$)alkyl- group --;
Line 44, cancel "a -($c_1$-$C_6$)alkyl group" and insert -- a -($C_1$-$C_6$)alkyl group --;
Line 53, after "antibody", insert -- , and a pharmaceutically acceptable excipient --;
Claim 33, Line 61 cancel "$R_5$" and insert -- $R_8$ --; and
Line 63, cancel "sub stituent" and insert -- substituent --.

Column 555, Claim 38, Line 16, cancel "$R_5$" and insert -- $R_8$ --;
Claim 39, Line 18; cancel "sub stituent" and insert -- substituent --;
Claim 42, Line 38; cancel "substituent" and insert -- substituent --;
Claim 43, Line 49, cancel "$R_5$" and insert -- $R_8$ --; and
Line 51, cancel "sub stituent" and insert -- substituent --.

Column 556, Claim 48, Line 48, Line 13, cancel "$R_5$" and insert -- $R_8$ --;
Claim 49, Line 16 cancel "sub stituent" and insert -- substituent --;
Claim 51, Line 26 cancel "sub stituent" and insert -- substituent --;
Claim 52, Line 36 cancel "sub stituent" and insert -- substituent --;
Claim 53, Line 47, cancel "$R_5$" and insert -- $R_8$ --; and Line 49,
cancel "sub stituent" and insert -- substituent --.